US009458471B2

(12) United States Patent
Weiss et al.

(10) Patent No.: US 9,458,471 B2
(45) **Date of Patent: *Oct. 4, 2016**

(54) ENGINEERED CELLULAR PATHWAYS FOR PROGRAMMED AUTOREGULATION OF DIFFERENTIATION

(71) Applicant: The Trustees of Princeton University, Princeton, NJ (US)

(72) Inventors: Ron Weiss, Princeton, NJ (US); Ihor Lemischka, Princeton, NJ (US); Priscilla Purnick, West Windsor, NJ (US); Christoph Schaniel, New York, NY (US); Miles Miller, Indianapolis, IN (US); Patrick Guye, Rupperswil (CH)

(73) Assignee: The Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/174,475

(22) Filed: Feb. 6, 2014

(65) Prior Publication Data

US 2014/0234957 A1 Aug. 21, 2014

Related U.S. Application Data

(63) Continuation of application No. 12/312,197, filed as application No. PCT/US2007/023227 on Nov. 1, 2007, now Pat. No. 8,685,720.

(60) Provisional application No. 60/858,531, filed on Nov. 3, 2006, provisional application No. 60/905,483, filed on Mar. 7, 2007.

(51) Int. Cl.

| | |
|---|---|
| ***C12N 15/00*** | (2006.01) |
| ***C12N 15/11*** | (2006.01) |
| ***C12N 15/09*** | (2006.01) |
| ***C12N 15/85*** | (2006.01) |

(52) U.S. Cl.

CPC ........... *C12N 15/85* (2013.01); *C12N 2800/40* (2013.01); *C12N 2830/002* (2013.01); *C12N 2830/003* (2013.01); *C12N 2830/005* (2013.01); *C12N 2830/006* (2013.01); *C12N 2830/008* (2013.01); *C12N 2830/15* (2013.01); *C12N 2830/55* (2013.01); *C12N 2830/85* (2013.01)

(58) Field of Classification Search

CPC .............. C12N 15/85; C12N 2800/40; C12N 2830/002; C12N 2830/85

See application file for complete search history.

(56) References Cited

U.S. PATENT DOCUMENTS

| | | | | |
|---|---|---|---|---|
| 5,061,620 | A | 10/1991 | Tsukamoto et al. | 435/7.21 |
| 5,139,941 | A | 8/1992 | Muzyczka et al. | 435/456 |
| 5,166,065 | A | 11/1992 | Williams et al. | 435/377 |
| 5,173,414 | A | 12/1992 | Lebkowski et al. | 435/91.4 |
| 5,197,985 | A | 3/1993 | Caplan et al. | 128/898 |
| 5,225,347 | A | 7/1993 | Goldberg et al. | 435/320.1 |
| 5,226,914 | A | 7/1993 | Caplan et al. | 435/325 |
| 5,340,740 | A | 8/1994 | Petitte et al. | 435/349 |
| 5,453,357 | A | 9/1995 | Hogan | 435/7.21 |
| 5,486,359 | A | 1/1996 | Caplan et al. | 424/93.7 |
| 5,512,421 | A | 4/1996 | Burns et al. | 435/320.1 |
| 5,523,226 | A | 6/1996 | Wheeler | 435/325 |
| 5,589,376 | A | 12/1996 | Anderson et al. | 435/325 |
| 5,591,625 | A | 1/1997 | Gerson et al. | 435/366 |
| 5,654,183 | A | 8/1997 | Anderson et al. | 435/456 |
| 5,672,499 | A | 9/1997 | Anderson et al. | 435/353 |
| 5,686,120 | A | 11/1997 | Mertz et al. | 435/353 |
| 5,716,827 | A | 2/1998 | Tsukamoto et al. | 435/325 |
| 5,719,055 | A | 2/1998 | Cooper | 435/320.1 |
| 5,750,376 | A | 5/1998 | Weiss et al. | 435/69.52 |
| 5,750,397 | A | 5/1998 | Tsukamoto et al. | 435/372 |
| 5,843,742 | A | 12/1998 | Natsoulis et al. | 435/465 |
| 5,843,780 | A | 12/1998 | Thomson | 435/363 |

(Continued)

FOREIGN PATENT DOCUMENTS

| | | |
|---|---|---|
| EP | 0117058 | 9/1989 |
| WO | WO/88/05486 | 7/1988 |

(Continued)

OTHER PUBLICATIONS

Ko and Takahasi, Molecular components of the mammalian circadian clock, Human Molecular Genetics, 2006, vol. 15, Review Issue No. 2 R271-R277.*

Agrawal, S. et al. (1988) "Oligodeoxynucleoside phosphoramidates and phosphorothioates as inhibitors of human immunodeficiency virus," *Proceedings of the National Academy of Sciences* 85(19), 7079-7083.

Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.

Boshart, M. et al. (1985) "A very strong enhancer is located upstream of an immediate early gene of human cytomegalovirus," *Cell* 41(2), 521-530.

Bosslet, K. et al. (1998) "Elucidation of the Mechanism Enabling Tumor Selective Prodrug Monotherapy," *Cancer Research* 58(6), 1195-1201.

(Continued)

*Primary Examiner* — Maria Marvich

(74) *Attorney, Agent, or Firm* — Medlen & Carroll, LLP

(57) ABSTRACT

The present invention provides compositions and methods for programming mammalian cells to perform desired functions. In particular, the present invention provides compositions and methods for programming stem cells to differentiate into a desired cell type. A quorum sensing systems that regulates the expression of cell fate regulators is introduced into mammalian host cells, such as stem cells. The quorum sensing systems generally comprises vectors that express the components of a bacterial quorum sensing pathway, including proteins which catalyze the synthesis of an autoinducer and a gene encoding a regulatory partner of the autoinducer, and vectors in which genes encoding cell fate regulators are operably linked to a promoter induced by the autoinducer/regulatory partner complex. The system can also comprise vectors in which genes encoding additional cell fate regulators are operably linked to a promoter that is induced by a factor synthesized in response to a first stage of differentiation, so that a second stage of differentiation is triggered.

6 Claims, 153 Drawing Sheets

(56) References Cited

U.S. PATENT DOCUMENTS

| | | | | |
|---|---|---|---|---|
| 5,849,553 | A | 12/1998 | Anderson et al. | 435/467 |
| 5,914,267 | A | 6/1999 | Mertz et al. | 435/320.1 |
| 5,958,775 | A | 9/1999 | Wickstrom et al. | 435/455 |
| 5,965,443 | A | 10/1999 | Reznikoff et al. | 435/473 |
| 5,968,785 | A | 10/1999 | Devine et al. | 435/91.41 |
| 5,968,829 | A | 10/1999 | Carpenter | 435/467 |
| 5,994,136 | A | 11/1999 | Naldini et al. | 435/455 |
| 6,013,516 | A | 1/2000 | Verma et al. | 435/325 |
| 6,027,722 | A | 2/2000 | Hodgson | 424/93.21 |
| 6,136,597 | A | 10/2000 | Hope et al. | 435/325 |
| 6,200,806 | B1 | 3/2001 | Thomson | 435/325 |
| 6,518,066 | B1 * | 2/2003 | Oulmassov | C12N 15/81 435/468 |
| 8,685,720 | B2 * | 4/2014 | Weiss et al. | 435/320.1 |
| 2004/0043924 | A1 | 3/2004 | Narhi et al. | 435/69.1 |
| 2006/0019922 | A1 | 1/2006 | Juliano et al. | 514/44 |
| 2006/0178430 | A1 * | 8/2006 | Blackwell | C07D 307/33 514/471 |

FOREIGN PATENT DOCUMENTS

| | | |
|---|---|---|
| WO | WO/92/01070 | 1/1992 |
| WO | WO/92/22584 | 12/1992 |
| WO | WO/93/03143 | 2/1993 |
| WO | WO/93/03769 | 3/1993 |
| WO | WO/99/14310 | 3/1999 |

OTHER PUBLICATIONS

Bradley, A. et al. (1984) "Formation of germ-line chimaeras from embryo-derived teratocarcinoma cell lines," *Nature* 309(5965), 255-256.
Burns, J. C. et al. (1993) "Vesicular stomatitis virus G glycoprotein pseudotyped retroviral vectors: concentration to very high titer and efficient gene transfer into mammalian and nonmammalian cells," *Proceedings of the National Academy of Sciences* 90(17), 8033-8037.
Burt, R. K. et al. (2004) "Embryonic Stem Cells as an Alternate Marrow Donor Source: Engraftment without Graft-Versus-Host Disease," *The Journal of Experimental Medicine* 199(7), 895-904.
Carter, B. J. (1992) "Adeno-associated virus vectors," *Current Opinion in Biotechnology* 3(5), 533-539.
Cech, T. R. et al. (1992) "RNA catalysis by a group I ribozyme. Developing a model for transition state stabilization," *Journal of Biological Chemistry* 267(25), 17479-17482.
Collins, C. A. et al. (2005) "Self-Renewal of the Adult Skeletal Muscle Satellite Cell," *Cell Cycle* 4(10), 1338-1341.
Couper, J. J. et al. (2003) "2: Recent advances in therapy of diabetes," *The Medical Journal of Australia* 179(8), 441-447.
Craig, N. L. (1996) "Transposon Tn7," *Current Topics in Microbiology and Immunology* 204, 27-48.
De La Cruz, N. B. et al. (1993) "Characterization of the Tn5 transposase and inhibitor proteins: a model for the inhibition of transposition," *Journal of Bacteriology* 175(21), 6932-6938.
Dijkema, R. et al. (1985) "Cloning and expression of the chromosomal immune interferon gene of the rat," *The EMBO Journal* 4(3), 761-767.
Doetschman, T. et al. (1988) "Establishment of hamster blastocyst-derived embryonic stem (ES) cells," *Developmental Biology* 127(1), 224-227.
Drubin, D. A. et al. (2007) "Designing biological systems," *Genes & Development* 21(3), 242-254.
Evans, M. J. et al. (1981) "Establishment in culture of pluripotential cells from mouse embryos," *Nature* 292(5819), 154-156.
Evans, M. J. et al. (1990) "Derivation and preliminary characterization of pluripotent cell lines from porcine and bovine blastocysts," *Theriogenology* 33(1), 125-128.
Giles, J. et al. (1993) "Pluripotency of cultured rabbit inner cell mass cells detected by isozyme analysis and eye pigmentation of fetuses following injection into blastocysts or morulae," *Molecular Reproduction and Development* 36(2), 130-138.
Gluckman, E. (2001) "Hematopoietic Stem-Cell Transplants Using Umbilical-Cord Blood," *New England Journal of Medicine* 344(24), 1860-1861.
Gorman, C. M. et al. (1982) "The Rous sarcoma virus long terminal repeat is a strong promoter when introduced into a variety of eukaryotic cells by DNA-mediated transfection," *Proceedings of the National Academy of Sciences of the United States of America* 79(22), 6777-6781.
Graham, F. L. et al. (1977) "Characteristics of a Human Cell Line Transformed by DNA from Human Adenovirus Type 5," *Journal of General Virology* 36(1), 59-72.
Graves, K. et al. (1993) "Derivation and characterization of putative pluripotential embryonic stem cells from preimplantation rabbit embryos," *Molecular Reproduction and Development* 36(4), 424-433.
Gray, G. L. et al. (1985) "Periplasmic production of correctly processed human growth hormone in *Escherichia coli*: natural and bacterial signal sequences are interchangeable," *Gene* 39(2-3), 247-254.
Haller, A. A. et al. (1992) "Linker scanning mutagenesis of the internal ribosome entry site of poliovirus RNA," *Journal of Virology* 66(8), 5075-5086.
Han, L. et al. (1991) "Inhibition of Moloney murine leukemia virus-induced leukemia in transgenic mice expressing antisense RNA complementary to the retroviral packaging sequences," *Proceedings of the National Academy of Sciences* 88(10), 4313-4317.
Heikkila, R. et al. (1987) "A c-myc antisense oligodeoxynucleotide inhibits entry into S phase but not progress from G0 to G1," *Nature* 328(6129), 445-449.
Hélène, C. et al. (1990) "Specific regulation of gene expression by antisense, sense and antigene nucleic acids," *Biochimica et Biophysica Acta (BBA)—Gene Structure and Expression* 1049(2), 99-125.
Hochedlinger, K. et al. (2003) "Nuclear Transplantation, Embryonic Stem Cells, and the Potential for Cell Therapy," *New England Journal of Medicine* 349(3), 275-286.
Iannaccone, P. M. et al. (1994) "Pluripotent Embryonic Stem Cells from the Rat are Capable of Producing Chimeras," *Developmental Biology* 163(1), 288-292.
Jang, S. K. et al. (1988) "A segment of the 5' nontranslated region of encephalomyocarditis virus RNA directs internal entry of ribosomes during in vitro translation," *Journal of Virology* 62(8), 2636-2643.
Kim, D. W. et al. (1990) "Use of the human elongation factor 1α promoter as a versatile and efficient expression system," *Gene* 91(2), 217-223.
Kotin, R. M. (1994) "Prospects for the Use of Adeno-Associated Virus as a Vector for Human Gene Therapy," *Human Gene Therapy* 5(7), 793-801.
Ku, H. T. et al. (2004) "Committing Embryonic Stem Cells to Early Endocrine Pancreas In Vitro," *Stem Cells* 22(7), 1205-1217.
Lagasse, E. et al. (2001) "Toward Regenerative Medicine," *Immunity* 14(4), 425-436.
Larson, R. S. et al. (1990) "The leukocyte integrin LFA-1 reconstituted by cDNA transfection in a nonhematopoietic cell line is functionally active and not transiently regulated," *Cell Regulation* 1(4), 359-367.
Lebkowski, J. S. et al. (1988) "Adeno-associated virus: a vector system for efficient introduction and integration of DNA into a variety of mammalian cell types," *Molecular and Cellular Biology* 8(10), 3988-3996.
Mandell, J. G. et al. (2006) "Zinc Finger Tools: custom DNA-binding domains for transcription factors and nucleases," *Nucleic Acids Research* 34(suppl 2), W516-W523.
Markowitz, D. et al. (1988) "A safe packaging line for gene transfer: separating viral genes on two different plasmids," *Journal of Virology* 62(4), 1120-1124.
Martial, J. A. et al. (1979) "Human growth hormone: complementary DNA cloning and expression in bacteria," *Science* 205(4406), 602-607.
Martin, G. R. (1981) "Isolation of a pluripotent cell line from early mouse embryos cultured in medium conditioned by teratocarcinoma stem cells," *Proceedings of the National Academy of Sciences of the United States of America* 78(12), 7634-7638.

(56) References Cited

OTHER PUBLICATIONS

Mastromarino, P. et al. (1987) "Characterization of Membrane Components of the Erythrocyte Involved in Vesicular Stomatitis Virus Attachment and Fusion at Acidic pH," *Journal of General Virology* 68(9), 2359-2369.
Mather, J. P. (1980) "Establishment and Characterization of Two Distinct Mouse Testicular Epithelial Cell Lines," *Biology of Reproduction* 23(1), 243-252.
Mather, J. P. et al. (1982) "Culture of Testicular Cells in Hormone-Supplemented Serum-Free Medium," *Annals of the New York Academy of Sciences* 383(1), 44-68.
Meyer, K. et al. (1995) "Interaction of eukaryotic initiation factor eIF-4B with a picornavirus internal translation initiation site," *Journal of Virology* 69(5), 2819-2824.
Miller, A. D. et al. (1986) "Redesign of retrovirus packaging cell lines to avoid recombination leading to helper virus production," *Molecular and Cellular Biology* 6(8), 2895-2902.
Mizushima, S. et al. (1990) "pEF-BOS, a powerful mammalian expression vector," *Nucleic Acids Research* 18(17), 5322.
Morisato, D. et al. (1987) "Tn10 transposition and circle formation in vitro," *Cell* 51(1), 101-111.
Muzyczka, N. (1992) "Use of adeno-associated virus as a general transduction vector for mammalian cells," *Current Topics in Microbiology and Immunology* 158, 97-129.
Nagy, A. et al. (1990) "Embryonic stem cells alone are able to support fetal development in the mouse," *Development* 110(3), 815-821.
Programmed Differentiation of Mouse Embryonic Stem Cells Using Artificial Signaling Pathways dated Oct. 2006.
Ritz-Laser, B. et al. (2005) "The Zinc Finger-Containing Transcription Factor Gata-4 is Expressed in the Developing Endocrine Pancreas and Activates Glucagon Gene Expression," *Molecular Endocrinology* 19(3), 759-770.
Sambrook, J. et al. (1989) in *Molecular Cloning: A Laboratory Manual* (Sambrook, J., et al., Eds.) 2nd ed., pp. 16.07-16.08, Cold Spring Harbor Laboratory Press, New York.
Sambrook, J. et al. (1989) in *Molecular Cloning: A Laboratory Manual* (Sambrook, J., et al., Eds.) 2nd ed., pp. 16.19-16.15, Cold Spring Harbor Laboratory Press, New York.
Scheper, G. C. et al. (1994) "Binding of eukaryotic initiation factor-2 and trans-acting factors to the 5' untranslated region of encephalomyocarditis virus RNA," *Biochimie* 76(8), 801-809.
Seshagiri, P. B. et al. (1993) "Non-surgical uterine flushing for the recovery of preimplantation embryos in rhesus monkeys: Lack of seasonal infertility," *American Journal of Primatology* 29(2), 81-91.
Shapiro, A. M. J. et al. (2006) "International Trial of the Edmonton Protocol for Islet Transplantation," *New England Journal of Medicine* 355(13), 1318-1330.
Shelling, A. N. et al. (1994) "Targeted integration of transfected and infected adeno-associated virus vectors containing the neomycin resistance gene," *Gene Therapy* 1(3), 165-169.
Shiner, E. K. et al. (2004) "Construction of a bacterial autoinducer detection system in mammalian cells," *Biological Procedures Online* 6, 268-276.
Soria, B. (2001) "In-vitro differentiation of pancreatic β-cells," *Differentiation* 68(4-5), 205-219.
Sukoyan, M. A. et al. (1992) "Isolation and cultivation of blastocyst-derived stem cell lines from American mink (*Mustela vison*)," *Molecular Reproduction and Development* 33(4), 418-431.
Sukoyan, M. A. et al. (1993) "Embryonic stem cells derived from morulae, inner cell mass, and blastocysts of mink: comparisons of their pluripotencies," *Molecular Reproduction and Development* 36(2), 148-158.
Thomson, J. A. et al. (1994) "Nonsurgical uterine stage preimplantation embryo collection from the common marmoset," *Journal of Medical Primatology* 23(6), 333-336.
Uetsuki, T. et al. (1989) "Isolation and characterization of the human chromosomal gene for polypeptide chain elongation factor-1 alpha," *Journal of Biological Chemistry* 264(10), 5791-5798.
Uhlmann, E. et al. (1990) "Antisense oligonucleotides: a new therapeutic principle," *Chemical Reviews* 90, 543-584.
Vincent, K. A. et al. (1990) "Replication and packaging of HIV envelope genes in a novel adeno-associated virus vector system," *Vaccines* (*Cold Spring Harbor*) 90, 353-359.
Voss, S. D. et al. (1986) "The role of enhancers in the regulation of cell-type-specific transcriptional control," *Trends in Biochemical Sciences* 11(7), 287-289.
Waters, C. M. et al. (2005) "Quorum Sensing: Cell-to-Cell Communication in Bacteria," *Annual Review of Cell and Developmental Biology* 21(1), 319-346.
Weber, W. et al. (2003) "Streptomyces-derived quorum-sensing systems engineered for adjustable transgene expression in mammalian cells and mice," *Nucleic Acids Research* 31(14), e71.
Weissman, I. L. (2000) "Translating Stem and Progenitor Cell Biology to the Clinic: Barriers and Opportunities," *Science* 287(5457), 1442-1446.
Zhou, S. Z. et al. (1994) "Adeno-associated virus 2-mediated high efficiency gene transfer into immature and mature subsets of hematopoietic progenitor cells in human umbilical cord blood," *Journal of Experimental Medicine* 179(6), 1867-1875.
Zwizinski, C. et al. (1980) "Purification and characterization of leader (signal) peptidase from *Escherichia coli*," *Journal of Biological Chemistry* 255(16), 7973-7977.

* cited by examiner

- AHL + AHL

MAMMALIAN RECEIVERS

MyoD (MYOBLASTS) PPAR (ADIPOCYTES) Nanog (SELF-RENEWAL)

mES CELL DIFFERENTIATION shRNA AND DIFFERENTIATION

ENRICHED POPULATION

SEQ ID NO:01:
cggccatcgataaggatccgcccctctccctcccccccccctaacgttactggccgaagccgcttgg
aataaggccggtgtgcgtttgtctatatgttattttccaccatattgccgtcttttggcaatgtgag
ggcccggaaacctggccctgtcttcttgacgagcattcctaggggtctttcccctctcgccaaagga
atgcaaggtctgttgaatgtcgtgaaggaagcagttcctctggaagcttcttgaagacaaacaacgt
ctgtagcgaccctttgcaggcagcggaaccccccacctggcgacaggtgcctctgcggccaaaagcc
acgtgtataagatacacctgcaaaggcggcacaaccccagtgccacgttgtgagttggatagttgtg
gaaagagtcaaatggctctcctcaagcgtattcaacaaggggctgaaggatgcccagaaggtacccc
attgtatgggatctgatctggggcctcggtgcacatgctttacatgtgtttagtcgaggttaaaaa
acgtctaggccccccgaaccacggggacgtggttttcctttgaaaaacacgatgataatatggccac
aaccatggcctcctccgaggacgtcatcaaggagttcatgcgcttcaaggtgcgcatggagggctcc
gtgaacggccacgagttcgagatcgagggcgagggcgagggccgcccctacgagggcacccagaccg
ccaagctgaaggtgaccaagggcggccccctgcccttcgcctgggacatcctgtcccccagttcca
gtacggctccaaggtgtacgtgaagcaccccgccgacatccccgactacaagaagctgtccttcccc
gagggcttcaagtgggagcgcgtgatgaacttcgaggacggcggcgtggtgaccgtgacccaggact
cctccctgcaggacggctccttcatctacaaggtgaagttcatcggcgtgaacttcccctccgacgg
ccccgtaatgcagaagaagactatgggctgggaggcctccaccgagcgcctgtaccccgcgacggc
gtgctgaagggcgagatccacaaggccctgaagctgaaggacggcggccactacctggtggagttca
agtccatctacatggccaagaagcccgtgcagctgcccggctactactacgtggactccaagctgga
catcacctcccacaacgaggactacaccatcgtggagcagtacgagcgcgccgagggccgccaccac
ctgttcctgtaggcggccgcaatcaacctctggattacaaaatttgtgaaagattgactggtattct
taactatgttgctccttttacgctatgtggatacgctgctttaatgcctttgtatcatgctattact
tcccgtacggctttcattttctcctccttgtataaatcctggttgctgtctctttatgaggagttgt
ggcccgttgtcaggcaacgtggcgtggtgtgcactgtgtttgctgacgcaacccccactggttgggg
cattgccaccacctatcaactcctttccgggactttcgctttccccctccctattgccacggcggaa
ctcattgccgcctgccttgcccgctgctggacaggggctcggctgttgggcactgacaattccgtgg
tgttgtcggggaagctgacgtcctttccatggctgctcgcctgtgttgccaactggattctgcgcgg
gacgtccttctgctacgtcccttcggccctcaatccagcggaccttccttcccgcggcctgctgccg
gttctgcggcctcttccgcgtcttcgccttcgccctcagacgagtcggatctccctttgggccgcct
ccccgcctgcctgcaggtttgtcgagacctagaaaaacatggagcaatcacaagtagcaatacagca
gctaccaatgctgattgtgcctggctagaagcacaagaggaggaggaggtgggttttccagtcacac
ctcaggtacctttaagaccaatgacttacaaggcagctgtagatcttagccactttttaaaagaaaa
ggggggactggaagggctaattcactcccaacgaagacaagatctgcttttttgcttgtactgggtct
ctctggttagaccagatctgagcctgggagctctctggctaactagggaacccactgcttaagcctc
aataaagcttgccttgagtgcttcaagtagtgtgtgcccgtctgttgtgtgactctggtaactagag
atccctcagacccttttagtcagtgtggaaaatctctagcagggcccgtttaaacccgctgatcagc
ctcgactgtgccttctagttgccagccatctgttgtttgcccctcccccgtgccttccttgaccctg
gaaggtgccactcccactgtcctttcctaataaaatgaggaaattgcatcgcattgtctgagtaggt
gtcattctattctggggggtggggtggggcaggacagcaagggggaggattgggaagacaatagcag
gcatgctggggatgcggtgggctctatggcttctgaggcggaaagaaccagctggggctctagggggg
tatccccacgcgccctgtagcggcgcattaagcgcggcgggtgtggtggttacgcgcagcgtgaccg
ctacacttgccagcgccctagcgcccgctcctttcgctttcttcccttcctttctcgccacgttcgc
cggctttccccgtcaagctctaaatcggggcatccctttagggttccgatttagtgctttacggcac
ctcgaccccaaaaaacttgattagggtgatggttcacgtagtgggccatcgccctgatagacggttt
ttcgccctttgacgttggagtccacgttctttaatagtggactcttgttccaaactggaacaacact
caaccctatctcggtctattcttttgatttataagggattttggggatttcggcctattggttaaaa
aatgagctgatttaacaaaaatttaacgcgaattaattctgtggaatgtgtgtcagttagggtgtgg
aaagtccccaggctccccaggcaggcagaagtatgcaaagcatgcatctcaattagtcagcaaccag
gtgtggaaagtccccaggctccccagcaggcagaagtatgcaaagcatgcatctcaattagtcagca
accatagtcccgcccctaactccgcccatcccgcccctaactccgcccagttccgcccattctccgc
cccatggctgactaatttttttatttatgcagaggccgaggccgcctctgcctctgagctattcca

FIG 5 gaagtagtgaggaggcttttttggaggcctaggcttttgcaaaaagctcccgggagcttgtatatcc
attttcggatctgatcagcacgtgttgacaattaatcatcggcatagtatatcggcatagtataata
cgacaaggtgaggaactaaaccatggccaagttgaccagtgccgttccggtgctcaccgcgcgcgac
gtcgccggagcggtcgagttctggaccgaccggctcgggttctcccgggacttcgtggaggacgact
tcgccggtgtggtccgggacgacgtgaccctgttcatcagcgcggtccaggaccaggtggtgccgga
caacaccctggcctgggtgtgggtgcgcggcctggacgagctgtacgccgagtggtcggaggtcgtg
tccacgaacttccgggacgcctccgggccggccatgaccgagatcggcgagcagccgtgggggcggg
agttcgccctgcgcgacccggccggcaactgcgtgcacttcgtggccgaggagcaggactgacacgt
gctacgagatttcgattccaccgccgccttctatgaaaggttgggcttcggaatcgttttccgggac
gccggctggatgatcctccagcgcggggatctcatgctggagttcttcgcccaccccaacttgttta
ttgcagcttataatggttacaaataaagcaatagcatcacaaatttcacaaataaagcatttttttc
actgcattctagttgtggtttgtccaaactcatcaatgtatcttatcatgtctgtataccgtcgacc
tctagctagagcttggcgtaatcatggtcatagctgtttcctgtgtgaaattgttatccgctcacaa
ttccacacaacatacgagccggaagcataaagtgtaaagcctggggtgcctaatgagtgagctaact
cacattaattgcgttgcgctcactgcccgctttccagtcgggaaacctgtcgtgccagctgcattaa
tgaatcggccaacgcgcggggagaggcggtttgcgtattgggcgctcttccgcttcctcgctcactg
actcgctgcgctcggtcgttcggctgcggcgagcggtatcagctcactcaaaggcggtaatacggtt
atccacagaatcaggggataacgcaggaaagaacatgtgagcaaaaggccagcaaaaggccaggaac
cgtaaaaaggccgcgttgctggcgtttttccataggctccgcccccctgacgagcatcacaaaaatc
gacgctcaagtcagaggtggcgaaacccgacaggactataaagataccaggcgtttccccctggaag
ctccctcgtgcgctctcctgttccgaccctgccgcttaccggatacctgtccgcctttctcccttcg
ggaagcgtggcgctttctcaatgctcacgctgtaggtatctcagttcggtgtaggtcgttcgctcca
agctgggctgtgtgcacgaaccccccgttcagcccgaccgctgcgccttatccggtaactatcgtct
tgagtccaacccggtaagacacgacttatcgccactggcagcagccactggtaacaggattagcaga
gcgaggtatgtaggcggtgctacagagttcttgaagtggtggcctaactacggctacactagaagga
cagtatttggtatctgcgctctgctgaagccagttaccttcggaaaaagagttggtagctcttgatc
cggcaaacaaaccaccgctggtagcggtggtttttttgtttgcaagcagcagattacgcgcagaaaa
aaaggatctcaagaagatcctttgatcttttctacggggtctgacgctcagtggaacgaaaactcac
gttaagggattttggtcatgagattatcaaaaaggatcttcacctagatccttttaaattaaaaatg
aagttttaaatcaatctaaagtatatatgagtaaacttggtctgacagttaccaatgcttaatcagt
gaggcacctatctcagcgatctgtctatttcgttcatccatagttgcctgactccccgtcgtgtaga
taactacgatacgggagggcttaccatctggccccagtgctgcaatgataccgcgagacccacgctc
accggctccagatttatcagcaataaaccagccagccggaagggccgagcgcagaagtggtcctgca
actttatccgcctccatccagtctattaattgttgccgggaagctagagtaagtagttcgccagtta
atagtttgcgcaacgttgttgccattgctacaggcatcgtggtgtcacgctcgtcgtttggtatggc
ttcattcagctccggttcccaacgatcaaggcgagttacatgatcccccatgttgtgcaaaaaagcg
gttagctccttcggtcctccgatcgttgtcagaagtaagttggccgcagtgttatcactcatggtta
tggcagcactgcataattctcttactgtcatgccatccgtaagatgcttttctgtgactggtgagta
ctcaaccaagtcattctgagaatagtgtatgcggcgaccgagttgctcttgcccggcgtcaatacgg
gataataccgcgccacatagcagaactttaaaagtgctcatcattggaaaacgttcttcggggcgaa
aactctcaaggatcttaccgctgttgagatccagttcgatgtaacccactcgtgcacccaactgatc
ttcagcatcttttactttcaccagcgtttctgggtgagcaaaaacaggaaggcaaaatgccgcaaaa
aagggaataagggcgacacggaaatgttgaatactcatactcttcctttttcaatattattgaagca
tttatcagggttattgtctcatgagcggatacatatttgaatgtatttagaaaaataaacaaatagg
ggttccgcgcacatttccccgaaaagtgccacctgacgtcgacggatcgggagatctcccgatcccc
tatggtgcactctcagtacaatctgctctgatgccgcatagttaagccagtatctgctccctgcttg
tgtgttggaggtcgctgagtagtgcgcgagcaaaatttaagctacaacaaggcaaggcttgaccgac
aattgcatgaagaatctgcttagggttaggcgttttgcgctgcttcgcgatgtacgggccagatata
cgcgttgacattgattattgactagttattaatagtaatcaattacggggtcattagttcatagccc
atatatggagttccgcgttacataacttacggtaaatggcccgcctggctgaccgcccaacgacccc
cgcccattgacgtcaataatgacgtatgttcccatagtaacgccaatagggactttccattgacgtc

FIG 5 CONT aatgggtggactatttacggtaaactgcccacttggcagtacatcaagtgtatcatatgccaagtac
gccccctattgacgtcaatgacggtaaatggcccgcctggcattatgcccagtacatgaccttatgg
gactttcctacttggcagtacatctacgtattagtcatcgctattaccatggtgatgcggttttggc
agtacatcaatgggcgtggatagcggtttgactcacggggatttccaagtctccaccccattgacgt
caatgggagtttgttttggcaccaaaatcaacgggactttccaaaatgtcgtaacaactccgcccca
ttgacgcaaatgggcggtaggcgtgtacggtgggaggtctatataagcagagctctctggctaacta
gagaacccactgcttactggcttatcgaaattaatacgactcactatagggagacccaagctggttt
aaacttaagcttggtaccgagctcactagtccagtgtggtggcagatatccagcacagtggcggccg
ctcgagtctagagggcccgtttgcctgtactgggtctctctggttagaccagatctgagcctggga
gctctctggctaactagggaacccactgcttaagcctcaataaagcttgccttgagtgcttcaagta
gtgtgtgcccgtctgttgtgtgactctggtaactagagatccctcagacccttttagtcagtgtgga
aaatctctagcagtggcgcccgaacagggacttgaaagcgaaagggaaaccagaggagctctctcga
cgcaggactcggcttgctgaagcgcgcacggcaagaggcgaggggcggcgactggtgagtacgccaa
aaatttgactagcggaggctagaaggagagagatgggtgcgagagcgtcagtattaagcgggggag
aattagatcgcgatgggaaaaaattcggttaaggccagggggaaagaaaaaatataaattaaaacat
atagtatgggcaagcagggagctagaacgattcgcagttaatcctggcctgttagaaacatcagaag
gctgtagacaaatactgggacagctacaaccatcccttcagacaggatcagaagaacttagatcatt
atataatacagtagcaaccctctattgtgtgcatcaaaggatagagataaaagacaccaaggaagct
ttagacaagatagaggaagagcaaaacaaaagtaagaccaccgcacagcaagcggccgctgatcttc
agacctggaggaggagatatgagggacaattggagaagtgaattatataaatataaagtagtaaaaa
ttgaaccattaggagtagcacccaccaaggcaaagagaagagtggtgcagagagaaaaaagagcagt
gggaataggagctttgttccttgggttcttgggagcagcaggaagcactatgggcgcagcgtcaatg
acgctgacggtacaggccagacaattattgtctggtatagtgcagcagcagaacaatttgctgaggg
ctattgaggcgcaacagcatctgttgcaactcacagtctggggcatcaagcagctccaggcaagaat
cctggctgtggaaagatacctaaaggatcaacagctcctggggatttggggttgctctggaaaactc
atttgcaccactgctgtgccttggaatgctagttggagtaataaatctctggaacagatttggaatc
acacgacctggatggagtgggacagagaaattaacaattacacaagcttaatacactccttaattga
agaatcgcaaaaccagcaagaaaagaatgaacaagaattattggaattagataaatgggcaagtttg
tggaattggtttaacataacaaattggctgtggtatataaaattattcataatgatagtaggaggct
tggtaggtttaagaatagtttttgctgtactttctatagtgaatagagttaggcagggatattcacc
attatcgtttcagacccacctcccaaccccgaggggacccgacaggcccttaattaattggctccgg
tgcccgtcagtgggcagagcgcacatcgcccacagtccccgagaagttggggggaggggtcggcaat
tgaaccggtgcctagagaaggtggcgcggggtaaactgggaaagtgatgtcgtgtactggctccgcc
tttttcccgagggtgggggagaaccgtatataagtgcagtagtcgccgtgaacgttctttttcgcaa
cgggtttgccgccagaacacaggtaagtgccgtgtgtggttcccgcgggcctggcctctttacgggt
tatggcccttgcgtgccttgaattacttccacctggctgcagtacgtgattcttgatcccgagcttc
gggttggaagtgggtgggagagttcgaggccttgcgcttaaggagccccttcgcctcgtgcttgagt
tgaggcctggcctgggcgctggggccgccgcgtgcgaatctggtggcaccttcgcgcctgtctcgct
gctttcgataagtctctagccatttaaaatttttgatgacctgctgcgacgctttttttctggcaag
atagtcttgtaaatgcgggccaagatctgcacactggtatttcggtttttggggccgcgggcggcga
cggggcccgtgcgtcccagcgcacatgttcggcgaggcggggcctgcgagcgcggccaccgagaatc
ggacgggggtagtctcaagctggccggcctgctctggtgcctggcctcgcgccgccgtgtatcgccc
cgccctgggcggcaaggctggcccggtcggcaccagttgcgtgagcggaaagatggccgcttcccgg
ccctgctgcagggagctcaaaatggaggacgcggcgctcgggagagcgggcgggtgagtcacccaca
caaaggaaaagggcctttccgtcctcagccgtcgcttcatgtgactccacggagtaccgggcgccgt
ccaggcacctcgattagttctcgagcttttggagtacgtcgtctttaggttggggggaggggtttta
tgcgatggagtttccccacactgagtgggtggagactgaagttaggccagcttggcacttgatgtaa
ttctccttggaatttgccctttttgagtttggatcttggttcattctcaagcctcagacagtggttc
aaagtttttttcttccatttcaggtgtcgtgaggaattcggccattacggcccgccaccatgaccat
catgatcaagaagagcgacttcctggccatccccagcgaggagtacaagggcatcctgagcctgaga
taccaggtgttcaagcagaggctggagtgggacctggtggtggagaacaacctggagagcgacgagt

FIG 5 CONT acgacaacagcaacgccgagtacatctacgcctgcgacgacaccgagaacgtgagcggctgctggcg
cctgctgcccaccaccggcgactacatgctgaagagcgtgttccccgagctgctgggccagcagagc
gcccccaaggaccccaacatcgtggagctgtccaggttcgccgtgggcaagaacagcagcaagatca
acaacagcgccagcgagatcaccatgaagctgttcgaggccatctacaagcacgccgtgagccaggg
catcaccgagtacgtgaccgtgaccagcaccgccatcgagagatttctgaagaggatcaaggtgccc
tgccacaggatcggcgacaaggagatccacgtcctgggcgacaccaagagcgtggtgctgtccatgc
ccatcaacgagcagttcaaaaaggccgtgctgaactgaggccgcct

FIG 5 CONT

```
FEATURES             Location/Qualifiers
     promoter        8835..10008
                     /vntifkey="29"
                     /label=PEF1-alpha
     promoter        6547..7198
                     /vntifkey="29"
                     /label=PCMV
     promoter        7201..7220
                     /vntifkey="29"
                     /label=T7\promoter
     misc_feature    2345..2558
                     /vntifkey="21"
                     /label=BGH\PolyA
     rep_origin      2621..3033
                     /vntifkey="33"
                     /label=f1\ori
     rep_origin      3099..3424
                     /vntifkey="33"
                     /label=SV40\ori
     promoter        3440..3505
                     /vntifkey="29"
                     /label=EM7
     CDS             3507..3881
                     /vntifkey="4"
                     /label=Zeocin(r)
     rep_origin      complement(4524..5197)
                     /vntifkey="33"
                     /label=pUC\ori
     promoter        complement(6203..6300)
                     /vntifkey="29"
                     /label=bla
     CDS             complement(5342..6202)
                     /vntifkey="4"
                     /label=Amp(r)
     misc_feature    1294..1885
                     /vntifkey="21"
                     /label=WPRE
     misc_feature    20..604
                     /vntifkey="21"
                     /label=IRES
     misc_feature    7233..7335
                     /vntifkey="21"
                     /label=MCS
     misc_feature    2085..2319
                     /vntifkey="21"
                     /label=deltaU3-3'LTR
     misc_feature    7336..7516
```

FIG 7

```
                     /vntifkey="21"
                     /label=5'\LTR
     CDS             608..1285
                     /vntifkey="4"
                     /label=DsRED2
     RBS             602..611
                     /vntifkey="32"
                     /label=Kozak\consensus
     CDS             10043..11728
                     /vntifkey="4"
                     /label=p65H4LuxRFmNLS
     RBS             10036..10046
                     /vntifkey="32"
                     /label=Kozak\consensus
BASE COUNT     2739 a      3198 c      3147 g      2652 t
SEQ ID NO:02
        1 cggccatcga taaggatccg cccctctccc tccccccccc ctaacgttac tggccgaagc
       61 cgcttggaat aaggccggtg tgcgtttgtc tatatgttat tttccaccat attgccgtct
      121 tttggcaatg tgagggcccg gaaacctggc cctgtcttct tgacgagcat tcctaggggt
      181 ctttcccctc tcgccaaagg aatgcaaggt ctgttgaatg tcgtgaagga agcagttcct
      241 ctggaagctt cttgaagaca aacaacgtct gtagcgaccc tttgcaggca gcggaacccc
      301 ccacctggcg acaggtgcct ctgcggccaa aagccacgtg tataagatac acctgcaaag
      361 gcggcacaac cccagtgcca cgttgtgagt tggatagttg tggaaagagt caaatggctc
      421 tcctcaagcg tattcaacaa ggggctgaag gatgcccaga aggtacccca ttgtatggga
      481 tctgatctgg ggcctcggtg cacatgcttt acatgtgttt agtcgaggtt aaaaaaacgt
      541 ctaggccccc cgaaccacgg ggacgtggtt ttcctttgaa aaacacgatg ataatatggc
      601 cacaaccatg gcctcctccg aggacgtcat caaggagttc atgcgcttca aggtgcgcat
      661 ggagggctcc gtgaacggcc acgagttcga gatcgagggc gagggcgagg gccgccccta
      721 cgagggcacc cagaccgcca agctgaaggt gaccaagggc ggccccctgc ccttcgcctg
      781 ggacatcctg tccccccagt tccagtacgg ctccaaggtg tacgtgaagc accccgccga
      841 catccccgac tacaagaagc tgtccttccc cgagggcttc aagtgggagc gcgtgatgaa
      901 cttcgaggac ggcggcgtgg tgaccgtgac ccaggactcc tccctgcagg acggctcctt
      961 catctacaag gtgaagttca tcggcgtgaa cttcccctcc gacggccccg taatgcagaa
     1021 gaagactatg ggctgggagg cctccaccga gcgcctgtac ccccgcgacg gcgtgctgaa
     1081 gggcgagatc cacaaggccc tgaagctgaa ggacggcggc cactacctgg tggagttcaa
     1141 gtccatctac atggccaaga agcccgtgca gctgcccggc tactactacg tggactccaa
     1201 gctggacatc acctcccaca acgaggacta caccatcgtg gagcagtacg agcgcgccga
     1261 gggccgccac cacctgttcc tgtaggcggc cgcaatcaac ctctggatta caaaatttgt
     1321 gaaagattga ctggtattct taactatgtt gctcctttta cgctatgtgg atacgctgct
     1381 ttaatgcctt tgtatcatgc tattacttcc cgtacggctt tcattttctc ctccttgtat
     1441 aaatcctggt tgctgtctct ttatgaggag ttgtggcccg ttgtcaggca acgtggcgtg
     1501 gtgtgcactg tgtttgctga cgcaaccccc actggttggg gcattgccac cacctatcaa
     1561 ctcctttccg ggactttcgc tttccccctc cctattgcca cggcggaact cattgccgcc
     1621 tgccttgccc gctgctggac aggggctcgg ctgttgggca ctgacaattc cgtggtgttg
     1681 tcggggaagc tgacgtcctt tccatggctg ctcgcctgtg ttgccaactg gattctgcgc
     1741 gggacgtcct tctgctacgt cccttcggcc ctcaatccag cggaccttcc ttcccgcggc
     1801 ctgctgccgg ttctgcggcc tcttccgcgt cttcgccttc gccctcagac gagtcggatc
     1861 tccctttggg ccgcctcccc gcctgcctgc aggtttgtcg agacctagaa aaacatggag
     1921 caatcacaag tagcaataca gcagctacca atgctgattg tgcctggcta gaagcacaag
     1981 aggaggagga ggtgggtttt ccagtcacac ctcaggtacc tttaagacca atgacttaca
     2041 aggcagctgt agatcttagc cactttttaa aagaaaaggg gggactggaa gggctaattc
     2101 actcccaacg aagacaagat ctgctttttg cttgtactgg gtctctctgg ttagaccaga
     2161 tctgagcctg ggagctctct ggctaactag ggaacccact gcttaagcct caataaagct
     2221 tgccttgagt gcttcaagta gtgtgtgccc gtctgttgtg tgactctggt aactagagat
```

FIG 7 CONT 2281 ccctcagacc cttttagtca gtgtggaaaa tctctagcag ggcccgttta aacccgctga
2341 tcagcctcga ctgtgccttc tagttgccag ccatctgttg tttgcccctc ccccgtgcct
2401 tccttgaccc tggaaggtgc cactcccact gtcctttcct aataaaatga ggaaattgca
2461 tcgcattgtc tgagtaggtg tcattctatt ctggggggtg gggtggggca ggacagcaag
2521 ggggaggatt gggaagacaa tagcaggcat gctggggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgcccgctc ctttcgcttt cttcccttcc tttctcgcca cgttcgccgg ctttccccgt
2761 caagctctaa atcgggggct ccctttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg gactcttgtt ccaaactgga
2941 acaacactca accctatctc ggtctattct tttgatttat aagggatttt ggggatttcg
3001 gcctattggt taaaaaatga gctgatttaa caaaaattta acgcgaatta attctgtgga
3061 atgtgtgtca gttagggtgt ggaaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtcccgcc cctaactccg
3241 cccatcccgc ccctaactcc gcccagttcc gcccattctc cgccccatgg ctgactaatt
3301 ttttttattt atgcagaggc cgaggccgcc tctgcctctg agctattcca gaagtagtga
3361 ggaggctttt ttggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgg ccaagttgac cagtgccgtt ccggtgctca
3541 ccgcgcgcga cgtcgccgga gcggtcgagt tctggaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttccgggac gcctccgggc
3781 cggccatgac cgagatcggc gagcagccgt gggggcggga gttcgccctg cgcgacccgg
3841 ccggcaactg cgtgcacttc gtggccgagg agcaggactg acacgtgcta cgagatttcg
3901 attccaccgc cgccttctat gaaaggttgg gcttcggaat cgttttccgg gacgccggct
3961 ggatgatcct ccagcgcggg gatctcatgc tggagttctt cgcccacccc aacttgttta
4021 ttgcagctta taatggttac aaataaagca atagcatcac aaatttcaca aataaagcat
4081 ttttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata aagtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcggggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg tttttccata ggctccgccc ccctgacgag catcacaaaa
4621 atcgacgctc aagtcagagg tggcgaaacc cgacaggact ataaagatac caggcgtttc
4681 cccctggaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaacccccc gttcagcccg
4861 accgctgcgc cttatccggt aactatcgtc ttgagtccaa cccggtaaga cacgacttat
4921 cgccactggc agcagccact ggtaacagga ttagcagagc gaggtatgta ggcggtgcta
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggtttttttg tttgcaagca gcagattacg cgcagaaaaa
5161 aaggatctca agaagatcct ttgatctttt ctacggggtc tgacgctcag tggaacgaaa
5221 actcacgtta agggattttg gtcatgagat tatcaaaaag gatcttcacc tagatccttt
5281 taaattaaaa atgaagtttt aaatcaatct aaagtatata tgagtaaact tggtctgaca
5341 gttaccaatg cttaatcagt gaggcaccta tctcagcgat ctgtctattt cgttcatcca
5401 tagttgcctg actccccgtc gtgtagataa ctacgatacg ggagggctta ccatctggcc
5461 ccagtgctgc aatgataccg cgagacccac gctcaccggc tccagattta tcagcaataa
5521 accagccagc cggaagggcc gagcgcagaa gtggtcctgc aactttatcc gcctccatcc
5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat

FIG 7 CONT 5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact ttaaaagtgc
6001 tcatcattgg aaaacgttct tcggggcgaa aactctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga ataagggcga
6181 cacggaaatg ttgaatactc atactcttcc tttttcaata ttattgaagc atttatcagg
6241 gttattgtct catgagcgga tacatatttg aatgtattta gaaaaataaa caaatagggg
6301 ttccgcgcac atttccccga aaagtgccac ctgacgtcga cggatcggga gatctcccga
6361 tcccctatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc cgcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgccccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat ttccaagtct
7021 ccaccccatt gacgtcaatg ggagtttgtt ttggcaccaa aatcaacggg actttccaaa
7081 atgtcgtaac aactccgccc cattgacgca aatgggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtggca gatatccagc acagtggcgg ccgctcgagt ctagagggcc
7321 cgtttttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagaccctt ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta gaaggagaga gatgggtgcg
7681 agagcgtcag tattaagcgg gggagaatta gatcgcgatg ggaaaaaatt cggttaaggc
7741 cagggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga agagcaaaac aaaagtaaga ccaccgcaca gcaagcggcc gctgatcttc
8041 agacctggag gaggagatat gagggacaat tggagaagtg aattatataa atataaagta
8101 gtaaaaattg aaccattagg agtagcaccc accaaggcaa agagaagagt ggtgcagaga
8161 gaaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag atacctaaag
8401 gatcaacagc tcctggggat ttggggttgc tctggaaaac tcatttgcac cactgctgtg
8461 ccttggaatg ctagttggag taataaatct ctggaacaga tttggaatca cacgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata taaaattatt cataatgata
8701 gtaggaggct tggtaggttt aagaatagtt tttgctgtac tttctatagt gaatagagtt
8761 aggcagggat attcaccatt atcgtttcag acccacctcc caaccccgag gggacccgac
8821 aggcccttaa ttaattggct ccggtgcccg tcagtgggca gagcgcacat cgcccacagt
8881 ccccgagaag ttggggggag gggtcggcaa ttgaaccggt gcctagagaa ggtggcgcgg
8941 ggtaaactgg gaaagtgatg tcgtgtactg gctccgcctt tttcccgagg gtgggggaga
9001 accgtatata agtgcagtag tcgccgtgaa cgttcttttt cgcaacgggt ttgccgccag
9061 aacacaggta agtgccgtgt gtggttcccg cgggcctggc ctctttacgg gttatggccc

FIG 7 CONT

```
 9121 ttgcgtgcct tgaattactt ccacctggct gcagtacgtg attcttgatc ccgagcttcg
 9181 ggttggaagt gggtgggaga gttcgaggcc ttgcgcttaa ggagcccctt cgcctcgtgc
 9241 ttgagttgag gcctggcctg ggcgctgggg ccgccgcgtg cgaatctggt ggcaccttcg
 9301 cgcctgtctc gctgctttcg ataagtctct agccatttaa aatttttgat gacctgctgc
 9361 gacgcttttt ttctggcaag atagtcttgt aaatgcgggc caagatctgc acactggtat
 9421 ttcggttttt ggggccgcgg gcggcgacgg ggcccgtgcg tcccagcgca catgttcggc
 9481 gaggcggggc ctgcgagcgc ggccaccgag aatcggacgg gggtagtctc aagctggccg
 9541 gcctgctctg gtgcctggcc tcgcgccgcc gtgtatcgcc ccgccctggg cggcaaggct
 9601 ggcccggtcg gcaccagttg cgtgagcgga aagatggccg cttcccggcc ctgctgcagg
 9661 gagctcaaaa tggaggacgc ggcgctcggg agagcgggcg ggtgagtcac ccacacaaag
 9721 gaaaagggcc tttccgtcct cagccgtcgc ttcatgtgac tccacggagt accgggcgcc
 9781 gtccaggcac ctcgattagt tctcgagctt ttggagtacg tcgtctttag gttgggggga
 9841 ggggttttat gcgatggagt ttccccacac tgagtgggtg gagactgaag ttaggccagc
 9901 ttggcacttg atgtaattct ccttggaatt tgcccttttt gagtttggat cttggttcat
 9961 tctcaagcct cagacagtgg ttcaaagttt ttttcttcca tttcaggtgt cgtgaggaat
10021 tcggccatta cggcctgcca ccatggacca gtacctgccc gacaccgacg acaggcacag
10081 gatcgaggag aagaggaaga ggacctacga gaccttcaag agcatcatga agaagagccc
10141 cttcaacggc cccaccgagc ccagaccccc caccaggcgg atcgccgtgc ccacaaggaa
10201 cagcaccagc gtgcccaagc ctgcccccca gccctacacc ttccccgcca gcctgagcac
10261 catcaacttc gacgagttca gccccatgct gctgcccagc ggccagatca gcaaccaggc
10321 cctggccctg gctcctagca gcgcccctgt gctggcccag accatggtgc ccagcagcgc
10381 catggtgcct ctggcccagc ctcctgcccc tgcccccgtg ctgacccctg gccccccctca
10441 gagcctgagc gccccagtgc ccaagagcac ccaggccggc gagggcacac tgagcgaggc
10501 cctgctgcac ctgcagttcg acgccgacga ggacctgggc gccctgctgg gcaacagcac
10561 cgacccgggc gtgttcaccg acctggccag cgtggacaac agcgagttcc agcagctgct
10621 gaaccagggc gtgagcatga gccacagcac cgccgagccc atgctgatgg agtaccccga
10681 ggccatcacc aggctggtga ccggcagcca gagacccccc gaccctgccc ctacccctct
10741 gggcaccagc ggcctgccca acggcctgag cggcgacgag gacttcagca gcatcgccga
10801 catggacttc tccgccctgc tgtcccagat cagctccctg gagctggccg aggccgctgc
10861 caaggaggct gccgctaagg aggccgctgc taaggaggct gctgccaagg ccgctgccat
10921 gaagaacatc aacgccgacg acacctacag gatcatcaac aagatcaagg cctgcagaag
10981 caacaacgac atcaaccagt gcctgagcga catggccaag atggtgcact gcgagtacta
11041 cctgctggcc ttcatctacc cccacagcat ggtgaagagc gacatcagca tcctggacaa
11101 ctaccccaag aagtggaggc agtactacga cgacgccaac ctgatcaagt acgaccccat
11161 cgtggactac agcaacagca accacagccc catcaactgg aacatcttcg agaacaacgc
11221 cgtgaacaaa aagtccccca acgtgatcaa ggaggccaag acagccggcc tgatcaccgg
11281 cttcagcttc cccatccaca ccgccaacaa cggcttcggc atgctgtcct tcgcccacag
11341 cgagaaggac aactacatcg acagcctgtt tctgcacgcc tgcatgaaca tcccccctgat
11401 cgtgcccagc ctggtggata actaccggaa gatcaacatc gccaacaaca agtccaacaa
11461 cgacctgacc aagcgggaga aggagtgcct ggcctgggcc tgcgagggca agagcagctg
11521 ggacatcagc aagatcctgg gctgcagcga gaggaccgtg accttccacc tgaccaacgc
11581 ccagatgaag ctgaacacca ccaacaggtg ccagagcatc agcaaggcca tcctgaccgg
11641 cgccatcgac tgcccctact tcaagaacag cagcctgagg cccccaaaa agaaaagaaa
11701 ggtgcaccac caccaccacc actgatgagg ccgcct
```

FIG 7 CONT

```
FEATURES             Location/Qualifiers
     misc_feature    7427..7607
                     /vntifkey="21"
                     /label=5'\LTR
     misc_feature    2176..2410
                     /vntifkey="21"
                     /label=deltaU3-3'LTR
     misc_feature    7324..7426
                     /vntifkey="21"
                     /label=MCS
     RBS             650..660
                     /vntifkey="32"
                     /label=Kozak\consensus
     CDS             657..1376
                     /vntifkey="4"
                     /label=EGFP
     misc_feature    69..653
                     /vntifkey="21"
                     /label=IRES2
     misc_feature    1385..1976
                     /vntifkey="21"
                     /label=WPRE
     CDS             complement(5433..6293)
                     /vntifkey="4"
                     /label=Amp(r)
     promoter        complement(6294..6391)
                     /vntifkey="29"
                     /label=bla
     rep_origin      complement(4615..5288)
                     /vntifkey="33"
                     /label=pUC\ori
     CDS             3598..3972
                     /vntifkey="4"
                     /label=Zeocin(r)
     promoter        3531..3596
                     /vntifkey="29"
                     /label=EM7
     rep_origin      3190..3515
                     /vntifkey="33"
                     /label=SV40\ori
     rep_origin      2712..3124
                     /vntifkey="33"
                     /label=f1\ori
     misc_feature    2436..2649
```

FIG 9

```
                     /vntifkey="21"
                     /label=BGH\PolyA
     promoter        7292..7311
                     /vntifkey="29"
                     /label=T7\promoter
     promoter        6638..7289
                     /vntifkey="29"
                     /label=PCMV
     promoter        9935..10045
                     /vntifkey="29"
                     /label=pminCMV
     protein_bind    9904..9923
                     /vntifkey="31"
                     /label=lux\box
     protein_bind    9861..9880
                     /vntifkey="31"
                     /label=lux\box
     protein_bind    9818..9837
                     /vntifkey="31"
                     /label=lux\box
     protein_bind    9775..9794
                     /vntifkey="31"
                     /label=lux\box
     protein_bind    9732..9751
                     /vntifkey="31"
                     /label=lux\box
     protein_bind    9689..9708
                     /vntifkey="31"
                     /label=lux\box
     protein_bind    9646..9665
                     /vntifkey="31"
                     /label=lux\box
BASE COUNT     2544 a      2506 c      2598 g      2402 t
ORIGIN
SEQ ID NO:03
        1 aattcggcca ttacggccgc tagcgttaac gtcgacggcc gcctcggcca tcgataagga
       61 tccggaatgc ccctctccct cccccccccc taacgttact ggccgaagcc gcttggaata
      121 aggccggtgt gcgtttgtct atatgttatt ttccaccata ttgccgtctt ttggcaatgt
      181 gagggcccgg aaacctggcc ctgtcttctt gacgagcatt cctaggggtc tttcccctct
      241 cgccaaagga atgcaaggtc tgttgaatgt cgtgaaggaa gcagttcctc tggaagcttc
      301 ttgaagacaa acaacgtctg tagcgaccct ttgcaggcag cggaaccccc cacctggcga
      361 caggtgcctc tgcggccaaa agccacgtgt ataagataca cctgcaaagg cggcacaacc
      421 ccagtgccac gttgtgagtt ggatagttgt ggaaagagtc aaatggctct cctcaagcgt
      481 attcaacaag gggctgaagg atgcccagaa ggtaccccat tgtatgggat ctgatctggg
      541 gcctcggtgc acatgcttta catgtgttta gtcgaggtta aaaaaacgtc taggcccccc
      601 gaaccacggg gacgtggttt tcctttgaaa aacacgatga taatatggcc acaaccatgg
      661 tgagcaaggg cgaggagctg ttcaccgggg tggtgcccat cctggtcgag ctggacggcg
      721 acgtaaacgg ccacaagttc agcgtgtccg gcgagggcga gggcgatgcc acctacggca
      781 agctgaccct gaagttcatc tgcaccaccg gcaagctgcc cgtgccctgg cccaccctcg
      841 tgaccaccct gacctacggc gtgcagtgct tcagccgcta ccccgaccac atgaagcagc
```

FIG 9 CONT

```
 901 acgacttctt caagtccgcc atgcccgaag gctacgtcca ggagcgcacc atcttcttca
 961 aggacgacgg caactacaag acccgcgccg aggtgaagtt cgagggcgac accctggtga
1021 accgcatcga gctgaagggc atcgacttca aggaggacgg caacatcctg gggcacaagc
1081 tggagtacaa ctacaacagc cacaacgtct atatcatggc cgacaagcag aagaacggca
1141 tcaaggtgaa cttcaagatc cgccacaaca tcgaggacgg cagcgtgcag ctcgccgacc
1201 actaccagca gaacaccccc atcggcgacg gccccgtgct gctgcccgac aaccactacc
1261 tgagcaccca gtccgccctg agcaaagacc ccaacgagaa gcgcgatcac atggtcctgc
1321 tggagttcgt gaccgccgcc gggatcactc tcggcatgga cgagctgtac aagtaagcgg
1381 ccgcaatcaa cctctggatt acaaaatttg tgaaagattg actggtattc ttaactatgt
1441 tgctcctttt acgctatgtg gatacgctgc tttaatgcct ttgtatcatg ctattacttc
1501 ccgtacggct ttcattttct cctccttgta taaatcctgg ttgctgtctc tttatgagga
1561 gttgtggccc gttgtcaggc aacgtggcgt ggtgtgcact gtgtttgctg acgcaacccc
1621 cactggttgg ggcattgcca ccacctatca actcctttcc gggactttcg ctttccccct
1681 ccctattgcc acggcggaac tcattgccgc ctgccttgcc cgctgctgga caggggctcg
1741 gctgttgggc actgacaatt ccgtggtgtt gtcggggaag ctgacgtcct ttccatggct
1801 gctcgcctgt gttgccaact ggattctgcg cgggacgtcc ttctgctacg tcccttcggc
1861 cctcaatcca gcggaccttc cttcccgcgg cctgctgccg gttctgcggc ctcttccgcg
1921 tcttcgcctt cgccctcaga cgagtcggat ctccctttgg gccgcctccc cgcctgcctg
1981 caggtttgtc gagacctaga aaaacatgga gcaatcacaa gtagcaatac agcagctacc
2041 aatgctgatt gtgcctggct agaagcacaa gaggaggagg aggtgggttt tccagtcaca
2101 cctcaggtac ctttaagacc aatgacttac aaggcagctg tagatcttag ccacttttta
2161 aaagaaaagg ggggactgga agggctaatt cactcccaac gaagacaaga tctgcttttt
2221 gcttgtactg ggtctctctg gttagaccag atctgagcct gggagctctc tggctaacta
2281 gggaacccac tgcttaagcc tcaataaagc ttgccttgag tgcttcaagt agtgtgtgcc
2341 cgtctgttgt gtgactctgg taactagaga tccctcagac ccttttagtc agtgtggaaa
2401 atctctagca gggcccgttt aaacccgctg atcagcctcg actgtgcctt ctagttgcca
2461 gccatctgtt gtttgcccct cccccgtgcc ttccttgacc ctggaaggtg ccactcccac
2521 tgtcctttcc taataaaatg aggaaattgc atcgcattgt ctgagtaggt gtcattctat
2581 tctggggggt ggggtggggc aggacagcaa gggggaggat tgggaagaca atagcaggca
2641 tgctggggat gcggtgggct ctatggcttc tgaggcggaa agaaccagct ggggctctag
2701 ggggtatccc cacgcgccct gtagcggcgc attaagcgcg gcgggtgtgg tggttacgcg
2761 cagcgtgacc gctacacttg ccagcgccct agcgcccgct cctttcgctt tcttcccttc
2821 ctttctcgcc acgttcgccg gctttccccg tcaagctcta aatcggggca tccctttagg
2881 gttccgattt agtgctttac ggcacctcga ccccaaaaaa cttgattagg gtgatggttc
2941 acgtagtggg ccatcgccct gatagacggt ttttcgccct ttgacgttgg agtccacgtt
3001 ctttaatagt ggactcttgt tccaaactgg aacaacactc aaccctatct cggtctattc
3061 ttttgattta taagggattt tggggatttc ggcctattgg ttaaaaaatg agctgattta
3121 acaaaaattt aacgcgaatt aattctgtgg aatgtgtgtc agttagggtg tggaaagtcc
3181 ccaggctccc caggcaggca gaagtatgca aagcatgcat ctcaattagt cagcaaccag
3241 gtgtggaaag tccccaggct ccccagcagg cagaagtatg caaagcatgc atctcaatta
3301 gtcagcaacc atagtcccgc ccctaactcc gcccatcccg cccctaactc cgcccagttc
3361 cgcccattct ccgccccatg gctgactaat tttttttatt tatgcagagg ccgaggccgc
3421 ctctgcctct gagctattcc agaagtagtg aggaggcttt tttggaggcc taggcttttg
3481 caaaaagctc ccgggagctt gtatatccat tttcggatct gatcagcacg tgttgacaat
3541 taatcatcgg catagtatat cggcatagta taatacgaca aggtgaggaa ctaaaccatg
3601 gccaagttga ccagtgccgt tccggtgctc accgcgcgcg acgtcgccgg agcggtcgag
3661 ttctggaccg accggctcgg gttctcccgg gacttcgtgg aggacgactt cgccggtgtg
3721 gtccgggacg acgtgaccct gttcatcagc gcggtccagg accaggtggt gccggacaac
3781 accctggcct gggtgtgggt gcgcggcctg gacgagctgt acgccgagtg gtcggaggtc
3841 gtgtccacga acttccggga cgcctccggg ccggccatga ccgagatcgg cgagcagccg
3901 tgggggcggg agttcgccct gcgcgacccg gccggcaact gcgtgcactt cgtggccgag
3961 gagcaggact gacacgtgct acgagatttc gattccaccg ccgccttcta tgaaaggttg
4021 ggcttcggaa tcgttttccg ggacgccggc tggatgatcc tccagcgcgg ggatctcatg
4081 ctggagttct tcgcccaccc caacttgttt attgcagctt ataatggtta caaataaagc
4141 aatagcatca caaatttcac aaataaagca tttttttcac tgcattctag ttgtggtttg
4201 tccaaactca tcaatgtatc ttatcatgtc tgtataccgt cgacctctag ctagagcttg
4261 gcgtaatcat ggtcatagct gtttcctgtg tgaaattgtt atccgctcac aattccacac
```

FIG 9 CONT

```
4321 aacatacgag ccggaagcat aaagtgtaaa gcctggggtg cctaatgagt gagctaactc
4381 acattaattg cgttgcgctc actgcccgct ttccagtcgg gaaacctgtc gtgccagctg
4441 cattaatgaa tcggccaacg cgcggggaga ggcggtttgc gtattgggcg ctcttccgct
4501 tcctcgctca ctgactcgct gcgctcggtc gttcggctgc ggcgagcggt atcagctcac
4561 tcaaaggcgg taatacggtt atccacagaa tcaggggata acgcaggaaa gaacatgtga
4621 gcaaaaggcc agcaaaaggc caggaaccgt aaaaaggccg cgttgctggc gtttttccat
4681 aggctccgcc cccctgacga gcatcacaaa aatcgacgct caagtcagag gtggcgaaac
4741 ccgacaggac tataaagata ccaggcgttt ccccctggaa gctccctcgt gcgctctcct
4801 gttccgaccc tgccgcttac cggatacctg tccgcctttc tcccttcggg aagcgtggcg
4861 ctttctcaat gctcacgctg taggtatctc agttcggtgt aggtcgttcg ctccaagctg
4921 ggctgtgtgc acgaaccccc cgttcagccc gaccgctgcg ccttatccgg taactatcgt
4981 cttgagtcca acccggtaag acacgactta tcgccactgg cagcagccac tggtaacagg
5041 attagcagag cgaggtatgt aggcggtgct acagagttct tgaagtggtg gcctaactac
5101 ggctacacta gaaggacagt atttggtatc tgcgctctgc tgaagccagt taccttcgga
5161 aaaagagttg gtagctcttg atccggcaaa caaaccaccg ctggtagcgg tggttttttt
5221 gtttgcaagc agcagattac gcgcagaaaa aaaggatctc aagaagatcc tttgatcttt
5281 tctacggggt ctgacgctca gtggaacgaa aactcacgtt aagggatttt ggtcatgaga
5341 ttatcaaaaa ggatcttcac ctagatcctt ttaaattaaa aatgaagttt taaatcaatc
5401 taaagtatat atgagtaaac ttggtctgac agttaccaat gcttaatcag tgaggcacct
5461 atctcagcga tctgtctatt tcgttcatcc atagttgcct gactccccgt cgtgtagata
5521 actacgatac gggagggctt accatctggc cccagtgctg caatgatacc gcgagaccca
5581 cgctcaccgg ctccagattt atcagcaata aaccagccag ccggaagggc cgagcgcaga
5641 agtggtcctg caactttatc cgcctccatc cagtctatta attgttgccg ggaagctaga
5701 gtaagtagtt cgccagttaa tagtttgcgc aacgttgttg ccattgctac aggcatcgtg
5761 gtgtcacgct cgtcgtttgg tatggcttca ttcagctccg gttcccaacg atcaaggcga
5821 gttacatgat cccccatgtt gtgcaaaaaa gcggttagct ccttcggtcc tccgatcgtt
5881 gtcagaagta agttggccgc agtgttatca ctcatggtta tggcagcact gcataattct
5941 cttactgtca tgccatccgt aagatgcttt tctgtgactg gtgagtactc aaccaagtca
6001 ttctgagaat agtgtatgcg gcgaccgagt tgctcttgcc cggcgtcaat acgggataat
6061 accgcgccac atagcagaac tttaaaagtg ctcatcattg gaaaacgttc ttcggggcga
6121 aaactctcaa ggatcttacc gctgttgaga tccagttcga tgtaacccac tcgtgcaccc
6181 aactgatctt cagcatcttt tactttcacc agcgtttctg ggtgagcaaa aacaggaagg
6241 caaaatgccg caaaaaaggg aataagggcg acacggaaat gttgaatact catactcttc
6301 ctttttcaat attattgaag catttatcag ggttattgtc tcatgagcgg atacatattt
6361 gaatgtattt agaaaaataa acaaataggg gttccgcgca catttccccg aaaagtgcca
6421 cctgacgtcg acggatcggg agatctcccg atcccctatg gtgcactctc agtacaatct
6481 gctctgatgc cgcatagtta agccagtatc tgctccctgc ttgtgtgttg gaggtcgctg
6541 agtagtgcgc gagcaaaatt taagctacaa caaggcaagg cttgaccgac aattgcatga
6601 agaatctgct tagggttagg cgttttgcgc tgcttcgcga tgtacgggcc agatatacgc
6661 gttgacattg attattgact agttattaat agtaatcaat tacggggtca ttagttcata
6721 gcccatatat ggagttccgc gttacataac ttacggtaaa tggcccgcct ggctgaccgc
6781 ccaacgaccc ccgcccattg acgtcaataa tgacgtatgt tcccatagta acgccaatag
6841 ggactttcca ttgacgtcaa tgggtggact atttacggta aactgcccac ttggcagtac
6901 atcaagtgta tcatatgcca agtacgcccc ctattgacgt caatgacggt aaatggcccg
6961 cctggcatta tgcccagtac atgaccttat gggactttcc tacttggcag tacatctacg
7021 tattagtcat cgctattacc atggtgatgc ggttttggca gtacatcaat gggcgtggat
7081 agcggtttga ctcacgggga tttccaagtc tccaccccat tgacgtcaat gggagtttgt
7141 tttggcacca aaatcaacgg gactttccaa aatgtcgtaa caactccgcc ccattgacgc
7201 aaatgggcgg taggcgtgta cggtgggagg tctatataag cagagctctc tggctaacta
7261 gagaacccac tgcttactgg cttatcgaaa ttaatacgac tcactatagg gagacccaag
7321 ctggtttaaa cttaagcttg gtaccgagct cactagtcca gtgtggtggc agatatccag
7381 cacagtggcg gccgctcgag tctagagggc ccgtttgcc tgtactgggt ctctctggtt
7441 agaccagatc tgagcctggg agctctctgg ctaactaggg aacccactgc ttaagcctca
7501 ataaagcttg ccttgagtgc ttcaagtagt gtgtgcccgt ctgttgtgtg actctggtaa
7561 ctagagatcc ctcagaccct tttagtcagt gtggaaaatc tctagcagtg gcgcccgaac
7621 agggacttga aagcgaaagg gaaaccagag gagctctctc gacgcaggac tcggcttgct
7681 gaagcgcgca cggcaagagg cgaggggcgg cgactggtga gtacgccaaa aattttgact
```

FIG 9 CONT

```
 7741 agcggaggct agaaggagag agatgggtgc gagagcgtca gtattaagcg ggggagaatt
 7801 agatcgcgat gggaaaaaat tcggttaagg ccagggggaa agaaaaaata taaattaaaa
 7861 catatagtat gggcaagcag ggagctagaa cgattcgcag ttaatcctgg cctgttagaa
 7921 acatcagaag gctgtagaca aatactggga cagctacaac catcccttca gacaggatca
 7981 gaagaactta gatcattata taatacagta gcaaccctct attgtgtgca tcaaaggata
 8041 gagataaaag acaccaagga agctttagac aagatagagg aagagcaaaa caaaagtaag
 8101 accaccgcac agcaagcggc cgctgatctt cagacctgga ggaggagata tgagggacaa
 8161 ttggagaagt gaattatata aatataaagt agtaaaaatt gaaccattag gagtagcacc
 8221 caccaaggca aagagaagag tggtgcagag agaaaaaaga gcagtgggaa taggagcttt
 8281 gttccttggg ttcttgggag cagcaggaag cactatgggc gcagcgtcaa tgacgctgac
 8341 ggtacaggcc agacaattat tgtctggtat agtgcagcag cagaacaatt tgctgagggc
 8401 tattgaggcg caacagcatc tgttgcaact cacagtctgg ggcatcaagc agctccaggc
 8461 aagaatcctg gctgtggaaa gatacctaaa ggatcaacag ctcctgggga tttggggttg
 8521 ctctggaaaa ctcatttgca ccactgctgt gccttggaat gctagttgga gtaataaatc
 8581 tctggaacag atttggaatc acacgacctg gatggagtgg gacagagaaa ttaacaatta
 8641 cacaagctta atacactcct taattgaaga atcgcaaaac cagcaagaaa agaatgaaca
 8701 agaattattg gaattagata aatgggcaag tttgtggaat tggtttaaca taacaaattg
 8761 gctgtggtat atagaaatta ttcataatga tagtaggagg cttggtaggt ttaagaatag
 8821 tttttgctgt actttctata gtgaatagag ttaggcaggg atattcacca ttatcgtttc
 8881 agacccacct cccaaccccg aggggacccg acaggcccga aggaatagaa gaagaaggtg
 8941 gagagagaga cagagacaga tccattcgat tagtgaacgg atcggcactg cgtgcgccaa
 9001 ttctgcagac aaatggcagt attcatccac aattttaaaa gaaaaggggg gattgggggg
 9061 tacagtgcag gggaaagaat agtagacata atagcaacag acatacaaac taaagaatta
 9121 caaaaacaaa ttacaaaaat tcaaaatttt cgggtttatt acagggacag cagagatcca
 9181 gtttggggtt gctctggaaa actcatttgc accactgctg tgccttggaa tgctagttgg
 9241 agtaataaat ctctggaaca gatttggaat cacacgacct ggatggagtg ggacagagaa
 9301 attaacaatt acacaagctt aatacactcc ttaattgaag aatcgcaaaa ccagcaagaa
 9361 aagaatgaac aagaattatt ggaattagat aaatgggcaa gtttgtggaa ttggtttaac
 9421 ataacaaatt ggctgtggta tataaaatta ttcataatga tagtaggagg cttggtaggt
 9481 ttaagaatag tttttgctgt actttctata gtgaatagag ttaggcaggg atattcacca
 9541 ttatcgtttc agacccacct cccaaccccg aggggacccg acaggccctt aattaatccc
 9601 ctgattctgt ggataaccgt attaccgcct ttgagtgagc tgcacacctg taggatcgta
 9661 caggtaaagt gaaaggctac aataggacac ctgtaggatc gtacaggtgg taaactcgag
 9721 agcgcccaat aacctgtagg atcgtacagg tagcgcacta gagagcgccc aataacctgt
 9781 aggatcgtac aggtaaagtg aaaggctaca ataggacacc tgtaggatcg tacaggtggt
 9841 aaactcgaga gcgcccaata acctgtagga tcgtacaggt aaagtgaaag gctacaatag
 9901 gacacctgta ggatcgtaca ggtggtaaac tcgacctata taagcagagc tcgtttagtg
 9961 aaccgtcaga tcgcctggag acgccatcca cgctgttttg acctccatag aagacaccgg
10021 gaccgatcca gcctccgcgg ccccgaattg
```

FIG 9 CONT

```
FEATURES             Location/Qualifiers
     promoter        8835..10008
                     /vntifkey="29"
                     /label=PEF1-alpha
     promoter        6547..7198
                     /vntifkey="29"
                     /label=PCMV
     promoter        7201..7220
                     /vntifkey="29"
                     /label=T7\promoter
     misc_feature    2345..2558
                     /vntifkey="21"
                     /label=BGH\PolyA
     rep_origin      2621..3033
                     /vntifkey="33"
                     /label=f1\ori
     rep_origin      3099..3424
                     /vntifkey="33"
                     /label=SV40\ori
     promoter        3440..3505
                     /vntifkey="29"
                     /label=EM7
     CDS             3507..3881
                     /vntifkey="4"
                     /label=Zeocin(r)
     rep_origin      complement(4524..5197)
                     /vntifkey="33"
                     /label=pUC\ori
     promoter        complement(6203..6300)
                     /vntifkey="29"
                     /label=bla
     CDS             complement(5342..6202)
                     /vntifkey="4"
                     /label=Amp(r)
     misc_feature    1294..1885
                     /vntifkey="21"
                     /label=WPRE
     misc_feature    20..604
                     /vntifkey="21"
                     /label=IRES
     misc_feature    7233..7335
                     /vntifkey="21"
                     /label=MCS
     misc_feature    2085..2319
                     /vntifkey="21"
                     /label=deltaU3-3'LTR
     misc_feature    7336..7516
```

FIG 11

```
                     /vntifkey="21"
                     /label=5'\LTR
     CDS             608..1285
                     /vntifkey="4"
                     /label=DsRED2
     RBS             602..611
                     /vntifkey="32"
                     /label=Kozak\consensus
     CDS             10043..10279
                     /vntifkey="4"
                     /label=ACPm
     RBS             10036..10046
                     /vntifkey="32"
                     /label=Kozak\consensus
BASE COUNT     2383 a     2649 c     2791 g     2464 t
ORIGIN
SEQ ID NO:04
        1 cggccatcga taaggatccg cccctctccc tccccccccc ctaacgttac tggccgaagc
       61 cgcttggaat aaggccggtg tgcgtttgtc tatatgttat tttccaccat attgccgtct
      121 tttggcaatg tgagggcccg gaaacctggc cctgtcttct tgacgagcat tcctaggggt
      181 ctttcccctc tcgccaaagg aatgcaaggt ctgttgaatg tcgtgaagga agcagttcct
      241 ctggaagctt cttgaagaca aacaacgtct gtagcgaccc tttgcaggca gcggaacccc
      301 ccacctggcg acaggtgcct ctgcggccaa aagccacgtg tataagatac acctgcaaag
      361 gcggcacaac cccagtgcca cgttgtgagt tggatagttg tggaaagagt caaatggctc
      421 tcctcaagcg tattcaacaa ggggctgaag gatgcccaga aggtacccca ttgtatggga
      481 tctgatctgg ggcctcggtg cacatgcttt acatgtgttt agtcgaggtt aaaaaaacgt
      541 ctaggccccc cgaaccacgg ggacgtggtt ttcctttgaa aaacacgatg ataatatggc
      601 cacaaccatg gcctcctccg aggacgtcat caaggagttc atgcgcttca aggtgcgcat
      661 ggagggctcc gtgaacggcc acgagttcga gatcgagggc gagggcgagg gccgccccta
      721 cgagggcacc cagaccgcca agctgaaggt gaccaagggc ggccccctgc ccttcgcctg
      781 ggacatcctg tcccccagt tccagtacgg ctccaaggtg tacgtgaagc accccgccga
      841 catccccgac tacaagaagc tgtccttccc cgagggcttc aagtgggagc gcgtgatgaa
      901 cttcgaggac ggcggcgtgg tgaccgtgac ccaggactcc tccctgcagg acggctcctt
      961 catctacaag gtgaagttca tcggcgtgaa cttcccctcc gacggccccg taatgcagaa
     1021 gaagactatg ggctgggagg cctccaccga gcgcctgtac ccccgcgacg gcgtgctgaa
     1081 gggcgagatc cacaaggccc tgaagctgaa ggacggcggc cactacctgg tggagttcaa
     1141 gtccatctac atggccaaga agcccgtgca gctgcccggc tactactacg tggactccaa
     1201 gctggacatc acctcccaca acgaggacta caccatcgtg gagcagtacg agcgcgccga
     1261 gggccgccac cacctgttcc tgtaggcggc cgcaatcaac ctctggatta caaaatttgt
     1321 gaaagattga ctggtattct taactatgtt gctcctttta cgctatgtgg atacgctgct
     1381 ttaatgcctt tgtatcatgc tattacttcc cgtacggctt tcattttctc ctccttgtat
     1441 aaatcctggt tgctgtctct ttatgaggag ttgtggcccg ttgtcaggca acgtggcgtg
     1501 gtgtgcactg tgtttgctga cgcaaccccc actggttggg gcattgccac cacctatcaa
     1561 ctcctttccg ggactttcgc tttccccctc cctattgcca cggcggaact cattgccgcc
     1621 tgccttgccc gctgctggac aggggctcgg ctgttgggca ctgacaattc cgtggtgttg
     1681 tcggggaagc tgacgtcctt tccatggctg ctcgcctgtg ttgccaactg gattctgcgc
     1741 gggacgtcct tctgctacgt cccttcggcc ctcaatccag cggaccttcc ttcccgcggc
     1801 ctgctgccgg ttctgcggcc tcttccgcgt cttcgccttc gccctcagac gagtcggatc
     1861 tccctttggg ccgcctcccc gcctgcctgc aggtttgtcg agacctagaa aaacatggag
     1921 caatcacaag tagcaataca gcagctacca atgctgattg tgcctggcta gaagcacaag
     1981 aggaggagga ggtgggtttt ccagtcacac ctcaggtacc tttaagacca atgacttaca
     2041 aggcagctgt agatcttagc cacttttaa aagaaaaggg gggactggaa gggctaattc
     2101 actcccaacg aagacaagat ctgcttttg cttgtactgg gtctctctgg ttagaccaga
```

FIG 11 CONT 2161 tctgagcctg ggagctctct ggctaactag ggaacccact gcttaagcct caataaagct
2221 tgccttgagt gcttcaagta gtgtgtgccc gtctgttgtg tgactctggt aactagagat
2281 ccctcagacc cttttagtca gtgtggaaaa tctctagcag ggcccgttta aacccgctga
2341 tcagcctcga ctgtgccttc tagttgccag ccatctgttg tttgcccctc ccccgtgcct
2401 tccttgaccc tggaaggtgc cactcccact gtcctttcct aataaaatga ggaaattgca
2461 tcgcattgtc tgagtaggtg tcattctatt ctggggggtg gggtggggca ggacagcaag
2521 ggggaggatt gggaagacaa tagcaggcat gctggggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgcccgctc ctttcgcttt cttcccttcc tttctcgcca cgttcgccgg ctttccccgt
2761 caagctctaa atcgggggcat ccctttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg gactcttgtt ccaaactgga
2941 acaacactca accctatctc ggtctattct tttgatttat aagggatttt ggggatttcg
3001 gcctattggt taaaaaatga gctgatttaa caaaaattta acgcgaatta attctgtgga
3061 atgtgtgtca gttagggtgt ggaaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtcccgcc cctaactccg
3241 cccatcccgc ccctaactcc gcccagttcc gcccattctc cgccccatgg ctgactaatt
3301 ttttttattt atgcagaggc cgaggccgcc tctgcctctg agctattcca gaagtagtga
3361 ggaggctttt ttggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgg ccaagttgac cagtgccgtt ccggtgctca
3541 ccgcgcgcga cgtcgccgga gcggtcgagt tctggaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttccgggac gcctccgggc
3781 cggccatgac cgagatcggc gagcagccgt gggggcggga gttcgccctg cgcgacccgg
3841 ccggcaactg cgtgcacttc gtggccgagg agcaggactg acacgtgcta cgagatttcg
3901 attccaccgc cgccttctat gaaaggttgg gcttcggaat cgttttccgg gacgccggct
3961 ggatgatcct ccagcgcggg gatctcatgc tggagttctt cgcccacccc aacttgttta
4021 ttgcagctta taatggttac aaataaagca atagcatcac aaatttcaca aataaagcat
4081 ttttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata aagtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcggggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg tttttccata ggctccgccc ccctgacgag catcacaaaa
4621 atcgacgctc aagtcagagg tggcgaaacc cgacaggact ataaagatac caggcgtttc
4681 cccctggaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaacccccc gttcagcccg
4861 accgctgcgc cttatccggt aactatcgtc ttgagtccaa cccggtaaga cacgacttat
4921 cgccactggc agcagccact ggtaacagga ttagcagagc gaggtatgta ggcggtgcta
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggtttttttg tttgcaagca gcagattacg cgcagaaaaa
5161 aaggatctca agaagatcct ttgatctttt ctacggggtc tgacgctcag tggaacgaaa
5221 actcacgtta agggattttg gtcatgagat tatcaaaaag gatcttcacc tagatccttt
5281 taaattaaaa atgaagtttt aaatcaatct aaagtatata tgagtaaact tggtctgaca
5341 gttaccaatg cttaatcagt gaggcaccta tctcagcgat ctgtctattt cgttcatcca
5401 tagttgcctg actccccgtc gtgtagataa ctacgatacg ggagggctta ccatctggcc
5461 ccagtgctgc aatgataccg cgagacccac gctcaccggc tccagattta tcagcaataa
5521 accagccagc cggaagggcc gagcgcagaa gtggtcctgc aactttatcc gcctccatcc

FIG 11 CONT 5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat
5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact ttaaaagtgc
6001 tcatcattgg aaaacgttct tcggggcgaa aactctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga ataagggcga
6181 cacggaaatg ttgaatactc atactcttcc tttttcaata ttattgaagc atttatcagg
6241 gttattgtct catgagcgga tacatatttg aatgtattta gaaaaataaa caaatagggg
6301 ttccgcgcac atttccccga aaagtgccac ctgacgtcga cggatcggga gatctcccga
6361 tcccctatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc cgcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgccccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat ttccaagtct
7021 ccaccccatt gacgtcaatg ggagtttgtt ttggcaccaa aatcaacggg actttccaaa
7081 atgtcgtaac aactccgccc cattgacgca aatgggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtggca gatatccagc acagtggcgg ccgctcgagt ctagagggcc
7321 cgttttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagaccctt ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta gaaggagaga gatgggtgcg
7681 agagcgtcag tattaagcgg gggagaatta gatcgcgatg ggaaaaaatt cggttaaggc
7741 cagggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga agagcaaaac aaaagtaaga ccaccgcaca gcaagcggcc gctgatcttc
8041 agacctggag gaggagatat gagggacaat tggagaagtg aattatataa atataaagta
8101 gtaaaaattg aaccattagg agtagcaccc accaaggcaa agagaagagt ggtgcagaga
8161 gaaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag atacctaaag
8401 gatcaacagc tcctggggat ttggggttgc tctggaaaac tcatttgcac cactgctgtg
8461 ccttggaatg ctagttggag taataaatct ctggaacaga tttggaatca cacgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata taaaattatt cataatgata
8701 gtaggaggct tggtaggttt aagaatagtt tttgctgtac tttctatagt gaatagagtt
8761 aggcagggat attcaccatt atcgtttcag acccacctcc caaccccgag gggacccgac
8821 aggcccttaa ttaattggct ccggtgcccg tcagtgggca gagcgcacat cgcccacagt
8881 ccccgagaag ttgggggggag gggtcggcaa ttgaaccggt gcctagagaa ggtggcgcgg
8941 ggtaaactgg gaaagtgatg tcgtgtactg gctccgcctt tttcccgagg gtgggggaga

FIG 11 CONT

```
 9001 accgtatata agtgcagtag tcgccgtgaa cgttcttttt cgcaacgggt ttgccgccag
 9061 aacacaggta agtgccgtgt gtggttcccg cgggcctggc ctctttacgg gttatggccc
 9121 ttgcgtgcct tgaattactt ccacctggct gcagtacgtg attcttgatc ccgagcttcg
 9181 ggttggaagt gggtgggaga gttcgaggcc ttgcgcttaa ggagcccctt cgcctcgtgc
 9241 ttgagttgag gcctggcctg ggcgctgggg ccgccgcgtg cgaatctggt ggcaccttcg
 9301 cgcctgtctc gctgctttcg ataagtctct agccatttaa aatttttgat gacctgctgc
 9361 gacgcttttt ttctggcaag atagtcttgt aaatgcgggc caagatctgc acactggtat
 9421 ttcggttttt ggggccgcgg gcggcgacgg ggcccgtgcg tcccagcgca catgttcggc
 9481 gaggcggggc ctgcgagcgc ggccaccgag aatcggacgg gggtagtctc aagctggccg
 9541 gcctgctctg gtgcctggcc tcgcgccgcc gtgtatcgcc ccgccctggg cggcaaggct
 9601 ggcccggtcg gcaccagttg cgtgagcgga aagatggccg cttcccggcc ctgctgcagg
 9661 gagctcaaaa tggaggacgc ggcgctcggg agagcgggcg ggtgagtcac ccacacaaag
 9721 gaaaagggcc tttccgtcct cagccgtcgc ttcatgtgac tccacggagt accgggcgcc
 9781 gtccaggcac ctcgattagt tctcgagctt ttggagtacg tcgtctttag gttgggggga
 9841 ggggttttat gcgatggagt ttccccacac tgagtgggtg gagactgaag ttaggccagc
 9901 ttggcacttg atgtaattct ccttggaatt tgcccttttt gagtttggat cttggttcat
 9961 tctcaagcct cagacagtgg ttcaaagttt ttttcttcca tttcaggtgt cgtgaggaat
10021 tcggccatta cggcccgcca ccatgagcac catcgaggag agggtgaaga agatcatcgg
10081 cgagcagctg ggcgtgaagc aggaggaggt caccaacaac gccagcttcg tggaggacct
10141 gggcgccgac agcctggaca ccgtggagct ggtgatggcc ctggaggagg agttcgacac
10201 cgagatcccc gacgaggagg ccgagaagat caccaccgtg caggccgcca tcgactacat
10261 caacggccac caggcctgag gccgcct
```

FIG 11 CONT

```
FEATURES             Location/Qualifiers
     misc_feature    7397..7577
                     /vntifkey="21"
                     /label=5'\LTR
     misc_feature    2146..2380
                     /vntifkey="21"
                     /label=deltaU3-3'LTR
     misc_feature    7294..7396
                     /vntifkey="21"
                     /label=MCS
     RBS             620..630
                     /vntifkey="32"
                     /label=Kozak\consensus
     CDS             627..1346
                     /vntifkey="4"
                     /label=EGFP
     misc_feature    39..623
                     /vntifkey="21"
                     /label=IRES
     promoter        8896..10516
                     /vntifkey="29"
                     /label=PEF1-alpha
     misc_feature    1355..1946
                     /vntifkey="21"
                     /label=WPRE
     CDS             complement(5403..6263)
                     /vntifkey="4"
                     /label=Amp(r)
     promoter        complement(6264..6361)
                     /vntifkey="29"
                     /label=bla
     rep_origin      complement(4585..5258)
                     /vntifkey="33"
                     /label=pUC\ori
     CDS             3568..3942
                     /vntifkey="4"
                     /label=Zeocin(r)
     promoter        3501..3566
                     /vntifkey="29"
                     /label=EM7
     rep_origin      3160..3485
                     /vntifkey="33"
                     /label=SV40\ori
     rep_origin      2682..3094
                     /vntifkey="33"
                     /label=f1\ori
```

FIG 13

```
     misc_feature    2406..2619
                     /vntifkey="21"
                     /label=BGH\PolyA
     promoter        7262..7281
                     /vntifkey="29"
                     /label=T7\promoter
     promoter        6608..7259
                     /vntifkey="29"
                     /label=PCMV
     CDS             10569..12728
                     /vntifkey="4"
                     /label=AAS
BASE COUNT     2991 a     3207 c     3449 g     3083 t
ORIGIN
SEQ ID NO:05
        1 cgcgccaagc tagcaagtta acaaatcgat ccggatccgc ccctctccct cccccccccc
       61 taacgttact ggccgaagcc gcttggaata aggccggtgt gcgtttgtct atatgttatt
      121 ttccaccata ttgccgtctt ttggcaatgt gagggcccgg aaacctggcc ctgtcttctt
      181 gacgagcatt cctaggggtc tttcccctct cgccaaagga atgcaaggtc tgttgaatgt
      241 cgtgaaggaa gcagttcctc tggaagcttc ttgaagacaa acaacgtctg tagcgaccct
      301 ttgcaggcag cggaaccccc cacctggcga caggtgcctc tgcggccaaa agccacgtgt
      361 ataagataca cctgcaaagg cggcacaacc ccagtgccac gttgtgagtt ggatagttgt
      421 ggaaagagtc aaatggctct cctcaagcgt attcaacaag gggctgaagg atgcccagaa
      481 ggtaccccat tgtatgggat ctgatctggg gcctcggtgc acatgcttta catgtgttta
      541 gtcgaggtta aaaaaacgtc taggcccccc gaaccacggg gacgtggttt tcctttgaaa
      601 aacacgatga taatatggcc acaaccatgg tgagcaaggg cgaggagctg ttcaccgggg
      661 tggtgcccat cctggtcgag ctggacggcg acgtaaacgg ccacaagttc agcgtgtccg
      721 gcgagggcga gggcgatgcc acctacggca agctgaccct gaagttcatc tgcaccaccg
      781 gcaagctgcc cgtgccctgg cccaccctcg tgaccaccct gacctacggc gtgcagtgct
      841 tcagccgcta ccccgaccac atgaagcagc acgacttctt caagtccgcc atgcccgaag
      901 gctacgtcca ggagcgcacc atcttcttca aggacgacgg caactacaag acccgcgccg
      961 aggtgaagtt cgagggcgac accctggtga accgcatcga gctgaagggc atcgacttca
     1021 aggaggacgg caacatcctg gggcacaagc tggagtacaa ctacaacagc cacaacgtct
     1081 atatcatggc cgacaagcag aagaacggca tcaaggtgaa cttcaagatc cgccacaaca
     1141 tcgaggacgg cagcgtgcag ctcgccgacc actaccagca gaacaccccc atcggcgacg
     1201 gccccgtgct gctgcccgac aaccactacc tgagcaccca gtccgccctg agcaaagacc
     1261 ccaacgagaa gcgcgatcac atggtcctgc tggagttcgt gaccgccgcc gggatcactc
     1321 tcggcatgga cgagctgtac aagtaagcgg ccgcaatcaa cctctggatt acaaaatttg
     1381 tgaaagattg actggtattc ttaactatgt tgctcctttt acgctatgtg gatacgctgc
     1441 tttaatgcct ttgtatcatg ctattacttc ccgtacggct ttcattttct cctccttgta
     1501 taaatcctgg ttgctgtctc tttatgagga gttgtggccc gttgtcaggc aacgtggcgt
     1561 ggtgtgcact gtgtttgctg acgcaacccc cactggttgg ggcattgcca ccacctatca
     1621 actcctttcc gggactttcg ctttccccct ccctattgcc acggcggaac tcattgccgc
     1681 ctgccttgcc cgctgctgga caggggctcg gctgttgggc actgacaatt ccgtggtgtt
     1741 gtcggggaag ctgacgtcct ttccatggct gctcgcctgt gttgccaact ggattctgcg
     1801 cgggacgtcc ttctgctacg tcccttcggc cctcaatcca gcggaccttc cttcccgcgg
     1861 cctgctgccg gttctgcggc ctcttccgcg tcttcgcctt cgccctcaga cgagtcggat
     1921 ctccctttgg gccgcctccc cgcctgcctg caggtttgtc gagacctaga aaaacatgga
     1981 gcaatcacaa gtagcaatac agcagctacc aatgctgatt gtgcctggct agaagcacaa
     2041 gaggaggagg aggtgggttt tccagtcaca cctcaggtac ctttaagacc aatgacttac
     2101 aaggcagctg tagatcttag ccacttttta aaagaaaagg ggggactgga agggctaatt
     2161 cactcccaac gaagacaaga tctgcttttt gcttgtactg ggtctctctg gttagaccag
     2221 atctgagcct gggagctctc tggctaacta gggaacccac tgcttaagcc tcaataaagc
     2281 ttgccttgag tgcttcaagt agtgtgtgcc cgtctgttgt gtgactctgg taactagaga
```

FIG 13 CONT

```
2341 tccctcagac cctttagtc agtgtggaaa atctctagca gggcccgttt aaacccgctg
2401 atcagcctcg actgtgcctt ctagttgcca gccatctgtt gtttgcccct cccccgtgcc
2461 ttccttgacc ctggaaggtg ccactcccac tgtcctttcc taataaaatg aggaaattgc
2521 atcgcattgt ctgagtaggt gtcattctat tctggggggt ggggtggggc aggacagcaa
2581 gggggaggat tgggaagaca atagcaggca tgctggggat gcggtgggct ctatggcttc
2641 tgaggcggaa agaaccagct ggggctctag ggggtatccc cacgcgccct gtagcggcgc
2701 attaagcgcg gcgggtgtgg tggttacgcg cagcgtgacc gctacacttg ccagcgccct
2761 agcgcccgct cctttcgctt tcttcccttc ctttctcgcc acgttcgccg gctttccccg
2821 tcaagctcta aatcggggca tccctttagg gttccgattt agtgctttac ggcacctcga
2881 ccccaaaaaa cttgattagg gtgatggttc acgtagtggg ccatcgccct gatagacggt
2941 ttttcgccct ttgacgttgg agtccacgtt ctttaatagt ggactcttgt tccaaactgg
3001 aacaacactc aaccctatct cggtctattc ttttgattta taagggattt tggggatttc
3061 ggcctattgg ttaaaaaatg agctgattta acaaaaattt aacgcgaatt aattctgtgg
3121 aatgtgtgtc agttagggtg tggaaagtcc ccaggctccc caggcaggca gaagtatgca
3181 aagcatgcat ctcaattagt cagcaaccag gtgtggaaag tccccaggct ccccagcagg
3241 cagaagtatg caaagcatgc atctcaatta gtcagcaacc atagtcccgc ccctaactcc
3301 gcccatcccg cccctaactc cgcccagttc cgcccattct ccgccccatg gctgactaat
3361 ttttttattt tatgcagagg ccgaggccgc ctctgcctct gagctattcc agaagtagtg
3421 aggaggcttt tttggaggcc taggcttttg caaaaagctc ccgggagctt gtatatccat
3481 tttcggatct gatcagcacg tgttgacaat taatcatcgg catagtatat cggcatagta
3541 taatacgaca aggtgaggaa ctaaaccatg gccaagttga ccagtgccgt tccggtgctc
3601 accgcgcgcg acgtcgccgg agcggtcgag ttctggaccg accggctcgg gttctcccgg
3661 gacttcgtgg aggacgactt cgccggtgtg gtccgggacg acgtgaccct gttcatcagc
3721 gcggtccagg accaggtggt gccggacaac accctggcct gggtgtgggt gcgcggcctg
3781 gacgagctgt acgccgagtg gtcggaggtc gtgtccacga acttccggga cgcctccggg
3841 ccggccatga ccgagatcgg cgagcagccg tgggggcggg agttcgccct gcgcgacccg
3901 gccggcaact gcgtgcactt cgtggccgag gagcaggact gacacgtgct acgagatttc
3961 gattccaccg ccgccttcta tgaaaggttg ggcttcggaa tcgttttccg ggacgccggc
4021 tggatgatcc tccagcgcgg ggatctcatg ctggagttct tcgcccaccc caacttgttt
4081 attgcagctt ataatggtta caaataaagc aatagcatca caaatttcac aaataaagca
4141 tttttttcac tgcattctag ttgtggtttg tccaaactca tcaatgtatc ttatcatgtc
4201 tgtataccgt cgacctctag ctagagcttg gcgtaatcat ggtcatagct gtttcctgtg
4261 tgaaattgtt atccgctcac aattccacac aacatacgag ccggaagcat aaagtgtaaa
4321 gcctggggtg cctaatgagt gagctaactc acattaattg cgttgcgctc actgcccgct
4381 ttccagtcgg gaaacctgtc gtgccagctg cattaatgaa tcggccaacg cgcggggaga
4441 ggcggtttgc gtattgggcg ctcttccgct tcctcgctca ctgactcgct gcgctcggtc
4501 gttcggctgc ggcgagcggt atcagctcac tcaaaggcgg taatacggtt atccacagaa
4561 tcaggggata acgcaggaaa gaacatgtga gcaaaaggcc agcaaaaggc caggaaccgt
4621 aaaaaggccg cgttgctggc gtttttccat aggctccgcc cccctgacga gcatcacaaa
4681 aatcgacgct caagtcagag gtggcgaaac ccgacaggac tataaagata ccaggcgttt
4741 ccccctggaa gctccctcgt gcgctctcct gttccgaccc tgccgcttac cggatacctg
4801 tccgcctttc tcccttcggg aagcgtggcg ctttctcaat gctcacgctg taggtatctc
4861 agttcggtgt aggtcgttcg ctccaagctg ggctgtgtgc acgaaccccc cgttcagccc
4921 gaccgctgcg ccttatccgg taactatcgt cttgagtcca acccggtaag acacgactta
4981 tcgccactgg cagcagccac tggtaacagg attagcagag cgaggtatgt aggcggtgct
5041 acagagttct tgaagtggtg gcctaactac ggctacacta gaaggacagt atttggtatc
5101 tgcgctctgc tgaagccagt taccttcgga aaaagagttg gtagctcttg atccggcaaa
5161 caaaccaccg ctggtagcgg tggttttttt gtttgcaagc agcagattac gcgcagaaaa
5221 aaaggatctc aagaagatcc tttgatcttt tctacggggt ctgacgctca gtggaacgaa
5281 aactcacgtt aagggatttt ggtcatgaga ttatcaaaaa ggatcttcac ctagatcctt
5341 ttaaattaaa aatgaagttt taaatcaatc taaagtatat atgagtaaac ttggtctgac
5401 agttaccaat gcttaatcag tgaggcacct atctcagcga tctgtctatt tcgttcatcc
5461 atagttgcct gactccccgt cgtgtagata actacgatac gggagggctt accatctggc
5521 cccagtgctg caatgatacc gcgagaccca cgctcaccgg ctccagattt atcagcaata
5581 aaccagccag ccggaagggc cgagcgcaga agtggtcctg caactttatc cgcctccatc
5641 cagtctatta attgttgccg ggaagctaga gtaagtagtt cgccagttaa tagtttgcgc
5701 aacgttgttg ccattgctac aggcatcgtg gtgtcacgct cgtcgtttgg tatggcttca
```

FIG 13 CONT

```
5761 ttcagctccg gttcccaacg atcaaggcga gttacatgat cccccatgtt gtgcaaaaaa
5821 gcggttagct ccttcggtcc tccgatcgtt gtcagaagta agttggccgc agtgttatca
5881 ctcatggtta tggcagcact gcataattct cttactgtca tgccatccgt aagatgcttt
5941 tctgtgactg gtgagtactc aaccaagtca ttctgagaat agtgtatgcg gcgaccgagt
6001 tgctcttgcc cggcgtcaat acgggataat accgcgccac atagcagaac tttaaaagtg
6061 ctcatcattg gaaaacgttc ttcggggcga aaactctcaa ggatcttacc gctgttgaga
6121 tccagttcga tgtaacccac tcgtgcaccc aactgatctt cagcatcttt tactttcacc
6181 agcgtttctg ggtgagcaaa aacaggaagg caaaatgccg caaaaaaggg aataagggcg
6241 acacggaaat gttgaatact catactcttc ctttttcaat attattgaag catttatcag
6301 ggttattgtc tcatgagcgg atacatattt gaatgtattt agaaaaataa acaaataggg
6361 gttccgcgca catttccccg aaaagtgcca cctgacgtcg acggatcggg agatctcccg
6421 atcccctatg gtgcactctc agtacaatct gctctgatgc cgcatagtta agccagtatc
6481 tgctccctgc ttgtgtgttg gaggtcgctg agtagtgcgc gagcaaaatt taagctacaa
6541 caaggcaagg cttgaccgac aattgcatga agaatctgct tagggttagg cgttttgcgc
6601 tgcttcgcga tgtacgggcc agatatacgc gttgacattg attattgact agttattaat
6661 agtaatcaat tacggggtca ttagttcata gcccatatat ggagttccgc gttacataac
6721 ttacggtaaa tggcccgcct ggctgaccgc ccaacgaccc ccgcccattg acgtcaataa
6781 tgacgtatgt tcccatagta acgccaatag ggactttcca ttgacgtcaa tgggtggact
6841 atttacggta aactgcccac ttggcagtac atcaagtgta tcatatgcca agtacgcccc
6901 ctattgacgt caatgacggt aaatggcccg cctggcatta tgcccagtac atgaccttat
6961 gggactttcc tacttggcag tacatctacg tattagtcat cgctattacc atggtgatgc
7021 ggttttggca gtacatcaat gggcgtggat agcggtttga ctcacgggga tttccaagtc
7081 tccaccccat tgacgtcaat gggagtttgt tttggcacca aaatcaacgg gactttccaa
7141 aatgtcgtaa caactccgcc ccattgacgc aaatgggcgg taggcgtgta cggtgggagg
7201 tctatataag cagagctctc tggctaacta gagaacccac tgcttactgg cttatcgaaa
7261 ttaatacgac tcactatagg gagacccaag ctggtttaaa cttaagcttg gtaccgagct
7321 cactagtcca gtgtggtggc agatatccag cacagtggcg gccgctcgag tctagagggc
7381 ccgttttgcc tgtactgggt ctctctggtt agaccagatc tgagcctggg agctctctgg
7441 ctaactaggg aacccactgc ttaagcctca ataaagcttg ccttgagtgc ttcaagtagt
7501 gtgtgcccgt ctgttgtgtg actctggtaa ctagagatcc ctcagaccct tttagtcagt
7561 gtggaaaatc tctagcagtg gcgcccgaac agggacttga aagcgaaagg gaaaccagag
7621 gagctctctc gacgcaggac tcggcttgct gaagcgcgca cggcaagagg cgaggggcgg
7681 cgactggtga gtacgccaaa aattttgact agcggaggct agaaggagag agatgggtgc
7741 gagagcgtca gtattaagcg ggggagaatt agatcgcgat gggaaaaaat tcggttaagg
7801 ccagggggaa agaaaaaata taaattaaaa catatagtat gggcaagcag ggagctagaa
7861 cgattcgcag ttaatcctgg cctgttagaa acatcagaag gctgtagaca aatactggga
7921 cagctacaac catcccttca gacaggatca gaagaactta gatcattata taatacagta
7981 gcaaccctct attgtgtgca tcaaaggata gagataaaag acaccaagga agctttagac
8041 aagatagagg aagagcaaaa caaaagtaag accaccgcac agcaagcggc cgctgatctt
8101 cagacctgga ggaggagata tgagggacaa ttggagaagt gaattatata aatataaagt
8161 agtaaaaatt gaaccattag gagtagcacc caccaaggca aagagaagag tggtgcagag
8221 agaaaaaaga gcagtgggaa taggagcttt gttccttggg ttcttgggag cagcaggaag
8281 cactatgggc gcagcgtcaa tgacgctgac ggtacaggcc agacaattat tgtctggtat
8341 agtgcagcag cagaacaatt tgctgagggc tattgaggcg caacagcatc tgttgcaact
8401 cacagtctgg ggcatcaagc agctccaggc aagaatcctg gctgtggaaa gatacctaaa
8461 ggatcaacag ctcctgggga tttggggttg ctctggaaaa ctcatttgca ccactgctgt
8521 gccttggaat gctagttgga gtaataaatc tctggaacag atttggaatc acacgacctg
8581 gatggagtgg gacagagaaa ttaacaatta cacaagctta atacactcct taattgaaga
8641 atcgcaaaac cagcaagaaa agaatgaaca agaattattg gaattagata aatgggcaag
8701 tttgtggaat tggtttaaca taacaaattg gctgtggtat ataaaattat tcataatgat
8761 agtaggaggc ttggtaggtt taagaatagt ttttgctgta ctttctatag tgaatagagt
8821 taggcaggga tattcaccat tatcgtttca gacccacctc ccaaccccga ggggacccga
8881 caggccctta attaagctac atcatcaata atatacctta ttttggattg aagccaatat
8941 gataatgagg gggtggagtt tgtgacgtgg cgcggggcgt gggaacgggg cgggtgacgt
9001 agtagtgtgg cggaagtgtg atgttgcaag tgtggcggaa cacatgtaag cgacggatgt
9061 ggcaaaagtg acgtttttgg tgtgcgccgg tgtacacagg aagtgacaat tttcgcgcgg
9121 ttttaggcgg atgttgtagt aaatttgggc gtaaccgagt aagatttggc cattttcgcg
```

FIG 13 CONT 9181 ggaaaactga ataagaggaa gtgaaatctg aataattttg tgttactcat agcgcgtaat
9241 atttgtctag ggagatccga gctttgcaaa gatggataaa gttttaaaca gagaggaatc
9301 tttgcagcta atggaccttc taggtcttga aaggagtggg aattggctcc ggtgcccgtc
9361 agtgggcaga gcgcacatcg cccacagtcc ccgagaagtt ggggggaggg gtcggcaatt
9421 gaaccggtgc ctagagaagg tggcgcgggg taaactggga aagtgatgtc gtgtactggc
9481 tccgcctttt tcccgagggt gggggagaac cgtatataag tgcagtagtc gccgtgaacg
9541 ttctttttcg caacgggttt gccgccagaa cacaggtaag tgccgtgtgt ggttcccgcg
9601 ggcctggcct ctttacgggt tatggccctt gcgtgccttg aattacttcc acctggctgc
9661 agtacgtgat tcttgatccc gagcttcggg ttggaagtgg gtgggagagt tcgaggcctt
9721 gcgcttaagg agccccttcg cctcgtgctt gagttgaggc ctggcctggg cgctggggcc
9781 gccgcgtgcg aatctggtgg caccttcgcg cctgtctcgc tgctttcgat aagtctctag
9841 ccatttaaaa tttttgatga cctgctgcga cgcttttttt ctggcaagat agtcttgtaa
9901 atgcgggcca agatctgcac actggtattt cggtttttgg ggccgcgggc ggcgacgggg
9961 cccgtgcgtc ccagcgcaca tgttcggcga ggcggggcct gcgagcgcgg ccaccgagaa
10021 tcggacgggg gtagtctcaa gctggccggc ctgctctggt gcctggcctc gcgccgccgt
10081 gtatcgcccc gccctgggcg gcaaggctgg cccggtcggc accagttgcg tgagcggaaa
10141 gatggccgct tcccggccct gctgcaggga gctcaaaatg gaggacgcgg cgctcgggag
10201 agcgggcggg tgagtcaccc acacaaagga aaagggcctt tccgtcctca gccgtcgctt
10261 catgtgactc cacggagtac cgggcgccgt ccaggcacct cgattagttc tcgagctttt
10321 ggagtacgtc gtctttaggt tggggggagg ggttttatgc gatggagttt ccccacactg
10381 agtgggtgga gactgaagtt aggccagctt ggcacttgat gtaattctcc ttggaatttg
10441 ccctttttga gtttggatct tggttcattc tcaagcctca gacagtggtt caaagttttt
10501 ttcttccatt tcaggtgtcg tgaggaattc gctactagct cgagaagaat tcaaggcgcg
10561 ccgccaccat gctttttagc tttttcgaa atttgtgccg tgttttgtat cgcgttcgcg
10621 ttacgggtga cacccaggca ctgaagggcg agcgcgttct aattacgcct aatcacgtct
10681 cttttattga tggcattttg cttggactgt ttttacctgt gcgtccagtg tttgccgttt
10741 acacctcaat aagccaacag tggtatatgc gttggctgaa atcatttatc gactttgttc
10801 ctctcgaccc gacgcaacct atggctatta aacatctggt acgtctggtg gaacagggcc
10861 gaccagtggt gattttccct gaaggacgca tcaccacgac aggctcgctg atgaaaatct
10921 acgatggcgc gggttttgtc gcggcgaagt ctggtgcaac ggttattcct gtgcgtattg
10981 aaggggcgga acttacgcac ttcagccgcc tgaaaggtct ggttaaacgt cgcttgttcc
11041 cgcaaattac tctgcatatt ttgccaccaa cgcaggtggc gatgccggat gcgccgcgtg
11101 cccgtgaccg tcgcaaaatc gctggcgaaa tgctgcatca aataatgatg gaagcgcgaa
11161 tggcggtgcg cccgcgtgaa acgctgtacg aatctttact gagtgcaatg taccgcttcg
11221 gagccgggaa gaaatgtgtc gaagacgtca actttacccc agactcctat cgcaaattgc
11281 ttacgaaaac gctgtttgtt ggacgcatcc ttgaaaaata cagtgttgaa ggcgaacgca
11341 tcggcttaat gctgcccaat gcaggcatca gtgcggcagt gatttttggg gccatcgccc
11401 gtcgccgcat gcccgcaatg atgaactaca ctgccggggt aaaagggctg accagtgcta
11461 ttacggcggc tgaaatcaaa accatcttca cttcccgcca gtttctcgat aaaggcaaac
11521 tctggcatct gccggagcaa cttactcagg tgcgctgggt ctatctggaa gatttaaaag
11581 cagatgtcac cactgccgac aaagtatgga tcttcgctca tttgctgatg ccgcgtctgg
11641 cacaggttaa acagcagccg gaagaagagg cgctgatcct ttttacctcc ggttctgaag
11701 gccatccgaa aggcgtcgtc catagccata aaagcattct ggcgaatgtc gagcagatta
11761 aaacgattgc cgacttcacc accaacgatc gctttatgtc ggcgttaccg ctgtttcact
11821 cctttgggct gacggtaggc ctgtttacgc cactgcttac aggtgcagaa gtgttccttt
11881 atccaagccc gctgcattac cgcattgtgc cggagttggt gtatgaccgc agttgcaccg
11941 tgttgttcgg cacctcgact ttcctcggtc actacgcgcg tttcgccaac ccgtatgact
12001 tctatcgtct acgctatgtg gtggcaggcg cagaaaaatt acaagaaagt accaaacagc
12061 tttggcagga taaatttggc ctgcgcatcc ttgaaggcta cggcgtgacc gaatgcgcgc
12121 ctgtcgtttc tatcaacgta ccgatggcgg cgaaacccgg tacggtaggg cgtattctac
12181 caggaatgga tgcgcgcctg ttgtcggtcc ctggtatcga agagggcgga cgcctgcaac
12241 tgaaagggcc gaacataatg aacggctatc tgcgggtgga gaagccaggt gtactggaag
12301 tgcccaccgc cgagaatgtt cgcggcgaaa tggagcgcgg ctggtatgac actggcgata
12361 ttgtgcgttt tgacgagcag ggctttgtgc agattcaggg ccgcgcaaaa cgctttgcca
12421 aaattgcagg cgaaatggtg tcgctggaaa tggtggaaca actggcactt ggtgtttcgc
12481 cagataaagt ccatgccact gcgattaaga gcgatgccag caaaggcgag gcactggtgc
12541 ttttcaccac agataacgaa ctgacgcgcg ataagttgca acagtatgcc cgcgagcacg

FIG 13 CONT 12601 gcgtgccgga gcttgctgta ccgcgcgata ttcgctatct gaaacagatg ccattacttg
12661 gcagcggcaa acctgacttt gtcacgttga aaagctgggt agacgaagcg gaacaacacg
12721 atgagtgagg

FIG 13 CONT

```
FEATURES             Location/Qualifiers
     promoter        8835..9884
                     /vntifkey="29"
                     /label=alpha-fetoprotein-promoter
     RBS             602..611
                     /vntifkey="32"
                     /label=Kozak\consensus
     CDS             608..1285
                     /vntifkey="4"
                     /label=DsRED2
     misc_feature    7336..7516
                     /vntifkey="21"
                     /label=5'\LTR
     misc_feature    2085..2319
                     /vntifkey="21"
                     /label=deltaU3-3'LTR
     misc_feature    7233..7335
                     /vntifkey="21"
                     /label=MCS
     misc_feature    20..604
                     /vntifkey="21"
                     /label=IRES
     misc_feature    1294..1885
                     /vntifkey="21"
                     /label=WPRE
     CDS             complement(5342..6202)
                     /vntifkey="4"
                     /label=Amp(r)
     promoter        complement(6203..6300)
                     /vntifkey="29"
                     /label=bla
     rep_origin      complement(4524..5197)
                     /vntifkey="33"
                     /label=pUC\ori
     CDS             3507..3881
                     /vntifkey="4"
                     /label=Zeocin(r)
     promoter        3440..3505
                     /vntifkey="29"
                     /label=EM7
     rep_origin      3099..3424
                     /vntifkey="33"
                     /label=SV40\ori
     rep_origin      2621..3033
                     /vntifkey="33"
                     /label=f1\ori
     misc_feature    2345..2558
```

FIG 15

```
                    /vntifkey="21"
                    /label=BGH\PolyA
     promoter       7201..7220
                    /vntifkey="29"
                    /label=T7\promoter
     promoter       6547..7198
                    /vntifkey="29"
                    /label=PCMV
     CDS            9911..10765
                    /vntifkey="4"
                    /label=Pdx1
BASE COUNT     2660 a     2758 c     2769 g     2586 t
ORIGIN
SEQ ID NO:06
        1 cggccatcga taaggatccg cccctctccc tccccccccc ctaacgttac tggccgaagc
       61 cgcttggaat aaggccggtg tgcgtttgtc tatatgttat tttccaccat attgccgtct
      121 tttggcaatg tgagggcccg gaaacctggc cctgtcttct tgacgagcat tcctaggggt
      181 ctttcccctc tcgccaaagg aatgcaaggt ctgttgaatg tcgtgaagga agcagttcct
      241 ctggaagctt cttgaagaca aacaacgtct gtagcgaccc tttgcaggca gcggaacccc
      301 ccacctggcg acaggtgcct ctgcggccaa aagccacgtg tataagatac acctgcaaag
      361 gcggcacaac cccagtgcca cgttgtgagt tggatagttg tggaaagagt caaatggctc
      421 tcctcaagcg tattcaacaa ggggctgaag gatgcccaga aggtacccca ttgtatggga
      481 tctgatctgg ggcctcggtg cacatgcttt acatgtgttt agtcgaggtt aaaaaaacgt
      541 ctaggccccc cgaaccacgg ggacgtggtt ttcctttgaa aaacacgatg ataatatggc
      601 cacaaccatg gcctcctccg aggacgtcat caaggagttc atgcgcttca aggtgcgcat
      661 ggagggctcc gtgaacggcc acgagttcga gatcgagggc gagggcgagg gccgccccta
      721 cgagggcacc cagaccgcca agctgaaggt gaccaagggc ggccccctgc ccttcgcctg
      781 ggacatcctg tcccccagt tccagtacgg ctccaaggtg tacgtgaagc accccgccga
      841 catccccgac tacaagaagc tgtccttccc cgagggcttc aagtgggagc gcgtgatgaa
      901 cttcgaggac ggcggcgtgg tgaccgtgac ccaggactcc tccctgcagg acggctcctt
      961 catctacaag gtgaagttca tcggcgtgaa cttcccctcc gacggccccg taatgcagaa
     1021 gaagactatg ggctgggagg cctccaccga gcgcctgtac cccgcgacg gcgtgctgaa
     1081 gggcgagatc cacaaggccc tgaagctgaa ggacggcggc cactacctgg tggagttcaa
     1141 gtccatctac atggccaaga agcccgtgca gctgcccggc tactactacg tggactccaa
     1201 gctggacatc acctcccaca acgaggacta caccatcgtg gagcagtacg agcgcgccga
     1261 gggccgccac cacctgttcc tgtaggcggc cgcaatcaac ctctggatta caaaatttgt
     1321 gaaagattga ctggtattct taactatgtt gctcctttta cgctatgtgg atacgctgct
     1381 ttaatgcctt tgtatcatgc tattacttcc cgtacggctt tcattttctc ctccttgtat
     1441 aaatcctggt tgctgtctct ttatgaggag ttgtggcccg ttgtcaggca acgtggcgtg
     1501 gtgtgcactg tgtttgctga cgcaaccccc actggttggg gcattgccac cacctatcaa
     1561 ctcctttccg ggactttcgc tttccccctc cctattgcca cggcggaact cattgccgcc
     1621 tgccttgccc gctgctggac aggggctcgg ctgttgggca ctgacaattc cgtggtgttg
     1681 tcggggaagc tgacgtcctt tccatggctg ctcgcctgtg ttgccaactg gattctgcgc
     1741 gggacgtcct tctgctacgt cccttcggcc ctcaatccag cggaccttcc ttcccgcggc
     1801 ctgctgccgg ttctgcggcc tcttccgcgt cttcgccttc gccctcagac gagtcggatc
     1861 tccctttggg ccgcctcccc gcctgcctgc aggtttgtcg agacctagaa aaacatggag
     1921 caatcacaag tagcaataca gcagctacca atgctgattg tgcctggcta gaagcacaag
     1981 aggaggagga ggtgggtttt ccagtcacac ctcaggtacc tttaagacca atgacttaca
     2041 aggcagctgt agatcttagc cactttttaa aagaaaaggg gggactggaa gggctaattc
     2101 actcccaacg aagacaagat ctgctttttg cttgtactgg gtctctctgg ttagaccaga
     2161 tctgagcctg ggagctctct ggctaactag ggaacccact gcttaagcct caataaagct
     2221 tgccttgagt gcttcaagta gtgtgtgccc gtctgttgtg tgactctggt aactagagat
     2281 ccctcagacc cttttagtca gtgtggaaaa tctctagcag ggcccgttta aacccgctga
     2341 tcagcctcga ctgtgccttc tagttgccag ccatctgttg tttgcccctc ccccgtgcct
```

FIG 15 CONT 2401 tccttgaccc tggaaggtgc cactcccact gtcctttcct aataaaatga ggaaattgca
2461 tcgcattgtc tgagtaggtg tcattctatt ctggggggtg gggtggggca ggacagcaag
2521 ggggaggatt gggaagacaa tagcaggcat gctggggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgcccgctc ctttcgcttt cttcccttcc tttctcgcca cgttcgccgg ctttccccgt
2761 caagctctaa atcgggggcat ccctttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg gactcttgtt ccaaactgga
2941 acaacactca accctatctc ggtctattct tttgatttat aagggatttt ggggatttcg
3001 gcctattggt taaaaaatga gctgatttaa caaaaattta acgcgaatta attctgtgga
3061 atgtgtgtca gttagggtgt ggaaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtcccgcc cctaactccg
3241 cccatcccgc ccctaactcc gcccagttcc gcccattctc cgccccatgg ctgactaatt
3301 ttttttattt atgcagaggc cgaggccgcc tctgcctctg agctattcca gaagtagtga
3361 ggaggctttt ttggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgg ccaagttgac cagtgccgtt ccggtgctca
3541 ccgcgcgcga cgtcgccgga gcggtcgagt tctggaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttccgggac gcctccgggc
3781 cggccatgac cgagatcggc gagcagccgt gggggcggga gttcgccctg cgcgacccgg
3841 ccggcaactg cgtgcacttc gtggccgagg agcaggactg acacgtgcta cgagatttcg
3901 attccaccgc cgccttctat gaaaggttgg gcttcggaat cgttttccgg gacgccggct
3961 ggatgatcct ccagcgcggg gatctcatgc tggagttctt cgcccacccc aacttgttta
4021 ttgcagctta taatggttac aaataaagca atagcatcac aaatttcaca aataaagcat
4081 tttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata aagtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcggggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg tttttccata ggctccgccc ccctgacgag catcacaaaa
4621 atcgacgctc aagtcagagg tggcgaaacc cgacaggact ataaagatac caggcgtttc
4681 cccctggaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaacccccc gttcagcccg
4861 accgctgcgc cttatccggt aactatcgtc ttgagtccaa cccggtaaga cacgacttat
4921 cgccactggc agcagccact ggtaacagga ttagcagagc gaggtatgta ggcggtgcta
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggtttttttg tttgcaagca gcagattacg cgcagaaaaa
5161 aaggatctca agaagatcct ttgatctttt ctacggggtc tgacgctcag tggaacgaaa
5221 actcacgtta agggattttg gtcatgagat tatcaaaaag gatcttcacc tagatccttt
5281 taaattaaaa atgaagtttt aaatcaatct aaagtatata tgagtaaact tggtctgaca
5341 gttaccaatg cttaatcagt gaggcaccta tctcagcgat ctgtctattt cgttcatcca
5401 tagttgcctg actccccgtc gtgtagataa ctacgatacg ggagggctta ccatctggcc
5461 ccagtgctgc aatgataccg cgagacccac gctcaccggc tccagattta tcagcaataa
5521 accagccagc cggaagggcc gagcgcagaa gtggtcctgc aactttatcc gcctccatcc
5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat
5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac

FIG 15 CONT

```
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact ttaaaagtgc
6001 tcatcattgg aaaacgttct tcggggcgaa aactctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga ataagggcga
6181 cacggaaatg ttgaatactc atactcttcc tttttcaata ttattgaagc atttatcagg
6241 gttattgtct catgagcgga tacatatttg aatgtattta gaaaaataaa caaatagggg
6301 ttccgcgcac atttccccga aaagtgccac ctgacgtcga cggatcggga gatctcccga
6361 tcccctatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc cgcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgccccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat ttccaagtct
7021 ccaccccatt gacgtcaatg ggagtttgtt ttggcaccaa aatcaacggg actttccaaa
7081 atgtcgtaac aactccgccc cattgacgca aatgggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtggca gatatccagc acagtggcgg ccgctcgagt ctagagggcc
7321 cgttttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagaccctt ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta gaaggagaga gatgggtgcg
7681 agagcgtcag tattaagcgg gggagaatta gatcgcgatg ggaaaaaatt cggttaaggc
7741 cagggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga agagcaaaac aaaagtaaga ccaccgcaca gcaagcggcc gctgatcttc
8041 agacctggag gaggagatat gagggacaat tggagaagtg aattatataa atataaagta
8101 gtaaaaattg aaccattagg agtagcaccc accaaggcaa agagaagagt ggtgcagaga
8161 gaaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag atacctaaag
8401 gatcaacagc tcctggggat ttggggttgc tctggaaaac tcatttgcac cactgctgtg
8461 ccttggaatg ctagttggag taataaatct ctggaacaga tttggaatca cacgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata taaaattatt cataatgata
8701 gtaggaggct tggtaggttt aagaatagtt tttgctgtac tttctatagt gaatagagtt
8761 aggcagggat attcaccatt atcgtttcag acccacctcc caaccccgag gggacccgac
8821 aggcccttaa ttaagccacc tatcctcttc agacctcttc aggaaacagc tatgcacata
8881 gcacacaggc atatgttcaa ccaaaacact gaaacacata aaagaaatgt ttaaagaatg
8941 aatttaaaaa aataaaaaat aaactcaact acatatgaag ccttagcaaa catgtctgga
9001 cctctagaca cacagactct gacacgccaa cgtctgagtt ctagtttcga tacgcactgg
9061 gaagttttaa aagttttcca tcaactctaa tgtgtagaga aatggaaact atcatagact
9121 ctacggcatt gagggtgaag gtatgagtga agcactctta gggtcagaag tatgtcagtg
9181 cccatttgtt gctgttagca tcatcatctt agggcttgag aggatgttgc agctgaccca
```

FIG 15 CONT

```
 9241 tgcacctgtg acatacatat ggaattattc tttggcacat aaaattagaa tgggagctgg
 9301 ctcatcaggt tttgtgctgt aagttttcta tgttaaacca gatgcgatac actaaataaa
 9361 ataaaatata cttgaccgat ggttttgagc gaaataataa ctggataatc aagaaatata
 9421 tccactaatg aatagcctga actactgaaa caatttgttc agtgcctagc atatggtgtg
 9481 cattttatta tttctttcaa aaagaatgta tttggagtta catagtaagt ctgctacctt
 9541 ttctttatgg ctatatctat gtcttatgtt gagatgaatg aattattctt caggggaaat
 9601 aatctatttg aacagtttag atggtgaaga acatttgcag catttgcaag atttttttcc
 9661 actctgaagt ggtctttgtc cttgaacata ggatacaagt gacccctgct ctgttaatta
 9721 ttggcaaatt gcctaacttc aacgtaagga aatagagtca tatgtttgct cactgaaggt
 9781 tactagttaa caggcatccc ttaaacagga tataaaagga cttcagcagg actgctcgaa
 9841 acatcccact tccagcactg cctgcggtga aggaaccagc agccgaattc ggccattacg
 9901 gcctgccacc atgaacagtg aggagcagta ctacgcggcc acacagctct acaaggaccc
 9961 gtgcgcattc cagaggggcc cggtgccaga gttcagcgct aacccccctg cgtgcctgta
10021 catgggccgc cagcccccac ctccgccgcc accccagttt acaagctcgc tgggatcact
10081 ggagcaggga agtcctccgg acatctcccc atacgaagtg cccccgctcg cctccgacga
10141 cccggctggc gctcacctcc accaccacct tccagctcag ctcgggctcg cccatccacc
10201 tcccggacct ttcccgaatg gaaccgagcc tgggggcctg gaagagccca accgcgtcca
10261 gctccctttc ccgtggatga aatccaccaa agctcacgcg tggaaaggcc agtgggcagg
10321 aggtgcttac acagcggaac ccgaggaaaa caagaggacc cgtactgcct acacccgggc
10381 gcagctgctg gagctggaga aggaattctt atttaacaaa tacatctccc ggcccccgccg
10441 ggtggagctg gcagtgatgt tgaacttgac cgagagacac atcaaaatct ggttccaaaa
10501 ccgtcgcatg aagtggaaaa aagaggaaga taagaaacgt agtagcggga ccccgagtgg
10561 gggcggtggg ggcgaagagc cggagcaaga ttgtgcggtg acctcgggcg aggagctgct
10621 ggcagtgcca ccgctgccac ctcccggagg tgccgtgccc ccaggcgtcc cagctgcagt
10681 ccgggagggc ctactgcctt cgggccttag cgtgtcgcca cagccctcca gcatcgcgcc
10741 actgcgaccg caggaacccc ggtgaggccg cct
```

FIG 15 CONT

```
FEATURES             Location/Qualifiers
     promoter        8835..9884
                     /vntifkey="29"
                     /label=alpha-fetoprotein-promoter
     RBS             602..611
                     /vntifkey="32"
                     /label=Kozak\consensus
     CDS             608..1285
                     /vntifkey="4"
                     /label=DsRED2
     misc_feature    7336..7516
                     /vntifkey="21"
                     /label=5'\LTR
     misc_feature    2085..2319
                     /vntifkey="21"
                     /label=deltaU3-3'LTR
     misc_feature    7233..7335
                     /vntifkey="21"
                     /label=MCS
     misc_feature    20..604
                     /vntifkey="21"
                     /label=IRES
     misc_feature    1294..1885
                     /vntifkey="21"
                     /label=WPRE
     CDS             complement(5342..6202)
                     /vntifkey="4"
                     /label=Amp(r)
     promoter        complement(6203..6300)
                     /vntifkey="29"
                     /label=bla
     rep_origin      complement(4524..5197)
                     /vntifkey="33"
                     /label=pUC\ori
     CDS             3507..3881
                     /vntifkey="4"
                     /label=Zeocin(r)
     promoter        3440..3505
                     /vntifkey="29"
                     /label=EM7
     rep_origin      3099..3424
                     /vntifkey="33"
                     /label=SV40\ori
     rep_origin      2621..3033
                     /vntifkey="33"
                     /label=f1\ori
     misc_feature    2345..2558
```

FIG 17

```
                     /vntifkey="21"
                     /label=BGH\PolyA
     promoter        7201..7220
                     /vntifkey="29"
                     /label=T7\promoter
     promoter        6547..7198
                     /vntifkey="29"
                     /label=PCMV
     RBS             9903..9913
                     /vntifkey="32"
                     /label=Kozak\consensus
     CDS             9910..10554
                     /vntifkey="4"
                     /label=NEUROG3
     misc_difference 10505..10505
                     /gene="NEUROG3"
                     /vntifkey="85"
                     /label=NEUROG3
                     /note="'C' in cDNA is 'T' in the human
genome; amino acid difference: 'S' in cDNA, 'F' in the human
genome.  The chimpanzee genome agrees with the cDNA sequence,
suggesting that this difference is unlikely to be due to an
artifact."
BASE COUNT     2594 a      2699 c      2725 g      2544 t
ORIGIN
SEQ ID NO:07
        1 cggccatcga taaggatccg cccctctccc tccccccccc ctaacgttac tggccgaagc
       61 cgcttggaat aaggccggtg tgcgtttgtc tatatgttat tttccaccat attgccgtct
      121 tttggcaatg tgagggcccg gaaacctggc cctgtcttct tgacgagcat tcctaggggt
      181 ctttcccctc tcgccaaagg aatgcaaggt ctgttgaatg tcgtgaagga agcagttcct
      241 ctggaagctt cttgaagaca aacaacgtct gtagcgaccc tttgcaggca gcggaacccc
      301 ccacctggcg acaggtgcct ctgcggccaa aagccacgtg tataagatac acctgcaaag
      361 gcggcacaac cccagtgcca cgttgtgagt tggatagttg tggaaagagt caaatggctc
      421 tcctcaagcg tattcaacaa ggggctgaag gatgcccaga aggtacccca ttgtatggga
      481 tctgatctgg ggcctcggtg cacatgcttt acatgtgttt agtcgaggtt aaaaaaacgt
      541 ctaggccccc cgaaccacgg ggacgtggtt ttcctttgaa aaacacgatg ataatatggc
      601 cacaaccatg gcctcctccg aggacgtcat caaggagttc atgcgcttca aggtgcgcat
      661 ggagggctcc gtgaacggcc acgagttcga gatcgagggc gagggcgagg gccgccccta
      721 cgagggcacc cagaccgcca agctgaaggt gaccaagggc ggccccctgc ccttcgcctg
      781 ggacatcctg tcccccagt tccagtacgg ctccaaggtg tacgtgaagc accccgccga
      841 catccccgac tacaagaagc tgtccttccc cgagggcttc aagtgggagc gcgtgatgaa
      901 cttcgaggac ggcggcgtgg tgaccgtgac ccaggactcc tccctgcagg acggctcctt
      961 catctacaag gtgaagttca tcggcgtgaa cttcccctcc gacggccccg taatgcagaa
     1021 gaagactatg ggctgggagg cctccaccga gcgcctgtac cccgcgacg gcgtgctgaa
     1081 gggcgagatc cacaaggccc tgaagctgaa ggacggcggc cactacctgg tggagttcaa
     1141 gtccatctac atggccaaga agcccgtgca gctgcccggc tactactacg tggactccaa
     1201 gctggacatc acctcccaca acgaggacta caccatcgtg gagcagtacg agcgcgccga
     1261 gggccgccac cacctgttcc tgtaggcggc cgcaatcaac ctctggatta caaaatttgt
     1321 gaaagattga ctggtattct taactatgtt gctcctttta cgctatgtgg atacgctgct
     1381 ttaatgcctt tgtatcatgc tattacttcc cgtacggctt tcattttctc ctccttgtat
     1441 aaatcctggt tgctgtctct ttatgaggag ttgtggcccg ttgtcaggca acgtggcgtg
     1501 gtgtgcactg tgtttgctga cgcaaccccc actggttggg gcattgccac cacctatcaa
```

FIG 17 CONT 1561 ctcctttccg ggactttcgc tttccccctc cctattgcca cggcggaact cattgccgcc
1621 tgccttgccc gctgctggac aggggctcgg ctgttgggca ctgacaattc cgtggtgttg
1681 tcggggaagc tgacgtcctt tccatggctg ctcgcctgtg ttgccaactg gattctgcgc
1741 gggacgtcct tctgctacgt cccttcggcc ctcaatccag cggaccttcc ttcccgcggc
1801 ctgctgccgg ttctgcggcc tcttccgcgt cttcgccttc gccctcagac gagtcggatc
1861 tccctttggg ccgcctcccc gcctgcctgc aggtttgtcg agacctagaa aaacatggag
1921 caatcacaag tagcaataca gcagctacca atgctgattg tgcctggcta gaagcacaag
1981 aggaggagga ggtgggtttt ccagtcacac ctcaggtacc tttaagacca atgacttaca
2041 aggcagctgt agatcttagc cactttttaa aagaaaaggg gggactggaa gggctaattc
2101 actcccaacg aagacaagat ctgctttttg cttgtactgg gtctctctgg ttagaccaga
2161 tctgagcctg ggagctctct ggctaactag ggaacccact gcttaagcct caataaagct
2221 tgccttgagt gcttcaagta gtgtgtgccc gtctgttgtg tgactctggt aactagagat
2281 ccctcagacc cttttagtca gtgtggaaaa tctctagcag ggcccgttta aacccgctga
2341 tcagcctcga ctgtgccttc tagttgccag ccatctgttg tttgcccctc ccccgtgcct
2401 tccttgaccc tggaaggtgc cactcccact gtcctttcct aataaaatga ggaaattgca
2461 tcgcattgtc tgagtaggtg tcattctatt ctggggggtg gggtggggca ggacagcaag
2521 ggggaggatt gggaagacaa tagcaggcat gctggggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgcccgctc ctttcgcttt cttcccttcc tttctcgcca cgttcgccgg ctttccccgt
2761 caagctctaa atcgggggct ccctttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg gactcttgtt ccaaactgga
2941 acaacactca accctatctc ggtctattct tttgatttat aagggatttt ggggatttcg
3001 gcctattggt taaaaaatga gctgatttaa caaaaattta acgcgaatta attctgtgga
3061 atgtgtgtca gttagggtgt ggaaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtcccgcc cctaactccg
3241 cccatcccgc ccctaactcc gcccagttcc gcccattctc cgccccatgg ctgactaatt
3301 ttttttattt atgcagaggc cgaggccgcc tctgcctctg agctattcca gaagtagtga
3361 ggaggctttt ttggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgg ccaagttgac cagtgccgtt ccggtgctca
3541 ccgcgcgcga cgtcgccgga gcggtcgagt tctggaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttccgggac gcctccgggc
3781 cggccatgac cgagatcggc gagcagccgt gggggcggga gttcgccctg cgcgacccgg
3841 ccggcaactg cgtgcacttc gtggccgagg agcaggactg acacgtgcta cgagatttcg
3901 attccaccgc cgccttctat gaaaggttgg gcttcggaat cgttttccgg gacgccggct
3961 ggatgatcct ccagcgcggg gatctcatgc tggagttctt cgcccacccc aacttgttta
4021 ttgcagctta taatggttac aaataaagca atagcatcac aaatttcaca aataaagcat
4081 tttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata aagtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcggggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg tttttccata ggctccgccc ccctgacgag catcacaaaa
4621 atcgacgctc aagtcagagg tggcgaaacc cgacaggact ataaagatac caggcgtttc
4681 cccctggaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaacccccc gttcagcccg
4861 accgctgcgc cttatccggt aactatcgtc ttgagtccaa cccggtaaga cacgacttat
4921 cgccactggc agcagccact ggtaacagga ttagcagagc gaggtatgta ggcggtgcta

FIG 17 CONT

```
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggtttttttg tttgcaagca gcagattacg cgcagaaaaa
5161 aaggatctca agaagatcct ttgatctttt ctacggggtc tgacgctcag tggaacgaaa
5221 actcacgtta agggattttg gtcatgagat tatcaaaaag gatcttcacc tagatccttt
5281 taaattaaaa atgaagtttt aaatcaatct aaagtatata tgagtaaact tggtctgaca
5341 gttaccaatg cttaatcagt gaggcaccta tctcagcgat ctgtctattt cgttcatcca
5401 tagttgcctg actccccgtc gtgtagataa ctacgatacg ggagggctta ccatctggcc
5461 ccagtgctgc aatgataccg cgagacccac gctcaccggc tccagattta tcagcaataa
5521 accagccagc cggaagggcc gagcgcagaa gtggtcctgc aactttatcc gcctccatcc
5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat
5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact ttaaaagtgc
6001 tcatcattgg aaaacgttct tcggggcgaa aactctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga ataagggcga
6181 cacggaaatg ttgaatactc atactcttcc tttttcaata ttattgaagc atttatcagg
6241 gttattgtct catgagcgga tacatatttg aatgtattta gaaaaataaa caaatagggg
6301 ttccgcgcac atttccccga aaagtgccac ctgacgtcga cggatcggga gatctcccga
6361 tcccctatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc cgcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgccccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat ttccaagtct
7021 ccaccccatt gacgtcaatg ggagtttgtt ttggcaccaa aatcaacggg actttccaaa
7081 atgtcgtaac aactccgccc cattgacgca aatgggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtggca gatatccagc acagtggcgg ccgctcgagt ctagagggcc
7321 cgtttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagaccctt ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta gaaggagaga gatgggtgcg
7681 agagcgtcag tattaagcgg gggagaatta gatcgcgatg ggaaaaaatt cggttaaggc
7741 caggggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga agagcaaaac aaaagtaaga ccaccgcaca gcaagcggcc gctgatcttc
8041 agacctggag gaggagatat gagggacaat tggagaagtg aattatataa atataaagta
8101 gtaaaaattg aaccattagg agtagcaccc accaaggcaa agagaagagt ggtgcagaga
8161 gaaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag atacctaaag
```

FIG 17 CONT 8401 gatcaacagc tcctggggat ttggggttgc tctggaaaac tcatttgcac cactgctgtg
8461 ccttggaatg ctagttggag taataaatct ctggaacaga tttggaatca cacgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata taaaattatt cataatgata
8701 gtaggaggct tggtaggttt aagaatagtt tttgctgtac tttctatagt gaatagagtt
8761 aggcagggat attcaccatt atcgtttcag acccacctcc caaccccgag gggacccgac
8821 aggcccttaa ttaagccacc tatcctcttc agacctcttc aggaaacagc tatgcacata
8881 gcacacaggc atatgttcaa ccaaaacact gaaacacata aaagaaatgt ttaaagaatg
8941 aatttaaaaa aataaaaaat aaactcaact acatatgaag ccttagcaaa catgtctgga
9001 cctctagaca cacagactct gacacgccaa cgtctgagtt ctagtttcga tacgcactgg
9061 gaagttttaa aagttttcca tcaactctaa tgtgtagaga aatggaaact atcatagact
9121 ctacggcatt gagggtgaag gtatgagtga agcactctta gggtcagaag tatgtcagtg
9181 cccatttgtt gctgttagca tcatcatctt agggcttgag aggatgttgc agctgaccca
9241 tgcacctgtg acatacatat ggaattattc tttggcacat aaaattagaa tgggagctgg
9301 ctcatcaggt tttgtgctgt aagttttcta tgttaaacca gatgcgatac actaaataaa
9361 ataaaatata cttgaccgat ggttttgagc gaaataataa ctggataatc aagaaatata
9421 tccactaatg aatagcctga actactgaaa caatttgttc agtgcctagc atatggtgtg
9481 cattttatta tttctttcaa aaagaatgta tttggagtta catagtaagt ctgctacctt
9541 ttctttatgg ctatatctat gtcttatgtt gagatgaatg aattattctt caggggaaat
9601 aatctatttg aacagtttag atggtgaaga acatttgcag catttgcaag attttttcc
9661 actctgaagt ggtctttgtc cttgaacata ggatacaagt gacccctgct ctgttaatta
9721 ttggcaaatt gcctaacttc aacgtaagga aatagagtca tatgtttgct cactgaaggt
9781 tactagttaa caggcatccc ttaaacagga tataaaagga cttcagcagg actgctcgaa
9841 acatcccact tccagcactg cctgcggtga aggaaccagc agccgaattc ggccattacg
9901 gccaccacca tgacgcctca accctcgggt gcgcccactg tccaagtgac ccgtgagacg
9961 gagcggtcct tccccagagc ctcggaagac gaagtgacct gccccacgtc cgccccgccc
10021 agccccactc gcacacgggg gaactgcgca gaggcggaag agggaggctg ccgagggcc
10081 ccgaggaagc tccgggcacg gcgcggggga cgcagccggc ctaagagcga gttggcactg
10141 agcaagcagc gacggagtcg gcgaaagaag gccaacgacc gcgagcgcaa tcgaatgcac
10201 aacctcaact cggcactgga cgccctgcgc ggtgtcctgc ccaccttccc agacgacgcg
10261 aagctcacca agatcgagac gctgcgcttc gcccacaact acatctgggc gctgactcaa
10321 acgctgcgca tagcggacca cagcttgtac gcgctggagc cgccggcgcc gcactgcggg
10381 gagctgggca gcccaggcgg ttcccccggg gactgggggt ccctctactc cccagtctcc
10441 caggctggca gcctgagtcc cgccgcgtcg ctggaggagc gacccgggct gctgggggcc
10501 acctcttccg cctgcttgag cccaggcagt ctggctttct cagattttct gtgaggccgc
10561 ct

FIG 17 CONT

```
FEATURES             Location/Qualifiers
     promoter        8835..9884
                     /vntifkey="29"
                     /label=alpha-fetoprotein-promoter
     RBS             602..611
                     /vntifkey="32"
                     /label=Kozak\consensus
     CDS             608..1285
                     /vntifkey="4"
                     /label=DsRED2
     misc_feature    7336..7516
                     /vntifkey="21"
                     /label=5'\LTR
     misc_feature    2085..2319
                     /vntifkey="21"
                     /label=deltaU3-3'LTR
     misc_feature    7233..7335
                     /vntifkey="21"
                     /label=MCS
     misc_feature    20..604
                     /vntifkey="21"
                     /label=IRES
     misc_feature    1294..1885
                     /vntifkey="21"
                     /label=WPRE
     CDS             complement(5342..6202)
                     /vntifkey="4"
                     /label=Amp(r)
     promoter        complement(6203..6300)
                     /vntifkey="29"
                     /label=bla
     rep_origin      complement(4524..5197)
                     /vntifkey="33"
                     /label=pUC\ori
     CDS             3507..3881
                     /vntifkey="4"
                     /label=Zeocin(r)
     promoter        3440..3505
                     /vntifkey="29"
                     /label=EM7
     rep_origin      3099..3424
                     /vntifkey="33"
                     /label=SV40\ori
     rep_origin      2621..3033
                     /vntifkey="33"
                     /label=f1\ori
     misc_feature    2345..2558
```

FIG 19

```
                  /vntifkey="21"
                  /label=BGH\PolyA
     promoter     7201..7220
                  /vntifkey="29"
                  /label=T7\promoter
     promoter     6547..7198
                  /vntifkey="29"
                  /label=PCMV
     RBS          9904..9914
                  /vntifkey="32"
                  /label=Kozak\consensus
     CDS          9911..10918
                  /vntifkey="4"
                  /label=tTR-KRAB
BASE COUNT     2787 a      2665 c      2762 g      2712 t
ORIGIN
SEQ ID NO:08
        1 cggccatcga taaggatccg cccctctccc tccccccccc ctaacgttac tggccgaagc
       61 cgcttggaat aaggccggtg tgcgtttgtc tatatgttat tttccaccat attgccgtct
      121 tttggcaatg tgagggcccg gaaacctggc cctgtcttct tgacgagcat tcctaggggt
      181 ctttcccctc tcgccaaagg aatgcaaggt ctgttgaatg tcgtgaagga agcagttcct
      241 ctggaagctt cttgaagaca aacaacgtct gtagcgaccc tttgcaggca gcggaacccc
      301 ccacctggcg acaggtgcct ctgcggccaa aagccacgtg tataagatac acctgcaaag
      361 gcggcacaac cccagtgcca cgttgtgagt tggatagttg tggaaagagt caaatggctc
      421 tcctcaagcg tattcaacaa ggggctgaag gatgcccaga aggtacccca ttgtatggga
      481 tctgatctgg ggcctcggtg cacatgcttt acatgtgttt agtcgaggtt aaaaaaacgt
      541 ctaggccccc cgaaccacgg ggacgtggtt ttcctttgaa aaacacgatg ataatatggc
      601 cacaaccatg gcctcctccg aggacgtcat caaggagttc atgcgcttca aggtgcgcat
      661 ggagggctcc gtgaacggcc acgagttcga gatcgagggc gagggcgagg gccgccccta
      721 cgagggcacc cagaccgcca agctgaaggt gaccaagggc ggccccctgc ccttcgcctg
      781 ggacatcctg tcccccagt tccagtacgg ctccaaggtg tacgtgaagc accccgccga
      841 catccccgac tacaagaagc tgtccttccc cgagggcttc aagtgggagc gcgtgatgaa
      901 cttcgaggac ggcggcgtgg tgaccgtgac ccaggactcc tccctgcagg acggctcctt
      961 catctacaag gtgaagttca tcggcgtgaa cttcccctcc gacggccccg taatgcagaa
     1021 gaagactatg ggctgggagg cctccaccga gcgcctgtac cccgcgacg gcgtgctgaa
     1081 gggcgagatc cacaaggccc tgaagctgaa ggacggcggc cactacctgg tggagttcaa
     1141 gtccatctac atggccaaga agcccgtgca gctgcccggc tactactacg tggactccaa
     1201 gctggacatc acctcccaca acgaggacta caccatcgtg gagcagtacg agcgcgccga
     1261 gggccgccac cacctgttcc tgtaggcggc cgcaatcaac ctctggatta caaaatttgt
     1321 gaaagattga ctggtattct taactatgtt gctcctttta cgctatgtgg atacgctgct
     1381 ttaatgcctt tgtatcatgc tattacttcc cgtacggctt tcattttctc ctccttgtat
     1441 aaatcctggt tgctgtctct ttatgaggag ttgtggcccg ttgtcaggca acgtggcgtg
     1501 gtgtgcactg tgtttgctga cgcaaccccc actggttggg gcattgccac cacctatcaa
     1561 ctcctttccg ggactttcgc tttccccctc cctattgcca cggcggaact cattgccgcc
     1621 tgccttgccc gctgctggac aggggctcgg ctgttgggca ctgacaattc cgtggtgttg
     1681 tcggggaagc tgacgtcctt tccatggctg ctcgcctgtg ttgccaactg gattctgcgc
     1741 gggacgtcct tctgctacgt cccttcggcc ctcaatccag cggaccttcc ttcccgcggc
     1801 ctgctgccgg ttctgcggcc tcttccgcgt cttcgccttc gccctcagac gagtcggatc
     1861 tccctttggg ccgcctcccc gcctgcctgc aggtttgtcg agacctagaa aaacatggag
     1921 caatcacaag tagcaataca gcagctacca atgctgattg tgcctggcta gaagcacaag
     1981 aggaggagga ggtgggtttt ccagtcacac ctcaggtacc tttaagacca atgacttaca
     2041 aggcagctgt agatcttagc cactttttaa aagaaaaggg gggactggaa gggctaattc
     2101 actcccaacg aagacaagat ctgctttttg cttgtactgg gtctctctgg ttagaccaga
```

FIG 19 CONT 2161 tctgagcctg ggagctctct ggctaactag ggaacccact gcttaagcct caataaagct
2221 tgccttgagt gcttcaagta gtgtgtgccc gtctgttgtg tgactctggt aactagagat
2281 ccctcagacc cttttagtca gtgtggaaaa tctctagcag ggcccgttta aacccgctga
2341 tcagcctcga ctgtgccttc tagttgccag ccatctgttg tttgcccctc ccccgtgcct
2401 tccttgaccc tggaaggtgc cactcccact gtcctttcct aataaaatga ggaaattgca
2461 tcgcattgtc tgagtaggtg tcattctatt ctggggggtg gggtggggca ggacagcaag
2521 ggggaggatt gggaagacaa tagcaggcat gctggggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgcccgctc ctttcgcttt cttcccttcc tttctcgcca cgttcgccgg ctttccccgt
2761 caagctctaa atcgggggct ccctttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg gactcttgtt ccaaactgga
2941 acaacactca accctatctc ggtctattct tttgatttat aagggatttt ggggatttcg
3001 gcctattggt taaaaaatga gctgatttaa caaaaattta acgcgaatta attctgtgga
3061 atgtgtgtca gttagggtgt ggaaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtcccgcc cctaactccg
3241 cccatcccgc ccctaactcc gcccagttcc gcccattctc cgccccatgg ctgactaatt
3301 ttttttattt atgcagaggc cgaggccgcc tctgcctctg agctattcca gaagtagtga
3361 ggaggctttt ttggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgg ccaagttgac cagtgccgtt ccggtgctca
3541 ccgcgcgcga cgtcgccgga gcggtcgagt tctggaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttccgggac gcctccgggc
3781 cggccatgac cgagatcggc gagcagccgt gggggcggga gttcgccctg cgcgacccgg
3841 ccggcaactg cgtgcacttc gtggccgagg agcaggactg acacgtgcta cgagatttcg
3901 attccaccgc cgccttctat gaaaggttgg gcttcggaat cgttttccgg gacgccggct
3961 ggatgatcct ccagcgcggg gatctcatgc tggagttctt cgcccacccc aacttgttta
4021 ttgcagctta taatggttac aaataaagca atagcatcac aaatttcaca aataaagcat
4081 ttttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata aagtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcggggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg tttttccata ggctccgccc ccctgacgag catcacaaaa
4621 atcgacgctc aagtcagagg tggcgaaacc cgacaggact ataaagatac caggcgtttc
4681 cccctggaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaacccccc gttcagcccg
4861 accgctgcgc cttatccggt aactatcgtc ttgagtccaa cccggtaaga cacgacttat
4921 cgccactggc agcagccact ggtaacagga ttagcagagc gaggtatgta ggcggtgcta
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggtttttttg tttgcaagca gcagattacg cgcagaaaaa
5161 aaggatctca agaagatcct ttgatctttt ctacggggtc tgacgctcag tggaacgaaa
5221 actcacgtta agggattttg gtcatgagat tatcaaaaag gatcttcacc tagatccttt
5281 taaattaaaa atgaagtttt aaatcaatct aaagtatata tgagtaaact tggtctgaca
5341 gttaccaatg cttaatcagt gaggcaccta tctcagcgat ctgtctattt cgttcatcca
5401 tagttgcctg actccccgtc gtgtagataa ctacgatacg ggagggctta ccatctggcc
5461 ccagtgctgc aatgataccg cgagacccac gctcaccggc tccagattta tcagcaataa
5521 accagccagc cggaagggcc gagcgcagaa gtggtcctgc aactttatcc gcctccatcc

FIG 19 CONT

```
5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat
5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact ttaaaagtgc
6001 tcatcattgg aaaacgttct tcggggcgaa aactctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga ataagggcga
6181 cacggaaatg ttgaatactc atactcttcc tttttcaata ttattgaagc atttatcagg
6241 gttattgtct catgagcgga tacatatttg aatgtattta gaaaaataaa caaatagggg
6301 ttccgcgcac atttccccga aaagtgccac ctgacgtcga cggatcggga gatctcccga
6361 tcccctatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc cgcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgccccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat ttccaagtct
7021 ccaccccatt gacgtcaatg ggagtttgtt ttggcaccaa aatcaacggg actttccaaa
7081 atgtcgtaac aactccgccc cattgacgca aatgggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtggca gatatccagc acagtggcgg ccgctcgagt ctagagggcc
7321 cgttttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagaccctt ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta gaaggagaga gatgggtgcg
7681 agagcgtcag tattaagcgg gggagaatta gatcgcgatg ggaaaaaatt cggttaaggc
7741 cagggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga agagcaaaac aaaagtaaga ccaccgcaca gcaagcggcc gctgatcttc
8041 agacctggag gaggagatat gagggacaat tggagaagtg aattatataa atataaagta
8101 gtaaaaattg aaccattagg agtagcaccc accaaggcaa agagaagagt ggtgcagaga
8161 gaaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag atacctaaag
8401 gatcaacagc tcctggggat ttggggttgc tctggaaaac tcatttgcac cactgctgtg
8461 ccttggaatg ctagttggag taataaatct ctggaacaga tttggaatca cacgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata taaaattatt cataatgata
8701 gtaggaggct tggtaggttt aagaatagtt tttgctgtac tttctatagt gaatagagtt
8761 aggcagggat attcaccatt atcgtttcag acccacctcc caaccccgag gggacccgac
8821 aggcccttaa ttaagccacc tatcctcttc agacctcttc aggaaacagc tatgcacata
8881 gcacacaggc atatgttcaa ccaaaacact gaaacacata aaagaaatgt ttaaagaatg
8941 aatttaaaaa aataaaaaat aaactcaact acatatgaag ccttagcaaa catgtctgga
```

FIG 19 CONT 9001 cctctagaca cacagactct gacacgccaa cgtctgagtt ctagtttcga tacgcactgg
9061 gaagttttaa aagttttcca tcaactctaa tgtgtagaga aatggaaact atcatagact
9121 ctacggcatt gagggtgaag gtatgagtga agcactctta gggtcagaag tatgtcagtg
9181 cccatttgtt gctgttagca tcatcatctt agggcttgag aggatgttgc agctgaccca
9241 tgcacctgtg acatacatat ggaattattc tttggcacat aaaattagaa tgggagctgg
9301 ctcatcaggt tttgtgctgt aagttttcta tgttaaacca gatgcgatac actaaataaa
9361 ataaaatata cttgaccgat ggttttgagc gaaataataa ctggataatc aagaaatata
9421 tccactaatg aatagcctga actactgaaa caatttgttc agtgcctagc atatggtgtg
9481 cattttatta tttctttcaa aaagaatgta tttggagtta catagtaagt ctgctacctt
9541 ttctttatgg ctatatctat gtcttatgtt gagatgaatg aattattctt caggggaaat
9601 aatctatttg aacagtttag atggtgaaga acatttgcag catttgcaag atttttttcc
9661 actctgaagt ggtctttgtc cttgaacata ggatacaagt gacccctgct ctgttaatta
9721 ttggcaaatt gcctaacttc aacgtaagga aatagagtca tatgtttgct cactgaaggt
9781 tactagttaa caggcatccc ttaaacagga tataaaagga cttcagcagg actgctcgaa
9841 acatcccact tccagcactg cctgcggtga aggaaccagc agccgaattc ggccattacg
9901 gcccgccacc atggctagat tagataaaag taaagtgatt aacagcgcat tagagctgct
9961 taatgaggtc ggaatcgaag gtttaacaac ccgtaaactc gcccagaagc taggtgtaga
10021 gcagcctaca ttgtattggc atgtaaaaaa taagcgggct ttgctcgacg ccttagccat
10081 tgagatgtta gataggcacc atactcactt ttgcccttta gaaggggaaa gctggcaaga
10141 tttttacgt aataacgcta aaagttttag atgtgcttta ctaagtcatc gcgatggagc
10201 aaaagtacat ttaggtacac ggcctacaga aaaacagtat gaaactctcg aaaatcaatt
10261 agcctttta tgccaacaag gtttttcact agagaatgca ttatatgcac tcagcgctgt
10321 ggggcatttt actttaggtt gcgtattgga agatcaagag catcaagtcg ctaaagaaga
10381 aagggaaaca cctactactg atagtatgcc gccattatta cgacaagcta tcgaattatt
10441 tgatcaccaa ggtgcagagc cagccttctt attcggcctt gaattgatca tatgcggatt
10501 agaaaaacaa cttaaatgtg aaagtgggtc gccaaaaaag aagagaaagg tcgacggcgg
10561 tggtgctttg tctcctcagc actctgctgt cactcaagga agtatcatca agaacaagga
10621 gggcatggat gctaagtcac taactgcctg gtcccggaca ctggtgacct tcaaggatgt
10681 atttgtggac ttcaccaggg aggagtggaa gctgctggac actgctcagc agatcgtgta
10741 cagaaatgtg atgctggaga actataagaa cctggtttcc ttgggttatc agcttactaa
10801 gccagatgtg atcctccggt tggagaaggg agaagagccc tggctggtgg agagagaaat
10861 tcaccaagag acccatcctg attcagagac tgcatttgaa atcaaatcat cagtttaagg
10921 ccgcct

FIG 19 CONT

```
COMMENT      VNTNAME|pLV-Hef1a-rhlI-IRES-DsRed2|

FEATURES             Location/Qualifiers
     promoter        8835..10008
                     /vntifkey="29"
                     /label=PEF1-alpha
     promoter        6547..7198
                     /vntifkey="29"
                     /label=PCMV
     promoter        7201..7220
                     /vntifkey="29"
                     /label=T7\promoter
     misc_feature    2345..2558
                     /vntifkey="21"
                     /label=BGH\PolyA
     rep_origin      2621..3033
                     /vntifkey="33"
                     /label=f1\ori
     rep_origin      3099..3424
                     /vntifkey="33"
                     /label=SV40\ori
     promoter        3440..3505
                     /vntifkey="29"
                     /label=EM7
     CDS             3507..3881
                     /vntifkey="4"
                     /label=Zeocin(r)
     rep_origin      complement(4524..5197)
                     /vntifkey="33"
                     /label=pUC\ori
     promoter        complement(6203..6300)
                     /vntifkey="29"
                     /label=bla
     CDS             complement(5342..6202)
                     /vntifkey="4"
                     /label=Amp(r)
     misc_feature    1294..1885
                     /vntifkey="21"
                     /label=WPRE
     misc_feature    20..604
                     /vntifkey="21"
                     /label=IRES
     misc_feature    7233..7335
                     /vntifkey="21"
                     /label=MCS
     misc_feature    2085..2319
                     /vntifkey="21"
```

FIG 21

```
                     /label=deltaU3-3'LTR
     misc_feature    7336..7516
                     /vntifkey="21"
                     /label=5'\LTR
     CDS             608..1285
                     /vntifkey="4"
                     /label=DsRED2
     RBS             602..611
                     /vntifkey="32"
                     /label=Kozak\consensus
     RBS             10036..10046
                     /vntifkey="32"
                     /label=Kozak\consensus
     CDS             10043..10648
                     /vntifkey="4"
                     /label=rhlI
BASE COUNT     2424 a     2785 c     2901 g     2546 t
ORIGIN
SEQ ID NO:09
        1 cggccatcga taaggatccg cccctctccc tccccccccc ctaacgttac tggccgaagc
       61 cgcttggaat aaggccggtg tgcgtttgtc tatatgttat tttccaccat attgccgtct
      121 tttggcaatg tgagggcccg gaaacctggc cctgtcttct tgacgagcat tcctaggggt
      181 ctttcccctc tcgccaaagg aatgcaaggt ctgttgaatg tcgtgaagga agcagttcct
      241 ctggaagctt cttgaagaca aacaacgtct gtagcgaccc tttgcaggca gcggaacccc
      301 ccacctggcg acaggtgcct ctgcggccaa aagccacgtg tataagatac acctgcaaag
      361 gcggcacaac cccagtgcca cgttgtgagt tggatagttg tggaaagagt caaatggctc
      421 tcctcaagcg tattcaacaa ggggctgaag gatgcccaga aggtacccca ttgtatggga
      481 tctgatctgg ggcctcggtg cacatgcttt acatgtgttt agtcgaggtt aaaaaaacgt
      541 ctaggccccc cgaaccacgg ggacgtggtt ttcctttgaa aaacacgatg ataatatggc
      601 cacaaccatg gcctcctccg aggacgtcat caaggagttc atgcgcttca aggtgcgcat
      661 ggagggctcc gtgaacggcc acgagttcga gatcgagggc gagggcgagg gccgccccta
      721 cgagggcacc cagaccgcca agctgaaggt gaccaagggc ggccccctgc ccttcgcctg
      781 ggacatcctg tccccccagt tccagtacgg ctccaaggtg tacgtgaagc accccgccga
      841 catccccgac tacaagaagc tgtccttccc cgagggcttc aagtgggagc gcgtgatgaa
      901 cttcgaggac ggcggcgtgg tgaccgtgac ccaggactcc tccctgcagg acggctcctt
      961 catctacaag gtgaagttca tcggcgtgaa cttcccctcc gacggccccg taatgcagaa
     1021 gaagactatg ggctgggagg cctccaccga gcgcctgtac ccccgcgacg gcgtgctgaa
     1081 gggcgagatc cacaaggccc tgaagctgaa ggacggcggc cactacctgg tggagttcaa
     1141 gtccatctac atggccaaga agcccgtgca gctgcccggc tactactacg tggactccaa
     1201 gctggacatc acctcccaca acgaggacta caccatcgtg gagcagtacg agcgcgccga
     1261 gggccgccac cacctgttcc tgtaggcggc cgcaatcaac ctctggatta caaaatttgt
     1321 gaaagattga ctggtattct taactatgtt gctcctttta cgctatgtgg atacgctgct
     1381 ttaatgcctt tgtatcatgc tattacttcc cgtacggctt tcattttctc ctccttgtat
     1441 aaatcctggt tgctgtctct ttatgaggag ttgtggcccg ttgtcaggca acgtggcgtg
     1501 gtgtgcactg tgtttgctga cgcaaccccc actggttggg gcattgccac cacctatcaa
     1561 ctcctttccg ggactttcgc tttccccctc cctattgcca cggcggaact cattgccgcc
     1621 tgccttgccc gctgctggac aggggctcgg ctgttgggca ctgacaattc cgtggtgttg
     1681 tcggggaagc tgacgtcctt tccatggctg ctcgcctgtg ttgccaactg gattctgcgc
     1741 gggacgtcct tctgctacgt cccttcggcc ctcaatccag cggaccttcc ttcccgcggc
     1801 ctgctgccgg ttctgcggcc tcttccgcgt cttcgccttc gccctcagac gagtcggatc
     1861 tccctttggg ccgcctcccc gcctgcctgc aggtttgtcg agacctagaa aaacatggag
     1921 caatcacaag tagcaataca gcagctacca atgctgattg tgcctggcta gaagcacaag
     1981 aggaggagga ggtgggtttt ccagtcacac ctcaggtacc tttaagacca atgacttaca
```

FIG 21 CONT 2041 aggcagctgt agatcttagc cactttttaa aagaaaaggg gggactggaa gggctaattc
2101 actcccaacg aagacaagat ctgctttttg cttgtactgg gtctctctgg ttagaccaga
2161 tctgagcctg ggagctctct ggctaactag ggaacccact gcttaagcct caataaagct
2221 tgccttgagt gcttcaagta gtgtgtgccc gtctgttgtg tgactctggt aactagagat
2281 ccctcagacc cttttagtca gtgtggaaaa tctctagcag ggcccgttta aacccgctga
2341 tcagcctcga ctgtgccttc tagttgccag ccatctgttg tttgcccctc ccccgtgcct
2401 tccttgaccc tggaaggtgc cactcccact gtcctttcct aataaaatga ggaaattgca
2461 tcgcattgtc tgagtaggtg tcattctatt ctggggggtg gggtggggca ggacagcaag
2521 ggggaggatt gggaagacaa tagcaggcat gctggggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgcccgctc ctttcgcttt cttcccttcc tttctcgcca cgttcgccgg ctttccccgt
2761 caagctctaa atcggggcat ccctttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg gactcttgtt ccaaactgga
2941 acaacactca accctatctc ggtctattct tttgatttat aagggatttt ggggatttcg
3001 gcctattggt taaaaaatga gctgatttaa caaaaattta acgcgaatta attctgtgga
3061 atgtgtgtca gttagggtgt ggaaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtcccgcc cctaactccg
3241 cccatcccgc ccctaactcc gcccagttcc gcccattctc cgccccatgg ctgactaatt
3301 ttttttattt atgcagaggc cgaggccgcc tctgcctctg agctattcca gaagtagtga
3361 ggaggctttt ttggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgg ccaagttgac cagtgccgtt ccggtgctca
3541 ccgcgcgcga cgtcgccgga gcggtcgagt tctggaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttccgggac gcctccgggc
3781 cggccatgac cgagatcggc gagcagccgt gggggcggga gttcgccctg cgcgacccgg
3841 ccggcaactg cgtgcacttc gtggccgagg agcaggactg acacgtgcta cgagatttcg
3901 attccaccgc cgccttctat gaaaggttgg gcttcggaat cgttttccgg gacgccggct
3961 ggatgatcct ccagcgcggg gatctcatgc tggagttctt cgcccacccc aacttgttta
4021 ttgcagctta taatggttac aaataaagca atagcatcac aaatttcaca aataaagcat
4081 ttttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata aagtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcggggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg tttttccata ggctccgccc ccctgacgag catcacaaaa
4621 atcgacgctc aagtcagagg tggcgaaacc cgacaggact ataaagatac caggcgtttc
4681 cccctggaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaacccccc gttcagcccg
4861 accgctgcgc cttatccggt aactatcgtc ttgagtccaa cccggtaaga cacgacttat
4921 cgccactggc agcagccact ggtaacagga ttagcagagc gaggtatgta ggcggtgcta
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggtttttttg tttgcaagca gcagattacg cgcagaaaaa
5161 aaggatctca agaagatcct ttgatctttt ctacggggtc tgacgctcag tggaacgaaa
5221 actcacgtta agggattttg gtcatgagat tatcaaaaag gatcttcacc tagatccttt
5281 taaattaaaa atgaagtttt aaatcaatct aaagtatata tgagtaaact tggtctgaca
5341 gttaccaatg cttaatcagt gaggcaccta tctcagcgat ctgtctattt cgttcatcca
5401 tagttgcctg actccccgtc gtgtagataa ctacgatacg ggagggctta ccatctggcc

FIG 21 CONT

```
5461 ccagtgctgc aatgataccg cgagacccac gctcaccggc tccagattta tcagcaataa
5521 accagccagc cggaagggcc gagcgcagaa gtggtcctgc aactttatcc gcctccatcc
5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat
5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact ttaaaagtgc
6001 tcatcattgg aaaacgttct tcggggcgaa aactctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga ataagggcga
6181 cacggaaatg ttgaatactc atactcttcc tttttcaata ttattgaagc atttatcagg
6241 gttattgtct catgagcgga tacatatttg aatgtattta gaaaaataaa caaatagggg
6301 ttccgcgcac atttccccga aaagtgccac ctgacgtcga cggatcggga gatctcccga
6361 tcccctatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc cgcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgccccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat ttccaagtct
7021 ccaccccatt gacgtcaatg ggagtttgtt ttggcaccaa aatcaacggg actttccaaa
7081 atgtcgtaac aactccgccc cattgacgca aatgggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtggca gatatccagc acagtggcgg ccgctcgagt ctagagggcc
7321 cgtttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagaccctt ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta gaaggagaga gatgggtgcg
7681 agagcgtcag tattaagcgg gggagaatta gatcgcgatg ggaaaaaatt cggttaaggc
7741 caggggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga agagcaaaac aaaagtaaga ccaccgcaca gcaagcggcc gctgatcttc
8041 agacctggag gaggagatat gagggacaat tggagaagtg aattatataa atataaagta
8101 gtaaaaattg aaccattagg agtagcaccc accaaggcaa agagaagagt ggtgcagaga
8161 gaaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag atacctaaag
8401 gatcaacagc tcctggggat ttggggttgc tctggaaaac tcatttgcac cactgctgtg
8461 ccttggaatg ctagttggag taataaatct ctggaacaga tttggaatca cacgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata taaaattatt cataatgata
8701 gtaggaggct tggtaggttt aagaatagtt tttgctgtac tttctatagt gaatagagtt
8761 aggcagggat attcaccatt atcgtttcag acccacctcc caaccccgag gggacccgac
8821 aggcccttaa ttaattggct ccggtgcccg tcagtgggca gagcgcacat cgcccacagt
```

FIG 21 CONT 8881 ccccgagaag ttggggggag gggtcggcaa ttgaaccggt gcctagagaa ggtggcgcgg
8941 ggtaaactgg gaaagtgatg tcgtgtactg gctccgcctt tttcccgagg gtgggggaga
9001 accgtatata agtgcagtag tcgccgtgaa cgttcttttt cgcaacgggt ttgccgccag
9061 aacacaggta agtgccgtgt gtggttcccg cgggcctggc ctctttacgg gttatggccc
9121 ttgcgtgcct tgaattactt ccacctggct gcagtacgtg attcttgatc ccgagcttcg
9181 ggttggaagt gggtgggaga gttcgaggcc ttgcgcttaa ggagcccctt cgcctcgtgc
9241 ttgagttgag gcctggcctg ggcgctgggg ccgccgcgtg cgaatctggt ggcaccttcg
9301 cgcctgtctc gctgctttcg ataagtctct agccatttaa aatttttgat gacctgctgc
9361 gacgcttttt ttctggcaag atagtcttgt aaatgcgggc caagatctgc acactggtat
9421 ttcggttttt ggggccgcgg gcggcgacgg ggcccgtgcg tcccagcgca catgttcggc
9481 gaggcggggc ctgcgagcgc ggccaccgag aatcggacgg gggtagtctc aagctggccg
9541 gcctgctctg gtgcctggcc tcgcgccgcc gtgtatcgcc ccgccctggg cggcaaggct
9601 ggcccggtcg gcaccagttg cgtgagcgga aagatggccg cttcccggcc ctgctgcagg
9661 gagctcaaaa tggaggacgc ggcgctcggg agagcgggcg ggtgagtcac ccacacaaag
9721 gaaaagggcc tttccgtcct cagccgtcgc ttcatgtgac tccacggagt accgggcgcc
9781 gtccaggcac ctcgattagt tctcgagctt ttggagtacg tcgtctttag gttgggggga
9841 ggggttttat gcgatggagt ttccccacac tgagtgggtg gagactgaag ttaggccagc
9901 ttggcacttg atgtaattct ccttggaatt tgcccttttt gagtttggat cttggttcat
9961 tctcaagcct cagacagtgg ttcaaagttt ttttcttcca tttcaggtgt cgtgaggaat
10021 tcggccatta cggcccgcca ccatgatcga attgctctct gaatcgctgg aagggctttc
10081 cgccgccatg atcgccgagc tgggacgcta ccggcatcag gtcttcatcg agaagctggg
10141 ctgggacgtg gtctccacct ccagggtccg cgaccaggaa ttcgaccagt tcgaccatcc
10201 gcaaacccgc tacatcgtcg ccatgagccg ccagggcatc tgcggttgcg cccgcctgct
10261 gccgacgacc gacgcctacc tgctcaagga cgtcttcgcc tacctgtgca gcgaaacccc
10321 gccgagcgat ccgtcggtct gggagctttc gcgctacgcc gccagcgcgg cggacgatcc
10381 gcagctggcg atgaagatat tctggtccag cctgcaatgc gcctggtacc tgggcgccag
10441 ttcggtggtg gcggtgacca ccacggccat ggagcgctat ttcgttcgca acggcgtgat
10501 cctccagcgc ctcggccccg cgcagaaggt caagggcgag acgctggtcg cgatcagctt
10561 cccggcctac caggagcgcg gcctggagat gctgctgcgc taccacccgg aatggctgca
10621 gggcgtaccg ctgtcgatgg cggtgtgagg ccgcct

FIG 21 CONT

SEQ ID NO: 10 gatccgcccctctccctcccccccccctaacgtttactggccgaagccgcttggaataaggccggtgtgcgtttgtctatatgttattttccaccatattgccgtc
ttttggcaatgtgagggcccggaaacctggccctgtcttcttgacgagcattcctaggggtctttcccctctcgccaaaggaatgcaaggtctgttgaatgtc
gtgaaggaagcagttcctctggaagcttcttgaagacaaacaacgtctgtagcgaccctttgcaggcagcggaaccccccacctggcgacaggtgcctct
gcggccaaaagccacgtgtataagatacacctgcaaaggcggcacaaccccagtgccacgttgtgagttggatagttgtggaaagagtcaaatggctctc
ctcaagcgtattcaacaaggggctgaaggatgcccagaaggtaccccattgtatgggatctgatctggggcctcggtgcacatgctttacatgtgtttagtc
gaggttaaaaaaacgtctaggccccccgaaccacggggacgtggttttcctttgaaaaacacgatgataatatggccacaaccatggtgagcaagggcg
aggagctgttcaccggggtggtgcccatcctggtcgagctggacggcgacgtaaacggccacaagttcagcgtgtccggcgagggcgagggcgatgc
cacctacggcaagctgaccctgaagttcatctgcaccaccggcaagctgcccgtgccctggcccaccctcgtgaccaccctgacctacggcgtgcagtg
cttcagccgctaccccgaccacatgaagcagcacgacttcttcaagtccgccatgcccgaaggctacgtccaggagcgcaccatcttcttcaaggacgac
ggcaactacaagacccgcgccgaggtgaagttcgagggcgacaccctggtgaaccgcatcgagctgaagggcatcgacttcaaggaggacggcaac
atcctggggcacaagctggagtacaactacaacagccacaacgtctatatcatggccgacaagcagaagaacggcatcaaggtgaacttcaagatccgc
cacaacatcgaggacggcagcgtgcagctcgccgaccactaccagcagaacacccccatcggcgacggccccgtgctgctgcccgacaaccactac
ctgagcacccagtccgccctgagcaaagaccccaacgagaagcgcgatcacatggtcctgctggagttcgtgaccgccgccgggatcactctcggcat

FIG. 23B ggacgagctgtacaagtaagcggccgcaatcaacctctggattacaaaatttgtg
aaagattgactggtattcttaactatgttgctccttttacgctatgtggatacgc
tgctttaatgcctttgtatcatgctattacttcccgtacggctttcattttctcc
tccttgtataaatcctggttgctgtctctttatgaggagttgtggcccgttgtca
ggcaacgtggcgtggtgtgcactgtgtttgctgacgcaacccccactggttgggg
cattgccaccacctatcaactcctttccgggactttcgctttccccctccctatt
gccacggcggaactcattgccgcctgccttgcccgctgctggacaggggctcggc
tgttgggcactgacaattccgtggtgttgtcggggaagctgacgtcctttccatg
gctgctcgcctgtgttgccaactggattctgcgcgggacgtccttctgctacgtc
ccttcggccctcaatccagcggaccttccttcccgcggcctgctgccggttctgc
ggcctcttccgcgtcttcgccttcgccctcagacgagtcggatctccctttgggc
cgcctccccgcctgcctgcaggtttgtcgagacctagaaaaacatggagcaatca
caagtagcaatacagcagctaccaatgctgattgtgcctggctagaagcacaaga
ggaggaggaggtgggttttccagtcacacctcaggtacctttaagaccaatgact
tacaaggcagctgtagatcttagccactttttaaaagaaaaggggggactggaag
ggctaattcactcccaacgaagacaagatctgcttttgcttgtactgggtctct
ctggttagaccagatctgagcctgggagctctctggctaactagggaacccactg
cttaagcctcaataaagcttgccttgagtgcttcaagtagtgtgtgcccgtctgt
tgtgtgactctggtaactagagatccctcagacccttttagtcagtgtggaaaat
ctctagcagggcccgtttaaacccgctgatcagcctcgactgtgccttctagttg
ccagccatctgttgtttgcccctcccccgtgccttccttgaccctggaaggtgcc
actcccactgtcctttcctaataaaatgaggaaattgcatcgcattgtctgagta
ggtgtcattctattctggggggtggggtggggcaggacagcaagggggaggattg
ggaagacaatagcaggcatgctggggatgcggtgggctctatggcttctgaggcg
gaaagaaccagctggggctctagggggtatccccacgcgccctgtagcggcgcat
taagcgcggcgggtgtggtggttacgcgcagcgtgaccgctacacttgccagcgc
cctagcgcccgctcctttcgctttcttcccttcctttctcgccacgttcgccggc
tttccccgtcaagctctaaatcggggcatccctttagggttccgatttagtgctt
tacggcacctcgaccccaaaaaacttgattagggtgatggttcacgtagtgggcc
atcgccctgatagacggtttttcgccctttgacgttggagtccacgttctttaat
agtggactcttgttccaaactggaacaacactcaaccctatctcggtctattctt
ttgatttataagggattttggggatttcggcctattggttaaaaaatgagctgat
ttaacaaaaatttaacgcgaattaattctgtggaatgtgtgtcagttagggtgtg
gaaagtccccaggctccccaggcaggcagaagtatgcaaagcatgcatctcaatt
agtcagcaaccaggtgtggaaagtccccaggctccccagcaggcagaagtatgca
aagcatgcatctcaattagtcagcaaccatagtcccgcccctaactccgcccatc
ccgcccctaactccgcccagttccgcccattctccgccccatggctgactaattt
tttttatttatgcagaggccgaggccgcctctgcctctgagctattccagaagta
gtgaggaggcttttttggaggcctaggcttttgcaaaaagctcccgggagcttgt
atatccattttcggatctgatcagcacgtgttgacaattaatcatcggcatagta

FIG 23B CONT tatcggcatagtataatacgacaaggtgaggaactaaaccatggccaagttgacc
agtgccgttccggtgctcaccgcgcgcgacgtcgccggagcggtcgagttctgga
ccgaccggctcgggttctcccgggacttcgtggaggacgacttcgccggtgtggt
ccgggacgacgtgaccctgttcatcagcgcggtccaggaccaggtggtgccggac
aacaccctggcctgggtgtgggtgcgcggcctggacgagctgtacgccgagtggt
cggaggtcgtgtccacgaacttccgggacgcctccgggccggccatgaccgagat
cggcgagcagccgtgggggcgggagttcgccctgcgcgacccggccggcaactgc
gtgcacttcgtggccgaggagcaggactgacacgtgctacgagatttcgattcca
ccgccgccttctatgaaaggttgggcttcggaatcgttttccgggacgccggctg
gatgatcctccagcgcggggatctcatgctggagttcttcgcccaccccaacttg
tttattgcagcttataatggttacaaataaagcaatagcatcacaaatttcacaa
ataaagcatttttttcactgcattctagttgtggtttgtccaaactcatcaatgt
atcttatcatgtctgtataccgtcgacctctagctagagcttggcgtaatcatgg
tcatagctgtttcctgtgtgaaattgttatccgctcacaattccacacaacatac
gagccggaagcataaagtgtaaagcctggggtgcctaatgagtgagctaactcac
attaattgcgttgcgctcactgcccgctttccagtcgggaaacctgtcgtgccag
ctgcattaatgaatcggccaacgcgcggggagaggcggtttgcgtattgggcgct
cttccgcttcctcgctcactgactcgctgcgctcggtcgttcggctgcggcgagc
ggtatcagctcactcaaaggcggtaatacggttatccacagaatcaggggataac
gcaggaaagaacatgtgagcaaaaggccagcaaaaggccaggaaccgtaaaaagg
ccgcgttgctggcgtttttccataggctccgcccccctgacgagcatcacaaaaa
tcgacgctcaagtcagaggtggcgaaacccgacaggactataaagataccaggcg
tttccccctggaagctccctcgtgcgctctcctgttccgaccctgccgcttaccg
gatacctgtccgcctttctcccttcgggaagcgtggcgctttctcaatgctcacg
ctgtaggtatctcagttcggtgtaggtcgttcgctccaagctgggctgtgtgcac
gaaccccccgttcagcccgaccgctgcgccttatccggtaactatcgtcttgagt
ccaacccggtaagacacgacttatcgccactggcagcagccactggtaacaggat
tagcagagcgaggtatgtaggcggtgctacagagttcttgaagtggtggcctaac
tacggctacactagaaggacagtatttggtatctgcgctctgctgaagccagtta
ccttcggaaaaagagttggtagctcttgatccggcaaacaaaccaccgctggtag
cggtggtttttttgtttgcaagcagcagattacgcgcagaaaaaaaggatctcaa
gaagatcctttgatcttttctacggggtctgacgctcagtggaacgaaaactcac
gttaagggattttggtcatgagattatcaaaaaggatcttcacctagatcctttt
aaattaaaaatgaagttttaaatcaatctaaagtatatatgagtaaacttggtct
gacagttaccaatgcttaatcagtgaggcacctatctcagcgatctgtctatttc
gttcatccatagttgcctgactccccgtcgtgtagataactacgatacgggaggg
cttaccatctggccccagtgctgcaatgataccgcgagacccacgctcaccggct
ccagatttatcagcaataaaccagccagccggaagggccgagcgcagaagtggtc
ctgcaactttatccgcctccatccagtctattaattgttgccgggaagctagagt
aagtagttcgccagttaatagtttgcgcaacgttgttgccattgctacaggcatc

FIG 23B CONT gtggtgtcacgctcgtcgtttggtatggcttcattcagctccggttcccaacgat
caaggcgagttacatgatcccccatgttgtgcaaaaaagcggttagctccttcgg
tcctccgatcgttgtcagaagtaagttggccgcagtgttatcactcatggttatg
gcagcactgcataattctcttactgtcatgccatccgtaagatgcttttctgtga
ctggtgagtactcaaccaagtcattctgagaatagtgtatgcggcgaccgagttg
ctcttgcccggcgtcaatacgggataataccgcgccacatagcagaactttaaaa
gtgctcatcattggaaaacgttcttcggggcgaaaactctcaaggatcttaccgc
tgttgagatccagttcgatgtaacccactcgtgcacccaactgatcttcagcatc
ttttactttcaccagcgtttctgggtgagcaaaaacaggaaggcaaaatgccgca
aaaaagggaataagggcgacacggaaatgttgaatactcatactcttcctttttc
aatattattgaagcatttatcagggttattgtctcatgagcggatacatatttga
atgtatttagaaaaataaacaaataggggttccgcgcacatttccccgaaaagtg
ccacctgacgtcgacggatcgggagatctcccgatcccctatggtgcactctcag
tacaatctgctctgatgccgcatagttaagccagtatctgctccctgcttgtgtg
ttggaggtcgctgagtagtgcgcgagcaaaatttaagctacaacaaggcaaggct
tgaccgacaattgcatgaagaatctgcttagggttaggcgttttgcgctgcttcg
cgatgtacgggccagatatacgcgttgacattgattattgactagttattaatag
taatcaattacggggtcattagttcatagcccatatatggagttccgcgttacat
aacttacggtaaatggcccgcctggctgaccgcccaacgacccccgcccattgac
gtcaataatgacgtatgttcccatagtaacgccaatagggactttccattgacgt
caatgggtggactatttacggtaaactgcccacttggcagtacatcaagtgtatc
atatgccaagtacgccccctattgacgtcaatgacggtaaatggcccgcctggca
ttatgcccagtacatgaccttatgggactttcctacttggcagtacatctacgta
ttagtcatcgctattaccatggtgatgcggttttggcagtacatcaatgggcgtg
gatagcggtttgactcacggggatttccaagtctccaccccattgacgtcaatgg
gagtttgttttggcaccaaaatcaacgggactttccaaaatgtcgtaacaactcc
gccccattgacgcaaatgggcggtaggcgtgtacggtgggaggtctatataagca
gagctctctggctaactagagaacccactgcttactggcttatcgaaattaatac
gactcactatagggagacccaagctggtttaaacttaagcttggtaccgagctca
ctagtccagtgtggtggcagatatccagcacagtggcggccgctcgagtctagag
ggcccgtttaaacnnnnngggtctctctggttagaccagatctgagcctgggagc
tctctggctaactagggaacccactgcttaagcctcaataaagcttgccttgagt
gcttcaagtagtgtgtgcccgtctgttgtgtgactctggtaactagagatccctc
agaccctttagtcagtgtggaaaatctctagcannnnnnnnnnccagcaactta
tctgtgtctgtccgattgtctagtgtctatgtttgatgttatgcgcctgcgtctg
tactagttagctaactagctctgtatctggcggacccgtggtggaactgacgagt
tctgaacacccggccgcaaccctgggagacgtcccagggactttgggggccgttt
ttgtggcccgacctgaggaagggagtcgatgtggaatccgaccccgtcaggatat
gtggttctggtaggagacgagaacctaaaacagttcccgcctccgtctgaatttt
tgctttcggtttggaaccgaagccgcgcgtcttgtctgctgcagcgctgcagcat

FIG 23B CONT cgttctgtgttgtctctgtctgactgtgtttctgtatttgtctgaaaattagggc
cagactgttaccactcccttaagtttgaccttaggtcactggaaagatgtcgagc
ggatcgctcacaaccagtcggtagatgtcaagaagagacgttgggttaccttctg
ctctgcagaatggccaacctttaacgtcggatggccgcgagacggcacctttaac
cgagacctcatcacccaggttaagatcaaggtcttttcacctggcccgcatggac
acccagaccaggtcccctacatcgtgacctgggaagccttggctttgacccccc
tccctgggtcaagccctttgtacaccctaagcctccgcctcctcttcctccatcc
gccccgtctctcccccttgaacctcctcgttcgaccccgcctcgatcctcccttt
atccagccctcactccttctctaggcgccnnnnnggaaaagtttagtaaaacacc
atatgtatgtttcagggaaagctaggggatggttttatagacatcactatgaaag
ccctcatccaagaataagttcagaagtacacatcccactaggggatgctagattg
gtaataacaacatattggggtctgcatacaggagaaagagactggcatctgggtc
agggagtctccatagaatggaggaaaaagagatatagcacacaagtagaccctga
actagcagaccaactaattcatctgtattactttgactgtttttcagactctgct
ataagaaaggccttattaggacatatagttagccctaggtgtgaatatcaagcag
gacataacaaggtaggatctctacaatacttggcactagcagcattaataacacc
aaaaaagataaagccacctttgcctagtgttacgaaactgacagaggatagatgg
aacaagccccagaagaccaagggccacagagggagccacacaatgaatggacact
agagctttagaggagcttaagaatgaagctgttagacattttcctaggatttgg
ctccatggcttagggcaacatatctatgaaacttatggggatacttgggcaggag
tggaagccataataatgcaacaactgctgtttatccatttcagaattgggtgtcg
acatagcagaataggcgttactcaacagaggagagcaagaaatggagccagtaga
tcctagactagagccctggaagcatccaggaagtcagcctaaaactgcttgtacc
acttgctattgtaaaaagtgttgctttcattgccaagtttgtttcacaacaaaag
ccttaggcatctcctatggcaggaagaagcggagacagcgacgaagacctcctca
aggcagtcagactcatcaagtttctctatcaaagcagtaagtagtacatgtaatg
caacctatacaaatagcaatagcagcattagtagtagcaataataatagcaatag
ttgtgtggtccatagtaatcatagaatataggaaaatattaagacaaagaaaaat
agacaggttaattgatagactaatnnnnnnnnggcccgaaggaatagaagaagaa
ggtggagagagagacagagacagatccattcgattagtgaacggatcggcactgc
gtgcgccaattctgcagacaaatggcagtattcatccacaattttaaaagaaaag
gggggattggggggtacagtgcaggggaaagaatagtagacataatagcaacaga
catacaaactaaagaattacaaaaacaaattacaaaaattcaaaattttcgggtt
tattacagggacagcagagatccagtttggttaattaatgctgctgagccacgtg
aagccttaagccgcagggagaccctgaaaatagactgtaagcaaccttggggtgg
ggtaagcctgttgcagcgttagtgtatccatgaactcctttaagatacaagctat
gtgtcattcctcatggagacgccggagagtcttgagcttacatgatggtcctgcg
gaggccttaaagtcctgtggggatgctcagggttgtccctgtgtgtcactgagac
ctccgaaagaatttaaatatcacagaaaaaaaaacataaagaagaccttaagcc
tttttaagttcccaaggagagccagaagtggtggtatatagctcaacttgggaga

FIG 23B CONT ctgaggcaaaaagactgactgagtttaagaccagcctagctacaccacaaagctc
ctttctcaaaagaaaaagctcccaaggaggttggatccccagtgagaccctcagc
aaggccctctggcctcactatggtcctgaggacacccctccacactgccctgatc
ttcttaccccatcctgcctgagctcttcacctgctctcctcttgcattcaaatat
cttctgctacagtaggtccactggagtctcccaggtacccagagtgtgaatgtct
gcagcactttctgggggacaaggagcagagagcaagggacccacaattcgggtct
agtgtctgtaaagccttgcggagggtagagttctagttcacacaaggcaccaagt
gtttttgctggttgcctaggaaacaggacagtgccaaatcaggaacagaaagagt
caaggaacccccaaccactccaagcggaggctgagaaaggttttgtagctggaat
agagcatgcactaacagatggagacagctggctttgagctctgaagcaagtatta
catatggagacttgctggccttcaggtgcttatcttgttattggatactgcagga
ggatgtaccacagggcttcagctcagctgacccccaagtgggatatggaaagaga
gatagaggaggagggaccattaagtgccttgctgcctgaattctgctttccttct
acctctgagagagagctggggactcggctgagttaagaacccagctatcaattgg
aactgtgaaacagtccaagggacaaagatactaggtccccaactgcaacttcctg
gggaatgatgtggaaaaatgctcagccaaggacaaagaaagcatcacccactctg
gaacaatgtcccctgctgtgaactggttcatcaggccatcagggccccttgttaa
gactctaattaccctaggactaagtagaggtgttgacgtccaatgagcgctttct
gcagacctagcaccagggaagtgtttggaaactgcagcttcagcccctctggcca
tctgctgacctaccccacctggagcccttaatgggtcaaacagcaaagtccaggg
ggcagagaggaggtgctttggtctataaaggtagtggggacccagtaaccaccgg
cgcgccaagctagcaagttaacaaatcgatccggatcctcccaccatgaaaccag
taacgttatacgatgtcgcagagtatgccggtgtctcttatcagaccgtttcccg
cgtggtgaaccaggccagccacgtttctgcgaaaacgcgggaaaaagtggaagcg
gcgatggcggagctgaattacattcccaaccgcgtggcacaacaactggcgggca
aacagtcgttgctgattggcgttgccacctccagtctggccctgcacgcgccgtc
gcaaattgtcgcggcgattaaatctcgcgccgatcaactgggtgccagcgtggtg
gtgtcgatggtagaacgaagcggcgtcgaagcctgtaaagcggcggtgcacaatc
ttctcgcgcaacgcgtcagtgggctgatcattaactatccgctggatgaccagga
tgccattgctgtggaagctgcctgcactaatgttccggcgttatttcttgatgtc
tctgaccagacacccatcaacagtattattttctcccatgaagacggtacgcgac
tgggcgtggagcatctggtcgcattgggtcaccagcaaatcgcgctgttagcggg
cccattaagttctgtctcggcgcgtctgcgtctggctggctggcataaatatctc
actcgcaatcaaattcagccgatagcggaacgggaaggcgactggagtgccatgt
ccggttttcaacaaaccatgcaaatgctgaatgagggcatcgttcccactgcgat
gctggttgccaacgatcagatggcgctgggcgcaatgcgcgccattaccgagtcc
gggctgcgcgttggtgcggatatctcggtagtgggatacgacgataccgaagaca
gctcatgttatatcccgccgttaaccaccatcaaacaggattttcgcctgctggg
gcaaaccagcgtggaccgcttgctgcaactctctcagggccaggcggtgaagggc
aatcagctgttgcccgtctcactggtgaaaagaaaaaccaccctggcgcccaata

FIG 23B CONT cgcaaaccgcctctccccgcgcgttggccgattcattaatgcagctggcacgaca
ggtttcccgactggaaagcgggcagagaccgccaaaaaagaagagaaaggtcgac
ggcggtggtgctttgtctcctcagcactctgctgtcactcaaggaagtatcatca
agaacaaggagggcatggatgctaagtcactaactgcctggtcccggacactggt
gaccttcaaggatgtatttgtggacttcaccagggaggagtggaagctgctggac
actgctcagcagatcgtgtacagaaatgtgatgctggagaactataagaacctgg
tttccttgggttatcagcttactaagccagatgtgatcctccggttggagaaggg
agaagagccctggctggtggagagagaaattcaccaagagacccatcctgattca
gagactgcatttgaaatcaaatcatcagtttgag

FIG 23B CONT

SEQ ID NO: 11 cgcgccaagctagcaagttaacaaatcgatccggatccnnnnngcccctctccctcccccccccctaacgttactggccgaagccgcttggaataaggc
cggtgtgcgtttgtctatatgttattttccaccatattgccgtcttttggcaatgtgagggcccggaaacctggccctgtcttcttgacgagcattcctaggggtc
tttcccctctcgccaaaggaatgcaaggtctgttgaatgtcgtgaaggaagcagttcctctggaagcttcttgaagacaaacaacgtctgtagcgaccctttg
caggcagcggaacccccccacctggcgacaggtgcctctgcggccaaaagccacgtgtataagatacacctgcaaaggcggcacaaccccagtgccac
gttgtgagttggatagttgtggaaagagtcaaatggctctcctcaagcgtattcaacaaggggctgaaggatgcccagaaggtaccccattgtatgggatct
gatctggggcctcggtgcacatgctttacatgtgtttagtcgaggttaaaaaaacgtctaggccccccgaaccacggggacgtggttttcctttgaaaaaca
cgatgataatatggccacaaccatggtgagcaagggcgaggagctgttcaccggggtggtgcccatcctggtcgagctggacggcgacgtaaacggcc
acaagttcagcgtgtccggcgagggcgagggcgatgccacctacggcaagctgaccctgaagttcatctgcaccaccggcaagctgcccgtgccctgg
cccaccctcgtgaccaccctgacctacggcgtgcagtgcttcagccgctaccccgaccacatgaagcagcacgacttcttcaagtccgccatgcccgaa
ggctacgtccaggagcgcaccatcttcttcaaggacgacggcaactacaagacccgcgccgaggtgaagttcgggcgacaccctggtgaaccgcat
cgagctgaagggcatcgacttcaaggaggacggcaacatcctggggcacaagctggattacaactacaacagccacaacgtctatatcatggccgaca
agcagaagaacggcatcaaggtgaacttcaagatccgccacaacatcgaggacggcagcgtgcagctcgccgaccactaccagcagaacacccccat
cggcgacggccccgtgctgctgcccgacaaccactacctgagcacccagtccgccctgagcaaagaccccaacgagaagcgcgatcacatggtcctg
ctggagttcgtgaccgccgccgggatcactctcggcatggacgagctgtacaagtaagcggccgcaatcaacctctggattacaaaatttgtgaaagattg
actggtattcttaactatgttgctccttttacgctatgtggatacgctgctttaatgcctttgtatcatgctattacttcccgtacggctttcattttctcctccttgtata

FIG. 24B aatcctggttgctgtctctttatgaggagttgtggcccgttgtcaggcaacgtgg
cgtggtgtgcactgtgtttgctgacgcaacccccactggttggggcattgccacc
acctatcaactcctttccgggactttcgctttccccctccctattgccacggcgg
aactcattgccgcctgccttgcccgctgctggacaggggctcggctgttgggcac
tgacaattccgtggtgttgtcggggaagctgacgtcctttccatggctgctcgcc
tgtgttgccaactggattctgcgcgggacgtccttctgctacgtcccttcggccc
tcaatccagcggaccttccttcccgcggcctgctgccggttctgcggcctcttcc
gcgtcttcgccttcgccctcagacgagtcggatctccctttgggccgcctccccg
cctgcctgcaggtttgtcgagacctagaaaaacatggagcaatcacaagtagcaa
tacagcagctaccaatgctgattgtgcctggctagaagcacaagaggaggaggag
gtgggttttccagtcacacctcaggtacctttaagaccaatgacttacaaggcag
ctgtagatcttagccactttttaaaagaaaaggggggactggaagggctaattca
ctcccaacgaagacaagatctgctttttgcttgtactgggtctctctggttagac
cagatctgagcctgggagctctctggctaactagggaacccactgcttaagcctc
aataaagcttgccttgagtgcttcaagtagtgtgtgcccgtctgttgtgtgactc
tggtaactagagatccctcagacccttttagtcagtgtggaaaatctctagcagg
gcccgtttaaacccgctgatcagcctcgactgtgccttctagttgccagccatct
gttgtttgcccctcccccgtgccttccttgaccctggaaggtgccactcccactg
tcctttcctaataaaatgaggaaattgcatcgcattgtctgagtaggtgtcattc
tattctggggggtggggtggggcaggacagcaagggggaggattgggaagacaat
agcaggcatgctggggatgcggtgggctctatggcttctgaggcggaaagaacca
gctggggctctagggggtatccccacgcgccctgtagcggcgcattaagcgcggc
gggtgtggtggttacgcgcagcgtgaccgctacacttgccagcgccctagcgccc
gctcctttcgctttcttcccttcctttctcgccacgttcgccggctttccccgtc
aagctctaaatcgggggcatccctttagggttccgatttagtgctttacggcacct
cgaccccaaaaaacttgattagggtgatggttcacgtagtgggccatcgccctga
tagacggtttttcgccctttgacgttggagtccacgttctttaatagtggactct
tgttccaaactggaacaacactcaaccctatctcggtctattcttttgatttata
agggattttggggatttcggcctattggttaaaaaatgagctgatttaacaaaaa
tttaacgcgaattaattctgtggaatgtgtgtcagttagggtgtggaaagtcccc
aggctccccaggcaggcagaagtatgcaaagcatgcatctcaattagtcagcaac
caggtgtggaaagtccccaggctccccagcaggcagaagtatgcaaagcatgcat
ctcaattagtcagcaaccatagtcccgcccctaactccgcccatcccgcccctaa
ctccgcccagttccgcccattctccgccccatggctgactaattttttttattta
tgcagaggccgaggccgcctctgcctctgagctattccagaagtagtgaggaggc
ttttttggaggcctaggcttttgcaaaaagctcccgggagcttgtatatccattt
tcggatctgatcagcacgtgttgacaattaatcatcggcatagtatatcggcata
gtataatacgacaaggtgaggaactaaaccatggccaagttgaccagtgccgttc
cggtgctcaccgcgcgcgacgtcgccggagcggtcgagttctggaccgaccggct
cgggttctcccgggacttcgtggaggacgacttcgccggtgtggtccgggacgac

FIG 24B CONT gtgaccctgttcatcagcgcggtccaggaccaggtggtgccggacaacaccctgg
cctgggtgtgggtgcgcggcctggacgagctgtacgccgagtggtcggaggtcgt
gtccacgaacttccgggacgcctccgggccggccatgaccgagatcggcgagcag
ccgtgggggcgggagttcgccctgcgcgacccggccggcaactgcgtgcacttcg
tggccgaggagcaggactgacacgtgctacgagatttcgattccaccgccgcctt
ctatgaaaggttgggcttcggaatcgttttccgggacgccggctggatgatcctc
cagcgcggggatctcatgctggagttcttcgcccaccccaacttgtttattgcag
cttataatggttacaaataaagcaatagcatcacaaatttcacaaataaagcatt
tttttcactgcattctagttgtggtttgtccaaactcatcaatgtatcttatcat
gtctgtataccgtcgacctctagctagagcttggcgtaatcatggtcatagctgt
ttcctgtgtgaaattgttatccgctcacaattccacacaacatacgagccggaag
cataaagtgtaaagcctggggtgcctaatgagtgagctaactcacattaattgcg
ttgcgctcactgcccgctttccagtcgggaaacctgtcgtgccagctgcattaat
gaatcggccaacgcgcggggagaggcggtttgcgtattgggcgctcttccgcttc
ctcgctcactgactcgctgcgctcggtcgttcggctgcggcgagcggtatcagct
cactcaaaggcggtaatacggttatccacagaatcaggggataacgcaggaaaga
acatgtgagcaaaaggccagcaaaaggccaggaaccgtaaaaaggccgcgttgct
ggcgtttttccataggctccgcccccctgacgagcatcacaaaaatcgacgctca
agtcagaggtggcgaaacccgacaggactataaagataccaggcgtttccccctg
gaagctccctcgtgcgctctcctgttccgaccctgccgcttaccggatacctgtc
cgcctttctcccttcgggaagcgtggcgctttctcaatgctcacgctgtaggtat
ctcagttcggtgtaggtcgttcgctccaagctgggctgtgtgcacgaaccccccg
ttcagcccgaccgctgcgccttatccggtaactatcgtcttgagtccaacccggt
aagacacgacttatcgccactggcagcagccactggtaacaggattagcagagcg
aggtatgtaggcggtgctacagagttcttgaagtggtggcctaactacggctaca
ctagaaggacagtatttggtatctgcgctctgctgaagccagttaccttcggaaa
aagagttggtagctcttgatccggcaaacaaaccaccgctggtagcggtggtttt
tttgtttgcaagcagcagattacgcgcagaaaaaaaggatctcaagaagatcctt
tgatcttttctacggggtctgacgctcagtggaacgaaaactcacgttaagggat
tttggtcatgagattatcaaaaaggatcttcacctagatccttttaaattaaaaa
tgaagttttaaatcaatctaaagtatatatgagtaaacttggtctgacagttacc
aatgcttaatcagtgaggcacctatctcagcgatctgtctatttcgttcatccat
agttgcctgactccccgtcgtgtagataactacgatacgggagggcttaccatct
ggccccagtgctgcaatgataccgcgagacccacgctcaccggctccagatttat
cagcaataaaccagccagccggaagggccgagcgcagaagtggtcctgcaacttt
atccgcctccatccagtctattaattgttgccgggaagctagagtaagtagttcg
ccagttaatagtttgcgcaacgttgttgccattgctacaggcatcgtggtgtcac
gctcgtcgtttggtatggcttcattcagctccggttcccaacgatcaaggcgagt
tacatgatcccccatgttgtgcaaaaaagcggttagctccttcggtcctccgatc
gttgtcagaagtaagttggccgcagtgttatcactcatggttatggcagcactgc

FIG 24B CONT ataattctcttactgtcatgccatccgtaagatgcttttctgtgactggtgagta
ctcaaccaagtcattctgagaatagtgtatgcggcgaccgagttgctcttgcccg
gcgtcaatacgggataataccgcgccacatagcagaactttaaaagtgctcatca
ttggaaaacgttcttcggggcgaaaactctcaaggatcttaccgctgttgagatc
cagttcgatgtaacccactcgtgcacccaactgatcttcagcatcttttactttc
accagcgtttctgggtgagcaaaaacaggaaggcaaaatgccgcaaaaaagggaa
taagggcgacacggaaatgttgaatactcatactcttcctttttcaatattattg
aagcatttatcagggttattgtctcatgagcggatacatatttgaatgtatttag
aaaaataaacaaataggggttccgcgcacatttccccgaaaagtgccacctgacg
tcgacggatcgggagatctcccgatcccctatggtgcactctcagtacaatctgc
tctgatgccgcatagttaagccagtatctgctccctgcttgtgtgttggaggtcg
ctgagtagtgcgcgagcaaaatttaagctacaacaaggcaaggcttgaccgacaa
ttgcatgaagaatctgcttagggttaggcgttttgcgctgcttcgcgatgtacgg
gccagatatacgcgttgacattgattattgactagttattaatagtaatcaatta
cggggtcattagttcatagcccatatatggagttccgcgttacataacttacggt
aaatggcccgcctggctgaccgcccaacgacccccgcccattgacgtcaataatg
acgtatgttcccatagtaacgccaatagggactttccattgacgtcaatgggtgg
actatttacggtaaactgcccacttggcagtacatcaagtgtatcatatgccaag
tacgccccctattgacgtcaatgacggtaaatggcccgcctggcattatgcccag
tacatgaccttatgggactttcctacttggcagtacatctacgtattagtcatcg
ctattaccatggtgatgcggttttggcagtacatcaatgggcgtggatagcggtt
tgactcacggggatttccaagtctccaccccattgacgtcaatgggagtttgttt
tggcaccaaaatcaacgggactttccaaaatgtcgtaacaactccgccccattga
cgcaaatgggcggtaggcgtgtacggtgggaggtctatataagcagagctctctg
gctaactagagaacccactgcttactggcttatcgaaattaatacgactcactat
agggagacccaagctggtttaaacttaagcttggtaccgagctcactagtccagt
gtggtggcagatatccagcacagtggcggccgctcgagtctagagggcccgttta
aacnnnnngggtctctctggttagaccagatctgagcctgggagctctctggcta
actagggaacccactgcttaagcctcaataaagcttgccttgagtgcttcaagta
gtgtgtgcccgtctgttgtgtgactctggtaactagagatccctcagaccctttt
agtcagtgtggaaaatctctagcannnnnnnnnnccagcaacttatctgtgtctg
tccgattgtctagtgtctatgtttgatgttatgcgcctgcgtctgtactagttag
ctaactagctctgtatctggcggacccgtggtggaactgacgagttctgaacacc
cggccgcaaccctgggagacgtcccagggactttgggggccgtttttgtggcccg
acctgaggaagggagtcgatgtggaatccgaccccgtcaggatatgtggttctgg
taggagacgagaacctaaaacagttcccgcctccgtctgaattttttgctttcggt
ttggaaccgaagccgcgcgtcttgtctgctgcagcgctgcagcatcgttctgtgt
tgtctctgtctgactgtgtttctgtatttgtctgaaaattagggccagactgtta
ccactcccttaagtttgaccttaggtcactggaaagatgtcgagcggatcgctca
caaccagtcggtagatgtcaagaagagacgttgggttaccttctgctctgcagaa

FIG 24B CONT tggccaacctttaacgtcggatggccgcgagacggcacctttaaccgagacctca
tcacccaggttaagatcaaggtcttttcacctggcccgcatggacacccagacca
ggtcccctacatcgtgacctgggaagccttggctttgacccccctccctgggtc
aagccctttgtacaccctaagcctccgcctcctcttcctccatccgccccgtctc
tccccccttgaacctcctcgttcgaccccgcctcgatcctccctttatccagccct
cactccttctctaggcgccnnnnnnggaaaagtttagtaaaacaccatatgtatgt
ttcagggaaagctaggggatggttttatagacatcactatgaaagccctcatcca
agaataagttcagaagtacacatcccactaggggatgctagattggtaataacaa
catattggggtctgcatacaggagaaagagactggcatctgggtcagggagtctc
catagaatggaggaaaaagagatatagcacacaagtagaccctgaactagcagac
caactaattcatctgtattactttgactgtttttcagactctgctataagaaagg
ccttattaggacatatagttagccctaggtgtgaatatcaagcaggacataacaa
ggtaggatctctacaatacttggcactagcagcattaataacaccaaaaaagata
aagccacctttgcctagtgttacgaaactgacagaggatagatggaacaagcccc
agaagaccaagggccacagagggagccacacaatgaatggacactagagctttta
gaggagcttaagaatgaagctgttagacattttcctaggatttggctccatggct
tagggcaacatatctatgaaacttatggggatacttgggcaggagtggaagccat
aataatgcaacaactgctgtttatccatttcagaattgggtgtcgacatagcaga
ataggcgttactcaacagaggagagcaagaaatggagccagtagatcctagacta
gagccctggaagcatccaggaagtcagcctaaaactgcttgtaccacttgctatt
gtaaaaagtgttgctttcattgccaagtttgtttcacaacaaaagccttaggcat
ctcctatggcaggaagaagcggagacagcgacgaagacctcctcaaggcagtcag
actcatcaagtttctctatcaaagcagtaagtagtacatgtaatgcaacctatac
aaatagcaatagcagcattagtagtagcaataataatagcaatagttgtgtggtc
catagtaatcatagaatataggaaaatattaagacaaagaaaaatagacaggtta
attgatagactaatnnnnnnnnggcccgaaggaatagaagaagaaggtggagaga
gagacagagacagatccattcgattagtgaacggatcggcactgcgtgcgccaat
tctgcagacaaatggcagtattcatccacaattttaaaagaaaaggggggattgg
ggggtacagtgcaggggaaagaatagtagacataatagcaacagacatacaaact
aaagaattacaaaaacaaattacaaaaattcaaaattttcgggtttattacaggg
acagcagagatccagtttggttaattaatgctgctgagccacgtgaagccttaag
ccgcagggagaccctgaaaatagactgtaagcaaccttggggtggggtaagcctg
ttgcagcgttagtgtatccatgaactcctttaagatacaagctatgtgtcattcc
tcatggagacgccggagagtcttgagcttacatgatggtcctgcggaggccttaa
agtcctgtggggatgctcagggttgtccctgtgtgtcactgagacctccgaaaga
atttaaatatcacagaaaaaaaaacataaagaagaccttaagccttttttaagtt
cccaaggagagccagaagtggtggtatatagctcaacttgggagactgaggcaaa
aagactgactgagtttaagaccagcctagctacaccacaaagctcctttctcaaa
agaaaaagctcccaaggaggttggatccccagtgagaccctcagcaaggccctct
ggcctcactatggtcctgaggacacccctccacactgccctgatcttcttacccc

FIG 24B CONT atcctgcctgagctcttcacctgctctcctcttgcattcaaatatcttctgctac
agtaggtccactggagtctcccaggtacccagagtgtgaatgtctgcagcacttt
ctgggggacaaggagcagagagcaagggacccacaattcgggtctagtgtctgta
aagccttgcggagggtagagttctagttcacacaaggcaccaagtgtttttgctg
gttgcctaggaaacaggacagtgccaaatcaggaacagaaagagtcaaggaaccc
ccaaccactccaagcggaggctgagaaaggttttgtagctggaatagagcatgca
ctaacagatggagacagctggctttgagctctgaagcaagtattacatatggaga
cttgctggccttcaggtgcttatcttgttattggatactgcaggaggatgtacca
cagggcttcagctcagctgacccccaagtgggatatggaaagagagatagaggag
gagggaccattaagtgccttgctgcctgaattctgctttccttctacctctgaga
gagagctggggactcggctgagttaagaacccagctatcaattggaactgtgaaa
cagtccaagggacaaagatactaggtccccaactgcaacttcctggggaatgatg
tggaaaaatgctcagccaaggacaaagaaagcatcacccactctggaacaatgtc
ccctgctgtgaactggttcatcaggccatcagggccccttgttaagactctaatt
accctaggactaagtagaggtgttgacgtccaatgagcgctttctgcagacctag
caccagggaagtgtttggaaactgcagcttcagcccctctggccatctgctgacc
taccccacctggagcccttaatgggtcaaacagcaaagtccagggggcagagagg
aggtgctttggtctataaaggtagtggggacccagtaaccaccgg

FIG 24B CONT

SEQ ID NO: 12 tacagtgcaggggaaagaatagtagacataatagcaacagacatacaaactaaagaattacaaaaacaaattacaaaaattcaaattttcggtttattaca
gggacagcagagatccagtttggttaattaattggctccggtgcccgtcagtgggcagagcgcacatcgcccacagtccccgagaagttgggggagg
ggtcggcaattgaaccggtgcctagagaaggtggcgcggggtaaactgggaaagtgatgtcgtgtactggctccgcctttttcccgagggtgggggaga
accgtatataagtgcagtagtcgccgtgaacgttctttttcgcaacgggtttgccgccagaacacaggtaagtgccgtgtgtggttcccgcgggcctggcct
ctttacgggttatggcccttgcgtgccttgaattacttccacctggctgcagtacgtgattcttgatcccgagcttcgggttggaagtgggtgggagagttcga
ggccttgcgcttaaggagccccttcgcctcgtgcttgagttgaggcctggcctgggcgctggggccgccgcgtgcgaatctggtggcaccttcgcgcctg
tctcgctgctttcgataagtctctagccatttaaaatttttgatgacctgctgcgacgctttttttctggcaagatagtcttgtaaatgcgggccaagatctgcaca
ctggtatttcggtttttggggccgcgggcggcgacggggcccgtgcgtcccagcgcacatgttcggcgaggcggggcctgcgagcgcggccaccgag
aatcggacgggggtagtctcaagctggccggcctgctctggtgcctggcctcgcgccgccgtgtatcgccccgccctgggcggcaaggctggcccggt
cggcaccagttgcgtgagcggaaagatggccgcttcccggccctgctgcagggagctcaaaatggaggacgcggcgctcgggagagcgggcgggt
gagtcacccacacaaaggaaaagggcctttccgtcctcagccgtcgcttcatgtgactccacggagtaccgggcgccgtccaggcacctcgattagttct
cgagcttttggagtacgtcgtctttaggttgggggggaggggttttatgcgatggagtttccccacactgagtgggtggagactgaagttaggccagcttggc
acttgatgtaattctccttggaatttgccctttttgagtttggatcttggttcattctcaagcctcagacagtggttcaaagtttttttcttccatttcaggtgtcgtgag
gaattcggccattacggcccgccaccatggctagattagataaaagtaaagtgattaacagcgcattagagctgcttaatgaggtcggaatcgaaggtttaa
caacccgtaaactcgcccagaagctaggtgtagagcagcctacattgtattggcatgtaaaaaataagcgggctttgctcgacgccttagccattgagatgt
tagataggcaccatactcacttttgccctttagaaggggaaagctggcaagatttttacgtaataacgctaaaagttttagatgtgctttactaagtcatcgcga

FIG. 25B tggagcaaaagtacatttaggtacacggcctacagaaaaacagtatgaaactctcg
aaaatcaattagcctttttatgccaacaaggttttcactagagaatgcattatat
gcactcagcgctgtggggcatttactttaggttgcgtattggaagatcaagagca
tcaagtcgctaaagaagaaagggaaacacctactactgatagtatgccgccattat
tacgacaagctatcgaattatttgatcaccaaggtgcagagccagccttcttattc
ggccttgaattgatcatatgcggattagaaaaacaacttaaatgtgaaagtgggtc
gccaaaaaagaagagaaaggtcgacggcggtggtgctttgtctcctcagcactctg
ctgtcactcaaggaagtatcatcaagaacaaggagggcatggatgctaagtcacta
actgcctggtcccggacactggtgaccttcaaggatgtatttgtggacttcaccag
ggaggagtggaagctgctggacactgctcagcagatcgtgtacagaaatgtgatgc
tggagaactataagaacctggtttccttgggttatcagcttactaagccagatgtg
atcctccggttggagaagggagaagagccctggctggtggagagagaaattcacca
agagacccatcctgattcagagactgcatttgaaatcaaatcatcagtttaaggcc
gcctcggccatcgataaggatccggaatgcccctctccctcccccccccctaacgt
tactggccgaagccgcttggaataaggccggtgtgcgtttgtctatatgttatttt
ccaccatattgccgtcttttggcaatgtgagggcccggaaacctggccctgtcttc
ttgacgagcattcctaggggtctttcccctctcgccaaaggaatgcaaggtctgtt
gaatgtcgtgaaggaagcagttcctctggaagcttcttgaagacaaacaacgtctg
tagcgaccctttgcaggcagcggaaccccccacctggcgacaggtgcctctgcggc
caaaagccacgtgtataagatacacctgcaaaggcggcacaaccccagtgccacgt
tgtgagttggatagttgtggaaagagtcaaatggctctcctcaagcgtattcaaca
aggggctgaaggatgcccagaaggtaccccattgtatgggatctgatctggggcct
cggtgcacatgctttacatgtgtttagtcgaggttaaaaaaacgtctaggccccc
gaaccacggggacgtggttttcctttgaaaaacacgatgataatatggccacaacc
atgaccgagtacaagcccacggtgcgcctcgccacccgcgacgacgtcccccgggc
cgtacgcaccctcgccgccgcgttcgccgactaccccgccacgcgccacaccgtcg
acccggaccgccacatcgagcgggtcaccgagctgcaagaactcttcctcacgcgc
gtcgggctcgacatcggcaaggtgtgggtcgcggacgacggcgccgcggtggcggt
ctggaccacgccggagagcgtcgaagcgggggcggtgttcgccgagatcggcccgc
gcatggccgagttgagcggttcccggctggccgcgcagcaacagatggaaggcctc
ctggcgccgcaccggcccaaggagcccgcgtggttcctggccaccgtcggcgtctc
gcccgaccaccagggcaagggtctgggcagcgccgtcgtgctccccggagtggagg
cggccgagcgcgccggggtgcccgccttcctggagacctccgcgccccgcaacctc
cccttctacgagcggctcggcttcaccgtcaccgccgacgtcgaggtgcccgaagg
accgcgcacctggtgcatgacccgcaagcccggtgcctgagcggccgcaatcaacc
tctggattacaaaatttgtgaaagattgactggtattcttaactatgttgctcctt
ttacgctatgtggatacgctgctttaatgcctttgtatcatgctattacttcccgt
acggctttcattttctcctccttgtataaatcctggttgctgtctctttatgagga
gttgtggcccgttgtcaggcaacgtggcgtggtgtgcactgtgtttgctgacgcaa
cccccactggttggggcattgccaccacctatcaactcctttccgggactttcgct
ttccccctccctattgccacggcggaactcattgccgcctgccttgcccgctgctg

FIG 25B CONT gacaggggctcggctgttgggcactgacaattccgtggtgttgtcggggaagctga
cgtcctttccatggctgctcgcctgtgttgccaactggattctgcgcgggacgtcc
ttctgctacgtcccttcggccctcaatccagcggaccttccttcccgcggcctgct
gccggttctgcggcctcttccgcgtcttcgccttcgccctcagacgagtcggatct
ccctttgggccgcctccccgcctgcctgcaggtttgtcgagacctagaaaaacatg
gagcaatcacaagtagcaatacagcagctaccaatgctgattgtgcctggctagaa
gcacaagaggaggaggaggtgggttttccagtcacacctcaggtacctttaagacc
aatgacttacaaggcagctgtagatcttagccactttttaaaagaaaaggggggac
tggaagggctaattcactcccaacgaagacaagatctgcttttgcttgtactggg
tctctctggttagaccagatctgagcctgggagctctctggctaactagggaaccc
actgcttaagcctcaataaagcttgccttgagtgcttcaagtagtgtgtgcccgtc
tgttgtgtgactctggtaactagagatccctcagacccttttagtcagtgtggaaa
atctctagcagggcccgtttaaacccgctgatcagcctcgactgtgccttctagtt
gccagccatctgttgtttgcccctcccccgtgccttccttgaccctggaaggtgcc
actcccactgtcctttcctaataaaatgaggaaattgcatcgcattgtctgagtag
gtgtcattctattctggggggtggggtggggcaggacagcaagggggaggattggg
aagacaatagcaggcatgctggggatgcggtgggctctatggcttctgaggcggaa
agaaccagctggggctctagggggtatccccacgcgccctgtagcggcgcattaag
cgcggcgggtgtggtggttacgcgcagcgtgaccgctacacttgccagcgccctag
cgcccgctcctttcgctttcttcccttcctttctcgccacgttcgccggctttccc
cgtcaagctctaaatcggggcatccctttagggttccgatttagtgctttacggca
cctcgaccccaaaaaacttgattagggtgatggttcacgtagtgggccatcgccct
gatagacggtttttcgccctttgacgttggagtccacgttctttaatagtggactc
ttgttccaaactggaacaacactcaaccctatctcggtctattcttttgatttata
agggattttggggatttcggcctattggttaaaaaatgagctgatttaacaaaaat
ttaacgcgaattaattctgtggaatgtgtgtcagttagggtgtggaaagtccccag
gctccccaggcaggcagaagtatgcaaagcatgcatctcaattagtcagcaaccag
gtgtggaaagtccccaggctccccagcaggcagaagtatgcaaagcatgcatctca
attagtcagcaaccatagtcccgcccctaactccgcccatcccgcccctaactccg
cccagttccgcccattctccgccccatggctgactaattttttttatttatgcaga
ggccgaggccgcctctgcctctgagctattccagaagtagtgaggaggcttttttg
gaggcctaggcttttgcaaaaagctcccgggagcttgtatatccatttcggatct
gatcagcacgtgttgacaattaatcatcggcatagtatatcggcatagtataatac
gacaaggtgaggaactaaaccatggccaagttgaccagtgccgttccggtgctcac
cgcgcgcgacgtcgccggagcggtcgagttctggaccgaccggctcgggttctccc
gggacttcgtggaggacgacttcgccggtgtggtccgggacgacgtgaccctgttc
atcagcgcggtccaggaccaggtggtgccggacaacaccctggcctgggtgtgggt
gcgcggcctggacgagctgtacgccgagtggtcggaggtcgtgtccacgaacttcc
gggacgcctccgggccggccatgaccgagatcggcgagcagccgtgggggcgggag
ttcgccctgcgcgacccggccggcaactgcgtgcacttcgtggccgaggagcagga
ctgacacgtgctacgagatttcgattccaccgccgccttctatgaaaggttgggct
tcggaatcgttttccgggacgccggctggatgatcctccagcgcggggatctcatg

FIG 25B CONT ctggagttcttcgcccaccccaacttgtttattgcagcttataatggttacaaata
aagcaatagcatcacaaatttcacaaataaagcatttttttcactgcattctagtt
gtggtttgtccaaactcatcaatgtatcttatcatgtctgtataccgtcgacctct
agctagagcttggcgtaatcatggtcatagctgtttcctgtgtgaaattgttatcc
gctcacaattccacacaacatacgagccggaagcataaagtgtaaagcctggggtg
cctaatgagtgagctaactcacattaattgcgttgcgctcactgcccgctttccag
tcgggaaacctgtcgtgccagctgcattaatgaatcggccaacgcgcggggagagg
cggtttgcgtattgggcgctcttccgcttcctcgctcactgactcgctgcgctcgg
tcgttcggctgcggcgagcggtatcagctcactcaaaggcggtaatacggttatcc
acagaatcaggggataacgcaggaaagaacatgtgagcaaaaggccagcaaaaggc
caggaaccgtaaaaaggccgcgttgctggcgtttttccataggctccgcccccctg
acgagcatcacaaaaatcgacgctcaagtcagaggtggcgaaacccgacaggacta
taaagataccaggcgtttccccctggaagctccctcgtgcgctctcctgttccgac
cctgccgcttaccggatacctgtccgcctttctcccttcgggaagcgtggcgcttt
ctcaatgctcacgctgtaggtatctcagttcggtgtaggtcgttcgctccaagctg
ggctgtgtgcacgaaccccccgttcagcccgaccgctgcgccttatccggtaacta
tcgtcttgagtccaacccggtaagacacgacttatcgccactggcagcagccactg
gtaacaggattagcagagcgaggtatgtaggcggtgctacagagttcttgaagtgg
tggcctaactacggctacactagaaggacagtatttggtatctgcgctctgctgaa
gccagttaccttcggaaaaagagttggtagctcttgatccggcaaacaaaccaccg
ctggtagcggtggtttttttgtttgcaagcagcagattacgcgcagaaaaaaagga
tctcaagaagatcctttgatcttttctacggggtctgacgctcagtggaacgaaaa
ctcacgttaagggattttggtcatgagattatcaaaaaggatcttcacctagatcc
ttttaaattaaaaatgaagttttaaatcaatctaaagtatatatgagtaaacttgg
tctgacagttaccaatgcttaatcagtgaggcacctatctcagcgatctgtctatt
tcgttcatccatagttgcctgactccccgtcgtgtagataactacgatacgggagg
gcttaccatctggccccagtgctgcaatgataccgcgagacccacgctcaccggct
ccagatttatcagcaataaaccagccagccggaagggccgagcgcagaagtggtcc
tgcaactttatccgcctccatccagtctattaattgttgccgggaagctagagtaa
gtagttcgccagttaatagtttgcgcaacgttgttgccattgctacaggcatcgtg
gtgtcacgctcgtcgtttggtatggcttcattcagctccggttcccaacgatcaag
gcgagttacatgatcccccatgttgtgcaaaaaagcggttagctccttcggtcctc
cgatcgttgtcagaagtaagttggccgcagtgttatcactcatggttatggcagca
ctgcataattctcttactgtcatgccatccgtaagatgcttttctgtgactggtga
gtactcaaccaagtcattctgagaatagtgtatgcggcgaccgagttgctcttgcc
cggcgtcaatacgggataataccgcgccacatagcagaactttaaaagtgctcatc
attggaaaacgttcttcggggcgaaaactctcaaggatcttaccgctgttgagatc
cagttcgatgtaacccactcgtgcacccaactgatcttcagcatcttttactttca
ccagcgtttctgggtgagcaaaaacaggaaggcaaaatgccgcaaaaaagggaata
agggcgacacggaaatgttgaatactcatactcttcctttttcaatattattgaag
catttatcagggttattgtctcatgagcggatacatatttgaatgtatttagaaaa
ataaacaaataggggttccgcgcacatttccccgaaaagtgccacctgacgtcgac

FIG 25B CONT ggatcgggagatctcccgatcccctatggtgcactctcagtacaatctgctctgat
gccgcatagttaagccagtatctgctccctgcttgtgtgttggaggtcgctgagta
gtgcgcgagcaaaatttaagctacaacaaggcaaggcttgaccgacaattgcatga
agaatctgcttagggttaggcgttttgcgctgcttcgcgatgtacgggccagatat
acgcgttgacattgattattgactagttattaatagtaatcaattacggggtcatt
agttcatagcccatatatggagttccgcgttacataacttacggtaaatggcccgc
ctggctgaccgcccaacgacccccgcccattgacgtcaataatgacgtatgttccc
atagtaacgccaatagggactttccattgacgtcaatgggtggactatttacggta
aactgcccacttggcagtacatcaagtgtatcatatgccaagtacgccccctattg
acgtcaatgacggtaaatggcccgcctggcattatgcccagtacatgaccttatgg
gactttcctacttggcagtacatctacgtattagtcatcgctattaccatggtgat
gcggttttggcagtacatcaatgggcgtggatagcggtttgactcacggggatttc
caagtctccaccccattgacgtcaatgggagtttgttttggcaccaaaatcaacgg
gactttccaaaatgtcgtaacaactccgccccattgacgcaaatgggcggtaggcg
tgtacggtgggaggtctatataagcagagcggtttaaacttaagcttggtaccgag
ctcactagtccagtgtggtggcagatatccagcacagtggcggccgctcgagtcta
gagggcccgtttgcctgtactgggtctctctggttagaccagatctgagcctggg
agctctctggctaactagggaacccactgcttaagcctcaataaagcttgccttga
gtgcttcaagtagtgtgtgcccgtctgttgtgtgactctggtaactagagatccct
cagaccctttagtcagtgtggaaaatctctagcagtggcgcccgaacagggactt
gaaagcgaaagggaaaccagaggagctctctcgacgcaggactcggcttgctgaag
cgcgcacggcaagaggcgaggggcggcgactggtgagtacgccaaaaattttgact
agcggaggctagaaggagagagatgggtgcgagagcgtcagtattaagcgggggag
aattagatcgcgatgggaaaaaattcggttaaggccagggggaaagaaaaaatata
aattaaaacatatagtatgggcaagcagggagctagaacgattcgcagttaatcct
ggcctgttagaaacatcagaaggctgtagacaaatactgggacagctacaaccatc
ccttcagacaggatcagaagaacttagatcattatataatacagtagcaaccctct
attgtgtgcatcaaaggatagagataaaagacaccaaggaagctttagacaagata
gaggaagagcaaaacaaaagtaagaccaccgcacagcaagcggccgctgatcttca
gacctggaggaggagatatgagggacaattggagaagtgaattatataaatataaa
gtagtaaaaattgaaccattaggagtagcacccaccaaggcaaagagaagagtggt
gcagagagaaaaaagagcagtgggaataggagctttgttccttgggttcttgggag
cagcaggaagcactatgggcgcagcgtcaatgacgctgacggtacaggccagacaa
ttattgtctggtatagtgcagcagcagaacaatttgctgagggctattgaggcgca
acagcatctgttgcaactcacagtctggggcatcaagcagctccaggcaagaatcc
tggctgtggaaagatacctaaaggatcaacagctcctggggatttggggttgctct
ggaaaactcatttgcaccactgctgtgccttggaatgctagttggagtaataaatc
tctggaacagatttggaatcacacgacctggatggagtgggacagagaaattaaca
attacacaagcttaatacactccttaattgaagaatcgcaaaaccagcaagaaaag
aatgaacaagaattattggaattagataaatgggcaagtttgtggaattggtttaa
cataacaaattggctgtggtatatagaaattattcataatgatagtaggaggcttg
gtaggtttaagaatagtttttgctgtactttctatagtgaatagagttaggcaggg

FIG 25B CONT atattcaccattatcgtttcagacccacctcccaaccccgaggggacccgacaggc
ccgaaggaatagaagaagaaggtggagagagagacagagacagatccattcgatta
gtgaacggatcggcactgcgtgcgccaattctgcagacaaatggcagtattcatcc
acaattttaaaagaaaagggggattgggggg

FIG 25B CONT aatgaagctactgtcttctatcgaacaagcatgcgatatttgccgacttaaaaagctcaagtgctccaaagaaaaaccgaagtgcg
ccaagtgtctgaagaacaactgggagtgtcgctactctcccaaaaccaaaaggtctccgctgactagggcacatctgacagaag
tggaatcaaggctagaaagactggaacagctatttctactgatttttcctcgagaagaccttgacatgattttgaaaatggattcttta
caggatataaaagcattgttaacaggattatttgtacaagataatgtgaataaagatgccgtcacagatagattggcttcagtggag
actgatatgcctctaacattgagacagcatagaataagtgcgacatcatcatcggaagagagtagtaacaaaggtcaaagacagt
tgactgtatcgattgactcggcagctcatcatgataactccacaattccgttggattttatgcccagggatgctcttcatggatttgatt
ggtctgaagaggatgacatgtcggatggcttgcccttcctgaaaacggaccccaacaataatgggttctttggcgacggttctctc
ttatgtattcttcgatctattggctttaaaccggaaaattacacgaactctaacgttaacaggctcccgaccatgattacggatagata
cacgttggcttctagatccacaacatcccgtttacttcaaagttatctcaataattttcacccctactgccctatcgtgcactcaccga
cgctaatgatgttgtataataaccagattgaaatcgcgtcgaaggatcaatggcaaatcctttttaactgcatattagccattggagc
ctggtgtatagaggggaatctactgatatagatgtttttactatcaaaatgctaaatctcatttgacgagcaaggtcttcgagtcag
gttccataattttggtgacagccctacatcttctgtcgcgatatacacagtggaggcagaaaacaaatactagctataattttcacag
cttttccataagaatggccatatcattgggcttgaatagggacctcccctcgtccttcagtgatagcagcattctggaacaaagacg
ccgaatttggtggtctgtctactcttgggagatccaattgtccctgctttatggtcgatccatccagctttctcagaatacaatctcctt
cccttcttctgtcgacgatgtgcagcgtaccacaacaggtcccaccatatatcatggcatcattgaaacagcaaggctcttacaag
ttttcacaaaaatctatgaactagacaaaacagtaactgcagaaaaaagtcctatatgtgcaaaaaaatgcttgatgatttgtaatga
gattgaggaggtttcgagacaggcaccaaagtttttacaaatggatatttccaccaccgctctaaccaatttgttgaaggaacaccc
ttggctatcctttacaagattcgaactgaagtggaaacagttgtctcttatcatttatgtattaagagatttttcactaattttacccaga
aaaagtcacaactagaacaggatcaaaatgatcatcaaagttatgaagttaaacgatgctccatcatgttaagcgatgcagcaca
aagaactgttatgtctgtaagtagctatatggacaatcataatgtcaccccatatttgcctggaattgttcttattacttgttcaatgca

FIG. 28B gtcctagtacccataaagactctactctcaaactcaaaatcgaatgctgagaata
acgagaccgcacaattattacaacaaattaacactgttctgatgctattaaaaaa
actggccactttaaaatccagacttgtgaaaatacattcaagtactggaagag
gtatgtgcgccgtttctgttatcacagtgtgcaatcccattaccgcatatcagtt
ataacaatagtaatggtagcgccattaaaaatattgtcggttctgcaactatcgc
ccaataccctactcttccggaggaaaatgtcaacaatatcagtgttaaatatgtt
tctcctggctcagtagggccttcacctgtgccattgaaatcaggagcaagtttca
gtgatctagtcaagctgttatctaaccgtccacccctctcgtaactctccagtgac
aataccaagaagcacaccttcgcatcgctcagtcacgcctttctagggcaacag
caacagctgcaatcattagtgccactgaccccgtctgctttgtttggtggcgcca
attttaatcaaagtgggaatattgctgatagctcattgtccttcactttcactaa
cagtagcaacggtccgaacctcataacaactcaaacaaattctcaagcgctttca
caaccaattgcctcctctaacgttcatgataacttcatgaataatgaaatcacgg
ctagtaaaattgatgatggtaataattcaaaaccactgtcacctggttggacgga
ccaaactgcgtataacgcgtttggaatcactacaggatgtttaataccactaca
atggatgatgtatataactatctattcgatgatgaagataccccaccaaacccaa
aaaaagagtaagaattcgatatcaagcttatcgataatcaacctctggattacaa
aatttgtgaaagattgactggtattcttaactatgttgctccttttacgctatgt
ggatacgctgctttaatgcctttgtatcatgctattacttcccgtacggctttca
ttttctcctccttgtataaatcctggttgctgtctctttatgaggagttgtggcc
cgttgtcaggcaacgtggcgtggtgtgcactgtgtttgctgacgcaacccccact
ggttggggcattgccaccacctatcaactcctttccgggactttcgctttccccc
tccctattgccacggcggaactcattgccgcctgccttgcccgctgctggacagg
ggctcggctgttgggcactgacaattccgtggtgttgtcggggaagctgacgtcc
tttccatggctgctcgcctgtgttgccaactggattctgcgcgggacgtccttct
gctacgtcccttcggccctcaatccagcggaccttccttcccgcggcctgctgcc
ggttctgcggcctcttccgcgtcttcgccttcgccctcagacgagtcggatctcc
ctttgggccgcctccccgcctgcctgcaggtttgtcgagacctagaaaaacatgg
agcaatcacaagtagcaatacagcagctaccaatgctgattgtgcctggctagaa
gcacaagaggaggaggaggtgggttttccagtcacacctcaggtacctttaagac
caatgacttacaaggcagctgtagatcttagccactttttaaaagaaaagggggg
actggaagggctaattcactcccaacgaagacaagatctgctttttgcttgtact
gggtctctctggttagaccagatctgagcctgggagctctctggctaactaggga
acccactgcttaagcctcaataaagcttgccttgagtgcttcaagtagtgtgtgc
ccgtctgttgtgtgactctggtaactagagatccctcagacccttttagtcagtg
tggaaaatctctagcagggcccgtttaaacccgctgatcagcctcgactgtgcct
tctagttgccagccatctgttgtttgcccctcccccgtgccttccttgaccctgg
aaggtgccactcccactgtcctttcctaataaaatgaggaaattgcatcgcattg
tctgagtaggtgtcattctattctggggggtggggtggggcaggacagcaagggg
gaggattgggaagacaatagcaggcatgctggggatgcggtgggctctatggctt

FIG 28B CONT ctgaggcggaaagaaccagctggggctctaggggtatccccacgcgccctgtag
cggcgcattaagcgcggcgggtgtggtggttacgcgcagcgtgaccgctacactt
gccagcgccctagcgcccgctcctttcgctttcttcccttcctttctcgccacgt
tcgccggctttccccgtcaagctctaaatcgggcatccctttagggttccgatt
tagtgctttacggcacctcgaccccaaaaaacttgattagggtgatggttcacgt
agtgggccatcgccctgatagacggtttttcgccctttgacgttggagtccacgt
tctttaatagtggactcttgttccaaactggaacaacactcaaccctatctcggt
ctattcttttgatttataagggattttggggatttcggcctattggttaaaaat
gagctgatttaacaaaaatttaacgcgaattaattctgtggaatgtgtgtcagtt
agggtgtggaaagtccccaggctccccaggcaggcagaagtatgcaaagcatgca
tctcaattagtcagcaaccaggtgtggaaagtccccaggctccccagcaggcaga
agtatgcaaagcatgcatctcaattagtcagcaaccatagtcccgcccctaactc
cgcccatcccgcccctaactccgcccagttccgcccattctccgccccatggctg
actaattttttttatttatgcagaggccgaggccgcctctgcctctgagctattc
cagaagtagtgaggaggcttttttggaggcctaggcttttgcaaaaagctcccgg
gagcttgtatatccattttcggatctgatcagcacgtgttgacaattaatcatcg
gcatagtatatcggcatagtataatacgacaaggtgaggaactaaaccatggcca
agttgaccagtgccgttccggtgctcaccgcgcgcgacgtcgccggagcggtcga
gttctggaccgaccggctcgggttctcccgggacttcgtggaggacgacttcgcc
ggtgtggtccgggacgacgtgaccctgttcatcagcgcggtccaggaccaggtgg
tgccggacaacaccctggcctgggtgtgggtgcgcggcctggacgagctgtacgc
cgagtggtcggaggtcgtgtccacgaacttccgggacgcctccgggccggccatg
accgagatcggcgagcagccgtgggggcgggagttcgccctgcgcgacccggccg
gcaactgcgtgcacttcgtggccgaggagcaggactgacacgtgctacgagattt
cgattccaccgccgccttctatgaaaggttgggcttcggaatcgttttccgggac
gccggctggatgatcctccagcgcggggatctcatgctggagttcttcgcccacc
ccaacttgtttattgcagcttataatggttacaaataaagcaatagcatcacaaa
tttcacaaataaagcatttttttcactgcattctagttgtggtttgtccaaactc
atcaatgtatcttatcatgtctgtataccgtcgacctctagctagagcttggcgt
aatcatggtcatagctgtttcctgtgtgaaattgttatccgctcacaattccaca
caacatacgagccggaagcataaagtgtaaagcctggggtgcctaatgagtgagc
taactcacattaattgcgttgcgctcactgcccgctttccagtcgggaaacctgt
cgtgccagctgcattaatgaatcggccaacgcgcggggagaggcggtttgcgtat
tgggcgctcttccgcttcctcgctcactgactcgctgcgctcggtcgttcggctg
cggcgagcggtatcagctcactcaaaggcggtaatacggttatccacagaatcag
gggataacgcaggaaagaacatgtgagcaaaaggccagcaaaaggccaggaaccg
taaaaaggccgcgttgctggcgtttttccataggctccgcccccctgacgagcat
cacaaaaatcgacgctcaagtcagaggtggcgaaacccgacaggactataaagat
accaggcgtttccccctggaagctccctcgtgcgctctcctgttccgaccctgcc
gcttaccggatacctgtccgcctttctcccttcgggaagcgtggcgctttctcaa

FIG 28B CONT tgctcacgctgtaggtatctcagttcggtgtaggtcgttcgctccaagctgggct
gtgtgcacgaaccccccgttcagcccgaccgctgcgccttatccggtaactatcg
tcttgagtccaacccggtaagacacgacttatcgccactggcagcagccactggt
aacaggattagcagagcgaggtatgtaggcggtgctacagagttcttgaagtggt
ggcctaactacggctacactagaaggacagtatttggtatctgcgctctgctgaa
gccagttaccttcggaaaaagagttggtagctcttgatccggcaaacaaaccacc
gctggtagcggtggtttttttgtttgcaagcagcagattacgcgcagaaaaaaag
gatctcaagaagatcctttgatcttttctacggggtctgacgctcagtggaacga
aaactcacgttaagggattttggtcatgagattatcaaaaaggatcttcacctag
atccttttaaattaaaaatgaagttttaaatcaatctaaagtatatatgagtaaa
cttggtctgacagttaccaatgcttaatcagtgaggcacctatctcagcgatctg
tctatttcgttcatccatagttgcctgactccccgtcgtgtagataactacgata
cgggagggcttaccatctggccccagtgctgcaatgataccgcgagacccacgct
caccggctccagatttatcagcaataaaccagccagccggaagggccgagcgcag
aagtggtcctgcaactttatccgcctccatccagtctattaattgttgccgggaa
gctagagtaagtagttcgccagttaatagtttgcgcaacgttgttgccattgcta
caggcatcgtggtgtcacgctcgtcgtttggtatggcttcattcagctccggttc
ccaacgatcaaggcgagttacatgatcccccatgttgtgcaaaaaagcggttagc
tccttcggtcctccgatcgttgtcagaagtaagttggccgcagtgttatcactca
tggttatggcagcactgcataattctcttactgtcatgccatccgtaagatgctt
ttctgtgactggtgagtactcaaccaagtcattctgagaatagtgtatgcggcga
ccgagttgctcttgcccggcgtcaatacgggataataccgcgccacatagcagaa
ctttaaaagtgctcatcattggaaaacgttcttcggggcgaaaactctcaaggat
cttaccgctgttgagatccagttcgatgtaacccactcgtgcacccaactgatct
tcagcatcttttactttcaccagcgtttctgggtgagcaaaaacaggaaggcaaa
atgccgcaaaaaagggaataagggcgacacggaaatgttgaatactcatactctt
cctttttcaatattattgaagcatttatcagggttattgtctcatgagcggatac
atatttgaatgtatttagaaaaataaacaaataggggttccgcgcacatttcccc
gaaaagtgccacctgacgtcgacggatcgggagatctcccgatcccctatggtgc
actctcagtacaatctgctctgatgccgcatagttaagccagtatctgctccctg
cttgtgtgttggaggtcgctgagtagtgcgcgagcaaaatttaagctacaacaag
gcaaggcttgaccgacaattgcatgaagaatctgcttagggttaggcgttttgcg
ctgcttcgcgatgtacgggccagatatacgcgttgacattgattattgactagtt
attaatagtaatcaattacggggtcattagttcatagcccatatatggagttccg
cgttacataacttacggtaaatggcccgcctggctgaccgcccaacgacccccgc
ccattgacgtcaataatgacgtatgttcccatagtaacgccaatagggactttcc
attgacgtcaatgggtggactatttacggtaaactgcccacttggcagtacatca
agtgtatcatatgccaagtacgccccctattgacgtcaatgacggtaaatggccc
gcctggcattatgcccagtacatgaccttatgggactttcctacttggcagtaca
tctacgtattagtcatcgctattaccatggtgatgcggttttggcagtacatcaa

FIG 28B CONT tgggcgtggatagcggtttgactcacggggatttccaagtctccaccccattgac
gtcaatgggagtttgttttggcaccaaaatcaacgggactttccaaaatgtcgta
acaactccgccccattgacgcaaatgggcggtaggcgtgtacggtgggaggtcta
tataagcagagctctctggctaactagagaacccactgcttactggcttatcgaa
attaatacgactcactatagggagacccaagctggtttaaacttaagcttggtac
cgagctcactagtccagtgtggtggcagatatccagcacagtggcggccgctcga
ggggcccgtttgcctgtactgggtctctctggttagaccagatctgagcctggg
agctctctggctaactagggaacccactgcttaagcctcaataaagcttgccttg
agtgcttcaagtagtgtgtgcccgtctgttgtgtgactctggtaactagagatcc
ctcagacccttttagtcagtgtggaaaatctctagcagtggcgcccgaacaggga
cttgaaagcgaaagggaaaccagaggagctctctcgacgcaggactcggcttgct
gaagcgcgcacggcaagaggcgaggggcggcgactggtgagtacgccaaaaattt
tgactagcggaggctagaaggagagagatgggtgcgagagcgtcagtattaagcg
ggggagaattagatcgcgatgggaaaaaattcggttaaggccagggggaaagaaa
aaatataaattaaaacatatagtatgggcaagcagggagctagaacgattcgcag
ttaatcctggcctgttagaaacatcagaaggctgtagacaaatactgggacagct
acaaccatcccttcagacaggatcagaagaacttagatcattatataatacagta
gcaaccctctattgtgtgcatcaaaggatagagataaaagacaccaaggaagctt
tagacaagatagaggaagagcaaaacaaaagtaagaccaccgcacagcaagcggc
cgctgatcttcagacctggaggaggagatatgagggacaattggagaagtgaatt
atataaatataaagtagtaaaaattgaaccattaggagtagcacccaccaaggca
aagagaagagtggtgcagagagaaaaaagagcagtgggaataggagctttgttcc
ttgggttcttgggagcagcaggaagcactatgggcgcagcgtcaatgacgctgac
ggtacaggccagacaattattgtctggtatagtgcagcagcagaacaatttgctg
agggctattgaggcgcaacagcatctgttgcaactcacagtctggggcatcaagc
agctccaggcaagaatcctggctgtggaaagatacctaaaggatcaacagctcct
ggggatttggggttgctctggaaaactcatttgcaccactgctgtgccttggaat
gctagttggagtaataaatctctggaacagatttggaatcacacgacctggatgg
agtgggacagagaaattaacaattacacaagcttaatacactccttaattgaaga
atcgcaaaaccagcaagaaaagaatgaacaagaattattggaattagataaatgg
gcaagtttgtggaattggtttaacataacaaattggctgtggtatataaaattat
tcataatgatagtaggaggcttggtaggtttaagaatagtttttgctgtactttc
tatagtgaatagagttaggcagggatattcaccattatcgtttcagacccacctc
ccaaccccgaggggacccgacaggcccttaattaatcccctgattctgtggataa
ccgtattaccgcctttgagtgagctgcacctagtacggattagaagccgccgagc
gggtgacagccctccgaaggaagactctcctccgtgcgtcctcgtcttcaccggt
cgcgttcctgaaacgcagatgtgcctcgcgccgcactgctccgaacaatgtcgac
tctagaggtaaactcgacctatataagcagagctcgtttagtgaaccgtcagatc
gcctggagacgccatccacgctgttttgacctccatagaagacaccgggaccgat

FIG 28B CONT ccagcctccgcggccccgaattgaattcgaagcaggagtagacgccggccattac
ggcctgccaccgttaat

FIG 28B CONT cgcgatcacatggtcctgctggagttcgtgaccgccgccgggatcactctcggcatggacgagctgtacaagtaagcggccgcaatcaa
cctctggattacaaaatttgtgaaagattgactggtattcttaactatgttgctccttttacgctatgtggatacgctgctttaatgcctttgtatcat
gctattacttcccgtacggctttcattttctcctccttgtataaatcctggttgctgtctctttatgaggagttgtggcccgttgtcaggcaacgtg
gcgtggtgtgcactgtgtttgctgacgcaacccccactggttggggcattgccaccacctatcaactcctttccgggactttcgctttccccc
tccctattgccacggcggaactcattgccgcctgccttgcccgctgctggacaggggctcggctgttgggcactgacaattccgtggtgtt
gtcggggaagctgacgtcctttccatggctgctcgcctgtgttgccaactggattctgcgcgggacgtccttctgctacgtcccttcggccc
tcaatccagcggaccttccttcccgcggcctgctgccggttctgcggcctcttccgcgtcttcgccttcgccctcagacgagtcggatctcc
ctttgggccgcctccccgcctgcctgcaggtttgtcgagacctagaaaaacatggagcaatcacaagtagcaatacagcagctaccaatg
ctgattgtgcctggctagaagcacaagaggaggaggaggtgggttttccagtcacacctcaggtacctttaagaccaatgacttacaagg
cagctgtagatcttagccactttttaaaagaaaaggggggactggaagggctaattcactcccaacgaagacaagatctgctttttgcttgta
ctgggtctctctggttagaccagatctgagcctgggagctctctggctaactagggaacccactgcttaagcctcaataaagcttgccttga
gtgcttcaagtagtgtgtgcccgtctgttgtgtgactctggtaactagagatccctcagacccttttagtcagtgtggaaaatctctagcaggg
cccgtttaaacccgctgatcagcctcgactgtgccttctagttgccagccatctgttgtttgcccctcccccgtgccttccttgaccctggaag
gtgccactcccactgtcctttcctaataaaatgaggaaattgcatcgcattgtctgagtaggtgtcattctattctggggggtggggtggggc
aggacagcaagggggaggattgggaagacaatagcaggcatgctggggatgcggtgggctctatggcttctgaggcggaaagaacc
agctggggctctagggggtatccccacgcgccctgtagcggcgcattaagcgcggcgggtgtggtggttacgcgcagcgtgaccgcta
cacttgccagcgccctagcgcccgctcctttcgctttcttcccttcctttctcgccacgttcgccggctttccccgtcaagctctaaatcgggg
catccctttagggttccgatttagtgctttacggcacctcgaccccaaaaaacttgattagggtgatggttcacgtagtggccatcgccctg
atagacggtttttcgccctttgacgttggagtccacgttctttaatagtggactcttgttccaaactggaacaacactcaaccctatctcggtct
attctttgatttataagggattttggggatttcggcctattggttaaaaaatgagctgatttaacaaaaatttaacgcgaattaattctgtggaa
gtgtgtcagttagggtgtggaaagtccccaggctccccaggcaggcagaagt

FIG. 29B atgcaaagcatgcatctcaattagtcagcaaccaggtgtggaaagtccccaggct
ccccagcaggcagaagtatgcaaagcatgcatctcaattagtcagcaaccatagt
cccgcccctaactccgcccatcccgcccctaactccgcccagttccgcccattct
ccgccccatggctgactaattttttttatttatgcagaggccgaggccgcctctg
cctctgagctattccagaagtagtgaggaggcttttttggaggcctaggcttttg
caaaaagctcccgggagcttgtatatccattttcggatctgatcagcacgtgttg
acaattaatcatcggcatagtatatcggcatagtataatacgacaaggtgaggaa
ctaaaccatggccaagttgaccagtgccgttccggtgctcaccgcgcgcgacgtc
gccggagcggtcgagttctggaccgaccggctcgggttctcccgggacttcgtgg
aggacgacttcgccggtgtggtccgggacgacgtgaccctgttcatcagcgcggt
ccaggaccaggtggtgccggacaacaccctggcctgggtgtgggtgcgcggcctg
gacgagctgtacgccgagtggtcggaggtcgtgtccacgaacttccgggacgcct
ccgggccggccatgaccgagatcggcgagcagccgtgggggcgggagttcgccct
gcgcgacccggccggcaactgcgtgcacttcgtggccgaggagcaggactgacac
gtgctacgagatttcgattccaccgccgccttctatgaaaggttgggcttcggaa
tcgttttccgggacgccggctggatgatcctccagcgcggggatctcatgctgga
gttcttcgcccaccccaacttgtttattgcagcttataatggttacaaataaagc
aatagcatcacaaatttcacaaataaagcatttttttcactgcattctagttgtg
gtttgtccaaactcatcaatgtatcttatcatgtctgtataccgtcgacctctag
ctagagcttggcgtaatcatggtcatagctgtttcctgtgtgaaattgttatccg
ctcacaattccacacaacatacgagccggaagcataaagtgtaaagcctggggtg
cctaatgagtgagctaactcacattaattgcgttgcgctcactgcccgctttcca
gtcgggaaacctgtcgtgccagctgcattaatgaatcggccaacgcgcggggaga
ggcggtttgcgtattgggcgctcttccgcttcctcgctcactgactcgctgcgct
cggtcgttcggctgcggcgagcggtatcagctcactcaaaggcggtaatacggtt
atccacagaatcaggggataacgcaggaaagaacatgtgagcaaaaggccagcaa
aaggccaggaaccgtaaaaaggccgcgttgctggcgtttttccataggctccgcc
cccctgacgagcatcacaaaaatcgacgctcaagtcagaggtggcgaaacccgac
aggactataaagataccaggcgtttccccctggaagctccctcgtgcgctctcct
gttccgaccctgccgcttaccggatacctgtccgcctttctcccttcgggaagcg
tggcgctttctcaatgctcacgctgtaggtatctcagttcggtgtaggtcgttcg
ctccaagctgggctgtgtgcacgaaccccccgttcagcccgaccgctgcgcctta
tccggtaactatcgtcttgagtccaacccggtaagacacgacttatcgccactgg
cagcagccactggtaacaggattagcagagcgaggtatgtaggcggtgctacaga
gttcttgaagtggtggcctaactacggctacactagaaggacagtatttggtatc
tgcgctctgctgaagccagttaccttcggaaaaagagttggtagctcttgatccg
gcaaacaaaccaccgctggtagcggtggtttttttgtttgcaagcagcagattac
gcgcagaaaaaaaggatctcaagaagatcctttgatcttttctacggggtctgac
gctcagtggaacgaaaactcacgttaagggattttggtcatgagattatcaaaaa
ggatcttcacctagatccttttaaattaaaaatgaagttttaaatcaatctaaag

FIG 29B CONT tatatatgagtaaacttggtctgacagttaccaatgcttaatcagtgaggcacct
atctcagcgatctgtctatttcgttcatccatagttgcctgactccccgtcgtgt
agataactacgatacgggagggcttaccatctggccccagtgctgcaatgatacc
gcgagacccacgctcaccggctccagatttatcagcaataaaccagccagccgga
agggccgagcgcagaagtggtcctgcaactttatccgcctccatccagtctatta
attgttgccgggaagctagagtaagtagttcgccagttaatagtttgcgcaacgt
tgttgccattgctacaggcatcgtggtgtcacgctcgtcgtttggtatggcttca
ttcagctccggttcccaacgatcaaggcgagttacatgatcccccatgttgtgca
aaaaagcggttagctccttcggtcctccgatcgttgtcagaagtaagttggccgc
agtgttatcactcatggttatggcagcactgcataattctcttactgtcatgcca
tccgtaagatgcttttctgtgactggtgagtactcaaccaagtcattctgagaat
agtgtatgcggcgaccgagttgctcttgcccggcgtcaatacgggataataccgc
gccacatagcagaactttaaaagtgctcatcattggaaaacgttcttcggggcga
aaactctcaaggatcttaccgctgttgagatccagttcgatgtaacccactcgtg
cacccaactgatcttcagcatcttttactttcaccagcgtttctgggtgagcaaa
aacaggaaggcaaaatgccgcaaaaaagggaataagggcgacacggaaatgttga
atactcatactcttcctttttcaatattattgaagcatttatcagggttattgtc
tcatgagcggatacatatttgaatgtatttagaaaaataaacaaataggggttcc
gcgcacatttccccgaaaagtgccacctgacgtcgacggatcgggagatctcccg
atcccctatggtgcactctcagtacaatctgctctgatgccgcatagttaagcca
gtatctgctccctgcttgtgtgttggaggtcgctgagtagtgcgcgagcaaaatt
taagctacaacaaggcaaggcttgaccgacaattgcatgaagaatctgcttaggg
ttaggcgttttgcgctgcttcgcgatgtacgggccagatatacgcgttgacattg
attattgactagttattaatagtaatcaattacggggtcattagttcatagccca
tatatggagttccgcgttacataacttacggtaaatggcccgcctggctgaccgc
ccaacgacccccgcccattgacgtcaataatgacgtatgttcccatagtaacgcc
aatagggactttccattgacgtcaatgggtggactatttacggtaaactgcccac
ttggcagtacatcaagtgtatcatatgccaagtacgccccctattgacgtcaatg
acggtaaatggcccgcctggcattatgcccagtacatgaccttatgggactttcc
tacttggcagtacatctacgtattagtcatcgctattaccatggtgatgcggttt
tggcagtacatcaatgggcgtggatagcggtttgactcacggggatttccaagtc
tccaccccattgacgtcaatgggagtttgttttggcaccaaaatcaacgggactt
tccaaaatgtcgtaacaactccgccccattgacgcaaatgggcggtaggcgtgta
cggtgggaggtctatataagcagagctctctggctaactagagaacccactgctt
actggcttatcgaaattaatacgactcactatagggagacccaagctggtttaaa
cttaagcttggtaccgagctcactagtccagtgtggtggcagatatccagcacag
tggcggccgctcgagtctagagggcccgtttgcctgtactgggtctctctggtt
agaccagatctgagcctgggagctctctggctaactagggaacccactgcttaag
cctcaataaagcttgccttgagtgcttcaagtagtgtgtgcccgtctgttgtgtg
actctggtaactagagatccctcagacccttttagtcagtgtggaaaatctctag

FIG 29B CONT cagtggcgcccgaacagggacttgaaagcgaaagggaaaccagaggagctctctc
gacgcaggactcggcttgctgaagcgcgcacggcaagaggcgaggggcggcgact
ggtgagtacgccaaaaattttgactagcggaggctagaaggagagagatgggtgc
gagagcgtcagtattaagcgggggagaattagatcgcgatgggaaaaaattcggt
taaggccagggggaaagaaaaaatataaattaaaacatatagtatgggcaagcag
ggagctagaacgattcgcagttaatcctggcctgttagaaacatcagaaggctgt
agacaaatactgggacagctacaaccatcccttcagacaggatcagaagaactta
gatcattatataatacagtagcaaccctctattgtgtgcatcaaaggatagagat
aaaagacaccaaggaagctttagacaagatagaggaagagcaaaacaaaagtaag
accaccgcacagcaagcggccgctgatcttcagacctggaggaggagatatgagg
gacaattggagaagtgaattatataaatataaagtagtaaaaattgaaccattag
gagtagcacccaccaaggcaaagagaagagtggtgcagagagaaaaaagagcagt
gggaataggagctttgttccttgggttcttgggagcagcaggaagcactatgggc
gcagcgtcaatgacgctgacggtacaggccagacaattattgtctggtatagtgc
agcagcagaacaatttgctgagggctattgaggcgcaacagcatctgttgcaact
cacagtctggggcatcaagcagctccaggcaagaatcctggctgtggaaagatac
ctaaaggatcaacagctcctggggatttggggttgctctggaaaactcatttgca
ccactgctgtgccttggaatgctagttggagtaataaatctctggaacagatttg
gaatcacacgacctggatggagtgggacagagaaattaacaattacacaagctta
atacactccttaattgaagaatcgcaaaaccagcaagaaaagaatgaacaagaat
tattggaattagataaatgggcaagtttgtggaattggtttaacataacaaattg
gctgtggtatatagaaattattcataatgatagtaggaggcttggtaggtttaag
aatagtttttgctgtactttctatagtgaatagagttaggcagggatattcacca
ttatcgtttcagacccacctcccaaccccgaggggacccgacaggcccgaaggaa
tagaagaagaaggtggagagagagacagagacagatccattcgattagtgaacgg
atcggcactgcgtgcgccaattctgcagacaaatggcagtattcatccacaattt
taaaagaaaaggggggattggggggtacagtgcaggggaaagaatagtagacata
atagcaacagacatacaaactaaagaattacaaaaacaaattacaaaaattcaaa
attttcgggtttattacagggacagcagagatccagtttggggttgctctggaaa
actcatttgcaccactgctgtgccttggaatgctagttggagtaataaatctctg
gaacagatttggaatcacacgacctggatggagtgggacagagaaattaacaatt
acacaagcttaatacactccttaattgaagaatcgcaaaaccagcaagaaaagaa
tgaacaagaattattggaattagataaatgggcaagtttgtggaattggtttaac
ataacaaattggctgtggtatataaaattattcataatgatagtaggaggcttgg
taggtttaagaatagtttttgctgtactttctatagtgaatagagttaggcaggg
atattcaccattatcgtttcagacccacctcccaaccccgaggggacccgacagg
cccttaattaattggctccggtgcccgtcagtgggcagagcgcacatcgcccaca
gtccccgagaagttggggggaggggtcggcaattgaaccggtgcctagagaaggt
ggcgcggggtaaactggaaagtgatgtcgtgtactggctccgcctttttcccga
gggtgggggagaaccgtatataagtgcagtagtcgccgtgaacgctagctccctat

FIG 29B CONT cagtgatagagatctccctatcagtgatagagagctagccgttctttttcgcaac
gggtttgccgccagaacacaggtaagtgccgtgtgtggttcccgcgggcctggcc
tctttacgggttatggcccttgcgtgccttgaattacttccacctggctgcagta
cgtgattcttgatcccgagcttcgggttggaagtgggtgggagagttcgaggcct
tgcgcttaaggagccccttcgcctcgtgcttgagttgaggcctggcctgggcgct
ggggccgccgcgtgcgaatctggtggcaccttcgcgcctgtctcgctgctttcga
taagtctctagccatttaaaatttttgatgacctgctgcgacgctttttttctgg
caagatagtcttgtaaatgcgggccaagatctgcacactggtatttcggtttttg
gggccgcgggcggcgacggggcccgtgcgtcccagcgcacatgttcggcgaggcg
gggcctgcgagcgcggccaccgagaatcggacgggggtagtctcaagctggccgg
cctgctctggtgcctggcctcgcgccgccgtgtatcgccccgccctgggcggcaa
ggctggcccggtcggcaccagttgcgtgagcggaaagatggccgcttcccggccc
tgctgcagggagctcaaaatggaggacgcggcgctcgggagagcgggcgggtgag
tcacccacacaaaggaaaagggcctttccgtcctcagccgtcgcttcatgtgact
ccacggagtaccgggcgccgtccaggcacctcgattagttctcgagcttttggag
tacgtcgtctttaggttggggggaggggttttatgcgatggagtttccccacact
gagtgggtggagactgaagttaggccagcttggcacttgatgtaattctccttgg
aatttgccctttttgagtttggatcttggttcattctcaagcctcagacagtggt
tcaaagtttttttcttccatttcaggtgaattcggccattacggcctcccaccat
gaaaccagtaacgttatacgatgtcgcagagtatgccggtgtctcttatcagacc
gtttcccgcgtggtgaaccaggccagccacgtttctgcgaaaacgcgggaaaaag
tggaagcggcgatggcggagctgaattacattcccaaccgcgtggcacaacaact
ggcgggcaaacagtcgttgctgattggcgttgccacctccagtctggccctgcac
gcgccgtcgcaaattgtcgcggcgattaaatctcgcgccgatcaactgggtgcca
gcgtggtggtgtcgatggtagaacgaagcggcgtcgaagcctgtaaagcggcggt
gcacaatcttctcgcgcaacgcgtcagtgggctgatcattaactatccgctggat
gaccaggatgccattgctgtggaagctgcctgcactaatgttccggcgttatttc
ttgatgtctctgaccagacacccatcaacagtattattttctcccatgaagacgg
tacgcgactgggcgtggagcatctggtcgcattgggtcaccagcaaatcgcgctg
ttagcgggcccattaagttctgtctcggcgcgtctgcgtctggctggctggcata
aatatctcactcgcaatcaaattcagccgatagcggaacgggaaggcgactggag
tgccatgtccggttttcaacaaaccatgcaaatgctgaatgagggcatcgttccc
actgcgatgctggttgccaacgatcagatggcgctgggcgcaatgcgcgccatta
ccgagtccgggctgcgcgttggtgcggatatctcggtagtgggatacgacgatac
cgaagacagctcatgttatatcccgccgttaaccaccatcaaacaggattttcgc
ctgctggggcaaaccagcgtggaccgcttgctgcaactctctcagggccaggcgg
tgaagggcaatcagctgttgcccgtctcactggtgaaaagaaaaaccaccctggc
gcccaatacgcaaaccgcctctccccgcgcgttggccgattcattaatgcagctg
gcacgacaggtttcccgactggaaagcgggcagccaaaaaagaagagaaaggtcg
acggcggtggtgctttgtctcctcagcactctgctgtcactcaaggaagtatcat

FIG 29B CONT caagaacaaggagggcatggatgctaagtcactaactgcctggtcccggacactg
gtgaccttcaaggatgtatttgtggacttcaccagggaggagtggaagctgctgg
acactgctcagcagatcgtgtacagaaatgtgatgctggagaactataagaacct
ggtttccttgggttatcagcttactaagccagatgtgatcctccggttggagaag
ggagaagagccctggctggtggagagagaaattcaccaagagacccatcctgatt
cagagactgcatttgaaatcaaatcatcagtttaaggccgcct

FIG 29B CONT ttattgccaccatgagcccgaaacgccgcacccaggcggaacgcgcgatggaaacccagggcaaactgattgcggcggcgctgggc
gtgctgcgcgaaaaaggctatgcgggctttcgcattgcggatgtgccgggcgcggcgggcgtgagccgcggcgcgcagagccatcat
tttccgaccaaactggaactgctgctggcgacctttgaatggctgtatgaacagattaccgaacgcagccgcgcgcgcctggcgaaactg
aaaccggaagatgatgtgattcagcagatgctggatgatgcggcggaatttttctggatgatgattttagcattagcctggatctgattgtgg
cggcggatcgcgatccggcgctgcgcgaaggcattcagcgcaccgtggaacgcaaccgctttgtggtggaagatatgtggctgggcgt
gctggtgagccgcggcctgagccgcgatgatgcggaagatattctgtggctgattttaacagcgtgcgcggcctggcggtgcgcagcc
tgtggcagaaagataaagaacgctttgaacgcgtgcgcaacagcaccctggaaattgcgcgcgaacgctatgcgaaatttaaacgcgc
gtacagccgcgcgcgtacgaaaaacaattacgggtctaccatcgagggcctgctcgatctcccggacgacgacgcccccgaagaggc
ggggctggcggctccgcgcctgtcctttctccccgcgggacacacgcgcagactgtcgacggcccccccgaccgatgtcagcctggg
ggacgagctccacttagacggcgaggacgtggcgatggcgcatgccgacgcgctagacgatttcgatctggacatgttgggggacgg
ggattccccgggtccgggatttacccccacgactccgcccccctacggcgctctggatatggccgacttcgagtttgagcagatgtttacc
gatgcccttggaattgacgagtacggtgggtaataagtgtgggagggctaagggcgcgccgttctagagaattcgatatcaagcttatcg
ataatcaacctctggattacaaaatttgtgaaagattgactggtattcttaactatgttgctccttttacgctatgtggatacgctgctttaatgcct
ttgtatcatgctattacttcccgtacggctttcattttctcctccttgtataaatcctggttgctgtctctttatgaggagttgtggcccgttgtcagg
caacgtggcgtggtgtgcactgtgtttgctgacgcaacccccactggttggggcattgccaccacctatcaactcctttccgggactttcgc
tttccccctccctattgccacggcggaactcattgccgcctgccttgcccgctgctggacaggggctcggctgttgggcactgacaattcc
gtggtgttgtcggggaagctgacgtcctttccatggctgctcgcctgtgttgccaactggattctgcgcgggacgtccttctgctacgtccct
tcggccctcaatccagcggaccttccttcccgcggcctgctgccggttctgcggcctcttccgcgtcttcgccttcgccctcagacgagtc
ggatctccctttgggccgcctccccgcctgcctgcaggtttgtcgagacctagaaaaacatggagca

FIG. 30B atcacaagtagcaatacagcagctaccaatgctgattgtgcctggctagaagcac
aagaggaggaggaggtgggttttccagtcacacctcaggtacctttaagaccaat
gacttacaaggcagctgtagatcttagccactttttaaaagaaaaggggggactg
gaagggctaattcactcccaacgaagacaagatctgctttttgcttgtactgggt
ctctctggttagaccagatctgagcctgggagctctctggctaactagggaaccc
actgcttaagcctcaataaagcttgccttgagtgcttcaagtagtgtgtgcccgt
ctgttgtgtgactctggtaactagagatccctcagacccttttagtcagtgtgga
aaatctctagcagggcccgtttaaacccgctgatcagcctcgactgtgccttcta
gttgccagccatctgttgtttgcccctcccccgtgccttccttgaccctggaagg
tgccactcccactgtcctttcctaataaaatgaggaaattgcatcgcattgtctg
agtaggtgtcattctattctggggggtggggtggggcaggacagcaagggggagg
attgggaagacaatagcaggcatgctggggatgcggtgggctctatggcttctga
ggcggaaagaaccagctggggctctagggggtatccccacgcgccctgtagcggc
gcattaagcgcggcgggtgtggtggttacgcgcagcgtgaccgctacacttgcca
gcgccctagcgcccgctcctttcgctttcttcccttcctttctcgccacgttcgc
cggctttccccgtcaagctctaaatcggggcatccctttagggttccgatttagt
gctttacggcacctcgaccccaaaaaacttgattagggtgatggttcacgtagtg
ggccatcgccctgatagacggtttttcgccctttgacgttggagtccacgttctt
taatagtggactcttgttccaaactggaacaacactcaaccctatctcggtctat
tcttttgatttataagggattttggggatttcggcctattggttaaaaaatgagc
tgatttaacaaaaatttaacgcgaattaattctgtggaatgtgtgtcagttaggg
tgtggaaagtccccaggctccccaggcaggcagaagtatgcaaagcatgcatctc
aattagtcagcaaccaggtgtggaaagtccccaggctccccagcaggcagaagta
tgcaaagcatgcatctcaattagtcagcaaccatagtcccgcccctaactccgcc
catcccgcccctaactccgcccagttccgcccattctccgccccatggctgacta
atttttttatttatgcagaggccgaggccgcctctgcctctgagctattccaga
agtagtgaggaggcttttttggaggcctaggcttttgcaaaaagctcccgggagc
ttgtatatccatttcggatctgatcagcacgtgttgacaattaatcatcggcat
agtatatcggcatagtataatacgacaaggtgaggaactaaaccatggccaagtt
gaccagtgccgttccggtgctcaccgcgcgcgacgtcgccggagcggtcgagttc
tggaccgaccggctcgggttctcccgggacttcgtggaggacgacttcgccggtg
tggtccgggacgacgtgaccctgttcatcagcgcggtccaggaccaggtggtgcc
ggacaacaccctggcctgggtgtgggtgcgcggcctggacgagctgtacgccgag
tggtcggaggtcgtgtccacgaacttccgggacgcctccgggccggccatgaccg
agatcggcgagcagccgtgggggcgggagttcgccctgcgcgacccggccggcaa
ctgcgtgcacttcgtggccgaggagcaggactgacacgtgctacgagatttcgat
tccaccgccgccttctatgaaaggttgggcttcggaatcgttttccgggacgccg
gctggatgatcctccagcgcggggatctcatgctggagttcttcgcccaccccaa
cttgtttattgcagcttataatggttacaaataaagcaatagcatcacaaatttc
acaaataaagcatttttttcactgcattctagttgtggtttgtccaaactcatca

FIG 30B CONT atgtatcttatcatgtctgtataccgtcgacctctagctagagcttggcgtaatc
atggtcatagctgtttcctgtgtgaaattgttatccgctcacaattccacacaac
atacgagccggaagcataaagtgtaaagcctggggtgcctaatgagtgagctaac
tcacattaattgcgttgcgctcactgcccgctttccagtcgggaaacctgtcgtg
ccagctgcattaatgaatcggccaacgcgcggggagaggcggtttgcgtattggg
cgctcttccgcttcctcgctcactgactcgctgcgctcggtcgttcggctgcggc
gagcggtatcagctcactcaaaggcggtaatacggttatccacagaatcagggga
taacgcaggaaagaacatgtgagcaaaaggccagcaaaaggccaggaaccgtaaa
aaggccgcgttgctggcgtttttccataggctccgcccccctgacgagcatcaca
aaaatcgacgctcaagtcagaggtggcgaaacccgacaggactataaagatacca
ggcgtttccccctggaagctccctcgtgcgctctcctgttccgaccctgccgctt
accggatacctgtccgcctttctcccttcgggaagcgtggcgctttctcaatgct
cacgctgtaggtatctcagttcggtgtaggtcgttcgctccaagctgggctgtgt
gcacgaaccccccgttcagcccgaccgctgcgccttatccggtaactatcgtctt
gagtccaacccggtaagacacgacttatcgccactggcagcagccactggtaaca
ggattagcagagcgaggtatgtaggcggtgctacagagttcttgaagtggtggcc
taactacggctacactagaaggacagtatttggtatctgcgctctgctgaagcca
gttaccttcggaaaaagagttggtagctcttgatccggcaaacaaaccaccgctg
gtagcggtggtttttttgtttgcaagcagcagattacgcgcagaaaaaaaggatc
tcaagaagatcctttgatcttttctacggggtctgacgctcagtggaacgaaaac
tcacgttaagggattttggtcatgagattatcaaaaaggatcttcacctagatcc
ttttaaattaaaaatgaagttttaaatcaatctaaagtatatatgagtaaacttg
gtctgacagttaccaatgcttaatcagtgaggcacctatctcagcgatctgtcta
tttcgttcatccatagttgcctgactccccgtcgtgtagataactacgatacggg
agggcttaccatctggccccagtgctgcaatgataccgcgagacccacgctcacc
ggctccagatttatcagcaataaaccagccagccggaagggccgagcgcagaagt
ggtcctgcaactttatccgcctccatccagtctattaattgttgccgggaagcta
gagtaagtagttcgccagttaatagtttgcgcaacgttgttgccattgctacagg
catcgtggtgtcacgctcgtcgtttggtatggcttcattcagctccggttcccaa
cgatcaaggcgagttacatgatcccccatgttgtgcaaaaaagcggttagctcct
tcggtcctccgatcgttgtcagaagtaagttggccgcagtgttatcactcatggt
tatggcagcactgcataattctcttactgtcatgccatccgtaagatgcttttct
gtgactggtgagtactcaaccaagtcattctgagaatagtgtatgcggcgaccga
gttgctcttgcccggcgtcaatacgggataataccgcgccacatagcagaacttt
aaaagtgctcatcattggaaaacgttcttcggggcgaaaactctcaaggatctta
ccgctgttgagatccagttcgatgtaacccactcgtgcacccaactgatcttcag
catcttttactttcaccagcgtttctgggtgagcaaaaacaggaaggcaaaatgc
cgcaaaaaagggaataagggcgacacggaaatgttgaatactcatactcttcctt
tttcaatattattgaagcatttatcagggttattgtctcatgagcggatacatat
ttgaatgtatttagaaaaataaacaaataggggttccgcgcacatttccccgaaa

FIG 30B CONT agtgccacctgacgtcgacggatcgggagatctcccgatcccctatggtgcactc
tcagtacaatctgctctgatgccgcatagttaagccagtatctgctccctgcttg
tgtgttggaggtcgctgagtagtgcgcgagcaaaatttaagctacaacaaggcaa
ggcttgaccgacaattgcatgaagaatctgcttagggttaggcgttttgcgctgc
ttcgcgatgtacgggccagatatacgcgttgacattgattattgactagttatta
atagtaatcaattacggggtcattagttcatagcccatatatggagttccgcgtt
acataacttacggtaaatggcccgcctggctgaccgcccaacgacccccgcccat
tgacgtcaataatgacgtatgttcccatagtaacgccaatagggactttccattg
acgtcaatgggtggactatttacggtaaactgcccacttggcagtacatcaagtg
tatcatatgccaagtacgccccctattgacgtcaatgacggtaaatggcccgcct
ggcattatgcccagtacatgaccttatgggactttcctacttggcagtacatcta
cgtattagtcatcgctattaccatggtgatgcggttttggcagtacatcaatggg
cgtggatagcggtttgactcacggggatttccaagtctccaccccattgacgtca
atgggagtttgttttggcaccaaaatcaacgggactttccaaaatgtcgtaacaa
ctccgccccattgacgcaaatgggcggtaggcgtgtacggtgggaggtctatata
agcagagctctctggctaactagagaacccactgcttactggcttatcgaaatta
atacgactcactatagggagacccaagctggtttaaacttaagcttggtaccgag
ctcactagtccagtgtggtggcagatatccagcacagtggcggccgctcgagggg
cccgttttgcctgtactgggtctctctggttagaccagatctgagcctgggagct
ctctggctaactagggaacccactgcttaagcctcaataaagcttgccttgagtg
cttcaagtagtgtgtgcccgtctgttgtgtgactctggtaactagagatccctca
gacccttttagtcagtgtggaaaatctctagcagtggcgcccgaacagggacttg
aaagcgaaagggaaaccagaggagctctctcgacgcaggactcggcttgctgaag
cgcgcacggcaagaggcgaggggcggcgactggtgagtacgccaaaaattttgac
tagcggaggctagaaggagagagatgggtgcgagagcgtcagtattaagcggggg
agaattagatcgcgatgggaaaaaattcggttaaggccagggggaaagaaaaaat
ataaattaaaacatatagtatgggcaagcagggagctagaacgattcgcagttaa
tcctggcctgttagaaacatcagaaggctgtagacaaatactgggacagctacaa
ccatcccttcagacaggatcagaagaacttagatcattatataatacagtagcaa
ccctctattgtgtgcatcaaaggatagagataaaagacaccaaggaagctttaga
caagatagaggaagagcaaaacaaaagtaagaccaccgcacagcaagcggccgct
gatcttcagacctggaggaggagatatgagggacaattggagaagtgaattatat
aaatataaagtagtaaaaattgaaccattaggagtagcacccaccaaggcaaaga
gaagagtggtgcagagagaaaaaagagcagtgggaataggagctttgttccttgg
gttcttgggagcagcaggaagcactatgggcgcagcgtcaatgacgctgacggta
caggccagacaattattgtctggtatagtgcagcagcagaacaatttgctgaggg
ctattgaggcgcaacagcatctgttgcaactcacagtctggggcatcaagcagct
ccaggcaagaatcctggctgtggaaagatacctaaaggatcaacagctcctgggg
atttggggttgctctggaaaactcatttgcaccactgctgtgccttggaatgcta
gttggagtaataaatctctggaacagatttggaatcacacgacctggatggagtg

FIG 30B CONT ggacagagaaattaacaattacacaagcttaatacactccttaattgaagaatcg
caaaaccagcaagaaaagaatgaacaagaattattggaattagataaatgggcaa
gtttgtggaattggtttaacataacaaattggctgtggtatataaaattattcat
aatgatagtaggaggcttggtaggtttaagaatagtttttgctgtactttctata
gtgaatagagttaggcagggatattcaccattatcgtttcagacccacctcccaa
ccccgaggggacccgacaggcccttaattaatcccctgattctgtggataaccgt
attaccgcctttgagtgagctgcacaactgccagatttcacaggaaaagtgaaag
gctacaataggacaactgccagatttcacaggaaaagtgaaaggctacaatagga
caactgccagatttcacaggaaaagtgaaaggctacaataggacaactgccagat
ttcacaggaaaagtgaaaggctacaataggacaactgccagatttcacaggaaaa
gtgaaaggctacaataggacaactgccagatttcacaggaaaagtgaaaggctac
aataggacaaagtgaaaggctacaataggacggtaaactcgacctatataagcag
agctcgtttagtgaaccgtcagatcgcctggagacgccatccacgctgttttgac
ctccatagaagacaccgggaccgatccagcctccgcggccccgaattgaattcga
tgctggtgttaaaaacatatgatgctggtgttaaaaacggccattacggcctgcc
acc

FIG 30B CONT ttatgtgtgggagggctaagggcgcgccgttctagagaattcgatatcaagcttatcgataatcaacctctggattacaaaatttgtgaaaga
ttgactggtattcttaactatgttgctccttttacgctatgtggatacgctgctttaatgcctttgtatcatgctattacttcccgtacggctttcatttt
ctcctccttgtataaatcctggttgctgtctctttatgaggagttgtggcccgttgtcaggcaacgtggcgtggtgtgcactgtgtttgctgacg
caacccccactggttggggcattgccaccacctatcaactcctttccgggactttcgctttccccctccctattgccacggcggaactcattg
ccgcctgccttgcccgctgctggacaggggctcggctgttgggcactgacaattccgtggtgttgtcggggaagctgacgtcctttccatg
gctgctcgcctgtgttgccaactggattctgcgcgggacgtccttctgctacgtcccttcggccctcaatccagcggaccttccttcccgcg
gcctgctgccggttctgcggcctcttccgcgtcttcgccttcgccctcagacgagtcggatctccctttgggccgcctccccgcctgcctgc
aggtttgtcgagacctagaaaaacatggagcaatcacaagtagcaatacagcagctaccaatgctgattgtgcctggctagaagcacaag
aggaggaggaggtgggttttccagtcacacctcaggtacctttaagaccaatgacttacaaggcagctgtagatcttagccactttttaaaa
gaaaaggggggactggaagggctaattcactcccaacgaagacaagatctgctttttgcttgtactgggtctctctggttagaccagatctg
agcctgggagctctctggctaactagggaacccactgcttaagcctcaataaagcttgccttgagtgcttcaagtagtgtgtgcccgtctgtt
gtgtgactctggtaactagagatccctcagacccttttagtcagtgtggaaaatctctagcagggcccgtttaaacccgctgatcagcctcg
actgtgccttctagttgccagccatctgttgtttgcccctcccccgtgccttccttgaccctggaaggtgccactcccactgtcctttcctaata
aaatgaggaaattgcatcgcattgtctgagtaggtgtcattctattctggggggtggggtggggcaggacagcaagggggaggattggg
aagacaatagcaggcatgctggggatgcggtgggctctatggcttctgaggcggaaagaaccagctggggctctagggggtatcccca
cgcgccctgtagcggcgcattaagcgcggcgggtgtggtggttacgcgcagcgtgaccgctacacttgccagcgccctagcgcccgct
cctttcgctttcttcccttcctttctcgccacgttcgccggctttccccgtcaagctctaaatcggggcatccctttagggttccgatttagtgctt
tacggcacctcgaccccaaaaaacttgattagggtgatggttcacgtagtgggccatcgccctgatagacggtttttcgccctttgacgttg
gagtccacgttctttaatagtggactcttgttccaaactggaacaacactcaaccctatctcggtctattcttttgatttataagggattttgggg
atttcggcctattggttaaaaaatgagctgatttaacaaaaatttaacgcgaattaattctgtg

FIG. 31B gaatgtgtgtcagttagggtgtggaaagtccccaggctccccaggcaggca
gaagtatgcaaagcatgcatctcaattagtcagcaaccaggtgtggaaagt
ccccaggctccccagcaggcagaagtatgcaaagcatgcatctcaattagt
cagcaaccatagtcccgcccctaactccgcccatcccgcccctaactccgc
ccagttccgcccattctccgccccatggctgactaattttttttatttatg
cagaggccgaggccgcctctgcctctgagctattccagaagtagtgaggag
gcttttttggaggcctaggcttttgcaaaaagctcccgggagcttgtatat
ccattttcggatctgatcagcacgtgttgacaattaatcatcggcatagta
tatcggcatagtataatacgacaaggtgaggaactaaaccatggccaagtt
gaccagtgccgttccggtgctcaccgcgcgcgacgtcgccggagcggtcga
gttctggaccgaccggctcgggttctcccgggacttcgtggaggacgactt
cgccggtgtggtccgggacgacgtgaccctgttcatcagcgcggtccagga
ccaggtggtgccggacaacaccctggcctgggtgtgggtgcgcggcctgga
cgagctgtacgccgagtggtcggaggtcgtgtccacgaacttccgggacgc
ctccgggccggccatgaccgagatcggcgagcagccgtgggggcgggagtt
cgccctgcgcgacccggccggcaactgcgtgcacttcgtggccgaggagca
ggactgacacgtgctacgagatttcgattccaccgccgccttctatgaaag
gttgggcttcggaatcgttttccgggacgccggctggatgatcctccagcg
cggggatctcatgctggagttcttcgcccaccccaacttgtttattgcagc
ttataatggttacaaataaagcaatagcatcacaaatttcacaaataaagc
atttttttcactgcattctagttgtggtttgtccaaactcatcaatgtatc
ttatcatgtctgtataccgtcgacctctagctagagcttggcgtaatcatg
gtcatagctgtttcctgtgtgaaattgttatccgctcacaattccacacaa
catacgagccggaagcataaagtgtaaagcctggggtgcctaatgagtgag
ctaactcacattaattgcgttgcgctcactgcccgctttccagtcgggaaa
cctgtcgtgccagctgcattaatgaatcggccaacgcgcggggagaggcgg
tttgcgtattgggcgctcttccgcttcctcgctcactgactcgctgcgctc
ggtcgttcggctgcggcgagcggtatcagctcactcaaaggcggtaatacg
gttatccacagaatcaggggataacgcaggaaagaacatgtgagcaaaagg
ccagcaaaaggccaggaaccgtaaaaaggccgcgttgctggcgtttttcca
taggctccgcccccctgacgagcatcacaaaaatcgacgctcaagtcagag
gtggcgaaacccgacaggactataaagataccaggcgtttccccctggaag
ctccctcgtgcgctctcctgttccgaccctgccgcttaccggatacctgtc
cgcctttctcccttcgggaagcgtggcgctttctcaatgctcacgctgtag
gtatctcagttcggtgtaggtcgttcgctccaagctgggctgtgtgcacga
accccccgttcagcccgaccgctgcgccttatccggtaactatcgtcttga
gtccaacccggtaagacacgacttatcgccactggcagcagccactggtaa
caggattagcagagcgaggtatgtaggcggtgctacagagttcttgaagtg
gtggcctaactacggctacactagaaggacagtatttggtatctgcgctct
gctgaagccagttaccttcggaaaaagagttggtagctcttgatccggcaa

FIG 31B CONT acaaaccaccgctggtagcggtggtttttttgtttgcaagcagcagattac
gcgcagaaaaaaaggatctcaagaagatcctttgatcttttctacggggtc
tgacgctcagtggaacgaaaactcacgttaagggattttggtcatgagatt
atcaaaaaggatcttcacctagatccttttaaattaaaaatgaagttttaa
atcaatctaaagtatatatgagtaaacttggtctgacagttaccaatgctt
aatcagtgaggcacctatctcagcgatctgtctatttcgttcatccatagt
tgcctgactccccgtcgtgtagataactacgatacgggagggcttaccatc
tggccccagtgctgcaatgataccgcgagacccacgctcaccggctccaga
tttatcagcaataaaccagccagccggaagggccgagcgcagaagtggtcc
tgcaactttatccgcctccatccagtctattaattgttgccgggaagctag
agtaagtagttcgccagttaatagtttgcgcaacgttgttgccattgctac
aggcatcgtggtgtcacgctcgtcgtttggtatggcttcattcagctccgg
ttcccaacgatcaaggcgagttacatgatcccccatgttgtgcaaaaaagc
ggttagctccttcggtcctccgatcgttgtcagaagtaagttggccgcagt
gttatcactcatggttatggcagcactgcataattctcttactgtcatgcc
atccgtaagatgcttttctgtgactggtgagtactcaaccaagtcattctg
agaatagtgtatgcggcgaccgagttgctcttgcccggcgtcaatacggga
taataccgcgccacatagcagaactttaaaagtgctcatcattggaaaacg
ttcttcggggcgaaaactctcaaggatcttaccgctgttgagatccagttc
gatgtaacccactcgtgcacccaactgatcttcagcatcttttactttcac
cagcgtttctgggtgagcaaaaacaggaaggcaaaatgccgcaaaaaaggg
aataagggcgacacggaaatgttgaatactcatactcttcctttttcaata
ttattgaagcatttatcagggttattgtctcatgagcggatacatatttga
atgtatttagaaaaataaacaaataggggttccgcgcacatttccccgaaa
agtgccacctgacgtcgacggatcgggagatctcccgatcccctatggtgc
actctcagtacaatctgctctgatgccgcatagttaagccagtatctgctc
cctgcttgtgtgttggaggtcgctgagtagtgcgcgagcaaaatttaagct
acaacaaggcaaggcttgaccgacaattgcatgaagaatctgcttagggtt
aggcgttttgcgctgcttcgcgatgtacgggccagatatacgcgttgacat
tgattattgactagttattaatagtaatcaattacggggtcattagttcat
agcccatatatggagttccgcgttacataacttacggtaaatggcccgcct
ggctgaccgcccaacgacccccgcccattgacgtcaataatgacgtatgtt
cccatagtaacgccaatagggactttccattgacgtcaatgggtggactat
ttacggtaaactgcccacttggcagtacatcaagtgtatcatatgccaagt
acgccccctattgacgtcaatgacggtaaatggcccgcctggcattatgcc
cagtacatgaccttatgggactttcctacttggcagtacatctacgtatta
gtcatcgctattaccatggtgatgcggttttggcagtacatcaatgggcgt
ggatagcggtttgactcacggggatttccaagtctccaccccattgacgtc
aatgggagtttgttttggcaccaaaatcaacgggactttccaaaatgtcgt
aacaactccgccccattgacgcaaatgggcggtaggcgtgtacggtgggag

FIG 31B CONT gtctatataagcagagctctctggctaactagagaacccactgcttactgg
cttatcgaaattaatacgactcactatagggagacccaagctggtttaaac
ttaagcttggtaccgagctcactagtccagtgtggtggcagatatccagca
cagtggcggccgctcgagggcccgtttgcctgtactgggtctctctggt
tagaccagatctgagcctgggagctctctggctaactagggaacccactgc
ttaagcctcaataaagcttgccttgagtgcttcaagtagtgtgtgcccgtc
tgttgtgtgactctggtaactagagatccctcagacccttttagtcagtgt
ggaaaatctctagcagtggcgcccgaacagggacttgaaagcgaaagggaa
accagaggagctctctcgacgcaggactcggcttgctgaagcgcgcacggc
aagaggcgaggggcggcgactggtgagtacgccaaaaattttgactagcgg
aggctagaaggagagagatgggtgcgagagcgtcagtattaagcgggggag
aattagatcgcgatgggaaaaaattcggttaaggccagggggaaagaaaaa
atataaattaaaacatatagtatgggcaagcagggagctagaacgattcgc
agttaatcctggcctgttagaaacatcagaaggctgtagacaaatactggg
acagctacaaccatcccttcagacaggatcagaagaacttagatcattata
taatacagtagcaaccctctattgtgtgcatcaaaggatagagataaaaga
caccaaggaagctttagacaagatagaggaagagcaaaacaaaagtaagac
caccgcacagcaagcggccgctgatcttcagacctggaggaggagatatga
gggacaattggagaagtgaattatataaatataaagtagtaaaaattgaac
cattaggagtagcacccaccaaggcaaagagaagagtggtgcagagagaaa
aaagagcagtgggaataggagctttgttccttgggttcttgggagcagcag
gaagcactatgggcgcagcgtcaatgacgctgacggtacaggccagacaat
tattgtctggtatagtgcagcagcagaacaatttgctgagggctattgagg
cgcaacagcatctgttgcaactcacagtctggggcatcaagcagctccagg
caagaatcctggctgtggaaagatacctaaaggatcaacagctcctgggga
tttggggttgctctggaaaactcatttgcaccactgctgtgccttggaatg
ctagttggagtaataaatctctggaacagatttggaatcacacgacctgga
tggagtgggacagagaaattaacaattacacaagcttaatacactccttaa
ttgaagaatcgcaaaaccagcaagaaaagaatgaacaagaattattggaat
tagataaatgggcaagtttgtggaattggtttaacataacaaattggctgt
ggtatataaaattattcataatgatagtaggaggcttggtaggtttaagaa
tagtttttgctgtactttctatagtgaatagagttaggcagggatattcac
cattatcgtttcagacccacctcccaaccccgaggggacccgacaggccct
taattaatcccctgattctgtggataaccgtattaccgcctttgagtgagc
tgcacaactgccagatttcacaggaaaagtgaaaggctacaataggacaac
tgccagatttcacaggaaaagtgaaaggctacaataggacaactgccagat
ttcacaggaaaagtgaaaggctacaataggacaactgccagatttcacagg
aaaagtgaaaggctacaataggacaactgccagatttcacaggaaaagtga
aaggctacaataggacaactgccagatttcacaggaaaagtgaaaggctac
aataggacaaagtgaaaggctacaataggacggtaaactcgacctatataa

FIG 31B CONT gcagagctcgtttagtgaaccgtcagatcgcctggagacgccatccacgct
gttttgacctccatagaagacaccgggaccgatccagcctccgcggccccg
aattgaattcgatgctggtgttaaaaacatatgatgctggtgttaaaaacg
gccattacggcctgccacc

FIG 31B CONT ttatgtgtgggagggctaagggcgcgccgttctagagaattcgatatcaagcttatcgataatcaacctctggattacaaaatttgtgaaaga
ttgactggtattcttaactatgttgctccttttacgctatgtggatacgctgctttaatgcctttgtatcatgctattacttcccgtacggctttcatttt
ctcctccttgtataaatcctggttgctgtctctttatgaggagttgtggcccgttgtcaggcaacgtggcgtggtgtgcactgtgtttgctgacg
caacccccactggttggggcattgccaccacctatcaactcctttccgggactttcgctttccccctccctattgccacggcggaactcattg
ccgcctgccttgcccgctgctggacaggggctcggctgttgggcactgacaattccgtggtgttgtcggggaagctgacgtcctttccatg
gctgctcgcctgtgttgccaactggattctgcgcgggacgtccttctgctacgtcccttcggccctcaatccagcggaccttccttcccgcg
gcctgctgccggttctgcggcctcttccgcgtcttcgccttcgccctcagacgagtcggatctccctttgggccgcctccccgcctgcctgc
aggtttgtcgagacctagaaaaacatggagcaatcacaagtagcaatacagcagctaccaatgctgattgtgcctggctagaagcacaag
aggaggaggaggtgggttttccagtcacacctcaggtacctttaagaccaatgacttacaaggcagctgtagatcttagccactttttaaaa
gaaaagggggactggaagggctaattcactcccaacgaagacaagatctgctttttgcttgtactgggtctctctggttagaccagatctg
agcctgggagctctctggctaactagggaacccactgcttaagcctcaataaagcttgccttgagtgcttcaagtagtgtgtgcccgtctgtt
gtgtgactctggtaactagagatccctcagacccttttagtcagtgtggaaaatctctagcagggcccgtttaaacccgctgatcagcctcg
actgtgccttctagttgccagccatctgttgtttgcccctcccccgtgccttccttgaccctggaaggtgccactcccactgtcctttcctaata
aaatgaggaaattgcatcgcattgtctgagtaggtgtcattctattctggggggtggggtggggcaggacagcaagggggaggattggg
aagacaatagcaggcatgctggggatgcggtgggctctatggcttctgaggcggaaagaaccagctggggctctagggggtatcccca
cgcgccctgtagcggcgcattaagcgcggcgggtgtggtggttacgcgcagcgtgaccgctacacttgccagcgccctagcgcccgct
cctttcgctttcttcccttcctttctcgccacgttcgccggctttccccgtcaagctctaaatcggggcatccctttaggg

FIG. 32B ttccgatttagtgctttacggcacctcgaccccaaaaaacttgattagggtgatg
gttcacgtagtgggccatcgccctgatagacggtttttcgccctttgacgttgga
gtccacgttctttaatagtggactcttgttccaaactggaacaacactcaaccct
atctcggtctattcttttgatttataagggattttggggatttcggcctattggt
taaaaaatgagctgatttaacaaaaatttaacgcgaattaattctgtggaatgtg
tgtcagttagggtgtggaaagtccccaggctccccaggcaggcagaagtatgcaa
agcatgcatctcaattagtcagcaaccaggtgtggaaagtccccaggctccccag
caggcagaagtatgcaaagcatgcatctcaattagtcagcaaccatagtcccgcc
cctaactccgcccatcccgcccctaactccgcccagttccgcccattctccgccc
catggctgactaattttttttatttatgcagaggccgaggccgcctctgcctctg
agctattccagaagtagtgaggaggcttttttggaggcctaggcttttgcaaaaa
gctcccgggagcttgtatatccatttcggatctgatcagcacgtgttgacaatt
aatcatcggcatagtatatcggcatagtataatacgacaaggtgaggaactaaac
catggccaagttgaccagtgccgttccggtgctcaccgcgcgcgacgtcgccgga
gcggtcgagttctggaccgaccggctcgggttctcccgggacttcgtggaggacg
acttcgccggtgtggtccgggacgacgtgaccctgttcatcagcgcggtccagga
ccaggtggtgccggacaacaccctggcctgggtgtgggtgcgcggcctggacgag
ctgtacgccgagtggtcggaggtcgtgtccacgaacttccgggacgcctccgggc
cggccatgaccgagatcggcgagcagccgtgggggcgggagttcgccctgcgcga
cccggccggcaactgcgtgcacttcgtggccgaggagcaggactgacacgtgcta
cgagatttcgattccaccgccgccttctatgaaaggttgggcttcggaatcgttt
tccgggacgccggctggatgatcctccagcgcggggatctcatgctggagttctt
cgcccaccccaacttgtttattgcagcttataatggttacaaataaagcaatagc
atcacaaatttcacaaataaagcatttttttcactgcattctagttgtggtttgt
ccaaactcatcaatgtatcttatcatgtctgtataccgtcgacctctagctagag
cttggcgtaatcatggtcatagctgtttcctgtgtgaaattgttatccgctcaca
attccacacaacatacgagccggaagcataaagtgtaaagcctggggtgcctaat
gagtgagctaactcacattaattgcgttgcgctcactgcccgctttccagtcggg
aaacctgtcgtgccagctgcattaatgaatcggccaacgcgcggggagaggcggt
ttgcgtattgggcgctcttccgcttcctcgctcactgactcgctgcgctcggtcg
ttcggctgcggcgagcggtatcagctcactcaaaggcggtaatacggttatccac
agaatcaggggataacgcaggaaagaacatgtgagcaaaaggccagcaaaaggcc
aggaaccgtaaaaaggccgcgttgctggcgtttttccataggctccgcccccctg
acgagcatcacaaaaatcgacgctcaagtcagaggtggcgaaacccgacaggact
ataaagataccaggcgtttccccctggaagctccctcgtgcgctctcctgttccg
accctgccgcttaccggatacctgtccgcctttctcccttcgggaagcgtggcgc
tttctcaatgctcacgctgtaggtatctcagttcggtgtaggtcgttcgctccaa
gctgggctgtgtgcacgaaccccccgttcagcccgaccgctgcgccttatccggt
aactatcgtcttgagtccaacccggtaagacacgacttatcgccactggcagcag
ccactggtaacaggattagcagagcgaggtatgtaggcggtgctacagagttctt

FIG 32B CONT gaagtggtggcctaactacggctacactagaaggacagtatttggtatctgcgct
ctgctgaagccagttaccttcggaaaaagagttggtagctcttgatccggcaaac
aaaccaccgctggtagcggtggtttttttgtttgcaagcagcagattacgcgcag
aaaaaaaggatctcaagaagatcctttgatcttttctacggggtctgacgctcag
tggaacgaaaactcacgttaagggattttggtcatgagattatcaaaaaggatct
tcacctagatccttttaaattaaaaatgaagttttaaatcaatctaaagtatata
tgagtaaacttggtctgacagttaccaatgcttaatcagtgaggcacctatctca
gcgatctgtctatttcgttcatccatagttgcctgactccccgtcgtgtagataa
ctacgatacgggagggcttaccatctggccccagtgctgcaatgataccgcgaga
cccacgctcaccggctccagatttatcagcaataaaccagccagccggaagggcc
gagcgcagaagtggtcctgcaactttatccgcctccatccagtctattaattgtt
gccgggaagctagagtaagtagttcgccagttaatagtttgcgcaacgttgttgc
cattgctacaggcatcgtggtgtcacgctcgtcgtttggtatggcttcattcagc
tccggttcccaacgatcaaggcgagttacatgatcccccatgttgtgcaaaaaag
cggttagctccttcggtcctccgatcgttgtcagaagtaagttggccgcagtgtt
atcactcatggttatggcagcactgcataattctcttactgtcatgccatccgta
agatgcttttctgtgactggtgagtactcaaccaagtcattctgagaatagtgta
tgcggcgaccgagttgctcttgcccggcgtcaatacgggataataccgcgccaca
tagcagaactttaaaagtgctcatcattggaaaacgttcttcggggcgaaaactc
tcaaggatcttaccgctgttgagatccagttcgatgtaacccactcgtgcaccca
actgatcttcagcatcttttactttcaccagcgtttctgggtgagcaaaaacagg
aaggcaaaatgccgcaaaaaagggaataagggcgacacggaaatgttgaatactc
atactcttcctttttcaatattattgaagcatttatcagggttattgtctcatga
gcggatacatatttgaatgtatttagaaaaataaacaaataggggttccgcgcac
atttccccgaaaagtgccacctgacgtcgacggatcgggagatctcccgatcccc
tatggtgcactctcagtacaatctgctctgatgccgcatagttaagccagtatct
gctccctgcttgtgtgttggaggtcgctgagtagtgcgcgagcaaaatttaagct
acaacaaggcaaggcttgaccgacaattgcatgaagaatctgcttagggttaggc
gttttgcgctgcttcgcgatgtacgggccagatatacgcgttgacattgattatt
gactagttattaatagtaatcaattacggggtcattagttcatagcccatatatg
gagttccgcgttacataacttacggtaaatggcccgcctggctgaccgcccaacg
acccccgcccattgacgtcaataatgacgtatgttcccatagtaacgccaatagg
gactttccattgacgtcaatgggtggactatttacggtaaactgcccacttggca
gtacatcaagtgtatcatatgccaagtacgccccctattgacgtcaatgacggta
aatggcccgcctggcattatgcccagtacatgaccttatgggactttcctacttg
gcagtacatctacgtattagtcatcgctattaccatggtgatgcggttttggcag
tacatcaatgggcgtggatagcggtttgactcacggggatttccaagtctccacc
ccattgacgtcaatgggagtttgttttggcaccaaaatcaacgggactttccaaa
atgtcgtaacaactccgccccattgacgcaaatgggcggtaggcgtgtacggtgg
gaggtctatataagcagagctctctggctaactagagaacccactgcttactggc

FIG 32B CONT ttatcgaaattaatacgactcactatagggagacccaagctggtttaaacttaag
cttggtaccgagctcactagtccagtgtggtggcagatatccagcacagtggcgg
ccgctcgagggggcccgtttgcctgtactgggtctctctggttagaccagatctg
agcctgggagctctctggctaactagggaacccactgcttaagcctcaataaagc
ttgccttgagtgcttcaagtagtgtgtgcccgtctgttgtgtgactctggtaact
agagatccctcagacccttttagtcagtgtggaaaatctctagcagtggcgcccg
aacagggacttgaaagcgaaagggaaaccagaggagctctctcgacgcaggactc
ggcttgctgaagcgcgcacggcaagaggcgaggggcggcgactggtgagtacgcc
aaaaattttgactagcggaggctagaaggagagagatgggtgcgagagcgtcagt
attaagcgggggagaattagatcgcgatgggaaaaaattcggttaaggccagggg
gaaagaaaaaatataaattaaaacatatagtatgggcaagcagggagctagaacg
attcgcagttaatcctggcctgttagaaacatcagaaggctgtagacaaatactg
ggacagctacaaccatcccttcagacaggatcagaagaacttagatcattatata
atacagtagcaaccctctattgtgtgcatcaaaggatagagataaaagacaccaa
ggaagctttagacaagatagaggaagagcaaaacaaaagtaagaccaccgcacag
caagcggccgctgatcttcagacctggaggaggagatatgagggacaattggaga
agtgaattatataaatataaagtagtaaaaattgaaccattaggagtagcaccca
ccaaggcaaagagaagagtggtgcagagagaaaaaagagcagtgggaataggagc
tttgttccttgggttcttgggagcagcaggaagcactatgggcgcagcgtcaatg
acgctgacggtacaggccagacaattattgtctggtatagtgcagcagcagaaca
atttgctgagggctattgaggcgcaacagcatctgttgcaactcacagtctgggg
catcaagcagctccaggcaagaatcctggctgtggaaagatacctaaaggatcaa
cagctcctggggatttggggttgctctggaaaactcatttgcaccactgctgtgc
cttggaatgctagttggagtaataaatctctggaacagatttggaatcacacgac
ctggatggagtgggacagagaaattaacaattacacaagcttaatacactcctta
attgaagaatcgcaaaaccagcaagaaaagaatgaacaagaattattggaattag
ataaatgggcaagtttgtggaattggtttaacataacaaattggctgtggtatat
aaaattattcataatgatagtaggaggcttggtaggtttaagaatagtttttgct
gtactttctatagtgaatagagttaggcagggatattcaccattatcgtttcaga
cccacctcccaaccccgaggggacccgacaggcccttaattaatcccctgattct
gtggataaccgtattaccgcctttgagtgagctgcacgggagcaattaatctata
gattaaaaagtgaaaggctacaataggacgggagcaattaatctatagattaaaa
agtgaaaggctacaataggacgggagcaattaatctatagattaaaaagtgaaag
gctacaataggacgggagcaattaatctatagattaaaaagtgaaaggctacaat
aggacgggagcaattaatctatagattaaaaagtgaaaggctacaataggacggg
agcaattaatctatagattaaaaagtgaaaggctacaataggacgggagcaatta
atctatagattaaaaagtgaaaggctacaataggacggtaaactcgacctatata
agcagagctcgtttagtgaaccgtcagatcgcctggagacgccatccacgctgtt
ttgacctccatagaagacaccgggaccgatccagcctccgcggccccgaattgaa
ttcggccattacggcctgccaccatgagcacaaaaaagaaaccattaacacaaga

FIG 32B CONT gcagcttgaggacgcacgtcgccttaaagcaatttatgaaaaaaagaaaaatgaa
cttggcttatcccaggaatctgtcgcagacaagatggggatggggcagtcaggcg
ttggtgctttatttaatggcatcaatgcattaaatgcttataacgccgcattgct
tgcaaaaattctcaaagttagcgttgaagaattcagcccttcaatcgccagagag
atctacgagatgtatgaagcggttagtatgcagccgtcacttagaagtgagtatg
agtaccctgtttttctcatgttcaggcagggatgttctcacctgagcttagaac
ctttaccaaaggtgatgcggagagatgggtaagcacaaccaaaaaagccagtgat
tctgcattctggcttgaggttgaaggtaattccatgaccgcaccaacaggctcca
agccaagctttcctgacggaatgttaattctcgttgaccctgagcaggctgttga
gcccggggatttctgcatagccagacttgggggtgatgagtttaccttcaagaaa
ctgatcagggatagcggtcaggtgtttttacaaccactaaacccacagtacccaa
tgatcccatgcaatgagagttgttccgttgtggggaaagttatcgctagtcagtg
gcctgaagagacgtttggcccaaaaaagaagagaaaggtcgacggcggtggtgct
ttgtctcctcagcactctgctgtcactcaaggaagtatcatcaagaacaaggagg
gcatggatgctaagtcactaactgcctggtcccggacactggtgaccttcaagga
tgtatttgtggacttcaccagggaggagtggaagctgctggacactgctcagcag
atcgtgtacagaaatgtgatgctggagaactataagaacctggtttccttgggtt
atcagcttactaagccagatgtgatcctccggttggagaagggagaagagccctg
gctggtggagagagaaattcaccaagagacccatcctgattcagagactgcattt
gaaatcaaatcatcagtttaatgccacc

FIG 32B CONT ttatgtgtgggagggctaagggcgcgccgttctagagaattcgatatcaagcttatcgataatcaacctctggattacaaaatttgtgaaaga
ttgactggtattcttaactatgttgctccttttacgctatgtggatacgctgctttaatgcctttgtatcatgctattacttcccgtacggctttcatttt
ctcctccttgtataaatcctggttgctgtctctttatgaggagttgtggcccgttgtcaggcaacgtggcgtggtgtgcactgtgtttgctgacg
caacccccactggttggggcattgccaccacctatcaactcctttccgggactttcgctttccccctccctattgccacggcggaactcattg
ccgcctgccttgcccgctgctggacaggggctcggctgttgggcactgacaattccgtggtgttgtcggggaagctgacgtcctttccatg
gctgctcgcctgtgttgccaactggattctgcgcgggacgtccttctgctacgtcccttcggccctcaatccagcggaccttccttcccgcg
gcctgctgccggttctgcggcctcttccgcgtcttcgccttcgccctcagacgagtcggatctccctttgggccgcctccccgcctgcctgc
aggtttgtcgagacctagaaaaacatggagcaatcacaagtagcaatacagcagctaccaatgctgattgtgcctggctagaagcacaag
aggaggaggaggtgggttttccagtcacacctcaggtacctttaagaccaatgacttacaaggcagctgtagatcttagccactttttaaaa
gaaaaggggggactggaagggctaattcactcccaacgaagacaagatctgctttttgcttgtactgggtctctctggttagaccagatctg
agcctgggagctctctggctaactagggaacccactgcttaagcctcaataaagcttgccttgagtgcttcaagtagtgtgtgcccgtctgtt
gtgtgactctggtaactagagatccctcagacccttttagtcagtgtggaaaatctctagcagggcccgtttaaacccgctgatcagcctcg
actgtgccttctagttgccagccatctgttgtttgcccctcccccgtgccttccttgaccctggaaggtgccactcccactgtcctttcctaata
aaatgagg

FIG. 33B aaattgcatcgcattgtctgagtaggtgtcattctattctggggggtggggtggg
gcaggacagcaagggggaggattgggaagacaatagcaggcatgctggggatgcg
gtgggctctatggcttctgaggcggaaagaaccagctggggctctagggggtatc
cccacgcgccctgtagcggcgcattaagcgcggcgggtgtggtggttacgcgcag
cgtgaccgctacacttgccagcgccctagcgcccgctcctttcgctttcttccct
tcctttctcgccacgttcgccggctttccccgtcaagctctaaatcggggcatcc
ctttagggttccgatttagtgctttacggcacctcgaccccaaaaaacttgatta
gggtgatggttcacgtagtgggccatcgccctgatagacggtttttcgccctttg
acgttggagtccacgttctttaatagtggactcttgttccaaactggaacaacac
tcaaccctatctcggtctattcttttgatttataagggattttggggatttcggc
ctattggttaaaaaatgagctgatttaacaaaaatttaacgcgaattaattctgt
ggaatgtgtgtcagttagggtgtggaaagtccccaggctccccaggcaggcagaa
gtatgcaaagcatgcatctcaattagtcagcaaccaggtgtggaaagtccccagg
ctccccagcaggcagaagtatgcaaagcatgcatctcaattagtcagcaaccata
gtcccgcccctaactccgcccatcccgcccctaactccgcccagttccgcccatt
ctccgccccatggctgactaattttttttatttatgcagaggccgaggccgcctc
tgcctctgagctattccagaagtagtgaggaggcttttttggaggcctaggcttt
tgcaaaaagctcccgggagcttgtatatccatttcggatctgatcagcacgtgt
tgacaattaatcatcggcatagtatatcggcatagtataatacgacaaggtgagg
aactaaaccatggccaagttgaccagtgccgttccggtgctcaccgcgcgcgacg
tcgccggagcggtcgagttctggaccgaccggctcgggttctcccgggacttcgt
ggaggacgacttcgccggtgtggtccgggacgacgtgaccctgttcatcagcgcg
gtccaggaccaggtggtgccggacaacaccctggcctgggtgtgggtgcgcggcc
tggacgagctgtacgccgagtggtcggaggtcgtgtccacgaacttccgggacgc
ctccgggccggccatgaccgagatcggcgagcagccgtgggggcgggagttcgcc
ctgcgcgacccggccggcaactgcgtgcacttcgtggccgaggagcaggactgac
acgtgctacgagatttcgattccaccgccgccttctatgaaaggttgggcttcgg
aatcgttttccgggacgccggctggatgatcctccagcgcggggatctcatgctg
gagttcttcgcccaccccaacttgtttattgcagcttataatggttacaaataaa
gcaatagcatcacaaatttcacaaataaagcatttttttcactgcattctagttg
tggtttgtccaaactcatcaatgtatcttatcatgtctgtataccgtcgacctct
agctagagcttggcgtaatcatggtcatagctgtttcctgtgtgaaattgttatc
cgctcacaattccacacaacatacgagccggaagcataaagtgtaaagcctgggg
tgcctaatgagtgagctaactcacattaattgcgttgcgctcactgcccgctttc
cagtcgggaaacctgtcgtgccagctgcattaatgaatcggccaacgcgcgggga
gaggcggtttgcgtattgggcgctcttccgcttcctcgctcactgactcgctgcg
ctcggtcgttcggctgcggcgagcggtatcagctcactcaaaggcggtaatacgg
ttatccacagaatcaggggataacgcaggaaagaacatgtgagcaaaaggccagc
aaaaggccaggaaccgtaaaaaggccgcgttgctggcgtttttccataggctccg
cccccctgacgagcatcacaaaaatcgacgctcaagtcagaggtggcgaaacccg

FIG 33B CONT acaggactataaagataccaggcgtttccccctggaagctccctcgtgcgctctc
ctgttccgaccctgccgcttaccggatacctgtccgcctttctcccttcgggaag
cgtggcgctttctcaatgctcacgctgtaggtatctcagttcggtgtaggtcgtt
cgctccaagctgggctgtgtgcacgaaccccccgttcagcccgaccgctgcgcct
tatccggtaactatcgtcttgagtccaacccggtaagacacgacttatcgccact
ggcagcagccactggtaacaggattagcagagcgaggtatgtaggcggtgctaca
gagttcttgaagtggtggcctaactacggctacactagaaggacagtatttggta
tctgcgctctgctgaagccagttaccttcggaaaaagagttggtagctcttgatc
cggcaaacaaaccaccgctggtagcggtggtttttttgtttgcaagcagcagatt
acgcgcagaaaaaaaggatctcaagaagatcctttgatcttttctacggggtctg
acgctcagtggaacgaaaactcacgttaagggattttggtcatgagattatcaaa
aaggatcttcacctagatccttttaaattaaaaatgaagttttaaatcaatctaa
agtatatatgagtaaacttggtctgacagttaccaatgcttaatcagtgaggcac
ctatctcagcgatctgtctatttcgttcatccatagttgcctgactccccgtcgt
gtagataactacgatacgggagggcttaccatctggccccagtgctgcaatgata
ccgcgagacccacgctcaccggctccagatttatcagcaataaaccagccagccg
gaagggccgagcgcagaagtggtcctgcaactttatccgcctccatccagtctat
taattgttgccgggaagctagagtaagtagttcgccagttaatagtttgcgcaac
gttgttgccattgctacaggcatcgtggtgtcacgctcgtcgtttggtatggctt
cattcagctccggttcccaacgatcaaggcgagttacatgatcccccatgttgtg
caaaaaagcggttagctccttcggtcctccgatcgttgtcagaagtaagttggcc
gcagtgttatcactcatggttatggcagcactgcataattctcttactgtcatgc
catccgtaagatgcttttctgtgactggtgagtactcaaccaagtcattctgaga
atagtgtatgcggcgaccgagttgctcttgcccggcgtcaatacgggataatacc
gcgccacatagcagaactttaaaagtgctcatcattggaaaacgttcttcggggc
gaaaactctcaaggatcttaccgctgttgagatccagttcgatgtaacccactcg
tgcacccaactgatcttcagcatcttttactttcaccagcgtttctgggtgagca
aaaacaggaaggcaaaatgccgcaaaaaagggaataagggcgacacggaaatgtt
gaatactcatactcttcctttttcaatattattgaagcatttatcagggttattg
tctcatgagcggatacatatttgaatgtatttagaaaaataaacaaataggggtt
ccgcgcacatttccccgaaaagtgccacctgacgtcgacggatcgggagatctcc
cgatcccctatggtgcactctcagtacaatctgctctgatgccgcatagttaagc
cagtatctgctccctgcttgtgtgttggaggtcgctgagtagtgcgcgagcaaaa
tttaagctacaacaaggcaaggcttgaccgacaattgcatgaagaatctgcttag
ggttaggcgttttgcgctgcttcgcgatgtacgggccagatatacgcgttgacat
tgattattgactagttattaatagtaatcaattacggggtcattagttcatagcc
catatatggagttccgcgttacataacttacggtaaatggcccgcctggctgacc
gcccaacgacccccgcccattgacgtcaataatgacgtatgttcccatagtaacg
ccaatagggactttccattgacgtcaatgggtggactatttacggtaaactgccc
acttggcagtacatcaagtgtatcatatgccaagtacgccccctattgacgtcaa

FIG 33B CONT tgacggtaaatggcccgcctggcattatgcccagtacatgaccttatgggacttt
cctacttggcagtacatctacgtattagtcatcgctattaccatggtgatgcggt
tttggcagtacatcaatgggcgtggatagcggtttgactcacggggatttccaag
tctccaccccattgacgtcaatgggagtttgttttggcaccaaaatcaacgggac
tttccaaaatgtcgtaacaactccgccccattgacgcaaatgggcggtaggcgtg
tacggtgggaggtctatataagcagagctctctggctaactagagaacccactgc
ttactggcttatcgaaattaatacgactcactatagggagacccaagctggttta
aacttaagcttggtaccgagctcactagtccagtgtggtggcagatatccagcac
agtggcggccgctcgagggggcccgtttgcctgtactgggtctctctggttagac
cagatctgagcctgggagctctctggctaactagggaacccactgcttaagcctc
aataaagcttgccttgagtgcttcaagtagtgtgtgcccgtctgttgtgtgactc
tggtaactagagatccctcagacccttttagtcagtgtggaaaatctctagcagt
ggcgcccgaacagggacttgaaagcgaaagggaaaccagaggagctctctcgacg
caggactcggcttgctgaagcgcgcacggcaagaggcgaggggcggcgactggtg
agtacgccaaaaattttgactagcggaggctagaaggagagagatgggtgcgaga
gcgtcagtattaagcgggggagaattagatcgcgatgggaaaaaattcggttaag
gccagggggaaagaaaaaatataaattaaaacatatagtatgggcaagcagggag
ctagaacgattcgcagttaatcctggcctgttagaaacatcagaaggctgtagac
aaatactgggacagctacaaccatcccttcagacaggatcagaagaacttagatc
attatataatacagtagcaaccctctattgtgtgcatcaaaggatagagataaaa
gacaccaaggaagctttagacaagatagaggaagagcaaaacaaaagtaagacca
ccgcacagcaagcggccgctgatcttcagacctggaggaggagatatgagggaca
attggagaagtgaattatataaatataaagtagtaaaaattgaaccattaggagt
agcacccaccaaggcaaagagaagagtggtgcagagagaaaaaagagcagtggga
ataggagctttgttccttgggttcttgggagcagcaggaagcactatgggcgcag
cgtcaatgacgctgacggtacaggccagacaattattgtctggtatagtgcagca
gcagaacaatttgctgagggctattgaggcgcaacagcatctgttgcaactcaca
gtctggggcatcaagcagctccaggcaagaatcctggctgtggaaagatacctaa
aggatcaacagctcctggggatttggggttgctctggaaaactcatttgcaccac
tgctgtgccttggaatgctagttggagtaataaatctctggaacagatttggaat
cacacgacctggatggagtgggacagagaaattaacaattacacaagcttaatac
actccttaattgaagaatcgcaaaaccagcaagaaaagaatgaacaagaattatt
ggaattagataaatgggcaagtttgtggaattggtttaacataacaaattggctg
tggtatataaaattattcataatgatagtaggaggcttggtaggtttaagaatag
tttttgctgtactttctatagtgaatagagttaggcagggatattcaccattatc
gtttcagacccacctcccaaccccgaggggacccgacaggcccttaattaatccc
ctgattctgtggataaccgtattaccgcctttgagtgagctgcacgggagcaatt
aatctatagattaaaaagtgaaaggctacaataggacgggagcaattaatctata
gattaaaaagtgaaaggctacaataggacgggagcaattaatctatagattaaaa
agtgaaaggctacaataggacgggagcaattaatctatagattaaaaagtgaaag

FIG 33B CONT gctacaataggacgggagcaattaatctatagattaaaaagtgaaaggctacaat
aggacgggagcaattaatctatagattaaaaagtgaaaggctacaataggacggg
agcaattaatctatagattaaaaagtgaaaggctacaataggacggtaaactcga
cctatataagcagagctcgtttagtgaaccgtcagatcgcctggagacgccatcc
acgctgttttgacctccatagaagacaccgggaccgatccagcctccgcggcccc
gaattgaattctccctatcagtgatagagatctccctatcagtgatagagaggcc
attacggcctgccaccatgttcgttatcatccaggctcacgaataccagaaatac
gctgctgttctggaccagatgttccgtctgcgtaaaaaagttttcgctgacaccc
tgtgctgggacgttccggttatcggtccgtacgaacgtgactcctacgactccct
ggctccggcttacctggtttggtgcaacgactcccgtacccgtctgtacggtggt
atgcgtctgatgccgaccaccggtccgaccctgctgtacgacgttttccgtgaaa
ccttcccggacgctgctgacctgatcgctccgggtatctgggaaggtacccgtat
gtgcatcgacgaagaagctatcgctaaagacttcccggaaatcgacgctggtcgt
gctttctccatgatgctgctggctctgtgcgaatgcgctctggaccacggtatcc
acaccatgatctccaactacgaaccgtacctgaaacgtgtttacaaacgtgctgg
tgctgaagttgaagaactgggtcgtgctgacggttacggtaaatacccggtttgc
tgcggtgctttcgaagtttccgaccgtgttctgcgtaaaatgcgtgctgctctgg
gtctgaccctgccgctgtacgttcgtcacgttccggctcgttccgttgttaccca
gttcctggaaatggctgctgctgctaacgacgaaaactacgctctggttgcttaa
taatgccacc

FIG 33B CONT cggccatcgataaggatccgcggccgcaatcaacctctggattacaaaatttgtgaaagattgactggtattcttaactatgttgctcctttta
cgctatgtggatacgctgctttaatgcctttgtatcatgctattacttcccgtacggctttcattttctcctccttgtataaatcctggttgctgtctct
ttatgaggagttgtggcccgttgtcaggcaacgtggcgtggtgtgcactgtgtttgctgacgcaacccccactggttggggcattgccacc
acctatcaactcctttccgggactttcgctttccccctccctattgccacggcggaactcattgccgcctgccttgcccgctgctggacagg
ggctcggctgttgggcactgacaattccgtggtgttgtcggggaagctgacgtcctttccatggctgctcgcctgtgttgccaactggattct
gcgcgggacgtccttctgctacgtcccttcggccctcaatccagcggaccttccttcccgcggcctgctgccggttctgcggcctcttccg
cgtcttcgccttcgccctcagacgagtcggatctccctttgggccgcctccccgcctgcctgcaggtttgtcgagacctagaaaaacatgg
agcaatcacaagtagcaatacagcagctaccaatgctgattgtgcct

FIG. 34B ggctagaagcacaagaggaggaggaggtgggttttccagtcacacctcaggtacc
tttaagaccaatgacttacaaggcagctgtagatcttagccactttttaaaagaa
aaggggggactggaagggctaattcactcccaacgaagacaagatctgcttttg
cttgtactgggtctctctggttagaccagatctgagcctgggagctctctggcta
actagggaacccactgcttaagcctcaataaagcttgccttgagtgcttcaagta
gtgtgtgcccgtctgttgtgtgactctggtaactagagatccctcagaccctttt
agtcagtgtggaaaatctctagcagggcccgtttaaacccgctgatcagcctcga
ctgtgccttctagttgccagccatctgttgtttgcccctcccccgtgccttcctt
gaccctggaaggtgccactcccactgtcctttcctaataaaatgaggaaattgca
tcgcattgtctgagtaggtgtcattctattctggggggtggggtggggcaggaca
gcaagggggaggattgggaagacaatagcaggcatgctggggatgcggtgggctc
tatggcttctgaggcggaaagaaccagctggggctctagggggtatccccacgcg
ccctgtagcggcgcattaagcgcggcgggtgtggtggttacgcgcagcgtgaccg
ctacacttgccagcgccctagcgcccgctcctttcgctttcttcccttcctttct
cgccacgttcgccggctttccccgtcaagctctaaatcggggcatccctttaggg
ttccgatttagtgctttacggcacctcgaccccaaaaaacttgattagggtgatg
gttcacgtagtgggccatcgccctgatagacggtttttcgccctttgacgttgga
gtccacgttctttaatagtggactcttgttccaaactggaacaacactcaaccct
atctcggtctattcttttgatttataagggattttggggatttcggcctattggt
taaaaaatgagctgatttaacaaaaatttaacgcgaattaattctgtggaatgtg
tgtcagttagggtgtggaaagtccccaggctccccaggcaggcagaagtatgcaa
agcatgcatctcaattagtcagcaaccaggtgtggaaagtccccaggctccccag
caggcagaagtatgcaaagcatgcatctcaattagtcagcaaccatagtcccgcc
cctaactccgcccatcccgcccctaactccgcccagttccgcccattctccgccc
catggctgactaattttttttatttatgcagaggccgaggccgcctctgcctctg
agctattccagaagtagtgaggaggcttttttggaggcctaggcttttgcaaaaa
gctcccgggagcttgtatatccatttcggatctgatcagcacgtgttgacaatt
aatcatcggcatagtatatcggcatagtataatacgacaaggtgaggaactaaac
catggccaagttgaccagtgccgttccggtgctcaccgcgcgcgacgtcgccgga
gcggtcgagttctggaccgaccggctcgggttctcccgggacttcgtggaggacg
acttcgccggtgtggtccgggacgacgtgaccctgttcatcagcgcggtccagga
ccaggtggtgccggacaacaccctggcctgggtgtgggtgcgcggcctggacgag
ctgtacgccgagtggtcggaggtcgtgtccacgaacttccgggacgcctccgggc
cggccatgaccgagatcggcgagcagccgtgggggcgggagttcgccctgcgcga
cccggccggcaactgcgtgcacttcgtggccgaggagcaggactgacacgtgcta
cgagatttcgattccaccgccgccttctatgaaaggttgggcttcggaatcgttt
tccgggacgccggctggatgatcctccagcgcggggatctcatgctggagttctt
cgcccaccccaacttgtttattgcagcttataatggttacaaataaagcaatagc
atcacaaatttcacaaataaagcatttttttcactgcattctagttgtggtttgt
ccaaactcatcaatgtatcttatcatgtctgtataccgtcgacctctagctagag

FIG 34B CONT cttggcgtaatcatggtcatagctgtttcctgtgtgaaattgttatccgctcaca
attccacacaacatacgagccggaagcataaagtgtaaagcctggggtgcctaat
gagtgagctaactcacattaattgcgttgcgctcactgcccgctttccagtcggg
aaacctgtcgtgccagctgcattaatgaatcggccaacgcgcggggagaggcggt
ttgcgtattgggcgctcttccgcttcctcgctcactgactcgctgcgctcggtcg
ttcggctgcggcgagcggtatcagctcactcaaaggcggtaatacggttatccac
agaatcaggggataacgcaggaaagaacatgtgagcaaaaggccagcaaaaggcc
aggaaccgtaaaaaggccgcgttgctggcgtttttccataggctccgcccccctg
acgagcatcacaaaaatcgacgctcaagtcagaggtggcgaaacccgacaggact
ataaagataccaggcgtttccccctggaagctccctcgtgcgctctcctgttccg
accctgccgcttaccggatacctgtccgcctttctcccttcgggaagcgtggcgc
tttctcaatgctcacgctgtaggtatctcagttcggtgtaggtcgttcgctccaa
gctgggctgtgtgcacgaaccccccgttcagcccgaccgctgcgccttatccggt
aactatcgtcttgagtccaacccggtaagacacgacttatcgccactggcagcag
ccactggtaacaggattagcagagcgaggtatgtaggcggtgctacagagttctt
gaagtggtggcctaactacggctacactagaaggacagtatttggtatctgcgct
ctgctgaagccagttaccttcggaaaaagagttggtagctcttgatccggcaaac
aaaccaccgctggtagcggtggtttttttgtttgcaagcagcagattacgcgcag
aaaaaaaggatctcaagaagatcctttgatcttttctacggggtctgacgctcag
tggaacgaaaactcacgttaagggattttggtcatgagattatcaaaaaggatct
tcacctagatccttttaaattaaaaatgaagttttaaatcaatctaaagtatata
tgagtaaacttggtctgacagttaccaatgcttaatcagtgaggcacctatctca
gcgatctgtctatttcgttcatccatagttgcctgactccccgtcgtgtagataa
ctacgatacgggagggcttaccatctggccccagtgctgcaatgataccgcgaga
cccacgctcaccggctccagatttatcagcaataaaccagccagccggaagggcc
gagcgcagaagtggtcctgcaactttatccgcctccatccagtctattaattgtt
gccgggaagctagagtaagtagttcgccagttaatagtttgcgcaacgttgttgc
cattgctacaggcatcgtggtgtcacgctcgtcgtttggtatggcttcattcagc
tccggttcccaacgatcaaggcgagttacatgatcccccatgttgtgcaaaaaag
cggttagctccttcggtcctccgatcgttgtcagaagtaagttggccgcagtgtt
atcactcatggttatggcagcactgcataattctcttactgtcatgccatccgta
agatgcttttctgtgactggtgagtactcaaccaagtcattctgagaatagtgta
tgcggcgaccgagttgctcttgcccggcgtcaatacgggataataccgcgccaca
tagcagaactttaaaagtgctcatcattggaaaacgttcttcggggcgaaaactc
tcaaggatcttaccgctgttgagatccagttcgatgtaacccactcgtgcaccca
actgatcttcagcatcttttactttcaccagcgtttctgggtgagcaaaaacagg
aaggcaaaatgccgcaaaaaagggaataagggcgacacggaaatgttgaatactc
atactcttcctttttcaatattattgaagcatttatcagggttattgtctcatga
gcggatacatatttgaatgtatttagaaaaataaacaaataggggttccgcgcac
atttccccgaaaagtgccacctgacgtcgacggatcgggagatctcccgatcccc

FIG 34B CONT tatggtgcactctcagtacaatctgctctgatgccgcatagttaagccagtatct
gctccctgcttgtgtgttggaggtcgctgagtagtgcgcgagcaaaatttaagct
acaacaaggcaaggcttgaccgacaattgcatgaagaatctgcttagggttaggc
gttttgcgctgcttcgcgatgtacgggccagatatacgcgttgacattgattatt
gactagttattaatagtaatcaattacggggtcattagttcatagcccatatatg
gagttccgcgttacataacttacggtaaatggcccgcctggctgaccgcccaacg
acccccgcccattgacgtcaataatgacgtatgttcccatagtaacgccaatagg
gactttccattgacgtcaatgggtggactatttacggtaaactgcccacttggca
gtacatcaagtgtatcatatgccaagtacgccccctattgacgtcaatgacggta
aatggcccgcctggcattatgcccagtacatgaccttatgggactttcctacttg
gcagtacatctacgtattagtcatcgctattaccatggtgatgcggttttggcag
tacatcaatgggcgtggatagcggtttgactcacggggatttccaagtctccacc
ccattgacgtcaatgggagtttgttttggcaccaaaatcaacgggactttccaaa
atgtcgtaacaactccgccccattgacgcaaatgggcggtaggcgtgtacggtgg
gaggtctatataagcagagctctctggctaactagagaacccactgcttactggc
ttatcgaaattaatacgactcactatagggagacccaagctggtttaaacttaag
cttggtaccgagctcactagtccagtgtggtggcagatatccagcacagtggcgg
ccgctcgagtctagagggcccgtttgcctgtactgggtctctctggttagacca
gatctgagcctgggagctctctggctaactagggaacccactgcttaagcctcaa
taaagcttgccttgagtgcttcaagtagtgtgtgcccgtctgttgtgtgactctg
gtaactagagatccctcagacccttttagtcagtgtggaaaatctctagcagtgg
cgcccgaacagggacttgaaagcgaaagggaaaccagaggagctctctcgacgca
ggactcggcttgctgaagcgcgcacggcaagaggcgaggggcggcgactggtgag
tacgccaaaaatttgactagcggaggctagaaggagagagatgggtgcgagagc
gtcagtattaagcgggggagaattagatcgcgatgggaaaaaattcggttaaggc
cagggggaaagaaaaaatataaattaaaacatatagtatgggcaagcagggagct
agaacgattcgcagttaatcctggcctgttagaaacatcagaaggctgtagacaa
atactgggacagctacaaccatcccttcagacaggatcagaagaacttagatcat
tatataatacagtagcaaccctctattgtgtgcatcaaaggatagagataaaaga
caccaaggaagctttagacaagatagaggaagagcaaaacaaaagtaagaccacc
gcacagcaagcggccgctgatcttcagacctggaggaggagatatgagggacaat
tggagaagtgaattatataaatataaagtagtaaaaattgaaccattaggagtag
cacccaccaaggcaaagagaagagtggtgcagagagaaaaaagagcagtgggaat
aggagctttgttccttgggttcttgggagcagcaggaagcactatgggcgcagcg
tcaatgacgctgacggtacaggccagacaattattgtctggtatagtgcagcagc
agaacaatttgctgagggctattgaggcgcaacagcatctgttgcaactcacagt
ctggggcatcaagcagctccaggcaagaatcctggctgtggaaagatacctaaag
gatcaacagctcctggggatttggggttgctctggaaaactcatttgcaccactg
ctgtgccttggaatgctagttggagtaataaatctctggaacagatttggaatca
cacgacctggatggagtgggacagagaaattaacaattacacaagcttaatacac

FIG 34B CONT tccttaattgaagaatcgcaaaaccagcaagaaaagaatgaacaagaattattgg
aattagataaatgggcaagtttgtggaattggtttaacataacaaattggctgtg
gtatataaaattattcataatgatagtaggaggcttggtaggtttaagaatagtt
tttgctgtactttctatagtgaatagagttaggcagggatattcaccattatcgt
ttcagacccacctcccaaccccgaggggacccgacaggcccttaattaattggct
ccggtgcccgtcagtgggcagagcgcacatcgcccacagtccccgagaagttggg
gggaggggtcggcaattgaaccggtgcctagagaaggtggcgcggggtaaactgg
gaaagtgatgtcgtgtactggctccgcctttttcccgagggtgggggagaaccgt
atataagtgcagtagtcgccgtgaagctagcaattgtgagcggataacaattcca
cagtcgaccctaggttgtgtcgcgagtgttggatcccagctgacaccaattgtga
gcgctcacaattgctagaagaatacaaccacgactatataagaatacaaccacga
ctccgttctttttcgcaacgggtttgccgccagaacacaggtaagtgccgtgtgt
ggttcccgcgggcctggcctctttacgggttatggcccttgcgtgccttgaatta
cttccacctggctgcagtacgtgattcttgatcccgagcttcgggttggaagtgg
gtgggagagttcgaggccttgcgcttaaggagccccttcgcctcgtgcttgagtt
gaggcctggcctgggcgctggggccgccgcgtgcgaatctggtggcaccttcgcg
cctgtctcgctgctttcgataagtctctagccatttaaaatttttgatgacctgc
tgcgacgctttttttctggcaagatagtcttgtaaatgcgggccaagatctgcac
actggtatttcggtttttggggccgcgggcggcgacggggcccgtgcgtcccagc
gcacatgttcggcgaggcggggcctgcgagcgcggccaccgagaatcggacgggg
gtagtctcaagctggccggcctgctctggtgcctggcctcgcgccgccgtgtatc
gccccgccctgggcggcaaggctggcccggtcggcaccagttgcgtgagcggaaa
gatggccgcttcccggccctgctgcagggagctcaaaatggaggacgcggcgctc
gggagagcgggcgggtgagtcacccacacaaaggaaaagggcctttccgtcctca
gccgtcgcttcatgtgactccacggagtaccgggcgccgtccaggcacctcgatt
agttctcgagcttttggagtacgtcgtctttaggttggggggaggggttttatgc
gatggagtttccccacactgagtgggtggagactgaagttaggccagcttggcac
ttgatgtaattctccttggaatttgccctttttgagtttggatcttggttcattc
tcaagcctcagacagtggttcaaagtttttttcttccatttcaggtgaattcggc
cattacggcccgccaccatggctagattagataaaagtaaagtgattaacagcgc
attagagctgcttaatgaggtcggaatcgaaggtttaacaacccgtaaactcgcc
cagaagctaggtgtagagcagcctacattgtattggcatgtaaaaaataagcggg
ctttgctcgacgccttagccattgagatgttagataggcaccatactcactttg
ccctttagaaggggaaagctggcaagattttttacgtaataacgctaaaagtttt
agatgtgctttactaagtcatcgcgatggagcaaaagtacatttaggtacacggc
ctacagaaaaacagtatgaaactctcgaaaatcaattagcctttttatgccaaca
aggtttttcactagagaatgcattatatgcactcagcgctgtggggcattttact
ttaggttgcgtattggaagatcaagagcatcaagtcgctaaagaagaaagggaaa
cacctactactgatagtatgccgccattattacgacaagctatcgaattatttga
tcaccaaggtgcagagccagccttcttattcggccttgaattgatcatatgcgga

FIG 34B CONT ttagaaaaacaacttaaatgtgaaagtgggtcgccaaaaaagaagagaaaggtcg
acggcggtggtgctttgtctcctcagcactctgctgtcactcaaggaagtatcat
caagaacaaggagggcatggatgctaagtcactaactgcctggtcccggacactg
gtgaccttcaaggatgtatttgtggacttcaccagggaggagtggaagctgctgg
acactgctcagcagatcgtgtacagaaatgtgatgctggagaactataagaacct
ggtttccttgggttatcagcttactaagccagatgtgatcctccggttggagaag
ggagaagagccctggctggtggagagagaaattcaccaagagacccatcctgatt
cagagactgcatttgaaatcaaatcatcagtttaaggccgcct

FIG 34B CONT agaattcgatatcaagcttatcgataatcaacctctggattacaaaatttgtgaaagattgactggtattcttaactatgttgctccttttacgctat
gtggatacgctgctttaatgcctttgtatcatgctattacttcccgtacggctttcattttctcctccttgtataaatcctggttgctgtctctttatga
ggagttgtggcccgttgtcaggcaacgtggcgtggtgtgcactgtgtttgctgacgcaacccccactggttggggcattgccaccacctat
caactcctttccgggactttcgctttccccctccctattgccacggcggaactcattgccgcctgccttgcccgctgctggacaggggctcg
gctgttgggcactgacaattccgtggtgttgtcggggaagctgacgtcctttccatggctgctcgcctgtgttgccaactggattctgcgcg
ggacgtccttctgctacgtcccttcggccctcaatccagcggaccttccttcccgcggcctgctgccggttctgcggcctcttccgcgtcttc
gccttcgccctcagacgagtcggatctccctttgggccgcctccccgcctgcctgcaggtttgtcgagacctagaaaaacatggagcaat
cacaagtagcaatacagcagctaccaatgctgattgtgcctggctagaagcacaagaggaggaggaggtgggttttccagtcacacctc
aggtacctttaagaccaatgacttacaaggcagctgtagatcttagccactttttaaaagaaaaggggggactggaagggctaattcactc
ccaacgaagacaagatctgctttttgcttgtactgggtctctctggttagaccagatctgagcctgggagctctctggctaactagggaacc
cactgcttaagcctcaataaagcttgccttgagtgcttcaagtagtgtgtgcccgtctgttgtgtgactctggtaactagagatccctcagacc
cttttagtcagtgtggaaaatctctagcagggcccgtttaaacccgctgatcagcctcgactgtgccttctagttgccagccatctgttgtttg
cccctcccccgtgccttccttgaccctggaaggtgccactcccactgtcctttcctaataaaatgaggaaattgcatcgcattgtctgagtag
gtgtcattctattctggggggtggggtggggcaggacagcaagggggaggattgggaagacaatagcaggcatgctggggatgcggt
gggctctatggcttctgaggcggaaagaaccagctggggctctagggggtatccccacgcgccctgtagcggcgcattaagcgcggc
gggtgtggtggttacgcgcagcgtgaccgctacacttgccagcgccctagcgcccgctcctttcgctttcttcccttcctttctcgccacgtt
cgccggctttccccgtcaagctctaaatcggggcatccctttagggttccgatttagtgctttacggcacctcgaccccaaaaaacttgatta
gggtgatggttcacgtagtgggccatcgccctgatagacggtttttcgccctttgacgttggagtccacgttctttaatagtggactcttgttcc
aaactggaacaacactcaaccctatctcggtctattcttttgatttataagggattttggggatttcggcctattggttaaaaaatgagctgattt
aacaaaaatttaacgcgaattaattctgtggaatgtgtgtcagttagggtgtggaaagtccccaggctccccaggcaggcagaagtatgca
aagcatgcatctcaattagtcagcaaccaggtgtggaaagtccccaggctccccagcag

FIG. 35B gcagaagtatgcaaagcatgcatctcaattagtcagcaaccatagtcccgcccct
aactccgcccatcccgcccctaactccgcccagttccgcccattctccgccccat
ggctgactaattttttttatttatgcagaggccgaggccgcctctgcctctgagc
tattccagaagtagtgaggaggcttttttggaggcctaggcttttgcaaaaagct
cccgggagcttgtatatccatttcggatctgatcagcacgtgttgacaattaat
catcggcatagtatatcggcatagtataatacgacaaggtgaggaactaaaccat
ggccaagttgaccagtgccgttccggtgctcaccgcgcgcgacgtcgccggagcg
gtcgagttctggaccgaccggctcgggttctcccgggacttcgtggaggacgact
tcgccggtgtggtccgggacgacgtgaccctgttcatcagcgcggtccaggacca
ggtggtgccggacaacaccctggcctgggtgtgggtgcgcggcctggacgagctg
tacgccgagtggtcggaggtcgtgtccacgaacttccgggacgcctccgggccgg
ccatgaccgagatcggcgagcagccgtgggggcgggagttcgccctgcgcgaccc
ggccggcaactgcgtgcacttcgtggccgaggagcaggactgacacgtgctacga
gatttcgattccaccgccgccttctatgaaaggttgggcttcggaatcgttttcc
gggacgccggctggatgatcctccagcgcggggatctcatgctggagttcttcgc
ccaccccaacttgtttattgcagcttataatggttacaaataaagcaatagcatc
acaaatttcacaaataaagcatttttttcactgcattctagttgtggtttgtcca
aactcatcaatgtatcttatcatgtctgtataccgtcgacctctagctagagctt
ggcgtaatcatggtcatagctgtttcctgtgtgaaattgttatccgctcacaatt
ccacacaacatacgagccggaagcataaagtgtaaagcctggggtgcctaatgag
tgagctaactcacattaattgcgttgcgctcactgcccgctttccagtcgggaaa
cctgtcgtgccagctgcattaatgaatcggccaacgcgcggggagaggcggtttg
cgtattgggcgctcttccgcttcctcgctcactgactcgctgcgctcggtcgttc
ggctgcggcgagcggtatcagctcactcaaaggcggtaatacggttatccacaga
atcaggggataacgcaggaaagaacatgtgagcaaaaggccagcaaaaggccagg
aaccgtaaaaaggccgcgttgctggcgtttttccataggctccgcccccctgacg
agcatcacaaaaatcgacgctcaagtcagaggtggcgaaacccgacaggactata
aagataccaggcgtttccccctggaagctccctcgtgcgctctcctgttccgacc
ctgccgcttaccggatacctgtccgcctttctcccttcgggaagcgtggcgcttt
ctcaatgctcacgctgtaggtatctcagttcggtgtaggtcgttcgctccaagct
gggctgtgtgcacgaaccccccgttcagcccgaccgctgcgccttatccggtaac
tatcgtcttgagtccaacccggtaagacacgacttatcgccactggcagcagcca
ctggtaacaggattagcagagcgaggtatgtaggcggtgctacagagttcttgaa
gtggtggcctaactacggctacactagaaggacagtatttggtatctgcgctctg
ctgaagccagttaccttcggaaaaagagttggtagctcttgatccggcaaacaaa
ccaccgctggtagcggtggtttttttgtttgcaagcagcagattacgcgcagaaa
aaaaggatctcaagaagatcctttgatcttttctacggggtctgacgctcagtgg
aacgaaaactcacgttaagggattttggtcatgagattatcaaaaaggatcttca
cctagatccttttaaattaaaaatgaagttttaaatcaatctaaagtatatatga
gtaaacttggtctgacagttaccaatgcttaatcagtgaggcacctatctcagcg

FIG 35B CONT atctgtctatttcgttcatccatagttgcctgactccccgtcgtgtagataacta
cgatacgggagggcttaccatctggccccagtgctgcaatgataccgcgagaccc
acgctcaccggctccagatttatcagcaataaaccagccagccggaagggccgag
cgcagaagtggtcctgcaactttatccgcctccatccagtctattaattgttgcc
gggaagctagagtaagtagttcgccagttaatagtttgcgcaacgttgttgccat
tgctacaggcatcgtggtgtcacgctcgtcgtttggtatggcttcattcagctcc
ggttcccaacgatcaaggcgagttacatgatcccccatgttgtgcaaaaaagcgg
ttagctccttcggtcctccgatcgttgtcagaagtaagttggccgcagtgttatc
actcatggttatggcagcactgcataattctcttactgtcatgccatccgtaaga
tgcttttctgtgactggtgagtactcaaccaagtcattctgagaatagtgtatgc
ggcgaccgagttgctcttgcccggcgtcaatacgggataataccgcgccacatag
cagaactttaaaagtgctcatcattggaaaacgttcttcggggcgaaaactctca
aggatcttaccgctgttgagatccagttcgatgtaacccactcgtgcacccaact
gatcttcagcatcttttactttcaccagcgtttctgggtgagcaaaaacaggaag
gcaaaatgccgcaaaaaagggaataagggcgacacggaaatgttgaatactcata
ctcttcctttttcaatattattgaagcatttatcagggttattgtctcatgagcg
gatacatatttgaatgtatttagaaaaataaacaaataggggttccgcgcacatt
tccccgaaaagtgccacctgacgtcgacggatcgggagatctcccgatcccctat
ggtgcactctcagtacaatctgctctgatgccgcatagttaagccagtatctgct
ccctgcttgtgtgttggaggtcgctgagtagtgcgcgagcaaaatttaagctaca
acaaggcaaggcttgaccgacaattgcatgaagaatctgcttagggttaggcgtt
ttgcgctgcttcgcgatgtacgggccagatatacgcgttgacattgattattgac
tagttattaatagtaatcaattacggggtcattagttcatagcccatatatggag
ttccgcgttacataacttacggtaaatggcccgcctggctgaccgcccaacgacc
cccgcccattgacgtcaataatgacgtatgttcccatagtaacgccaatagggac
tttccattgacgtcaatgggtggactatttacggtaaactgcccacttggcagta
catcaagtgtatcatatgccaagtacgccccctattgacgtcaatgacggtaaat
ggcccgcctggcattatgcccagtacatgaccttatgggactttcctacttggca
gtacatctacgtattagtcatcgctattaccatggtgatgcggttttggcagtac
atcaatgggcgtggatagcggtttgactcacggggatttccaagtctccacccca
ttgacgtcaatgggagtttgttttggcaccaaaatcaacgggactttccaaaatg
tcgtaacaactccgccccattgacgcaaatgggcggtaggcgtgtacggtgggag
gtctatataagcagagctctctggctaactagagaacccactgcttactggctta
tcgaaattaatacgactcactatagggagacccaagctggtttaaacttaagctt
ggtaccgagctcactagtccagtgtggtggcagatatccagcacagtggcggccg
ctcgagggggcccgtttttgcctgtactgggtctctctggttagaccagatctgagc
ctgggagctctctggctaactagggaacccactgcttaagcctcaataaagcttg
ccttgagtgcttcaagtagtgtgtgcccgtctgttgtgtgactctggtaactaga
gatccctcagacccttttagtcagtgtggaaaatctctagcagtggcgcccgaac
agggacttgaaagcgaaagggaaaccagaggagctctctcgacgcaggactcggc

FIG 35B CONT ttgctgaagcgcgcacggcaagaggcgaggggcggcgactggtgagtacgccaaa
aattttgactagcggaggctagaaggagagagatgggtgcgagagcgtcagtatt
aagcgggggagaattagatcgcgatgggaaaaaattcggttaaggccagggggaa
agaaaaaatataaattaaaacatatagtatgggcaagcagggagctagaacgatt
cgcagttaatcctggcctgttagaaacatcagaaggctgtagacaaatactggga
cagctacaaccatcccttcagacaggatcagaagaacttagatcattatataata
cagtagcaaccctctattgtgtgcatcaaaggatagagataaaagacaccaagga
agctttagacaagatagaggaagagcaaaacaaaagtaagaccaccgcacagcaa
gcggccgctgatcttcagacctggaggaggagatatgagggacaattggagaagt
gaattatataaatataaagtagtaaaaattgaaccattaggagtagcacccacca
aggcaaagagaagagtggtgcagagagaaaaaagagcagtgggaataggagcttt
gttccttgggttcttgggagcagcaggaagcactatgggcgcagcgtcaatgacg
ctgacggtacaggccagacaattattgtctggtatagtgcagcagcagaacaatt
tgctgagggctattgaggcgcaacagcatctgttgcaactcacagtctggggcat
caagcagctccaggcaagaatcctggctgtggaaagatacctaaaggatcaacag
ctcctggggatttggggttgctctggaaaactcatttgcaccactgctgtgcctt
ggaatgctagttggagtaataaatctctggaacagatttggaatcacacgacctg
gatggagtgggacagagaaattaacaattacacaagcttaatacactccttaatt
gaagaatcgcaaaaccagcaagaaaagaatgaacaagaattattggaattagata
aatgggcaagtttgtggaattggtttaacataacaaattggctgtggtatataaa
attattcataatgatagtaggaggcttggtaggtttaagaatagtttttgctgta
ctttctatagtgaatagagttaggcagggatattcaccattatcgtttcagaccc
acctcccaaccccgaggggacccgacaggcccttaattaatcccctgattctgtg
gataaccgtattaccgcctttgagtgagctgcacctagtacggattagaagccgc
cgagcgggtgacagccctccgaaggaagactctcctccgtgcgtcctcgtcttca
ccggtcgcgttcctgaaacgcagatgtgcctcgcgccgcactgctccgaacaatg
tcgactctagaggtaaactcgacctatataagcagagctcgtttagtgaaccgtc
agatcgcctggagacgccatccacgctgttttgacctccatagaagacaccggga
ccgatccagcctccgcggccccgaattgaattcggccattacggcctgccaccgt
gccaccatgctggagcccggcgagaagccctacaagtgccccgagtgcggcaaga
gcttcagcgactgcagggacctggccaggcaccagaggacccacaccggcgagaa
gccctacaagtgccccgagtgcggcaagagcttcagcgaccccggcaacctggtg
aggcaccagaggacccacaccggcgagaagccctacaagtgccccgagtgcggca
agagcttcagccagagcagcagcctggtgaggcaccagaggacccacaccggcga
gaagccctacaagtgccccgagtgcggcaagagcttcagccagagggcccacctg
gagaggcaccagaggacccacaccggcgagaagccctacaagtgccccgagtgcg
gcaagagcttcagccagagcggcgacctgaggaggcaccagaggacccacaccgg
cgagaagccctacaagtgccccgagtgcggcaagagcttcagccagagcagcaac
ctggtgaggcaccagaggacccacaccggcaagaagaccagcggcccaggcggcc
gatgctaagtcactgactgcctggtcccggacactggtgaccttcaaggatgtgt

FIG 35B CONT ttgtggacttcaccagggaggagtggaagctgctggacactgctcagcagatcct
gtacagaaatgtgatgctggagaactataagaacctggtttccttgggttatcag
cttactaagccagatgtgatcctccggttggagaagggagaagagccctggctgg
tggagagagaaattcaccaagagacccatcctgattcagagactgcatttgaaat
caaatcatcagttgggcgcgccgacgcgctggacgatttcgatctcgacatgctg
ggttctgatgccctcgatgactttgacctggatatgttgggaagcgacgcattgg
atgactttgatctggacatgctcggctccgatgctctggacgatttcgatctcga
tatgttaattaactaattaat

FIG 35B CONT agaattcgatatcaagcttatcgataatcaacctctggattacaaaatttgtgaaagattgactggtattcttaactatgttgctcctttta
cgctatgtggatacgctgctttaatgcctttgtatcatgctattacttcccgtacggctttcattttctcctccttgtataaatcctggttgc
tgtctctttatgaggagttgtggcccgttgtcaggcaacgtggcgtggtgtgcactgtgtttgctgacgcaacccccactggttggg
gcattgccaccacctatcaactcctttccgggactttcgctttccccctccctattgccacggcggaactcattgccgcctgccttgc
ccgctgctggacaggggctcggctgttgggcactgacaattccgtggtgttgtcggggaagctgacgtcctttccatggctgctc
gcctgtgttgccaactggattctgcgcgggacgtccttctgctacgtcccttcggccctcaatccagcggaccttccttcccgcgg
cctgctgccggttctgcggcctcttccgcgtcttcgccttcgccctcagacgagtcggatctccctttgggccgcctccccgcctg
cctgcaggtttgtcgagacctagaaaaacatggagcaatcacaagtagcaatacagcagctaccaatgctgattgtgcctggcta
gaagcacaagaggaggaggaggtgggttttccagtcacacctcaggtacctttaagaccaatgacttacaaggcagctgtagat
cttagccactttttaaaagaaaaggggggactggaagggctaattcactcccaacgaagacaagatctgctttttgcttgtactgg
gtctctctggttagaccagatctgagcctgggagctctctggctaactagggaacccactgcttaagcctcaataaagcttgccttg
agtgcttcaagtagtgtgtgcccgtctgttgtgtgactctggtaactagagatccctcagacccttttagtcagtgtggaaaatctcta
gcagggcccgtttaaacccgctgatcagcctcgactgtgccttctagttgccagccatctgttgtttgcccctcccccgtgccttcct
tgaccctggaaggtgccactcccactgtcctttcctaataaaatgaggaaattgcatcgcattgtctgagtaggtgtcattctattctg
gggggtggggtggggcaggacagcaagggggaggattgggaagacaatagcaggcatgctggggatgcggtgggctctat
ggcttctgaggcggaaagaaccagctggggctctagggggtatccccacgcgccctgtagcggcgcattaagcgcggcggg
tgtggtggttacgcgcagcgtgaccgctacacttgccagcgccctagcgcccgctcctttcgctttcttcccttcctttctcgccac

FIG. 36B gttcgccggctttccccgtcaagctctaaatcggggcatccctttagggttccga
tttagtgctttacggcacctcgaccccaaaaaacttgattagggtgatggttcac
gtagtgggccatcgccctgatagacggtttttcgccctttgacgttggagtccac
gttctttaatagtggactcttgttccaaactggaacaacactcaaccctatctcg
gtctattcttttgatttataagggattttggggatttcggcctattggttaaaaa
atgagctgatttaacaaaaatttaacgcgaattaattctgtggaatgtgtgtcag
ttagggtgtggaaagtccccaggctccccaggcaggcagaagtatgcaaagcatg
catctcaattagtcagcaaccaggtgtggaaagtccccaggctccccagcaggca
gaagtatgcaaagcatgcatctcaattagtcagcaaccatagtcccgcccctaac
tccgcccatcccgcccctaactccgcccagttccgcccattctccgccccatggc
tgactaattttttttatttatgcagaggccgaggccgcctctgcctctgagctat
tccagaagtagtgaggaggcttttttggaggcctaggcttttgcaaaaagctccc
gggagcttgtatatccatttcggatctgatcagcacgtgttgacaattaatcat
cggcatagtatatcggcatagtataatacgacaaggtgaggaactaaaccatggc
caagttgaccagtgccgttccggtgctcaccgcgcgcgacgtcgccggagcggtc
gagttctggaccgaccggctcgggttctcccgggacttcgtggaggacgacttcg
ccggtgtggtccgggacgacgtgaccctgttcatcagcgcggtccaggaccaggt
ggtgccggacaacaccctggcctgggtgtgggtgcgcggcctggacgagctgtac
gccgagtggtcggaggtcgtgtccacgaacttccgggacgcctccgggccggcca
tgaccgagatcggcgagcagccgtgggggcgggagttcgccctgcgcgacccggc
cggcaactgcgtgcacttcgtggccgaggagcaggactgacacgtgctacgagat
ttcgattccaccgccgccttctatgaaaggttgggcttcggaatcgttttccggg
acgccggctggatgatcctccagcgcggggatctcatgctggagttcttcgccca
ccccaacttgtttattgcagcttataatggttacaaataaagcaatagcatcaca
aatttcacaaataaagcatttttttcactgcattctagttgtggtttgtccaaac
tcatcaatgtatcttatcatgtctgtataccgtcgacctctagctagagcttggc
gtaatcatggtcatagctgtttcctgtgtgaaattgttatccgctcacaattcca
cacaacatacgagccggaagcataaagtgtaaagcctggggtgcctaatgagtga
gctaactcacattaattgcgttgcgctcactgcccgctttccagtcgggaaacct
gtcgtgccagctgcattaatgaatcggccaacgcgcggggagaggcggtttgcgt
attgggcgctcttccgcttcctcgctcactgactcgctgcgctcggtcgttcggc
tgcggcgagcggtatcagctcactcaaaggcggtaatacggttatccacagaatc
aggggataacgcaggaaagaacatgtgagcaaaaggccagcaaaaggccaggaac
cgtaaaaaggccgcgttgctggcgtttttccataggctccgcccccctgacgagc
atcacaaaaatcgacgctcaagtcagaggtggcgaaacccgacaggactataaag
ataccaggcgtttccccctggaagctccctcgtgcgctctcctgttccgaccctg
ccgcttaccggatacctgtccgcctttctcccttcgggaagcgtggcgctttctc
aatgctcacgctgtaggtatctcagttcggtgtaggtcgttcgctccaagctggg
ctgtgtgcacgaacccccgttcagcccgaccgctgcgccttatccggtaactat
cgtcttgagtccaacccggtaagacacgacttatcgccactggcagcagccactg

FIG 36B CONT gtaacaggattagcagagcgaggtatgtaggcggtgctacagagttcttgaagtg
gtggcctaactacggctacactagaaggacagtatttggtatctgcgctctgctg
aagccagttaccttcggaaaaagagttggtagctcttgatccggcaaacaaacca
ccgctggtagcggtggtttttttgtttgcaagcagcagattacgcgcagaaaaaa
aggatctcaagaagatcctttgatcttttctacggggtctgacgctcagtggaac
gaaaactcacgttaagggattttggtcatgagattatcaaaaaggatcttcacct
agatccttttaaattaaaaatgaagttttaaatcaatctaaagtatatatgagta
aacttggtctgacagttaccaatgcttaatcagtgaggcacctatctcagcgatc
tgtctatttcgttcatccatagttgcctgactccccgtcgtgtagataactacga
tacgggagggcttaccatctggccccagtgctgcaatgataccgcgagacccacg
ctcaccggctccagatttatcagcaataaaccagccagccggaagggccgagcgc
agaagtggtcctgcaactttatccgcctccatccagtctattaattgttgccggg
aagctagagtaagtagttcgccagttaatagtttgcgcaacgttgttgccattgc
tacaggcatcgtggtgtcacgctcgtcgtttggtatggcttcattcagctccggt
tcccaacgatcaaggcgagttacatgatcccccatgttgtgcaaaaaagcggtta
gctccttcggtcctccgatcgttgtcagaagtaagttggccgcagtgttatcact
catggttatggcagcactgcataattctcttactgtcatgccatccgtaagatgc
ttttctgtgactggtgagtactcaaccaagtcattctgagaatagtgtatgcggc
gaccgagttgctcttgcccggcgtcaatacgggataataccgcgccacatagcag
aactttaaaagtgctcatcattggaaaacgttcttcggggcgaaaactctcaagg
atcttaccgctgttgagatccagttcgatgtaacccactcgtgcacccaactgat
cttcagcatcttttactttcaccagcgtttctgggtgagcaaaaacaggaaggca
aaatgccgcaaaaaagggaataagggcgacacggaaatgttgaatactcatactc
ttcctttttcaatattattgaagcatttatcagggttattgtctcatgagcggat
acatatttgaatgtatttagaaaaataaacaaataggggttccgcgcacatttcc
ccgaaaagtgccacctgacgtcgacggatcgggagatctcccgatcccctatggt
gcactctcagtacaatctgctctgatgccgcatagttaagccagtatctgctccc
tgcttgtgtgttggaggtcgctgagtagtgcgcgagcaaaatttaagctacaaca
aggcaaggcttgaccgacaattgcatgaagaatctgcttagggttaggcgttttg
cgctgcttcgcgatgtacgggccagatatacgcgttgacattgattattgactag
ttattaatagtaatcaattacggggtcattagttcatagcccatatatggagttc
cgcgttacataacttacggtaaatggcccgcctggctgaccgcccaacgacccccc
gcccattgacgtcaataatgacgtatgttcccatagtaacgccaatagggacttt
ccattgacgtcaatgggtggactatttacggtaaactgcccacttggcagtacat
caagtgtatcatatgccaagtacgccccctattgacgtcaatgacggtaaatggc
ccgcctggcattatgcccagtacatgaccttatgggactttcctacttggcagta
catctacgtattagtcatcgctattaccatggtgatgcggttttggcagtacatc
aatgggcgtggatagcggtttgactcacggggatttccaagtctccaccccattg
acgtcaatgggagtttgttttggcaccaaaatcaacgggactttccaaaatgtcg
taacaactccgccccattgacgcaaatgggcggtaggcgtgtacggtgggaggtc

FIG 36B CONT tatataagcagagctctctggctaactagagaacccactgcttactggcttatcg
aaattaatacgactcactatagggagacccaagctggtttaaacttaagcttggt
accgagctcactagtccagtgtggtggcagatatccagcacagtggcggccgctc
gaggggcccgttttgcctgtactgggtctctctggttagaccagatctgagcctg
ggagctctctggctaactagggaacccactgcttaagcctcaataaagcttgcct
tgagtgcttcaagtagtgtgtgcccgtctgttgtgtgactctggtaactagagat
ccctcagacccttttagtcagtgtggaaaatctctagcagtggcgcccgaacagg
gacttgaaagcgaaagggaaaccagaggagctctctcgacgcaggactcggcttg
ctgaagcgcgcacggcaagaggcgaggggcggcgactggtgagtacgccaaaaat
tttgactagcggaggctagaaggagagagatgggtgcgagagcgtcagtattaag
cgggggagaattagatcgcgatgggaaaaaattcggttaaggccagggggaaaga
aaaaatataaattaaaacatatagtatgggcaagcagggagctagaacgattcgc
agttaatcctggcctgttagaaacatcagaaggctgtagacaaatactgggacag
ctacaaccatcccttcagacaggatcagaagaacttagatcattatataatacag
tagcaaccctctattgtgtgcatcaaaggatagagataaaagacaccaaggaagc
tttagacaagatagaggaagagcaaaacaaaagtaagaccaccgcacagcaagcg
gccgctgatcttcagacctggaggaggagatatgagggacaattggagaagtgaa
ttatataaatataaagtagtaaaaattgaaccattaggagtagcacccaccaagg
caaagagaagagtggtgcagagagaaaaaagagcagtgggaataggagctttgtt
ccttgggttcttgggagcagcaggaagcactatgggcgcagcgtcaatgacgctg
acggtacaggccagacaattattgtctggtatagtgcagcagcagaacaatttgc
tgagggctattgaggcgcaacagcatctgttgcaactcacagtctggggcatcaa
gcagctccaggcaagaatcctggctgtggaaagatacctaaaggatcaacagctc
ctggggatttggggttgctctggaaaactcatttgcaccactgctgtgccttgga
atgctagttggagtaataaatctctggaacagatttggaatcacacgacctggat
ggagtgggacagagaaattaacaattacacaagcttaatacactccttaattgaa
gaatcgcaaaaccagcaagaaaagaatgaacaagaattattggaattagataaat
gggcaagtttgtggaattggtttaacataacaaattggctgtggtatataaaatt
attcataatgatagtaggaggcttggtaggtttaagaatagtttttgctgtactt
tctatagtgaatagagttaggcagggatattcaccattatcgtttcagacccacc
tcccaaccccgaggggacccgacaggcccttaattaatcccctgattctgtggat
aaccgtattaccgcctttgagtgagctgcacctagtacggattagaagccgccga
gcgggtgacagccctccgaaggaagactctcctccgtgcgtcctcgtcttcaccg
gtcgcgttcctgaaacgcagatgtgcctcgcgccgcactgctccgaacaatgtcg
actctagaggtaaactcgacctatataagcagagctcgtttagtgaaccgtcaga
tcgcctggagacgccatccacgctgttttgacctccatagaagacaccgggaccg
atccagcctccgcggccccgaattgaattcggccattacggcctgccaccgtgcc
accatgctggagcccggcgagaagccctacaagtgccccgagtgcggcaagagct
tcagcaggagcgacgagctggtgaggcaccagaggacccacaccggcgagaagcc
ctacaagtgccccgagtgcggcaagagcttcagcaggagcgacaagctggtgagg

FIG 36B CONT caccagaggacccacaccggcgagaagccctacaagtgccccgagtgcggcaaga
gcttcagcaggagcgacgacctggtgaggcaccagaggacccacaccggcgagaa
gccctacaagtgccccgagtgcggcaagagcttcagcaggagcgacaacctggtg
aggcaccagaggacccacaccggcgagaagccctacaagtgccccgagtgcggca
agagcttcagcgaccccggcgccctggtgaggcaccagaggacccacaccggcga
gaagccctacaagtgccccgagtgcggcaagagcttcagcgaccccggccacctg
gtgaggcaccagaggacccacaccggcaagaagaccagcggcccaggcggccgat
gctaagtcactgactgcctggtcccggacactggtgaccttcaaggatgtgtttg
tggacttcaccagggaggagtggaagctgctggacactgctcagcagatcctgta
cagaaatgtgatgctggagaactataagaacctggtttccttgggttatcagctt
actaagccagatgtgatcctccggttggagaagggagaagagccctggctggtgg
agagagaaattcaccaagagacccatcctgattcagagactgcatttgaaatcaa
atcatcagttgggcgcgccgacgcgctggacgatttcgatctcgacatgctgggt
tctgatgccctcgatgactttgacctggatatgttgggaagcgacgcattggatg
actttgatctggacatgctcggctccgatgctctggacgatttcgatctcgatat
gttaattaactaattaat

FIG 36B CONT cgtgccaccatgctggagcccggcgagaagccctacaagtgccccgagtgcggcaagagcttcagcgacagcggcaacctgagggt
gcaccagaggacccacaccggcgagaagccctacaagtgccccgagtgcggcaagagcttcagccagagggccaacctgagggcc
caccagaggacccacaccggcgagaagccctacaagtgccccgagtgcggcaagagcttcagcaccagcggcagcctggtgaggc
accagaggacccacaccggcgagaagccctacaagtgccccgagtgcggcaagagcttcagcaccagcggccacctggtgaggca
ccagaggacccacaccggcgagaagccctacaagtgccccgagtgcggcaagagcttcagcaccagcggcgagctggtgaggcac
cagaggacccacaccggcgagaagccctacaagtgccccgagtgcggcaagagcttcagcaccagcggcaacctggtgaggcacc
agaggacccacaccggcaagaagaccagcggcccaggcggccgatgctaagtcactgactgcctggtcccggacactggtgaccttc
aaggatgtgtttgtggacttcaccagggaggagtggaagctgctggacactgctcagcagatcctgtacagaaatgtgatgctggagaac
tataagaacctggtttccttgggttatcagcttactaagccagatgtgatcctccggttggagaagggagaagagccctggctggtggaga
gagaaattcaccaagagacccatcctgattcagagactgcatttgaaatcaaatcatcagttgggcgcgccgacgcgctggacgatttcg
atctcgacatgctgggttctgatgccctcgatgactttgacctggatatgttgggaagcgacgcattggatgactttgatctggacatgctcg
gctccgatgctctggacgatttcga

FIG. 37B tctcgatatgttaattaactaacgatcacatggtcctgctggagttcgtgaccgc
cgccgggatcactctcggcatggacgagctgtacaagtaagcggccgcaatcaac
ctctggattacaaaatttgtgaaagattgactggtattcttaactatgttgctcc
ttttacgctatgtggatacgctgctttaatgcctttgtatcatgctattacttcc
cgtacggctttcattttctcctccttgtataaatcctggttgctgtctctttatg
aggagttgtggcccgttgtcaggcaacgtggcgtggtgtgcactgtgtttgctga
cgcaacccccactggttggggcattgccaccacctatcaactcctttccgggact
ttcgctttccccctccctattgccacggcggaactcattgccgcctgccttgccc
gctgctggacaggggctcggctgttgggcactgacaattccgtggtgttgtcggg
gaagctgacgtcctttccatggctgctcgcctgtgttgccaactggattctgcgc
gggacgtccttctgctacgtcccttcggccctcaatccagcggaccttccttccc
gcggcctgctgccggttctgcggcctcttccgcgtcttcgccttcgccctcagac
gagtcggatctccctttgggccgcctccccgcctgcctgcaggtttgtcgagacc
tagaaaaacatggagcaatcacaagtagcaatacagcagctaccaatgctgattg
tgcctggctagaagcacaagaggaggaggaggtgggttttccagtcacacctcag
gtacctttaagaccaatgacttacaaggcagctgtagatcttagccactttttaa
aagaaaaggggggactggaagggctaattcactcccaacgaagacaagatctgct
ttttgcttgtactgggtctctctggttagaccagatctgagcctgggagctctct
ggctaactagggaacccactgcttaagcctcaataaagcttgccttgagtgcttc
aagtagtgtgtgcccgtctgttgtgtgactctggtaactagagatccctcagacc
cttttagtcagtgtggaaaatctctagcagggcccgtttaaacccgctgatcagc
ctcgactgtgccttctagttgccagccatctgttgtttgcccctcccccgtgcct
tccttgaccctggaaggtgccactcccactgtcctttcctaataaaatgaggaaa
ttgcatcgcattgtctgagtaggtgtcattctattctggggggtggggtggggca
ggacagcaagggggaggattgggaagacaatagcaggcatgctggggatgcggtg
ggctctatggcttctgaggcggaaagaaccagctggggctctagggggtatcccc
acgcgccctgtagcggcgcattaagcgcggcgggtgtggtggttacgcgcagcgt
gaccgctacacttgccagcgccctagcgcccgctcctttcgctttcttcccttcc
tttctcgccacgttcgccggctttccccgtcaagctctaaatcgggggcatccctt
tagggttccgatttagtgctttacggcacctcgaccccaaaaaacttgattaggg
tgatggttcacgtagtgggccatcgccctgatagacggtttttcgccctttgacg
ttggagtccacgttctttaatagtggactcttgttccaaactggaacaacactca
accctatctcggtctattcttttgatttataagggattttggggatttcggccta
ttggttaaaaaatgagctgatttaacaaaaatttaacgcgaattaattctgtgga
atgtgtgtcagttagggtgtggaaagtccccaggctccccaggcaggcagaagta
tgcaaagcatgcatctcaattagtcagcaaccaggtgtggaaagtccccaggctc
cccagcaggcagaagtatgcaaagcatgcatctcaattagtcagcaaccatagtc
ccgcccctaactccgcccatcccgcccctaactccgcccagttccgcccattctc
cgccccatggctgactaattttttttatttatgcagaggccgaggccgcctctgc
ctctgagctattccagaagtagtgaggaggcttttttggaggcctaggcttttgc

FIG 37B CONT aaaaagctcccgggagcttgtatatccattttcggatctgatcagcacgtgttga
caattaatcatcggcatagtatatcggcatagtataatacgacaaggtgaggaac
taaaccatggccaagttgaccagtgccgttccggtgctcaccgcgcgcgacgtcg
ccggagcggtcgagttctggaccgaccggctcgggttctcccgggacttcgtgga
ggacgacttcgccggtgtggtccgggacgacgtgaccctgttcatcagcgcggtc
caggaccaggtggtgccggacaacaccctggcctgggtgtgggtgcgcggcctgg
acgagctgtacgccgagtggtcggaggtcgtgtccacgaacttccgggacgcctc
cgggccggccatgaccgagatcggcgagcagccgtgggggcgggagttcgccctg
cgcgacccggccggcaactgcgtgcacttcgtggccgaggagcaggactgacacg
tgctacgagatttcgattccaccgccgccttctatgaaaggttgggcttcggaat
cgttttccgggacgccggctggatgatcctccagcgcggggatctcatgctggag
ttcttcgcccaccccaacttgtttattgcagcttataatggttacaaataaagca
atagcatcacaaatttcacaaataaagcatttttttcactgcattctagttgtgg
tttgtccaaactcatcaatgtatcttatcatgtctgtataccgtcgacctctagc
tagagcttggcgtaatcatggtcatagctgtttcctgtgtgaaattgttatccgc
tcacaattccacacaacatacgagccggaagcataaagtgtaaagcctggggtgc
ctaatgagtgagctaactcacattaattgcgttgcgctcactgcccgctttccag
tcgggaaacctgtcgtgccagctgcattaatgaatcggccaacgcgcggggagag
gcggtttgcgtattgggcgctcttccgcttcctcgctcactgactcgctgcgctc
ggtcgttcggctgcggcgagcggtatcagctcactcaaaggcggtaatacggtta
tccacagaatcaggggataacgcaggaaagaacatgtgagcaaaaggccagcaaa
aggccaggaaccgtaaaaaggccgcgttgctggcgtttttccataggctccgccc
ccctgacgagcatcacaaaaatcgacgctcaagtcagaggtggcgaaacccgaca
ggactataaagataccaggcgtttccccctggaagctccctcgtgcgctctcctg
ttccgaccctgccgcttaccggatacctgtccgcctttctcccttcgggaagcgt
ggcgctttctcaatgctcacgctgtaggtatctcagttcggtgtaggtcgttcgc
tccaagctgggctgtgtgcacgaaccccccgttcagcccgaccgctgcgccttat
ccggtaactatcgtcttgagtccaacccggtaagacacgacttatcgccactggc
agcagccactggtaacaggattagcagagcgaggtatgtaggcggtgctacagag
ttcttgaagtggtggcctaactacggctacactagaaggacagtatttggtatct
gcgctctgctgaagccagttaccttcggaaaaagagttggtagctcttgatccgg
caaacaaaccaccgctggtagcggtggtttttttgtttgcaagcagcagattacg
cgcagaaaaaaaggatctcaagaagatcctttgatcttttctacggggtctgacg
ctcagtggaacgaaaactcacgttaagggattttggtcatgagattatcaaaaag
gatcttcacctagatccttttaaattaaaaatgaagttttaaatcaatctaaagt
atatatgagtaaacttggtctgacagttaccaatgcttaatcagtgaggcaccta
tctcagcgatctgtctatttcgttcatccatagttgcctgactccccgtcgtgta
gataactacgatacgggagggcttaccatctggccccagtgctgcaatgataccg
cgagacccacgctcaccggctccagatttatcagcaataaaccagccagccggaa
gggccgagcgcagaagtggtcctgcaactttatccgcctccatccagtctattaa

FIG 37B CONT ttgttgccgggaagctagagtaagtagttcgccagttaatagtttgcgcaacgtt
gttgccattgctacaggcatcgtggtgtcacgctcgtcgtttggtatggcttcat
tcagctccggttcccaacgatcaaggcgagttacatgatcccccatgttgtgcaa
aaaagcggttagctccttcggtcctccgatcgttgtcagaagtaagttggccgca
gtgttatcactcatggttatggcagcactgcataattctcttactgtcatgccat
ccgtaagatgcttttctgtgactggtgagtactcaaccaagtcattctgagaata
gtgtatgcggcgaccgagttgctcttgcccggcgtcaatacgggataataccgcg
ccacatagcagaactttaaaagtgctcatcattggaaaacgttcttcggggcgaa
aactctcaaggatcttaccgctgttgagatccagttcgatgtaacccactcgtgc
acccaactgatcttcagcatcttttactttcaccagcgtttctgggtgagcaaaa
acaggaaggcaaaatgccgcaaaaaagggaataagggcgacacggaaatgttgaa
tactcatactcttcctttttcaatattattgaagcatttatcagggttattgtct
catgagcggatacatatttgaatgtatttagaaaaataaacaaataggggttccg
cgcacatttccccgaaaagtgccacctgacgtcgacggatcgggagatctcccga
tcccctatggtgcactctcagtacaatctgctctgatgccgcatagttaagccag
tatctgctccctgcttgtgtgttggaggtcgctgagtagtgcgcgagcaaaattt
aagctacaacaaggcaaggcttgaccgacaattgcatgaagaatctgcttagggt
taggcgttttgcgctgcttcgcgatgtacgggccagatatacgcgttgacattga
ttattgactagttattaatagtaatcaattacggggtcattagttcatagcccat
atatggagttccgcgttacataacttacggtaaatggcccgcctggctgaccgcc
caacgacccccgcccattgacgtcaataatgacgtatgttcccatagtaacgcca
atagggactttccattgacgtcaatgggtggactatttacggtaaactgcccact
tggcagtacatcaagtgtatcatatgccaagtacgccccctattgacgtcaatga
cggtaaatggcccgcctggcattatgcccagtacatgaccttatgggactttcct
acttggcagtacatctacgtattagtcatcgctattaccatggtgatgcggtttt
ggcagtacatcaatgggcgtggatagcggtttgactcacggggatttccaagtct
ccaccccattgacgtcaatgggagtttgttttggcaccaaaatcaacgggacttt
ccaaaatgtcgtaacaactccgccccattgacgcaaatgggcggtaggcgtgtac
ggtgggaggtctatataagcagagctctctggctaactagagaacccactgctta
ctggcttatcgaaattaatacgactcactatagggagacccaagctggtttaaac
ttaagcttggtaccgagctcactagtccagtgtggtggcagatatccagcacagt
ggcggccgctcgagtctagagggcccgttttgcctgtactgggtctctctggtta
gaccagatctgagcctgggagctctctggctaactagggaacccactgcttaagc
ctcaataaagcttgccttgagtgcttcaagtagtgtgtgcccgtctgttgtgtga
ctctggtaactagagatccctcagacccttttagtcagtgtggaaaatctctagc
agtggcgcccgaacagggacttgaaagcgaaagggaaaccagaggagctctctcg
acgcaggactcggcttgctgaagcgcgcacggcaagaggcgaggggcggcgactg
gtgagtacgccaaaaattttgactagcggaggctagaaggagagagatgggtgcg
agagcgtcagtattaagcgggggagaattagatcgcgatgggaaaaaattcggtt
aaggccagggggaaagaaaaaatataaattaaaacatatagtatgggcaagcagg

FIG 37B CONT gagctagaacgattcgcagttaatcctggcctgttagaaacatcagaaggctgta
gacaaatactgggacagctacaaccatcccttcagacaggatcagaagaacttag
atcattatataatacagtagcaaccctctattgtgtgcatcaaaggatagagata
aaagacaccaaggaagctttagacaagatagaggaagagcaaaacaaaagtaaga
ccaccgcacagcaagcggccgctgatcttcagacctggaggaggagatatgaggg
acaattggagaagtgaattatataaatataaagtagtaaaaattgaaccattagg
agtagcacccaccaaggcaaagagaagagtggtgcagagagaaaaaagagcagtg
ggaataggagctttgttccttgggttcttgggagcagcaggaagcactatgggcg
cagcgtcaatgacgctgacggtacaggccagacaattattgtctggtatagtgca
gcagcagaacaatttgctgagggctattgaggcgcaacagcatctgttgcaactc
acagtctggggcatcaagcagctccaggcaagaatcctggctgtggaaagatacc
taaaggatcaacagctcctggggatttggggttgctctggaaaactcatttgcac
cactgctgtgccttggaatgctagttggagtaataaatctctggaacagatttgg
aatcacacgacctggatggagtgggacagagaaattaacaattacacaagcttaa
tacactccttaattgaagaatcgcaaaaccagcaagaaaagaatgaacaagaatt
attggaattagataaatgggcaagtttgtggaattggtttaacataacaaattgg
ctgtggtatatagaaattattcataatgatagtaggaggcttggtaggtttaaga
atagtttttgctgtactttctatagtgaatagagttaggcagggatattcaccat
tatcgtttcagacccacctcccaaccccgaggggacccgacaggcccgaaggaat
agaagaagaaggtggagagagagacagagacagatccattcgattagtgaacgga
tcggcactgcgtgcgccaattctgcagacaaatggcagtattcatccacaatttt
aaaagaaaaggggggattggggggtacagtgcaggggaaagaatagtagacataa
tagcaacagacatacaaactaaagaattacaaaaacaaattacaaaaattcaaaa
ttttcgggtttattacagggacagcagagatccagtttggggttgctctggaaaa
ctcatttgcaccactgctgtgccttggaatgctagttggagtaataaatctctgg
aacagatttggaatcacacgacctggatggagtgggacagagaaattaacaatta
cacaagcttaatacactccttaattgaagaatcgcaaaaccagcaagaaaagaat
gaacaagaattattggaattagataaatgggcaagtttgtggaattggtttaaca
taacaaattggctgtggtatataaaattattcataatgatagtaggaggcttggt
aggtttaagaatagtttttgctgtactttctatagtgaatagagttaggcaggga
tattcaccattatcgtttcagacccacctcccaaccccgaggggacccgacaggc
ccttaattaattggctccggtgcccgtcagtgggcagagcgcacatcgcccacag
tccccgagaagttggggggaggggtcggcaattgaaccggtgcctagagaaggtg
gcgcggggtaaactgggaaagtgatgtcgtgtactggctccgcctttttcccgag
ggtgggggagaaccgtatataagtgcagtagtcgccgtgaagctagcggcgtcga
ggcgggggtgatatggcgtcgaggcgggggtggctagccgttctttttcgcaacg
ggtttgccgccagaacacaggtaagtgccgtgtgtggttcccgcgggcctggcct
ctttacgggttatggcccttgcgtgccttgaattacttccacctggctgcagtac
gtgattcttgatcccgagcttcgggttggaagtgggtgggagagttcgaggcctt
gcgcttaaggagccccttcgcctcgtgcttgagttgaggcctggcctgggcgctg

FIG 37B CONT gggccgccgcgtgcgaatctggtggcaccttcgcgcctgtctcgctgctttcgat
aagtctctagccatttaaaatttttgatgacctgctgcgacgctttttttctggc
aagatagtcttgtaaatgcgggccaagatctgcacactggtatttcggtttttgg
ggccgcgggcggcgacggggcccgtgcgtcccagcgcacatgttcggcgaggcgg
ggcctgcgagcgcggccaccgagaatcggacgggggtagtctcaagctggccggc
ctgctctggtgcctggcctcgcgccgccgtgtatcgccccgccctgggcggcaag
gctggcccggtcggcaccagttgcgtgagcggaaagatggccgcttcccggccct
gctgcagggagctcaaaatggaggacgcggcgctcgggagagcgggcgggtgagt
cacccacacaaaggaaaagggcctttccgtcctcagccgtcgcttcatgtgactc
cacggagtaccgggcgccgtccaggcacctcgattagttctcgagcttttggagt
acgtcgtctttaggttgggggggaggggttttatgcgatggagtttccccacactg
agtgggtggagactgaagttaggccagcttggcacttgatgtaattctccttgga
atttgccctttttgagtttggatcttggttcattctcaagcctcagacagtggtt
caaagtttttttcttccatttcaggtgaattcggccattacggcctcccaccggc
cgcct

FIG 37B CONT ttgccaccatgctggagcccggcgagaagccctacaagtgccccgagtgcggcaagagcttcagcacccacctggacctgatcaggc
accagaggacccacaccggcgagaagccctacaagtgccccgagtgcggcaagagcttcagcaggaccgacaccctgagggacca
ccagaggacccacaccggcgagaagccctacaagtgccccgagtgcggcaagagcttcagcgacaagaaggacctgaccaggcac
cagaggacccacaccggcgagaagccctacaagtgccccgagtgcggcaagagcttcagcagccccgccgacctgaccaggcacc
agaggacccacaccggcgagaagccctacaagtgccccgagtgcggcaagagcttcagcaccaccggcaacctgaccgtgcaccag
aggacccacaccggcgagaagccctacaagtgccccgagtgcggcaagagcttc

FIG. 38B agcaggaaggacaacctgaagaaccaccagaggacccacaccggcaagaagacca
gcggcccaggcggccgatgctaagtcactgactgcctggtcccggacactggtga
ccttcaaggatgtgtttgtggacttcaccagggaggagtggaagctgctggacac
tgctcagcagatcctgtacagaaatgtgatgctggagaactataagaacctggtt
tccttgggttatcagcttactaagccagatgtgatcctccggttggagaagggag
aagagccctggctggtggagagagaaattcaccaagagacccatcctgattcaga
gactgcatttgaaatcaaatcatcagttgggcgcgccgacgcgctggacgatttc
gatctcgacatgctgggttctgatgccctcgatgactttgacctggatatgttgg
gaagcgacgcattggatgactttgatctggacatgctcggctccgatgctctgga
cgatttcgatctcgatatgttaattaactaatatgtgtgggagggctaagggcgc
gccgttctagagaattcgatatcaagcttatcgataatcaacctctggattacaa
aatttgtgaaagattgactggtattcttaactatgttgctccttttacgctatgt
ggatacgctgctttaatgcctttgtatcatgctattacttcccgtacggctttca
ttttctcctccttgtataaatcctggttgctgtctctttatgaggagttgtggcc
cgttgtcaggcaacgtggcgtggtgtgcactgtgtttgctgacgcaacccccact
ggttggggcattgccaccacctatcaactcctttccgggactttcgctttccccc
tccctattgccacggcggaactcattgccgcctgccttgcccgctgctggacagg
ggctcggctgttgggcactgacaattccgtggtgttgtcggggaagctgacgtcc
tttccatggctgctcgcctgtgttgccaactggattctgcgcgggacgtccttct
gctacgtcccttcggccctcaatccagcggaccttccttcccgcggcctgctgcc
ggttctgcggcctcttccgcgtcttcgccttcgccctcagacgagtcggatctcc
ctttgggccgcctccccgcctgcctgcaggtttgtcgagacctagaaaaacatgg
agcaatcacaagtagcaatacagcagctaccaatgctgattgtgcctggctagaa
gcacaagaggaggaggaggtgggttttccagtcacacctcaggtacctttaagac
caatgacttacaaggcagctgtagatcttagccactttttaaaagaaaagggggg
actggaagggctaattcactcccaacgaagacaagatctgctttttgcttgtact
gggtctctctggttagaccagatctgagcctgggagctctctggctaactaggga
acccactgcttaagcctcaataaagcttgccttgagtgcttcaagtagtgtgtgc
ccgtctgttgtgtgactctggtaactagagatccctcagacccttttagtcagtg
tggaaaatctctagcagggcccgtttaaacccgctgatcagcctcgactgtgcct
tctagttgccagccatctgttgtttgcccctcccccgtgccttccttgaccctgg
aaggtgccactcccactgtcctttcctaataaaatgaggaaattgcatcgcattg
tctgagtaggtgtcattctattctggggggtggggtggggcaggacagcaagggg
gaggattgggaagacaatagcaggcatgctggggatgcggtgggctctatggctt
ctgaggcggaaagaaccagctggggctctagggggtatccccacgcgccctgtag
cggcgcattaagcgcggcgggtgtggtggttacgcgcagcgtgaccgctacactt
gccagcgccctagcgcccgctcctttcgctttcttcccttcctttctcgccacgt
tcgccggctttccccgtcaagctctaaatcgggggcatccctttagggttccgatt
tagtgctttacggcacctcgaccccaaaaaacttgattagggtgatggttcacgt
agtgggccatcgccctgatagacggtttttcgccctttgacgttggagtccacgt

FIG 38B CONT tctttaatagtggactcttgttccaaactggaacaacactcaaccctatctcggt
ctattcttttgatttataagggattttggggatttcggcctattggttaaaaaat
gagctgatttaacaaaaatttaacgcgaattaattctgtggaatgtgtgtcagtt
agggtgtggaaagtccccaggctccccaggcaggcagaagtatgcaaagcatgca
tctcaattagtcagcaaccaggtgtggaaagtccccaggctccccagcaggcaga
agtatgcaaagcatgcatctcaattagtcagcaaccatagtcccgcccctaactc
cgcccatcccgcccctaactccgcccagttccgcccattctccgccccatggctg
actaatttttttatttatgcagaggccgaggccgcctctgcctctgagctattc
cagaagtagtgaggaggcttttttggaggcctaggcttttgcaaaaagctcccgg
gagcttgtatatccattttcggatctgatcagcacgtgttgacaattaatcatcg
gcatagtatatcggcatagtataatacgacaaggtgaggaactaaaccatggcca
agttgaccagtgccgttccggtgctcaccgcgcgcgacgtcgccggagcggtcga
gttctggaccgaccggctcgggttctcccgggacttcgtggaggacgacttcgcc
ggtgtggtccgggacgacgtgaccctgttcatcagcgcggtccaggaccaggtgg
tgccggacaacaccctggcctgggtgtgggtgcgcggcctggacgagctgtacgc
cgagtggtcggaggtcgtgtccacgaacttccgggacgcctccgggccggccatg
accgagatcggcgagcagccgtgggggcgggagttcgccctgcgcgacccggccg
gcaactgcgtgcacttcgtggccgaggagcaggactgacacgtgctacgagattt
cgattccaccgccgccttctatgaaaggttgggcttcggaatcgttttccgggac
gccggctggatgatcctccagcgcggggatctcatgctggagttcttcgcccacc
ccaacttgtttattgcagcttataatggttacaaataaagcaatagcatcacaaa
tttcacaaataaagcatttttttcactgcattctagttgtggtttgtccaaactc
atcaatgtatcttatcatgtctgtataccgtcgacctctagctagagcttggcgt
aatcatggtcatagctgtttcctgtgtgaaattgttatccgctcacaattccaca
caacatacgagccggaagcataaagtgtaaagcctggggtgcctaatgagtgagc
taactcacattaattgcgttgcgctcactgcccgctttccagtcgggaaacctgt
cgtgccagctgcattaatgaatcggccaacgcgcggggagaggcggtttgcgtat
tgggcgctcttccgcttcctcgctcactgactcgctgcgctcggtcgttcggctg
cggcgagcggtatcagctcactcaaaggcggtaatacggttatccacagaatcag
gggataacgcaggaaagaacatgtgagcaaaaggccagcaaaaggccaggaaccg
taaaaaggccgcgttgctggcgtttttccataggctccgcccccctgacgagcat
cacaaaaatcgacgctcaagtcagaggtggcgaaacccgacaggactataaagat
accaggcgtttccccctggaagctccctcgtgcgctctcctgttccgaccctgcc
gcttaccggatacctgtccgcctttctcccttcgggaagcgtggcgctttctcaa
tgctcacgctgtaggtatctcagttcggtgtaggtcgttcgctccaagctgggct
gtgtgcacgaaccccccgttcagcccgaccgctgcgccttatccggtaactatcg
tcttgagtccaacccggtaagacacgacttatcgccactggcagcagccactggt
aacaggattagcagagcgaggtatgtaggcggtgctacagagttcttgaagtggt
ggcctaactacggctacactagaaggacagtatttggtatctgcgctctgctgaa
gccagttaccttcggaaaaagagttggtagctcttgatccggcaaacaaaccacc

FIG 38B CONT gctggtagcggtggtttttttgtttgcaagcagcagattacgcgcagaaaaaaag
gatctcaagaagatcctttgatcttttctacggggtctgacgctcagtggaacga
aaactcacgttaagggattttggtcatgagattatcaaaaaggatcttcacctag
atccttttaaattaaaaatgaagttttaaatcaatctaaagtatatatgagtaaa
cttggtctgacagttaccaatgcttaatcagtgaggcacctatctcagcgatctg
tctatttcgttcatccatagttgcctgactccccgtcgtgtagataactacgata
cgggagggcttaccatctggccccagtgctgcaatgataccgcgagacccacgct
caccggctccagatttatcagcaataaaccagccagccggaagggccgagcgcag
aagtggtcctgcaactttatccgcctccatccagtctattaattgttgccgggaa
gctagagtaagtagttcgccagttaatagtttgcgcaacgttgttgccattgcta
caggcatcgtggtgtcacgctcgtcgtttggtatggcttcattcagctccggttc
ccaacgatcaaggcgagttacatgatcccccatgttgtgcaaaaaagcggttagc
tccttcggtcctccgatcgttgtcagaagtaagttggccgcagtgttatcactca
tggttatggcagcactgcataattctcttactgtcatgccatccgtaagatgctt
ttctgtgactggtgagtactcaaccaagtcattctgagaatagtgtatgcggcga
ccgagttgctcttgcccggcgtcaatacgggataataccgcgccacatagcagaa
ctttaaaagtgctcatcattggaaaacgttcttcggggcgaaaactctcaaggat
cttaccgctgttgagatccagttcgatgtaacccactcgtgcacccaactgatct
tcagcatcttttactttcaccagcgtttctgggtgagcaaaaacaggaaggcaaa
atgccgcaaaaaagggaataagggcgacacggaaatgttgaatactcatactctt
cctttttcaatattattgaagcatttatcagggttattgtctcatgagcggatac
atatttgaatgtatttagaaaaataaacaaataggggttccgcgcacatttcccc
gaaaagtgccacctgacgtcgacggatcgggagatctcccgatcccctatggtgc
actctcagtacaatctgctctgatgccgcatagttaagccagtatctgctccctg
cttgtgtgttggaggtcgctgagtagtgcgcgagcaaaatttaagctacaacaag
gcaaggcttgaccgacaattgcatgaagaatctgcttagggttaggcgttttgcg
ctgcttcgcgatgtacgggccagatatacgcgttgacattgattattgactagtt
attaatagtaatcaattacggggtcattagttcatagcccatatatggagttccg
cgttacataacttacggtaaatggcccgcctggctgaccgcccaacgacccccgc
ccattgacgtcaataatgacgtatgttcccatagtaacgccaatagggactttcc
attgacgtcaatgggtggactatttacggtaaactgcccacttggcagtacatca
agtgtatcatatgccaagtacgccccctattgacgtcaatgacggtaaatggccc
gcctggcattatgcccagtacatgaccttatgggactttcctacttggcagtaca
tctacgtattagtcatcgctattaccatggtgatgcggttttggcagtacatcaa
tgggcgtggatagcggtttgactcacggggatttccaagtctccaccccattgac
gtcaatgggagtttgttttggcaccaaaatcaacgggactttccaaaatgtcgta
acaactccgccccattgacgcaaatgggcggtaggcgtgtacggtgggaggtcta
tataagcagagctctctggctaactagagaacccactgcttactggcttatcgaa
attaatacgactcactatagggagacccaagctggtttaaacttaagcttggtac
cgagctcactagtccagtgtggtggcagatatccagcacagtggcggccgctcga

FIG 38B CONT ggggcccgtttgcctgtactgggtctctctggttagaccagatctgagcctggg
agctctctggctaactagggaacccactgcttaagcctcaataaagcttgccttg
agtgcttcaagtagtgtgtgcccgtctgttgtgtgactctggtaactagagatcc
ctcagacccttttagtcagtgtggaaaatctctagcagtggcgcccgaacaggga
cttgaaagcgaaagggaaaccagaggagctctctcgacgcaggactcggcttgct
gaagcgcgcacggcaagaggcgaggggcggcgactggtgagtacgccaaaaattt
tgactagcggaggctagaaggagagagatgggtgcgagagcgtcagtattaagcg
ggggagaattagatcgcgatgggaaaaaattcggttaaggccagggggaaagaaa
aaatataaattaaaacatatagtatgggcaagcagggagctagaacgattcgcag
ttaatcctggcctgttagaaacatcagaaggctgtagacaaatactgggacagct
acaaccatcccttcagacaggatcagaagaacttagatcattatataatacagta
gcaaccctctattgtgtgcatcaaaggatagagataaaagacaccaaggaagctt
tagacaagatagaggaagagcaaaacaaaagtaagaccaccgcacagcaagcggc
cgctgatcttcagacctggaggaggagatatgagggacaattggagaagtgaatt
atataaatataaagtagtaaaaattgaaccattaggagtagcacccaccaaggca
aagagaagagtggtgcagagagaaaaaagagcagtgggaataggagctttgttcc
ttgggttcttgggagcagcaggaagcactatgggcgcagcgtcaatgacgctgac
ggtacaggccagacaattattgtctggtatagtgcagcagcagaacaatttgctg
agggctattgaggcgcaacagcatctgttgcaactcacagtctggggcatcaagc
agctccaggcaagaatcctggctgtggaaagatacctaaaggatcaacagctcct
ggggatttggggttgctctggaaaactcatttgcaccactgctgtgccttggaat
gctagttggagtaataaatctctggaacagatttggaatcacacgacctggatgg
agtgggacagagaaattaacaattacacaagcttaatacactccttaattgaaga
atcgcaaaaccagcaagaaaagaatgaacaagaattattggaattagataaatgg
gcaagtttgtggaattggtttaacataacaaattggctgtggtatataaaattat
tcataatgatagtaggaggcttggtaggtttaagaatagtttttgctgtactttc
tatagtgaatagagttaggcagggatattcaccattatcgtttcagacccacctc
ccaaccccgaggggacccgacaggcccttaattaatcccctgattctgtggataa
ccgtattaccgcctttgagtgagctgcacaaagaaacaaaccaacctgtctgtat
tatcaaagtgaaaggctacaataggacaaagaaacaaaccaacctgtctgtatta
tcaaagtgaaaggctacaataggacaaagaaacaaaccaacctgtctgtattatc
aaagtgaaaggctacaataggacaaagaaacaaaccaacctgtctgtattatcaa
agtgaaaggctacaataggacaaagaaacaaaccaacctgtctgtattatcaaag
tgaaaggctacaataggacaaagaaacaaaccaacctgtctgtattatcaaagtg
aaaggctacaataggacaaagaaacaaaccaacctgtctgtattatcaaagtgaa
aggctacaataggacggtaaactcgacctatataagcagagctcgtttagtgaac
cgtcagatcgcctggagacgccatccacgctgttttgacctccatagaagacacc
gggaccgatccagcctccgcggccccgaattgaattctaacaccgtgcgtgttga
ctattttacctctggcggtgataggccattacggcctgccacc

FIG 38B CONT

ENGINEERED CELLULAR PATHWAYS FOR PROGRAMMED AUTOREGULATION OF DIFFERENTIATION

This application is a continuation of, and claims priority to, co-pending U.S. application Ser. No. 12/312,197, filed on Apr. 29, 2009, which is the U.S. National stage filing of PCT Application No. PCT/US2007/023227, filed on Nov. 1, 2007, now which claims priority to U.S. provisional Patent Application Ser. No. 60/856,531 filed on Nov. 3, 2006, and to U.S. provisional Patent Application Ser. No. 60/905,483 filed on Mar. 7, 2007, each of which is herein incorporated by reference in its entirety for all purposes.

FIELD OF THE INVENTION

The present invention provides compositions and methods for programming mammalian cells to perform desired functions. In particular, the present invention provides compositions and methods for programming stem cells to differentiate into a desired cell type.

BACKGROUND OF THE INVENTION

Diabetes Mellitus is a heterogeneous mix of genetic abnormalities in the insulin-producing machinery ranging from the body's inability to produce enough insulin to the body's inability to recognize and/or use insulin. Type I diabetes is an autoimmune disease which systematically destroys insulin-producing β cells in the pancreas. Type II diabetes is caused by various genetic abnormalities in the pancreas and onset is directly correlated to obesity. The current standard treatment for diabetes is to maintain insulin levels by monitoring blood glucose and diet, to provide exogenous doses of insulin when necessary and to treat the consequences of diabetes such as loss of circulation to the extremities, glaucoma, and sepsis, as the disease progresses [Couper et al., Medical Journal of Australia, 179(8):441-447, 2003]. More radical treatments include full organ transplants, islet cell transplants or β cell transplants. Pancreatic transplantation candidates are put on a long waiting list for a suitable organ. Even when patients are lucky enough to be chosen for an allogeneic pancreatic organ transplant, they must take immunosuppressants in order to battle graft vs. host disease. A recent attempt to use islet cell transplant therapy provided short-lived relief in most patients but the transplanted β cells subsequently died or ceased to produce insulin in a majority of the initial successful transplants [Shapiro et al., New England Journal of Medicine, 355(13):1318-1330, 2006]. Clearly another approach is necessary to alleviate the problems caused by diabetes and address the root cause of the disease.

Recent developments in genome technologies, tissue engineering and synthetic biology offer possibilities to establish highly accurate and robust approaches for predictable and controllable cell fate regulation both temporally and spatially. Stem cell research promises to revolutionize the way many inherited and acquired diseases are treated and will also provide unprecedented insights into fetal development and the etiology of numerous disorders [Hochedlinger et al., N Engl J Med, 349(3):275-286, July 2003; Weissman, Science, 287(5457):1442-1446, February 2000; Lagasse et al., Immunity, 14(4):425-436, April 2001; Reya et al., Nature, 414(6859):105-111, November 2001]. Mouse embryonic stem (mES) cells are an attractive platform for this research because they are amenable to extensive genetic manipulation. When introduced into the appropriate in vitro or in vivo contexts, mES cells contribute to all tissue types of adult mice, including the germ line [Nagy et al., Development, 110(3):815-821, November 1990].

Consequently, there has been much excitement about the potential of these cells as an unlimited source of differentiated cell populations for transplantation or other therapies. Although potentially exciting and ground-breaking, ES cell-based therapies depend on the ability to reliably and controllably produce the necessary mature cell populations. In addition, directed differentiation must be absolute, given the tumorigenic potential of ES cells. With few exceptions, such directed production of desired cell populations has not been possible yet.

Current approaches towards tissue engineering and transplantation rely on carefully creating environments that induce cells to differentiate into desired tissues or organs. While these approaches have proven partially effective for certain applications, they are inherently limited since they rely on innate cellular response to existing host conditions or exogenous cues. Often, naturally occurring host conditions are insufficient to trigger the correct differentiation pathways. In those instances, researchers have attempted to provide appropriate environmental cues using scaffolds and exogenous signals. However, it is often difficult, if not impossible, to create and maintain the precise conditions that are required for tissue regeneration using such means.

What is needed in the art are systems and methods that can be used to cause stem cells to reliably differentiate into a desired cell type based on expression of genes introduced into the stem cells.

SUMMARY OF THE INVENTION

The present invention provides compositions and methods for programming mammalian cells to perform desired functions. In particular, the present invention provides compositions and methods for programming stem cells to differentiate into a desired cell type. Accordingly, in some embodiments, the present invention provides systems for directing differentiation of an undifferentiated cell type comprising: a) a first mammalian vector comprising a first gene encoding a protein that synthesizes an autoinducer; b) a second mammalian vector comprising a second gene encoding a regulatory protein that interacts with the autoinducer; c) a third mammalian vector comprising a promoter that binds to the regulatory protein in the presence of the autoinducer, the promoter operably linked to a third gene of interest encoding a first cell fate regulator. In some embodiments, the systems of the present invention further comprise a fourth mammalian vector comprising a promoter comprising a response element that binds to a regulatory protein produced in response to expression of the first cell fate regulator. The present invention is not limited to the use of any particular type of mammalian vector. Indeed, the use of a variety of mammalian vectors is contemplated, including, but not limited to lentiviral vectors, retroviral vectors, pseudotyped retroviral or lentiviral vectors, adenoviral vectors, AAV vectors, plasmids, artificial chromosomes, transposon vectors and the like.

In some embodiments, the first mammalian vector further comprises a promoter operably linked to the first gene. The present invention is not limited to the use of any particular promoter. Indeed, the use of a variety of promoters is contemplated. In some embodiments, the promoter is a repressible promoter. In some embodiments the promoter comprises a lac repressor. In some embodiments, the promoter is an inducible promoter. In some embodiments, the inducible promoter is a Tet promoter. The present invention is not limited to vectors encoding genes that synthesize any particular autoinducer. Indeed, the use of a variety of autoinducers is contemplated, including, but not limited to 30C6HSL, C4HSL, and 3OC14HSL. The present invention is not limited to the use of genes encoding any particular autoinducer. Indeed, the use of several genes that encode proteins that catalyze the synthesis of autoinducers is contemplated, included but not limited to the LuxI, Rh1I, and CinI proteins. The present inventions is not limited to the use of the any particular genes encoding LuxI, Rh1I, or CinI. In some embodiments, the genes comprise codons that are optimized for expression in mammalian cells. In other embodiments, the genes utilized are at least 70%, 80%, 90% or 95% identical to the wild type LuxI, Rh1I or CinI wild-type genes.

In some preferred embodiments, the second mammalian vector comprises a gene encoding a regulatory protein that interacts with the autoinducer synthesized by the protein encoded by the gene of interest in the first vector. The present invention is not limited to the use of any particular regulatory protein. Indeed, the use of a variety of regulatory proteins is contemplated, including, but not limited to LuxR, Rh1R, and CinR. The present inventions is not limited to the use of the any particular genes encoding LuxR, Rh1R, or CinR. In some embodiments, the genes comprise codons that are optimized for expression in mammalian cells. In other embodiments, the genes utilized are at least 70%, 80%, 90% or 95% identical to the wild type LuxR, Rh1R or CinR wild-type genes.

The present invention is not limited to the use of any particular promoter in the third vector of the system of the present invention. In some embodiments, the third mammalian vector comprises a promoter selected from the group consisting of lux and LasR promoters. In some preferred embodiments, the lux promoter comprises multiple repeats of the lux binding sequence, which binds LuxR/autoinducer complex. Likewise, the vectors for use in the systems of the present invention may comprise promoters comprising multiple repeats of the binding sequences recognized by the Rh1I and CinI autoinducer complexes. The present invention is not limited to the use of vectors encoding any particular cell fate regulator. In some embodiments, the first cell fate regulator is selected from the group consisting of Sox17, Gata4, and Gata6 and combinations thereof. In further embodiments, the vectors used in the systems of the present invention encode two or more of the cell fate regulators selected from the group consisting of Sox17, Gata4, Gata6, Pdx1, Ngn3, Nkx6.1, Nkx2.2, Fgf4, BRA, Wnt9, NCAD, CER, FoxA2, CxcR4, Hnf1B, Hnf4A, Hnf6, H1xB9, Pax4, Cgc, GHRL, SST, PPY, Activin, Fgf10, Cyc, RA, Ex4, DAPT, HGF and Igf1.

In some embodiments of the systems of the present invention, the fourth mammalian vector further comprises a gene encoding a second cell fate regulator. The present invention is not limited to the use of any particular second cell fate messenger. In some embodiments, the second cell fate regulator is selected from the group consisting of Pdx1, Ngn3, Nkx6.1, Nkx2.2, Fgf4, BRA, Wnt9, NCAD, CER, FoxA2, CxcR4, Hnf1B, Hnf4A, Hnf6, H1xB9, Pax4, Cgc, GHRL, SST, PPY, Activin, Fgf10, Cyc, RA, Ex4, DAPT, HGF and Igf1. In some embodiments, the systems of the present invention comprise multiple vectors encoding one or more of the foregoing cell fate regulators. The fourth vectors of the systems of the present invention are not limited to the use of any particular promoter. Indeed, a variety of stage specific promoters may be utilized. In some embodiments, the promoter comprising a response element that binds to a regulatory protein produced in response to expression of the first cell fate regulator comprises an α-fetoprotein promoter.

In some embodiments, the systems of the present invention comprise vectors encoding additional proteins involved in a quorum sensing pathway. Accordingly, in some embodiments, the systems of the present invention comprise a fifth mammalian vector comprising a gene encoding an acyl carrier protein (ACP). In further embodiments, the systems of the present invention comprise a sixth mammalian vector comprising a gene encoding acyl-acyl carrier protein synthase (AAS). The present invention is not limited to vectors comprising any particular ACP or AAS genes. In some embodiments, the genes comprise codons optimized for expression in a mammalian cells. In further embodiments, the genes are at least 70%, 80%, 90% or 95% identical to the wild type ACP or ASS genes.

In some embodiments, the systems of the present invention further comprise a separate vector encoding comprising a gene encoding Rh1R. In some embodiments, the systems of the present invention further comprise a separate mammalian vector comprising a gene encoding Growth Arrest Factor. In some embodiments, the systems of the present invention further comprise a mammalian vector comprising a gene encoding TetR. In some embodiments, the systems of the present invention further comprise a separate mammalian vector comprising a gene of interest encoding a protein selected from the group consisting of TetR, LacI, and CinI operably linked to a Mouse Insulin promoter.

In some embodiments, the present invention provides a culture of mammalian cells comprising one or more of the foregoing vectors of the system of the present invention. In some embodiments, the present invention provides a mammalian cell comprising one or more of the foregoing vectors of the system of the present invention. The present invention is not limited to the use of any particular type of mammalian cells. In some embodiments, the cell is totipotent cell. In some embodiments, the cell is a multipotent cell. In some embodiments, the cell is a differentiated cell. In some embodiments, the cell or cell culture comprises cells selected from the group consisting of embryonic stem cells, adult stem cells or cord blood stem cells. The present invention is not limited to mammalian cells of any particular species. In some embodiments, the cells are human, primate, mouse, cow, hamster, rat, pig, sheep or goat cells. In some embodiments, the differentiated cells are β-cells. In some embodiments, the cells produce insulin.

In some embodiments, the present invention provides methods of treating a patient comprising: providing a patient in need of treatment and the mammalian cells described in the foregoing paragraphs, and introducing the cells into the patient. In some embodiments, the patient is diabetic. In some embodiments, the mammalian cells produce insulin after introduction into the patient.

In some embodiments, the present invention provides methods of programming mammalian cells comprising: introducing a quorum sensing system into a mammalian cell, wherein the system causes production of an autoinducer molecule and a regulatory partner of the autoinducer; introducing an expression system for at least one cell fate regulator into the mammalian cell; culturing the cell under conditions such that the cell produces the autoinducer, wherein the autoinducer interacts with the regulatory partner to induce expression of the at least one cell fate regulator.

In some embodiments, the present invention provides methods of programming mammalian cells comprising 1) providing i) a mammalian cell, ii) a first vector encoding a protein that synthesizes an autoinducer molecule; iii) a second vector encoding a regulatory partner of the autoinducer; iv) a third vector encoding a gene of interest operably linked to a promoter activated by the interaction of the autoinducer and the regulatory partner; 2)

introducing the vectors into the mammalian cell; 3) culturing the mammalian cell under conditions such that the regulatory partner and the autoinducer are synthesized and activate expression of the gene of interest.

In some embodiments, the present invention provides a mammalian cell comprising an exogenous gene selected from the group consisting of genes encoding LuxI, LuxR, Rh1I, Rh1R, CinI, and CinR. In some embodiments, the present invention provides a mammalian cell comprising an exogenous gene selected from the group consisting of Sox17, Gata4, and Gata6, wherein the exogenous gene is operably linked to a lux promoter. In some embodiments, the present invention provides a mammalian cell comprising an exogenous gene selected from the group consisting of Pdx1, Ngn3, Nkx6.1, Nkx2.2, Fgf4, BRA, Wnt9, NCAD, CER, FoxA2, CxcR4, Hnf1B, Hnf4A, Hnf6, H1xB9, Pax4, Cgc, GHRL, SST, PPY, Activin, Fgf10, Cyc, RA, Ex4, DAPT, HGF and Igf1, wherein the exogenous gene is operably linked to a endoderm specific promoter. In some embodiments, the endoderm specific promoter is the α-fetoprotein promoter.

In some embodiments, the present invention provides a mammalian cell comprising a quorum sensing pathway. In some embodiments, the quorum sensing pathway comprises one or more exogenous genes encoding Lux1, LuxR, acyl carrier protein and acyl-acyl carrier protein synthase.

In some embodiments, the present invention provides a system for use in establishing tissue homeostasis in a differentiating cell system comprising mammalian vectors encoding at least one cell-cell communication system, wherein said at least a first cell-cell communication system controls proliferation or differentiation of cells in said differentiating cell system. In some embodiments, the systems further comprise at least a second cell-cell communication system, wherein said first and second cell-cell communication systems interact to establish homeostasis in said differentiating cell system. In some embodiments, the differentiating cells system comprises differentiable cells and differentiated cells produced from said differentiable cells. In some embodiments, the homeostasis is characterized by the controlled proliferation of said differentiable cells comprising said at least two cell-cell communication systems and the controlled production of said differentiated cells. In further embodiments, the at least two cell-cell communication systems interact to establish tissue homeostasis in a differentiating cell system comprising differentiable cells and differentiated cells by sensing the number of differentiating cells via the first cell-cell communication system and the number of differentiated cells via the second cell-cell communication system so that when the number of differentiable cells is low proliferation of the differentiable cells is induced, when the number of differentiable cells is high the proliferation of the differentiable is cells in inhibited, when the number of differentiated cells is low the differentiation of the differentiable cells is induced and the proliferation of the differentiable cells is induced, and when the number of differentiated cells is high the differentiation of the differentiable cells is inhibited. The present invention is not limited to the use of any particular cell-cell communication systems. Indeed, the use of a variety of cell-cell communication systems is contemplated. In some embodiments, the at least one cell-cell communication system is a bacterial cell-cell communication systems. In other embodiments, the at least one cell-cell communication system is selected from the group consisting of the LuxI, Rh1I, and CinI cell-cell communication systems. The present invention is not limited to the use of any particular type of vector. Indeed, the use of a variety of vectors is contemplated. In some embodiments, the mammalian vectors are retroviral vectors. In further embodiments, the systems of the present invention further comprise a cell differentiation control system.

In some embodiments, the present invention provides a differentiable cell comprising the foregoing systems, wherein said differentiable cell is cultured in vitro. In further embodiments, the present invention provides a differentiable mammalian cell comprising at least a first cell-cell communication pathway, wherein said first cell-cell communication pathway is encoded by exogenous genes. In some embodiments, the cells further comprise at least a second cell communication pathway. In some embodiments, the cell differentiates into a target differentiated cell. The present invention is not limited to any particular type of cell. Indeed, the use of a variety of cell types is contemplated. In some embodiments, the cell is a pluripotent, multipotent or totipotent cell. The present invention is not limited to the use of any particular cell-cell communication systems. Indeed, the use of a variety of cell-cell communication systems is contemplated. In some embodiments, the at least one cell-cell communication system is a bacterial cell-cell communication systems. In other embodiments, the at least one cell-cell communication system is selected from the group consisting of the LuxI, Rh1I, and CinI cell-cell communication systems. In some embodiments, the cell further comprises an exogenous cell differentiation pathway. In some embodiments, the first cell-cell communication pathway is a CinI/CinR cell-cell communication pathway. In some embodiments, the CinI/CinR cell-cell communication pathway comprises at least a first gene encoding CinI, a second gene encoding CinR, and a third gene of interest operably linked to a CinR/30C14HSL inducible promoter. In some embodiments, the second cell-cell communication pathway is a Rh1I/Rh1R cell-cell communication pathway. In some embodiments, the Rh1I/Rh1R cell-cell communication pathway comprises at least a first gene encoding Rh1I, a second gene encoding Rh1R, and a third gene of interest operably linked to a Rh1R/C4HSL inducible promoter. In some embodiments, the cell comprises a cell differentiation pathway. In some embodiments, the cell differentiation pathway comprises at least one exogenous gene encoding a cell fate regulator. The present invention is not limited to the use of any particular cell fate regulator. Indeed, the use of a variety of cell fate regulators is contemplated, including, but not limited to, Sox17, Gata4, Gata6, Pdx1, Ngn3, Nkx6.1, Nkx2.2, Fgf4, BRA, Wnt9, NCAD, CER, FoxA2, CxcR4, Hnf1B, Hnf4A, Hnf6, H1xB9, Pax4, Cgc, GHRL, SST, PPY, Activin, Fgf10, Cyc, RA, Ex4, DAPT, HGF and Igf1. In some embodiments, the third gene of interest operably linked to a Rh1R/C4HSL inducible promoter is a protein that inhibits growth in a cell. In further embodiments, the protein that inhibits growth in a cell is Growth Arrest Factor. In some embodiments, the third gene of interest operably linked to a CinR/30C14HSL inducible promoter is a repressor. In some embodiments, the repressor is lambda repressor. In some embodiments, the first and second cell-cell communication pathways interact to control proliferation and differentiation of said mammalian cell. In some embodiments, the cell differentiation pathway comprises at least one gene encoding a protein that causes said cell to differentiate into a target differentiated cell. In some embodiments, the target differentiated cell is a beta cell. In some embodiments, the second cell-cell communication pathway is activated in said target differentiated cell and comprises at least one gene encoding a protein that inhibits the proliferation of undifferentiated cells comprising said first and second cell-cell communication pathways. In some embodiments, the cell differentiation pathway is activated in said target differentiated cell and comprises at least one gene encoding a protein that regulates expression of said at least one gene encoding a protein that causes undifferentiated cells comprising said first and second cell-cell communication pathways to differentiate into a target differentiated cell. In some embodiments, the gene encoding a protein that regulates expression of said at least one gene encoding a protein that causes undifferentiated cells comprising said first and second cell-cell communication pathways to differentiate into a target differentiated cell is a repressor. In some embodiments, the repressor is a lambda repressor. In some embodiments, the cell is maintained in vitro.

The present invention further provides methods of controlling proliferation and differentiation of a differentiable cell comprising: a) providing: i) a differentiable cell; and ii) at least one cell-cell communication pathway; and b) introducing said at least one cell-cell communication pathway into said differentiable cell so that when said at least one cell-cell communication pathway is expressed in said differentiable cell, the proliferation and differentiation of said differentiable cell is controlled. In some embodiments, the two cell-cell communication pathways are introduced into said differentiable cells and wherein said two cell communication pathways interact to control proliferation and differentiation of said differentiable cell and proliferation of target differentiated cells that differentiate from said differentiable cells. In some embodiments, the at least one of said two cell-cell communication pathways provides regulatory feedback on differentiation of said differentiable cells. The present invention is not limited to the use of any particular cell-cell communication pathway. Indeed, the use of a variety of cell-cell communication pathways is contemplated. In some embodiments, the at least one cell-cell communication pathway is a bacterial cell-cell communication systems. In other embodiments, the at least one cell-cell communication pathway is selected from the group consisting of the LuxI, Rh1I, and CinI cell-cell communication systems.

In some embodiments, the present invention provides methods of treating a subject comprising: a) providing a plurality of mammalian cells as described above; and b) introducing said cells into a subject under conditions such that the proliferation and differentiation of said cells is controlled to provide a source of differentiated target cells in said subject. In some embodiments, the subject is human.

In some embodiments, the present invention provides a symmetry breaking system for mammalian cells comprising a first vector comprising an activator operably linked to a promoter responsive to the activator and a repressor and a second vector encoding a repressor operably linked to promoter responsive to said activator. In some embodiments, the present invention provides a population of cells comprising the symmetry breaking system, wherein expression of the activator causes activation of the activator and the repressor and expression of the repressor causes repression of the activator, so that at any given time only a portion of the cells within the population have high levels of expression of the activator as compared to the repressor.

In some embodiments, the present invention provides a cascade system for mammalian cells comprising a first vector encoding a first repressor operably linked to a promoter responsive to a first activator, a second vector encoding a second repressor operably linked to promoter repressed by said first repressor, and a third vector encoding a second activator operably linked to a promoter repressed by said second repressor, and a fourth vector encoding a repressor operably linked to a promoter that is activated by said second activator and repressed by a third repressor. In some embodiments, the present invention provides a population of cells comprising the cascade system.

In some embodiments, the present invention provides a toggle switch system for mammalian cells comprising a first vector encoding first repressor operably linked to a promoter repressed by a second repressor and a second vector encoding said second repressor operably linked to a promoter repressed by said first repressor. In some embodiments, the first repressor is TetR and said second repressor is LacI. In some embodiments, the present invention provides cells comprising the toggle switch system.

In some embodiments, the present invention provides a population of uncommitted and committed cells comprising: a) a cell population control module comprising a first cell-cell communication pathway; b) a cell commitment module comprising a symmetry breaking system and a second cell-cell communication system; and c) a cell differentiation module; wherein said cell population control module senses the concentration of uncommitted cells in the population via said first cell-cell communication system, the cell commitment module senses the concentration of committed cells in the population via said second cell-cell communication system and controls which cells within the population are allowed to commit via said symmetry breaking system, so that when the concentration of uncommitted cells in the population is high, the concentration of committed cells in the population is low, and there are cells that allowed to commit, said cell differentiation module is activated. In some embodiments, the cell communication module further comprises a cascade system and a toggle switch system that interact with said symmetry breaking system and said second cell-cell communication system to control the commitment of cells within the population to differentiate. In some embodiments, the cells further comprise an apoptosis module. In some embodiments, the apoptosis module comprises a vectors encoding a repressor operably linked to a tissue-specific promoter and a vector encoding an apoptosis gene operably linked to a promoter regulated by said repressor, so that said apoptosis gene is not expressed in a tissue wherein said tissue-specific promoter is active.

In some embodiments, the present invention provides a fusion protein comprising a secretion signal, cell penetrating polypeptide, and trans acting domain in operable combination, wherein at least one of said secretion signal, cell penetrating polypeptide and trans acting domain are from different proteins. The present invention is not limited to the use of any particular secretion signal. Indeed, the use of a variety of secretion signals is contemplated, including, but not limited to IgG, t PA, serum albumin, lactoferrin, and growth hormone secretion signals. The present invention is not limited to the use of any particular cell penetrating polypeptide. Indeed, the use of a variety of cell penetrating polypeptides is contemplated, including, but not limited to, TAT cell penetrating polypeptide and penetratin. The present invention is not limited to the use of any particular trans-acting domain. Indeed, the use of variety of trans-acting domains is contemplated, including, but not limited to, zinc finger binding domains. In further embodiments, the present invention provides nucleic acids encoding the fusion proteins. In further embodiments, the present invention provides a vector comprising the nucleic acid encoding the fusion protein. In still further embodiments, the present invention provides a cell comprising the nucleic acid.

In some embodiments, the present invention provides a cell-cell communication system comprising: a) a first vector comprising a nucleic acid encoding a fusion protein comprising a secretion signal, cell penetrating polypeptide, and trans-acting domain in operable combination and b) a second vector comprising a nucleic acid encoding a promoter comprising an element that binds said trans-acting domain operably linked to a protein of interest. In further embodiments, the present invention provides a population of cells comprising the system.

DESCRIPTION OF THE FIGURES

FIG. 5 provides the sequence (SEQ ID NO:01) for the LuxI vector-pLV-Hef1a-LuxIm-IRES2-DsRed2.

FIG. 7 provides a description and sequence (SEQ ID NO:02) for the LuxR vector-pLV-Hef1a-p65H4LuxRFm-IRES2-DsRed2.

FIG. 9 provides a description and sequence (SEQ ID NO:03) for the lux promoter vector for expression of Gata4/Sox17-pLV-minCMVLuxO7-IRES2-EGFP.

FIG. 11 provides a description and sequence (SEQ ID NO:04) for the ACP vector-pLV-Hef1a-ACPm-IRES2-DsRed2

FIG. 13 provides a description and sequence (SEQ ID NO:05) for the AAS vector-pLV-Hef1a-AAS-IRES2-EGFP.

FIG. 15 provides a description and sequence (SEQ ID NO:06) for the AFP promoter vector PDX1-pLV-AFP-Pdx1-IRES2-DsRed2.

FIG. 17 provides a description and sequence (SEQ ID NO:07) for the AFP promoter vector Ngn3-pLV-AFP-Ngn3-IRES2-DsRed2.

FIG. 19 provides a description and sequence (SEQ ID NO:08) for the AFP promoter vector for TetRKRAB-pLV-AFP-TetRKRAB-IRES2-DsRed2.

FIG. 21 provides a description and sequence (SEQ ID NO:09) for the Rh1I vector-pLV-Hef1a-Rh1I-IRES2-DsRed2.

DEFINITIONS

Figure 1A:
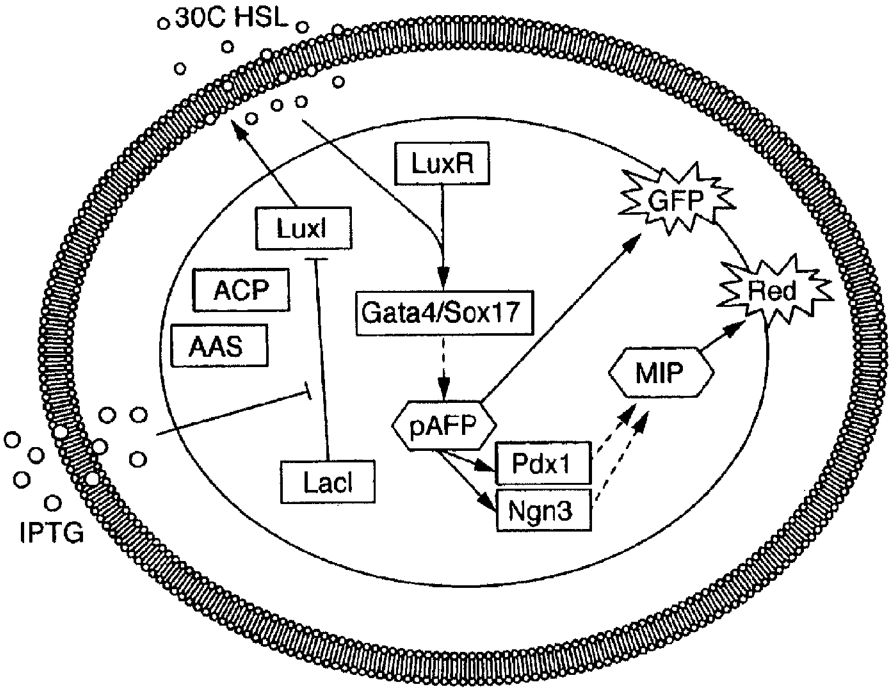
FIG. 1: Autoregulated quorum sensing based two-step differentiation from mES to endoderm to β cells. (a) Circuit diagram of the system. Details are in the text. Gata4/Sox17 activates the α-fetoprotein promoter (pAFP) indirectly by stimulating expression of AFP (dashed line). Likewise, Pdx1 and Ngn3 activate the Mouse Insulin Promoter (MIP) indirectly by stimulating insulin production (dashed lines). AFP production results in green fluorescence and insulin production results in red fluorescence. (b) Progress of system from a single cell to a collection of β cells. Due to quorum sensing, a population of mES cells is necessary in order to differentiate into endoderm.
Figure 1B:
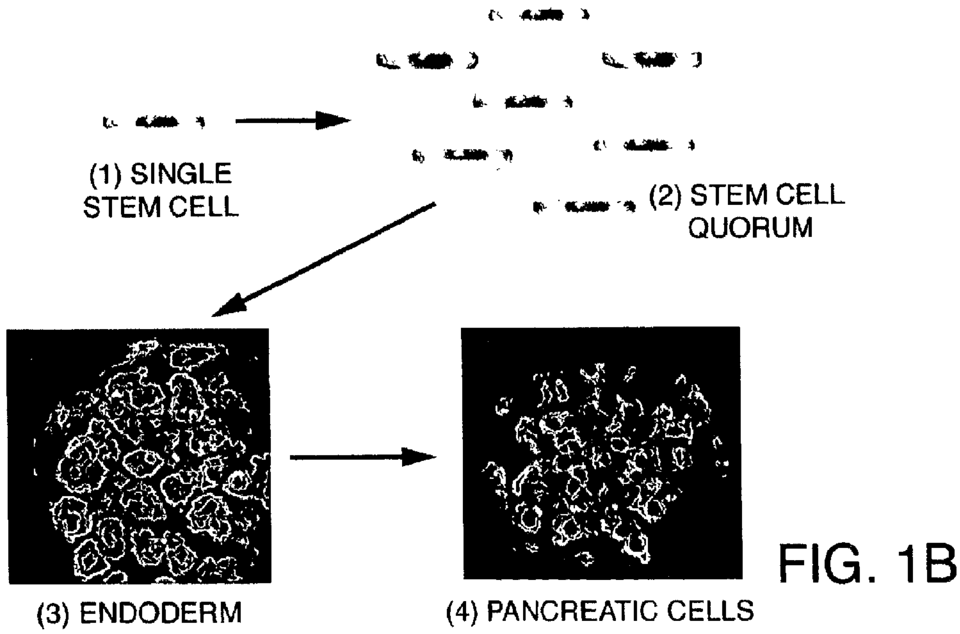

As used herein, the term "quorum sensing" refers to the detection of the density of a cell type by means of cell-cell communications. In some embodiments, "quorum sensing" is associated with an action upon achievement of a certain cell density.

As used herein, the term "quorum sensing system" refers to a system of genes that provides components for quorum sensing.

As used herein, the term "totipotent" means the ability of a cell to differentiate into any type of cell in a differentiated organism.

As used herein, the term "pluripotent" refers to a cell line capable of differentiating into several differentiated cell types.

As used herein, the term "multipotent" refers to a cell line capable of differentiating into at least two differentiated cell types.

As used herein, the term "host cell" refers to any eukaryotic cell (e.g., mammalian cells, avian cells, amphibian cells, plant cells, fish cells, and insect cells), whether located in vitro or in vivo.

As use herein, the term "stem cells" means cells that are totipotent or pluripotent and are capable of differentiating into one or more different cell types.

As use herein, the term "embryonic stem cells" means stem cells derived from an embryo.

As used herein, the term "adult stem cells" means stem cells derived from an organism after birth.

As used herein, the term "mesodermal cell line" means a cell line displaying characteristics associated with mesodermal cells.

As used herein, the term "endodermal cell line" means a cell line displaying characteristics normally associated with endodermal cells.

As used herein, the term "neural cell line" means a cell line displaying characteristics normally associated with neural cell lines. Examples of such characteristics include, but are not limited to, expression of GFAP, neuron-specific enolase, Neu-N, neurofilament-N, or tau.

As used herein the term "differentiable cell" refers to a cell that can differentiate into another cell type and includes multipotent, pluripotent and totipotent cells.

As used herein, the term "target differentiated cell" refers to a predetermined cell type that differentiates from a differentiable cell.

As used herein, the term "differentiating cell system" refers to a population of differentiable cells and target differentiated cells.

As used herein, the term "tissue homeostasis" refers to a steady state achieved between a population of differentiable cells and target differentiated cells in a differentiating cell system wherein cell-cell communication between the differentiable cells and the target differentiated cells controls the number of differentiable cells and target differentiated cells in the system.

As used herein, the term "proliferation" as used with respect to cells in a differentiating cell system refers to the production of cells of like type from a given cell population, such as the production of additional differentiable cells from a population of differentiable cells.

As used herein, the term "differentiation" as used with respect to cells in a differentiating cell system refers to the process by which cells differentiate from one cell type (e.g., a multipotent, totipotent or pluripotent differentiable cell) to another cell type such as a target differentiated cell (e.g., a beta cell).

The term "cell-cell communication pathway" refers to a network of two or more genes encoding proteins (e.g., LuxR, CinR, Rh1R) and proteins that synthesize products (e.g., $3OC_6HSL$, $C_{14}HSL$, $C_4HSL$) that are involved in cell-cell communication. Exemplary cell-cell communication pathways include, but are not limited to the LuxI/LuxR, CinI/CinR, Rh1I/Rh1R. As a further example, the LuxI/LuxR cell-cell communication pathway can include the LuxI and LuxR genes. Additionally the LuxI/LuxR cell-cell communication pathway can include a gene of interest operably linked to promoter induced by LuxR/$3OC_6HSL$. The CinI/CinR cell-cell communication pathway can include the CinI and CinR genes. Additionally the CinI/CinR cell-cell communication pathway can include a gene of interest operably linked to promoter induced by CinR/$C_{14}HSL$. The Rh1I/Rh1R cell-cell communication pathway can include the Rh1I and Rh1R genes. Additionally the Rh1I/Rh1R cell-cell communication pathway can include a gene of interest operably linked to promoter induced by Rh1R/$C_4HSL$.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "multiplicity of infection" or "MOI" refers to the ratio of integrating vectors:host cells used during transfection or transduction of host cells. For example, if 100,000 vectors are used to transduce 100,000 host cells, the multiplicity of infection is 1. The use of this term is not limited to events involving transduction, but instead encompasses introduction of a vector into a host by methods such as lipofection, microinjection, calcium phosphate precipitation, and electroporation.

As used herein, the term "genome" refers to the genetic material (e.g., chromosomes) of an organism.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

As used herein, the term "exogenous gene" refers to a gene that is not naturally present in a host organism or cell, or is artificially introduced into a host organism or cell.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$=81.5+0.41(% G+C), when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "selectable marker" refers to a gene that encodes an enzymatic activity that confers the ability to grow in medium lacking what would otherwise be an essential nutrient (e.g. the HISS gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene, which is used in conjunction with CAD-deficient cells, and the mammalian hypoxanthine-guanine phosphoribosyl transferase (hprt) gene, which is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter.

Regulatory elements may be tissue specific or cell specific. The term "tissue specific" as it applies to a regulatory element refers to a regulatory element that is capable of directing selective expression of a nucleotide sequence of interest to a specific type of tissue (e.g., liver) in the relative absence of expression of the same nucleotide sequence of interest in a different type of tissue (e.g., lung).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

The term "cell type specific" as applied to a regulatory element refers to a regulatory element that is capable of directing selective expression of a nucleotide sequence of interest in a specific type of cell in the relative absence of expression of the same nucleotide sequence of interest in a different type of cell within the same tissue. The term "cell type specific" when applied to a regulatory element also means a regulatory element capable of promoting selective expression of a nucleotide sequence of interest in a region within a single tissue.

Cell type specificity of a regulatory element may be assessed using methods well known in the art (e.g., immunohistochemical staining and/or Northern blot analysis). Briefly, for immunohistochemical staining, tissue sections are embedded in paraffin, and paraffin sections are reacted with a primary antibody specific for the polypeptide product encoded by the nucleotide sequence of interest whose expression is regulated by the regulatory element. A labeled (e.g., peroxidase conjugated) secondary antibody specific for the primary antibody is allowed to bind to the sectioned tissue and specific binding detected (e.g., with avidin/biotin) by microscopy. Briefly, for Northern blot analysis, RNA is isolated from cells and electrophoresed on agarose gels to fractionate the RNA according to size followed by transfer of the RNA from the gel to a solid support (e.g., nitrocellulose or a nylon membrane). The immobilized RNA is then probed with a labeled oligo-deoxyribonucleotide probe or DNA probe to detect RNA species complementary to the probe used. Northern blots are a standard tool of molecular biologists.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one that is capable of directing a level of transcription of an operably linked nucleic acid sequence in the presence of a stimulus (e.g., heat shock, chemicals, etc.), which is different from the level of transcription of the operably linked nucleic acid sequence in the absence of the stimulus.

As used herein, the term "nucleic acid binding protein" refers to proteins that bind to nucleic acid, and in particular to proteins that cause increased (i.e., activators or transcription factors) or decreased (i.e., inhibitors, repressors) transcription from a gene.

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

As used herein, the term "long terminal repeat" of "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

As used herein, the terms "RNA export element" or "Pre-mRNA Processing Enhancer (PPE)" refer to 3' and 5' cis-acting post-transcriptional regulatory elements that enhance export of RNA from the nucleus. "PPE" elements include, but are not limited to Mertz sequences (described in U.S. Pat. Nos. 5,914,267 and 5,686,120, all of which are incorporated herein by reference) and woodchuck mRNA processing enhancer (WPRE; WO99/14310 and U.S. Pat. No. 6,136,597, each of which is incorporated herein by reference).

As used herein, the term "polycistronic" refers to an mRNA encoding more than polypeptide chain (See, e.g., WO 93/03143, WO 88/05486, and European Pat. No. 117058, all of which are incorporated herein by reference). Likewise, the term "arranged in polycistronic sequence" refers to the arrangement of genes encoding two different polypeptide chains in a single mRNA.

As used herein, the term "internal ribosome entry site" or "IRES" refers to a sequence located between polycistronic genes that permits the production of the expression product originating from the second gene by internal initiation of the translation of the dicistronic mRNA. Examples of internal ribosome entry sites include, but are not limited to, those derived from foot and mouth disease virus (FDV), encephalomyocarditis virus, poliovirus and RDV (Scheper et al., Biochem. 76: 801-809 [1994]; Meyer et al., J. Virol. 69: 2819-2824 [1995]; Jang et al., 1988, J. Virol. 62: 2636-2643 [1998]; Haller et al., J. Virol. 66: 5075-5086 [1995]). Vectors incorporating IRES's may be assembled as is known in the art. For example, a retroviral vector containing a polycistronic sequence may contain the following elements in operable association: nucleotide polylinker, gene of interest, an internal ribosome entry site and a mammalian selectable marker or another gene of interest. The polycistronic cassette is situated within the retroviral vector between the 5' LTR and the 3' LTR at a position such that transcription from the 5' LTR promoter transcribes the polycistronic message cassette. The transcription of the polycistronic message cassette may also be driven by an internal promoter (e.g., cytomegalovirus promoter) or an inducible promoter, which may be preferable depending on the use. The polycistronic message cassette can further comprise a cDNA or genomic DNA (gDNA) sequence operatively associated within the polylinker. Any mammalian selectable marker can be utilized as the polycistronic message cassette mammalian selectable marker. Such mammalian selectable markers are well known to those of skill in the art and can include, but are not limited to, kanamycin/G418, hygromycin B or mycophenolic acid resistance markers.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell. The term "retrovirus" encompasses Oncovirinae (e.g., Moloney murine leukemia virus (MoMOLV), Moloney murine sarcoma virus (MoMSV), and Mouse mammary tumor virus (MMTV), Spumavirinae, amd Lentivirinae (e.g., Human immunodeficiency virus, Simian immunodeficiency virus, Equine infection anemia virus, and Caprine arthritis-encephalitis virus; See, e.g., U.S. Pat. Nos. 5,994,136 and 6,013,516, both of which are incorporated herein by reference).

As used herein, the term "retroviral vector" refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells that are susceptible to infection by the retrovirus. Through well known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

The term "pseudotyped retroviral vector" refers to a retroviral vector containing a heterologous membrane protein. The term "membrane-associated protein" refers to a protein (e.g., a viral envelope glycoprotein or the G proteins of viruses in the Rhabdoviridae family such as VSV, Piry, Chandipura and Mokola) that are associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

The term "heterologous membrane-associated protein" refers to a membrane-associated protein which is derived from a virus that is not a member of the same viral class or family as that from which the nucleocapsid protein of the vector particle is derived. "Viral class or family" refers to the taxonomic rank of class or family, as assigned by the International Committee on Taxonomy of Viruses.

The term "Rhabdoviridae" refers to a family of enveloped RNA viruses that infect animals, including humans, and plants. The Rhabdoviridae family encompasses the genus Vesiculovirus that includes vesicular stomatitis virus (VSV), Cocal virus, Piry virus, Chandipura virus, and Spring viremia of carp virus (sequences encoding the Spring viremia of carp virus are available under GenBank accession number U18101). The G proteins of viruses in the Vesiculovirus genera are virally-encoded integral membrane proteins that form externally projecting homotrimeric spike glycoproteins complexes that are required for receptor binding and membrane fusion. The G proteins of viruses in the Vesiculovirus genera have a covalently bound palmititic acid ($C_{16}$) moiety. The amino acid sequences of the G proteins from the Vesiculoviruses are fairly well conserved. For example, the Piry virus G protein share about 38% identity and about 55% similarity with the VSV G proteins (several strains of VSV are known, e.g., Indiana, New Jersey, Orsay, San Juan, etc., and their G proteins are highly homologous). The Chandipura virus G protein and the VSV G proteins share about 37% identity and 52% similarity. Given the high degree of conservation (amino acid sequence) and the related functional characteristics (e.g., binding of the virus to the host cell and fusion of membranes, including syncytia formation) of the G proteins of the Vesiculoviruses, the G proteins from non-VSV Vesiculoviruses may be used in place of the VSV G protein for the pseudotyping of viral particles. The G proteins of the Lyssa viruses (another genera within the Rhabdoviridae family) also share a fair degree of conservation with the VSV G proteins and function in a similar manner (e.g., mediate fusion of membranes) and therefore may be used in place of the VSV G protein for the pseudotyping of viral particles. The Lyssa viruses include the Mokola virus and the Rabies viruses (several strains of Rabies virus are known and their G proteins have been cloned and sequenced). The Mokola virus G protein shares stretches of homology (particularly over the extracellular and transmembrane domains) with the VSV G proteins which show about 31% identity and 48% similarity with the VSV G proteins. Preferred G proteins share at least 25% identity, preferably at least 30% identity and most preferably at least 35% identity with the VSV G proteins. The VSV G protein from which New Jersey strain (the sequence of this G protein is provided in GenBank accession numbers M27165 and M21557) is employed as the reference VSV G protein.

As used herein, the term "lentivirus vector" refers to retroviral vectors derived from the Lentiviridae family (e.g., human immunodeficiency virus, simian immunodeficiency virus, equine infectious anemia virus, and caprine arthritis-encephalitis virus) that are capable of integrating into non-dividing cells (See, e.g., U.S. Pat. Nos. 5,994,136 and 6,013,516, both of which are incorporated herein by reference).

The term "pseudotyped lentivirus vector" refers to lentivirus vector containing a heterologous membrane protein (e.g., a viral envelope glycoprotein or the G proteins of viruses in the Rhabdoviridae family such as VSV, Piry, Chandipura and Mokola).

As used herein, the term "transposon" refers to transposable elements (e.g., Tn5, Tn7, and Tn10) that can move or transpose from one position to another in a genome. In general, the transposition is controlled by a transposase. The term "transposon vector," as used herein, refers to a vector encoding a nucleic acid of interest flanked by the terminal ends of transposon. Examples of transposon vectors include, but are not limited to, those described in U.S. Pat. Nos. 6,027,722; 5,958,775; 5,968,785; 5,965,443; and 5,719,055, all of which are incorporated herein by reference.

As used herein, the term "adeno-associated virus (AAV) vector" refers to a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences.

AAV vectors can be constructed using recombinant techniques that are known in the art to include one or more heterologous nucleotide sequences flanked on both ends (5' and 3') with functional AAV ITRs. In the practice of the invention, an AAV vector can include at least one AAV ITR and a suitable promoter sequence positioned upstream of the heterologous nucleotide sequence and at least one AAV ITR positioned downstream of the heterologous sequence. A "recombinant AAV vector plasmid" refers to one type of recombinant AAV vector wherein the vector comprises a plasmid. As with AAV vectors in general, 5' and 3' ITRs flank the selected heterologous nucleotide sequence.

AAV vectors can also include transcription sequences such as polyadenylation sites, as well as selectable markers or reporter genes, enhancer sequences, and other control elements that allow for the induction of transcription. Such control elements are described above.

As used herein, the term "AAV virion" refers to a complete virus particle. An AAV virion may be a wild type AAV virus particle (comprising a linear, single-stranded AAV nucleic acid genome associated with an AAV capsid, i.e., a protein coat), or a recombinant AAV virus particle (described below). In this regard, single-stranded AAV nucleic acid molecules (either the sense/coding strand or the anti-sense/anticoding strand as those terms are generally defined) can be packaged into an AAV virion; both the sense and the antisense strands are equally infectious.

As used herein, the term "recombinant AAV virion" or "rAAV" is defined as an infectious, replication-defective virus composed of an AAV protein shell encapsidating (i.e., surrounding with a protein coat) a heterologous nucleotide sequence, which in turn is flanked 5' and 3' by AAV ITRs. A number of techniques for constructing recombinant AAV virions are known in the art (See, e.g., U.S. Pat. No. 5,173,414; WO 92/01070; WO 93/03769; Lebkowski et al., Molec. Cell. Biol. 8:3988-3996 [1988]; Vincent et al., Vaccines 90 [1990] (Cold Spring Harbor Laboratory Press); Carter, Current Opinion in Biotechnology 3:533-539 [1992]; Muzyczka, Current Topics in Microbiol. and Immunol. 158:97-129 [1992]; Kotin, Human Gene Therapy 5:793-801 [1994]; Shelling and Smith, Gene Therapy 1:165-169 [1994]; and Zhou et al., J. Exp. Med. 179:1867-1875 [1994], all of which are incorporated herein by reference).

Suitable nucleotide sequences for use in AAV vectors (and, indeed, any of the vectors described herein) include any functionally relevant nucleotide sequence. Thus, the AAV vectors of the present invention can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Suitable genes include those used for the treatment of inflammatory diseases, autoimmune, chronic and infectious diseases, including such disorders as AIDS, cancer, neurological diseases, cardiovascular disease, hypercholestemia; various blood disorders including various anemias, thalasemias and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA) that are useful in antisense therapy for cancer and for viral diseases have been described in the art. (See, e.g., Han et al., Proc. Natl. Acad. Sci. USA 88:4313-4317 [1991]; Uhlmann et al., Chem. Rev. 90:543-584 [1990]; Helene et al., Biochim. Biophys. Acta. 1049:99-125 [1990]; Agarwal et al., Proc. Natl. Acad. Sci. USA 85:7079-7083 [1989]; and Heikkila et al., Nature 328:445-449 [1987]). For a discussion of suitable ribozymes, see, e.g., Cech et al. (1992) J. Biol. Chem. 267:17479-17482 and U.S. Pat. No. 5,225,347, incorporated herein by reference.

By "adeno-associated virus inverted terminal repeats" or "AAV ITRs" is meant the art-recognized palindromic regions found at each end of the AAV genome which function together in cis as origins of DNA replication and as packaging signals for the virus. For use with the present invention, flanking AAV ITRs are positioned 5' and 3' of one or more selected heterologous nucleotide sequences and, together with the rep coding region or the Rep expression product, provide for the integration of the selected sequences into the genome of a target cell.

The nucleotide sequences of AAV ITR regions are known (See, e.g., Kotin, Human Gene Therapy 5:793-801 [1994]; Berns, K. I. "Parvoviridae and their Replication" in Fundamental Virology, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. The 5' and 3' ITRs which flank a selected heterologous nucleotide sequence need not necessarily be identical or derived from the same AAV serotype or isolate, so long as they function as intended, i.e., to allow for the integration of the associated heterologous sequence into the target cell genome when the rep gene is present (either on the same or on a different vector), or when the Rep expression product is present in the target cell.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "passage" refers to the process of diluting a culture of cells that has grown to a particular density or confluency (e.g., 70% or 80% confluent), and then allowing the diluted cells to regrow to the particular density or confluency desired (e.g., by replating the cells or establishing a new roller bottle culture with the cells.

As used herein, the term "stable," when used in reference to genome, refers to the stable maintenance of the information content of the genome from one generation to the next, or, in the particular case of a cell line, from one passage to the next. Accordingly, a genome is considered to be stable if no gross changes occur in the genome (e.g., a gene is deleted or a chromosomal translocation occurs). The term "stable" does not exclude subtle changes that may occur to the genome such as point mutations.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

GENERAL DESCRIPTION OF THE INVENTION

The present invention uses the novel paradigm of utilizing exogenous cell-cell communication pathways to autoregulate cell proliferation and differentiation. In some embodiments, the present invention provides a variety of cell-cell communication pathways and regulatory motifs that can be incorporated into any desired cell type.

In some preferred embodiments, the systems, compositions and methods of the present invention allow for tissue homeostasis to be achieved between a source of differentiable cells such as stem cells and target differentiated cells produced from the differentiable cells so that both cell populations are maintained. In some embodiments, the systems, compositions and methods control the proliferation and differentiation of the differentiable cell population so that a population of differentiable cells is maintained over time that can differentiate into the desired target differentiated cells. In preferred embodiments, the differentiable cells are subject to a regulatory feedback mechanism that controls a) the proliferation or inhibition of proliferation of differentiable cells into additional differentiable cells so that a source of differentiable cells is stably maintained and b) the differentiation of differentiable cells into target differentiated cells so that a stable population of target differentiated cells is maintained.

In some embodiments, the present invention utilizes a series of modules to control proliferation and differentiation of differentiable cells. In some embodiments, the modules each comprise one more genes. In further embodiments, the genes are provided on vectors that can be introduced into a desired cell line. In some embodiments, the first module comprises one or more nucleic acid constructs that interact to provide population control for a population of proliferating cells. In some embodiments, the proliferating cells are differentiable cells. In some embodiments, the second module comprises one or more nucleic acid constructs that interact to control commitment of the differentiable cells to differentiate. In some preferred embodiments, if the differentiable cell population is above a certain threshold and the target differentiated cells are below a certain threshold, some of the differentiable cells commit to differentiate into the target differentiated cells. In some embodiments, the third module comprises one or more nucleic acid constructs that interact to cause differentiation of differentiable cells into target differentiated cells. In some embodiments, the fourth module comprises one or more nucleic acid constructs that trigger apoptosis if the differentiable cell migrates out of a desired location.

Precise in vivo control of stem cell differentiation into desired cell types, such as insulin-producing cells, the cell type that is adversely affected in Diabetes Mellitus, is achievable through use of the compositions and methods described herein. In some preferred embodiments, the approaches described herein ensure a constant and steady supply of precursor cells and β cells which autoregulate insulin production. This approach also has the potential to bypass graft vs. host disease by using naive embryonic stem cells [Burt et al., Journal of Experimental Medicine, 199(7): 895-904, 2004] or the patient's own adult stem cells. Finally, the approach is modular, controllable and flexible, allowing us to genetically engineer pathways that best address a patient's disease state.

This approach represents a paradigm shift in tissue engineering and diabetes treatment. Artificial cell-cell communication coordinates cell population behavior and the formation of insulin-producing β cells by precisely controlling gene expression in a two-step differentiation process. In the systems of the present invention, cells are not simply induced exogenously to differentiate, but rather are programmed to sense and respond to changes in their environment and coordinate their collective behavior based on the needs of the organism. It is important to initially build a large, undifferentiated reservoir of cells. Quorum sensing allows for controlled growth of mES cells until they reach the required density before they are directed to differentiate. Once mES cells have terminally differentiated into beta cells, they either stop dividing or divide at a very slow rate. Importantly, once these beta cells lose function or die due for example to an attack by the immune system, the ES cell reservoir detects this condition and produces new beta cells.

DETAILED DESCRIPTION OF THE INVENTION

Figure 3:
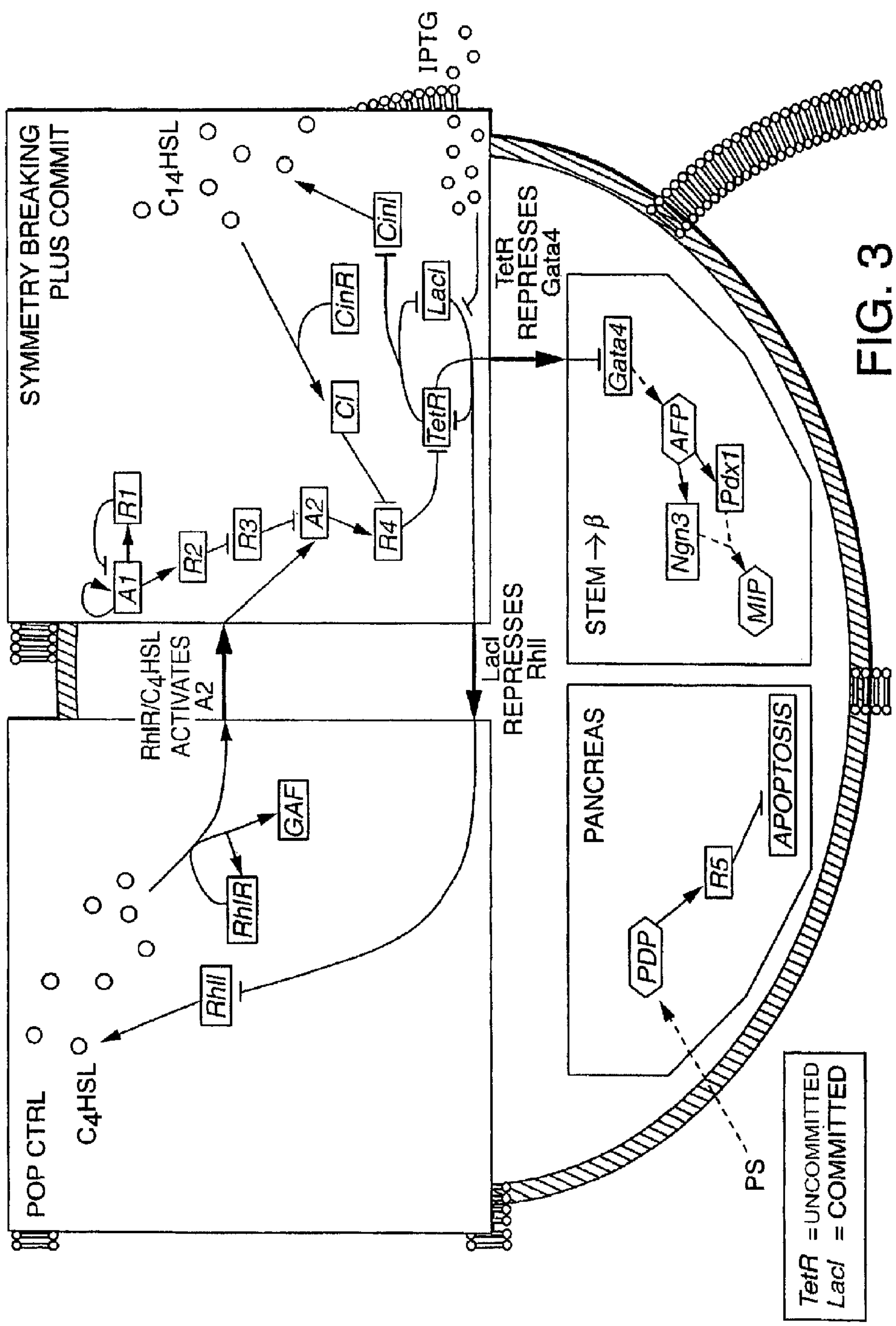
FIG. 3: Diagram of a four module system for cell proliferation and differentiation control.

The present invention utilizes artificial cell-cell communication pathways to control proliferation and differentiation of a population of differentiable cells. In some embodiments, multiple exogenous cell-cell communication pathways are introduced into a population of differentiable cells to provide a regulatory feedback control system. A schematic representation of an exemplary system is provided in FIG. 3. FIG. 3 depicts a modular system for control of proliferation and differentiation of cells. In preferred embodiments, the cells of the present invention comprise one or more of the depicted modules or components of the depicted modules. The depicted modules comprise stem cell population control modules, commitment to differentiation modules, cell differentiation modules, and apoptosis modules. In some preferred embodiments, the cells of the present invention comprise at least one population control module and commitment module that interface with a differentiation module and an apoptosis module. In some preferred embodiments, the cell population control module and commitment module interface to control the number of uncommitted cells in the population (i.e., cells that retain the ability to differentiate) and the number of committed cells in the population (i.e., cells that have committed to differentiate, but have not necessarily differentiated into the desired target cell type).

In preferred embodiments, the modules of the present invention comprise separate motifs or circuit designs that interact to produce a desired outcome. In particularly preferred embodiments, cell-cell communication, oscillator, cascade, and/or toggle switch motifs are incorporated into one or more of the modules of the present invention. In preferred embodiments, these motifs interact to provide a symmetry breaking condition so that a population of stem cells is maintained and not exhausted. These individual components and their interaction with one another is described in detail below.

In some embodiments, the present invention provides artificial cell-cell communication systems for use in mammalian cells. In some embodiments, cell-cell communication systems are derived from bacterial cell-cell communication systems from organisms such as *Pseudomonas aeruginosa, Rhizobium leguminosarum*, and *Vibrio fischeri*. These systems comprise genes that catalyze the synthesis of chemical signals of the acyl-homoserine lactone (AHL) family. In other embodiments, the cell-cell communication systems utilize secretion signals and viral internalization signals.

A. Population Control Module

As shown in FIG. 3, in some embodiments, the present invention provides a population control module comprising a pathway of exogenous genes that are preferably introduced into a population of stem cells. The population control module interacts with the commitment module to control the proliferation and differentiation of the cells within the system. The population control module is utilized to detect the number of stem cells in the system. If the stem cell population is low, then stem cell proliferation is allowed. If the stem cell population is high, then proliferation is inhibited. The commitment module (explained in more detail below) is used to detect the number of differentiated cells in the system (in this example, beta cells). If the beta cell population is high, proliferation of stem cells in inhibited. If the beta cell population is low, differentiation of stem cells is induced along with stem cell proliferation. A third module, described in more detail below, interacts with the two cell-cell communication modules to cause differentiation of stem cells into the desired target differentiated cell, in this example beta cells.

Referring to FIG. 3, in some embodiments, the population control module preferably comprises genes encoding a cell-cell communication pathway, preferably a Rh1I/Rh1R cell-cell communication pathway. The invention is not limited to the use of any particular cell-cell communication pathway in the first module. In other embodiments, Lux1/LuxR, CinI/CinR, or viral-based cell-cell communication systems are utilized. In preferred embodiments, bacterial cell-cell signaling pathways are utilized. As shown in FIG. 3, the population control module senses the density of the stem cell population. In some embodiments, the population control module comprises an exogenous Rh1I gene operably linked to a repressor element, preferably a Lad repressor element. In the absence of the repressor, the exogenous Rh1I gene catalyzes the synthesis of $C_4$HSL. The population control module further comprises an exogenous RhrR gene and an exogenous gene comprising a Growth Arrest Factor (GAF) operably linked to a promoter responsive to the $C_4$HSL/RhrR complex. Under conditions of a high density of stem cells, the corresponding high amount of $C_4$HSL interacts with the gene product of RhrR to form a complex, which activates expression of GAF, thus inhibiting proliferation of the stem cells.

Exemplary vectors for the components shown in FIG. 3 are provided in FIGS. 28-37, where A1=Gal4, R1=ZF1, R2=ZF2, R3=ZF3, R4=ZF4, A2=CymVP16, and P is either Hef1a or minCMV.

B. Commitment Module

Referring to FIG. 3, in some embodiments, the present invention provides a commitment module comprising multiple motifs or circuit elements that allow for symmetry breaking and control the commitment of cell to differentiate. In some embodiments, the module comprises one or more of the following motifs: an oscillator, a cascade, a toggle switch, and a cell-cell communication pathway. In some preferred embodiments, these motifs interact, as described in detail below, to allow commitment to differentiate when three conditions are met within the population of cells containing the modules: a) there is a high level of uncommitted cells; b) there are cells that allowed to commit; and c) there is a low level of committed cells.

Referring to FIG. 3, an embodiment of an oscillator is depicted by A1 and R1. In preferred embodiments, A1 is an activator and R1 is a repressor that are connected in way so that they oscillate. In some embodiments, as depicted, the activator A1 activates itself and the repressor R1 and the repressor R1 represses the activator A1. This oscillation provides symmetry breaking for the population of cells containing the motif. Due to the oscillation of activator A1 and repressor R1, the population of cells containing activator A1 and repressor R1 is asynchronous. At any given time, only a portion of the cells in the population will have a high level of activator A1. In some embodiments, as depicted, only cells with high activator A1 are allowed to commit to differentiate, thus the remaining portion of the cells with low levels of activator A1 is reserved in an uncommitted state. This ensures that a population of uncommitted stem cells will be maintained. Otherwise, all uncommitted stem cells could commit to differentiate, allowing the exhaustion of the stem cells from the population.

Referring to FIG. 3, an embodiment of a cascade is depicted by repressor R2, repressor R3, activator A2, and repressor R4. In some embodiments, activator A2 is operably linked to a promoter responsive to $C_4$HSL/RhrR and thus interfaces with the population control module. In some embodiments, as depicted, activator A1 from the oscillator activates repressor R2, which in turn represses repressor R3, which is a repressor of activator A2. Activator A2 interfaces with the population control module and is activated by the $C_4$HSL/RhrR complex. Thus, if the level of activator A1 is high, repressor R2 is activated which represses repressor R3, allowing the level of activator A2 to be high if there is a concomitant high concentration of uncommitted stem cells that are producing $C_4$HSL/RhrR. As a result, the level of activator A2 can only be high when two conditions are met: 1) there is a high level of A1 within the cell; and 2) there is a high concentration of uncommitted stem cells. When these two conditions are met, activator A2 in turn activates repressor R4, which interfaces with the cell-cell communication and toggle switch motifs.

Still referring to FIG. 3, in order for cells within the population to commit as described above, a third condition must be met: a low concentration of committed cells. In some embodiments, the level of committed cells is detected via a cell-cell communication pathway, preferably a CinI/CinR cell-cell communication pathway. The invention is not limited to the use of any particular cell-cell communication pathway in the second module, although the particular cell-cell communication pathway utilized should preferably be different than the cell-cell communication pathway selected for the cell population module. In other embodiments, Lux1/LuxR, Rh1I/Rh1R, or viral-based cell-cell communication systems are utilized.

In some embodiments, as depicted in FIG. 3, the cell-cell communication pathway comprises an exogenous CinI gene, and exogenous CinR gene, and an exogenous gene encoding the repressor CI operably linked to a promoter responsive to the $C_{14}$HSL/CinR complex. High levels of $C_{14}$HSL are indicative of a high concentration of committed cells. Under these conditions, repressor CI is activated and in turn represses repressor R4. In some embodiments, repressor R4 interacts with the toggle switch motif as detailed below. When the level of repressor R4 is low, there is no commitment. As can be seen, the level of R4 can only be high when the level of activator A2 is high and the level of CI is low. Low levels of $C_{14}$HSL are indicative of a low concentration of committed cells and under these conditions, the level of repressor CI is low, allowing the level repressor R4 to be high.

Still referring to FIG. 3, in some embodiments, the commitment module further comprises a toggle switch motif that switches cells between an uncommitted state and a committed state. In some embodiments, as depicted in FIG. 3, the toggle switch motif comprises two repressors, in preferred embodiments, TetR and Lad. In some embodiments, TetR and LacI cross repress each other. High levels of TetR within a cell are indicative of an uncommitted state. As shown in FIG. 3, IPTG can be added to the cells to repress LacI, thus causing the cells to enter into an uncommitted state. Alternatively, as described above, repressor R4 is high in cells where activator A1 is high and where there is a high concentration of uncommitted stem cells. When these two conditions are met, along with the condition of low number of committed cells, repressor R4 represses TetR, allowing a high level of LacI. High levels of LacI in a cell trigger the transition from an uncommitted cell to a committed cell by repressing TetR. As depicted in FIG. 3, when LacI is high, repression of CinI is released, causing the synthesis of $C_{14}$HSL, the activation of CI and the repression of R4. These events are indicative of a committed cell. As also depicted in FIG. 3, high LacI within a cell represses Rh1I of the cell population module, inhibiting synthesis of $C_4$HSL.

Exemplary vectors for the components shown in FIG. 3 are provided in FIGS. 28-37, where A1=Gal4, R1=ZF1, R2=ZF2, R3=ZF3, R4=ZF4, A2=CymVP16, and P is either Hef1a or minCMV.

C. Cell Differentiation Module

As shown in FIG. 3, in some embodiments, the present invention provides a cell differentiation module that is responsive to the commitment module. In some embodiments, the cell-differentiation module comprises at least an exogenous gene encoding a first cell fate regulator that is operably linked to a repressor, such as the TetR repressor. In some embodiments, as depicted in FIG. 3, the TetR/LacI toggle switch controls the expression of the cell fate regulator. When the three conditions of a) high level of uncommitted cells, b) cell that that is allowed to commit, and c) low level of committed cells are met, TetR is repressed, releasing the repression of the a cell fate regulator such as Gata4 or Sox 17 (not shown). Gata4 expression is the initial step in the programmed two-step differentiation of ES cells into β cells using established cell fate regulators. In some preferred embodiments, two-step differentiation of ES cells first to visceral or definitive endoderm and then to pancreatic β cells is facilitated by using controlled expression of established cell fate regulators triggered by cell-cell communication. A preferred system for the integration of the relevant cell fate regulators with the cell population and commitment modules is shown in FIG. 3. When the three conditions are met, either Gata4 is expressed. These two cell fate regulators were chosen because they are both expressed in mammalian visceral endoderm [Ritz-Laser et al., Molecular Endocrinology, 19(3):759-770, 2005; Ku et al., Stem Cells, 22:1205-1217, 2004]. Both Gata4 and Sox17 are required transcription factors in pancreatic organogenesis. Gata4 is present in very early visceral endoderm that differentiates into both insulin-producing and glucagon-producing cells [42]. Sox17 is expressed exclusively in insulin-producing cells and appears slightly later than Gata4 [43]. In preferred embodiments, endoderm differentiation is verified by visualizing the presence of endodermal markers such as Hnf3β or lamininB1 using immunohistochemistry and Western blots. Cells that remain in the stem cell state are identified by staining with alkaline phosphatase in a standard ES cell assay.

In some preferred embodiments, the cell-cell communication systems of the present invention comprise vectors that express cell fate regulators that regulate the differentiation of endoderm to β cells. Differentiation into endoderm triggers the expression of endoderm specific factors. In preferred embodiments, the genes encoding cell fate regulators are operably linked to a promoter that is regulated (preferably induced) by one or more endoderm specific factors. It is contemplated that cells that differentiate into endoderm naturally express the endodermal marker α-fetoprotein (AFP) which binds the AFP promoter. In the third module of the present invention, AFP regulates expression of Ngn3, Pdx1 and/or other cell fate regulators such as EGFP via the AFP promoter, hence the differentiation from ES to endoderm is visualized with the appearance of green fluorescence. In vivo, Ngn3 and Pdx1 are both expressed at various points during cellular differentiation from endoderm to β cells [Soria, Differentiation, 68:205-219, 2001] and both have been found to be necessary for terminal differentiation into β cells. Naturally occurring in vivo specialization of endodermal cells into β cells depends on the existence of a complex set of environmental cues which may not be present in the disease state. In the engineered system of the present invention, however, differentiation of mES cells into endoderm internally forces the cell to subsequently specialize into β cells. Upon terminal β cell differentiation, insulin production activates DsRed expression from the Mouse Insulin Promoter (MIP). Cells expressing the fluorescent red protein are assayed for terminal differentiation by immunohistochemical assays and Western blotting of β cell markers such as C-peptide, insulin and Nkx6.1. Cells not expressing fluorescent red protein are histochemically assayed for the presence of AFP, Pdx1, Ngn3 and also for stem cell character using the standard ES cell assay. Cells not initially induced with IPTG should not fluoresce red and should remain in the ES cell state.

In other preferred embodiments, other cell fate regulators are expressed via the differentiation module. Examples of the cell fate regulators include, but are not limited to, Nkx6.1, Nkx2.2, Isl-1, NeuroD, Pax6, Fgf4, BRA, Wnt9, NCAD, CER, FoxA2, CxcR4, Hnf1B, Hnf4A, Hnf6, H1xB9, Pax4, Cgc, GHRL, SST, PPY, Activin, Fgf10, Cyc, RA, Ex4, DAPT, HGF and Igf1. In preferred embodiments, these cell fate regulators are inserted into lentiviral vectors and introduced into the cell line of interest. In some preferred embodiments, the cell fate regulators are operably linked to a stage specific promoter. Stage specific promoters are promoters that are expressed at a particular stage of differentiation, such as differentiation into endoderm, ectoderm or mesoderm. In some preferred embodiments, the cell fate regulators are operably linked to an AFP promoter.

Exemplary vectors for the components shown in FIG. 3 are provided in FIGS. 28-37, where A1=Gal4, R1=ZF1, R2=ZF2, R3=ZF3, R4=ZF4, A2=CymVP16, and P is either Hef1a or minCMV.

D. Apoptosis Module

As shown in Figure, in some embodiments, the cells of the present invention further comprise an apoptosis module. In some embodiments, the apopstosis module comprises a series of vectors comprising genes that trigger apoptosis is the cell migrate to an undesired location. In preferred embodiments, the stem cells of the present invention would undergo apoptosis if the cells leave the pancreas. As shown in FIG. 3, genes encoding an apoptosis pathway are operably linked to a repressor element responsive to a repressor that is synthesized in the presence of a signal for the pancreas (PS). In the absence of PS, the repressor is not synthesized and apoptosis is triggered.

E. Cell Penetration Element Based Cell-Cell Communication Systems

In some embodiments, the present invention provides cell-cell communication systems that utilize cell penetrating polypeptide elements. In some embodiments, the present invention provides a fusion protein comprising a secretion signal, cell penetrating polypeptide, and trans acting domain in operable combination, wherein at least one of said secretion signal, cell penetrating polypeptide and trans acting domain are from at least two different proteins. In further embodiments, the present invention provides a nucleic acid encoding the fusion protein. In further preferred embodiments, the present invention provides vectors comprising a nucleic acid encoding the fusion protein. In still other embodiments, the present invention provides cells that express the fusion protein. In some embodiments, the present invention further provides a nucleic acid comprising a promoter comprising an element that binds or is responsive to the trans-acting domain, wherein the promoter is operably linked to a protein of interest.

The present invention is not limited to the use of any particular secretion signals, cell penetrating polypeptides or trans-acting domains. Indeed, the present invention contemplates a modular and highly expandable library of artificial cell-cell communication signals by using translational fusions of cell permeable peptides with in silico designed zinc finger proteins and an enhancer or repressor. Such fusion proteins are exported by sender cells, translocate to the nucleus of receiver cells, where they control expression of genes in synthetic as well as endogenous signaling pathways by binding their cognate DNA binding sites.

CPPs are peptide sequences with the ability to translocate across the plasma membrane and to reach cytoplasmic and/or nuclear compartments in live cells after internalization. CPPs have been first described in the HIV TAT-1 and the Antennapedia proteins, where the translocation seems to reflect in vivo biological process. In the last decade, fusion proteins containing such CPPs have been widely used to deliver effector proteins into the cytoplasm or nucleus of target cells, predominantly by adding the purified fusion protein to the cell culture supernatant or injecting it intraperitoneally in vivo. The binding of TAT to the cell surface thought to involve heparan sulfate proteoglycans, and in vitro evidences suggest that the uptake is mediated by an energy-depending endocytic process involving lipid rafts. The release from these endocytic vesicles into the cytoplasm is less well understood, and has been shown to be a rate-limiting step in the transduction process. For TAT, the subsequent localization to the nucleus is achieved through an effective nuclear localization sequence (NLS), endogenously present in this protein.

The present invention is not limited to the use any particular CPP peptide. The following CPP peptides find use in the present invention:

TAT:
SGYGRKKRRQRRRC (SEQ ID NO: 24)

Antp:
SGRQIKIWFQNRRMKWKKC (SEQ ID NO: 25)

TAT:
GRKKRRQRRRPPQG (SEQ ID NO: 26)

TAT: (47-60),
N-Cys-Tyr$^{47}$-Gly-Arg-Lys-Lys-Arg-Arg-Gln-Arg-Arg-Arg-Pro-Pro-Gln$^{60}$-COOH (SEQ ID NO: 27);

ANTP:
N-Cys-Arg$^{43}$-Gln-Ile-Lys-Ile-Trp-Phe-Gln-Asn-Arg-Arg-Met-Lys-Trp-Lys-Lys$^{58}$-COOH (SEQ ID NO: 28)

Vectocell ®
DPV3 sense,
5' GATCCCGTAAAAAGCGTCGTCGAGAAAGCCGTAAGAAACGTCGACGTGAAAGCA-3' (SEQ ID NO: 29);

DPV3 antisense,
5'-AGCTTGCTTTCACGTCGACGTTTCTTACGGCTTTCTCGACGACGCTTTTTACGG-3' (SEQ ID NO: 30);

DPV15b sense,
5'-GATCCGGTGCGTATGATCTGCGTCGTCGAGAACGTCAGAGCCGTCTGCGTCGACGTGAAAGACAGAGCAGAA-3' (SEQ ID NO: 31);

-continued

DPV3 antisense,
5'-AGCTTTCTGCTCTGTCTTTCACGTCGACGCAGACGGCTCTGACGTT

CTCGACGACGCAGATCATACGCACCG-3' (SEQ ID NO: 32);

DPV1047 sense,
5'-GATCCGTTAAACGTGGACTGAAACTTCGTCATGTTCGTCCGCGTGT

GACCCGTGATGTGA-3' (SEQ ID NO: 33);

DPV1047 antisense,
5'-AGCTTCACATCACGGGTCACACGCGGACGAACATGACGAAGTTTCA

GTCCACGTTTAACG-3' (SEQ ID NO: 34).

ZFs of the Cys2His2 type contain about 30 amino acids that code for two b-strands and an a-helix that mediates interaction with a nucleotide triplet. The human genome contains at least 4000 such domains in over 700 proteins, which represents about 2% of human genes. ZFs recognizing many of the 64 triplets possible have been isolated and described. Such a ZF domain can be treated as modular, which means that multiple concatenated ZF domains (polydactyl ZFs) do bind to DTS with a multiple of three triplets length. Recently, databases and tools became available to easily engineer ZFP-DTS pairs in silico to further streamline this process (16-18). The optimal linker sequences to connect such single ZF domains to a ZFP have also been described, as well as the optimal positioning of transcriptional activators or inhibitors.

A translational fusion of a CPP with a ZFP, when exported by a sender cell, translocates into the nucleus of receiver cells. The transcellular delivery of such ZFPs would massively expand the possibilities we have at our disposition to manipulate synthetic as well as endogenous signaling pathways in stem cells. This would facilitate the programmed differentiation of stem cells into tissue patterns by design. By engineering cells that can be manipulated to decide between cell fates based on the given signal and working within a 3D matrix system in vitro, we will study the potential of this system in promoting organogenesis and tissue repair. The long-term goal would be to have safe self-regulating and self-regenerating tissue/organs for clinical applications. Another purpose is to elucidate the architecture and dynamics of endogenous cell fate regulatory networks as they function to promote lineage choices.

An additional application for such an artificial cell-cell communication system would be the delivery of cell-permeable therapeutic proteins influencing cell signaling at the level of protein-protein interactions in a controlled fashion in vivo. As an example, the secretion of cell-permeable peptides of the wild-type tumor suppressor p53 from artificially engineered cells or tissue, would restore cell growth control of tumor cells with mutated forms of p53, which are present in almost all human cancers.

The present invention is likewise not limited to the use of any particular secretion signal. A secretion signal is any DNA sequence which when operably linked to a recombinant DNA sequence encodes a signal peptide which is capable of causing the secretion of the recombinant polypeptide. In general, the signal peptides comprise a series of about 15 to 30 hydrophobic amino acid residues (See, e.g., Zwizinski et al., J. Biol. Chem. 255(16): 7973-77 [1980], Gray et al., Gene 39(2): 247-54 [1985], and Martial et al., Science 205: 602-607 [1979]). Such secretion signal sequences are preferably derived from genes encoding polypeptides secreted from the cell type targeted for tissue specific expression. Secretory DNA sequences, however, are not limited to such sequences. Secretory DNA sequences from proteins secreted from many cell types and organisms may also be used (e.g., the secretion signals for t PA, serum albumin, lactoferrin, and growth hormone, and secretion signals from microbial genes encoding secreted polypeptides such as from yeast, filamentous fungi, and bacteria).

Figure 26A:
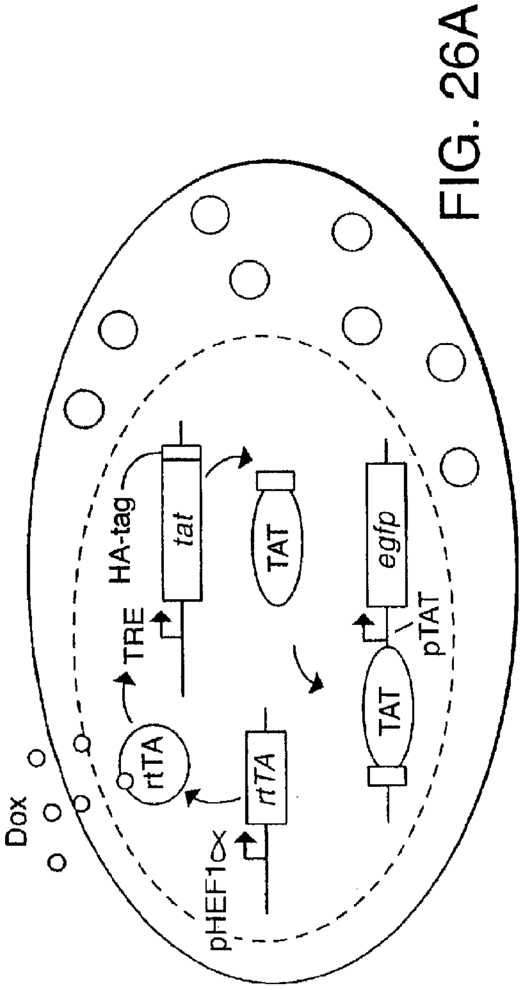
FIG. 26 provides a diagram of a synthetic signaling circuit utilizing cell penetrating polypeptide elements.

FIGS. 26 and 27 provide examples of a synthetic cell-cell communication circuit that utilizes CPP elements. Panel (A) depicts internal signaling. TAT is expressed upon the addition of Dox, binds to is promoter pTAT, and induces expression of EGFP. Panel (B) depicts cell-cell signaling. Sender and receiver circuits are infected into separate cells. Sender cells express TAT upon addition of Dox; TAT is secreted, and enters receiver cells, where is localizes to the nucleus and induces the expression of EGFP.

F. Vector Systems

In some embodiments, the various exogenous genes described above are provided on vectors that are introduced into the desired cell line, such as a stem cell line. In some preferred embodiments, the vectors are lentiviral vectors. In some embodiments, additional genes required for the synthesis of precursors of $C_4$HSL, $C_{14}$HSL, or 30$C_6$HSL are also introduced into the desired cell line. In some preferred embodiments, vectors encoding one or more genes from the Type II bacterial fatty acid synthesis (FAS) system are also introduced into mammalian cells. In some embodiments, the vectors encode Acyl Carrier Protein and Acyl-Acyl Carrier (ACP) Protein Synthase (AAS) including ACP and AAS.

In preferred embodiments, the components of the cell-cell communication system are included in separate vectors. The individual vectors are then introduced into the desired cell line. In preferred embodiments, where lentiviral vectors are utilized, the target cell line is transduced with the lentiviral vectors. The cell line may be co-infected with the vectors or the vectors may be introduced serially.

In some preferred embodiments, the genes for the components of the cell-cell communication system of the present invention (e.g., LuxI, ACP, and AAS) are optimized for expression in mammalian cells. In other embodiments, genes comprising the entire bacterial Type II Fatty Acid Synthase system are included on vectors and introduced in the cell line.

In preferred embodiments, as described in more detail below, the components of the cell-cell communication systems are introduced into a mammalian cell line. The present invention is not limited to the use of any particular cell lines. In some embodiments, the cell lines are pluripotent, multipotent or totipotent cell lines. In some preferred embodiments, the cells lines are stem cell lines. In preferred embodiments, the components are incorporated into expression vectors that are introduced into mammalian cells. In some preferred embodiments, the genes encoding the components of the cell-cell communication system are operably linked to exogenous promoters.

The modules and motifs of the present invention generally comprise multiple exogenous genes operably linked to promoters. In preferred embodiments, the exogenous genes operably linked to promoters are included in a vector. In preferred embodiments, the vectors are introduced into a cell. The present invention is not limited to the use of any particular vector system. Indeed, the use of a variety of vector systems is contemplated. In some preferred embodiments, the vectors are lentiviral vectors. In other embodiments, the vectors are retroviral vectors, pseudotyped retroviral vectors, pseudotyped lentiviral vectors, adenovirus vectors, plasmids, transposons, or artificial chromosomes.

The present invention also contemplates the use of lentiviral vectors to generate high copy number cell lines. The lentiviruses (e.g., equine infectious anemia virus, caprine arthritis-encephalitis virus, human immunodeficiency virus) are a subfamily of retroviruses that are able to integrate into non-dividing cells. The lentiviral genome and the proviral DNA have the three genes found in all retroviruses: gag, pol, and env, which are flanked by two LTR sequences. The gag gene encodes the internal structural proteins (e.g., matrix, capsid, and nucleocapsid proteins); the pol gene encodes the reverse transcriptase, protease, and integrase proteins; and the pol gene encodes the viral envelope glycoproteins. The 5' and 3' LTRs control transcription and polyadenylation of the viral RNAs. Additional genes in the lentiviral genome include the vif, vpr, tat, rev, vpu, nef, and vpx genes.

A variety of lentiviral vectors and packaging cell lines are known in the art and find use in the present invention (See, e.g., U.S. Pat. Nos. 5,994,136 and 6,013,516, both of which are herein incorporated by reference). Furthermore, the VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV. The lentiviral vectors may also be modified as described above to contain various regulatory sequences (e.g., signal peptide sequences, RNA export elements, and IRES's). After the lentiviral vectors are produced, they may be used to transfect host cells as described above for retroviral vectors.

In general, retroviruses (family Retroviridae) are divided into three groups: the spumaviruses (e.g., human foamy virus); the lentiviruses (e.g., human immunodeficiency virus and sheep visna virus) and the oncoviruses (e.g., MLV, Rous sarcoma virus).

Retroviruses are enveloped (i.e., surrounded by a host cell-derived lipid bilayer membrane) single-stranded RNA viruses which infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products), which is surrounded by a lipid bilayer membrane derived from the host cell containing the viral envelope glycoproteins (also referred to as membrane-associated proteins).

The organization of the genomes of numerous retroviruses is well known to the art and this has allowed the adaptation of the retroviral genome to produce retroviral vectors. The production of a recombinant retroviral vector carrying a gene of interest is typically achieved in two stages.

First, the gene of interest is inserted into a retroviral vector which contains the sequences necessary for the efficient expression of the gene of interest (including promoter and/or enhancer elements which may be provided by the viral long terminal repeats (LTRs) or by an internal promoter/enhancer and relevant splicing signals), sequences required for the efficient packaging of the viral RNA into infectious virions (e.g., the packaging signal (Psi), the tRNA primer binding site (−PBS), the 3' regulatory sequences required for reverse transcription (−PBS)) and the viral LTRs. The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); therefore, the resulting virus is said to be replication defective.

Second, following the construction of the recombinant vector, the vector DNA is introduced into a packaging cell line. Packaging cell lines provide proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles that lack a membrane-associated protein (e.g., an env protein). In order to produce viral particles containing a membrane associated protein that will permit entry of the virus into a cell, the packaging cell line containing the retroviral sequences is transfected with sequences encoding a membrane-associated protein (e.g., the G protein of vesicular stomatitis virus (VSV)). The transfected packaging cell will then produce viral particles, which contain the membrane-associated protein expressed by the transfected packaging cell line; these viral particles, which contain viral genomic RNA derived from one virus encapsidated by the envelope proteins of another virus are said to be pseudotyped virus particles.

The retroviral vectors of the present invention can be further modified to include additional regulatory sequences. As described above, the retroviral vectors of the present invention include the following elements in operable association: a) a 5' LTR; b) a packaging signal; c) a 3' LTR and d) a nucleic acid encoding a protein of interest located between the 5' and 3' LTRs. In some embodiments, the nucleic acid of interest is operably linked to a promoter of interest. As described above, in preferred embodiments, the nucleic acid of interest is a gene encoding a protein from a quorum sensing system, or a gene encoding a cell fate regulator. In some preferred embodiments, the promoter is a promoter responsive to an autoinducer/regulatory partner complex synthesized by the quorum sensing pathway, an inducible promoter, a repressible promoter, or a stage specific promoter such as the AFP promoter. In some embodiments of the present invention, the nucleic acid of interest may be arranged in opposite orientation to the 5' LTR when transcription from an internal promoter is desired.

In other embodiments of the present invention, the vectors are modified by incorporating an RNA export element (See, e.g., U.S. Pat. Nos. 5,914,267; 6,136,597; and 5,686,120; and WO99/14310, all of which are incorporated herein by reference) either 3' or 5' to the nucleic acid sequence encoding the protein of interest. It is contemplated that the use of RNA export elements allows high levels of expression of the protein of interest without incorporating splice signals or introns in the nucleic acid sequence encoding the protein of interest.

In still other embodiments, the vector further comprises at least one internal ribosome entry site (IRES) sequence. The sequences of several suitable IRES's are available, including, but not limited to, those derived from foot and mouth disease virus (FDV), encephalomyocarditis virus, and poliovirus. The IRES sequence can be interposed between two transcriptional units (e.g., nucleic acids encoding different proteins of interest or subunits of a multisubunit protein such as an antibody) to form a polycistronic sequence so that the two transcriptional units are transcribed from the same promoter.

The retroviral vectors of the present invention may also further comprise a selectable marker allowing selection of transformed cells. A number of selectable markers find use in the present invention, including, but not limited to the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. In some embodiments, the selectable marker gene is provided as part of polycistronic sequence that also encodes the protein of interest.

Viral vectors, including recombinant lentiviral vectors, provide a more efficient means of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

The most commonly used recombinant retroviral vectors are derived from the amphotropic Moloney murine leukemia virus (MoMLV) (See e.g., Miller and Baltimore Mol. Cell. Biol. 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (e.g., the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the proteins required for particle assembly (Markowitz et al., J. Virol. 62:1120 [1988]).

In some preferred embodiments, the retroviral vector is pseudotyped. (See, e.g., U.S. Pat. No. 5,512,421, which is incorporated herein by reference). In some preferred embodiments, the pseudotyped retrovirus contains the G protein of VSV as the membrane associated protein. Unlike retroviral envelope proteins that bind to a specific cell surface protein receptor to gain entry into a cell, the VSV G protein interacts with a phospholipid component of the plasma membrane (Mastromarino et al., J. Gen. Virol. 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al, Proc. Natl. Acad. Sci. USA 90:8033 [1993]).

The present invention also contemplates the use of adeno associated virus (AAV) vectors. AAV is a human DNA parvovirus, which belongs to the genus Dependovirus. The AAV genome is composed of a linear, single-stranded DNA molecule that contains approximately 4680 bases. The genome includes inverted terminal repeats (ITRs) at each end that function in cis as origins of DNA replication and as packaging signals for the virus. The internal nonrepeated portion of the genome includes two large open reading frames, known as the AAV rep and cap regions, respectively. These regions code for the viral proteins involved in replication and packaging of the virion. A family of at least four viral proteins are synthesized from the AAV rep region, Rep 78, Rep 68, Rep 52 and Rep 40, named according to their apparent molecular weight. The AAV cap region encodes at least three proteins, VP1, VP2 and VP3 (for a detailed description of the AAV genome, see e.g., Muzyczka, Current Topics Microbiol. Immunol. 158:97-129 [1992]; Kotin, Human Gene Therapy 5:793-801 [1994]).

AAV requires coinfection with an unrelated helper virus, such as adenovirus, a herpesvirus or vaccinia, in order for a productive infection to occur. In the absence of such coinfection, AAV establishes a latent state by insertion of its genome into a host cell chromosome. Subsequent infection by a helper virus rescues the integrated copy, which can then replicate to produce infectious viral progeny. Unlike the non-pseudotyped retroviruses, AAV has a wide host range and is able to replicate in cells from any species so long as there is coinfection with a helper virus that will also multiply in that species. Thus, for example, human AAV will replicate in canine cells coinfected with a canine adenovirus. Furthermore, unlike the retroviruses, AAV is not associated with any human or animal disease, does not appear to alter the biological properties of the host cell upon integration and is able to integrate into nondividing cells. It has also recently been found that AAV is capable of site-specific integration into a host cell genome.

In light of the above-described properties, a number of recombinant AAV vectors have been developed for gene delivery (See, e.g., U.S. Pat. Nos. 5,173,414; 5,139,941; WO 92/01070 and WO 93/03769, both of which are incorporated herein by reference; Lebkowski et al., Molec. Cell. Biol. 8:3988-3996 [1988]; Carter, Current Opinion in Biotechnology 3:533-539 [1992]; Muzyczka, Current Topics in Microbiol. and Immunol. 158:97-129 [1992]; Kotin, (1994) Human Gene Therapy 5:793-801; Shelling and Smith, Gene Therapy 1:165-169 [1994]; and Zhou et al., J. Exp. Med. 179:1867-1875 [1994]).

Recombinant AAV virions can be produced in a suitable host cell that has been transfected with both an AAV helper plasmid and an AAV vector. An AAV helper plasmid generally includes AAV rep and cap coding regions, but lacks AAV ITRs. Accordingly, the helper plasmid can neither replicate nor package itself. An AAV vector generally includes a selected gene of interest bounded by AAV ITRs that provide for viral replication and packaging functions. Both the helper plasmid and the AAV vector bearing the selected gene are introduced into a suitable host cell by transient transfection. The transfected cell is then infected with a helper virus, such as an adenovirus, which transactivates the AAV promoters present on the helper plasmid that direct the transcription and translation of AAV rep and cap regions. Recombinant AAV virions harboring the selected gene are formed and can be purified from the preparation. Once the AAV vectors are produced, they may be used to transfect (See, e.g., U.S. Pat. No. 5,843,742, herein incorporated by reference) host cells at the desired multiplicity of infection to produce high copy number host cells. As will be understood by those skilled in the art, the AAV vectors may also be modified as described above to contain various regulatory sequences (e.g., signal peptide sequences, RNA export elements, and IRES's).

The present invention also contemplates the use of transposon vectors. Transposons are mobile genetic elements that can move or transpose from one location another in the genome. Transposition within the genome is controlled by a transposase enzyme that is encoded by the transposon. Many examples of transposons are known in the art, including, but not limited to, Tn5 (See e.g., de la Cruz et al., J. Bact. 175: 6932-38 [1993], Tn7 (See e.g., Craig, Curr. Topics Microbiol. Immunol. 204: 27-48 [1996]), and Tn10 (See e.g., Morisato and Kleckner, Cell 51:101-111 [1987]). The ability of transposons to integrate into genomes has been utilized to create transposon vectors (See, e.g., U.S. Pat. Nos. 5,719,055; 5,968,785; 5,958,775; and 6,027,722; all of which are incorporated herein by reference.) Because transposons are not infectious, transposon vectors are introduced into host cells via methods known in the art (e.g., electroporation, lipofection, or microinjection). Therefore, the ratio of transposon vectors to host cells may be adjusted to provide the desired multiplicity of infection to produce the high copy number host cells of the present invention.

Transposon vectors suitable for use in the present invention generally comprise a nucleic acid encoding a protein of interest interposed between two transposon insertion sequences. Some vectors also comprise a nucleic acid sequence encoding a transposase enzyme. In these vectors, the one of the insertion sequences is positioned between the transposase enzyme and the nucleic acid encoding the protein of interest so that it is not incorporated into the genome of the host cell during recombination. Alternatively, the transposase enzyme may be provided by a suitable method (e.g., lipofection or microinjection). As will be understood by those skilled in the art, the transposon vectors may also be modified as described above to contain various regulatory sequences (e.g., signal peptide sequences, RNA export elements, and IRES's).

Figure 6:
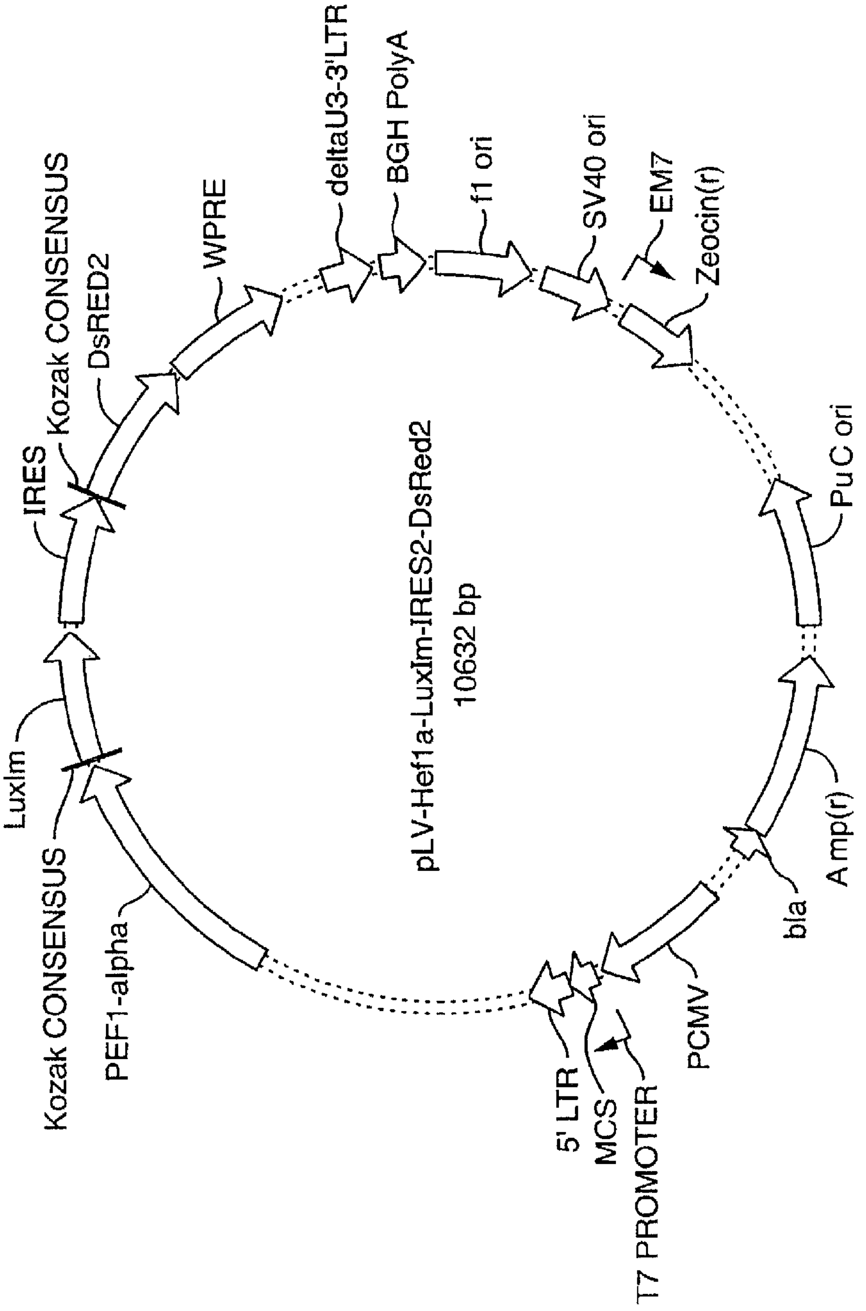
FIG. 6 provides a diagram of the vector of FIG. 5.
Figure 8:
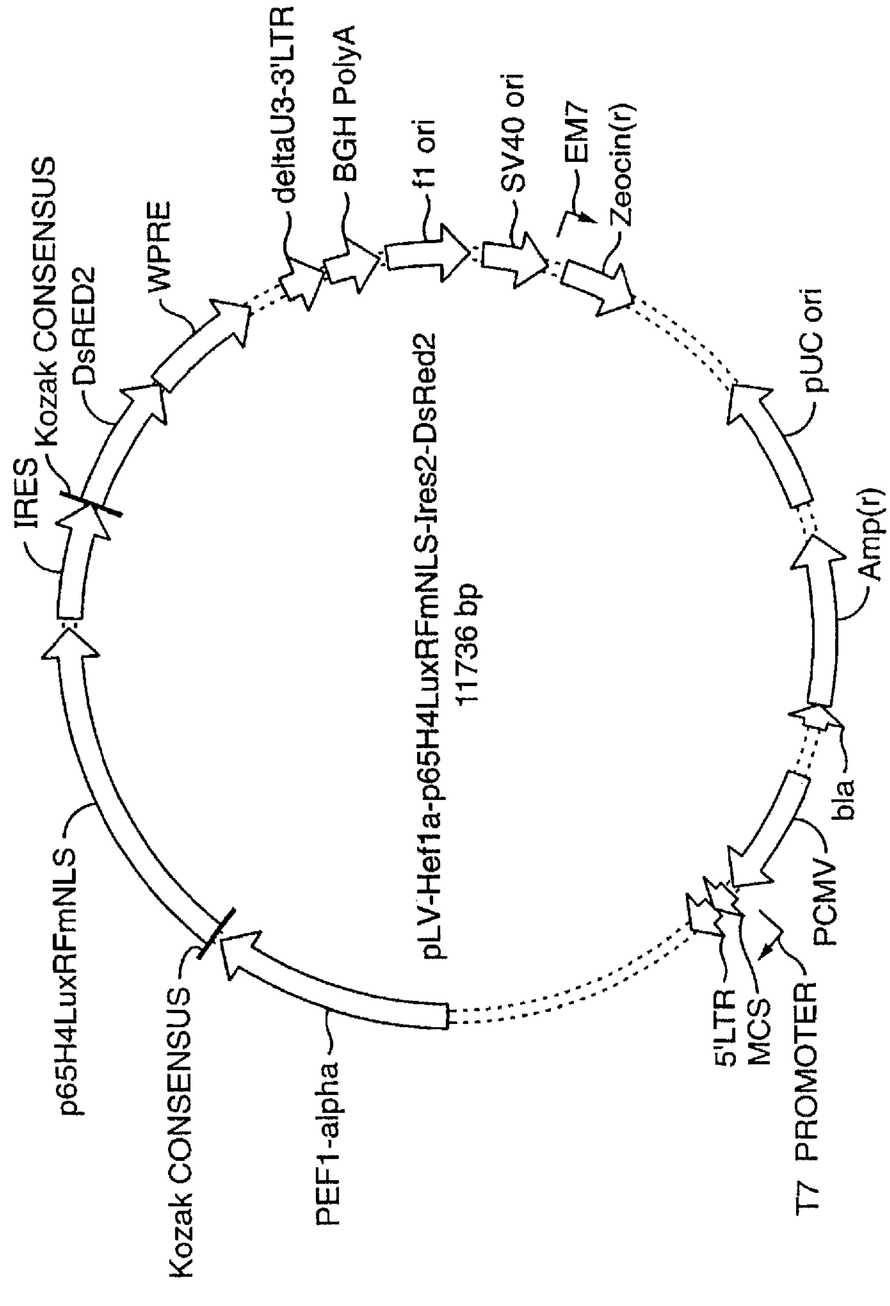
FIG. 8 provides a diagram of the vector of FIG. 7.
Figure 10:
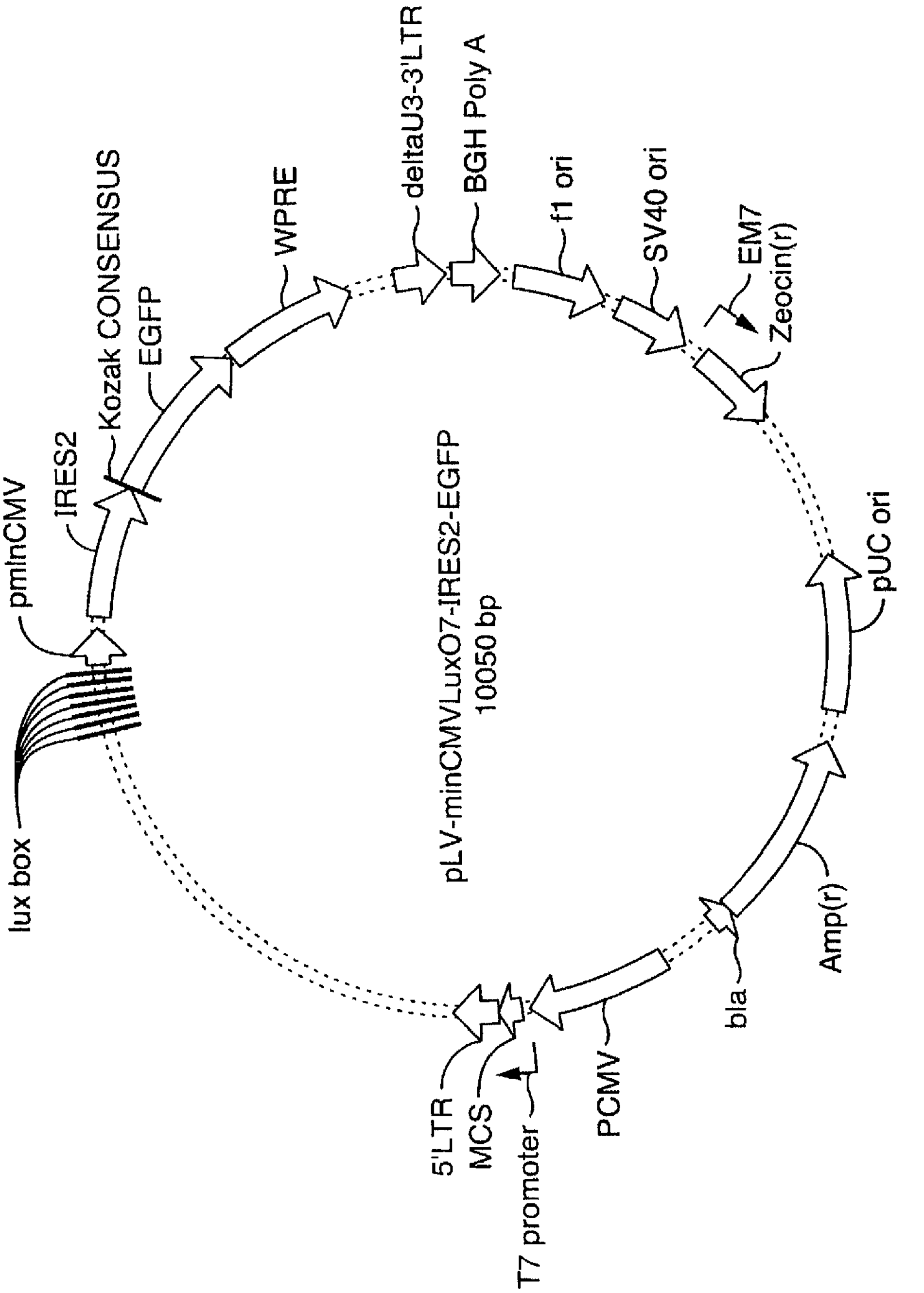
FIG. 10 provides a diagram of the vector of FIG. 9.
Figure 12:
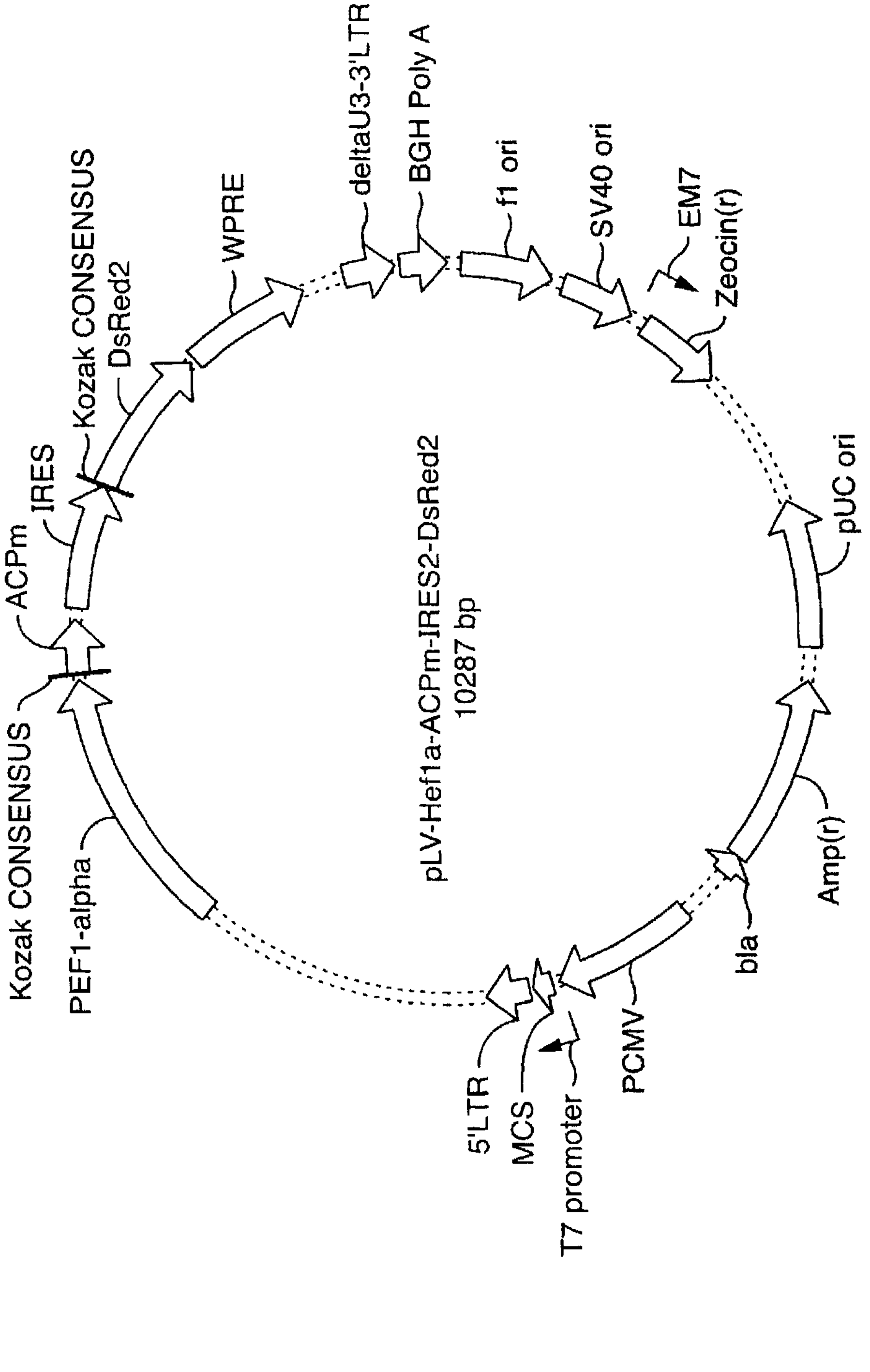
FIG. 12 provides a diagram of the vector of FIG. 11.
Figure 14:
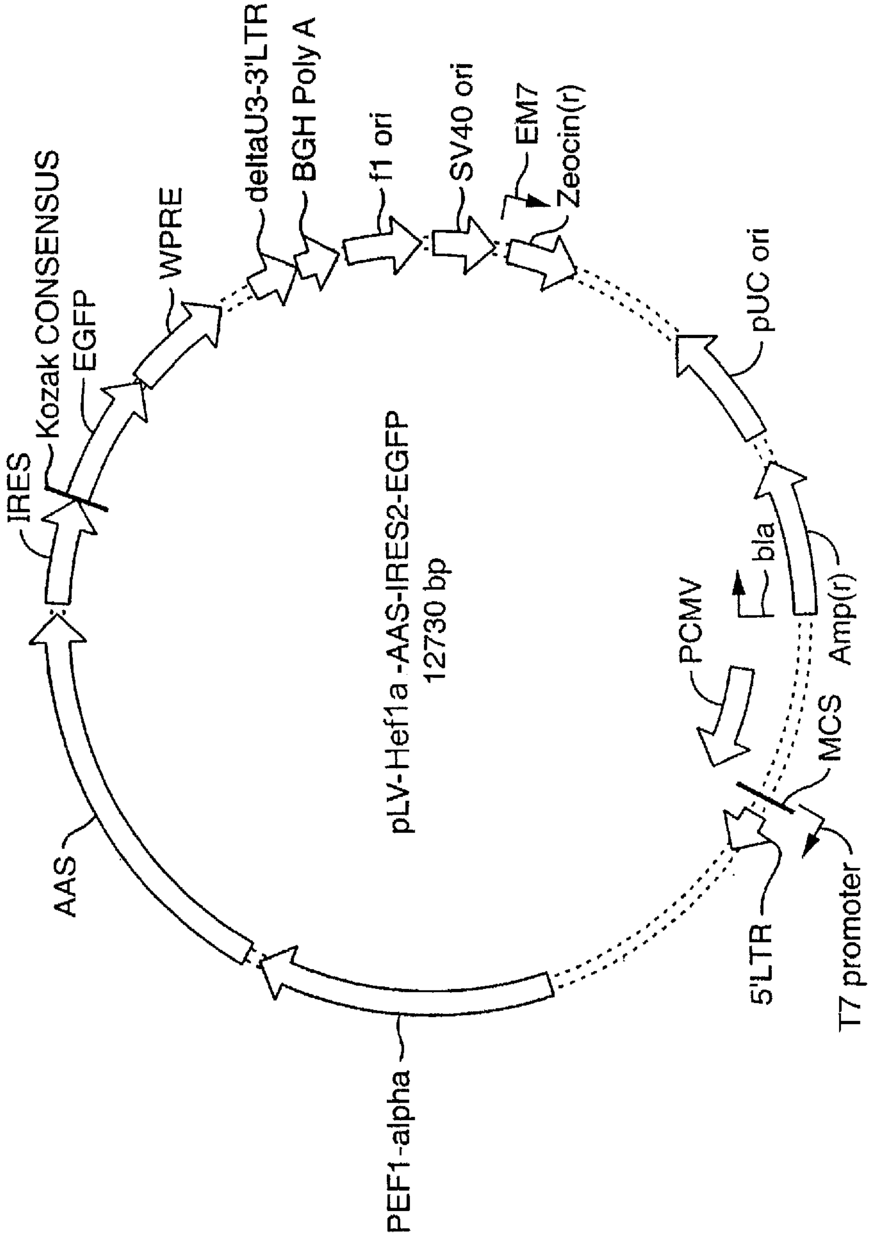
FIG. 14 provides a diagram of the vector of FIG. 13.
Figure 16:
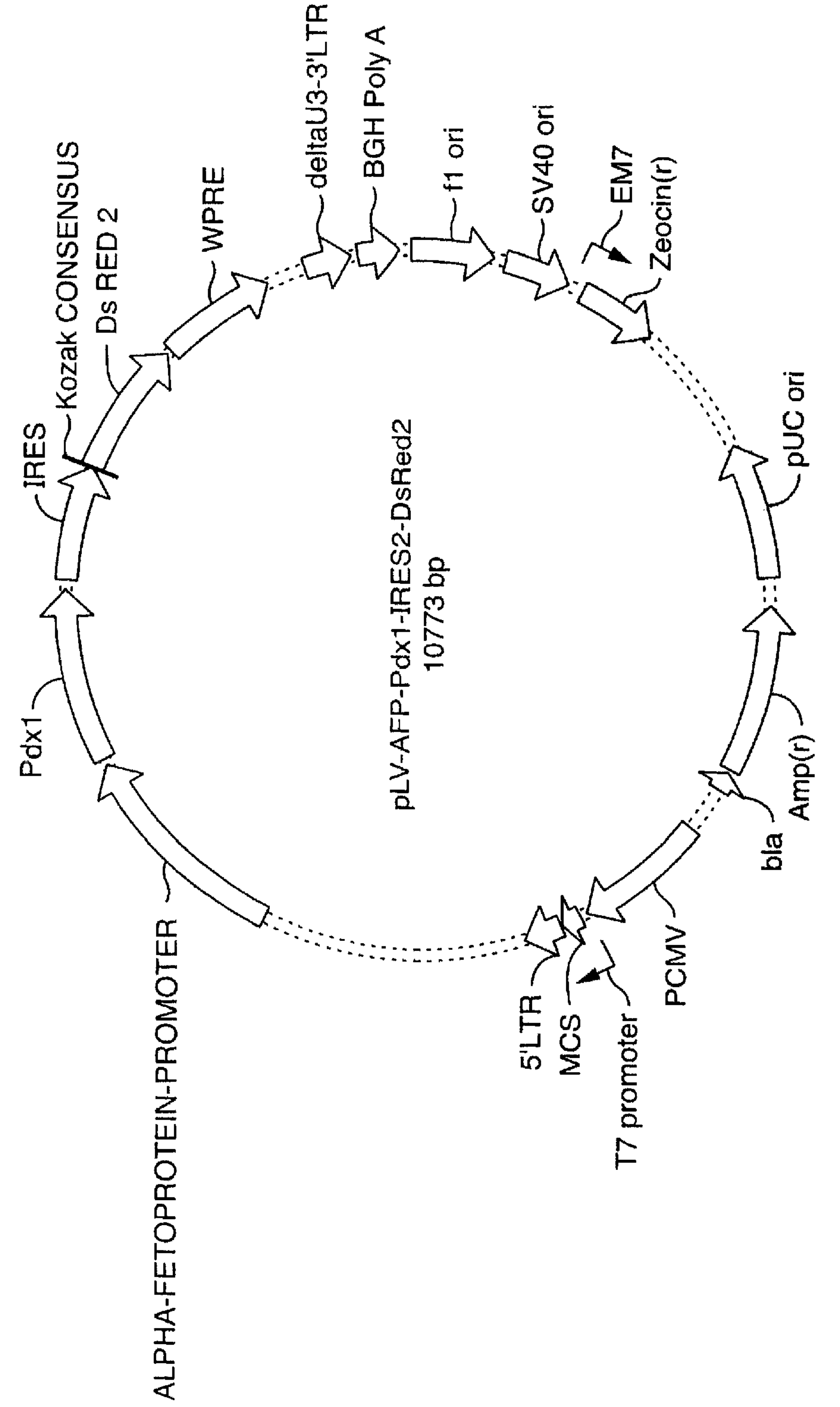
FIG. 16 provides a diagram of the vector of FIG. 15.
Figure 18:
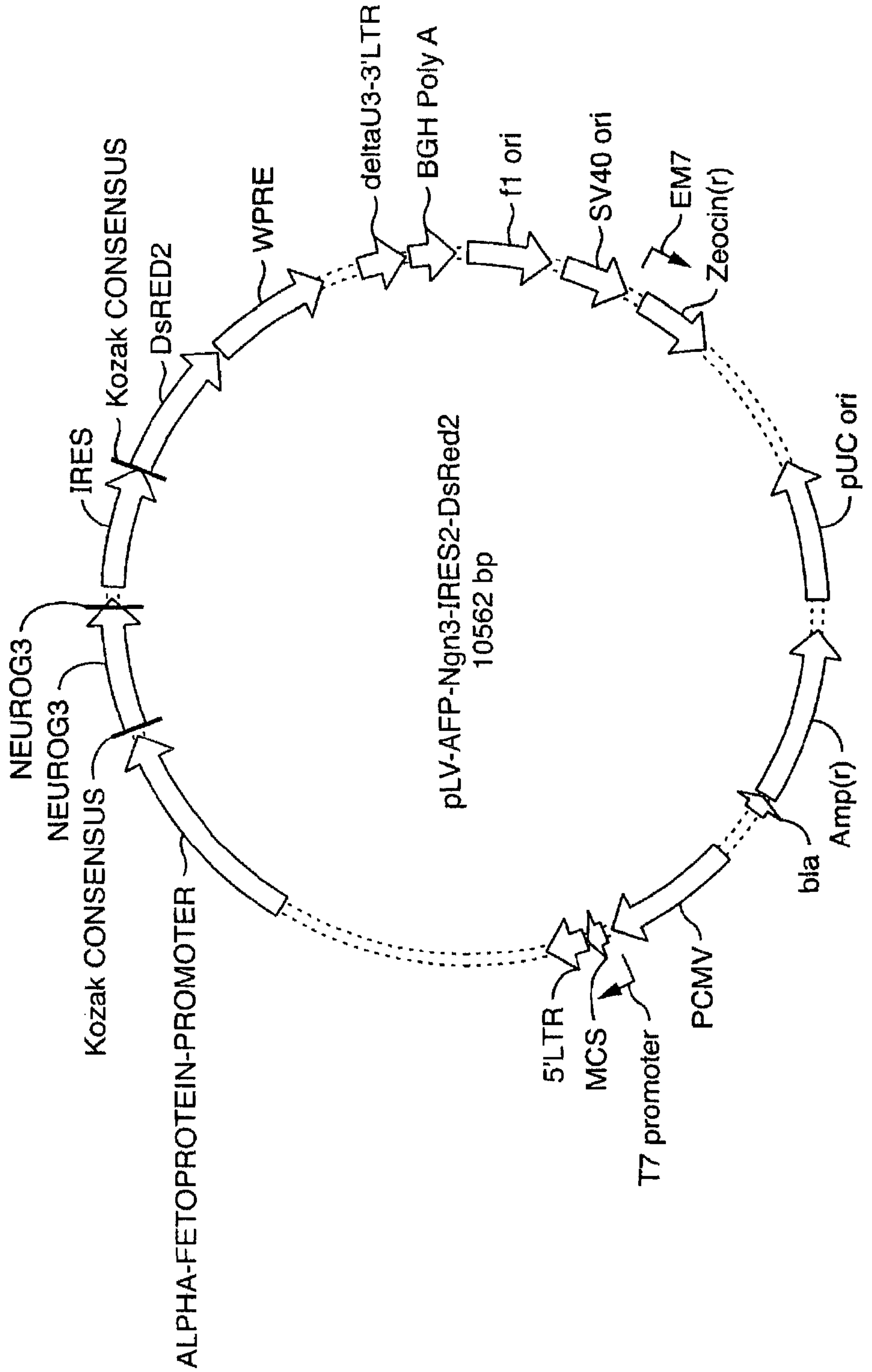
FIG. 18 provides a diagram of the vector of FIG. 17.
Figure 20:
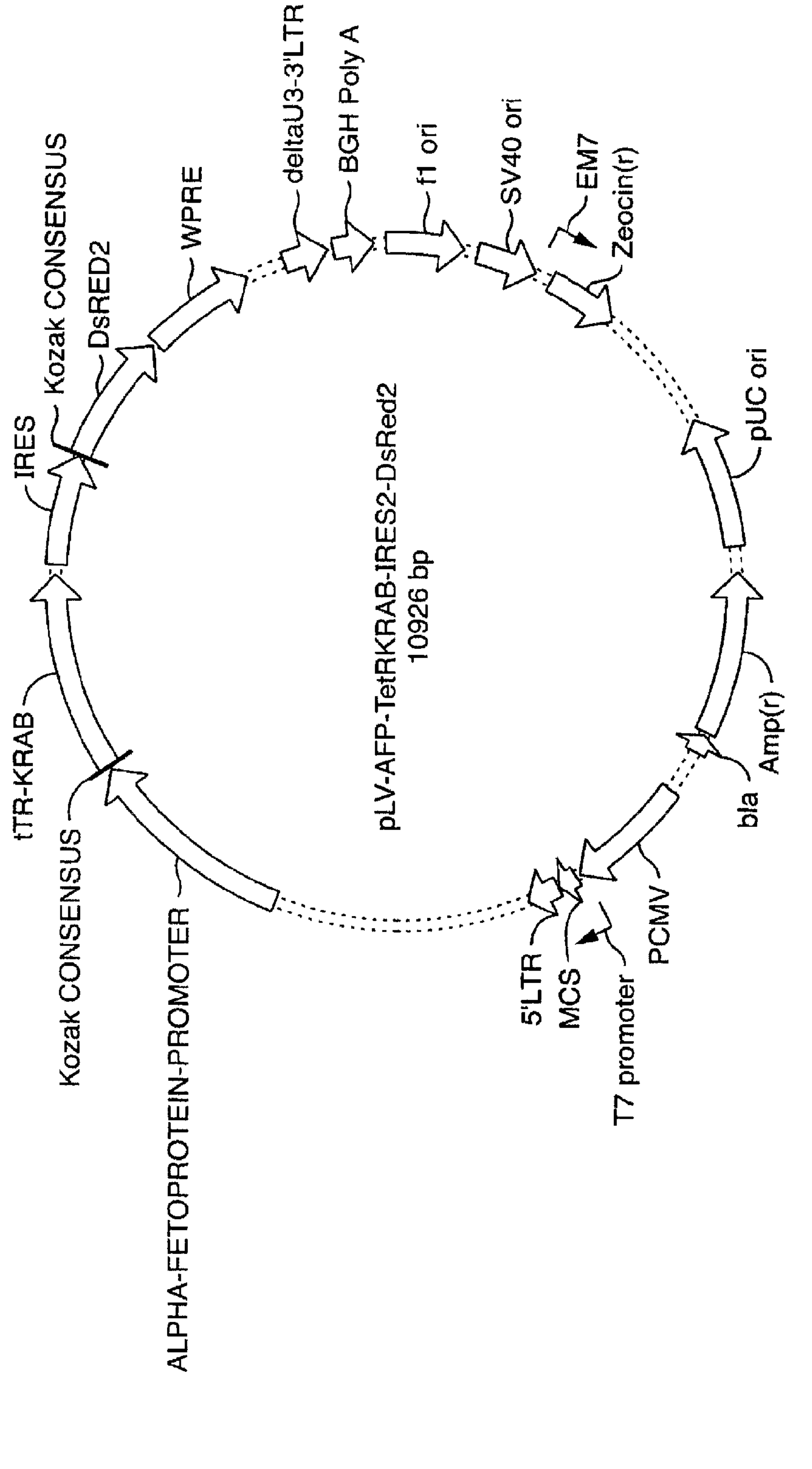
FIG. 20 provides a diagram of the vector of FIG. 19.
Figure 22:
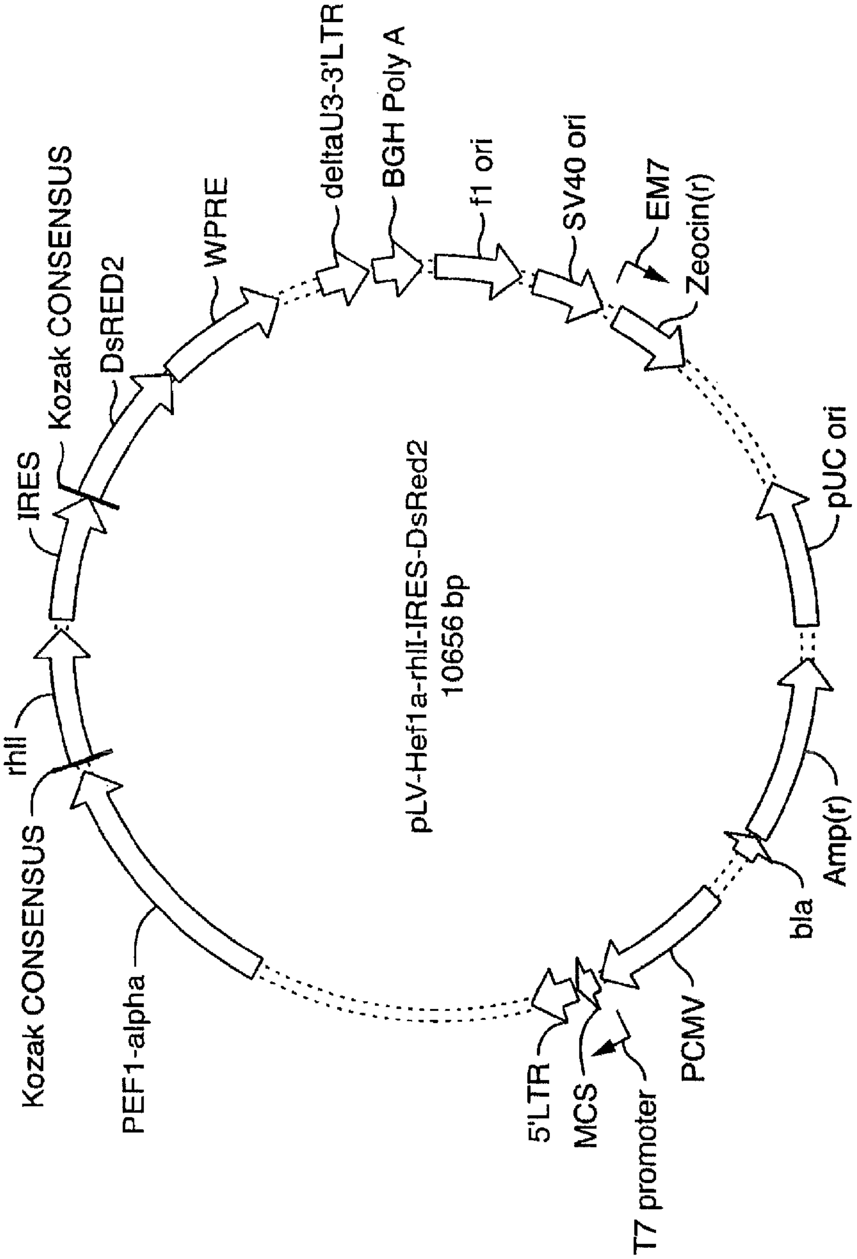
FIG. 22 provides a diagram of the vector of FIG. 21.
Figure 23A:
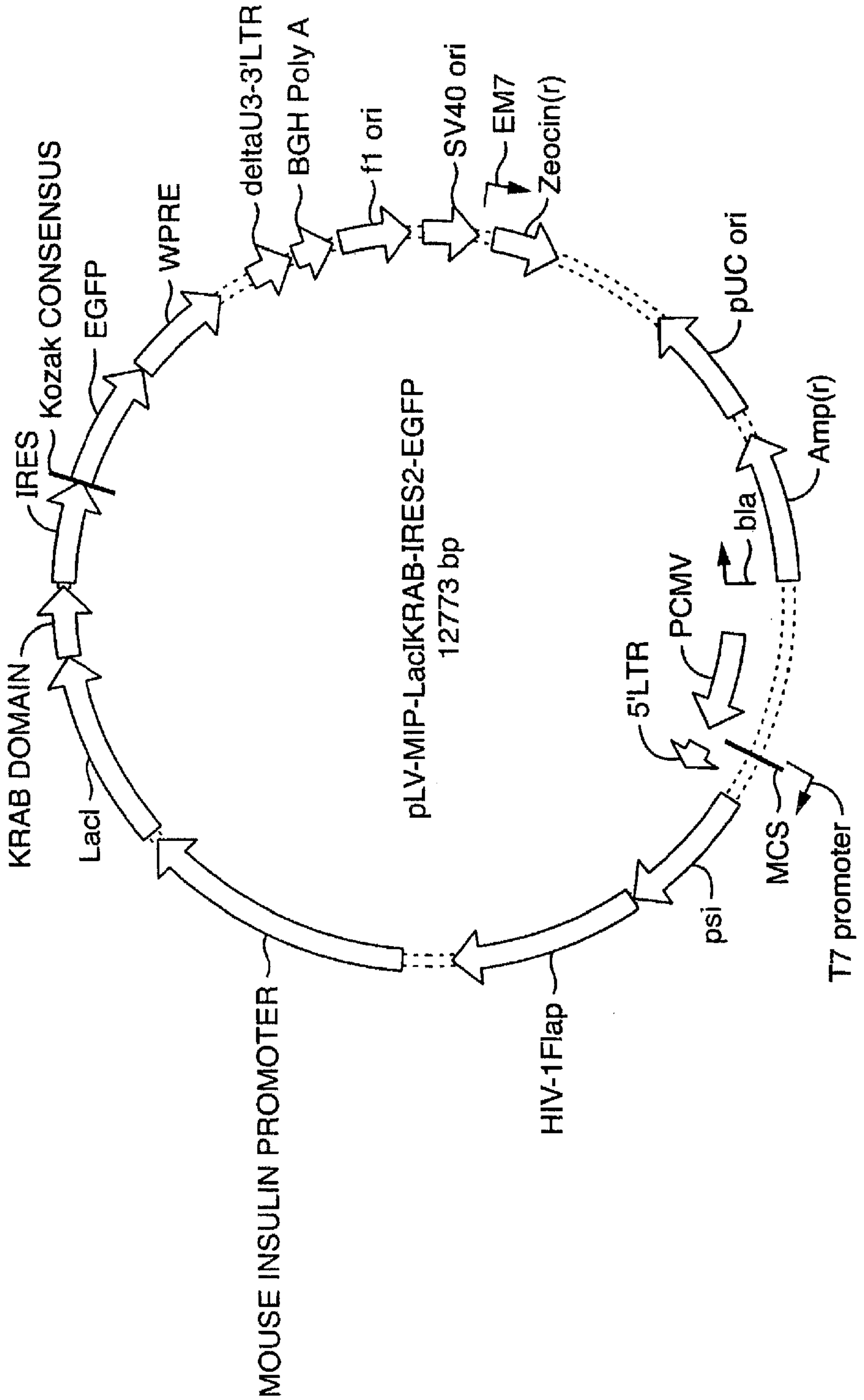
FIG. 23 provides a diagram and sequence (SEQ ID NO:10) for the vector pLV-MIP-LacIKRAB-IRES2-EGFP FIG. 24 provides a diagram and sequence (SEQ ID NO:11) for the vector pLV-MIP-IRES2-EGFP.
Figure 24A:
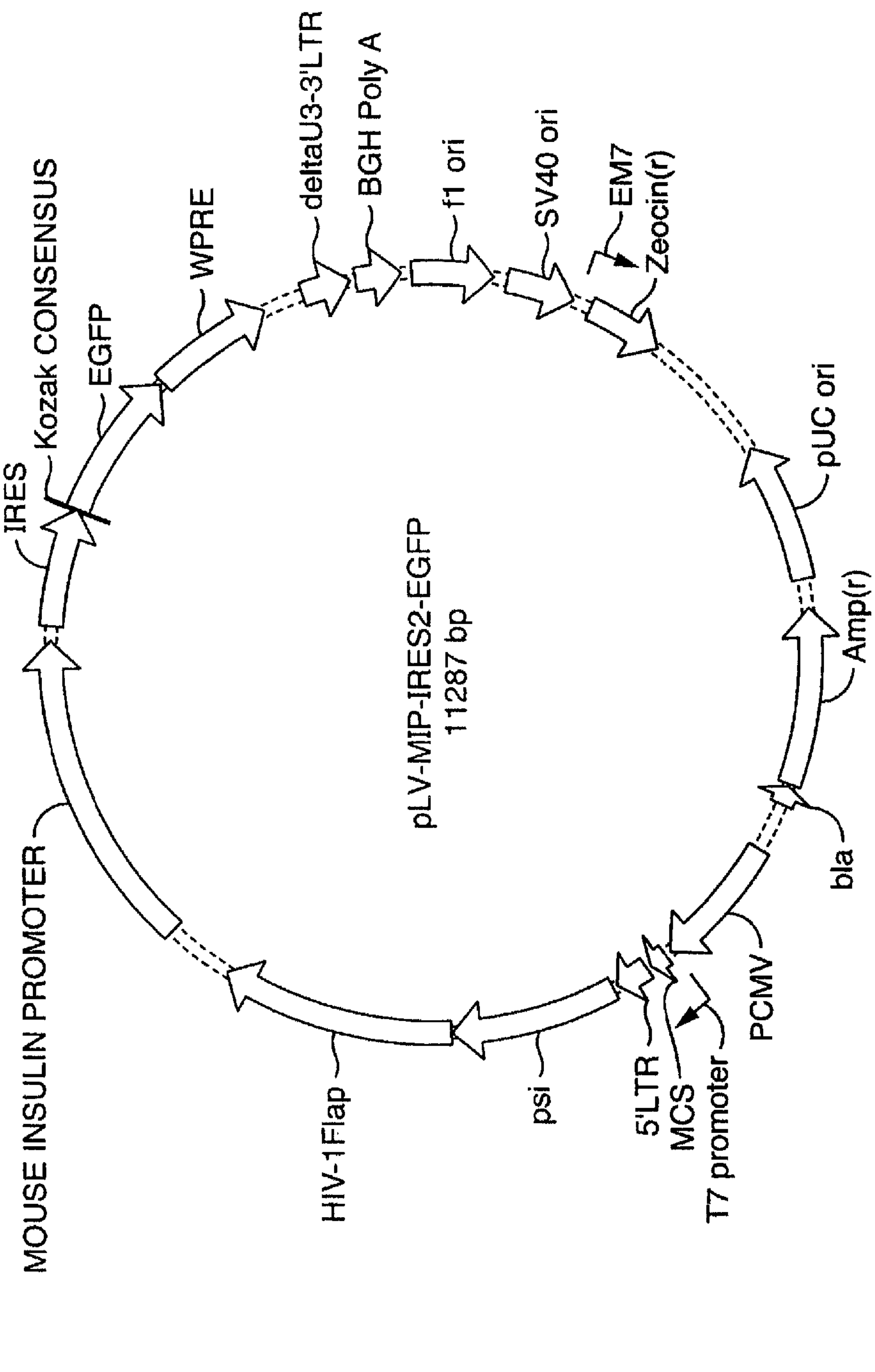
Figure 25A:
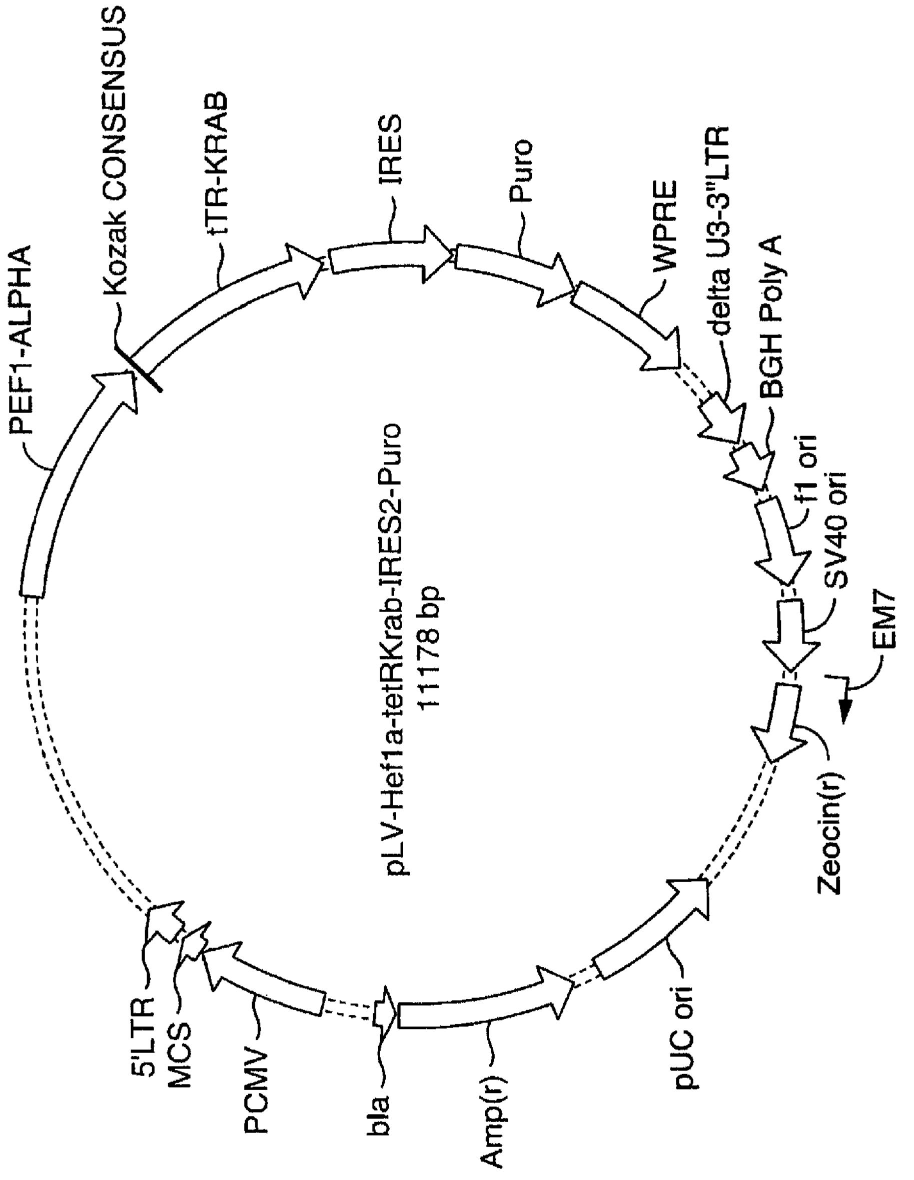
FIG. 25 provides a diagram and sequence for SEQ ID NO:12) for the vector pLV-TetRKRAB-IRES2-Puro.

In some preferred embodiments, the quorum sensing system of the present invention comprises one or more of the vectors described in FIGS. 5-25, and SEQ ID Nos:01-12. FIGS. 5 and 6 provide a map and sequence (SEQ ID NO:01) for the LuxI vector-pLV-Hef1a-LuxIm-IRES2-DsRed2; FIGS. 7 and 8 provide a map and sequence (SEQ ID NO:02) for the LuxR vector-pLV-Hef1a-p65H4LuxRFm-IRES2-DsRed2; FIGS. 9 and 10 provide a map and sequence (SEQ ID NO:03) for the lux promoter vector for expression of Gata4/Sox17-pLV-minCMVLuxO7-IRES2-EGFP; FIGS. 11 and 12 provide a map and sequence (SEQ ID NO:04) for the ACP vector-pLV-Hef1a-ACPm-IRES2-DsRed2; FIGS. 13 and 14 provide a map and sequence (SEQ ID NO:05) for the AAS vector-pLV-Hef1a-AAS-IRES2-EGFP; FIGS. 15 and 16 provide a map and sequence (SEQ ID NO:06) for the AFP promoter vector PDX1-pLV-AFP-Pdx1-IRES2-DsRed2; FIGS. 17 and 18 provide a map and sequence (SEQ ID NO:07) for the AFP promoter vector Ngn3-pLV-AFP-Ngn3-IRES2-DsRed2; FIGS. 19 and 20 provide a map and sequence (SEQ ID NO:08) for the AFP promoter vector for TetRKRAB-pLV-AFP-TetRKRAB-IRES2-DsRed2; FIGS. 21 and 22 provide a map and sequence (SEQ ID NO:09) for the Rh1I vector-pLV-Hef1a-Rh1I-IRES2-DsRed2.

It will be recognized that forgoing vectors are plasmid vectors utilized for the production of lentiviral vectors that are used to transducer target cells such as embryonic stems cells or adult stem cells. The quorum sensing pathway components are derived from bacterial genes. In preferred embodiments, the bacterial genes are codon optimized for expression in mammalian cells. It will also be recognized that the sequences of the components of the vectors may be varied. Accordingly, the present invention encompasses the use of vector components, including the genes of interest such as LuxI, CinI, Rh1I, LuxR, CinR, Rh1R, and any of the cell fate regulators that are at least 50%, 70%, 80%, 90%, or 95% identical to the wild type gene of interest and maintain the function of the gene of interest. Likewise, the present invention encompasses the use of promoters that that are at least 50%, 70%, 80%, 90%, or 95% identical to the promoter sequences described herein such as the lux promoter, AFP promoter, etc. In some preferred embodiments, the genes encoding LuxR, CinR, or Rh1R are modified to include a mammalian activation domain. In preferred embodiments, the mammalian activation domain is the P65 mammalian activation domain. In preferred embodiments, the LuxR-, CinR-, or Rh1I-regulator proteins are therefore a fusion with a mammalian activation domain. Accordingly, in some embodiments, the present invention provides vectors and systems comprising vectors that comprise a gene encoding a regulator protein-mammalian activation domain fusion protein.

In further embodiments, the present invention provides promoters that are inducible by a regulatory protein-autoinducer complex. In some embodiments, the promoter comprises at least one, and preferably 2, 3, 4, 5, 6, 7, 8, 9, or 10 sequences that bind the regulatory protein-autoinducer complex. In some embodiments, the promoter further comprises a minimal element from a mammalian promoter. In some embodiments, the minimal element is derived from the cytomegalovirus promoter, an example of such a promoter is provided in FIGS. 9 and 10, SEQ ID NO:3.

Accordingly, in some preferred embodiments, the present invention provides vectors with the following components in operable association:

5'LTR-Promoter-Mammalian codon optimized LuxI-3'LTR

5'LTR-Promoter-Mammalian codon optimized LuxI-IRES-Reporter-3'LTR

5'LTR-Repressible promoter-Mammalian codon optimized LuxI-3'LTR

5'LTR-LacI promoter-Mammalian codon optimized LuxI-3'LTR

5'LTR-Promoter-Mammalian codon optimized Rh1I-3'LTR

5'LTR-Promoter-Mammalian codon optimized Rh1I-IRES-Reporter-3'LTR

5'LTR-Repressible promoter-Mammalian codon optimized Rh1I-3'LTR

5'LTR-LacI promoter-Mammalian codon optimized Rh1I-3'LTR

5'LTR-Promoter-Mammalian codon optimized CinI-3'LTR

5'LTR-Promoter-Mammalian codon optimized CinI-IRES-Reporter-3'LTR

5'LTR-Repressible promoter-Mammalian codon optimized CinI-3'LTR

5'LTR-LacI promoter-Mammalian codon optimized CinI-3'LTR

5'LTR-Promoter-Mammalian codon optimized LuxR-3'LTR

5'LTR-Promoter-Mammalian codon optimized LuxR-IRES-Reporter-3'LTR

5'LTR-Repressible promoter-Mammalian codon optimized LuxR-3'LTR

5'LTR-LacI promoter-Mammalian codon optimized LuxR-3'LTR

5'LTR-Promoter-Mammalian codon optimized Rh1R-3'LTR

5'LTR-Promoter-Mammalian codon optimized Rh1R-IRES-Reporter-3'LTR

5'LTR-Repressible promoter-Mammalian codon optimized Rh1R-3'LTR

5'LTR-LacI promoter-Mammalian codon optimized Rh1R-3'LTR

5'LTR-Promoter-Mammalian codon optimized CinR-3'LTR

5'LTR-Promoter-Mammalian codon optimized CinR-IRES-Reporter-3'LTR

5'LTR-Repressible promoter-Mammalian codon optimized CinR-3'LTR

5'LTR-LacI promoter-Mammalian codon optimized CinR-3'LTR

5'LTR-Promoter-Mammalian codon optimized LuxR P65 fusion-3'LTR

5'LTR-Promoter-Mammalian codon optimized LuxR P65 fusion-IRES-Reporter-3'LTR

5'LTR-Repressible promoter-Mammalian codon optimized LuxR P65 fusion-3'LTR

5'LTR-LacI promoter-Mammalian codon optimized LuxR P65 fusion-3'LTR

5'LTR-Promoter-Mammalian codon optimized Rh1R P65 fusion-3'LTR

5'LTR-Promoter-Mammalian codon optimized Rh1R P65 fusion-IRES-Reporter-3'LTR

5'LTR-Repressible promoter-Mammalian codon optimized Rh1R P65 fusion-3'LTR

5'LTR-LacI promoter-Mammalian codon optimized Rh1R P65 fusion-3'LTR

5'LTR-Promoter-Mammalian codon optimized CinR P65 fusion-3'LTR

5'LTR-Promoter-Mammalian codon optimized CinR P65 fusion-IRES-Reporter-3'LTR

5'LTR-Repressible promoter-Mammalian codon optimized CinR P65 fusion-3'LTR

5'LTR-LacI promoter-Mammalian codon optimized CinR P65 fusion-3'LTR

5'LTR-regulatory protein/autoinducer responsive promoter-cell fate regulator gene-3'LTR 5'LTR-regulatory protein/autoinducer responsive promoter-cell fate regulator gene-IRES-reporter gene-3'LTR 5'LTR-regulatory protein/autoinducer responsive promoter-cell fate regulator gene-IRES-selectable marker-3'LTR 5'LTR-lux promoter-cell fate regulator gene-3'LTR 5'LTR-regulatory protein/autoinducer responsive promoter-Gata4 gene-3'LTR 5'LTR-regulatory protein/autoinducer responsive promoter-Sox17-3'LTR 5'LTR-promoter-mammalian codon optimized ACP-3'LTR 5'LTR-promoter-mammalian codon optimized AAS-3'LTR 5'LTR-stage specific promoter-cell fate regulator-3'LTR 5'LTR-AFP promoter-cell fate regulator-3'LTR 5'LTR-stage specific promoter-cell fate regulator-IRES-reporter-3'LTR 5'LTR-AFP promoter-cell fate regulator-IRES-reporter-3'LTR 5'LTR-stage specific promoter-cell fate regulator-IRES-selectable marker-3'LTR 5'LTR-AFP promoter-cell fate regulator-IRES-selectable marker-3'LTR 5'LTR-stage specific promoter-Pdx1 gene-3'LTR 5'LTR-AFP promoter-Pdx1 gene-3'LTR 5'LTR-stage specific promoter-Pdx1 gene-IRES-reporter-3'LTR 5'LTR-AFP promoter-Pdx1 gene-IRES-reporter-3'LTR 5'LTR-stage specific promoter-Pdx1 gene-IRES-selectable marker-3'LTR 5'LTR-AFP promoter-Pdx1 gene-IRES-selectable marker-3'LTR 5'LTR-stage specific promoter-Ngn3 gene-3'LTR 5'LTR-AFP promoter-Ngn3 gene-3'LTR 5'LTR-stage specific promoter-Ngn3 gene-IRES-reporter-3'LTR 5'LTR-AFP promoter-Ngn3 gene-IRES-reporter-3'LTR 5'LTR-stage specific promoter-Ngn3 gene-IRES-selectable marker-3'LTR 5'LTR-AFP promoter-Ngn3 gene-IRES-selectable marker-3'LTR 5'LTR-stage specific promoter-TetR-3'LTR 5'LTR-AFP promoter-TetRr-3'LTR 5'LTR-stage specific promoter-TetR-IRES-reporter-3'LTR 5'LTR-AFP promoter-TetR-IRES-reporter-3'LTR 5'LTR-stage specific promoter-TetR-IRES-selectable marker-3'LTR 5'LTR-AFP promoter-TetR-IRES-selectable marker-3'LTR 5'LTR-terminal differentiation promoter-repressor-3'LTR 5'LTR-MIP promoter-repressor-3'LTR 5'LTR-stage specific promoter-repressor-IRES-reporter-3'LTR 5'LTR-MIP promoter-repressor-IRES-reporter-3'LTR 5'LTR-stage specific promoter-repressor-IRES-selectable marker-3'LTR 5'LTR-MIP promoter-repressor-IRES-selectable marker-3'LTR 5'LTR-terminal differentiation promoter-LacI-3'LTR 5'LTR-MIP promoter-LacI-3'LTR 5'LTR-stage specific promoter-LacI-IRES-reporter-3'LTR 5'LTR-MIP promoter-LacI-IRES-reporter-3'LTR 5'LTR-stage specific promoter-LacI-IRES-selectable marker-3'LTR 5' LTR-MIP promoter-LacI-IRES-selectable marker-3'LTR In the vectors described above, the 5' and 3' LTRs are preferably retroviral LTRs and most preferably lentiviral LTRs. The vectors can preferably comprise additional elements in additional to the listed elements.

G. Cells

The quorum sensing system of the present invention may be introduced into a variety of mammalian cell types. In preferred embodiments, the quorum sensing system is introduced into embryonic or adult stem cells. However, the quorum sensing systems may be introduced into any mammalian cell lines, including, but not limited to, 293 cells, to Chinese hamster ovary cells (CHO-K1, ATCC CCl-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC 5 cells; FS4 cells; rat fibroblasts (208F cells); MDBK cells (bovine kidney cells); and a human hepatoma line (Hep G2).

The present invention is not limited to the use of any particular type of embryonic stem cells. Indeed, the use of embryonic stem cells from a number of animal species is contemplated. Methods for obtaining totipotent or pluripotent cells from humans, monkeys, mice, rats, pigs, cattle and sheep have been previously described. See, e.g., U.S. Pat. Nos. 5,453,357; 5,523,226; 5,589,376; 5,340,740; and 5,166,065 (all of which are specifically incorporated herein by reference); as well as, Evans, et al., Theriogenology 33(1):125-128, 1990; Evans, et al., Theriogenology 33(1): 125-128, 1990; Notarianni, et al., J. Reprod. Fertil. 41(Suppl.):51-56, 1990; Giles, et al., Mol. Reprod. Dev. 36:130-138, 1993; Graves, et al., Mol. Reprod. Dev. 36:424-433, 1993; Sukoyan, et al., Mol. Reprod. Dev. 33:418-431, 1992; Sukoyan, et al., Mol. Reprod. Dev. 36:148-158, 1993; Iannaccone, et al., Dev. Biol. 163:288-292, 1994; Evans & Kaufman, Nature 292:154-156, 1981; Martin, Proc Natl Acad Sci USA 78:7634-7638, 1981; Doetschman et al. Dev Biol 127:224-227, 1988); Giles et al. Mol Reprod Dev 36:130-138, 1993; Graves & Moreadith, Mol Reprod Dev 36:424-433, 1993 and Bradley, et al., Nature 309:255-256, 1984.

Primate embryonic stem cells may be preferably obtained by the methods disclosed in U.S. Pat. Nos. 5,843,780 and 6,200,806, each of which is incorporated herein by reference. Primate (including human) stem cells may also be obtained from commercial sources such as WiCell, Madison, Wis. A preferable medium for isolation of embryonic stem cells is "ES medium." ES medium consists of 80% Dulbecco's modified Eagle's medium (DMEM; no pyruvate, high glucose formulation, Gibco BRL), with 20% fetal bovine serum (FBS; Hyclone), 0.1 mM β-mercaptoethanol (Sigma), 1% non-essential amino acid stock (Gibco BRL). Preferably, fetal bovine serum batches are compared by testing clonal plating efficiency of a low passage mouse ES cell line ($ES_{jt3}$), a cell line developed just for the purpose of this test. FBS batches must be compared because it has been found that batches vary dramatically in their ability to support embryonic cell growth, but any other method of assaying the competence of FBS batches for support of embryonic cells will work as an alternative.

Primate ES cells are isolated on a confluent layer of murine embryonic fibroblast in the presence of ES cell medium. Embryonic fibroblasts are preferably obtained from 12 day old fetuses from outbred CF1 mice (SASCO), but other strains may be used as an alternative. Tissue culture dishes are preferably treated with 0.1% gelatin (type I; Sigma). Recovery of rhesus monkey embryos has been demonstrated, with recovery of an average 0.4 to 0.6 viable embryos per rhesus monkey per month, Seshagiri et al. Am J Primatol 29:81-91, 1993. Embryo collection from marmoset monkey is also well documented (Thomson et al. "Non-surgical uterine stage preimplantation embryo collection from the common marmoset," J Med Primatol, 23:333-336 (1994)). Here, the zona pellucida is removed from blastocysts by brief exposure to pronase (Sigma). For immunosurgery, blastocysts are exposed to a 1:50 dilution of rabbit anti-marmoset spleen cell antiserum (for marmoset blastocysts) or a 1:50 dilution of rabbit anti-rhesus monkey (for rhesus monkey blastocysts) in DMEM for 30 minutes, then washed for 5 minutes three times in DMEM, then exposed to a 1:5 dilution of Guinea pig complement (Gibco) for 3 minutes.

After two further washes in DMEM, lysed trophectoderm cells are removed from the intact inner cell mass (ICM) by gentle pipetting, and the ICM plated on mouse inactivated (3000 rads gamma irradiation) embryonic fibroblasts. After 7-21 days, ICM-derived masses are removed from endoderm outgrowths with a micropipette with direct observation under a stereo microscope, exposed to 0.05% Trypsin-EDTA (Gibco) supplemented with 1% chicken serum for 3-5 minutes and gently dissociated by gentle pipetting through a flame polished micropipette.

Dissociated cells are replated on embryonic feeder layers in fresh ES medium, and observed for colony formation. Colonies demonstrating ES-like morphology are individually selected, and split again as described above. The ES-like morphology is defined as compact colonies having a high nucleus to cytoplasm ratio and prominent nucleoli. Resulting ES cells are then routinely split by brief trypsinization or exposure to Dulbecco's Phosphate Buffered Saline (without calcium or magnesium and with 2 mM EDTA) every 1-2 weeks as the cultures become dense. Early passage cells are also frozen and stored in liquid nitrogen.

The present invention is not limited to the use of any particular adult stem cell. The adult stem cell is an undifferentiated (unspecialized) cell that is found in a differentiated (specialized) tissue; it can renew itself and become specialized to yield specialized cell types of the tissue from which it originated. These precursor cells exist within the differentiated tissues of the adult of all multicellular organisms. Precursor cells derived from adults can be divided into three categories based on their potential for differentiation. These three categories of precursor cells are epiblast-like stem cells, germ layer lineage stem cells, and progenitor cells. Precursor cells have been isolated from a wide variety of tissues, including, but not limited to, skeletal muscle, dermis, fat, cardiac muscle, granulation tissue, periosteum, perichondrium, brain, meninges, nerve sheaths, ligaments, tendons, blood vessels, bone marrow, trachea, lungs, esophagus, stomach, liver, intestines, spleen, pancreas, kidney, urinary bladder, and testis. Precursor cells can be released from the connective tissue compartments throughout the body by mechanical disruption and/or enzymatic digestion and have been isolated from, but not limited to, newborns, adolescent, and geriatric mice, rats and humans, and adult rabbits, dogs, goats, sheep, and pigs.

The first category of precursor cells, epiblast-like stem cells (ELSCs), consists of a stem cell that will form cells from all three embryonic germ layer lineages. Stem cells from adult rats and stem cells from adult humans can be released from the connective tissue compartments throughout the body by mechanical disruption and/or enzymatic digestion. The stem cells from either adult rats or adult humans can be preferentially slow frozen and stored at −80° C.±5° C. using 7.5% ultra-pure dimethyl sulfoxide. Fast thawing of stem cells from both species from the frozen state to ambient temperature yields recovery rates exceeding 98%. These cells in the undifferentiated state express the Oct-3/4 gene that is characteristic of embryonic stem cells. ELSCs do not spontaneously differentiate in a serum free environment lacking progression agents, proliferation agents, lineage-induction agents, and/or inhibitory factors, such as recombinant human leukemia inhibitory factor (LIF), recombinant murine leukemia inhibitory factor (ESGRO), or recombinant human anti-differentiation factor (ADF). Embryonic stem cells spontaneously differentiate under these conditions. In contrast, ELSCs derived from both species remain quiescent unless acted upon by specific proliferative and/or inductive agents and/or environment.

ELSCs proliferate to form multiple confluent layers of cells in vitro in the presence of proliferation agents such as platelet-derived growth factors and respond to lineage-induction agents. ELSCs respond to hepatocyte growth factor by forming cells belonging to the endodermal lineage. Cell lines have expressed phenotypic markers for many discrete cell types of ectodermal, mesodermal, and endodermal origin when exposed to general and specific induction agents.

The second category of precursor cells consists of three separate stem cells. Each of the cells forms cells of a specific embryonic germ layer lineage (ectodermal stem cells, mesodermal stem cells and endodermal stem cells). When exposed to general and specific inductive agents, germ layer lineage ectodermal stem cells can differentiated into, for example, neuronal progenitor cells, neurons, ganglia, oligodendrocytes, astrocytes, synaptic vesicles, radial glial cells, and keratinocytes.

The third category of precursor cells present in adult tissues is composed of a multitude of multipotent, tripotent, bipotent, and unipotent progenitor cells. In solid tissues these cells are located near their respective differentiated cell types. Progenitor cells do not typically display phenotypic expression markers for pluripotent ELSCs, such as stage specific embryonic antigen-4, stage-specific embryonic antigen-1 or stage-specific embryonic antigen-3, or carcinoembryonic antigen cell adhesion molecule-1. Similarly, progenitor cells do not typically display phenotypic expression markers for germ layer lineage stem cells, such as nestin for cells of the ectodermal lineage or fetoprotein for cells of the endodermal lineage.

A progenitor cell may be multipotent, having the ability to form multiple cell types. A precursor cell of ectodermal origin residing in the adenohypophysis and designated the adenohypophyseal progenitor cell is an example of a multipotent progenitor cell. This cell will form gonadotrophs, somatotrophs, thyrotrophs, corticotrophs, and mammotrophs. Progenitor cells for particular cell lineages have unique profiles of cell surface cluster of differentiation (CD) markers and unique profiles of phenotypic differentiation expression markers. Progenitor cells do not typically spontaneously differentiate in serum-free defined medium in the absence of a differentiation agent, such as LIF or ADF. Thus, unlike embryonic stem cells which spontaneously differentiate under these conditions, progenitor cells remain quiescent unless acted upon by proliferative agents (such as platelet-derived growth factor) and/or progressive agents (such as insulin, insulin-like growth factor-I or insulin-like growth factor-II).

Progenitor cells can regulate their behavior according to changing demands such that after transplantation they activate from quiescence to proliferate and generate both new satellite cells and substantial amounts of new differentiated cells. For example, the contractile units of muscle are myofibers, elongated syncytial cells each containing many hundreds of postmitotic myonuclei. Satellite cells are resident beneath the basal lamina of myofibers and function as myogenic precursors during muscle regeneration. In response to muscle injury, satellite cells are activated, proliferate, and differentiate, during which they fuse together to repair or replace damaged myofibers. When satellite cells are removed from their myofibers by a non-enzymatic physical titration method, they retain their ability to generate substantial quantities of new muscle after grafting that they are not able to attain by enzymatic digestion. Conventional enzymatic disaggregation techniques impair myogenic potential. Collins and Partridge "Self-Renewal of the Adult Skeletal Muscle Satellite Cell" Cell Cycle 4:10, 1338-1341 (2005).

Accordingly, the present invention also contemplates the use of non-embryonic stem cells, such as those described above. In some embodiments, mesenchymal stem cells (MSCs) can be derived from marrow, periosteum, dermis and other tissues of mesodermal origin (See, e.g., U.S. Pat. Nos. 5,591,625 and 5,486,359, each of which is incorporated herein by reference). MSCs are the formative pluripotential blast cells that differentiate into the specific types of connective tissues (i.e. the tissues of the body that support the specialized elements; particularly adipose, areolar, osseous, cartilaginous, elastic, marrow stroma, muscle, and fibrous connective tissues) depending upon various in vivo or in vitro environmental influences. Although these cells are normally present at very low frequencies in bone marrow, various methods have been described for isolating, purifying, and greatly replicating the marrow-derived mesenchymal stems cells in culture, i.e. in vitro (See also U.S. Pat. Nos. 5,197,985 and 5,226,914 and PCT Publication No. WO 92/22584, each of which are incorporated herein by reference).

Various methods have also been described for the isolation of hematopoietic stem cells (See, e.g., U.S. Pat. Nos. 5,061,620; 5,750,397; 5,716,827 all of which are incorporated herein by reference). It is contemplated that the methods of the present invention can be used to produce lymphoid, myeloid and erythroid cells from hematopoietic stem cells. The lymphoid lineage, comprising B-cells and T-cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers.

Accordingly, the present invention also contemplates the use of neural stem cells, which are generally isolated from developing fetuses. The isolation, culture, and use of neural stem cells are described in U.S. Pat. Nos. 5,654,183; 5,672,499; 5,750,376; 5,849,553; and 5,968,829, all of which are incorporated herein by reference. It is contemplated that the methods of the present invention can use neural stem cells to produce neurons, glia, melanocytes, cartilage and connective tissue of the head and neck, stroma of various secretory glands and cells in the outflow tract of the heart.

In some embodiments, the quorum sensing systems are incorporated into cord blood cells. Transplantation of umbilical-cord blood has been successfully performed to treat individuals with blood-diseases; donors, used have been newborn siblings being perfect HLA matches for the affects sibling. The advantages of cord blood as a source of hematopoietic stem cells for transplantation are clear. First, the proliferative capacity of hematopoietic stem cells in cord blood is superior to that of cells in marrow or blood from adults. Because they proliferate rapidly, the stem cells in a single unit of cord blood can reconstitute the entire hematopoietic system. Second, the use of cord blood reduces the risk of graft-versus-host disease, the main obstacle to the success of allogeneic transplantation of hematopoietic stem cells. Graft-versus-host disease is caused by a reaction of T cells in the graft to HLA antigens in the recipient; the immaturity of lymphocytes in cord blood dampens that reaction. A joint European study showed that recipients of cord blood from HLA-identical siblings had a lower risk of acute or chronic graft-versus-host disease than recipients of marrow from HLA-identical siblings. Children with acute leukemia who received HLA-mismatched cord blood from an unrelated donor also had a lower risk of graft-versus-host disease than recipients of HLA-mismatched marrow from an unrelated donor (Hematopoietic stem-cell transplants using umbilical-cord blood, *New England Journal of Medicine,* 2001, 344(24):1860-1861, editorial). Cord blood cells from siblings or children with matching HLA could be used to produce cell lines for use as contemplated by this invention.

H. Treatment Methods

In preferred embodiments, cells incorporating the vectors or systems of vectors described are introduced into a subject in need of treatment. In some embodiments, where the subject is diabetic, synthetic β cells comprising the quorum sensing system described above are introduced into the diabetic subject. In preferred embodiments, the synthetic β cells produce insulin. It will be recognized that the systems described above can be adapted to cause the differentiation of embryonic stem cells, adult stem cells and cord blood stem cells into a variety of cell types that can be utilized for therapeutic purposes, including neurons, chondrocytes, myocytes, and keratinocytes of various types.

In some embodiments, banks of cells comprising the quorum sensing systems described above are provided. In preferred embodiments, the banks of cells include cell lines that are programmed to attain a particular differentiated states, such as β cells. In some embodiments, the banks of cells comprise multiple cell lines expressing different combinations of HLA antigens. It is contemplated that such banks will result in an increased likelihood of obtaining a 6-6, 10-10 or greater match for a particular subject.

I. Identification of Additional Genes Involved in Beta Cell Differentiation

In some embodiments, the systems of the present invention are used to identify genes involved in pancreatic β cell differentiation using RNAi knockdown assays. In preferred embodiments, the assays utilize a large library of shRNAs comprising >100,000 hairpins which target ~21,000 human and ~17,000 mouse genes, 30,000 of which are cloned into a tet-inducible microRNA-embedded shRNA lentiviral vector.

Figure 4A:
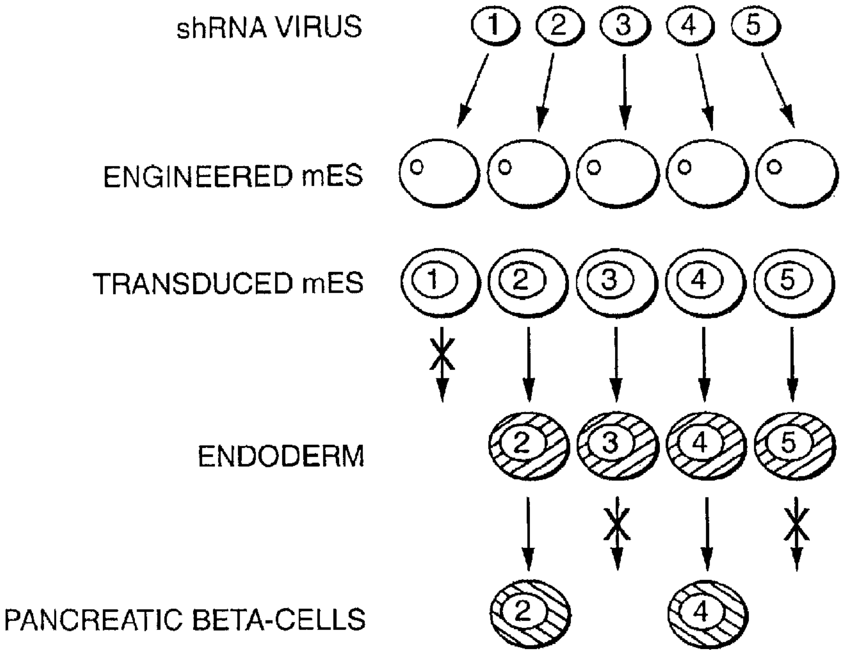
FIG. 4: (a) shRNA is transduced into engineered mES cells and cells are allowed to differentiate into pancreatic β cells. (b) Before differentiation, shRNAs will be uniformly present in mES cells. After differentiation there will be different pools of cell types (undifferentiated mES cells, endodermal cells or pancreatic β cells, e.g.) depending on the effect of the transduced shRNAs. The resulting shRNA ratios compared with the shRNA ratios before differentiation will allow identification of genes necessary for differentiation.
Figure 4B:
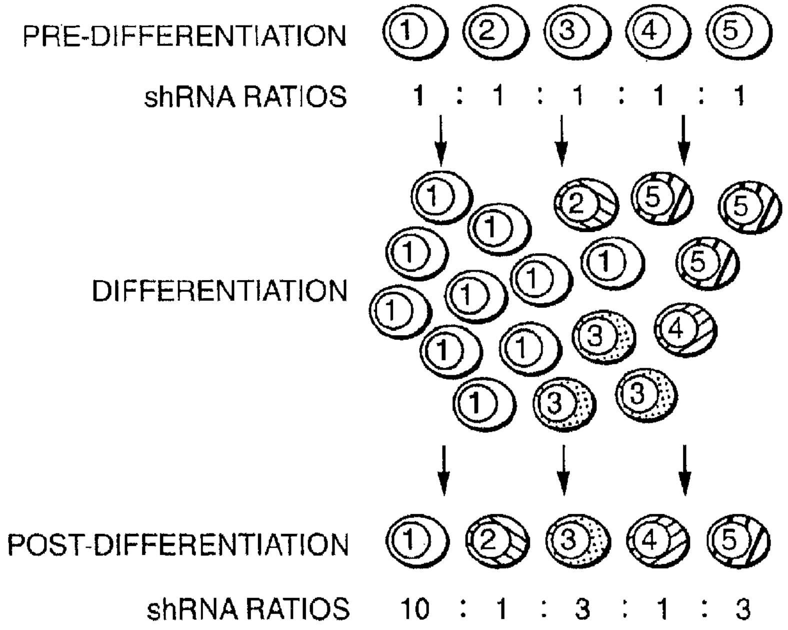

The RNAi knockdown assay is illustrated in FIG. 4. First, engineered ES cells are transduced with a lentiviral shRNA library at an MOI of 1, so that each post-transduction cell will have one shRNA. After quorum sensing and two-step differentiation occurs in the transduced cells, three unique pools of cells emerge in the population. The first consists of cells in which shRNA interferes with the differentiation of mES cells to endoderm, causing cells to retain stem cell character and proliferate rapidly. The second pool consists of cells in which shRNA interferes with the differentiation of endodermal cells to β cells, causing cells to retain endoderm character and proliferate more slowly than the stem cells. The last pool consists of cells in which shRNA does not interfere with the two-step differentiation process from mES cells, resulting in slowly- or non-dividing β cells. Two populations of cells, a sample of the initial population after transduction and a sample of the population directed to differentiate, will be subjected to microarray analysis. Comparisons of the relative ratios of individual shRNA will allow identification of genes that are involved at each step of the differentiation process.

EXAMPLES

Example 1

Figure 2A:
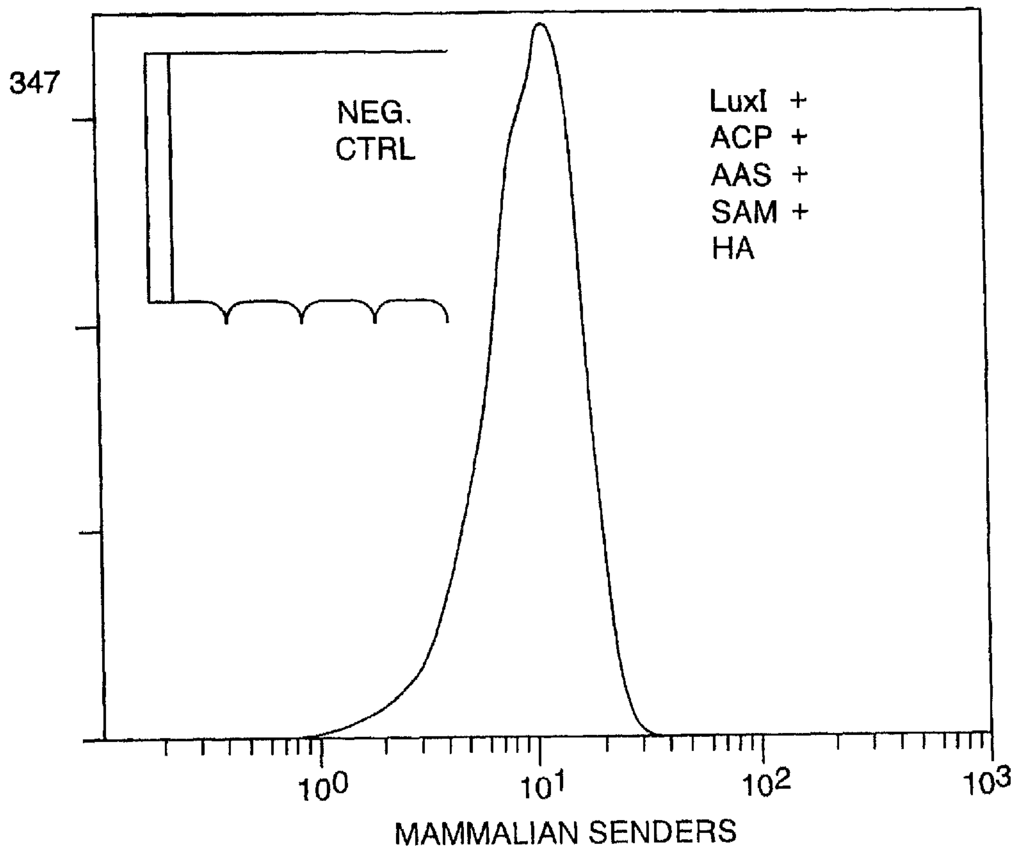
FIG. 2: (a) 30C6HSL synthesis by mammalian 293FT cells. Supernatant from the cells' growth media was collected and filter sterilized. Histograms show the fluorescence intensities of bacterial cells sensitive to 30C6HSL grown in the filtered supernatant, expressing green fluorescent protein due to 30C6HSL from the mammalian cells. (b) 30C6HSL detection by mammalian receiver cells. 293FT Cells express DsRed constitutively, but express EGFP only upon induction with exogenous 30C6HSL. (c) Controlled stem cell differentiation with genetically inducible systems. Three different lentiviral genetic constructs were built, enabling exogenous chemical induction into myoblasts, adipocytes, or maintenance of stem cell properties. Dox-induced mES cells expressing MyoD causes visible changes to a myoblast morphology. In addition, the marker protein for myoblasts, dystrophin, was expressed from these cells (data not shown). PPARγ expression resulted in an adipocyte morphology. In a separate experiment, induced expression of Nanog supplanted the need for a growth factor usually required to maintain the overall character of mES cells.
Figure 2B:
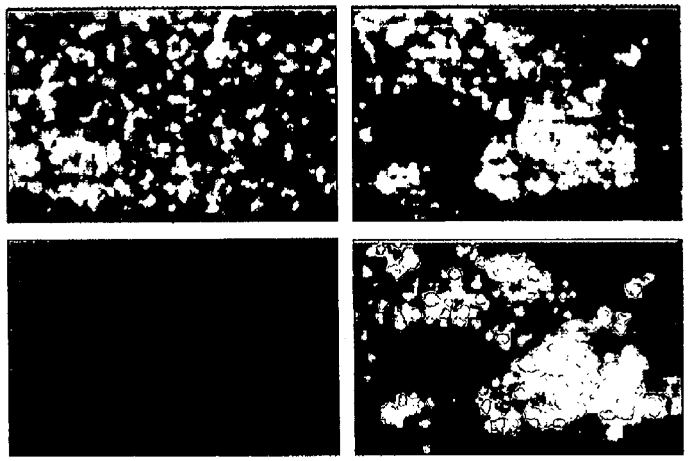
Figure 2C:
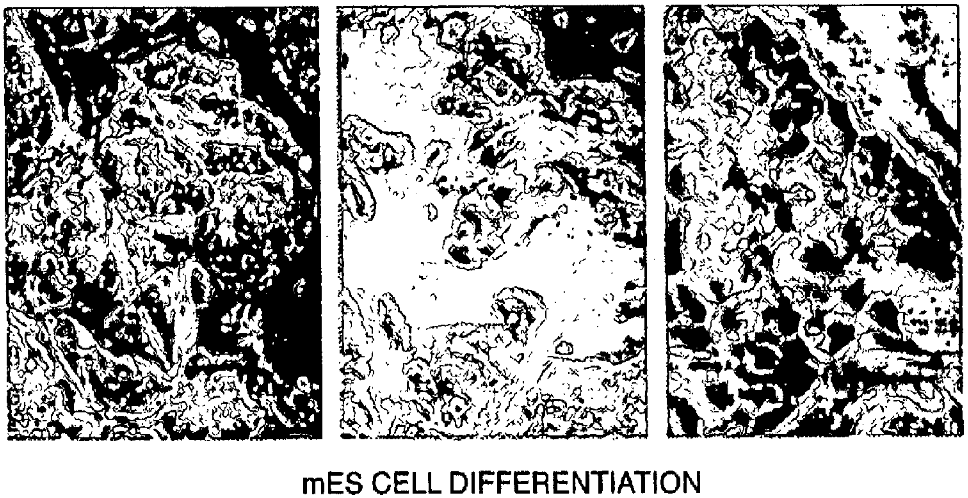

293FT cells that were genetically engineered to synthesize 30C6HSL were grown in liquid media, and this media was found to contain 30C6HSL (FIG. 2*a*). The 30C6HSL detection pathway consists of a signal transducer that binds 30C6HSL and activates transcription of genes controlled by a synthetic lux promoter. The 30C6HSL signal transducer is a chimeric LuxR-activator protein created by the fusion of a P65 mammalian activation domain to a codon optimized mammalian version of a bacterial LuxR. Initial testing of the mammalian version of LuxR in 293FT cells shows a strong response to the addition of 30C6HSL (FIG. 2*b*).

Example 2

Synthetic Gene Networks in Mammalian Cells—the rtTA Switch

A reverse Tetracycline-controlled transactivator (rtTA) switch, where gene expression is upregulated by the addition of Doxycycline (Dox), has been implemented. rtTA is constitutively expressed in the Ainv15 mES cell line and activates transcription of a give cell fate regulator (CFR) and a EGFP as control from the TRE promoter in the presence of Dox. A dosage response curve (not shown) demonstrates that the expression level (as measured by flourescence depending of the Dox concentration.

Controlled Induction of Cell Fate Regulators in mES.

Ngn1, MyoD and Nanog Ainv15 mES stem cells constitutively expressing the Dox-inducible circuit can be infected with a virus encoding Ngn1/EGFP or MyoD/EGFP under the control of a TRE promoter. The cell maintains self-renewal in the absence of Dox, while the presence of Dox results in the differentiation into either cells with a neuronal morphology (Ngn1), muscle cell morphology (MyoD).

Matrigel-Embedded mES—MyoD Expression.

To verify the conditions required for mES cell growth and differentiation in semi-solid media, embedded mES cells were infected with the Dox inducible circuit encoding MyoD/EGFP in Matrigel and subsequently induced with 1 mg/ml Dox over several days. Cells not induced with Dox grow, do not express EGFP and maintained stem cell morphology in a Matrigel matrix. The addition of Dox results in EGFP expression and formation of multinucleated syncitia 60 hours post induction, which is one key development step in formation of muscle fibers.

Example 3

293FT and CHO cells were infected with virus encoding pLV-pTat-IRES2-EGFP, and then exposed three different types of TAT communication molecules with various secretion tags. The 293FT cells are able to internalize the TAT protein, while CHO cells cannot. In the experiment, sender cells were grown for 2 days, and then receiver 293FT cells were grown in the supernatant. As expected, the supernatant from 293FT cells that can internalize the TAT molecule did not yield much communication, while supernatant from the CHO cells was able to active GFP expression significantly in the receiver cells.

Example 4

This example describes the assessment of the transactivatory properties of TAT and the functionality of the signaling modules by having sender and receiver modules in the same cell. Sender cells expressing TAT containing a secretion signal and receiver cells containing the detection module separated by a permeable barrier (e.g. transwell inserts), are used to validate and optimize the cell-cell transducing capabilities of TAT. A hemagglutinin tag (HA-tag) is added as a translational fusion to the C-terminus of TAT, to confirm its expression by means of immunofluorescence (IF) and western blotting (WB).

Engineering TAT Internal Signaling:

By having receiver and mock TAT sender (no secretion signal for export) in the same cell, the transactivatory properties of TAT as well as the detector functionality is validated. As described above, the rtTA switch, where gene expression is upregulated by the addition of Dox, is operational. Full-length HIV-1 TAT with a C-terminal HA-tag is placed under the control of the TRE promoter, enabling induction of TAT expression by adding Dox to the cell culture media. The receiver contains the wild-type HIV-1 pTAT promoter with the TAR element driving expression of EGFP upon TAT binding. To test, the TAT transactivation capabilities, Dox is added to cells, whereupon TAT expression is induced. TAT binds to pTAT and induces the expression of EGFP, which is detected by FACS and/or fluorescence microscopy (FIG. 26).

Figure 26B:
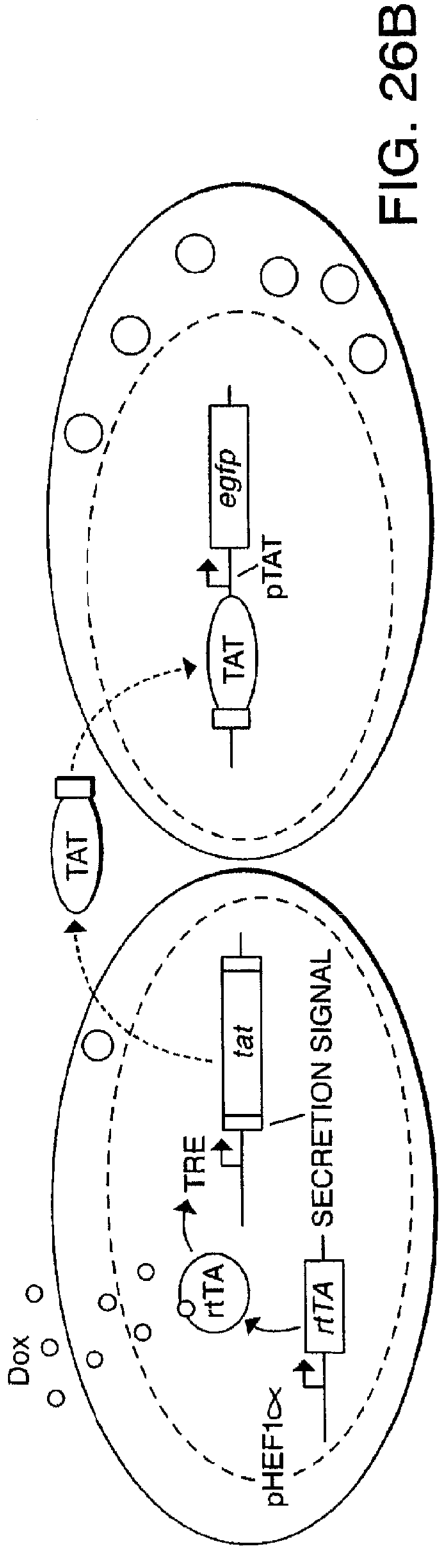

Engineering TAT Senders:

By co-infecting the rtTA switch and the TAT gene with an N-terminal secretion tag and an C-terminal HA-tag under control of the pTRE promoter into cells, Dox-inducible secretion of TAT is achieved (FIG. 26*b*). To get a high level of secretion to the extracellular milieu, the N-terminal export signal sequence present in IL-2 to the N-terminus of TAT is added. To verify protein expression and export, cell lysates and cell supernatants is checked by a WB against the HA tag. Low levels of TAT in the supernatant can be concentrated by precipitation of the protein fraction with triacetic acid.

Engineering TAT Receivers:

By infecting the module containing the pTAT promoter controlling the expression of EGFP, TAT-inducible expression is of EGFP achieved (FIG. 26*b*). Using the TAT senders secreting the protein into the supernatant described in the previous paragraph, EGFP expression in receivers is detectable by fluorescence microscopy or FACS. The uptake of TAT by receiver cells will also be confirmed by IF staining against the HA-tag. Using transwell inserts as a permeable barrier to keep sender and receiver cells separate, cell-cell communication of the secreted TAT can be assessed by measuring the EGFP protein expression levels in the receiver cells (FACS/fluorescence microscopy).

The presence of TAT in the sender cell, in the supernatant, in the cytoplasm or nucleus of the receiver cell will be confirmed by IF and WB against the HA-tag in TAT. Recently, reports have suggested the release from macropinosomes is the limiting factor in the transduction of cells by using a HIS-tag purified TAT-peptide/Cre fusion protein. The addition of an N-terminal 20 amino acids of the influenza virus hemagglutinin protein HA2—which is a fusogenic peptide that destabilizes lipid membranes at low pH in mature endosomes—to the C-terminus of the TAT-peptide, markedly increased its release from the macropinosomes, and subsequently the effectiveness of transduction. As a consequence, the addition of this fusogenic peptide might also increase the effectiveness of cell-cell transduction.

If TAT receiver sensitivity is too low, a TAT-Cre fusion protein with a secretion signal in the sender cells will be made and used to transduce a reporter module into receiver cells where the expression of EGFP from a constitutive promoter is blocked by a terminator with two loxP sites. In principle, the translocation of one TAT-Cre molecule into the nucleus of a receiver cell should be sufficient to trigger the Cre mediated recombination/removal of the terminator, hence full expression of EGFP. Such a TAT-Cre fusion expressing module could also be very useful in tracing the dispersion of TAT in vivo, by using a reporter mouse cell line expressing EGFP upon recombination of a terminator located in its promoter.

Example 5

This example describes the assessment of the effectiveness of in silico designed ZFP-DTS pairs and the functionality of the signaling modules by having sender and receiver modules in the same cell. In a second step, sender cells expressing TAT-ZFP fusions and receiver cells containing the detection module separated by a barrier (e.g. transwell inserts) are used to check and optimize the cell-cell transducing capabilities of TAT-ZFP fusion proteins with their cognate DTS.

Published in silico designed ZFP-DTS pairs, as for example Jazz, EPOZFP-862c and ZFP-809 binding to the DTSs "GCTGCTGCG", "GCGGTGGCT", "G(G/c)GGG (T/a)G(A/g)C" (5-fold, 15-fold and 46-130 fold induction of reporter genes respectively) (37-39) will be used first to demonstrate the functionality of my reporter system. Subsequently, novel in silico ZFP-DTS pairs are designed.

Engineering ZFP-DTS Pairs (in Silico):

Described ZF-nucleotide triplet interactions will be used to assemble novel ZFP-DTS pairs in silico by using existing knowledge on how to engineer translational fusions of such single zinc finger to a ZFP, which is also integrated into the online ZFP design toolset "ZF Tools" developed by the Barbas group (Mandell, J. G. & Barbas, C. F., 3rd (2006) Nucleic acids research 34, W516-523; Mandell, J. G. (2006) (on the world wide web at scripps.edu/mb/barbas/zfdesign/zfdesignhome.php), p. Zinc Finger Tools Version 3.0). Care will be taken to design ZFP-DTS pairs for which the DTS has no significant homologies in the human or mouse genome (nucleotide blast against the genome sequence), to reduce the probability of ZFP binding to endogenous sequences.

Engineering the Internal ZFP-DTS Signaling:

By having receiver and mock sender (no secretion signal for export) in the same cell, the transactivatory properties of the ZFP-DTS pairs as well as the detector functionality will be validated. As described above, the reverse Tetracycline-controlled transactivator (rtTA) switch, where gene expression is upregulated by the addition of Dox is operational. For the mock secretion module, a TAT-ZFP-VP64 fusion (VP64 as a strong enhancer) will be placed under the control of the TRE promoter, enabling induction of TAT-ZFP-VP64 expression by adding Dox to the cell culture media. The receiver module contains a minimal CMV promoter with the cognate DTS for the ZFP driving the expression of EGFP upon TAT-ZFP-VP64 binding. To test the transactivation capabilities, Dox is added to cells containing the artificial network, whereupon TAT-ZFP-VP64 is expressed, exported to the extracellular milieu by the virtue of its N-terminal IL-2 signal peptide, re-enter the cell with the help of the transducing TAT domain and localize to the nucleus where binds to its cognate DTS. The binding of fusion protein to the minimal CMV promoter will induce expression of EGFP (detectable by FACS and/or fluorescence microscopy) (FIG. 27a).

Figures 27A, 27B:
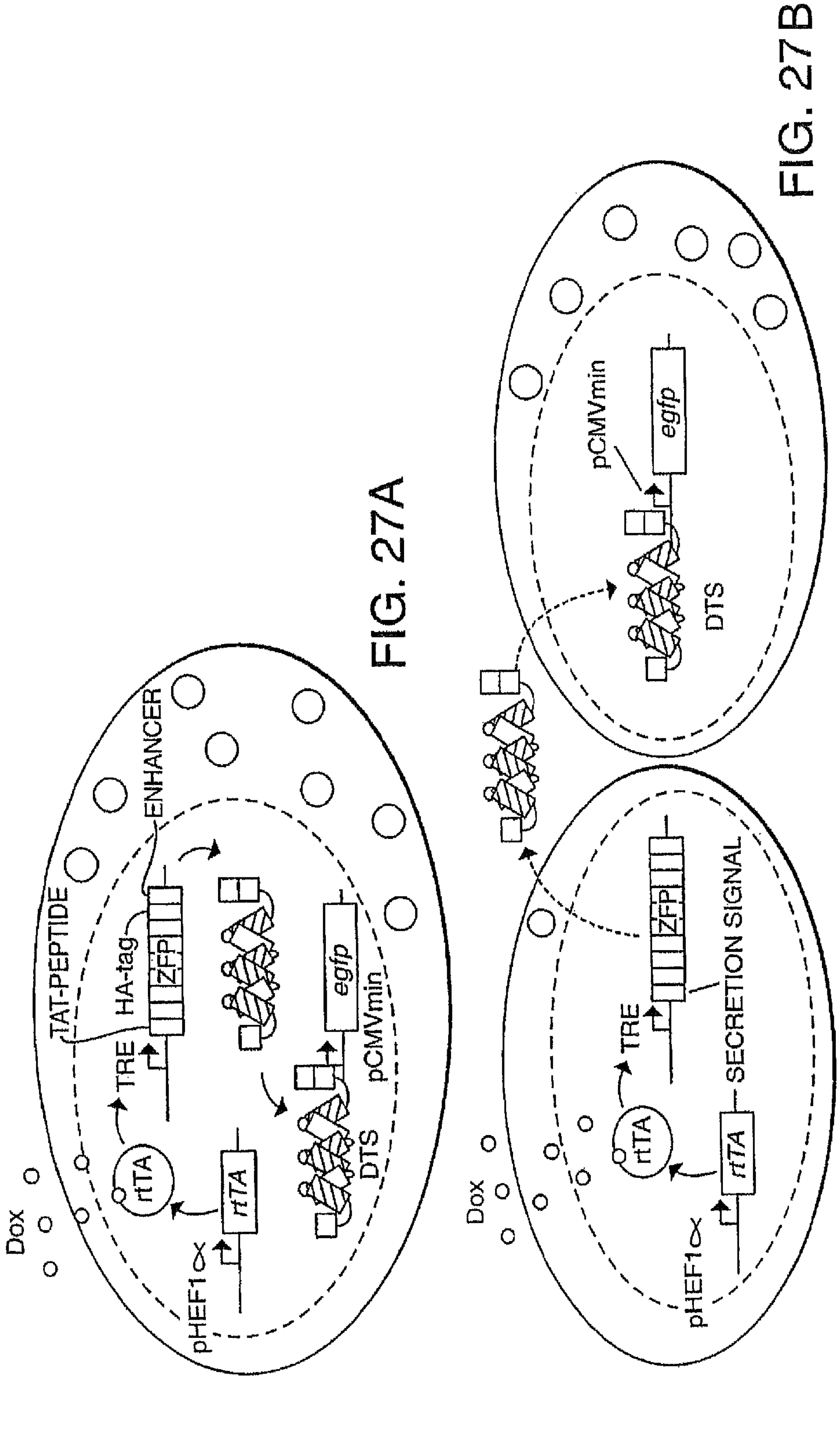
FIG. 27 provides a diagram of a synthetic signaling circuit utilizing cell penetrating polypeptide elements.
Figure 28A:
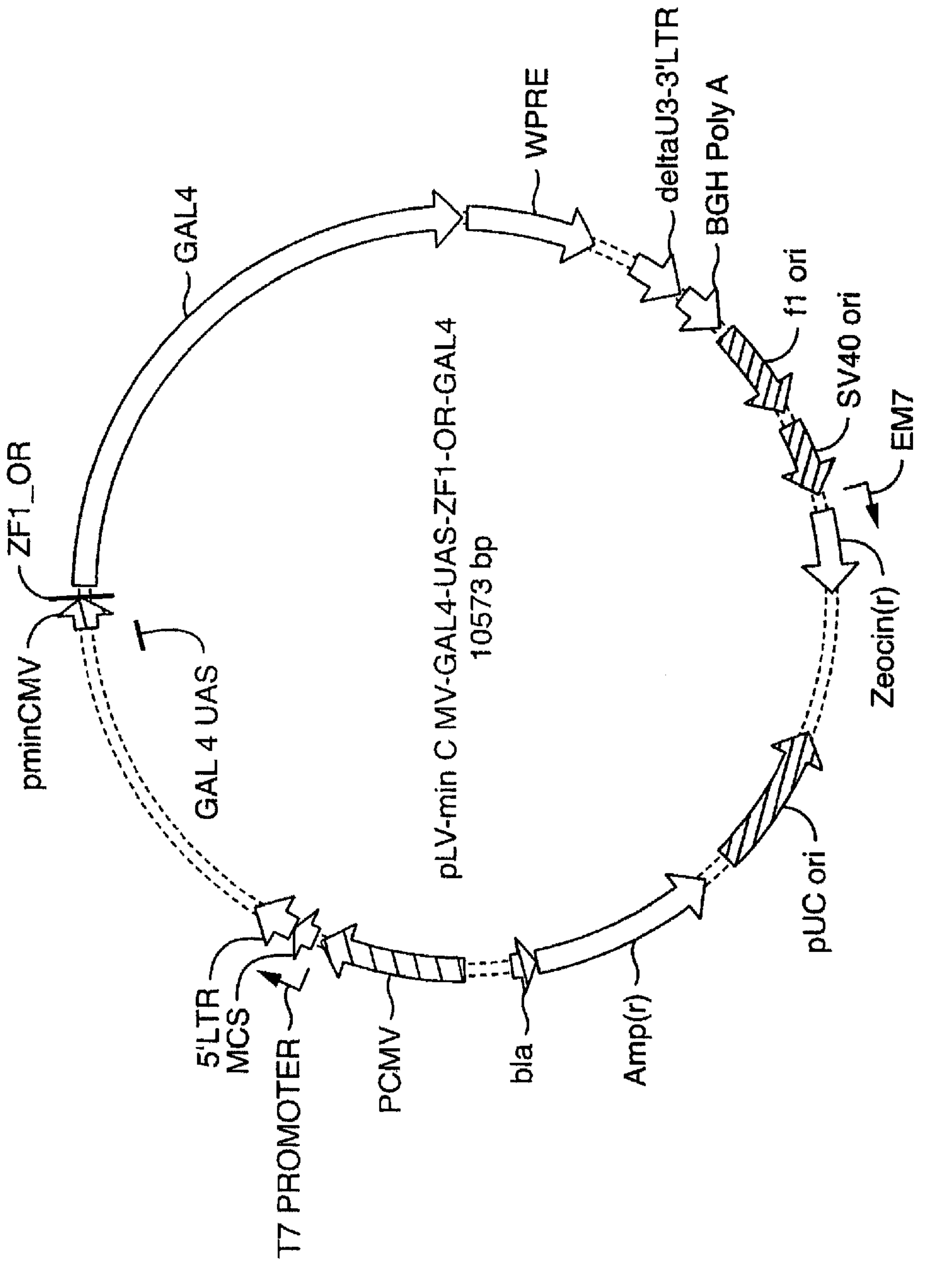
FIG. 28 provides a plasmid and sequence for P_A1_R1/A1 (SEQ ID NO: 13).
Figure 29A:
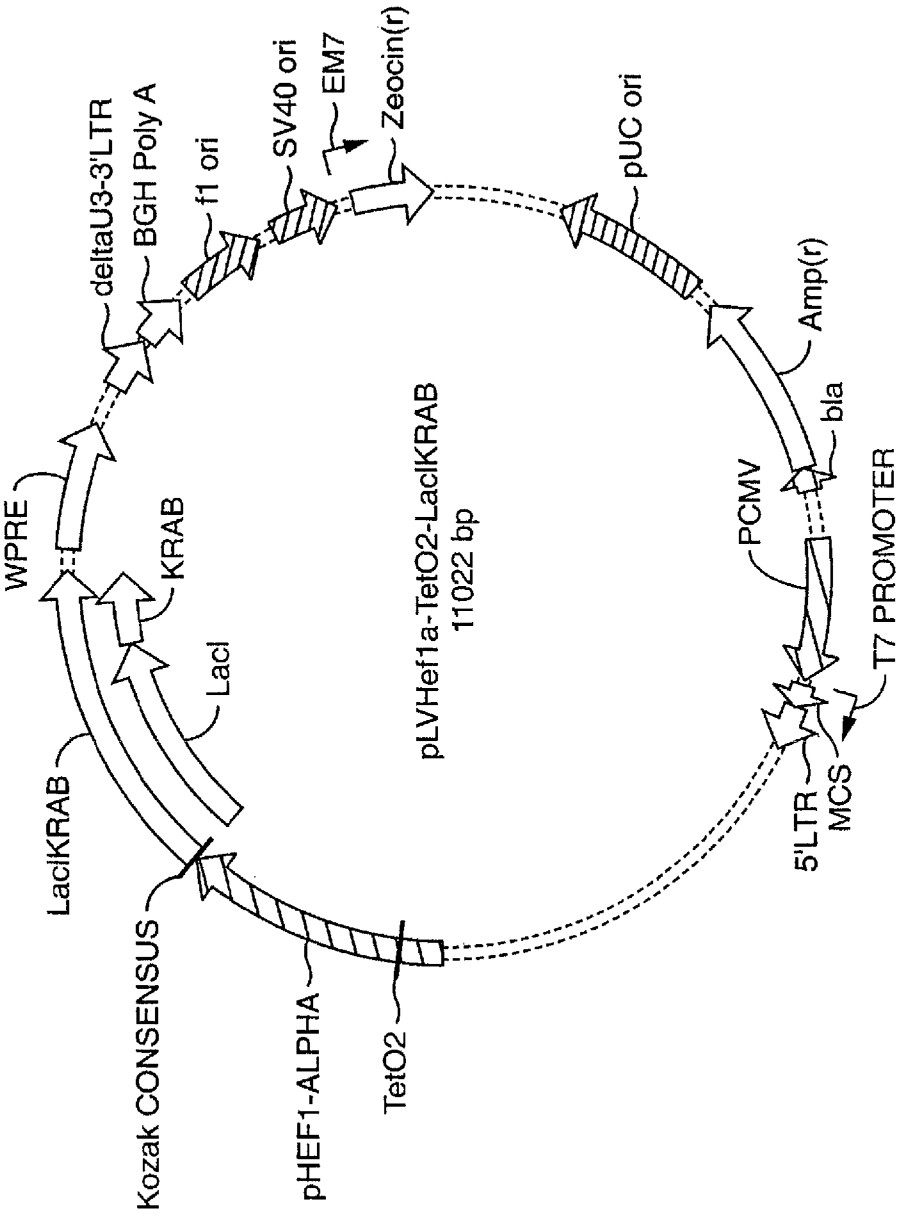
FIG. 29 provides a plasmid and sequence for p_tetO/LacI (SEQ ID NO: 14).
Figure 30A:
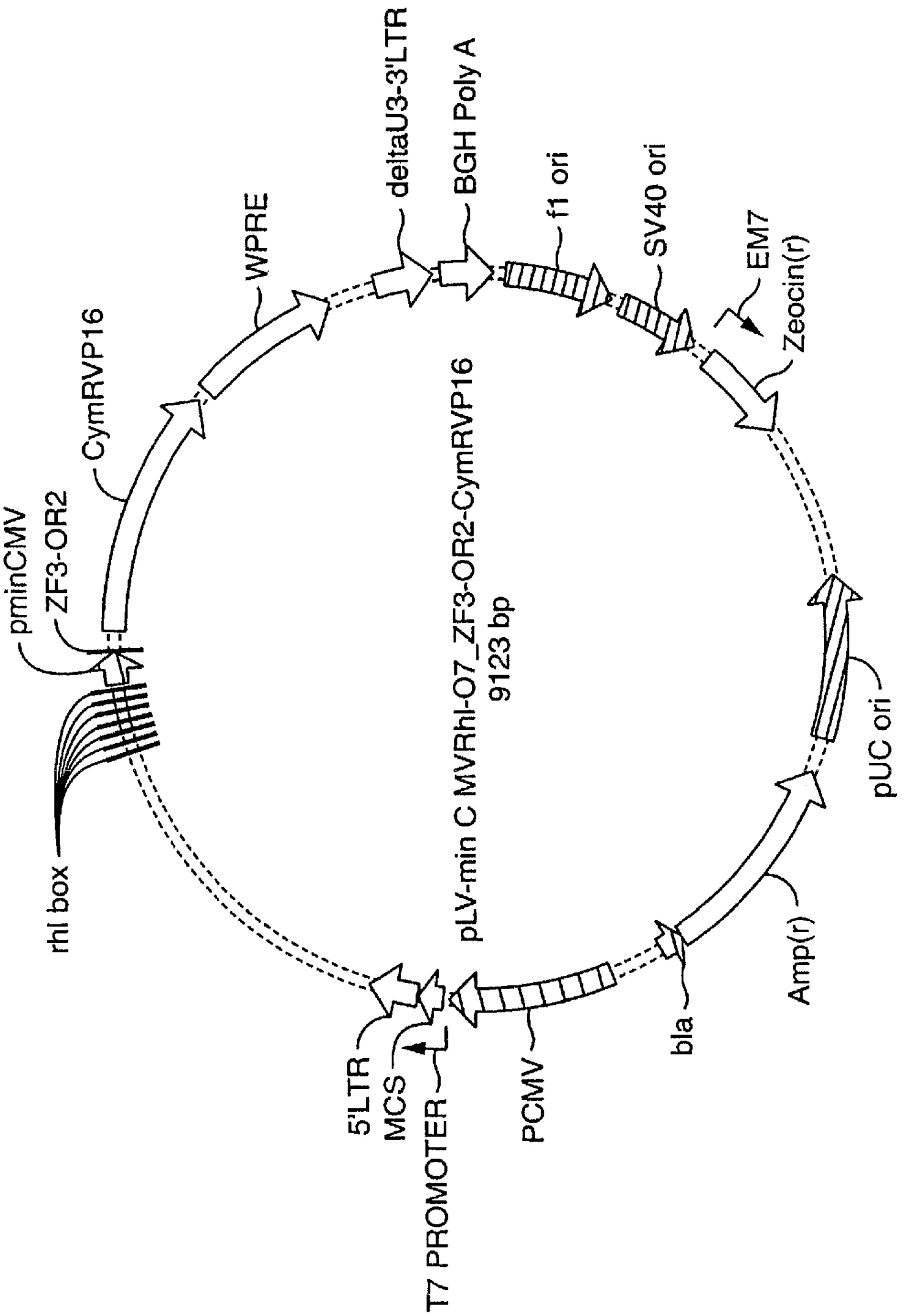
FIG. 30 provides a plasmid and sequence for p_Rh1I_R3/A2 (SEQ ID NO: 15).
Figure 31A:
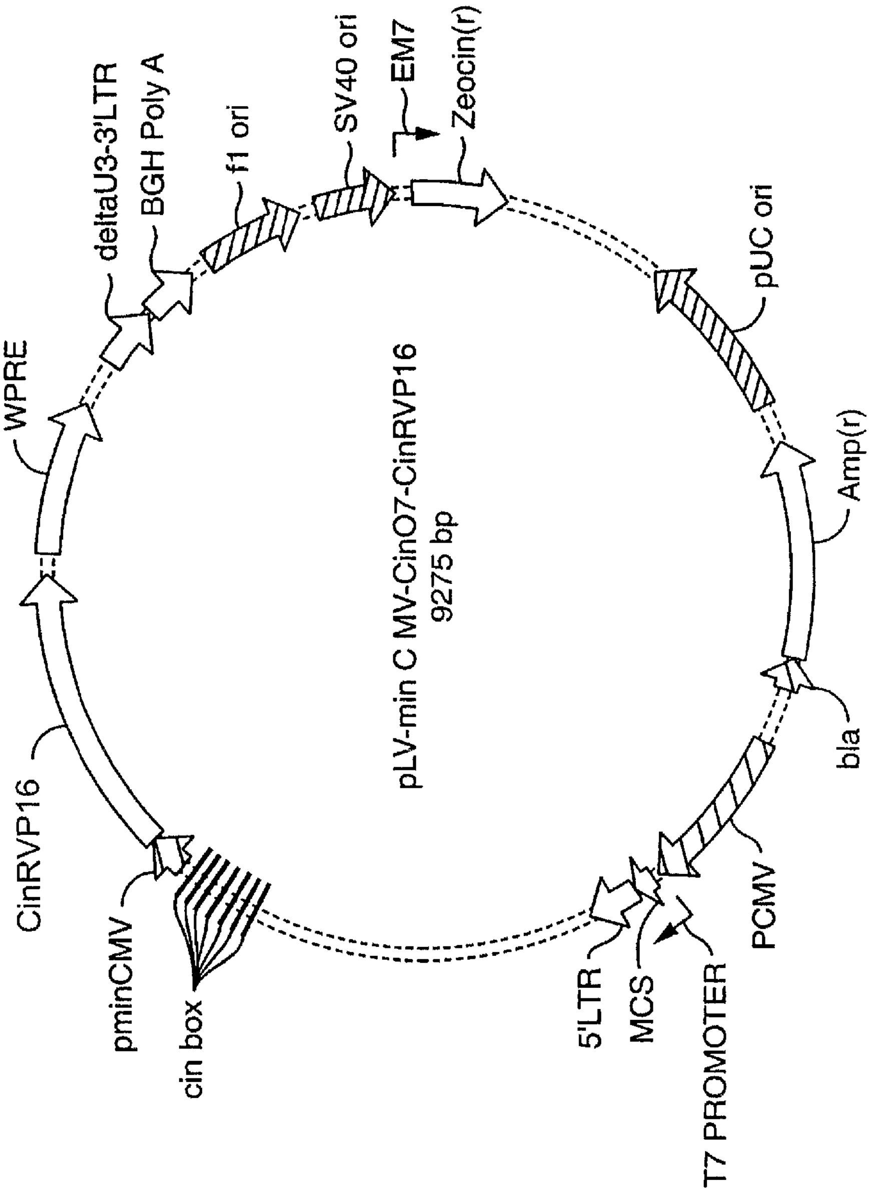
FIG. 31 provides a plasmid and sequence for P_Cin/CinR (SEQ ID NO: 16).
Figure 32A:
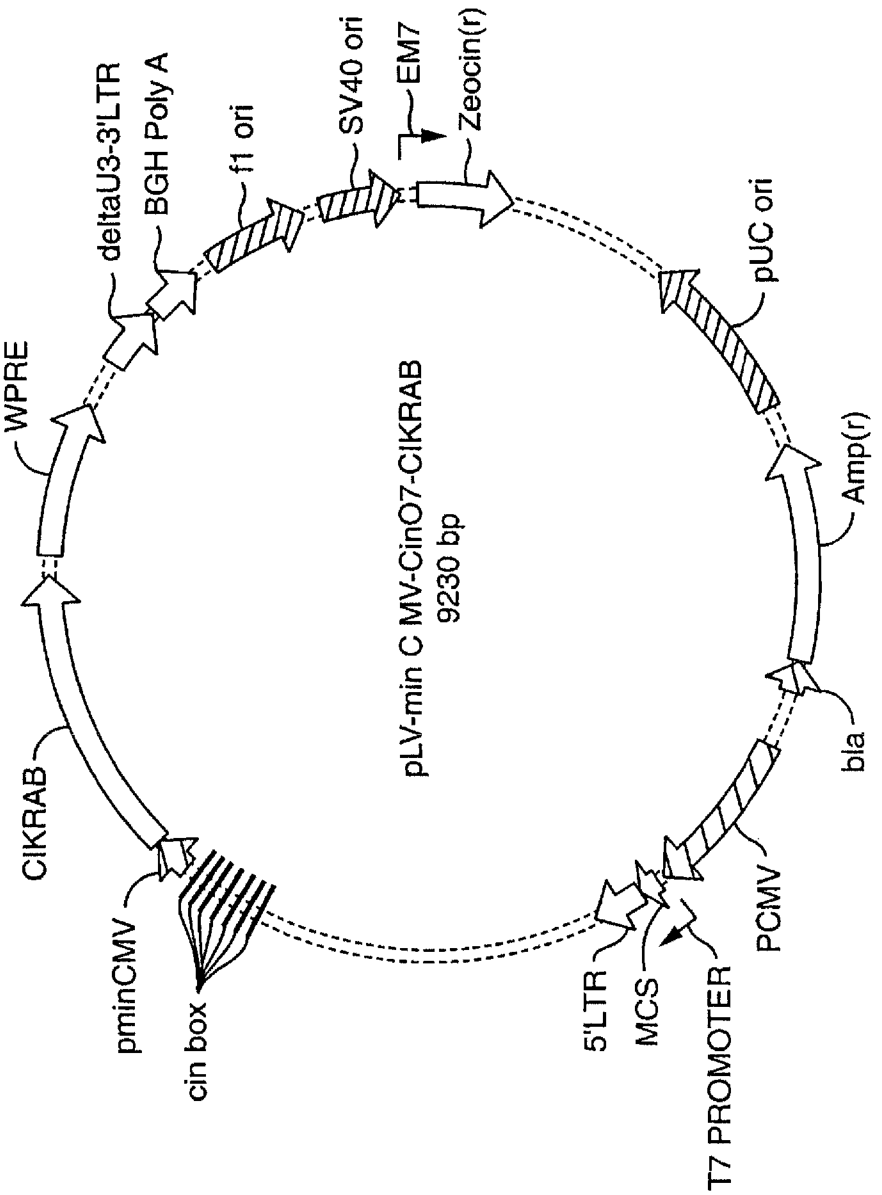
FIG. 32 provides a plasmid and sequence for P_Cin/CI (SEQ ID NO: 17).
Figure 33A:
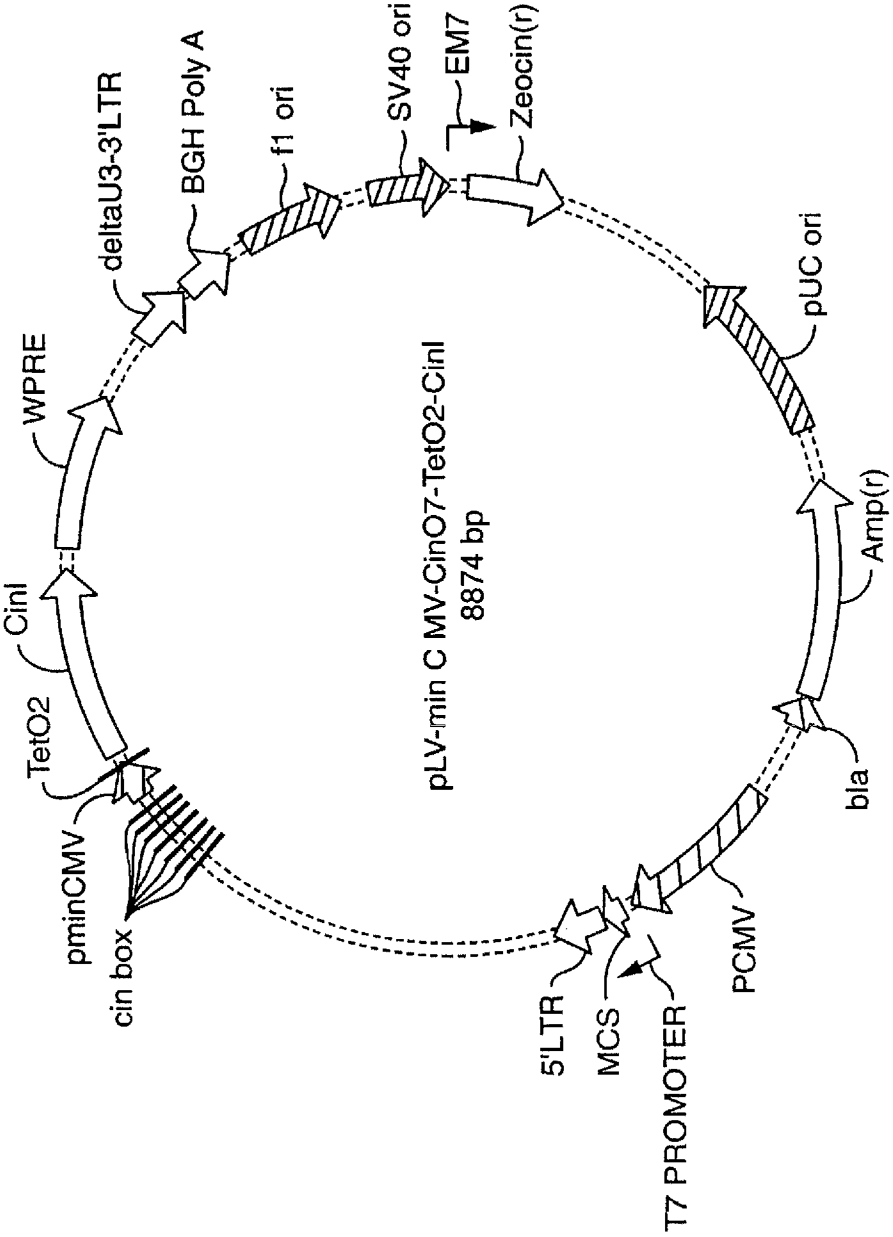
FIG. 33 provides a plasmid and sequence for P_Cin_tetO/CinI (SEQ ID NO: 18).
Figure 34A:
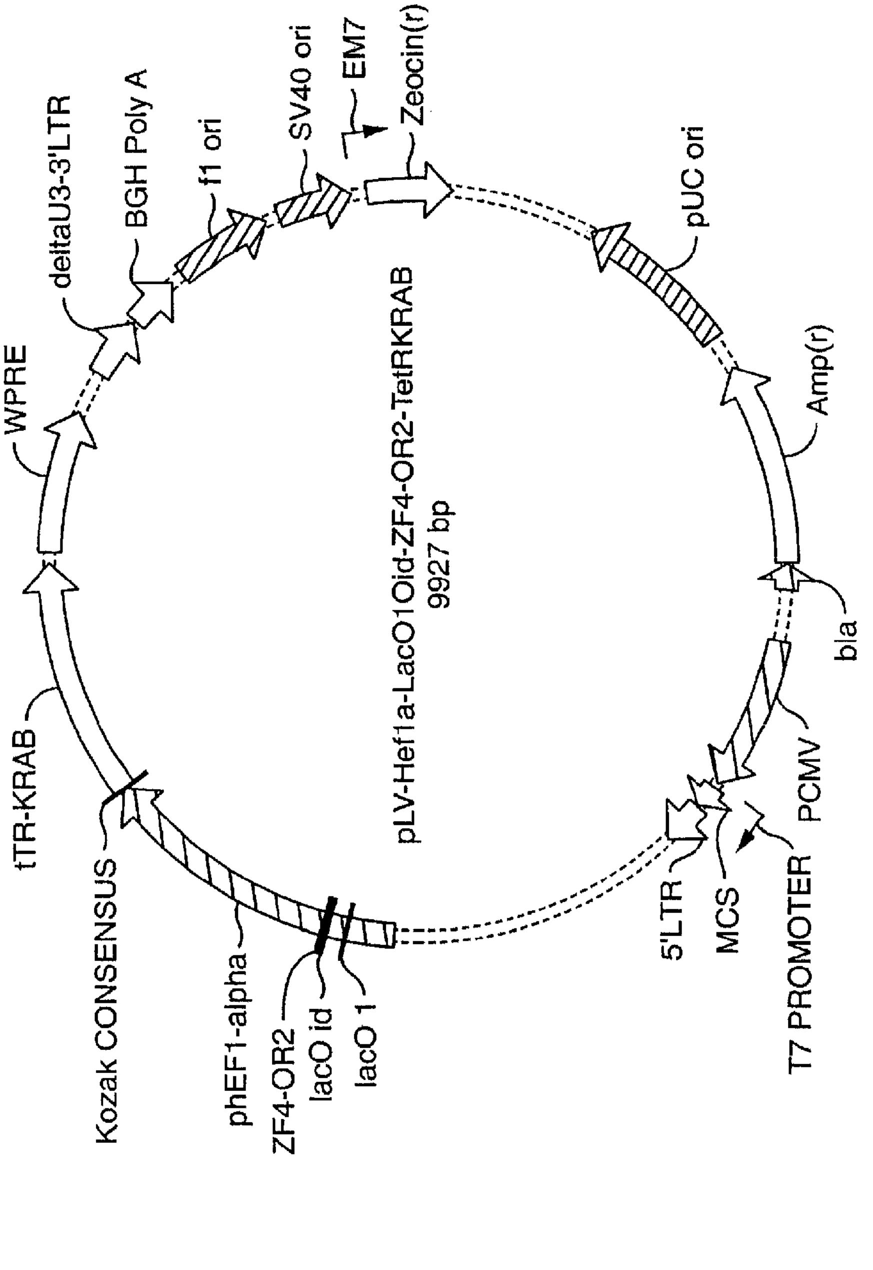
FIG. 34 provides a plasmid and sequence for P_lacO_R4/TetR (SEQ ID NO: 19).
Figure 35A:
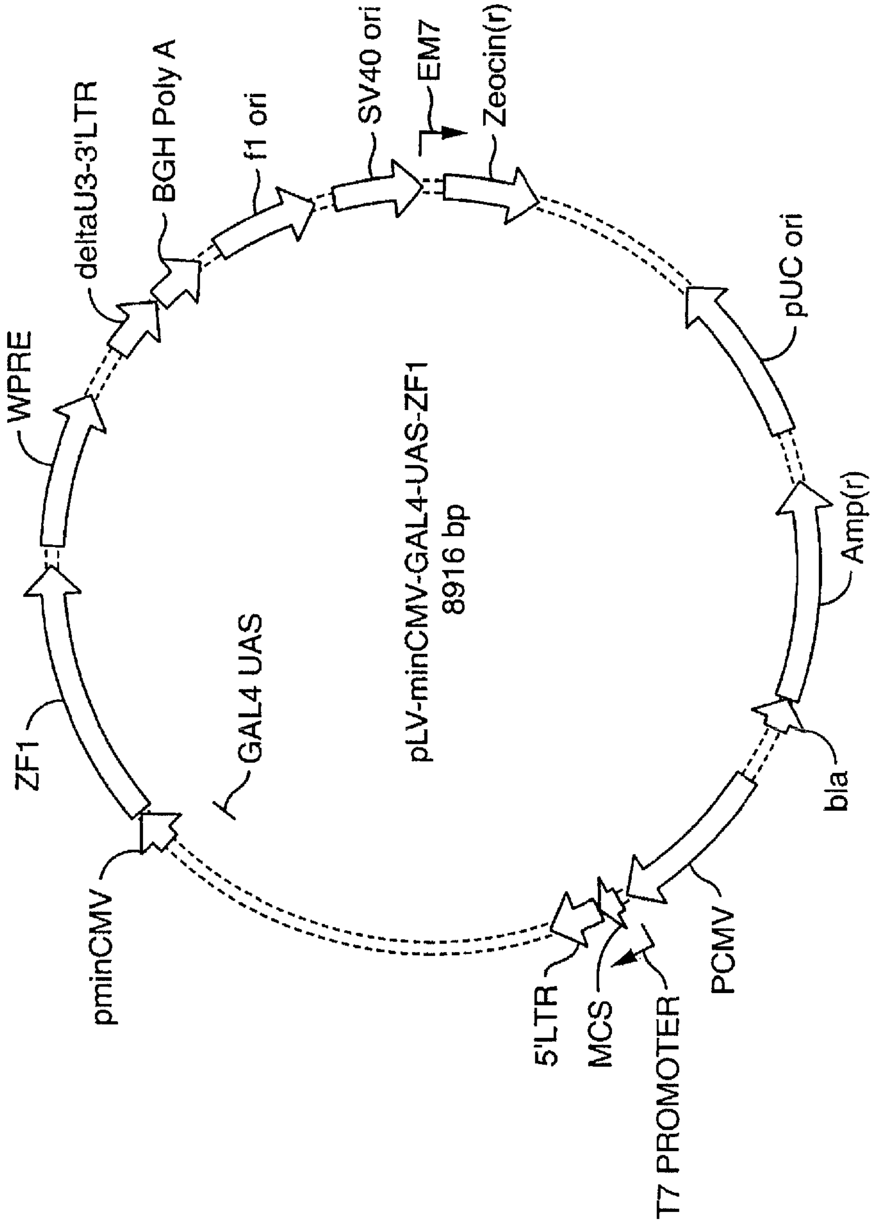
FIG. 35 provides a plasmid and sequence for P_A1/R1 (SEQ ID NO: 20).
Figure 36A:
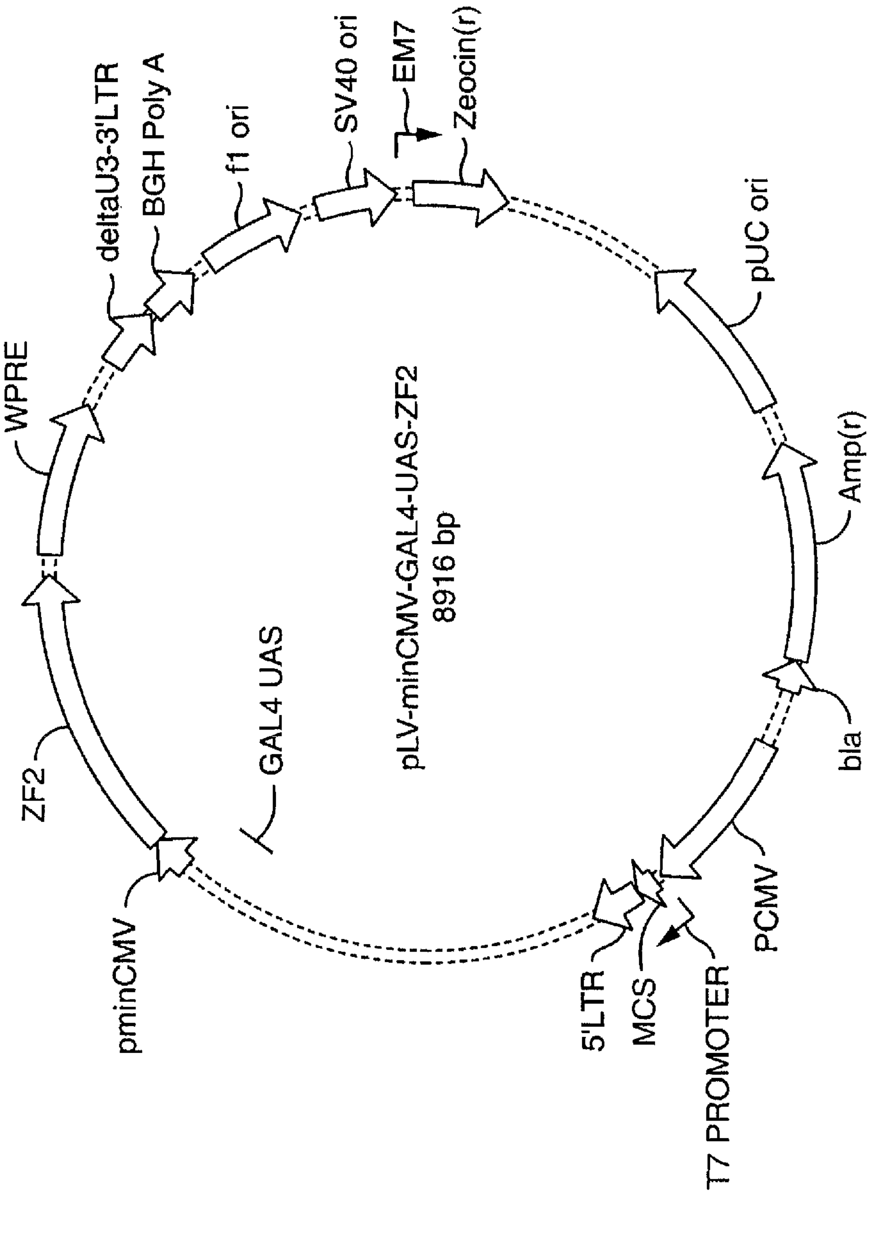
FIG. 36 provides a plasmid and sequence for P_A1/R2 (SEQ ID NO: 21).
Figure 37A:
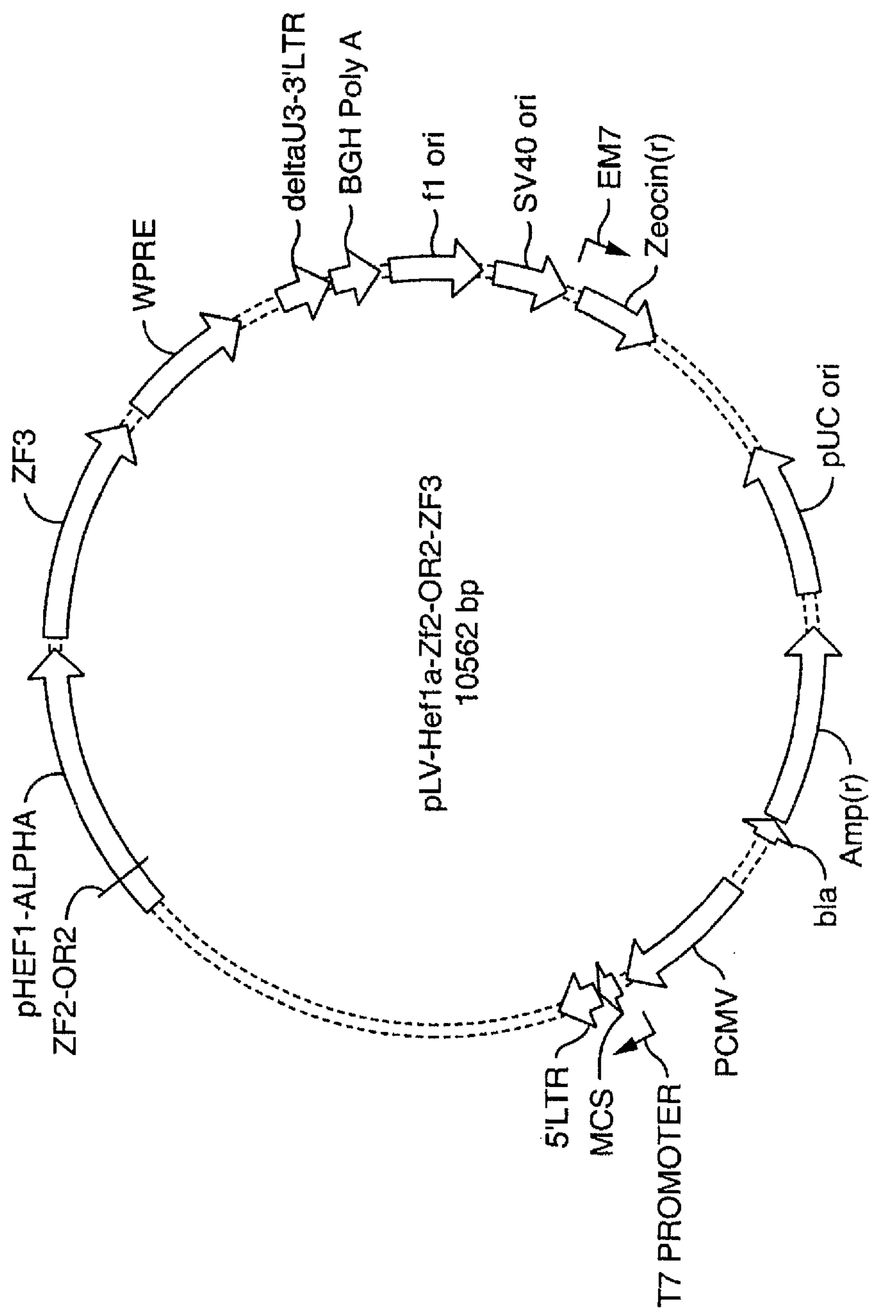
FIG. 37 provides a plasmid and sequence for P_R2/R3 (SEQ ID NO: 22).
Figure 38A:
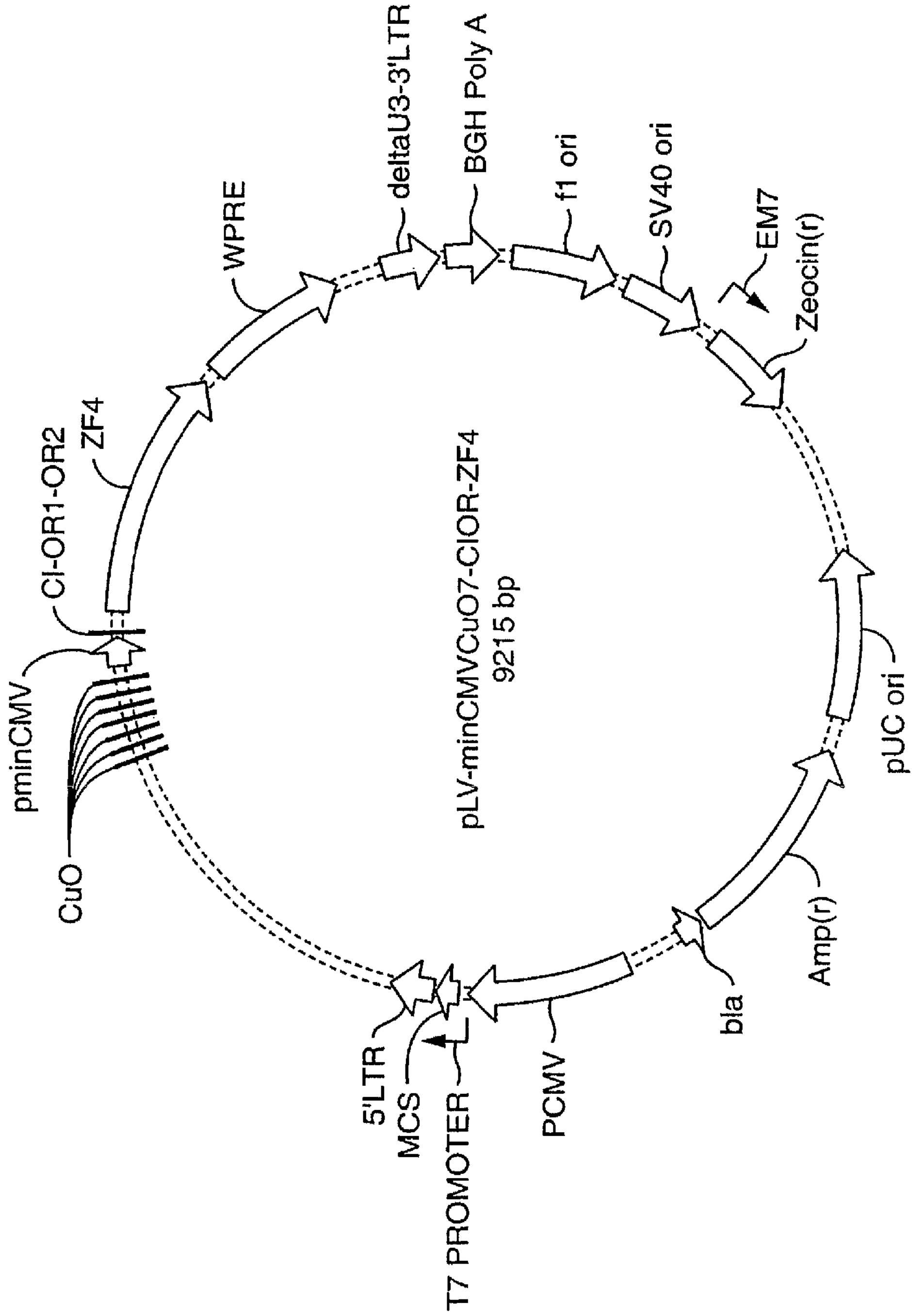
FIG. 38 provides a plasmid and sequence for P_A2/CIOR/R4 (SEQ ID NO: 23).

Engineering ZFP Senders:

By co-infecting the rtTA switch and the TAT-ZFP-VP64 fusion gene with a secretion signal under control of the TRE promoter into cells, Dox-inducible secretion of TAT-ZFP-VP64 is achieved (FIG. 27b). This fusion protein is exported by the virtue of its N-terminal secretion system to the extracellular milieu, where it can be detected by using receiver cells, or, at an earlier stage, by WB. The expression of the fusion protein in the sender cells can be verified by WB of cell lysates or IF staining against the HA-tag.

Engineering ZFP Receivers:

By infecting the module containing the minimal CMV promoter with the DTS for the cognate ZFP controlling the expression of EGFP, TAT-ZFP-VP64-inducible expression of EGFP is achieved (FIG. 27b). Specifically, the secretion signal-containing TAT-ZFP-VP64 fusion protein is exported by sender cells separated by a transwell membrane into in the cell supernatant will transduce into receiver cells, localize to the nucleus and bind its cognate DTS in the minimal CMV promoter, thereby expressing EGFP (detectable by FACS and/or fluorescence microscopy). The uptake of the fusion protein will also be tracked by IF staining against the HA-tag.

If the engineering of cognate ZFP-DBP pairs and/or the export of ZFPs is problematic, the ZFP will be replaced by Gal4 and use the well-described Gal4 DTS in the receiver cells. This library could then be expanded by replacing Gal4 with known DNA-binding proteins/transcription factors (e.g. LacI, cI, TetR, rtTA) and their cognate DTS on the receiver side. Also, different endocytic domains and different secretion tags (from IL-11, GM-CSF . . . ) can be used.

Full length TAT might bind to endogenous regulatory elements, where it would have undesirable effects on the expression of endogenous genes. By using only a minimal TAT-peptide of 10 amino acids needed for cellular uptake and nuclear localization, it should be possible to reduce these undesirable interactions. Alternatively, other transducing/NLS-containing peptide sequences could be used in the delivery, as for example the 34 amino acid sequence of the Beta2/NeuroD transcription factor or the third a-helix of the Antennapedia homeoprotein.

Example 6

This example demonstrates that the artificial cell-cell communication signals described in Example 5 can be used to induce differentiation of mouse embryonic stem cells in vitro. Two types of sender cells will express TAT-ZFP1-VP64 or TAT-ZFP2-VP64. ZFP1 activates MyoD expression, while ZFP2 activates Ngn1 expression. By placing patches of sender cells on a Matrigel matrix with embedded receiver cells, the gradient of the two synthetic morphogens should induce differentiation of the receiver cells into a myoblast- or neuron-like morphology, depending on their location.

Engineering Senders:

By infecting the rtTA switch, the TAT-ZFP-VP64 fusion expressing module from above and additionally a module with a distinct ZFP (TAT-ZFP2-VP64), two sender cell types are created expressing TAT-ZFP-VP64 or TAT-ZFP2-VP64 upon addition of Dox.

Engineering Receivers:

By co-infecting the two modules containing a DTS1 or DTS2, a minimal CMV promoter, the myoD or ngn1 genes, an internal ribosome entry site (IRES) and a egfp or dsred2 gene into receiver cells, they will express MyoD and EGFP in response to ZFP1, Ngn1 and DsRed2 in response to ZFP2. These signaling circuits will be first tested with mES in liquid cell culture. If the communication and differentiation in the liquid media with transwell insert works, the receiver mES cells will be embedded in a Matrigel matrix and the sender cells filled into holes of various diameter at the surface of this matrix. This to induce three-dimensional differentiation patterns in the receiver cells. The differentiation success in both liquid as well matrix approach can be assessed by morphological changes, IF stainings, or RT-PCR for relevant markers (e.g. Desmin, Mef2, Cx2 for myocyte assays; Lim 1/2, Map2 and NSE for neural assays)

Other substrates than Matrigel might provide better growth and differentiation capabilities for mES, as for example a collagen-agarose matrix. The diffusion properties of the TAT-ZFP fusions proteins will be critical, as well as the positioning and the number the sender cells on the matrix. Suboptimal expression of MyoD/Ngn1 could be overcome by incorporating signal amplifying circuits into the receiver cells. Crosstalk between the ZFP-DTS pairs should have been ruled out earlier in the ZFP-DTS optimization procedure, nevertheless the ZFP and/or DTS coding sequences could be exchanged for other variants.

What is claimed is:

1. A composition comprising one or more recombinant mammalian vectors, wherein the one or more vectors comprise:

a) a first nucleic acid sequence comprising a first promoter that is operably linked to a first DNA sequence encoding a first cell-cell communication molecule, b) a second nucleic acid sequence comprising a second promoter that is operably linked to second DNA sequence encoding a second cell-cell communication molecule that binds with said first cell-cell communication molecule to produce a first binding molecule, c) a third nucleic acid sequence comprising a third promoter that is operably linked to a third DNA sequence encoding a first cell fate regulator protein that induces differentiation of a first cell type into a second cell type that expresses a marker protein of said second cell type, d) a fourth nucleic acid sequence comprising a fourth promoter that is operably linked to a fourth DNA sequence encoding a first repressor, and e) a fifth nucleic acid sequence comprising a fifth promoter that is operably linked to a fifth DNA sequence encoding a first activator, wherein i) said first repressor represses expression of said first activator, and ii) said first activator activates expression of;

1) said first repressor, and 2) said first activator.

2. A composition comprising one or more recombinant mammalian vectors, wherein the one or more vectors comprise:

a) a first nucleic acid sequence comprising a first promoter that is operably linked to a first DNA sequence encoding a first cell-cell communication molecule, b) a second nucleic acid sequence comprising a second promoter that is operably linked to second DNA sequence encoding a second cell-cell communication molecule that binds with said first cell-cell communication molecule to produce a first binding molecule, c) a third nucleic acid sequence comprising a third promoter that is operably linked to a third DNA sequence encoding a first cell fate regulator protein that induces differentiation of a first cell type into a second cell type that expresses a marker protein of said second cell type, d) a fourth nucleic acid sequence comprising a fourth promoter that is operably linked to a fourth DNA sequence encoding a first repressor, and e) a fifth nucleic acid sequence comprising a fifth promoter that is operably linked to a fifth DNA sequence encoding a first activator, wherein i) said first repressor represses expression of said first activator, and ii) said first activator activates expression of;

1) said first repressor, and 2) said first activator, wherein said one or more vectors further comprises:

f) a sixth nucleic acid sequence comprising a sixth promoter that is operably linked to a sixth DNA sequence encoding a second repressor, g) a seventh nucleic acid sequence comprising a seventh promoter that is operably linked to a seventh DNA sequence encoding a third repressor, h) an eighth nucleic acid sequence comprising an eighth promoter that is operably linked to an eighth DNA sequence encoding a second activator, i) a ninth nucleic acid sequence comprising a ninth promoter that is operably linked to a ninth DNA sequence encoding a fourth repressor, wherein i) said second repressor represses expression of said third repressor, ii) said third repressor represses expression of said second activator, iii) said second activator activates expression of said fourth repressor, and iv) said first activator activates expression of said second repressor.

3. The composition of claim 2, wherein said one or more vectors further comprises:

j) a tenth nucleic acid sequence comprising a tenth promoter that is operably linked to a tenth DNA sequence encoding a fifth repressor, and k) an eleventh nucleic acid sequence comprising an eleventh promoter that is operably linked to an eleventh DNA sequence encoding a sixth repressor, wherein i) said fifth repressor represses expression of said sixth repressor and of said first cell-cell communication molecule, ii) said sixth repressor represses expression of said fifth repressor, and iii) said fourth repressor represses expression of said fifth repressor.

4. The composition of claim 3, wherein said one or more vectors further comprises:

l) a twelfth nucleic acid sequence comprising a twelfth promoter that is operably linked to a twelfth DNA sequence encoding a seventh repressor, wherein i) said first binding molecule induces expression of said seventh repressor, and ii) said seventh repressor represses expression of said fourth repressor.

5. The composition of claim 3, wherein said fifth repressor represses expression of said twelfth nucleic acid sequence.

6. A composition comprising one or more recombinant mammalian vectors, wherein the one or more vectors comprise:

a) a first nucleic acid sequence comprising a first promoter that is operably linked to a first DNA sequence encoding a first cell-cell communication molecule, b) a second nucleic acid sequence comprising a second promoter that is operably linked to second DNA sequence encoding a second cell-cell communication molecule that binds with said first cell-cell communication molecule to produce a first binding molecule, c) a third nucleic acid sequence comprising a third promoter that is operably linked to a third DNA sequence encoding a first cell fate regulator protein that induces differentiation of a first cell type into a second cell type that expresses a marker protein of said second cell type, d) a fourth nucleic acid sequence comprising a fourth promoter that is operably linked to a fourth DNA sequence encoding a repressor, wherein said fourth promoter is a tissue specific promoter, and e) a fifth nucleic acid sequence comprising a fifth promoter that is operably linked to a fifth DNA sequence encoding an apoptosis protein, wherein expression of said repressor represses expression of said apoptosis protein, and wherein the absence of expression of said repressor induces expression of said apoptosis protein.

* * * * *

SEQUENCE LISTING

```
<160> NUMBER OF SEQ ID NOS: 34

<210> SEQ ID NO 1
<211> LENGTH: 10632
<212> TYPE: DNA
<213> ORGANISM: Artificial Sequence
<220> FEATURE:
<223> OTHER INFORMATION: Synthetic

<400> SEQUENCE: 1

cggccatcga taaggatccg cccctctccc tccccccccc ctaacgttac tggccgaagc      60

cgcttggaat aaggccggtg tgcgtttgtc tatatgttat tttccaccat attgccgtct    120
```

-continued

```
tttggcaatg tgagggcccg gaaacctggc cctgtcttct tgacgagcat tcctaggggt    180
ctttcccctc tcgccaaagg aatgcaaggt ctgttgaatg tcgtgaagga agcagttcct    240
ctggaagctt cttgaagaca aacaacgtct gtagcgaccc tttgcaggca gcggaacccc    300
ccacctggcg acaggtgcct ctgcggccaa aagccacgtg tataagatac acctgcaaag    360
gcggcacaac cccagtgcca cgttgtgagt tggatagttg tggaaagagt caaatggctc    420
tcctcaagcg tattcaacaa ggggctgaag gatgcccaga aggtacccca ttgtatggga    480
tctgatctgg ggcctcggtg cacatgcttt acatgtgttt agtcgaggtt aaaaaaacgt    540
ctaggccccc cgaaccacgg ggacgtggtt ttcctttgaa aaacacgatg ataatatggc    600
cacaaccatg gcctcctccg aggacgtcat caaggagttc atgcgcttca aggtgcgcat    660
ggagggctcc gtgaacggcc acgagttcga gatcgagggc gagggcgagg gccgccccta    720
cgagggcacc cagaccgcca agctgaaggt gaccaagggc ggccccctgc ccttcgcctg    780
ggacatcctg tccccccagt tccagtacgg ctccaaggtg tacgtgaagc accccgccga    840
catccccgac tacaagaagc tgtccttccc cgagggcttc aagtgggagc gcgtgatgaa    900
cttcgaggac ggcggcgtgg tgaccgtgac ccaggactcc tccctgcagg acggctcctt    960
catctacaag gtgaagttca tcggcgtgaa cttcccctcc gacggccccg taatgcagaa   1020
gaagactatg ggctgggagg cctccaccga gcgcctgtac ccccgcgacg gcgtgctgaa   1080
gggcgagatc cacaaggccc tgaagctgaa ggacggcggc cactacctgg tggagttcaa   1140
gtccatctac atggccaaga agcccgtgca gctgcccggc tactactacg tggactccaa   1200
gctggacatc acctcccaca acgaggacta caccatcgtg gagcagtacg agcgcgccga   1260
gggccgccac cacctgttcc tgtaggcggc cgcaatcaac ctctggatta caaaatttgt   1320
gaaagattga ctggtattct taactatgtt gctcctttta cgctatgtgg atacgctgct   1380
ttaatgcctt tgtatcatgc tattacttcc cgtacggctt tcattttctc ctccttgtat   1440
aaatcctggt tgctgtctct ttatgaggag ttgtggcccg ttgtcaggca acgtggcgtg   1500
gtgtgcactg tgtttgctga cgcaaccccc actggttggg gcattgccac cacctatcaa   1560
ctcctttccg ggactttcgc tttccccctc cctattgcca cggcggaact cattgccgcc   1620
tgccttgccc gctgctggac aggggctcgg ctgttgggca ctgacaattc cgtggtgttg   1680
tcggggaagc tgacgtcctt tccatggctg ctcgcctgtg ttgccaactg gattctgcgc   1740
gggacgtcct tctgctacgt cccttcggcc ctcaatccag cggaccttcc ttcccgcggc   1800
ctgctgccgg ttctgcggcc tcttccgcgt cttcgccttc gccctcagac gagtcggatc   1860
tccctttggg ccgcctcccc gcctgcctgc aggtttgtcg agacctagaa aaacatggag   1920
caatcacaag tagcaataca gcagctacca atgctgattg tgcctggcta gaagcacaag   1980
aggaggagga ggtgggtttt ccagtcacac ctcaggtacc tttaagacca atgacttaca   2040
aggcagctgt agatcttagc cactttttaa aagaaaaggg gggactggaa gggctaattc   2100
actcccaacg aagacaagat ctgctttttg cttgtactgg gtctctctgg ttagaccaga   2160
tctgagcctg ggagctctct ggctaactag ggaacccact gcttaagcct caataaagct   2220
tgccttgagt gcttcaagta gtgtgtgccc gtctgttgtg tgactctggt aactagagat   2280
ccctcagacc cttttagtca gtgtggaaaa tctctagcag ggcccgttta aacccgctga   2340
tcagcctcga ctgtgccttc tagttgccag ccatctgttg tttgcccctc ccccgtgcct   2400
tccttgaccc tggaaggtgc cactcccact gtcctttcct aataaaatga ggaaattgca   2460
tcgcattgtc tgagtaggtg tcattctatt ctggggggtg gggtggggca ggacagcaag   2520
```

-continued

```
ggggaggatt gggaagacaa tagcaggcat gctggggatg cggtgggctc tatggcttct   2580
gaggcggaaa gaaccagctg gggctctagg gggtatcccc acgcgccctg tagcggcgca   2640
ttaagcgcgg cgggtgtggt ggttacgcgc agcgtgaccg ctacacttgc cagcgcccta   2700
gcgcccgctc ctttcgcttt cttcccttcc tttctcgcca cgttcgccgg ctttccccgt   2760
caagctctaa atcggggcat ccctttaggg ttccgattta gtgctttacg gcacctcgac   2820
cccaaaaaac ttgattaggg tgatggttca cgtagtgggc catcgccctg atagacggtt   2880
tttcgccctt tgacgttgga gtccacgttc tttaatagtg gactcttgtt ccaaactgga   2940
acaacactca accctatctc ggtctattct tttgatttat aagggatttt ggggatttcg   3000
gcctattggt taaaaaatga gctgatttaa caaaaattta acgcgaatta attctgtgga   3060
atgtgtgtca gttagggtgt ggaaagtccc caggctcccc aggcaggcag aagtatgcaa   3120
agcatgcatc tcaattagtc agcaaccagg tgtggaaagt ccccaggctc cccagcaggc   3180
agaagtatgc aaagcatgca tctcaattag tcagcaacca tagtcccgcc cctaactccg   3240
cccatcccgc ccctaactcc gcccagttcc gcccattctc cgccccatgg ctgactaatt   3300
ttttttattt atgcagaggc cgaggccgcc tctgcctctg agctattcca gaagtagtga   3360
ggaggctttt ttggaggcct aggcttttgc aaaaagctcc cgggagcttg tatatccatt   3420
ttcggatctg atcagcacgt gttgacaatt aatcatcggc atagtatatc ggcatagtat   3480
aatacgacaa ggtgaggaac taaaccatgg ccaagttgac cagtgccgtt ccggtgctca   3540
ccgcgcgcga cgtcgccgga gcggtcgagt tctggaccga ccggctcggg ttctcccggg   3600
acttcgtgga ggacgacttc gccggtgtgg tccgggacga cgtgaccctg ttcatcagcg   3660
cggtccagga ccaggtggtg ccggacaaca ccctggcctg ggtgtgggtg cgcggcctgg   3720
acgagctgta cgccgagtgg tcggaggtcg tgtccacgaa cttccgggac gcctccgggc   3780
cggccatgac cgagatcggc gagcagccgt gggggcggga gttcgccctg cgcgacccgg   3840
ccggcaactg cgtgcacttc gtggccgagg agcaggactg acacgtgcta cgagatttcg   3900
attccaccgc cgccttctat gaaaggttgg gcttcggaat cgttttccgg gacgccggct   3960
ggatgatcct ccagcgcggg gatctcatgc tggagttctt cgcccacccc aacttgttta   4020
ttgcagctta taatggttac aaataaagca atagcatcac aaatttcaca aataaagcat   4080
tttttcact gcattctagt tgtggtttgt ccaaactcat caatgtatct tatcatgtct   4140
gtataccgtc gacctctagc tagagcttgg cgtaatcatg gtcatagctg tttcctgtgt   4200
gaaattgtta tccgctcaca attccacaca acatacgagc cggaagcata aagtgtaaag   4260
cctggggtgc ctaatgagtg agctaactca cattaattgc gttgcgctca ctgcccgctt   4320
tccagtcggg aaacctgtcg tgccagctgc attaatgaat cggccaacgc gcggggagag   4380
gcggtttgcg tattgggcgc tcttccgctt cctcgctcac tgactcgctg cgctcggtcg   4440
ttcggctgcg gcgagcggta tcagctcact caaaggcggt aatacggtta tccacagaat   4500
caggggataa cgcaggaaag aacatgtgag caaaaggcca gcaaaaggcc aggaaccgta   4560
aaaaggccgc gttgctggcg tttttccata ggctccgccc ccctgacgag catcacaaaa   4620
atcgacgctc aagtcagagg tggcgaaacc cgacaggact ataaagatac caggcgtttc   4680
cccctggaag ctccctcgtg cgctctcctg ttccgaccct gccgcttacc ggatacctgt   4740
ccgcctttct cccttcggga agcgtggcgc tttctcaatg ctcacgctgt aggtatctca   4800
gttcggtgta ggtcgttcgc tccaagctgg gctgtgtgca cgaacccccc gttcagcccg   4860
```

-continued

```
accgctgcgc cttatccggt aactatcgtc ttgagtccaa cccggtaaga cacgacttat   4920
cgccactggc agcagccact ggtaacagga ttagcagagc gaggtatgta ggcggtgcta   4980
cagagttctt gaagtggtgg cctaactacg gctacactag aaggacagta tttggtatct   5040
gcgctctgct gaagccagtt accttcggaa aaagagttgg tagctcttga tccggcaaac   5100
aaaccaccgc tggtagcggt ggtttttttg tttgcaagca gcagattacg cgcagaaaaa   5160
aaggatctca agaagatcct ttgatctttt ctacggggtc tgacgctcag tggaacgaaa   5220
actcacgtta agggattttg gtcatgagat tatcaaaaag gatcttcacc tagatccttt   5280
taaattaaaa atgaagtttt aaatcaatct aaagtatata tgagtaaact tggtctgaca   5340
gttaccaatg cttaatcagt gaggcaccta tctcagcgat ctgtctattt cgttcatcca   5400
tagttgcctg actccccgtc gtgtagataa ctacgatacg ggagggctta ccatctggcc   5460
ccagtgctgc aatgataccg cgagacccac gctcaccggc tccagattta tcagcaataa   5520
accagccagc cggaagggcc gagcgcagaa gtggtcctgc aactttatcc gcctccatcc   5580
agtctattaa ttgttgccgg gaagctagag taagtagttc gccagttaat agtttgcgca   5640
acgttgttgc cattgctaca ggcatcgtgg tgtcacgctc gtcgtttggt atggcttcat   5700
tcagctccgg ttcccaacga tcaaggcgag ttacatgatc ccccatgttg tgcaaaaaag   5760
cggttagctc cttcggtcct ccgatcgttg tcagaagtaa gttggccgca gtgttatcac   5820
tcatggttat ggcagcactg cataattctc ttactgtcat gccatccgta agatgctttt   5880
ctgtgactgg tgagtactca accaagtcat tctgagaata gtgtatgcgg cgaccgagtt   5940
gctcttgccc ggcgtcaata cgggataata ccgcgccaca tagcagaact ttaaaagtgc   6000
tcatcattgg aaaacgttct tcggggcgaa aactctcaag gatcttaccg ctgttgagat   6060
ccagttcgat gtaacccact cgtgcaccca actgatcttc agcatctttt actttcacca   6120
gcgtttctgg gtgagcaaaa acaggaaggc aaaatgccgc aaaaaaggga ataagggcga   6180
cacggaaatg ttgaatactc atactcttcc tttttcaata ttattgaagc atttatcagg   6240
gttattgtct catgagcgga tacatatttg aatgtattta gaaaaataaa caaatagggg   6300
ttccgcgcac atttccccga aaagtgccac ctgacgtcga cggatcggga gatctcccga   6360
tcccctatgg tgcactctca gtacaatctg ctctgatgcc gcatagttaa gccagtatct   6420
gctccctgct tgtgtgttgg aggtcgctga gtagtgcgcg agcaaaattt aagctacaac   6480
aaggcaaggc ttgaccgaca attgcatgaa gaatctgctt agggttaggc gttttgcgct   6540
gcttcgcgat gtacgggcca gatatacgcg ttgacattga ttattgacta gttattaata   6600
gtaatcaatt acggggtcat tagttcatag cccatatatg gagttccgcg ttacataact   6660
tacggtaaat ggcccgcctg gctgaccgcc caacgacccc cgcccattga cgtcaataat   6720
gacgtatgtt cccatagtaa cgccaatagg gactttccat tgacgtcaat gggtggacta   6780
tttacggtaa actgcccact tggcagtaca tcaagtgtat catatgccaa gtacgccccc   6840
tattgacgtc aatgacggta aatggcccgc ctggcattat gcccagtaca tgaccttatg   6900
ggactttcct acttggcagt acatctacgt attagtcatc gctattacca tggtgatgcg   6960
gttttggcag tacatcaatg ggcgtggata gcggtttgac tcacggggat ttccaagtct   7020
ccaccccatt gacgtcaatg ggagtttgtt ttggcaccaa aatcaacggg actttccaaa   7080
atgtcgtaac aactccgccc cattgacgca aatgggcggt aggcgtgtac ggtgggaggt   7140
ctatataagc agagctctct ggctaactag agaacccact gcttactggc ttatcgaaat   7200
taatacgact cactataggg agacccaagc tggtttaaac ttaagcttgg taccgagctc   7260
```

-continued actagtccag tgtggtggca gatatccagc acagtggcgg ccgctcgagt ctagagggcc 7320
cgttttgcct gtactgggtc tctctggtta gaccagatct gagcctggga gctctctggc 7380
taactaggga acccactgct taagcctcaa taaagcttgc cttgagtgct tcaagtagtg 7440
tgtgcccgtc tgttgtgtga ctctggtaac tagagatccc tcagaccctt ttagtcagtg 7500
tggaaaatct ctagcagtgg cgcccgaaca gggacttgaa agcgaaaggg aaaccagagg 7560
agctctctcg acgcaggact cggcttgctg aagcgcgcac ggcaagaggc gaggggcggc 7620
gactggtgag tacgccaaaa attttgacta gcggaggcta gaaggagaga gatgggtgcg 7680
agagcgtcag tattaagcgg gggagaatta gatcgcgatg ggaaaaaatt cggttaaggc 7740
caggggggaaa gaaaaaatat aaattaaaac atatagtatg ggcaagcagg gagctagaac 7800
gattcgcagt taatcctggc ctgttagaaa catcagaagg ctgtagacaa atactgggac 7860
agctacaacc atcccttcag acaggatcag aagaacttag atcattatat aatacagtag 7920
caaccctcta ttgtgtgcat caaaggatag agataaaaga caccaaggaa gctttagaca 7980
agatagagga agagcaaaac aaaagtaaga ccaccgcaca gcaagcggcc gctgatcttc 8040
agacctggag gaggagatat gagggacaat tggagaagtg aattatataa atataaagta 8100
gtaaaaattg aaccattagg agtagcaccc accaaggcaa agagaagagt ggtgcagaga 8160
gaaaaaagag cagtgggaat aggagctttg ttccttgggt tcttgggagc agcaggaagc 8220
actatgggcg cagcgtcaat gacgctgacg gtacaggcca gacaattatt gtctggtata 8280
gtgcagcagc agaacaattt gctgagggct attgaggcgc aacagcatct gttgcaactc 8340
acagtctggg gcatcaagca gctccaggca agaatcctgg ctgtggaaag atacctaaag 8400
gatcaacagc tcctggggat ttggggttgc tctggaaaac tcatttgcac cactgctgtg 8460
ccttggaatg ctagttggag taataaatct ctggaacaga tttggaatca cacgacctgg 8520
atggagtggg acagagaaat taacaattac acaagcttaa tacactcctt aattgaagaa 8580
tcgcaaaacc agcaagaaaa gaatgaacaa gaattattgg aattagataa atgggcaagt 8640
ttgtggaatt ggtttaacat aacaaattgg ctgtggtata taaaattatt cataatgata 8700
gtaggaggct tggtaggttt aagaatagtt tttgctgtac tttctatagt gaatagagtt 8760
aggcagggat attcaccatt atcgtttcag acccacctcc caaccccgag gggacccgac 8820
aggcccttaa ttaattggct ccggtgcccg tcagtgggca gagcgcacat cgcccacagt 8880
ccccgagaag ttggggggag gggtcggcaa ttgaaccggt gcctagagaa ggtggcgcgg 8940
ggtaaactgg gaaagtgatg tcgtgtactg gctccgcctt tttcccgagg gtgggggaga 9000
accgtatata agtgcagtag tcgccgtgaa cgttcttttt cgcaacgggt ttgccgccag 9060
aacacaggta agtgccgtgt gtggttcccg cgggcctggc ctctttacgg gttatggccc 9120
ttgcgtgcct tgaattactt ccacctggct gcagtacgtg attcttgatc ccgagcttcg 9180
ggttggaagt gggtgggaga gttcgaggcc ttgcgcttaa ggagcccctt cgcctcgtgc 9240
ttgagttgag gcctggcctg ggcgctgggg ccgccgcgtg cgaatctggt ggcaccttcg 9300
cgcctgtctc gctgctttcg ataagtctct agccatttaa aatttttgat gacctgctgc 9360
gacgcttttt ttctggcaag atagtcttgt aaatgcgggc caagatctgc acactggtat 9420
ttcggttttt ggggccgcgg gcggcgacgg ggcccgtgcg tcccagcgca catgttcggc 9480
gaggcggggc ctgcgagcgc ggccaccgag aatcggacgg gggtagtctc aagctggccg 9540
gcctgctctg gtgcctggcc tcgcgccgcc gtgtatcgcc ccgccctggg cggcaaggct 9600
ggcccggtcg gcaccagttg cgtgagcgga aagatggccg cttcccggcc ctgctgcagg 9660
gagctcaaaa tggaggacgc ggcgctcggg agagcgggcg ggtgagtcac ccacacaaag 9720
gaaaagggcc tttccgtcct cagccgtcgc ttcatgtgac tccacggagt accgggcgcc 9780
gtccaggcac ctcgattagt tctcgagctt ttggagtacg tcgtctttag gttgggggga 9840
ggggttttat gcgatggagt ttccccacac tgagtgggtg gagactgaag ttaggccagc 9900
ttggcacttg atgtaattct ccttggaatt tgcccttttt gagtttggat cttggttcat 9960
tctcaagcct cagacagtgg ttcaaagttt ttttcttcca tttcaggtgt cgtgaggaat 10020
tcggccatta cggcccgcca ccatgaccat catgatcaag aagagcgact tcctggccat 10080
ccccagcgag gagtacaagg gcatcctgag cctgagatac caggtgttca agcagaggct 10140
ggagtgggac ctggtggtgg agaacaacct ggagagcgac gagtacgaca acagcaacgc 10200
cgagtacatc tacgcctgcg acgacaccga gaacgtgagc ggctgctggc gcctgctgcc 10260
caccaccggc gactacatgc tgaagagcgt gttccccgag ctgctgggcc agcagagcgc 10320
ccccaaggac cccaacatcg tggagctgtc caggttcgcc gtgggcaaga acagcagcaa 10380
gatcaacaac agcgccagcg agatcaccat gaagctgttc gaggccatct acaagcacgc 10440
cgtgagccag ggcatcaccg agtacgtgac cgtgaccagc accgccatcg agagatttct 10500
gaagaggatc aaggtgccct gccacaggat cggcgacaag gagatccacg tcctgggcga 10560
caccaagagc gtggtgctgt ccatgcccat caacgagcag ttcaaaaagg ccgtgctgaa 10620
ctgaggccgc ct 10632

<210> SEQ ID NO 2
<211> LENGTH: 11736
<212> TYPE: DNA
<213> ORGANISM: Artificial Sequence
<220> FEATURE:
<223> OTHER INFORMATION: Synthetic

<400> SEQUENCE: 2
cggccatcga taaggatccg cccctctccc tccccccccc ctaacgttac tggccgaagc 60
cgcttggaat aaggccggtg tgcgtttgtc tatatgttat tttccaccat attgccgtct 120
tttggcaatg tgagggcccg gaaacctggc cctgtcttct tgacgagcat tcctaggggt 180
ctttcccctc tcgccaaagg aatgcaaggt ctgttgaatg tcgtgaagga agcagttcct 240
ctggaagctt cttgaagaca aacaacgtct gtagcgaccc tttgcaggca gcggaacccc 300
ccacctggcg acaggtgcct ctgcggccaa aagccacgtg tataagatac acctgcaaag 360
gcggcacaac cccagtgcca cgttgtgagt tggatagttg tggaaagagt caaatggctc 420
tcctcaagcg tattcaacaa ggggctgaag gatgcccaga aggtacccca ttgtatggga 480
tctgatctgg ggcctcggtg cacatgcttt acatgtgttt agtcgaggtt aaaaaaacgt 540
ctaggccccc cgaaccacgg ggacgtggtt ttcctttgaa aaacacgatg ataatatggc 600
cacaaccatg gcctcctccg aggacgtcat caaggagttc atgcgcttca aggtgcgcat 660
ggagggctcc gtgaacggcc acgagttcga gatcgagggc gagggcgagg gccgccccta 720
cgagggcacc cagaccgcca agctgaaggt gaccaagggc ggcccccctgc ccttcgcctg 780 ggacatcctg tccccccagt tccagtacgg ctccaaggtg tacgtgaagc accccgccga 840
catccccgac tacaagaagc tgtccttccc cgagggcttc aagtgggagc gcgtgatgaa 900
cttcgaggac ggcggcgtgg tgaccgtgac ccaggactcc tccctgcagg acggctcctt 960
catctacaag gtgaagttca tcggcgtgaa cttcccctcc gacggccccg taatgcagaa 1020

-continued gaagactatg ggctgggagg cctccaccga gcgcctgtac ccccgcgacg gcgtgctgaa 1080
gggcgagatc cacaaggccc tgaagctgaa ggacggcggc cactacctgg tggagttcaa 1140
gtccatctac atggccaaga agcccgtgca gctgcccggc tactactacg tggactccaa 1200
gctggacatc acctcccaca acgaggacta caccatcgtg gagcagtacg agcgcgccga 1260
gggccgccac cacctgttcc tgtaggcggc cgcaatcaac ctctggatta caaaatttgt 1320
gaaagattga ctggtattct taactatgtt gctcctttta cgctatgtgg atacgctgct 1380
ttaatgcctt tgtatcatgc tattacttcc cgtacggctt tcattttctc ctccttgtat 1440
aaatcctggt tgctgtctct ttatgaggag ttgtggcccg ttgtcaggca acgtggcgtg 1500
gtgtgcactg tgtttgctga cgcaaccccc actggttggg gcattgccac cacctatcaa 1560
ctcctttccg ggactttcgc tttccccctc cctattgcca cggcggaact cattgccgcc 1620
tgccttgccc gctgctggac aggggctcgg ctgttgggca ctgacaattc cgtggtgttg 1680
tcggggaagc tgacgtcctt tccatggctg ctcgcctgtg ttgccaactg gattctgcgc 1740
gggacgtcct tctgctacgt cccttcggcc ctcaatccag cggaccttcc ttcccgcggc 1800
ctgctgccgg ttctgcggcc tcttccgcgt cttcgccttc gccctcagac gagtcggatc 1860
tccctttggg ccgcctcccc gcctgcctgc aggtttgtcg agacctagaa aaacatggag 1920
caatcacaag tagcaataca gcagctacca atgctgattg tgcctggcta gaagcacaag 1980
aggaggagga ggtgggtttt ccagtcacac ctcaggtacc tttaagacca atgacttaca 2040
aggcagctgt agatcttagc cactttttaa aagaaaaggg gggactggaa gggctaattc 2100
actcccaacg aagacaagat ctgctttttg cttgtactgg gtctctctgg ttagaccaga 2160
tctgagcctg ggagctctct ggctaactag ggaacccact gcttaagcct caataaagct 2220
tgccttgagt gcttcaagta gtgtgtgccc gtctgttgtg tgactctggt aactagagat 2280
ccctcagacc cttttagtca gtgtggaaaa tctctagcag ggcccgttta aacccgctga 2340
tcagcctcga ctgtgccttc tagttgccag ccatctgttg tttgcccctc ccccgtgcct 2400
tccttgaccc tggaaggtgc cactcccact gtcctttcct aataaaatga ggaaattgca 2460
tcgcattgtc tgagtaggtg tcattctatt ctggggggtg gggtggggca ggacagcaag 2520
ggggaggatt gggaagacaa tagcaggcat gctggggatg cggtgggctc tatggcttct 2580
gaggcggaaa gaaccagctg gggctctagg gggtatcccc acgcgccctg tagcggcgca 2640
ttaagcgcgg cgggtgtggt ggttacgcgc agcgtgaccg ctacacttgc cagcgcccta 2700
gcgcccgctc ctttcgcttt cttcccttcc tttctcgcca cgttcgccgg ctttccccgt 2760
caagctctaa atcggggcat ccctttaggg ttccgattta gtgctttacg gcacctcgac 2820
cccaaaaaac ttgattaggg tgatggttca cgtagtgggc catcgccctg atagacggtt 2880
tttcgccctt tgacgttgga gtccacgttc tttaatagtg gactcttgtt ccaaactgga 2940
acaacactca accctatctc ggtctattct tttgatttat aagggatttt ggggatttcg 3000
gcctattggt taaaaaatga gctgatttaa caaaaattta acgcgaatta attctgtgga 3060
atgtgtgtca gttagggtgt ggaaagtccc caggctcccc aggcaggcag aagtatgcaa 3120
agcatgcatc tcaattagtc agcaaccagg tgtggaaagt ccccaggctc cccagcaggc 3180
agaagtatgc aaagcatgca tctcaattag tcagcaacca tagtcccgcc cctaactccg 3240
cccatcccgc ccctaactcc gcccagttcc gcccattctc cgccccatgg ctgactaatt 3300
ttttttattt atgcagaggc cgaggccgcc tctgcctctg agctattcca gaagtagtga 3360

-continued

```
ggaggctttt ttggaggcct aggcttttgc aaaaagctcc cgggagcttg tatatccatt   3420
ttcggatctg atcagcacgt gttgacaatt aatcatcggc atagtatatc ggcatagtat   3480
aatacgacaa ggtgaggaac taaaccatgg ccaagttgac cagtgccgtt ccggtgctca   3540
ccgcgcgcga cgtcgccgga gcggtcgagt tctggaccga ccggctcggg ttctcccggg   3600
acttcgtgga ggacgacttc gccggtgtgg tccgggacga cgtgaccctg ttcatcagcg   3660
cggtccagga ccaggtggtg ccggacaaca ccctggcctg ggtgtgggtg cgcggcctgg   3720
acgagctgta cgccgagtgg tcggaggtcg tgtccacgaa cttccgggac gcctccgggc   3780
cggccatgac cgagatcggc gagcagccgt gggggcggga gttcgccctg cgcgacccgg   3840
ccggcaactg cgtgcacttc gtggccgagg agcaggactg acacgtgcta cgagatttcg   3900
attccaccgc cgccttctat gaaaggttgg gcttcggaat cgttttccgg gacgccggct   3960
ggatgatcct ccagcgcggg gatctcatgc tggagttctt cgcccacccc aacttgttta   4020
ttgcagctta taatggttac aaataaagca atagcatcac aaatttcaca aataaagcat   4080
tttttcact gcattctagt tgtggtttgt ccaaactcat caatgtatct tatcatgtct   4140
gtataccgtc gacctctagc tagagcttgg cgtaatcatg gtcatagctg tttcctgtgt   4200
gaaattgtta tccgctcaca attccacaca acatacgagc cggaagcata aagtgtaaag   4260
cctggggtgc ctaatgagtg agctaactca cattaattgc gttgcgctca ctgcccgctt   4320
tccagtcggg aaacctgtcg tgccagctgc attaatgaat cggccaacgc gcggggagag   4380
gcggtttgcg tattgggcgc tcttccgctt cctcgctcac tgactcgctg cgctcggtcg   4440
ttcggctgcg gcgagcggta tcagctcact caaaggcggt aatacggtta tccacagaat   4500
caggggataa cgcaggaaag aacatgtgag caaaaggcca gcaaaaggcc aggaaccgta   4560
aaaaggccgc gttgctggcg tttttccata ggctccgccc ccctgacgag catcacaaaa   4620
atcgacgctc aagtcagagg tggcgaaacc cgacaggact ataaagatac caggcgtttc   4680
cccctggaag ctccctcgtg cgctctcctg ttccgaccct gccgcttacc ggatacctgt   4740
ccgcctttct cccttcggga agcgtggcgc tttctcaatg ctcacgctgt aggtatctca   4800
gttcggtgta ggtcgttcgc tccaagctgg gctgtgtgca cgaacccccc gttcagcccg   4860
accgctgcgc cttatccggt aactatcgtc ttgagtccaa cccggtaaga cacgacttat   4920
cgccactggc agcagccact ggtaacagga ttagcagagc gaggtatgta ggcggtgcta   4980
cagagttctt gaagtggtgg cctaactacg gctacactag aaggacagta tttggtatct   5040
gcgctctgct gaagccagtt accttcggaa aaagagttgg tagctcttga tccggcaaac   5100
aaaccaccgc tggtagcggt ggtttttttg tttgcaagca gcagattacg cgcagaaaaa   5160
aaggatctca agaagatcct ttgatctttt ctacggggtc tgacgctcag tggaacgaaa   5220
actcacgtta agggattttg gtcatgagat tatcaaaaag gatcttcacc tagatccttt   5280
taaattaaaa atgaagtttt aaatcaatct aaagtatata tgagtaaact tggtctgaca   5340
gttaccaatg cttaatcagt gaggcaccta tctcagcgat ctgtctattt cgttcatcca   5400
tagttgcctg actccccgtc gtgtagataa ctacgatacg ggagggctta ccatctggcc   5460
ccagtgctgc aatgataccg cgagacccac gctcaccggc tccagattta tcagcaataa   5520
accagccagc cggaagggcc gagcgcagaa gtggtcctgc aactttatcc gcctccatcc   5580
agtctattaa ttgttgccgg gaagctagag taagtagttc gccagttaat agtttgcgca   5640
acgttgttgc cattgctaca ggcatcgtgg tgtcacgctc gtcgtttggt atggcttcat   5700
tcagctccgg ttcccaacga tcaaggcgag ttacatgatc ccccatgttg tgcaaaaaag   5760
```

-continued

```
cggttagctc cttcggtcct ccgatcgttg tcagaagtaa gttggccgca gtgttatcac   5820
tcatggttat ggcagcactg cataattctc ttactgtcat gccatccgta agatgctttt   5880
ctgtgactgg tgagtactca accaagtcat tctgagaata gtgtatgcgg cgaccgagtt   5940
gctcttgccc ggcgtcaata cgggataata ccgcgccaca tagcagaact ttaaaagtgc   6000
tcatcattgg aaaacgttct tcggggcgaa aactctcaag gatcttaccg ctgttgagat   6060
ccagttcgat gtaacccact cgtgcaccca actgatcttc agcatctttt actttcacca   6120
gcgtttctgg gtgagcaaaa acaggaaggc aaaatgccgc aaaaaaggga ataagggcga   6180
cacggaaatg ttgaatactc atactcttcc tttttcaata ttattgaagc atttatcagg   6240
gttattgtct catgagcgga tacatatttg aatgtattta gaaaaataaa caaatagggg   6300
ttccgcgcac atttccccga aaagtgccac ctgacgtcga cggatcggga gatctcccga   6360
tcccctatgg tgcactctca gtacaatctg ctctgatgcc gcatagttaa gccagtatct   6420
gctccctgct tgtgtgttgg aggtcgctga gtagtgcgcg agcaaaattt aagctacaac   6480
aaggcaaggc ttgaccgaca attgcatgaa gaatctgctt agggttaggc gttttgcgct   6540
gcttcgcgat gtacgggcca gatatacgcg ttgacattga ttattgacta gttattaata   6600
gtaatcaatt acggggtcat tagttcatag cccatatatg gagttccgcg ttacataact   6660
tacggtaaat ggcccgcctg gctgaccgcc caacgacccc cgcccattga cgtcaataat   6720
gacgtatgtt cccatagtaa cgccaatagg gactttccat tgacgtcaat gggtggacta   6780
tttacggtaa actgcccact tggcagtaca tcaagtgtat catatgccaa gtacgccccc   6840
tattgacgtc aatgacggta aatggcccgc ctggcattat gcccagtaca tgaccttatg   6900
ggactttcct acttggcagt acatctacgt attagtcatc gctattacca tggtgatgcg   6960
gttttggcag tacatcaatg ggcgtggata gcggtttgac tcacggggat ttccaagtct   7020
ccaccccatt gacgtcaatg ggagtttgtt ttggcaccaa aatcaacggg actttccaaa   7080
atgtcgtaac aactccgccc cattgacgca aatgggcggt aggcgtgtac ggtgggaggt   7140
ctatataagc agagctctct ggctaactag agaacccact gcttactggc ttatcgaaat   7200
taatacgact cactataggg agacccaagc tggtttaaac ttaagcttgg taccgagctc   7260
actagtccag tgtggtggca gatatccagc acagtggcgg ccgctcgagt ctagagggcc   7320
cgttttgcct gtactgggtc tctctggtta gaccagatct gagcctggga gctctctggc   7380
taactaggga acccactgct taagcctcaa taaagcttgc cttgagtgct tcaagtagtg   7440
tgtgcccgtc tgttgtgtga ctctggtaac tagagatccc tcagaccctt ttagtcagtg   7500
tggaaaatct ctagcagtgg cgcccgaaca gggacttgaa agcgaaaggg aaaccagagg   7560
agctctctcg acgcaggact cggcttgctg aagcgcgcac ggcaagaggc gaggggcggc   7620
gactggtgag tacgccaaaa attttgacta gcggaggcta gaaggagaga gatgggtgcg   7680
agagcgtcag tattaagcgg gggagaatta gatcgcgatg ggaaaaaatt cggttaaggc   7740
cagggggaaa gaaaaaatat aaattaaaac atatagtatg ggcaagcagg gagctagaac   7800
gattcgcagt taatcctggc ctgttagaaa catcagaagg ctgtagacaa atactgggac   7860
agctacaacc atcccttcag acaggatcag aagaacttag atcattatat aatacagtag   7920
caaccctcta ttgtgtgcat caaaggatag agataaaaga caccaaggaa gctttagaca   7980
agatagagga agagcaaaac aaaagtaaga ccaccgcaca gcaagcggcc gctgatcttc   8040
agacctggag gaggagatat gagggacaat tggagaagtg aattatataa atataaagta   8100
```

-continued

```
gtaaaaattg aaccattagg agtagcaccc accaaggcaa agagaagagt ggtgcagaga   8160
gaaaaaagag cagtgggaat aggagctttg ttccttgggt tcttgggagc agcaggaagc   8220
actatgggcg cagcgtcaat gacgctgacg gtacaggcca gacaattatt gtctggtata   8280
gtgcagcagc agaacaattt gctgagggct attgaggcgc aacagcatct gttgcaactc   8340
acagtctggg gcatcaagca gctccaggca agaatcctgg ctgtggaaag atacctaaag   8400
gatcaacagc tcctggggat ttggggttgc tctggaaaac tcatttgcac cactgctgtg   8460
ccttggaatg ctagttggag taataaatct ctggaacaga tttggaatca cacgacctgg   8520
atggagtggg acagagaaat taacaattac acaagcttaa tacactcctt aattgaagaa   8580
tcgcaaaacc agcaagaaaa gaatgaacaa gaattattgg aattagataa atgggcaagt   8640
ttgtggaatt ggtttaacat aacaaattgg ctgtggtata taaaattatt cataatgata   8700
gtaggaggct tggtaggttt aagaatagtt tttgctgtac tttctatagt gaatagagtt   8760
aggcagggat attcaccatt atcgtttcag acccacctcc caaccccgag gggacccgac   8820
aggcccttaa ttaattggct ccggtgcccg tcagtgggca gagcgcacat cgcccacagt   8880
ccccgagaag ttgggggggag gggtcggcaa ttgaaccggt gcctagagaa ggtggcgcgg   8940
ggtaaactgg gaaagtgatg tcgtgtactg gctccgcctt tttcccgagg gtgggggaga   9000
accgtatata agtgcagtag tcgccgtgaa cgttcttttt cgcaacgggt ttgccgccag   9060
aacacaggta agtgccgtgt gtggttcccg cgggcctggc ctctttacgg gttatggccc   9120
ttgcgtgcct tgaattactt ccacctggct gcagtacgtg attcttgatc ccgagcttcg   9180
ggttggaagt gggtgggaga gttcgaggcc ttgcgcttaa ggagcccctt cgcctcgtgc   9240
ttgagttgag gcctggcctg ggcgctgggg ccgccgcgtg cgaatctggt ggcaccttcg   9300
cgcctgtctc gctgctttcg ataagtctct agccatttaa aatttttgat gacctgctgc   9360
gacgcttttt ttctggcaag atagtcttgt aaatgcgggc caagatctgc acactggtat   9420
ttcggttttt ggggccgcgg gcggcgacgg ggcccgtgcg tcccagcgca catgttcggc   9480
gaggcggggc ctgcgagcgc ggccaccgag aatcggacgg gggtagtctc aagctggccg   9540
gcctgctctg gtgcctggcc tcgcgccgcc gtgtatcgcc ccgccctggg cggcaaggct   9600
ggcccggtcg gcaccagttg cgtgagcgga aagatggccg cttcccggcc ctgctgcagg   9660
gagctcaaaa tggaggacgc ggcgctcggg agagcgggcg ggtgagtcac ccacacaaag   9720
gaaaagggcc tttccgtcct cagccgtcgc ttcatgtgac tccacggagt accgggcgcc   9780
gtccaggcac ctcgattagt tctcgagctt ttggagtacg tcgtctttag gttgggggga   9840
ggggttttat gcgatggagt ttccccacac tgagtgggtg gagactgaag ttaggccagc   9900
ttggcacttg atgtaattct ccttggaatt tgcccttttt gagtttggat cttggttcat   9960
tctcaagcct cagacagtgg ttcaaagttt ttttcttcca tttcaggtgt cgtgaggaat  10020
tcggccatta cggcctgcca ccatggacca gtacctgccc gacaccgacg acaggcacag  10080
gatcgaggag aagaggaaga ggacctacga gaccttcaag agcatcatga agaagagccc  10140
cttcaacggc cccaccgagc ccagaccccc caccaggcgg atcgccgtgc ccacaaggaa  10200
cagcaccagc gtgcccaagc ctgcccccca gccctacacc ttccccgcca gcctgagcac  10260
catcaacttc gacgagttca gccccatgct gctgcccagc ggccagatca gcaaccaggc  10320
cctggccctg gctcctagca gcgcccctgt gctggcccag accatggtgc ccagcagcgc  10380
catggtgcct ctggcccagc ctcctgcccc tgcccccgtg ctgacccctg gcccccctca  10440
gagcctgagc gccccagtgc ccaagagcac ccaggccggc gagggcacac tgagcgaggc  10500
```

```
cctgctgcac ctgcagttcg acgccgacga ggacctgggc gccctgctgg gcaacagcac  10560

cgaccccggc gtgttcaccg acctggccag cgtggacaac agcgagttcc agcagctgct  10620

gaaccagggc gtgagcatga gccacagcac cgccgagccc atgctgatgg agtaccccga  10680

ggccatcacc aggctggtga ccggcagcca gagacccccc gaccctgccc ctacccctct  10740

gggcaccagc ggcctgccca acggcctgag cggcgacgag gacttcagca gcatcgccga  10800

catggacttc tccgccctgc tgtcccagat cagctccctg gagctggccg aggccgctgc  10860

caaggaggct gccgctaagg aggccgctgc taaggaggct gctgccaagg ccgctgccat  10920

gaagaacatc aacgccgacg acacctacag gatcatcaac aagatcaagg cctgcagaag  10980

caacaacgac atcaaccagt gcctgagcga catggccaag atggtgcact gcgagtacta  11040

cctgctggcc ttcatctacc cccacagcat ggtgaagagc gacatcagca tcctggacaa  11100

ctaccccaag aagtggaggc agtactacga cgacgccaac ctgatcaagt acgaccccat  11160

cgtggactac agcaacagca accacagccc catcaactgg aacatcttcg agaacaacgc  11220

cgtgaacaaa aagtccccca acgtgatcaa ggaggccaag acagccggcc tgatcaccgg  11280

cttcagcttc cccatccaca ccgccaacaa cggcttcggc atgctgtcct tcgcccacag  11340

cgagaaggac aactacatcg acagcctgtt tctgcacgcc tgcatgaaca tcccccctgat  11400

cgtgcccagc ctggtggata actaccggaa gatcaacatc gccaacaaca agtccaacaa  11460

cgacctgacc aagcgggaga aggagtgcct ggcctgggcc tgcgagggca agagcagctg  11520

ggacatcagc aagatcctgg gctgcagcga gaggaccgtg accttccacc tgaccaacgc  11580

ccagatgaag ctgaacacca ccaacaggtg ccagagcatc agcaaggcca tcctgaccgg  11640

cgccatcgac tgcccctact tcaagaacag cagcctgagg ccccccaaaa agaaaagaaa  11700

ggtgcaccac caccaccacc actgatgagg ccgcct                            11736
```

<210> SEQ ID NO 3
<211> LENGTH: 10050
<212> TYPE: DNA
<213> ORGANISM: Artificial Sequence
<220> FEATURE:
<223> OTHER INFORMATION: Synthetic

<400> SEQUENCE: 3

```
aattcggcca ttacggccgc tagcgttaac gtcgacggcc gcctcggcca tcgataagga     60

tccggaatgc ccctctccct cccccccccc taacgttact ggccgaagcc gcttggaata    120

aggccggtgt gcgtttgtct atatgttatt ttccaccata ttgccgtctt ttggcaatgt    180

gagggcccgg aaacctggcc ctgtcttctt gacgagcatt cctaggggtc tttcccctct    240

cgccaaagga atgcaaggtc tgttgaatgt cgtgaaggaa gcagttcctc tggaagcttc    300

ttgaagacaa acaacgtctg tagcgaccct ttgcaggcag cggaaccccc cacctggcga    360

caggtgcctc tgcggccaaa agccacgtgt ataagataca cctgcaaagg cggcacaacc    420

ccagtgccac gttgtgagtt ggatagttgt ggaaagagtc aaatggctct cctcaagcgt    480

attcaacaag gggctgaagg atgcccagaa ggtaccccat tgtatgggat ctgatctggg    540

gcctcggtgc acatgcttta catgtgttta gtcgaggtta aaaaaacgtc taggcccccc    600

gaaccacggg gacgtggttt tcctttgaaa aacacgatga taatatggcc acaaccatgg    660

tgagcaaggg cgaggagctg ttcaccgggg tggtgcccat cctggtcgag ctggacggcg    720

acgtaaacgg ccacaagttc agcgtgtccg gcgagggcga gggcgatgcc acctacggca    780
```

-continued

```
agctgaccct gaagttcatc tgcaccaccg gcaagctgcc cgtgccctgg cccaccctcg    840
tgaccaccct gacctacggc gtgcagtgct tcagccgcta ccccgaccac atgaagcagc    900
acgacttctt caagtccgcc atgcccgaag gctacgtcca ggagcgcacc atcttcttca    960
aggacgacgg caactacaag acccgcgccg aggtgaagtt cgagggcgac accctggtga   1020
accgcatcga gctgaagggc atcgacttca aggaggacgg caacatcctg gggcacaagc   1080
tggagtacaa ctacaacagc cacaacgtct atatcatggc cgacaagcag aagaacggca   1140
tcaaggtgaa cttcaagatc cgccacaaca tcgaggacgg cagcgtgcag ctcgccgacc   1200
actaccagca gaacaccccc atcggcgacg gccccgtgct gctgcccgac aaccactacc   1260
tgagcaccca gtccgccctg agcaaagacc ccaacgagaa gcgcgatcac atggtcctgc   1320
tggagttcgt gaccgccgcc gggatcactc tcggcatgga cgagctgtac aagtaagcgg   1380
ccgcaatcaa cctctggatt acaaaatttg tgaaagattg actggtattc ttaactatgt   1440
tgctcctttt acgctatgtg gatacgctgc tttaatgcct ttgtatcatg ctattacttc   1500
ccgtacggct ttcattttct cctccttgta taaatcctgg ttgctgtctc tttatgagga   1560
gttgtggccc gttgtcaggc aacgtggcgt ggtgtgcact gtgtttgctg acgcaacccc   1620
cactggttgg ggcattgcca ccacctatca actcctttcc gggactttcg ctttccccct   1680
ccctattgcc acggcggaac tcattgccgc ctgccttgcc cgctgctgga caggggctcg   1740
gctgttgggc actgacaatt ccgtggtgtt gtcggggaag ctgacgtcct ttccatggct   1800
gctcgcctgt gttgccaact ggattctgcg cgggacgtcc ttctgctacg tcccttcggc   1860
cctcaatcca gcggaccttc cttcccgcgg cctgctgccg gttctgcggc ctcttccgcg   1920
tcttcgcctt cgccctcaga cgagtcggat ctccctttgg gccgcctccc cgcctgcctg   1980
caggtttgtc gagacctaga aaaacatgga gcaatcacaa gtagcaatac agcagctacc   2040
aatgctgatt gtgcctggct agaagcacaa gaggaggagg aggtgggttt tccagtcaca   2100
cctcaggtac ctttaagacc aatgacttac aaggcagctg tagatcttag ccacttttta   2160
aaagaaaagg ggggactgga agggctaatt cactcccaac gaagacaaga tctgcttttt   2220
gcttgtactg ggtctctctg gttagaccag atctgagcct gggagctctc tggctaacta   2280
gggaacccac tgcttaagcc tcaataaagc ttgccttgag tgcttcaagt agtgtgtgcc   2340
cgtctgttgt gtgactctgg taactagaga tccctcagac ccttttagtc agtgtggaaa   2400
atctctagca gggcccgttt aaacccgctg atcagcctcg actgtgcctt ctagttgcca   2460
gccatctgtt gtttgcccct cccccgtgcc ttccttgacc ctggaaggtg ccactcccac   2520
tgtcctttcc taataaaatg aggaaattgc atcgcattgt ctgagtaggt gtcattctat   2580
tctggggggt ggggtggggc aggacagcaa gggggaggat tgggaagaca atagcaggca   2640
tgctggggat gcggtgggct ctatggcttc tgaggcggaa agaaccagct ggggctctag   2700
ggggtatccc cacgcgccct gtagcggcgc attaagcgcg gcgggtgtgg tggttacgcg   2760
cagcgtgacc gctacacttg ccagcgccct agcgcccgct cctttcgctt tcttcccttc   2820
ctttctcgcc acgttcgccg gctttccccg tcaagctcta aatcggggca tccctttagg   2880
gttccgattt agtgctttac ggcacctcga ccccaaaaaa cttgattagg gtgatggttc   2940
acgtagtggg ccatcgccct gatagacggt ttttcgccct ttgacgttgg agtccacgtt   3000
ctttaatagt ggactcttgt tccaaactgg aacaacactc aaccctatct cggtctattc   3060
ttttgattta taagggattt tggggatttc ggcctattgg ttaaaaaatg agctgattta   3120
acaaaaattt aacgcgaatt aattctgtgg aatgtgtgtc agttagggtg tggaaagtcc   3180
```

```
ccaggctccc caggcaggca gaagtatgca aagcatgcat ctcaattagt cagcaaccag   3240
gtgtggaaag tccccaggct ccccagcagg cagaagtatg caaagcatgc atctcaatta   3300
gtcagcaacc atagtcccgc ccctaactcc gcccatcccg cccctaactc cgcccagttc   3360
cgcccattct ccgccccatg gctgactaat tttttttatt tatgcagagg ccgaggccgc   3420
ctctgcctct gagctattcc agaagtagtg aggaggcttt tttggaggcc taggcttttg   3480
caaaaagctc ccgggagctt gtatatccat tttcggatct gatcagcacg tgttgacaat   3540
taatcatcgg catagtatat cggcatagta taatacgaca aggtgaggaa ctaaaccatg   3600
gccaagttga ccagtgccgt tccggtgctc accgcgcgcg acgtcgccgg agcggtcgag   3660
ttctggaccg accggctcgg gttctcccgg gacttcgtgg aggacgactt cgccggtgtg   3720
gtccgggacg acgtgaccct gttcatcagc gcggtccagg accaggtggt gccggacaac   3780
accctggcct gggtgtgggt gcgcggcctg gacgagctgt acgccgagtg gtcggaggtc   3840
gtgtccacga acttccggga cgcctccggg ccggccatga ccgagatcgg cgagcagccg   3900
tgggggcggg agttcgccct gcgcgacccg gccggcaact gcgtgcactt cgtggccgag   3960
gagcaggact gacacgtgct acgagatttc gattccaccg ccgccttcta tgaaaggttg   4020
ggcttcggaa tcgttttccg ggacgccggc tggatgatcc tccagcgcgg ggatctcatg   4080
ctggagttct tcgcccaccc caacttgttt attgcagctt ataatggtta caaataaagc   4140
aatagcatca caaatttcac aaataaagca tttttttcac tgcattctag ttgtggtttg   4200
tccaaactca tcaatgtatc ttatcatgtc tgtataccgt cgacctctag ctagagcttg   4260
gcgtaatcat ggtcatagct gtttcctgtg tgaaattgtt atccgctcac aattccacac   4320
aacatacgag ccggaagcat aaagtgtaaa gcctggggtg cctaatgagt gagctaactc   4380
acattaattg cgttgcgctc actgcccgct ttccagtcgg gaaacctgtc gtgccagctg   4440
cattaatgaa tcggccaacg cgcggggaga ggcggtttgc gtattgggcg ctcttccgct   4500
tcctcgctca ctgactcgct gcgctcggtc gttcggctgc ggcgagcggt atcagctcac   4560
tcaaaggcgg taatacggtt atccacagaa tcaggggata acgcaggaaa gaacatgtga   4620
gcaaaaggcc agcaaaaggc caggaaccgt aaaaaggccg cgttgctggc gtttttccat   4680
aggctccgcc cccctgacga gcatcacaaa aatcgacgct caagtcagag gtggcgaaac   4740
ccgacaggac tataaagata ccaggcgttt ccccctggaa gctccctcgt gcgctctcct   4800
gttccgaccc tgccgcttac cggatacctg tccgcctttc tcccttcggg aagcgtggcg   4860
ctttctcaat gctcacgctg taggtatctc agttcggtgt aggtcgttcg ctccaagctg   4920
ggctgtgtgc acgaaccccc cgttcagccc gaccgctgcg ccttatccgg taactatcgt   4980
cttgagtcca acccggtaag acacgactta tcgccactgg cagcagccac tggtaacagg   5040
attagcagag cgaggtatgt aggcggtgct acagagttct tgaagtggtg gcctaactac   5100
ggctacacta gaaggacagt atttggtatc tgcgctctgc tgaagccagt taccttcgga   5160
aaaagagttg gtagctcttg atccggcaaa caaaccaccg ctggtagcgg tggttttttt   5220
gtttgcaagc agcagattac gcgcagaaaa aaaggatctc aagaagatcc tttgatcttt   5280
tctacggggt ctgacgctca gtggaacgaa aactcacgtt aagggatttt ggtcatgaga   5340
ttatcaaaaa ggatcttcac ctagatcctt ttaaattaaa aatgaagttt taaatcaatc   5400
taaagtatat atgagtaaac ttggtctgac agttaccaat gcttaatcag tgaggcacct   5460
atctcagcga tctgtctatt tcgttcatcc atagttgcct gactccccgt cgtgtagata   5520
```

-continued

```
actacgatac gggagggctt accatctggc cccagtgctg caatgatacc gcgagaccca   5580
cgctcaccgg ctccagattt atcagcaata aaccagccag ccggaagggc cgagcgcaga   5640
agtggtcctg caactttatc cgcctccatc cagtctatta attgttgccg ggaagctaga   5700
gtaagtagtt cgccagttaa tagtttgcgc aacgttgttg ccattgctac aggcatcgtg   5760
gtgtcacgct cgtcgtttgg tatggcttca ttcagctccg gttcccaacg atcaaggcga   5820
gttacatgat cccccatgtt gtgcaaaaaa gcggttagct ccttcggtcc tccgatcgtt   5880
gtcagaagta agttggccgc agtgttatca ctcatggtta tggcagcact gcataattct   5940
cttactgtca tgccatccgt aagatgcttt tctgtgactg gtgagtactc aaccaagtca   6000
ttctgagaat agtgtatgcg gcgaccgagt tgctcttgcc cggcgtcaat acgggataat   6060
accgcgccac atagcagaac tttaaaagtg ctcatcattg gaaaacgttc ttcggggcga   6120
aaactctcaa ggatcttacc gctgttgaga tccagttcga tgtaacccac tcgtgcaccc   6180
aactgatctt cagcatcttt tactttcacc agcgtttctg ggtgagcaaa aacaggaagg   6240
caaaatgccg caaaaaaggg aataagggcg acacggaaat gttgaatact catactcttc   6300
ctttttcaat attattgaag catttatcag ggttattgtc tcatgagcgg atacatattt   6360
gaatgtattt agaaaaataa acaaataggg gttccgcgca catttccccg aaaagtgcca   6420
cctgacgtcg acggatcggg agatctcccg atcccctatg gtgcactctc agtacaatct   6480
gctctgatgc cgcatagtta agccagtatc tgctccctgc ttgtgtgttg gaggtcgctg   6540
agtagtgcgc gagcaaaatt taagctacaa caaggcaagg cttgaccgac aattgcatga   6600
agaatctgct tagggttagg cgttttgcgc tgcttcgcga tgtacgggcc agatatacgc   6660
gttgacattg attattgact agttattaat agtaatcaat tacggggtca ttagttcata   6720
gcccatatat ggagttccgc gttacataac ttacggtaaa tggcccgcct ggctgaccgc   6780
ccaacgaccc ccgcccattg acgtcaataa tgacgtatgt tcccatagta acgccaatag   6840
ggactttcca ttgacgtcaa tgggtggact atttacggta aactgcccac ttggcagtac   6900
atcaagtgta tcatatgcca agtacgcccc ctattgacgt caatgacggt aaatggcccg   6960
cctggcatta tgcccagtac atgaccttat gggactttcc tacttggcag tacatctacg   7020
tattagtcat cgctattacc atggtgatgc ggttttggca gtacatcaat gggcgtggat   7080
agcggtttga ctcacgggga tttccaagtc tccaccccat tgacgtcaat gggagtttgt   7140
tttggcacca aaatcaacgg gactttccaa aatgtcgtaa caactccgcc ccattgacgc   7200
aaatgggcgg taggcgtgta cggtgggagg tctatataag cagagctctc tggctaacta   7260
gagaacccac tgcttactgg cttatcgaaa ttaatacgac tcactatagg gagacccaag   7320
ctggtttaaa cttaagcttg gtaccgagct cactagtcca gtgtggtggc agatatccag   7380
cacagtggcg gccgctcgag tctagagggc ccgttttgcc tgtactgggt ctctctggtt   7440
agaccagatc tgagcctggg agctctctgg ctaactaggg aacccactgc ttaagcctca   7500
ataaagcttg ccttgagtgc ttcaagtagt gtgtgcccgt ctgttgtgtg actctggtaa   7560
ctagagatcc ctcagaccct tttagtcagt gtggaaaatc tctagcagtg gcgcccgaac   7620
agggacttga aagcgaaagg gaaaccagag gagctctctc gacgcaggac tcggcttgct   7680
gaagcgcgca cggcaagagg cgaggggcgg cgactggtga gtacgccaaa aattttgact   7740
agcggaggct agaaggagag agatgggtgc gagagcgtca gtattaagcg ggggagaatt   7800
agatcgcgat gggaaaaaat tcggttaagg ccagggggaa agaaaaaata taaattaaaa   7860
catatagtat gggcaagcag ggagctagaa cgattcgcag ttaatcctgg cctgttagaa   7920
```

-continued acatcagaag gctgtagaca aatactggga cagctacaac catcccttca gacaggatca 7980
gaagaactta gatcattata taatacagta gcaaccctct attgtgtgca tcaaaggata 8040
gagataaaag acaccaagga agctttagac aagatagagg aagagcaaaa caaaagtaag 8100
accaccgcac agcaagcggc cgctgatctt cagacctgga ggaggagata tgagggacaa 8160
ttggagaagt gaattatata aatataaagt agtaaaaatt gaaccattag gagtagcacc 8220
caccaaggca aagagaagag tggtgcagag agaaaaaaga gcagtgggaa taggagcttt 8280
gttccttggg ttcttgggag cagcaggaag cactatgggc gcagcgtcaa tgacgctgac 8340
ggtacaggcc agacaattat tgtctggtat agtgcagcag cagaacaatt tgctgagggc 8400
tattgaggcg caacagcatc tgttgcaact cacagtctgg ggcatcaagc agctccaggc 8460
aagaatcctg gctgtggaaa gatacctaaa ggatcaacag ctcctgggga tttggggttg 8520
ctctggaaaa ctcatttgca ccactgctgt gccttggaat gctagttgga gtaataaatc 8580
tctggaacag atttggaatc acacgacctg gatggagtgg gacagagaaa ttaacaatta 8640
cacaagctta atacactcct taattgaaga atcgcaaaac cagcaagaaa agaatgaaca 8700
agaattattg gaattagata aatgggcaag tttgtggaat tggtttaaca taacaaattg 8760
gctgtggtat atagaaatta ttcataatga tagtaggagg cttggtaggt ttaagaatag 8820
tttttgctgt actttctata gtgaatagag ttaggcaggg atattcacca ttatcgtttc 8880
agacccacct cccaaccccg aggggacccg acaggcccga aggaatagaa gaagaaggtg 8940
gagagagaga cagagacaga tccattcgat tagtgaacgg atcggcactg cgtgcgccaa 9000
ttctgcagac aaatggcagt attcatccac aattttaaaa gaaaaggggg gattgggggg 9060
tacagtgcag gggaaagaat agtagacata atagcaacag acatacaaac taaagaatta 9120
caaaaacaaa ttacaaaaat tcaaaatttt cgggtttatt acagggacag cagagatcca 9180
gtttggggtt gctctggaaa actcatttgc accactgctg tgccttggaa tgctagttgg 9240
agtaataaat ctctggaaca gatttggaat cacacgacct ggatggagtg ggacagagaa 9300
attaacaatt acacaagctt aatacactcc ttaattgaag aatcgcaaaa ccagcaagaa 9360
aagaatgaac aagaattatt ggaattagat aaatgggcaa gtttgtggaa ttggtttaac 9420
ataacaaatt ggctgtggta tataaaatta ttcataatga tagtaggagg cttggtaggt 9480
ttaagaatag tttttgctgt actttctata gtgaatagag ttaggcaggg atattcacca 9540
ttatcgtttc agacccacct cccaaccccg aggggacccg acaggccctt aattaatccc 9600
ctgattctgt ggataaccgt attaccgcct ttgagtgagc tgcacacctg taggatcgta 9660
caggtaaagt gaaaggctac aataggacac ctgtaggatc gtacaggtgg taaactcgag 9720
agcgcccaat aacctgtagg atcgtacagg tagcgcacta gagagcgccc aataacctgt 9780
aggatcgtac aggtaaagtg aaaggctaca ataggacacc tgtaggatcg tacaggtggt 9840
aaactcgaga gcgcccaata acctgtagga tcgtacaggt aaagtgaaag gctacaatag 9900
gacacctgta ggatcgtaca ggtggtaaac tcgacctata taagcagagc tcgtttagtg 9960
aaccgtcaga tcgcctggag acgccatcca cgctgttttg acctccatag aagacaccgg 10020
gaccgatcca gcctccgcgg ccccgaattg 10050

<210> SEQ ID NO 4
<211> LENGTH: 10287
<212> TYPE: DNA
<213> ORGANISM: Artificial Sequence
<220> FEATURE:

-continued

<223> OTHER INFORMATION: Synthetic

<400> SEQUENCE: 4

```
cggccatcga taaggatccg cccctctccc tccccccccc ctaacgttac tggccgaagc     60
cgcttggaat aaggccggtg tgcgtttgtc tatatgttat tttccaccat attgccgtct    120
tttggcaatg tgagggcccg gaaacctggc cctgtcttct tgacgagcat tcctaggggt    180
ctttcccctc tcgccaaagg aatgcaaggt ctgttgaatg tcgtgaagga agcagttcct    240
ctggaagctt cttgaagaca aacaacgtct gtagcgaccc tttgcaggca gcggaacccc    300
ccacctggcg acaggtgcct ctgcggccaa aagccacgtg tataagatac acctgcaaag    360
gcggcacaac cccagtgcca cgttgtgagt tggatagttg tggaaagagt caaatggctc    420
tcctcaagcg tattcaacaa ggggctgaag gatgcccaga aggtacccca ttgtatggga    480
tctgatctgg ggcctcggtg cacatgcttt acatgtgttt agtcgaggtt aaaaaaacgt    540
ctaggccccc cgaaccacgg ggacgtggtt ttcctttgaa aaacacgatg ataatatggc    600
cacaaccatg gcctcctccg aggacgtcat caaggagttc atgcgcttca aggtgcgcat    660
ggagggctcc gtgaacggcc acgagttcga gatcgagggc gagggcgagg gccgccccta    720
cgagggcacc cagaccgcca agctgaaggt gaccaagggc ggccccctgc ccttcgcctg    780
ggacatcctg tccccccagt tccagtacgg ctccaaggtg tacgtgaagc accccgccga    840
catccccgac tacaagaagc tgtccttccc cgagggcttc aagtgggagc gcgtgatgaa    900
cttcgaggac ggcggcgtgg tgaccgtgac ccaggactcc tccctgcagg acggctcctt    960
catctacaag gtgaagttca tcggcgtgaa cttcccctcc gacggccccg taatgcagaa   1020
gaagactatg ggctgggagg cctccaccga gcgcctgtac ccccgcgacg gcgtgctgaa   1080
gggcgagatc cacaaggccc tgaagctgaa ggacggcggc cactacctgg tggagttcaa   1140
gtccatctac atggccaaga agcccgtgca gctgcccggc tactactacg tggactccaa   1200
gctggacatc acctcccaca acgaggacta caccatcgtg gagcagtacg agcgcgccga   1260
gggccgccac cacctgttcc tgtaggcggc cgcaatcaac ctctggatta caaaatttgt   1320
gaaagattga ctggtattct taactatgtt gctcctttta cgctatgtgg atacgctgct   1380
ttaatgcctt tgtatcatgc tattacttcc cgtacggctt tcattttctc ctccttgtat   1440
aaatcctggt tgctgtctct ttatgaggag ttgtggcccg ttgtcaggca acgtggcgtg   1500
gtgtgcactg tgtttgctga cgcaaccccc actggttggg gcattgccac cacctatcaa   1560
ctcctttccg ggactttcgc tttccccctc cctattgcca cggcggaact cattgccgcc   1620
tgccttgccc gctgctggac aggggctcgg ctgttgggca ctgacaattc cgtggtgttg   1680
tcggggaagc tgacgtcctt tccatggctg ctcgcctgtg ttgccaactg gattctgcgc   1740
gggacgtcct tctgctacgt cccttcggcc ctcaatccag cggaccttcc ttcccgcggc   1800
ctgctgccgg ttctgcggcc tcttccgcgt cttcgccttc gccctcagac gagtcggatc   1860
tccctttggg ccgcctcccc gcctgcctgc aggtttgtcg agacctagaa aaacatggag   1920
caatcacaag tagcaataca gcagctacca atgctgattg tgcctggcta gaagcacaag   1980
aggaggagga ggtgggtttt ccagtcacac ctcaggtacc tttaagacca atgacttaca   2040
aggcagctgt agatcttagc cactttttaa aagaaaaggg gggactggaa gggctaattc   2100
actcccaacg aagacaagat ctgctttttg cttgtactgg gtctctctgg ttagaccaga   2160
tctgagcctg ggagctctct ggctaactag ggaacccact gcttaagcct caataaagct   2220
tgccttgagt gcttcaagta gtgtgtgccc gtctgttgtg tgactctggt aactagagat   2280
```

-continued

```
ccctcagacc cttttagtca gtgtggaaaa tctctagcag ggcccgttta aacccgctga   2340
tcagcctcga ctgtgccttc tagttgccag ccatctgttg tttgcccctc ccccgtgcct   2400
tccttgaccc tggaaggtgc cactcccact gtcctttcct aataaaatga ggaaattgca   2460
tcgcattgtc tgagtaggtg tcattctatt ctggggggtg gggtggggca ggacagcaag   2520
ggggaggatt gggaagacaa tagcaggcat gctggggatg cggtgggctc tatggcttct   2580
gaggcggaaa gaaccagctg gggctctagg gggtatcccc acgcgccctg tagcggcgca   2640
ttaagcgcgg cgggtgtggt ggttacgcgc agcgtgaccg ctacacttgc cagcgcccta   2700
gcgcccgctc ctttcgcttt cttcccttcc tttctcgcca cgttcgccgg ctttccccgt   2760
caagctctaa atcggggcat ccctttaggg ttccgattta gtgctttacg gcacctcgac   2820
cccaaaaaac ttgattaggg tgatggttca cgtagtgggc catcgccctg atagacggtt   2880
tttcgccctt tgacgttgga gtccacgttc tttaatagtg gactcttgtt ccaaactgga   2940
acaacactca accctatctc ggtctattct tttgatttat aagggatttt ggggatttcg   3000
gcctattggt taaaaaatga gctgatttaa caaaaattta acgcgaatta attctgtgga   3060
atgtgtgtca gttagggtgt ggaaagtccc caggctcccc aggcaggcag aagtatgcaa   3120
agcatgcatc tcaattagtc agcaaccagg tgtggaaagt ccccaggctc cccagcaggc   3180
agaagtatgc aaagcatgca tctcaattag tcagcaacca tagtcccgcc cctaactccg   3240
cccatcccgc ccctaactcc gcccagttcc gcccattctc cgccccatgg ctgactaatt   3300
ttttttattt atgcagaggc cgaggccgcc tctgcctctg agctattcca gaagtagtga   3360
ggaggctttt ttggaggcct aggcttttgc aaaaagctcc cgggagcttg tatatccatt   3420
ttcggatctg atcagcacgt gttgacaatt aatcatcggc atagtatatc ggcatagtat   3480
aatacgacaa ggtgaggaac taaaccatgg ccaagttgac cagtgccgtt ccggtgctca   3540
ccgcgcgcga cgtcgccgga gcggtcgagt tctggaccga ccggctcggg ttctcccggg   3600
acttcgtgga ggacgacttc gccggtgtgg tccgggacga cgtgaccctg ttcatcagcg   3660
cggtccagga ccaggtggtg ccggacaaca ccctggcctg ggtgtgggtg cgcggcctgg   3720
acgagctgta cgccgagtgg tcggaggtcg tgtccacgaa cttccgggac gcctccgggc   3780
cggccatgac cgagatcggc gagcagccgt gggggcggga gttcgccctg cgcgacccgg   3840
ccggcaactg cgtgcacttc gtggccgagg agcaggactg acacgtgcta cgagatttcg   3900
attccaccgc cgccttctat gaaaggttgg gcttcggaat cgttttccgg gacgccggct   3960
ggatgatcct ccagcgcggg gatctcatgc tggagttctt cgcccacccc aacttgttta   4020
ttgcagctta taatggttac aaataaagca atagcatcac aaatttcaca aataaagcat   4080
tttttcact gcattctagt tgtggtttgt ccaaactcat caatgtatct tatcatgtct   4140
gtataccgtc gacctctagc tagagcttgg cgtaatcatg gtcatagctg tttcctgtgt   4200
gaaattgtta tccgctcaca attccacaca acatacgagc cggaagcata aagtgtaaag   4260
cctggggtgc ctaatgagtg agctaactca cattaattgc gttgcgctca ctgcccgctt   4320
tccagtcggg aaacctgtcg tgccagctgc attaatgaat cggccaacgc gcggggagag   4380
gcggtttgcg tattgggcgc tcttccgctt cctcgctcac tgactcgctg cgctcggtcg   4440
ttcggctgcg gcgagcggta tcagctcact caaaggcggt aatacggtta tccacagaat   4500
caggggataa cgcaggaaag aacatgtgag caaaaggcca gcaaaaggcc aggaaccgta   4560
aaaaggccgc gttgctggcg tttttccata ggctccgccc ccctgacgag catcacaaaa   4620
```

-continued

```
atcgacgctc aagtcagagg tggcgaaacc cgacaggact ataaagatac caggcgtttc   4680
cccctggaag ctccctcgtg cgctctcctg ttccgaccct gccgcttacc ggatacctgt   4740
ccgcctttct cccttcggga agcgtggcgc tttctcaatg ctcacgctgt aggtatctca   4800
gttcggtgta ggtcgttcgc tccaagctgg gctgtgtgca cgaacccccc gttcagcccg   4860
accgctgcgc cttatccggt aactatcgtc ttgagtccaa cccggtaaga cacgacttat   4920
cgccactggc agcagccact ggtaacagga ttagcagagc gaggtatgta ggcggtgcta   4980
cagagttctt gaagtggtgg cctaactacg gctacactag aaggacagta tttggtatct   5040
gcgctctgct gaagccagtt accttcggaa aaagagttgg tagctcttga tccggcaaac   5100
aaaccaccgc tggtagcggt ggtttttttg tttgcaagca gcagattacg cgcagaaaaa   5160
aaggatctca agaagatcct ttgatctttt ctacggggtc tgacgctcag tggaacgaaa   5220
actcacgtta agggattttg gtcatgagat tatcaaaaag gatcttcacc tagatccttt   5280
taaattaaaa atgaagtttt aaatcaatct aaagtatata tgagtaaact tggtctgaca   5340
gttaccaatg cttaatcagt gaggcaccta tctcagcgat ctgtctattt cgttcatcca   5400
tagttgcctg actccccgtc gtgtagataa ctacgatacg ggagggctta ccatctggcc   5460
ccagtgctgc aatgataccg cgagacccac gctcaccggc tccagattta tcagcaataa   5520
accagccagc cggaagggcc gagcgcagaa gtggtcctgc aactttatcc gcctccatcc   5580
agtctattaa ttgttgccgg gaagctagag taagtagttc gccagttaat agtttgcgca   5640
acgttgttgc cattgctaca ggcatcgtgg tgtcacgctc gtcgtttggt atggcttcat   5700
tcagctccgg ttcccaacga tcaaggcgag ttacatgatc ccccatgttg tgcaaaaaag   5760
cggttagctc cttcggtcct ccgatcgttg tcagaagtaa gttggccgca gtgttatcac   5820
tcatggttat ggcagcactg cataattctc ttactgtcat gccatccgta agatgctttt   5880
ctgtgactgg tgagtactca accaagtcat tctgagaata gtgtatgcgg cgaccgagtt   5940
gctcttgccc ggcgtcaata cgggataata ccgcgccaca tagcagaact ttaaaagtgc   6000
tcatcattgg aaaacgttct tcggggcgaa aactctcaag gatcttaccg ctgttgagat   6060
ccagttcgat gtaacccact cgtgcaccca actgatcttc agcatctttt actttcacca   6120
gcgtttctgg gtgagcaaaa acaggaaggc aaaatgccgc aaaaaaggga ataagggcga   6180
cacggaaatg ttgaatactc atactcttcc tttttcaata ttattgaagc atttatcagg   6240
gttattgtct catgagcgga tacatatttg aatgtattta gaaaaataaa caaatagggg   6300
ttccgcgcac atttccccga aaagtgccac ctgacgtcga cggatcggga gatctcccga   6360
tcccctatgg tgcactctca gtacaatctg ctctgatgcc gcatagttaa gccagtatct   6420
gctccctgct tgtgtgttgg aggtcgctga gtagtgcgcg agcaaaattt aagctacaac   6480
aaggcaaggc ttgaccgaca attgcatgaa gaatctgctt agggttaggc gttttgcgct   6540
gcttcgcgat gtacgggcca gatatacgcg ttgacattga ttattgacta gttattaata   6600
gtaatcaatt acggggtcat tagttcatag cccatatatg gagttccgcg ttacataact   6660
tacggtaaat ggcccgcctg gctgaccgcc caacgacccc cgcccattga cgtcaataat   6720
gacgtatgtt cccatagtaa cgccaatagg gactttccat tgacgtcaat gggtggacta   6780
tttacggtaa actgcccact tggcagtaca tcaagtgtat catatgccaa gtacgccccc   6840
tattgacgtc aatgacggta aatggcccgc ctggcattat gcccagtaca tgaccttatg   6900
ggactttcct acttggcagt acatctacgt attagtcatc gctattacca tggtgatgcg   6960
gttttggcag tacatcaatg ggcgtggata gcggtttgac tcacggggat ttccaagtct   7020
```

ccaccccatt gacgtcaatg ggagtttgtt ttggcaccaa aatcaacggg actttccaaa 7080
atgtcgtaac aactccgccc cattgacgca aatgggcggt aggcgtgtac ggtgggaggt 7140
ctatataagc agagctctct ggctaactag agaacccact gcttactggc ttatcgaaat 7200
taatacgact cactataggg agacccaagc tggtttaaac ttaagcttgg taccgagctc 7260
actagtccag tgtggtggca gatatccagc acagtggcgg ccgctcgagt ctagagggcc 7320
cgttttgcct gtactgggtc tctctggtta gaccagatct gagcctggga gctctctggc 7380
taactaggga acccactgct taagcctcaa taaagcttgc cttgagtgct tcaagtagtg 7440
tgtgcccgtc tgttgtgtga ctctggtaac tagagatccc tcagaccctt ttagtcagtg 7500
tggaaaatct ctagcagtgg cgcccgaaca gggacttgaa agcgaaaggg aaaccagagg 7560
agctctctcg acgcaggact cggcttgctg aagcgcgcac ggcaagaggc gaggggcggc 7620
gactggtgag tacgccaaaa attttgacta gcggaggcta gaaggagaga gatgggtgcg 7680
agagcgtcag tattaagcgg gggagaatta gatcgcgatg ggaaaaaatt cggttaaggc 7740
cagggggaaa gaaaaaatat aaattaaaac atatagtatg ggcaagcagg gagctagaac 7800
gattcgcagt taatcctggc ctgttagaaa catcagaagg ctgtagacaa atactgggac 7860
agctacaacc atcccttcag acaggatcag aagaacttag atcattatat aatacagtag 7920
caaccctcta ttgtgtgcat caaaggatag agataaaaga caccaaggaa gctttagaca 7980
agatagagga agagcaaaac aaaagtaaga ccaccgcaca gcaagcggcc gctgatcttc 8040
agacctggag gaggagatat gagggacaat tggagaagtg aattatataa atataaagta 8100
gtaaaaattg aaccattagg agtagcaccc accaaggcaa agagaagagt ggtgcagaga 8160
gaaaaaagag cagtgggaat aggagctttg ttccttgggt tcttgggagc agcaggaagc 8220
actatgggcg cagcgtcaat gacgctgacg gtacaggcca gacaattatt gtctggtata 8280
gtgcagcagc agaacaattt gctgagggct attgaggcgc aacagcatct gttgcaactc 8340
acagtctggg gcatcaagca gctccaggca agaatcctgg ctgtggaaag atacctaaag 8400
gatcaacagc tcctggggat ttggggttgc tctggaaaac tcatttgcac cactgctgtg 8460
ccttggaatg ctagttggag taataaatct ctggaacaga tttggaatca cacgacctgg 8520
atggagtggg acagagaaat taacaattac acaagcttaa tacactcctt aattgaagaa 8580
tcgcaaaacc agcaagaaaa gaatgaacaa gaattattgg aattagataa atgggcaagt 8640
ttgtggaatt ggtttaacat aacaaattgg ctgtggtata taaaattatt cataatgata 8700
gtaggaggct tggtaggttt aagaatagtt tttgctgtac tttctatagt gaatagagtt 8760
aggcagggat attcaccatt atcgtttcag acccacctcc caaccccgag gggacccgac 8820
aggcccttaa ttaattggct ccggtgcccg tcagtgggca gagcgcacat cgcccacagt 8880
ccccgagaag ttggggggag gggtcggcaa ttgaaccggt gcctagagaa ggtggcgcgg 8940
ggtaaactgg gaaagtgatg tcgtgtactg gctccgcctt tttcccgagg gtgggggaga 9000
accgtatata agtgcagtag tcgccgtgaa cgttcttttt cgcaacgggt ttgccgccag 9060
aacacaggta agtgccgtgt gtggttcccg cgggcctggc ctctttacgg gttatggccc 9120
ttgcgtgcct tgaattactt ccacctggct gcagtacgtg attcttgatc ccgagcttcg 9180
ggttggaagt gggtgggaga gttcgaggcc ttgcgcttaa ggagcccctt cgcctcgtgc 9240
ttgagttgag gcctggcctg ggcgctgggg ccgccgcgtg cgaatctggt ggcaccttcg 9300
cgcctgtctc gctgctttcg ataagtctct agccatttaa aatttttgat gacctgctgc 9360

-continued

```
gacgcttttt ttctggcaag atagtcttgt aaatgcgggc caagatctgc acactggtat   9420

ttcggttttt ggggccgcgg gcggcgacgg ggcccgtgcg tcccagcgca catgttcggc   9480

gaggcggggc ctgcgagcgc ggccaccgag aatcggacgg gggtagtctc aagctggccg   9540

gcctgctctg gtgcctggcc tcgcgccgcc gtgtatcgcc ccgccctggg cggcaaggct   9600

ggcccggtcg gcaccagttg cgtgagcgga aagatggccg cttcccggcc ctgctgcagg   9660

gagctcaaaa tggaggacgc ggcgctcggg agagcgggcg ggtgagtcac ccacacaaag   9720

gaaaagggcc tttccgtcct cagccgtcgc ttcatgtgac tccacggagt accgggcgcc   9780

gtccaggcac ctcgattagt tctcgagctt ttggagtacg tcgtctttag gttgggggga   9840

ggggttttat gcgatggagt ttccccacac tgagtgggtg gagactgaag ttaggccagc   9900

ttggcacttg atgtaattct ccttggaatt tgcccttttt gagtttggat cttggttcat   9960

tctcaagcct cagacagtgg ttcaaagttt ttttcttcca tttcaggtgt cgtgaggaat  10020

tcggccatta cggcccgcca ccatgagcac catcgaggag agggtgaaga agatcatcgg  10080

cgagcagctg ggcgtgaagc aggaggaggt caccaacaac gccagcttcg tggaggacct  10140

gggcgccgac agcctggaca ccgtggagct ggtgatggcc ctggaggagg agttcgacac  10200

cgagatcccc gacgaggagg ccgagaagat caccaccgtg caggccgcca tcgactacat  10260

caacggccac caggcctgag gccgcct                                     10287
```

<210> SEQ ID NO 5
<211> LENGTH: 12730
<212> TYPE: DNA
<213> ORGANISM: Artificial Sequence
<220> FEATURE:
<223> OTHER INFORMATION: Synthetic

<400> SEQUENCE: 5

```
cgcgccaagc tagcaagtta acaaatcgat ccggatccgc cctctccct cccccccccc     60

taacgttact ggccgaagcc gcttggaata aggccggtgt gcgtttgtct atatgttatt    120

ttccaccata ttgccgtctt ttggcaatgt gagggcccgg aaacctggcc ctgtcttctt    180

gacgagcatt cctaggggtc tttcccctct cgccaaagga atgcaaggtc tgttgaatgt    240

cgtgaaggaa gcagttcctc tggaagcttc ttgaagacaa acaacgtctg tagcgaccct    300

ttgcaggcag cggaaccccc cacctggcga caggtgcctc tgcggccaaa agccacgtgt    360

ataagataca cctgcaaagg cggcacaacc ccagtgccac gttgtgagtt ggatagttgt    420

ggaaagagtc aaatggctct cctcaagcgt attcaacaag gggctgaagg atgcccagaa    480

ggtaccccat tgtatgggat ctgatctggg gcctcggtgc acatgcttta catgtgttta    540

gtcgaggtta aaaaaacgtc taggcccccc gaaccacggg gacgtggttt tcctttgaaa    600

aacacgatga taatatggcc acaaccatgg tgagcaaggg cgaggagctg ttcaccgggg    660

tggtgcccat cctggtcgag ctggacggcg acgtaaacgg ccacaagttc agcgtgtccg    720

gcgagggcga gggcgatgcc acctacggca agctgaccct gaagttcatc tgcaccaccg    780

gcaagctgcc cgtgccctgg cccaccctcg tgaccaccct gacctacggc gtgcagtgct    840

tcagccgcta ccccgaccac atgaagcagc acgacttctt caagtccgcc atgcccgaag    900

gctacgtcca ggagcgcacc atcttcttca aggacgacgg caactacaag acccgcgccg    960

aggtgaagtt cgagggcgac accctggtga accgcatcga gctgaagggc atcgacttca   1020

aggaggacgg caacatcctg gggcacaagc tggagtacaa ctacaacagc cacaacgtct   1080

atatcatggc cgacaagcag aagaacggca tcaaggtgaa cttcaagatc cgccacaaca   1140
```

tcgaggacgg cagcgtgcag ctcgccgacc actaccagca gaacaccccc atcggcgacg 1200
gccccgtgct gctgcccgac aaccactacc tgagcaccca gtccgccctg agcaaagacc 1260
ccaacgagaa gcgcgatcac atggtcctgc tggagttcgt gaccgccgcc gggatcactc 1320
tcggcatgga cgagctgtac aagtaagcgg ccgcaatcaa cctctggatt acaaaatttg 1380
tgaaagattg actggtattc ttaactatgt tgctcctttt acgctatgtg gatacgctgc 1440
tttaatgcct ttgtatcatg ctattacttc ccgtacggct ttcattttct cctccttgta 1500
taaatcctgg ttgctgtctc tttatgagga gttgtggccc gttgtcaggc aacgtggcgt 1560
ggtgtgcact gtgtttgctg acgcaacccc cactggttgg ggcattgcca ccacctatca 1620
actcctttcc gggactttcg ctttccccct ccctattgcc acggcggaac tcattgccgc 1680
ctgccttgcc cgctgctgga caggggctcg gctgttgggc actgacaatt ccgtggtgtt 1740
gtcggggaag ctgacgtcct ttccatggct gctcgcctgt gttgccaact ggattctgcg 1800
cgggacgtcc ttctgctacg tcccttcggc cctcaatcca gcggaccttc cttcccgcgg 1860
cctgctgccg gttctgcggc ctcttccgcg tcttcgcctt cgccctcaga cgagtcggat 1920
ctccctttgg gccgcctccc cgcctgcctg caggtttgtc gagacctaga aaaacatgga 1980
gcaatcacaa gtagcaatac agcagctacc aatgctgatt gtgcctggct agaagcacaa 2040
gaggaggagg aggtgggttt tccagtcaca cctcaggtac ctttaagacc aatgacttac 2100
aaggcagctg tagatcttag ccacttttta aaagaaaagg ggggactgga agggctaatt 2160
cactcccaac gaagacaaga tctgcttttt gcttgtactg ggtctctctg gttagaccag 2220
atctgagcct gggagctctc tggctaacta gggaacccac tgcttaagcc tcaataaagc 2280
ttgccttgag tgcttcaagt agtgtgtgcc cgtctgttgt gtgactctgg taactagaga 2340
tccctcagac ccttttagtc agtgtggaaa atctctagca gggcccgttt aaacccgctg 2400
atcagcctcg actgtgcctt ctagttgcca gccatctgtt gtttgcccct cccccgtgcc 2460
ttccttgacc ctggaaggtg ccactcccac tgtcctttcc taataaaatg aggaaattgc 2520
atcgcattgt ctgagtaggt gtcattctat tctggggggt ggggtggggc aggacagcaa 2580
gggggaggat tgggaagaca atagcaggca tgctggggat gcggtgggct ctatggcttc 2640
tgaggcggaa agaaccagct ggggctctag ggggtatccc cacgcgccct gtagcggcgc 2700
attaagcgcg gcgggtgtgg tggttacgcg cagcgtgacc gctacacttg ccagcgccct 2760
agcgcccgct cctttcgctt tcttcccttc ctttctcgcc acgttcgccg gctttccccg 2820
tcaagctcta aatcgggggca tccctttagg gttccgattt agtgctttac ggcacctcga 2880
ccccaaaaaa cttgattagg gtgatggttc acgtagtggg ccatcgccct gatagacggt 2940
ttttcgccct ttgacgttgg agtccacgtt ctttaatagt ggactcttgt tccaaactgg 3000
aacaacactc aaccctatct cggtctattc ttttgattta taagggattt tggggatttc 3060
ggcctattgg ttaaaaaatg agctgattta acaaaaattt aacgcgaatt aattctgtgg 3120
aatgtgtgtc agttagggtg tggaaagtcc ccaggctccc caggcaggca gaagtatgca 3180
aagcatgcat ctcaattagt cagcaaccag gtgtggaaag tccccaggct ccccagcagg 3240
cagaagtatg caaagcatgc atctcaatta gtcagcaacc atagtcccgc ccctaactcc 3300
gcccatcccg cccctaactc cgcccagttc cgcccattct ccgccccatg gctgactaat 3360 ttttttttatt tatgcagagg ccgaggccgc ctctgcctct gagctattcc agaagtagtg 3420
aggaggcttt tttggaggcc taggcttttg caaaaagctc ccgggagctt gtatatccat 3480

-continued

```
tttcggatct gatcagcacg tgttgacaat taatcatcgg catagtatat cggcatagta   3540
taatacgaca aggtgaggaa ctaaaccatg gccaagttga ccagtgccgt tccggtgctc   3600
accgcgcgcg acgtcgccgg agcggtcgag ttctggaccg accggctcgg gttctcccgg   3660
gacttcgtgg aggacgactt cgccggtgtg gtccgggacg acgtgaccct gttcatcagc   3720
gcggtccagg accaggtggt gccggacaac accctggcct gggtgtgggt gcgcggcctg   3780
gacgagctgt acgccgagtg gtcggaggtc gtgtccacga acttccggga cgcctccggg   3840
ccggccatga ccgagatcgg cgagcagccg tgggggcggg agttcgccct gcgcgacccg   3900
gccggcaact gcgtgcactt cgtggccgag gagcaggact gacacgtgct acgagatttc   3960
gattccaccg ccgccttcta tgaaaggttg ggcttcggaa tcgttttccg ggacgccggc   4020
tggatgatcc tccagcgcgg ggatctcatg ctggagttct tcgcccaccc caacttgttt   4080
attgcagctt ataatggtta caaataaagc aatagcatca caaatttcac aaataaagca   4140
tttttttcac tgcattctag ttgtggtttg tccaaactca tcaatgtatc ttatcatgtc   4200
tgtataccgt cgacctctag ctagagcttg gcgtaatcat ggtcatagct gtttcctgtg   4260
tgaaattgtt atccgctcac aattccacac aacatacgag ccggaagcat aaagtgtaaa   4320
gcctggggtg cctaatgagt gagctaactc acattaattg cgttgcgctc actgcccgct   4380
ttccagtcgg gaaacctgtc gtgccagctg cattaatgaa tcggccaacg cgcggggaga   4440
ggcggtttgc gtattgggcg ctcttccgct tcctcgctca ctgactcgct gcgctcggtc   4500
gttcggctgc ggcgagcggt atcagctcac tcaaaggcgg taatacggtt atccacagaa   4560
tcaggggata acgcaggaaa gaacatgtga gcaaaaggcc agcaaaaggc caggaaccgt   4620
aaaaaggccg cgttgctggc gtttttccat aggctccgcc cccctgacga gcatcacaaa   4680
aatcgacgct caagtcagag gtggcgaaac ccgacaggac tataaagata ccaggcgttt   4740
ccccctggaa gctccctcgt gcgctctcct gttccgaccc tgccgcttac cggatacctg   4800
tccgcctttc tcccttcggg aagcgtggcg ctttctcaat gctcacgctg taggtatctc   4860
agttcggtgt aggtcgttcg ctccaagctg ggctgtgtgc acgaaccccc cgttcagccc   4920
gaccgctgcg ccttatccgg taactatcgt cttgagtcca acccggtaag acacgactta   4980
tcgccactgg cagcagccac tggtaacagg attagcagag cgaggtatgt aggcggtgct   5040
acagagttct tgaagtggtg gcctaactac ggctacacta gaaggacagt atttggtatc   5100
tgcgctctgc tgaagccagt taccttcgga aaaagagttg gtagctcttg atccggcaaa   5160
caaaccaccg ctggtagcgg tggttttttt gtttgcaagc agcagattac gcgcagaaaa   5220
aaaggatctc aagaagatcc tttgatcttt tctacggggt ctgacgctca gtggaacgaa   5280
aactcacgtt aagggatttt ggtcatgaga ttatcaaaaa ggatcttcac ctagatcctt   5340
ttaaattaaa aatgaagttt taaatcaatc taaagtatat atgagtaaac ttggtctgac   5400
agttaccaat gcttaatcag tgaggcacct atctcagcga tctgtctatt tcgttcatcc   5460
atagttgcct gactccccgt cgtgtagata actacgatac gggagggctt accatctggc   5520
cccagtgctg caatgatacc gcgagaccca cgctcaccgg ctccagattt atcagcaata   5580
aaccagccag ccggaagggc cgagcgcaga agtggtcctg caactttatc cgcctccatc   5640
cagtctatta attgttgccg ggaagctaga gtaagtagtt cgccagttaa tagtttgcgc   5700
aacgttgttg ccattgctac aggcatcgtg gtgtcacgct cgtcgtttgg tatggcttca   5760
ttcagctccg gttcccaacg atcaaggcga gttacatgat cccccatgtt gtgcaaaaaa   5820
gcggttagct ccttcggtcc tccgatcgtt gtcagaagta agttggccgc agtgttatca   5880
```

-continued

```
ctcatggtta tggcagcact gcataattct cttactgtca tgccatccgt aagatgcttt   5940
tctgtgactg gtgagtactc aaccaagtca ttctgagaat agtgtatgcg gcgaccgagt   6000
tgctcttgcc cggcgtcaat acgggataat accgcgccac atagcagaac tttaaaagtg   6060
ctcatcattg gaaaacgttc ttcggggcga aaactctcaa ggatcttacc gctgttgaga   6120
tccagttcga tgtaacccac tcgtgcaccc aactgatctt cagcatcttt tactttcacc   6180
agcgtttctg ggtgagcaaa aacaggaagg caaaatgccg caaaaaaggg aataagggcg   6240
acacggaaat gttgaatact catactcttc ctttttcaat attattgaag catttatcag   6300
ggttattgtc tcatgagcgg atacatattt gaatgtattt agaaaaataa acaaataggg   6360
gttccgcgca catttccccg aaaagtgcca cctgacgtcg acggatcggg agatctcccg   6420
atcccctatg gtgcactctc agtacaatct gctctgatgc cgcatagtta agccagtatc   6480
tgctccctgc ttgtgtgttg gaggtcgctg agtagtgcgc gagcaaaatt taagctacaa   6540
caaggcaagg cttgaccgac aattgcatga agaatctgct tagggttagg cgttttgcgc   6600
tgcttcgcga tgtacgggcc agatatacgc gttgacattg attattgact agttattaat   6660
agtaatcaat tacggggtca ttagttcata gcccatatat ggagttccgc gttacataac   6720
ttacggtaaa tggcccgcct ggctgaccgc ccaacgaccc ccgcccattg acgtcaataa   6780
tgacgtatgt tcccatagta acgccaatag ggactttcca ttgacgtcaa tgggtggact   6840
atttacggta aactgcccac ttggcagtac atcaagtgta tcatatgcca agtacgcccc   6900
ctattgacgt caatgacggt aaatggcccg cctggcatta tgcccagtac atgaccttat   6960
gggactttcc tacttggcag tacatctacg tattagtcat cgctattacc atggtgatgc   7020
ggttttggca gtacatcaat gggcgtggat agcggtttga ctcacgggga tttccaagtc   7080
tccaccccat tgacgtcaat gggagtttgt tttggcacca aaatcaacgg gactttccaa   7140
aatgtcgtaa caactccgcc ccattgacgc aaatgggcgg taggcgtgta cggtgggagg   7200
tctatataag cagagctctc tggctaacta gagaacccac tgcttactgg cttatcgaaa   7260
ttaatacgac tcactatagg gagacccaag ctggtttaaa cttaagcttg gtaccgagct   7320
cactagtcca gtgtggtggc agatatccag cacagtggcg gccgctcgag tctagagggc   7380
ccgttttgcc tgtactgggt ctctctggtt agaccagatc tgagcctggg agctctctgg   7440
ctaactaggg aacccactgc ttaagcctca ataaagcttg ccttgagtgc ttcaagtagt   7500
gtgtgcccgt ctgttgtgtg actctggtaa ctagagatcc ctcagaccct tttagtcagt   7560
gtggaaaatc tctagcagtg gcgcccgaac agggacttga aagcgaaagg gaaaccagag   7620
gagctctctc gacgcaggac tcggcttgct gaagcgcgca cggcaagagg cgaggggcgg   7680
cgactggtga gtacgccaaa aattttgact agcggaggct agaaggagag agatgggtgc   7740
gagagcgtca gtattaagcg ggggagaatt agatcgcgat gggaaaaaat tcggttaagg   7800
ccagggggaa agaaaaaata taaattaaaa catatagtat gggcaagcag ggagctagaa   7860
cgattcgcag ttaatcctgg cctgttagaa acatcagaag gctgtagaca aatactggga   7920
cagctacaac catcccttca gacaggatca gaagaactta gatcattata taatacagta   7980
gcaaccctct attgtgtgca tcaaaggata gagataaaag acaccaagga agctttagac   8040
aagatagagg aagagcaaaa caaaagtaag accaccgcac agcaagcggc cgctgatctt   8100
cagacctgga ggaggagata tgagggacaa ttggagaagt gaattatata aatataaagt   8160
agtaaaaatt gaaccattag gagtagcacc caccaaggca aagagaagag tggtgcagag   8220
```

-continued

```
agaaaaaaga gcagtgggaa taggagcttt gttccttggg ttcttgggag cagcaggaag   8280
cactatgggc gcagcgtcaa tgacgctgac ggtacaggcc agacaattat tgtctggtat   8340
agtgcagcag cagaacaatt tgctgagggc tattgaggcg caacagcatc tgttgcaact   8400
cacagtctgg ggcatcaagc agctccaggc aagaatcctg gctgtggaaa gatacctaaa   8460
ggatcaacag ctcctgggga tttggggttg ctctggaaaa ctcatttgca ccactgctgt   8520
gccttggaat gctagttgga gtaataaatc tctggaacag atttggaatc acacgacctg   8580
gatggagtgg gacagagaaa ttaacaatta cacaagctta atacactcct taattgaaga   8640
atcgcaaaac cagcaagaaa agaatgaaca agaattattg gaattagata aatgggcaag   8700
tttgtggaat tggtttaaca taacaaattg gctgtggtat ataaaattat tcataatgat   8760
agtaggaggc ttggtaggtt taagaatagt tttgctgtta ctttctatag tgaatagagt   8820
taggcaggga tattcaccat tatcgtttca gacccacctc ccaaccccga ggggacccga   8880
caggccctta attaagctac atcatcaata atataccttta ttttggattg aagccaatat   8940
gataatgagg gggtggagtt tgtgacgtgg cgcggggcgt gggaacgggg cgggtgacgt   9000
agtagtgtgg cggaagtgtg atgttgcaag tgtggcggaa cacatgtaag cgacggatgt   9060
ggcaaaagtg acgtttttgg tgtgcgccgg tgtacacagg aagtgacaat tttcgcgcgg   9120
ttttaggcgg atgttgtagt aaatttgggc gtaaccgagt aagatttggc cattttcgcg   9180
ggaaaactga ataagaggaa gtgaaatctg aataattttg tgttactcat agcgcgtaat   9240
atttgtctag ggagatccga gctttgcaaa gatggataaa gttttaaaca gagaggaatc   9300
tttgcagcta atggaccttc taggtcttga aaggagtggg aattggctcc ggtgcccgtc   9360
agtgggcaga gcgcacatcg cccacagtcc ccgagaagtt ggggggaggg gtcggcaatt   9420
gaaccggtgc ctagagaagg tggcgcgggg taaactggga aagtgatgtc gtgtactggc   9480
tccgcctttt tcccgagggt gggggagaac cgtatataag tgcagtagtc gccgtgaacg   9540
ttctttttcg caacgggttt gccgccagaa cacaggtaag tgccgtgtgt ggttcccgcg   9600
ggcctggcct ctttacgggt tatggccctt gcgtgccttg aattacttcc acctggctgc   9660
agtacgtgat tcttgatccc gagcttcggg ttggaagtgg gtgggagagt tcgaggcctt   9720
gcgcttaagg agccccttcg cctcgtgctt gagttgaggc ctggcctggg cgctggggcc   9780
gccgcgtgcg aatctggtgg caccttcgcg cctgtctcgc tgctttcgat aagtctctag   9840
ccatttaaaa tttttgatga cctgctgcga cgcttttttt ctggcaagat agtcttgtaa   9900
atgcgggcca agatctgcac actggtattt cggtttttgg ggccgcgggc ggcgacgggg   9960
cccgtgcgtc ccagcgcaca tgttcggcga ggcggggcct gcgagcgcgg ccaccgagaa  10020
tcggacgggg gtagtctcaa gctggccggc ctgctctggt gcctggcctc gcgccgccgt  10080
gtatcgcccc gccctgggcg gcaaggctgg cccggtcggc accagttgcg tgagcggaaa  10140
gatggccgct tcccggccct gctgcaggga gctcaaaatg gaggacgcgg cgctcgggag  10200
agcgggcggg tgagtcaccc acacaaagga aaagggcctt tccgtcctca gccgtcgctt  10260
catgtgactc cacggagtac cgggcgccgt ccaggcacct cgattagttc tcgagctttt  10320
ggagtacgtc gtctttaggt tggggggagg ggttttatgc gatggagttt ccccacactg  10380
agtgggtgga gactgaagtt aggccagctt ggcacttgat gtaattctcc ttggaatttg  10440
ccctttttga gtttggatct tggttcattc tcaagcctca gacagtggtt caaagttttt  10500
ttcttccatt tcaggtgtcg tgaggaattc gctactagct cgagaagaat tcaaggcgcg  10560
ccgccaccat gctttttagc ttttttcgaa atttgtgccg tgttttgtat cgcgttcgcg  10620
```

```
ttacgggtga cacccaggca ctgaagggcg agcgcgttct aattacgcct aatcacgtct  10680
cttttattga tggcattttg cttggactgt ttttacctgt gcgtccagtg tttgccgttt  10740
acacctcaat aagccaacag tggtatatgc gttggctgaa atcatttatc gactttgttc  10800
ctctcgaccc gacgcaacct atggctatta aacatctggt acgtctggtg gaacagggcc  10860
gaccagtggt gattttccct gaaggacgca tcaccacgac aggctcgctg atgaaaatct  10920
acgatggcgc gggttttgtc gcggcgaagt ctggtgcaac ggttattcct gtgcgtattg  10980
aaggggcgga acttacgcac ttcagccgcc tgaaaggtct ggttaaacgt cgcttgttcc  11040
cgcaaattac tctgcatatt ttgccaccaa cgcaggtggc gatgccggat gcgccgcgtg  11100
cccgtgaccg tcgcaaaatc gctggcgaaa tgctgcatca aataatgatg gaagcgcgaa  11160
tggcggtgcg cccgcgtgaa acgctgtacg aatctttact gagtgcaatg taccgcttcg  11220
gagccgggaa gaaatgtgtc gaagacgtca actttacccc agactcctat cgcaaattgc  11280
ttacgaaaac gctgtttgtt ggacgcatcc ttgaaaaata cagtgttgaa ggcgaacgca  11340
tcggcttaat gctgcccaat gcaggcatca gtgcggcagt gatttttggg gccatcgccc  11400
gtcgccgcat gcccgcaatg atgaactaca ctgccggggt aaaagggctg accagtgcta  11460
ttacggcggc tgaaatcaaa accatcttca cttcccgcca gtttctcgat aaaggcaaac  11520
tctggcatct gccggagcaa cttactcagg tgcgctgggt ctatctggaa gatttaaaag  11580
cagatgtcac cactgccgac aaagtatgga tcttcgctca tttgctgatg ccgcgtctgg  11640
cacaggttaa acagcagccg gaagaagagg cgctgatcct tttacctcc ggttctgaag  11700
gccatccgaa aggcgtcgtc catagccata aaagcattct ggcgaatgtc gagcagatta  11760
aaacgattgc cgacttcacc accaacgatc gctttatgtc ggcgttaccg ctgtttcact  11820
cctttgggct gacggtaggc ctgtttacgc cactgcttac aggtgcagaa gtgttccttt  11880
atccaagccc gctgcattac cgcattgtgc cggagttggt gtatgaccgc agttgcaccg  11940
tgttgttcgg cacctcgact ttcctcggtc actacgcgcg tttcgccaac ccgtatgact  12000
tctatcgtct acgctatgtg gtggcaggcg cagaaaaatt acaagaaagt accaaacagc  12060
tttggcagga taaatttggc ctgcgcatcc ttgaaggcta cggcgtgacc gaatgcgcgc  12120
ctgtcgtttc tatcaacgta ccgatggcgg cgaaacccgg tacggtaggg cgtattctac  12180
caggaatgga tgcgcgcctg ttgtcggtcc ctggtatcga agagggcgga cgcctgcaac  12240
tgaaagggcc gaacataatg aacggctatc tgcgggtgga gaagccaggt gtactggaag  12300
tgcccaccgc cgagaatgtt cgcggcgaaa tggagcgcgg ctggtatgac actggcgata  12360
ttgtgcgttt tgacgagcag ggctttgtgc agattcaggg ccgcgcaaaa cgctttgcca  12420
aaattgcagg cgaaatggtg tcgctggaaa tggtggaaca actggcactt ggtgtttcgc  12480
cagataaagt ccatgccact gcgattaaga gcgatgccag caaaggcgag gcactggtgc  12540
ttttcaccac agataacgaa ctgacgcgcg ataagttgca acagtatgcc cgcgagcacg  12600
gcgtgccgga gcttgctgta ccgcgcgata ttcgctatct gaaacagatg ccattacttg  12660
gcagcggcaa acctgacttt gtcacgttga aaagctgggt agacgaagcg gaacaacacg  12720
atgagtgagg                                                         12730
```

<210> SEQ ID NO 6
<211> LENGTH: 10773
<212> TYPE: DNA
<213> ORGANISM: Artificial Sequence
<220> FEATURE:

<223> OTHER INFORMATION: Synthetic

<400> SEQUENCE: 6

```
cggccatcga taaggatccg cccctctccc tccccccccc ctaacgttac tggccgaagc     60
cgcttggaat aaggccggtg tgcgtttgtc tatatgttat tttccaccat attgccgtct    120
tttggcaatg tgagggcccg gaaacctggc cctgtcttct tgacgagcat tcctaggggt    180
ctttcccctc tcgccaaagg aatgcaaggt ctgttgaatg tcgtgaagga agcagttcct    240
ctggaagctt cttgaagaca aacaacgtct gtagcgaccc tttgcaggca gcggaacccc    300
ccacctggcg acaggtgcct ctgcggccaa aagccacgtg tataagatac acctgcaaag    360
gcggcacaac cccagtgcca cgttgtgagt tggatagttg tggaaagagt caaatggctc    420
tcctcaagcg tattcaacaa ggggctgaag gatgcccaga aggtacccca ttgtatggga    480
tctgatctgg ggcctcggtg cacatgcttt acatgtgttt agtcgaggtt aaaaaaacgt    540
ctaggccccc cgaaccacgg ggacgtggtt ttcctttgaa aaacacgatg ataatatggc    600
cacaaccatg gcctcctccg aggacgtcat caaggagttc atgcgcttca aggtgcgcat    660
ggagggctcc gtgaacggcc acgagttcga gatcgagggc gagggcgagg gccgccccta    720
cgagggcacc cagaccgcca agctgaaggt gaccaagggc ggcccccctgc ccttcgcctg    780
ggacatcctg tcccccagt tccagtacgg ctccaaggtg tacgtgaagc accccgccga     840
catccccgac tacaagaagc tgtccttccc cgagggcttc aagtgggagc gcgtgatgaa    900
cttcgaggac ggcggcgtgg tgaccgtgac ccaggactcc tccctgcagg acggctcctt    960
catctacaag gtgaagttca tcggcgtgaa cttcccctcc gacggccccg taatgcagaa   1020
gaagactatg ggctgggagg cctccaccga gcgcctgtac ccccgcgacg gcgtgctgaa   1080
gggcgagatc cacaaggccc tgaagctgaa ggacggcggc cactacctgg tggagttcaa   1140
gtccatctac atggccaaga agcccgtgca gctgcccggc tactactacg tggactccaa   1200
gctggacatc acctcccaca acgaggacta caccatcgtg gagcagtacg agcgcgccga   1260
gggccgccac cacctgttcc tgtaggcggc cgcaatcaac ctctggatta caaaatttgt   1320
gaaagattga ctggtattct taactatgtt gctcctttta cgctatgtgg atacgctgct   1380
ttaatgcctt tgtatcatgc tattacttcc cgtacggctt tcattttctc ctccttgtat   1440
aaatcctggt tgctgtctct ttatgaggag ttgtggcccg ttgtcaggca acgtggcgtg   1500
gtgtgcactg tgtttgctga cgcaaccccc actggttggg gcattgccac cacctatcaa   1560
ctcctttccg ggactttcgc tttcccccctc cctattgcca cggcggaact cattgccgcc  1620
tgccttgccc gctgctggac aggggctcgg ctgttgggca ctgacaattc cgtggtgttg   1680
tcggggaagc tgacgtcctt tccatggctg ctcgcctgtg ttgccaactg gattctgcgc   1740
gggacgtcct tctgctacgt cccttcggcc ctcaatccag cggaccttcc ttcccgcggc   1800
ctgctgccgg ttctgcggcc tcttccgcgt cttcgccttc gccctcagac gagtcggatc   1860
tccctttggg ccgcctcccc gcctgcctgc aggtttgtcg agacctagaa aaacatggag   1920
caatcacaag tagcaataca gcagctacca atgctgattg tgcctggcta gaagcacaag   1980
aggaggagga ggtgggtttt ccagtcacac ctcaggtacc tttaagacca atgacttaca   2040
aggcagctgt agatcttagc cactttttaa aagaaaaggg gggactggaa gggctaattc   2100
actcccaacg aagacaagat ctgctttttg cttgtactgg gtctctctgg ttagaccaga   2160
tctgagcctg ggagctctct ggctaactag ggaacccact gcttaagcct caataaagct   2220
tgccttgagt gcttcaagta gtgtgtgccc gtctgttgtg tgactctggt aactagagat   2280
```

-continued

```
ccctcagacc cttttagtca gtgtggaaaa tctctagcag ggcccgttta aacccgctga   2340
tcagcctcga ctgtgccttc tagttgccag ccatctgttg tttgcccctc ccccgtgcct   2400
tccttgaccc tggaaggtgc cactcccact gtcctttcct aataaaatga ggaaattgca   2460
tcgcattgtc tgagtaggtg tcattctatt ctggggggtg gggtggggca ggacagcaag   2520
ggggaggatt gggaagacaa tagcaggcat gctggggatg cggtgggctc tatggcttct   2580
gaggcggaaa gaaccagctg gggctctagg gggtatcccc acgcgccctg tagcggcgca   2640
ttaagcgcgg cgggtgtggt ggttacgcgc agcgtgaccg ctacacttgc cagcgcccta   2700
gcgcccgctc ctttcgcttt cttcccttcc tttctcgcca cgttcgccgg ctttccccgt   2760
caagctctaa atcggggcat ccctttaggg ttccgattta gtgctttacg gcacctcgac   2820
cccaaaaaac ttgattaggg tgatggttca cgtagtgggc catcgccctg atagacggtt   2880
tttcgccctt tgacgttgga gtccacgttc tttaatagtg gactcttgtt ccaaactgga   2940
acaacactca accctatctc ggtctattct tttgatttat aagggatttt ggggatttcg   3000
gcctattggt taaaaaatga gctgatttaa caaaaattta acgcgaatta attctgtgga   3060
atgtgtgtca gttagggtgt ggaaagtccc caggctcccc aggcaggcag aagtatgcaa   3120
agcatgcatc tcaattagtc agcaaccagg tgtggaaagt ccccaggctc cccagcaggc   3180
agaagtatgc aaagcatgca tctcaattag tcagcaacca tagtcccgcc cctaactccg   3240
cccatcccgc ccctaactcc gcccagttcc gcccattctc cgccccatgg ctgactaatt   3300
ttttttattt atgcagaggc cgaggccgcc tctgcctctg agctattcca gaagtagtga   3360
ggaggctttt ttggaggcct aggcttttgc aaaaagctcc cgggagcttg tatatccatt   3420
ttcggatctg atcagcacgt gttgacaatt aatcatcggc atagtatatc ggcatagtat   3480
aatacgacaa ggtgaggaac taaaccatgg ccaagttgac cagtgccgtt ccggtgctca   3540
ccgcgcgcga cgtcgccgga gcggtcgagt tctggaccga ccggctcggg ttctcccggg   3600
acttcgtgga ggacgacttc gccggtgtgg tccgggacga cgtgaccctg ttcatcagcg   3660
cggtccagga ccaggtggtg ccggacaaca ccctggcctg ggtgtgggtg cgcggcctgg   3720
acgagctgta cgccgagtgg tcggaggtcg tgtccacgaa cttccgggac gcctccgggc   3780
cggccatgac cgagatcggc gagcagccgt gggggcggga gttcgccctg cgcgacccgg   3840
ccggcaactg cgtgcacttc gtggccgagg agcaggactg acacgtgcta cgagatttcg   3900
attccaccgc cgccttctat gaaaggttgg gcttcggaat cgttttccgg gacgccggct   3960
ggatgatcct ccagcgcggg gatctcatgc tggagttctt cgcccacccc aacttgttta   4020
ttgcagctta taatggttac aaataaagca atagcatcac aaatttcaca aataaagcat   4080
ttttttcact gcattctagt tgtggtttgt ccaaactcat caatgtatct tatcatgtct   4140
gtataccgtc gacctctagc tagagcttgg cgtaatcatg gtcatagctg tttcctgtgt   4200
gaaattgtta tccgctcaca attccacaca acatacgagc cggaagcata aagtgtaaag   4260
cctggggtgc ctaatgagtg agctaactca cattaattgc gttgcgctca ctgcccgctt   4320
tccagtcggg aaacctgtcg tgccagctgc attaatgaat cggccaacgc gcggggagag   4380
gcggtttgcg tattgggcgc tcttccgctt cctcgctcac tgactcgctg cgctcggtcg   4440
ttcggctgcg gcgagcggta tcagctcact caaaggcggt aatacggtta tccacagaat   4500
caggggataa cgcaggaaag aacatgtgag caaaaggcca gcaaaaggcc aggaaccgta   4560
aaaaggccgc gttgctggcg tttttccata ggctccgccc ccctgacgag catcacaaaa   4620
```

-continued

```
atcgacgctc aagtcagagg tggcgaaacc cgacaggact ataaagatac caggcgtttc   4680
cccctggaag ctccctcgtg cgctctcctg ttccgaccct gccgcttacc ggatacctgt   4740
ccgcctttct cccttcggga agcgtggcgc tttctcaatg ctcacgctgt aggtatctca   4800
gttcggtgta ggtcgttcgc tccaagctgg gctgtgtgca cgaacccccc gttcagcccg   4860
accgctgcgc cttatccggt aactatcgtc ttgagtccaa cccggtaaga cacgacttat   4920
cgccactggc agcagccact ggtaacagga ttagcagagc gaggtatgta ggcggtgcta   4980
cagagttctt gaagtggtgg cctaactacg gctacactag aaggacagta tttggtatct   5040
gcgctctgct gaagccagtt accttcggaa aaagagttgg tagctcttga tccggcaaac   5100
aaaccaccgc tggtagcggt ggtttttttg tttgcaagca gcagattacg cgcagaaaaa   5160
aaggatctca agaagatcct ttgatctttt ctacggggtc tgacgctcag tggaacgaaa   5220
actcacgtta agggattttg gtcatgagat tatcaaaaag gatcttcacc tagatccttt   5280
taaattaaaa atgaagtttt aaatcaatct aaagtatata tgagtaaact tggtctgaca   5340
gttaccaatg cttaatcagt gaggcaccta tctcagcgat ctgtctattt cgttcatcca   5400
tagttgcctg actccccgtc gtgtagataa ctacgatacg ggagggctta ccatctggcc   5460
ccagtgctgc aatgataccg cgagacccac gctcaccggc tccagattta tcagcaataa   5520
accagccagc cggaagggcc gagcgcagaa gtggtcctgc aactttatcc gcctccatcc   5580
agtctattaa ttgttgccgg gaagctagag taagtagttc gccagttaat agtttgcgca   5640
acgttgttgc cattgctaca ggcatcgtgg tgtcacgctc gtcgtttggt atggcttcat   5700
tcagctccgg ttcccaacga tcaaggcgag ttacatgatc ccccatgttg tgcaaaaaag   5760
cggttagctc cttcggtcct ccgatcgttg tcagaagtaa gttggccgca gtgttatcac   5820
tcatggttat ggcagcactg cataattctc ttactgtcat gccatccgta agatgctttt   5880
ctgtgactgg tgagtactca accaagtcat tctgagaata gtgtatgcgg cgaccgagtt   5940
gctcttgccc ggcgtcaata cgggataata ccgcgccaca tagcagaact ttaaaagtgc   6000
tcatcattgg aaaacgttct tcggggcgaa aactctcaag gatcttaccg ctgttgagat   6060
ccagttcgat gtaacccact cgtgcaccca actgatcttc agcatctttt actttcacca   6120
gcgtttctgg gtgagcaaaa acaggaaggc aaaatgccgc aaaaaaggga ataagggcga   6180
cacggaaatg ttgaatactc atactcttcc tttttcaata ttattgaagc atttatcagg   6240
gttattgtct catgagcgga tacatatttg aatgtattta gaaaaataaa caaatagggg   6300
ttccgcgcac atttccccga aaagtgccac ctgacgtcga cggatcggga gatctcccga   6360
tcccctatgg tgcactctca gtacaatctg ctctgatgcc gcatagttaa gccagtatct   6420
gctccctgct tgtgtgttgg aggtcgctga gtagtgcgcg agcaaaattt aagctacaac   6480
aaggcaaggc ttgaccgaca attgcatgaa gaatctgctt agggttaggc gttttgcgct   6540
gcttcgcgat gtacgggcca gatatacgcg ttgacattga ttattgacta gttattaata   6600
gtaatcaatt acggggtcat tagttcatag cccatatatg gagttccgcg ttacataact   6660
tacggtaaat ggcccgcctg gctgaccgcc caacgacccc cgcccattga cgtcaataat   6720
gacgtatgtt cccatagtaa cgccaatagg gactttccat tgacgtcaat gggtggacta   6780
tttacggtaa actgcccact tggcagtaca tcaagtgtat catatgccaa gtacgccccc   6840
tattgacgtc aatgacggta aatggcccgc ctggcattat gcccagtaca tgaccttatg   6900
ggactttcct acttggcagt acatctacgt attagtcatc gctattacca tggtgatgcg   6960
gttttggcag tacatcaatg ggcgtggata gcggtttgac tcacggggat ttccaagtct   7020
```

ccaccccatt gacgtcaatg ggagtttgtt ttggcaccaa aatcaacggg actttccaaa 7080
atgtcgtaac aactccgccc cattgacgca aatgggcggt aggcgtgtac ggtgggaggt 7140
ctatataagc agagctctct ggctaactag agaacccact gcttactggc ttatcgaaat 7200
taatacgact cactataggg agacccaagc tggtttaaac ttaagcttgg taccgagctc 7260
actagtccag tgtggtggca gatatccagc acagtggcgg ccgctcgagt ctagagggcc 7320
cgttttgcct gtactgggtc tctctggtta gaccagatct gagcctggga gctctctggc 7380
taactaggga acccactgct taagcctcaa taaagcttgc cttgagtgct tcaagtagtg 7440
tgtgcccgtc tgttgtgtga ctctggtaac tagagatccc tcagaccctt ttagtcagtg 7500
tggaaaatct ctagcagtgg cgcccgaaca gggacttgaa agcgaaaggg aaaccagagg 7560
agctctctcg acgcaggact cggcttgctg aagcgcgcac ggcaagaggc gaggggcggc 7620
gactggtgag tacgccaaaa attttgacta gcggaggcta gaaggagaga gatgggtgcg 7680
agagcgtcag tattaagcgg gggagaatta gatcgcgatg ggaaaaaatt cggttaaggc 7740
cagggggaaa gaaaaaatat aaattaaaac atatagtatg ggcaagcagg gagctagaac 7800
gattcgcagt taatcctggc ctgttagaaa catcagaagg ctgtagacaa atactgggac 7860
agctacaacc atcccttcag acaggatcag aagaacttag atcattatat aatacagtag 7920
caaccctcta ttgtgtgcat caaaggatag agataaaaga caccaaggaa gctttagaca 7980
agatagagga agagcaaaac aaaagtaaga ccaccgcaca gcaagcggcc gctgatcttc 8040
agacctggag gaggagatat gagggacaat tggagaagtg aattatataa atataaagta 8100
gtaaaaattg aaccattagg agtagcaccc accaaggcaa agagaagagt ggtgcagaga 8160
gaaaaaagag cagtgggaat aggagctttg ttccttgggt tcttgggagc agcaggaagc 8220
actatgggcg cagcgtcaat gacgctgacg gtacaggcca gacaattatt gtctggtata 8280
gtgcagcagc agaacaattt gctgagggct attgaggcgc aacagcatct gttgcaactc 8340
acagtctggg gcatcaagca gctccaggca agaatcctgg ctgtggaaag atacctaaag 8400
gatcaacagc tcctggggat ttggggttgc tctggaaaac tcatttgcac cactgctgtg 8460
ccttggaatg ctagttggag taataaatct ctggaacaga tttggaatca cacgacctgg 8520
atggagtggg acagagaaat taacaattac acaagcttaa tacactcctt aattgaagaa 8580
tcgcaaaacc agcaagaaaa gaatgaacaa gaattattgg aattagataa atgggcaagt 8640
ttgtggaatt ggtttaacat aacaaattgg ctgtggtata taaaattatt cataatgata 8700
gtaggaggct tggtaggttt aagaatagtt tttgctgtac tttctatagt gaatagagtt 8760
aggcagggat attcaccatt atcgtttcag acccacctcc caaccccgag gggacccgac 8820
aggcccttaa ttaagccacc tatcctcttc agacctcttc aggaaacagc tatgcacata 8880
gcacacaggc atatgttcaa ccaaaacact gaaacacata aaagaaatgt ttaaagaatg 8940
aatttaaaaa aataaaaaat aaactcaact acatatgaag ccttagcaaa catgtctgga 9000
cctctagaca cacagactct gacacgccaa cgtctgagtt ctagtttcga tacgcactgg 9060
gaagttttaa aagttttcca tcaactctaa tgtgtagaga aatggaaact atcatagact 9120
ctacggcatt gagggtgaag gtatgagtga agcactctta gggtcagaag tatgtcagtg 9180
cccatttgtt gctgttagca tcatcatctt agggcttgag aggatgttgc agctgaccca 9240
tgcacctgtg acatacatat ggaattattc tttggcacat aaaattagaa tgggagctgg 9300
ctcatcaggt tttgtgctgt aagttttcta tgttaaacca gatgcgatac actaaataaa 9360

-continued

```
ataaaatata cttgaccgat ggttttgagc gaaataataa ctggataatc aagaaatata   9420
tccactaatg aatagcctga actactgaaa caatttgttc agtgcctagc atatggtgtg   9480
cattttatta tttctttcaa aaagaatgta tttggagtta catagtaagt ctgctacctt   9540
ttctttatgg ctatatctat gtcttatgtt gagatgaatg aattattctt caggggaaat   9600
aatctatttg aacagtttag atggtgaaga acatttgcag catttgcaag atttttttcc   9660
actctgaagt ggtctttgtc cttgaacata ggatacaagt gacccctgct ctgttaatta   9720
ttggcaaatt gcctaacttc aacgtaagga aatagagtca tatgtttgct cactgaaggt   9780
tactagttaa caggcatccc ttaaacagga tataaaagga cttcagcagg actgctcgaa   9840
acatcccact tccagcactg cctgcggtga aggaaccagc agccgaattc ggccattacg   9900
gcctgccacc atgaacagtg aggagcagta ctacgcggcc acacagctct acaaggaccc   9960
gtgcgcattc cagaggggcc cggtgccaga gttcagcgct aacccccctg cgtgcctgta  10020
catgggccgc cagcccccac ctccgccgcc accccagttt acaagctcgc tgggatcact  10080
ggagcaggga agtcctccgg acatctcccc atacgaagtg cccccgctcg cctccgacga  10140
cccggctggc gctcacctcc accaccacct tccagctcag ctcgggctcg cccatccacc  10200
tcccggacct ttcccgaatg gaaccgagcc tgggggcctg gaagagccca accgcgtcca  10260
gctccctttc ccgtggatga aatccaccaa agctcacgcg tggaaaggcc agtgggcagg  10320
aggtgcttac acagcggaac ccgaggaaaa caagaggacc cgtactgcct acacccgggc  10380
gcagctgctg gagctggaga aggaattctt atttaacaaa tacatctccc ggccccgccg  10440
ggtggagctg gcagtgatgt tgaacttgac cgagagacac atcaaaatct ggttccaaaa  10500
ccgtcgcatg aagtggaaaa aagaggaaga taagaaacgt agtagcggga ccccgagtgg  10560
gggcggtggg ggcgaagagc cggagcaaga ttgtgcggtg acctcgggcg aggagctgct  10620
ggcagtgcca ccgctgccac ctcccggagg tgccgtgccc ccaggcgtcc cagctgcagt  10680
ccgggagggc ctactgcctt cgggccttag cgtgtcgcca cagccctcca gcatcgcgcc  10740
actgcgaccg caggaacccc ggtgaggccg cct                               10773
```

<210> SEQ ID NO 7
<211> LENGTH: 10562
<212> TYPE: DNA
<213> ORGANISM: Artificial Sequence
<220> FEATURE:
<223> OTHER INFORMATION: Synthetic

<400> SEQUENCE: 7

```
cggccatcga taaggatccg cccctctccc tccccccccc ctaacgttac tggccgaagc     60
cgcttggaat aaggccggtg tgcgtttgtc tatatgttat tttccaccat attgccgtct    120
tttggcaatg tgagggcccg gaaacctggc cctgtcttct tgacgagcat tcctaggggt    180
ctttcccctc tcgccaaagg aatgcaaggt ctgttgaatg tcgtgaagga agcagttcct    240
ctggaagctt cttgaagaca aacaacgtct gtagcgaccc tttgcaggca gcggaacccc    300
ccacctggcg acaggtgcct ctgcggccaa aagccacgtg tataagatac acctgcaaag    360
gcggcacaac cccagtgcca cgttgtgagt tggatagttg tggaaagagt caaatggctc    420
tcctcaagcg tattcaacaa ggggctgaag gatgcccaga aggtacccca ttgtatggga    480
tctgatctgg ggcctcggtg cacatgcttt acatgtgttt agtcgaggtt aaaaaaacgt    540
ctaggccccc cgaaccacgg ggacgtggtt ttcctttgaa aaacacgatg ataatatggc    600
cacaaccatg gcctcctccg aggacgtcat caaggagttc atgcgcttca aggtgcgcat    660
```

```
ggagggctcc gtgaacggcc acgagttcga gatcgagggc gagggcgagg gccgccccta    720
cgagggcacc cagaccgcca agctgaaggt gaccaagggc ggccccctgc ccttcgcctg    780
ggacatcctg tccccccagt tccagtacgg ctccaaggtg tacgtgaagc accccgccga    840
catccccgac tacaagaagc tgtccttccc cgagggcttc aagtgggagc gcgtgatgaa    900
cttcgaggac ggcggcgtgg tgaccgtgac ccaggactcc tccctgcagg acggctcctt    960
catctacaag gtgaagttca tcggcgtgaa cttcccctcc gacggccccg taatgcagaa   1020
gaagactatg ggctgggagg cctccaccga gcgcctgtac ccccgcgacg gcgtgctgaa   1080
gggcgagatc cacaaggccc tgaagctgaa ggacggcggc cactacctgg tggagttcaa   1140
gtccatctac atggccaaga agcccgtgca gctgcccggc tactactacg tggactccaa   1200
gctggacatc acctcccaca acgaggacta caccatcgtg gagcagtacg agcgcgccga   1260
gggccgccac cacctgttcc tgtaggcggc cgcaatcaac ctctggatta caaaatttgt   1320
gaaagattga ctggtattct taactatgtt gctcctttta cgctatgtgg atacgctgct   1380
ttaatgcctt tgtatcatgc tattacttcc cgtacggctt tcattttctc ctccttgtat   1440
aaatcctggt tgctgtctct ttatgaggag ttgtggcccg ttgtcaggca acgtggcgtg   1500
gtgtgcactg tgtttgctga cgcaaccccc actggttggg gcattgccac cacctatcaa   1560
ctcctttccg ggactttcgc tttccccctc cctattgcca cggcggaact cattgccgcc   1620
tgccttgccc gctgctggac aggggctcgg ctgttgggca ctgacaattc cgtggtgttg   1680
tcggggaagc tgacgtcctt tccatggctg ctcgcctgtg ttgccaactg gattctgcgc   1740
gggacgtcct tctgctacgt cccttcggcc ctcaatccag cggaccttcc ttcccgcggc   1800
ctgctgccgg ttctgcggcc tcttccgcgt cttcgccttc gccctcagac gagtcggatc   1860
tccctttggg ccgcctcccc gcctgcctgc aggtttgtcg agacctagaa aaacatggag   1920
caatcacaag tagcaataca gcagctacca atgctgattg tgcctggcta gaagcacaag   1980
aggaggagga ggtgggtttt ccagtcacac ctcaggtacc tttaagacca atgacttaca   2040
aggcagctgt agatcttagc cactttttaa aagaaaaggg gggactggaa gggctaattc   2100
actcccaacg aagacaagat ctgctttttg cttgtactgg gtctctctgg ttagaccaga   2160
tctgagcctg ggagctctct ggctaactag ggaacccact gcttaagcct caataaagct   2220
tgccttgagt gcttcaagta gtgtgtgccc gtctgttgtg tgactctggt aactagagat   2280
ccctcagacc cttttagtca gtgtggaaaa tctctagcag ggcccgttta aacccgctga   2340
tcagcctcga ctgtgccttc tagttgccag ccatctgttg tttgcccctc ccccgtgcct   2400
tccttgaccc tggaaggtgc cactcccact gtcctttcct aataaaatga ggaaattgca   2460
tcgcattgtc tgagtaggtg tcattctatt ctggggggtg gggtggggca ggacagcaag   2520
ggggaggatt gggaagacaa tagcaggcat gctggggatg cggtgggctc tatggcttct   2580
gaggcggaaa gaaccagctg gggctctagg gggtatcccc acgcgccctg tagcggcgca   2640
ttaagcgcgg cgggtgtggt ggttacgcgc agcgtgaccg ctacacttgc cagcgcccta   2700
gcgcccgctc ctttcgcttt cttcccttcc tttctcgcca cgttcgccgg ctttccccgt   2760
caagctctaa atcggggcat ccctttaggg ttccgattta gtgctttacg gcacctcgac   2820
cccaaaaaac ttgattaggg tgatggttca cgtagtgggc catcgccctg atagacggtt   2880
tttcgccctt tgacgttgga gtccacgttc tttaatagtg gactcttgtt ccaaactgga   2940
acaacactca accctatctc ggtctattct tttgatttat aagggatttt ggggatttcg   3000
```

-continued

```
gcctattggt taaaaaatga gctgatttaa caaaaattta acgcgaatta attctgtgga   3060
atgtgtgtca gttagggtgt ggaaagtccc caggctcccc aggcaggcag aagtatgcaa   3120
agcatgcatc tcaattagtc agcaaccagg tgtggaaagt ccccaggctc cccagcaggc   3180
agaagtatgc aaagcatgca tctcaattag tcagcaacca tagtcccgcc cctaactccg   3240
cccatcccgc ccctaactcc gcccagttcc gcccattctc cgccccatgg ctgactaatt   3300
ttttttattt atgcagaggc cgaggccgcc tctgcctctg agctattcca gaagtagtga   3360
ggaggctttt ttggaggcct aggcttttgc aaaaagctcc cgggagcttg tatatccatt   3420
ttcggatctg atcagcacgt gttgacaatt aatcatcggc atagtatatc ggcatagtat   3480
aatacgacaa ggtgaggaac taaaccatgg ccaagttgac cagtgccgtt ccggtgctca   3540
ccgcgcgcga cgtcgccgga gcggtcgagt tctggaccga ccggctcggg ttctcccggg   3600
acttcgtgga ggacgacttc gccggtgtgg tccgggacga cgtgaccctg ttcatcagcg   3660
cggtccagga ccaggtggtg ccggacaaca ccctggcctg ggtgtgggtg cgcggcctgg   3720
acgagctgta cgccgagtgg tcggaggtcg tgtccacgaa cttccgggac gcctccgggc   3780
cggccatgac cgagatcggc gagcagccgt gggggcggga gttcgccctg cgcgacccgg   3840
ccggcaactg cgtgcacttc gtggccgagg agcaggactg acacgtgcta cgagatttcg   3900
attccaccgc cgccttctat gaaaggttgg gcttcggaat cgttttccgg gacgccggct   3960
ggatgatcct ccagcgcggg gatctcatgc tggagttctt cgcccacccc aacttgttta   4020
ttgcagctta taatggttac aaataaagca atagcatcac aaatttcaca aataaagcat   4080
tttttcact gcattctagt tgtggtttgt ccaaactcat caatgtatct tatcatgtct   4140
gtataccgtc gacctctagc tagagcttgg cgtaatcatg gtcatagctg tttcctgtgt   4200
gaaattgtta tccgctcaca attccacaca acatacgagc cggaagcata aagtgtaaag   4260
cctggggtgc ctaatgagtg agctaactca cattaattgc gttgcgctca ctgcccgctt   4320
tccagtcggg aaacctgtcg tgccagctgc attaatgaat cggccaacgc gcggggagag   4380
gcggtttgcg tattgggcgc tcttccgctt cctcgctcac tgactcgctg cgctcggtcg   4440
ttcggctgcg gcgagcggta tcagctcact caaaggcggt aatacggtta tccacagaat   4500
caggggataa cgcaggaaag aacatgtgag caaaaggcca gcaaaaggcc aggaaccgta   4560
aaaaggccgc gttgctggcg tttttccata ggctccgccc ccctgacgag catcacaaaa   4620
atcgacgctc aagtcagagg tggcgaaacc cgacaggact ataaagatac caggcgtttc   4680
cccctggaag ctccctcgtg cgctctcctg ttccgaccct gccgcttacc ggatacctgt   4740
ccgcctttct cccttcggga agcgtggcgc tttctcaatg ctcacgctgt aggtatctca   4800
gttcggtgta ggtcgttcgc tccaagctgg gctgtgtgca cgaacccccc gttcagcccg   4860
accgctgcgc cttatccggt aactatcgtc ttgagtccaa cccggtaaga cacgacttat   4920
cgccactggc agcagccact ggtaacagga ttagcagagc gaggtatgta ggcggtgcta   4980
cagagttctt gaagtggtgg cctaactacg gctacactag aaggacagta tttggtatct   5040
gcgctctgct gaagccagtt accttcggaa aaagagttgg tagctcttga tccggcaaac   5100
aaaccaccgc tggtagcggt ggtttttttg tttgcaagca gcagattacg cgcagaaaaa   5160
aaggatctca agaagatcct ttgatctttt ctacggggtc tgacgctcag tggaacgaaa   5220
actcacgtta agggattttg gtcatgagat tatcaaaaag gatcttcacc tagatccttt   5280
taaattaaaa atgaagtttt aaatcaatct aaagtatata tgagtaaact tggtctgaca   5340
gttaccaatg cttaatcagt gaggcaccta tctcagcgat ctgtctattt cgttcatcca   5400
```

-continued

```
tagttgcctg actccccgtc gtgtagataa ctacgatacg ggagggctta ccatctggcc   5460
ccagtgctgc aatgataccg cgagacccac gctcaccggc tccagattta tcagcaataa   5520
accagccagc cggaagggcc gagcgcagaa gtggtcctgc aactttatcc gcctccatcc   5580
agtctattaa ttgttgccgg gaagctagag taagtagttc gccagttaat agtttgcgca   5640
acgttgttgc cattgctaca ggcatcgtgg tgtcacgctc gtcgtttggt atggcttcat   5700
tcagctccgg ttcccaacga tcaaggcgag ttacatgatc ccccatgttg tgcaaaaaag   5760
cggttagctc cttcggtcct ccgatcgttg tcagaagtaa gttggccgca gtgttatcac   5820
tcatggttat ggcagcactg cataattctc ttactgtcat gccatccgta agatgctttt   5880
ctgtgactgg tgagtactca accaagtcat tctgagaata gtgtatgcgg cgaccgagtt   5940
gctcttgccc ggcgtcaata cgggataata ccgcgccaca tagcagaact ttaaaagtgc   6000
tcatcattgg aaaacgttct tcggggcgaa aactctcaag gatcttaccg ctgttgagat   6060
ccagttcgat gtaacccact cgtgcaccca actgatcttc agcatctttt actttcacca   6120
gcgtttctgg gtgagcaaaa acaggaaggc aaaatgccgc aaaaaaggga ataagggcga   6180
cacggaaatg ttgaatactc atactcttcc tttttcaata ttattgaagc atttatcagg   6240
gttattgtct catgagcgga tacatatttg aatgtattta gaaaaataaa caaatagggg   6300
ttccgcgcac atttccccga aaagtgccac ctgacgtcga cggatcggga gatctcccga   6360
tcccctatgg tgcactctca gtacaatctg ctctgatgcc gcatagttaa gccagtatct   6420
gctccctgct tgtgtgttgg aggtcgctga gtagtgcgcg agcaaaattt aagctacaac   6480
aaggcaaggc ttgaccgaca attgcatgaa gaatctgctt agggttaggc gttttgcgct   6540
gcttcgcgat gtacgggcca gatatacgcg ttgacattga ttattgacta gttattaata   6600
gtaatcaatt acggggtcat tagttcatag cccatatatg gagttccgcg ttacataact   6660
tacggtaaat ggcccgcctg gctgaccgcc caacgacccc cgcccattga cgtcaataat   6720
gacgtatgtt cccatagtaa cgccaatagg gactttccat tgacgtcaat gggtggacta   6780
tttacggtaa actgcccact tggcagtaca tcaagtgtat catatgccaa gtacgccccc   6840
tattgacgtc aatgacggta aatggcccgc ctggcattat gcccagtaca tgaccttatg   6900
ggactttcct acttggcagt acatctacgt attagtcatc gctattacca tggtgatgcg   6960
gttttggcag tacatcaatg ggcgtggata gcggtttgac tcacggggat ttccaagtct   7020
ccaccccatt gacgtcaatg ggagtttgtt ttggcaccaa aatcaacggg actttccaaa   7080
atgtcgtaac aactccgccc cattgacgca aatgggcggt aggcgtgtac ggtgggaggt   7140
ctatataagc agagctctct ggctaactag agaacccact gcttactggc ttatcgaaat   7200
taatacgact cactataggg agacccaagc tggtttaaac ttaagcttgg taccgagctc   7260
actagtccag tgtggtggca gatatccagc acagtggcgg ccgctcgagt ctagagggcc   7320
cgttttgcct gtactgggtc tctctggtta gaccagatct gagcctggga gctctctggc   7380
taactaggga acccactgct taagcctcaa taaagcttgc cttgagtgct tcaagtagtg   7440
tgtgcccgtc tgttgtgtga ctctggtaac tagagatccc tcagaccctt ttagtcagtg   7500
tggaaaatct ctagcagtgg cgcccgaaca gggacttgaa agcgaaaggg aaaccagagg   7560
agctctctcg acgcaggact cggcttgctg aagcgcgcac ggcaagaggc gaggggcggc   7620
gactggtgag tacgccaaaa attttgacta gcggaggcta gaaggagaga gatgggtgcg   7680
agagcgtcag tattaagcgg gggagaatta gatcgcgatg ggaaaaaatt cggttaaggc   7740
```

-continued

```
caggggggaaa gaaaaaatat aaattaaaac atatagtatg ggcaagcagg gagctagaac   7800
gattcgcagt taatcctggc ctgttagaaa catcagaagg ctgtagacaa atactgggac   7860
agctacaacc atcccttcag acaggatcag aagaacttag atcattatat aatacagtag   7920
caaccctcta ttgtgtgcat caaaggatag agataaaaga caccaaggaa gctttagaca   7980
agatagagga agagcaaaac aaaagtaaga ccaccgcaca gcaagcggcc gctgatcttc   8040
agacctggag gaggagatat gagggacaat tggagaagtg aattatataa atataaagta   8100
gtaaaaattg aaccattagg agtagcaccc accaaggcaa agagaagagt ggtgcagaga   8160
gaaaaaagag cagtgggaat aggagctttg ttccttgggt tcttgggagc agcaggaagc   8220
actatgggcg cagcgtcaat gacgctgacg gtacaggcca gacaattatt gtctggtata   8280
gtgcagcagc agaacaattt gctgagggct attgaggcgc aacagcatct gttgcaactc   8340
acagtctggg gcatcaagca gctccaggca agaatcctgg ctgtggaaag atacctaaag   8400
gatcaacagc tcctggggat ttggggttgc tctggaaaac tcatttgcac cactgctgtg   8460
ccttggaatg ctagttggag taataaatct ctggaacaga tttggaatca cacgacctgg   8520
atggagtggg acagagaaat taacaattac acaagcttaa tacactcctt aattgaagaa   8580
tcgcaaaacc agcaagaaaa gaatgaacaa gaattattgg aattagataa atgggcaagt   8640
ttgtggaatt ggtttaacat aacaaattgg ctgtggtata taaaattatt cataatgata   8700
gtaggaggct tggtaggttt aagaatagtt tttgctgtac tttctatagt gaatagagtt   8760
aggcagggat attcaccatt atcgtttcag acccacctcc caaccccgag gggacccgac   8820
aggcccttaa ttaagccacc tatcctcttc agacctcttc aggaaacagc tatgcacata   8880
gcacacaggc atatgttcaa ccaaaacact gaaacacata aaagaaatgt ttaaagaatg   8940
aatttaaaaa aataaaaaat aaactcaact acatatgaag ccttagcaaa catgtctgga   9000
cctctagaca cacagactct gacacgccaa cgtctgagtt ctagtttcga tacgcactgg   9060
gaagttttaa aagttttcca tcaactctaa tgtgtagaga aatggaaact atcatagact   9120
ctacggcatt gagggtgaag gtatgagtga agcactctta gggtcagaag tatgtcagtg   9180
cccatttgtt gctgttagca tcatcatctt agggcttgag aggatgttgc agctgaccca   9240
tgcacctgtg acatacatat ggaattattc tttggcacat aaaattagaa tgggagctgg   9300
ctcatcaggt tttgtgctgt aagttttcta tgttaaacca gatgcgatac actaaataaa   9360
ataaaatata cttgaccgat ggttttgagc gaaataataa ctggataatc aagaaatata   9420
tccactaatg aatagcctga actactgaaa caatttgttc agtgcctagc atatggtgtg   9480
cattttatta tttctttcaa aaagaatgta tttggagtta catagtaagt ctgctacctt   9540
ttctttatgg ctatatctat gtcttatgtt gagatgaatg aattattctt caggggaaat   9600
aatctatttg aacagtttag atggtgaaga acatttgcag catttgcaag attttttttcc   9660
actctgaagt ggtctttgtc cttgaacata ggatacaagt gacccctgct ctgttaatta   9720
ttggcaaatt gcctaacttc aacgtaagga aatagagtca tatgtttgct cactgaaggt   9780
tactagttaa caggcatccc ttaaacagga tataaaagga cttcagcagg actgctcgaa   9840
acatcccact tccagcactg cctgcggtga aggaaccagc agccgaattc ggccattacg   9900
gccaccacca tgacgcctca accctcgggt gcgcccactg tccaagtgac ccgtgagacg   9960
gagcggtcct tccccagagc ctcggaagac gaagtgacct gccccacgtc cgccccgccc  10020
agccccactc gcacacgggg gaactgcgca gaggcggaag agggaggctg ccgaggggcc  10080
ccgaggaagc tccgggcacg gcgcggggga cgcagccggc ctaagagcga gttggcactg  10140
```

```
agcaagcagc gacggagtcg gcgaaagaag gccaacgacc gcgagcgcaa tcgaatgcac  10200

aacctcaact cggcactgga cgccctgcgc ggtgtcctgc ccaccttccc agacgacgcg  10260

aagctcacca agatcgagac gctgcgcttc gcccacaact acatctgggc gctgactcaa  10320

acgctgcgca tagcggacca cagcttgtac gcgctggagc cgccggcgcc gcactgcggg  10380

gagctgggca gcccaggcgg ttcccccggg gactgggggt ccctctactc cccagtctcc  10440

caggctggca gcctgagtcc cgccgcgtcg ctggaggagc gacccgggct gctgggggcc  10500

acctcttccg cctgcttgag cccaggcagt ctggctttct cagattttct gtgaggccgc  10560

ct                                                                 10562
```

<210> SEQ ID NO 8
<211> LENGTH: 10926
<212> TYPE: DNA
<213> ORGANISM: Artificial Sequence
<220> FEATURE:
<223> OTHER INFORMATION: Synthetic

<400> SEQUENCE: 8

```
cggccatcga taaggatccg cccctctccc tcccccccc ctaacgttac tggccgaagc     60

cgcttggaat aaggccggtg tgcgtttgtc tatatgttat tttccaccat attgccgtct    120

tttggcaatg tgagggcccg gaaacctggc cctgtcttct tgacgagcat tcctaggggt    180

ctttcccctc tcgccaaagg aatgcaaggt ctgttgaatg tcgtgaagga agcagttcct    240

ctggaagctt cttgaagaca aacaacgtct gtagcgaccc tttgcaggca gcggaacccc    300

ccacctggcg acaggtgcct ctgcggccaa aagccacgtg tataagatac acctgcaaag    360

gcggcacaac cccagtgcca cgttgtgagt tggatagttg tggaaagagt caaatggctc    420

tcctcaagcg tattcaacaa ggggctgaag gatgcccaga aggtacccca ttgtatggga    480

tctgatctgg ggcctcggtg cacatgcttt acatgtgttt agtcgaggtt aaaaaaacgt    540

ctaggccccc cgaaccacgg ggacgtggtt ttcctttgaa aaacacgatg ataatatggc    600

cacaaccatg gcctcctccg aggacgtcat caaggagttc atgcgcttca aggtgcgcat    660

ggagggctcc gtgaacggcc acgagttcga gatcgagggc gagggcgagg gccgccccta    720

cgagggcacc cagaccgcca agctgaaggt gaccaagggc ggcccccctgc ccttcgcctg    780

ggacatcctg tccccccagt tccagtacgg ctccaaggtg tacgtgaagc accccgccga    840

catccccgac tacaagaagc tgtccttccc cgagggcttc aagtgggagc gcgtgatgaa    900

cttcgaggac ggcggcgtgg tgaccgtgac ccaggactcc tccctgcagg acggctcctt    960

catctacaag gtgaagttca tcggcgtgaa cttcccctcc gacggccccg taatgcagaa   1020

gaagactatg ggctgggagg cctccaccga gcgcctgtac ccccgcgacg gcgtgctgaa   1080

gggcgagatc cacaaggccc tgaagctgaa ggacggcggc cactacctgg tggagttcaa   1140

gtccatctac atggccaaga agcccgtgca gctgcccggc tactactacg tggactccaa   1200

gctggacatc acctcccaca acgaggacta caccatcgtg gagcagtacg agcgcgccga   1260

gggccgccac cacctgttcc tgtaggcggc cgcaatcaac ctctggatta caaaatttgt   1320

gaaagattga ctggtattct taactatgtt gctcctttta cgctatgtgg atacgctgct   1380

ttaatgcctt tgtatcatgc tattacttcc cgtacggctt tcattttctc ctccttgtat   1440

aaatcctggt tgctgtctct ttatgaggag ttgtggcccg ttgtcaggca acgtggcgtg   1500

gtgtgcactg tgtttgctga cgcaaccccc actggttggg gcattgccac cacctatcaa   1560
```

-continued

```
ctcctttccg ggactttcgc tttccccctc cctattgcca cggcggaact cattgccgcc   1620
tgccttgccc gctgctggac aggggctcgg ctgttgggca ctgacaattc cgtggtgttg   1680
tcggggaagc tgacgtcctt tccatggctg ctcgcctgtg ttgccaactg gattctgcgc   1740
gggacgtcct tctgctacgt cccttcggcc ctcaatccag cggaccttcc ttcccgcggc   1800
ctgctgccgg ttctgcggcc tcttccgcgt cttcgccttc gccctcagac gagtcggatc   1860
tccctttggg ccgcctcccc gcctgcctgc aggtttgtcg agacctagaa aaacatggag   1920
caatcacaag tagcaataca gcagctacca atgctgattg tgcctggcta gaagcacaag   1980
aggaggagga ggtgggtttt ccagtcacac ctcaggtacc tttaagacca atgacttaca   2040
aggcagctgt agatcttagc cactttttaa aagaaaaggg gggactggaa gggctaattc   2100
actcccaacg aagacaagat ctgctttttg cttgtactgg gtctctctgg ttagaccaga   2160
tctgagcctg ggagctctct ggctaactag ggaacccact gcttaagcct caataaagct   2220
tgccttgagt gcttcaagta gtgtgtgccc gtctgttgtg tgactctggt aactagagat   2280
ccctcagacc cttttagtca gtgtggaaaa tctctagcag ggcccgttta aacccgctga   2340
tcagcctcga ctgtgccttc tagttgccag ccatctgttg tttgcccctc ccccgtgcct   2400
tccttgaccc tggaaggtgc cactcccact gtcctttcct aataaaatga ggaaattgca   2460
tcgcattgtc tgagtaggtg tcattctatt ctggggggtg gggtggggca ggacagcaag   2520
ggggaggatt gggaagacaa tagcaggcat gctggggatg cggtgggctc tatggcttct   2580
gaggcggaaa gaaccagctg gggctctagg gggtatcccc acgcgccctg tagcggcgca   2640
ttaagcgcgg cgggtgtggt ggttacgcgc agcgtgaccg ctacacttgc cagcgcccta   2700
gcgcccgctc ctttcgcttt cttcccttcc tttctcgcca cgttcgccgg ctttccccgt   2760
caagctctaa atcggggcat ccctttaggg ttccgattta gtgctttacg gcacctcgac   2820
cccaaaaaac ttgattaggg tgatggttca cgtagtgggc catcgccctg atagacggtt   2880
tttcgccctt tgacgttgga gtccacgttc tttaatagtg gactcttgtt ccaaactgga   2940
acaacactca accctatctc ggtctattct tttgatttat aagggatttt ggggatttcg   3000
gcctattggt taaaaaatga gctgatttaa caaaaattta acgcgaatta attctgtgga   3060
atgtgtgtca gttagggtgt ggaaagtccc caggctcccc aggcaggcag aagtatgcaa   3120
agcatgcatc tcaattagtc agcaaccagg tgtggaaagt ccccaggctc cccagcaggc   3180
agaagtatgc aaagcatgca tctcaattag tcagcaacca tagtcccgcc cctaactccg   3240
cccatcccgc ccctaactcc gcccagttcc gcccattctc cgccccatgg ctgactaatt   3300
ttttttattt atgcagaggc cgaggccgcc tctgcctctg agctattcca gaagtagtga   3360
ggaggctttt ttggaggcct aggcttttgc aaaaagctcc cgggagcttg tatatccatt   3420
ttcggatctg atcagcacgt gttgacaatt aatcatcggc atagtatatc ggcatagtat   3480
aatacgacaa ggtgaggaac taaaccatgg ccaagttgac cagtgccgtt ccggtgctca   3540
ccgcgcgcga cgtcgccgga gcggtcgagt tctggaccga ccggctcggg ttctcccggg   3600
acttcgtgga ggacgacttc gccggtgtgg tccgggacga cgtgaccctg ttcatcagcg   3660
cggtccagga ccaggtggtg ccggacaaca ccctggcctg ggtgtgggtg cgcggcctgg   3720
acgagctgta cgccgagtgg tcggaggtcg tgtccacgaa cttccgggac gcctccgggc   3780
cggccatgac cgagatcggc gagcagccgt gggggcggga gttcgccctg cgcgacccgg   3840
ccggcaactg cgtgcacttc gtggccgagg agcaggactg acacgtgcta cgagatttcg   3900
attccaccgc cgccttctat gaaaggttgg gcttcggaat cgttttccgg gacgccggct   3960
```

-continued

```
ggatgatcct ccagcgcggg gatctcatgc tggagttctt cgcccacccc aacttgttta   4020
ttgcagctta taatggttac aaataaagca atagcatcac aaatttcaca aataaagcat   4080
tttttcact gcattctagt tgtggtttgt ccaaactcat caatgtatct tatcatgtct    4140
gtataccgtc gacctctagc tagagcttgg cgtaatcatg gtcatagctg tttcctgtgt   4200
gaaattgtta tccgctcaca attccacaca acatacgagc cggaagcata aagtgtaaag   4260
cctggggtgc ctaatgagtg agctaactca cattaattgc gttgcgctca ctgcccgctt   4320
tccagtcggg aaacctgtcg tgccagctgc attaatgaat cggccaacgc gcggggagag   4380
gcggtttgcg tattgggcgc tcttccgctt cctcgctcac tgactcgctg cgctcggtcg   4440
ttcggctgcg gcgagcggta tcagctcact caaaggcggt aatacggtta tccacagaat   4500
caggggataa cgcaggaaag aacatgtgag caaaaggcca gcaaaaggcc aggaaccgta   4560
aaaaggccgc gttgctggcg tttttccata ggctccgccc ccctgacgag catcacaaaa   4620
atcgacgctc aagtcagagg tggcgaaacc cgacaggact ataaagatac caggcgtttc   4680
cccctggaag ctccctcgtg cgctctcctg ttccgaccct gccgcttacc ggatacctgt   4740
ccgcctttct cccttcggga agcgtggcgc tttctcaatg ctcacgctgt aggtatctca   4800
gttcggtgta ggtcgttcgc tccaagctgg gctgtgtgca cgaacccccc gttcagcccg   4860
accgctgcgc cttatccggt aactatcgtc ttgagtccaa cccggtaaga cacgacttat   4920
cgccactggc agcagccact ggtaacagga ttagcagagc gaggtatgta ggcggtgcta   4980
cagagttctt gaagtggtgg cctaactacg gctacactag aaggacagta tttggtatct   5040
gcgctctgct gaagccagtt accttcggaa aaagagttgg tagctcttga tccggcaaac   5100
aaaccaccgc tggtagcggt ggtttttttg tttgcaagca gcagattacg cgcagaaaaa   5160
aaggatctca agaagatcct ttgatctttt ctacggggtc tgacgctcag tggaacgaaa   5220
actcacgtta agggattttg gtcatgagat tatcaaaaag gatcttcacc tagatccttt   5280
taaattaaaa atgaagtttt aaatcaatct aaagtatata tgagtaaact tggtctgaca   5340
gttaccaatg cttaatcagt gaggcaccta tctcagcgat ctgtctattt cgttcatcca   5400
tagttgcctg actccccgtc gtgtagataa ctacgatacg ggagggctta ccatctggcc   5460
ccagtgctgc aatgataccg cgagacccac gctcaccggc tccagattta tcagcaataa   5520
accagccagc cggaagggcc gagcgcagaa gtggtcctgc aactttatcc gcctccatcc   5580
agtctattaa ttgttgccgg gaagctagag taagtagttc gccagttaat agtttgcgca   5640
acgttgttgc cattgctaca ggcatcgtgg tgtcacgctc gtcgtttggt atggcttcat   5700
tcagctccgg ttcccaacga tcaaggcgag ttacatgatc ccccatgttg tgcaaaaaag   5760
cggttagctc cttcggtcct ccgatcgttg tcagaagtaa gttggccgca gtgttatcac   5820
tcatggttat ggcagcactg cataattctc ttactgtcat gccatccgta agatgctttt   5880
ctgtgactgg tgagtactca accaagtcat tctgagaata gtgtatgcgg cgaccgagtt   5940
gctcttgccc ggcgtcaata cgggataata ccgcgccaca tagcagaact ttaaaagtgc   6000
tcatcattgg aaaacgttct tcggggcgaa aactctcaag gatcttaccg ctgttgagat   6060
ccagttcgat gtaacccact cgtgcaccca actgatcttc agcatctttt actttcacca   6120
gcgtttctgg gtgagcaaaa acaggaaggc aaaatgccgc aaaaaaggga ataagggcga   6180
cacggaaatg ttgaatactc atactcttcc tttttcaata ttattgaagc atttatcagg   6240
gttattgtct catgagcgga tacatatttg aatgtattta gaaaaataaa caaatagggg   6300
```

-continued

```
ttccgcgcac atttccccga aaagtgccac ctgacgtcga cggatcggga gatctcccga   6360
tcccctatgg tgcactctca gtacaatctg ctctgatgcc gcatagttaa gccagtatct   6420
gctccctgct tgtgtgttgg aggtcgctga gtagtgcgcg agcaaaattt aagctacaac   6480
aaggcaaggc ttgaccgaca attgcatgaa gaatctgctt agggttaggc gttttgcgct   6540
gcttcgcgat gtacgggcca gatatacgcg ttgacattga ttattgacta gttattaata   6600
gtaatcaatt acggggtcat tagttcatag cccatatatg gagttccgcg ttacataact   6660
tacggtaaat ggcccgcctg gctgaccgcc caacgacccc cgcccattga cgtcaataat   6720
gacgtatgtt cccatagtaa cgccaatagg gactttccat tgacgtcaat gggtggacta   6780
tttacggtaa actgcccact tggcagtaca tcaagtgtat catatgccaa gtacgccccc   6840
tattgacgtc aatgacggta aatggcccgc ctggcattat gcccagtaca tgaccttatg   6900
ggactttcct acttggcagt acatctacgt attagtcatc gctattacca tggtgatgcg   6960
gttttggcag tacatcaatg ggcgtggata gcggtttgac tcacggggat ttccaagtct   7020
ccaccccatt gacgtcaatg ggagtttgtt ttggcaccaa aatcaacggg actttccaaa   7080
atgtcgtaac aactccgccc cattgacgca aatgggcggt aggcgtgtac ggtgggaggt   7140
ctatataagc agagctctct ggctaactag agaacccact gcttactggc ttatcgaaat   7200
taatacgact cactataggg agacccaagc tggtttaaac ttaagcttgg taccgagctc   7260
actagtccag tgtggtggca gatatccagc acagtggcgg ccgctcgagt ctagagggcc   7320
cgttttgcct gtactgggtc tctctggtta gaccagatct gagcctggga gctctctggc   7380
taactaggga acccactgct taagcctcaa taaagcttgc cttgagtgct tcaagtagtg   7440
tgtgcccgtc tgttgtgtga ctctggtaac tagagatccc tcagaccctt ttagtcagtg   7500
tggaaaatct ctagcagtgg cgcccgaaca gggacttgaa agcgaaaggg aaaccagagg   7560
agctctctcg acgcaggact cggcttgctg aagcgcgcac ggcaagaggc gaggggcggc   7620
gactggtgag tacgccaaaa attttgacta gcggaggcta gaaggagaga gatgggtgcg   7680
agagcgtcag tattaagcgg gggagaatta gatcgcgatg ggaaaaaatt cggttaaggc   7740
cagggggaaa gaaaaaatat aaattaaaac atatagtatg ggcaagcagg gagctagaac   7800
gattcgcagt taatcctggc ctgttagaaa catcagaagg ctgtagacaa atactgggac   7860
agctacaacc atcccttcag acaggatcag aagaacttag atcattatat aatacagtag   7920
caaccctcta ttgtgtgcat caaaggatag agataaaaga caccaaggaa gctttagaca   7980
agatagagga agagcaaaac aaaagtaaga ccaccgcaca gcaagcggcc gctgatcttc   8040
agacctggag gaggagatat gagggacaat tggagaagtg aattatataa atataaagta   8100
gtaaaaattg aaccattagg agtagcaccc accaaggcaa agagaagagt ggtgcagaga   8160
gaaaaaagag cagtgggaat aggagctttg ttccttgggt tcttgggagc agcaggaagc   8220
actatgggcg cagcgtcaat gacgctgacg gtacaggcca gacaattatt gtctggtata   8280
gtgcagcagc agaacaattt gctgagggct attgaggcgc aacagcatct gttgcaactc   8340
acagtctggg gcatcaagca gctccaggca agaatcctgg ctgtggaaag atacctaaag   8400
gatcaacagc tcctggggat ttggggttgc tctggaaaac tcatttgcac cactgctgtg   8460
ccttggaatg ctagttggag taataaatct ctggaacaga tttggaatca cacgacctgg   8520
atggagtggg acagagaaat taacaattac acaagcttaa tacactcctt aattgaagaa   8580
tcgcaaaacc agcaagaaaa gaatgaacaa gaattattgg aattagataa atgggcaagt   8640
ttgtggaatt ggtttaacat aacaaattgg ctgtggtata taaaattatt cataatgata   8700
```

```
gtaggaggct tggtaggttt aagaatagtt tttgctgtac tttctatagt gaatagagtt   8760
aggcagggat attcaccatt atcgtttcag acccacctcc caaccccgag gggacccgac   8820
aggcccttaa ttaagccacc tatcctcttc agacctcttc aggaaacagc tatgcacata   8880
gcacacaggc atatgttcaa ccaaaacact gaaacacata aaagaaatgt ttaaagaatg   8940
aatttaaaaa aataaaaaat aaactcaact acatatgaag ccttagcaaa catgtctgga   9000
cctctagaca cacagactct gacacgccaa cgtctgagtt ctagtttcga tacgcactgg   9060
gaagttttaa aagttttcca tcaactctaa tgtgtagaga aatggaaact atcatagact   9120
ctacggcatt gagggtgaag gtatgagtga agcactctta gggtcagaag tatgtcagtg   9180
cccatttgtt gctgttagca tcatcatctt agggcttgag aggatgttgc agctgaccca   9240
tgcacctgtg acatacatat ggaattattc tttggcacat aaaattagaa tgggagctgg   9300
ctcatcaggt tttgtgctgt aagttttcta tgttaaacca gatgcgatac actaaataaa   9360
ataaaatata cttgaccgat ggttttgagc gaaataataa ctggataatc aagaaatata   9420
tccactaatg aatagcctga actactgaaa caatttgttc agtgcctagc atatggtgtg   9480
cattttatta tttctttcaa aaagaatgta tttggagtta catagtaagt ctgctacctt   9540
ttctttatgg ctatatctat gtcttatgtt gagatgaatg aattattctt caggggaaat   9600
aatctatttg aacagtttag atggtgaaga acatttgcag catttgcaag atttttttcc   9660
actctgaagt ggtctttgtc cttgaacata ggatacaagt gacccctgct ctgttaatta   9720
ttggcaaatt gcctaacttc aacgtaagga aatagagtca tatgtttgct cactgaaggt   9780
tactagttaa caggcatccc ttaaacagga tataaaagga cttcagcagg actgctcgaa   9840
acatcccact tccagcactg cctgcggtga aggaaccagc agccgaattc ggccattacg   9900
gcccgccacc atggctagat tagataaaag taaagtgatt aacagcgcat tagagctgct   9960
taatgaggtc ggaatcgaag gtttaacaac ccgtaaactc gcccagaagc taggtgtaga  10020
gcagcctaca ttgtattggc atgtaaaaaa taagcgggct ttgctcgacg ccttagccat  10080
tgagatgtta gataggcacc atactcactt ttgccctttta gaaggggaaa gctggcaaga  10140
ttttttacgt aataacgcta aaagttttag atgtgcttta ctaagtcatc gcgatggagc  10200
aaaagtacat ttaggtacac ggcctacaga aaaacagtat gaaactctcg aaaatcaatt  10260
agcctttta tgccaacaag gtttttcact agagaatgca ttatatgcac tcagcgctgt  10320
ggggcatttt actttaggtt gcgtattgga agatcaagag catcaagtcg ctaaagaaga  10380
aagggaaaca cctactactg atagtatgcc gccattatta cgacaagcta tcgaattatt  10440
tgatcaccaa ggtgcagagc cagccttctt attcggcctt gaattgatca tatgcggatt  10500
agaaaaacaa cttaaatgtg aaagtgggtc gccaaaaaag aagagaaagg tcgacggcgg  10560
tggtgctttg tctcctcagc actctgctgt cactcaagga agtatcatca agaacaagga  10620
gggcatggat gctaagtcac taactgcctg gtcccggaca ctggtgacct tcaaggatgt  10680
atttgtggac ttcaccaggg aggagtggaa gctgctggac actgctcagc agatcgtgta  10740
cagaaatgtg atgctggaga actataagaa cctggtttcc ttgggttatc agcttactaa  10800
gccagatgtg atcctccggt tggagaaggg agaagagccc tggctggtgg agagagaaat  10860
tcaccaagag acccatcctg attcagagac tgcatttgaa atcaaatcat cagtttaagg  10920
ccgcct                                                             10926
```

<210> SEQ ID NO 9

<211> LENGTH: 10656
<212> TYPE: DNA
<213> ORGANISM: Artificial Sequence
<220> FEATURE:
<223> OTHER INFORMATION: Synthetic

<400> SEQUENCE: 9
cggccatcga taaggatccg cccctctccc tcccccccc ctaacgttac tggccgaagc 60
cgcttggaat aaggccggtg tgcgtttgtc tatatgttat tttccaccat attgccgtct 120
tttggcaatg tgagggcccg gaaacctggc cctgtcttct tgacgagcat tcctaggggt 180
ctttcccctc tcgccaaagg aatgcaaggt ctgttgaatg tcgtgaagga agcagttcct 240
ctggaagctt cttgaagaca aacaacgtct gtagcgaccc tttgcaggca gcggaacccc 300
ccacctggcg acaggtgcct ctgcggccaa aagccacgtg tataagatac acctgcaaag 360
gcggcacaac cccagtgcca cgttgtgagt tggatagttg tggaaagagt caaatggctc 420
tcctcaagcg tattcaacaa ggggctgaag gatgcccaga aggtacccca ttgtatggga 480
tctgatctgg ggcctcggtg cacatgcttt acatgtgttt agtcgaggtt aaaaaaacgt 540
ctaggccccc cgaaccacgg ggacgtggtt ttcctttgaa aaacacgatg ataatatggc 600
cacaaccatg gcctcctccg aggacgtcat caaggagttc atgcgcttca aggtgcgcat 660
ggagggctcc gtgaacggcc acgagttcga gatcgagggc gagggcgagg gccgccccta 720
cgagggcacc cagaccgcca agctgaaggt gaccaagggc ggcccctgc ccttcgcctg 780 ggacatcctg tccccccagt tccagtacgg ctccaaggtg tacgtgaagc accccgccga 840
catccccgac tacaagaagc tgtccttccc cgagggcttc aagtgggagc gcgtgatgaa 900
cttcgaggac ggcggcgtgg tgaccgtgac ccaggactcc tccctgcagg acggctcctt 960
catctacaag gtgaagttca tcggcgtgaa cttcccctcc gacggccccg taatgcagaa 1020
gaagactatg ggctgggagg cctccaccga gcgcctgtac ccccgcgacg gcgtgctgaa 1080
gggcgagatc cacaaggccc tgaagctgaa ggacggcggc cactacctgg tggagttcaa 1140
gtccatctac atggccaaga agcccgtgca gctgcccggc tactactacg tggactccaa 1200
gctggacatc acctcccaca acgaggacta caccatcgtg gagcagtacg agcgcgccga 1260
gggccgccac cacctgttcc tgtaggcggc cgcaatcaac ctctggatta caaaatttgt 1320
gaaagattga ctggtattct taactatgtt gctcctttta cgctatgtgg atacgctgct 1380
ttaatgcctt tgtatcatgc tattacttcc cgtacggctt tcattttctc ctccttgtat 1440
aaatcctggt tgctgtctct ttatgaggag ttgtggcccg ttgtcaggca acgtggcgtg 1500
gtgtgcactg tgtttgctga cgcaaccccc actggttggg gcattgccac cacctatcaa 1560
ctcctttccg ggactttcgc tttccccctc cctattgcca cggcggaact cattgccgcc 1620
tgccttgccc gctgctggac aggggctcgg ctgttgggca ctgacaattc cgtggtgttg 1680
tcggggaagc tgacgtcctt tccatggctg ctcgcctgtg ttgccaactg gattctgcgc 1740
gggacgtcct tctgctacgt cccttcggcc ctcaatccag cggaccttcc ttcccgcggc 1800
ctgctgccgg ttctgcggcc tcttccgcgt cttcgccttc gccctcagac gagtcggatc 1860
tccctttggg ccgcctcccc gcctgcctgc aggtttgtcg agacctagaa aaacatggag 1920
caatcacaag tagcaataca gcagctacca atgctgattg tgcctggcta gaagcacaag 1980
aggaggagga ggtgggtttt ccagtcacac ctcaggtacc tttaagacca atgacttaca 2040
aggcagctgt agatcttagc cactttttaa aagaaaaggg gggactggaa gggctaattc 2100
actcccaacg aagacaagat ctgctttttg cttgtactgg gtctctctgg ttagaccaga 2160

-continued

```
tctgagcctg ggagctctct ggctaactag ggaacccact gcttaagcct caataaagct   2220
tgccttgagt gcttcaagta gtgtgtgccc gtctgttgtg tgactctggt aactagagat   2280
ccctcagacc cttttagtca gtgtggaaaa tctctagcag ggcccgttta aacccgctga   2340
tcagcctcga ctgtgccttc tagttgccag ccatctgttg tttgcccctc ccccgtgcct   2400
tccttgaccc tggaaggtgc cactcccact gtcctttcct aataaaatga ggaaattgca   2460
tcgcattgtc tgagtaggtg tcattctatt ctggggggtg gggtggggca ggacagcaag   2520
ggggaggatt gggaagacaa tagcaggcat gctggggatg cggtgggctc tatggcttct   2580
gaggcggaaa gaaccagctg gggctctagg gggtatcccc acgcgccctg tagcggcgca   2640
ttaagcgcgg cgggtgtggt ggttacgcgc agcgtgaccg ctacacttgc cagcgcccta   2700
gcgcccgctc ctttcgcttt cttcccttcc tttctcgcca cgttcgccgg ctttccccgt   2760
caagctctaa atcggggcat ccctttaggg ttccgattta gtgctttacg gcacctcgac   2820
cccaaaaaac ttgattaggg tgatggttca cgtagtgggc catcgccctg atagacggtt   2880
tttcgccctt tgacgttgga gtccacgttc tttaatagtg gactcttgtt ccaaactgga   2940
acaacactca accctatctc ggtctattct tttgatttat aagggatttt ggggatttcg   3000
gcctattggt taaaaaatga gctgatttaa caaaaattta acgcgaatta attctgtgga   3060
atgtgtgtca gttagggtgt ggaaagtccc caggctcccc aggcaggcag aagtatgcaa   3120
agcatgcatc tcaattagtc agcaaccagg tgtggaaagt ccccaggctc cccagcaggc   3180
agaagtatgc aaagcatgca tctcaattag tcagcaacca tagtcccgcc cctaactccg   3240
cccatcccgc ccctaactcc gcccagttcc gcccattctc cgccccatgg ctgactaatt   3300
ttttttattt atgcagaggc cgaggccgcc tctgcctctg agctattcca gaagtagtga   3360
ggaggctttt ttggaggcct aggcttttgc aaaaagctcc cgggagcttg tatatccatt   3420
ttcggatctg atcagcacgt gttgacaatt aatcatcggc atagtatatc ggcatagtat   3480
aatacgacaa ggtgaggaac taaaccatgg ccaagttgac cagtgccgtt ccggtgctca   3540
ccgcgcgcga cgtcgccgga gcggtcgagt tctggaccga ccggctcggg ttctcccggg   3600
acttcgtgga ggacgacttc gccggtgtgg tccgggacga cgtgaccctg ttcatcagcg   3660
cggtccagga ccaggtggtg ccggacaaca ccctggcctg ggtgtgggtg cgcggcctgg   3720
acgagctgta cgccgagtgg tcggaggtcg tgtccacgaa cttccgggac gcctccgggc   3780
cggccatgac cgagatcggc gagcagccgt gggggcggga gttcgccctg cgcgacccgg   3840
ccggcaactg cgtgcacttc gtggccgagg agcaggactg acacgtgcta cgagatttcg   3900
attccaccgc cgccttctat gaaaggttgg gcttcggaat cgttttccgg gacgccggct   3960
ggatgatcct ccagcgcggg gatctcatgc tggagttctt cgcccacccc aacttgttta   4020
ttgcagctta taatggttac aaataaagca atagcatcac aaatttcaca aataaagcat   4080
ttttttcact gcattctagt tgtggtttgt ccaaactcat caatgtatct tatcatgtct   4140
gtataccgtc gacctctagc tagagcttgg cgtaatcatg gtcatagctg tttcctgtgt   4200
gaaattgtta tccgctcaca attccacaca acatacgagc cggaagcata aagtgtaaag   4260
cctggggtgc ctaatgagtg agctaactca cattaattgc gttgcgctca ctgcccgctt   4320
tccagtcggg aaacctgtcg tgccagctgc attaatgaat cggccaacgc gcggggagag   4380
gcggtttgcg tattgggcgc tcttccgctt cctcgctcac tgactcgctg cgctcggtcg   4440
ttcggctgcg gcgagcggta tcagctcact caaaggcggt aatacggtta tccacagaat   4500
```

-continued

```
caggggataa cgcaggaaag aacatgtgag caaaaggcca gcaaaaggcc aggaaccgta   4560
aaaaggccgc gttgctggcg tttttccata ggctccgccc ccctgacgag catcacaaaa   4620
atcgacgctc aagtcagagg tggcgaaacc cgacaggact ataaagatac caggcgtttc   4680
cccctggaag ctccctcgtg cgctctcctg ttccgaccct gccgcttacc ggatacctgt   4740
ccgcctttct cccttcggga agcgtggcgc tttctcaatg ctcacgctgt aggtatctca   4800
gttcggtgta ggtcgttcgc tccaagctgg gctgtgtgca cgaacccccc gttcagcccg   4860
accgctgcgc cttatccggt aactatcgtc ttgagtccaa cccggtaaga cacgacttat   4920
cgccactggc agcagccact ggtaacagga ttagcagagc gaggtatgta ggcggtgcta   4980
cagagttctt gaagtggtgg cctaactacg gctacactag aaggacagta tttggtatct   5040
gcgctctgct gaagccagtt accttcggaa aaagagttgg tagctcttga tccggcaaac   5100
aaaccaccgc tggtagcggt ggtttttttg tttgcaagca gcagattacg cgcagaaaaa   5160
aaggatctca agaagatcct ttgatctttt ctacggggtc tgacgctcag tggaacgaaa   5220
actcacgtta agggattttg gtcatgagat tatcaaaaag gatcttcacc tagatccttt   5280
taaattaaaa atgaagtttt aaatcaatct aaagtatata tgagtaaact tggtctgaca   5340
gttaccaatg cttaatcagt gaggcaccta tctcagcgat ctgtctattt cgttcatcca   5400
tagttgcctg actccccgtc gtgtagataa ctacgatacg ggagggctta ccatctggcc   5460
ccagtgctgc aatgataccg cgagacccac gctcaccggc tccagattta tcagcaataa   5520
accagccagc cggaagggcc gagcgcagaa gtggtcctgc aactttatcc gcctccatcc   5580
agtctattaa ttgttgccgg gaagctagag taagtagttc gccagttaat agtttgcgca   5640
acgttgttgc cattgctaca ggcatcgtgg tgtcacgctc gtcgtttggt atggcttcat   5700
tcagctccgg ttcccaacga tcaaggcgag ttacatgatc ccccatgttg tgcaaaaaag   5760
cggttagctc cttcggtcct ccgatcgttg tcagaagtaa gttggccgca gtgttatcac   5820
tcatggttat ggcagcactg cataattctc ttactgtcat gccatccgta agatgctttt   5880
ctgtgactgg tgagtactca accaagtcat tctgagaata gtgtatgcgg cgaccgagtt   5940
gctcttgccc ggcgtcaata cgggataata ccgcgccaca tagcagaact ttaaaagtgc   6000
tcatcattgg aaaacgttct tcggggcgaa aactctcaag gatcttaccg ctgttgagat   6060
ccagttcgat gtaacccact cgtgcaccca actgatcttc agcatctttt actttcacca   6120
gcgtttctgg gtgagcaaaa acaggaaggc aaaatgccgc aaaaaaggga ataagggcga   6180
cacggaaatg ttgaatactc atactcttcc tttttcaata ttattgaagc atttatcagg   6240
gttattgtct catgagcgga tacatatttg aatgtattta gaaaaataaa caaatagggg   6300
ttccgcgcac atttccccga aaagtgccac ctgacgtcga cggatcggga gatctcccga   6360
tcccctatgg tgcactctca gtacaatctg ctctgatgcc gcatagttaa gccagtatct   6420
gctccctgct tgtgtgttgg aggtcgctga gtagtgcgcg agcaaaattt aagctacaac   6480
aaggcaaggc ttgaccgaca attgcatgaa gaatctgctt agggttaggc gttttgcgct   6540
gcttcgcgat gtacgggcca gatatacgcg ttgacattga ttattgacta gttattaata   6600
gtaatcaatt acggggtcat tagttcatag cccatatatg gagttccgcg ttacataact   6660
tacggtaaat ggcccgcctg gctgaccgcc caacgacccc cgcccattga cgtcaataat   6720
gacgtatgtt cccatagtaa cgccaatagg gactttccat tgacgtcaat gggtggacta   6780
tttacggtaa actgcccact tggcagtaca tcaagtgtat catatgccaa gtacgccccc   6840
tattgacgtc aatgacggta aatggcccgc ctggcattat gcccagtaca tgaccttatg   6900
```

```
ggactttcct acttggcagt acatctacgt attagtcatc gctattacca tggtgatgcg   6960
gttttggcag tacatcaatg ggcgtggata gcggtttgac tcacggggat ttccaagtct   7020
ccaccccatt gacgtcaatg ggagtttgtt ttggcaccaa aatcaacggg actttccaaa   7080
atgtcgtaac aactccgccc cattgacgca aatgggcggt aggcgtgtac ggtgggaggt   7140
ctatataagc agagctctct ggctaactag agaacccact gcttactggc ttatcgaaat   7200
taatacgact cactataggg agacccaagc tggtttaaac ttaagcttgg taccgagctc   7260
actagtccag tgtggtggca gatatccagc acagtggcgg ccgctcgagt ctagagggcc   7320
cgttttgcct gtactgggtc tctctggtta gaccagatct gagcctggga gctctctggc   7380
taactaggga acccactgct taagcctcaa taaagcttgc cttgagtgct tcaagtagtg   7440
tgtgcccgtc tgttgtgtga ctctggtaac tagagatccc tcagaccctt ttagtcagtg   7500
tggaaaatct ctagcagtgg cgcccgaaca gggacttgaa agcgaaaggg aaaccagagg   7560
agctctctcg acgcaggact cggcttgctg aagcgcgcac ggcaagaggc gaggggcggc   7620
gactggtgag tacgccaaaa attttgacta gcggaggcta gaaggagaga gatgggtgcg   7680
agagcgtcag tattaagcgg gggagaatta gatcgcgatg ggaaaaaatt cggttaaggc   7740
caggggggaaa gaaaaaatat aaattaaaac atatagtatg ggcaagcagg gagctagaac   7800
gattcgcagt taatcctggc ctgttagaaa catcagaagg ctgtagacaa atactgggac   7860
agctacaacc atcccttcag acaggatcag aagaacttag atcattatat aatacagtag   7920
caaccctcta ttgtgtgcat caaaggatag agataaaaga caccaaggaa gctttagaca   7980
agatagagga agagcaaaac aaaagtaaga ccaccgcaca gcaagcggcc gctgatcttc   8040
agacctggag gaggagatat gagggacaat tggagaagtg aattatataa atataaagta   8100
gtaaaaattg aaccattagg agtagcaccc accaaggcaa agagaagagt ggtgcagaga   8160
gaaaaaagag cagtgggaat aggagctttg ttccttgggt tcttgggagc agcaggaagc   8220
actatgggcg cagcgtcaat gacgctgacg gtacaggcca gacaattatt gtctggtata   8280
gtgcagcagc agaacaattt gctgagggct attgaggcgc aacagcatct gttgcaactc   8340
acagtctggg gcatcaagca gctccaggca agaatcctgg ctgtggaaag atacctaaag   8400
gatcaacagc tcctggggat ttggggttgc tctggaaaac tcatttgcac cactgctgtg   8460
ccttggaatg ctagttggag taataaatct ctggaacaga tttggaatca cacgacctgg   8520
atggagtggg acagagaaat taacaattac acaagcttaa tacactcctt aattgaagaa   8580
tcgcaaaacc agcaagaaaa gaatgaacaa gaattattgg aattagataa atgggcaagt   8640
ttgtggaatt ggtttaacat aacaaattgg ctgtggtata taaaattatt cataatgata   8700
gtaggaggct tggtaggttt aagaatagtt tttgctgtac tttctatagt gaatagagtt   8760
aggcagggat attcaccatt atcgtttcag acccacctcc caaccccgag gggacccgac   8820
aggcccttaa ttaattggct ccggtgcccg tcagtgggca gagcgcacat cgcccacagt   8880
ccccgagaag ttggggggag gggtcggcaa ttgaaccggt gcctagagaa ggtggcgcgg   8940
ggtaaactgg gaaagtgatg tcgtgtactg gctccgcctt tttcccgagg gtgggggaga   9000
accgtatata agtgcagtag tcgccgtgaa cgttcttttt cgcaacgggt ttgccgccag   9060
aacacaggta agtgccgtgt gtggttcccg cgggcctggc ctctttacgg gttatggccc   9120
ttgcgtgcct tgaattactt ccacctggct gcagtacgtg attcttgatc ccgagcttcg   9180
ggttggaagt gggtgggaga gttcgaggcc ttgcgcttaa ggagcccctt cgcctcgtgc   9240
```

ttgagttgag gcctggcctg ggcgctgggg ccgccgcgtg cgaatctggt ggcaccttcg 9300
cgcctgtctc gctgctttcg ataagtctct agccatttaa aatttttgat gacctgctgc 9360
gacgcttttt ttctggcaag atagtcttgt aaatgcgggc caagatctgc acactggtat 9420
ttcggttttt ggggccgcgg gcggcgacgg ggcccgtgcg tcccagcgca catgttcggc 9480
gaggcggggc ctgcgagcgc ggccaccgag aatcggacgg gggtagtctc aagctggccg 9540
gcctgctctg gtgcctggcc tcgcgccgcc gtgtatcgcc ccgccctggg cggcaaggct 9600
ggcccggtcg gcaccagttg cgtgagcgga aagatggccg cttcccggcc ctgctgcagg 9660
gagctcaaaa tggaggacgc ggcgctcggg agagcgggcg ggtgagtcac ccacacaaag 9720
gaaaagggcc tttccgtcct cagccgtcgc ttcatgtgac tccacggagt accgggcgcc 9780
gtccaggcac ctcgattagt tctcgagctt ttggagtacg tcgtctttag gttgggggga 9840
ggggttttat gcgatggagt ttccccacac tgagtgggtg gagactgaag ttaggccagc 9900
ttggcacttg atgtaattct ccttggaatt tgcccttttt gagtttggat cttggttcat 9960
tctcaagcct cagacagtgg ttcaaagttt ttttcttcca tttcaggtgt cgtgaggaat 10020
tcggccatta cggcccgcca ccatgatcga attgctctct gaatcgctgg aagggctttc 10080
cgccgccatg atcgccgagc tgggacgcta ccggcatcag gtcttcatcg agaagctggg 10140
ctgggacgtg gtctccacct ccagggtccg cgaccaggaa ttcgaccagt tcgaccatcc 10200
gcaaacccgc tacatcgtcg ccatgagccg ccagggcatc tgcggttgcg cccgcctgct 10260
gccgacgacc gacgcctacc tgctcaagga cgtcttcgcc tacctgtgca gcgaaacccc 10320
gccgagcgat ccgtcggtct gggagctttc gcgctacgcc gccagcgcgg cggacgatcc 10380
gcagctggcg atgaagatat tctggtccag cctgcaatgc gcctggtacc tgggcgccag 10440
ttcggtggtg gcggtgacca ccacggccat ggagcgctat ttcgttcgca acggcgtgat 10500
cctccagcgc ctcggcccgc cgcagaaggt caagggcgag acgctggtcg cgatcagctt 10560
cccggcctac caggagcgcg gcctggagat gctgctgcgc taccacccgg aatggctgca 10620
gggcgtaccg ctgtcgatgg cggtgtgagg ccgcct 10656

<210> SEQ ID NO 10
<211> LENGTH: 12768
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7358)..(7362)
<223> OTHER INFORMATION: n is a, c, g, or t
<220> FEATURE:
<221> NAME/KEY: misc_feature
<222> LOCATION: (7544)..(7553)
<223> OTHER INFORMATION: n is a, c, g, or t
<220> FEATURE:
<221> NAME/KEY: misc_feature
<222> LOCATION: (8364)..(8368)
<223> OTHER INFORMATION: n is a, c, g, or t
<220> FEATURE:
<221> NAME/KEY: misc_feature
<222> LOCATION: (9459)..(9466)
<223> OTHER INFORMATION: n is a, c, g, or t

<400> SEQUENCE: 10
gatccgcccc tctccctccc ccccccctaa cgttactggc cgaagccgct tggaataagg 60
ccggtgtgcg tttgtctata tgttattttc caccatattg ccgtcttttg gcaatgtgag 120
ggcccggaaa cctggccctg tcttcttgac gagcattcct aggggtcttt cccctctcgc 180

-continued

```
caaaggaatg caaggtctgt tgaatgtcgt gaaggaagca gttcctctgg aagcttcttg    240
aagacaaaca acgtctgtag cgaccctttg caggcagcgg aaccccccac ctggcgacag    300
gtgcctctgc ggccaaaagc cacgtgtata agatacacct gcaaaggcgg cacaacccca    360
gtgccacgtt gtgagttgga tagttgtgga aagagtcaaa tggctctcct caagcgtatt    420
caacaagggg ctgaaggatg cccagaaggt accccattgt atgggatctg atctggggcc    480
tcggtgcaca tgctttacat gtgtttagtc gaggttaaaa aaacgtctag gccccccgaa    540
ccacggggac gtggttttcc tttgaaaaac acgatgataa tatggccaca accatggtga    600
gcaagggcga ggagctgttc accggggtgg tgcccatcct ggtcgagctg gacggcgacg    660
taaacggcca caagttcagc gtgtccggcg agggcgaggg cgatgccacc tacggcaagc    720
tgaccctgaa gttcatctgc accaccggca agctgcccgt gccctggccc accctcgtga    780
ccaccctgac ctacggcgtg cagtgcttca gccgctaccc cgaccacatg aagcagcacg    840
acttcttcaa gtccgccatg cccgaaggct acgtccagga gcgcaccatc ttcttcaagg    900
acgacggcaa ctacaagacc cgcgccgagg tgaagttcga gggcgacacc ctggtgaacc    960
gcatcgagct gaagggcatc gacttcaagg aggacggcaa catcctgggg cacaagctgg   1020
agtacaacta caacagccac aacgtctata tcatggccga caagcagaag aacggcatca   1080
aggtgaactt caagatccgc cacaacatcg aggacggcag cgtgcagctc gccgaccact   1140
accagcagaa cacccccatc ggcgacggcc ccgtgctgct gcccgacaac cactacctga   1200
gcacccagtc cgccctgagc aaagacccca acgagaagcg cgatcacatg gtcctgctgg   1260
agttcgtgac cgccgccggg atcactctcg gcatggacga gctgtacaag taagcggccg   1320
caatcaacct ctggattaca aaatttgtga aagattgact ggtattctta actatgttgc   1380
tccttttacg ctatgtggat acgctgcttt aatgcctttg tatcatgcta ttacttcccg   1440
tacggctttc attttctcct ccttgtataa atcctggttg ctgtctcttt atgaggagtt   1500
gtggcccgtt gtcaggcaac gtggcgtggt gtgcactgtg tttgctgacg caacccccac   1560
tggttggggc attgccacca cctatcaact cctttccggg actttcgctt tccccctccc   1620
tattgccacg gcggaactca ttgccgcctg ccttgcccgc tgctggacag gggctcggct   1680
gttgggcact gacaattccg tggtgttgtc ggggaagctg acgtcctttc catggctgct   1740
cgcctgtgtt gccaactgga ttctgcgcgg gacgtccttc tgctacgtcc cttcggccct   1800
caatccagcg gaccttcctt cccgcggcct gctgccggtt ctgcggcctc ttccgcgtct   1860
tcgccttcgc cctcagacga gtcggatctc cctttgggcc gcctccccgc ctgcctgcag   1920
gtttgtcgag acctagaaaa acatggagca atcacaagta gcaatacagc agctaccaat   1980
gctgattgtg cctggctaga agcacaagag gaggaggagg tgggttttcc agtcacacct   2040
caggtacctt taagaccaat gacttacaag gcagctgtag atcttagcca ctttttaaaa   2100
gaaaaggggg gactggaagg gctaattcac tcccaacgaa gacaagatct gctttttgct   2160
tgtactgggt ctctctggtt agaccagatc tgagcctggg agctctctgg ctaactaggg   2220
aacccactgc ttaagcctca ataaagcttg ccttgagtgc ttcaagtagt gtgtgcccgt   2280
ctgttgtgtg actctggtaa ctagagatcc ctcagaccct tttagtcagt gtggaaaatc   2340
tctagcaggg cccgtttaaa cccgctgatc agcctcgact gtgccttcta gttgccagcc   2400
atctgttgtt tgcccctccc ccgtgccttc cttgaccctg gaaggtgcca ctcccactgt   2460
cctttcctaa taaaatgagg aaattgcatc gcattgtctg agtaggtgtc attctattct   2520
```

-continued

```
gggggggtggg gtggggcagg acagcaaggg ggaggattgg gaagacaata gcaggcatgc   2580
tggggatgcg gtgggctcta tggcttctga ggcggaaaga accagctggg gctctagggg   2640
gtatccccac gcgccctgta gcggcgcatt aagcgcggcg ggtgtggtgg ttacgcgcag   2700
cgtgaccgct acacttgcca gcgccctagc gcccgctcct ttcgctttct tcccttcctt   2760
tctcgccacg ttcgccggct ttccccgtca agctctaaat cggggcatcc ctttagggtt   2820
ccgatttagt gctttacggc acctcgaccc caaaaaactt gattagggtg atggttcacg   2880
tagtgggcca tcgccctgat agacggtttt tcgccctttg acgttggagt ccacgttctt   2940
taatagtgga ctcttgttcc aaactggaac aacactcaac cctatctcgg tctattcttt   3000
tgatttataa gggattttgg ggatttcggc ctattggtta aaaaatgagc tgatttaaca   3060
aaaatttaac gcgaattaat tctgtggaat gtgtgtcagt tagggtgtgg aaagtcccca   3120
ggctccccag gcaggcagaa gtatgcaaag catgcatctc aattagtcag caaccaggtg   3180
tggaaagtcc ccaggctccc cagcaggcag aagtatgcaa agcatgcatc tcaattagtc   3240
agcaaccata gtcccgcccc taactccgcc catcccgccc ctaactccgc ccagttccgc   3300
ccattctccg ccccatggct gactaatttt ttttatttat gcagaggccg aggccgcctc   3360
tgcctctgag ctattccaga agtagtgagg aggctttttt ggaggcctag gcttttgcaa   3420
aaagctcccg ggagcttgta tatccatttt cggatctgat cagcacgtgt tgacaattaa   3480
tcatcggcat agtatatcgg catagtataa tacgacaagg tgaggaacta aaccatggcc   3540
aagttgacca gtgccgttcc ggtgctcacc gcgcgcgacg tcgccggagc ggtcgagttc   3600
tggaccgacc ggctcgggtt ctcccgggac ttcgtggagg acgacttcgc cggtgtggtc   3660
cgggacgacg tgaccctgtt catcagcgcg gtccaggacc aggtggtgcc ggacaacacc   3720
ctggcctggg tgtgggtgcg cggcctggac gagctgtacg ccgagtggtc ggaggtcgtg   3780
tccacgaact tccgggacgc ctccgggccg gccatgaccg agatcggcga gcagccgtgg   3840
gggcgggagt tcgccctgcg cgacccggcc ggcaactgcg tgcacttcgt ggccgaggag   3900
caggactgac acgtgctacg agatttcgat tccaccgccg ccttctatga aaggttgggc   3960
ttcggaatcg ttttccggga cgccggctgg atgatcctcc agcgcgggga tctcatgctg   4020
gagttcttcg cccaccccaa cttgtttatt gcagcttata atggttacaa ataaagcaat   4080
agcatcacaa atttcacaaa taaagcattt ttttcactgc attctagttg tggtttgtcc   4140
aaactcatca atgtatctta tcatgtctgt ataccgtcga cctctagcta gagcttggcg   4200
taatcatggt catagctgtt tcctgtgtga aattgttatc cgctcacaat tccacacaac   4260
atacgagccg gaagcataaa gtgtaaagcc tggggtgcct aatgagtgag ctaactcaca   4320
ttaattgcgt tgcgctcact gcccgctttc cagtcgggaa acctgtcgtg ccagctgcat   4380
taatgaatcg gccaacgcgc ggggagaggc ggtttgcgta ttgggcgctc ttccgcttcc   4440
tcgctcactg actcgctgcg ctcggtcgtt cggctgcggc gagcggtatc agctcactca   4500
aaggcggtaa tacggttatc cacagaatca ggggataacg caggaaagaa catgtgagca   4560
aaaggccagc aaaaggccag gaaccgtaaa aaggccgcgt tgctggcgtt tttccatagg   4620
ctccgccccc ctgacgagca tcacaaaaat cgacgctcaa gtcagaggtg gcgaaacccg   4680
acaggactat aaagatacca ggcgtttccc cctggaagct ccctcgtgcg ctctcctgtt   4740
ccgaccctgc cgcttaccgg atacctgtcc gcctttctcc cttcgggaag cgtggcgctt   4800
tctcaatgct cacgctgtag gtatctcagt tcggtgtagg tcgttcgctc caagctgggc   4860
tgtgtgcacg aaccccccgt tcagcccgac cgctgcgcct tatccggtaa ctatcgtctt   4920
```

-continued

```
gagtccaacc cggtaagaca cgacttatcg ccactggcag cagccactgg taacaggatt   4980
agcagagcga ggtatgtagg cggtgctaca gagttcttga agtggtggcc taactacggc   5040
tacactagaa ggacagtatt tggtatctgc gctctgctga agccagttac cttcggaaaa   5100
agagttggta gctcttgatc cggcaaacaa accaccgctg gtagcggtgg tttttttgtt   5160
tgcaagcagc agattacgcg cagaaaaaaa ggatctcaag aagatccttt gatcttttct   5220
acggggtctg acgctcagtg gaacgaaaac tcacgttaag ggattttggt catgagatta   5280
tcaaaaagga tcttcaccta gatcctttta aattaaaaat gaagttttaa atcaatctaa   5340
agtatatatg agtaaacttg gtctgacagt taccaatgct taatcagtga ggcacctatc   5400
tcagcgatct gtctatttcg ttcatccata gttgcctgac tccccgtcgt gtagataact   5460
acgatacggg agggcttacc atctggcccc agtgctgcaa tgataccgcg agacccacgc   5520
tcaccggctc cagatttatc agcaataaac cagccagccg gaagggccga gcgcagaagt   5580
ggtcctgcaa ctttatccgc ctccatccag tctattaatt gttgccggga agctagagta   5640
agtagttcgc cagttaatag tttgcgcaac gttgttgcca ttgctacagg catcgtggtg   5700
tcacgctcgt cgtttggtat ggcttcattc agctccggtt cccaacgatc aaggcgagtt   5760
acatgatccc ccatgttgtg caaaaaagcg gttagctcct tcggtcctcc gatcgttgtc   5820
agaagtaagt tggccgcagt gttatcactc atggttatgg cagcactgca taattctctt   5880
actgtcatgc catccgtaag atgcttttct gtgactggtg agtactcaac caagtcattc   5940
tgagaatagt gtatgcggcg accgagttgc tcttgcccgg cgtcaatacg ggataatacc   6000
gcgccacata gcagaacttt aaaagtgctc atcattggaa aacgttcttc ggggcgaaaa   6060
ctctcaagga tcttaccgct gttgagatcc agttcgatgt aacccactcg tgcacccaac   6120
tgatcttcag catcttttac tttcaccagc gtttctgggt gagcaaaaac aggaaggcaa   6180
aatgccgcaa aaaagggaat aagggcgaca cggaaatgtt gaatactcat actcttcctt   6240
tttcaatatt attgaagcat ttatcagggt tattgtctca tgagcggata catatttgaa   6300
tgtatttaga aaaataaaca aataggggtt ccgcgcacat ttccccgaaa agtgccacct   6360
gacgtcgacg gatcgggaga tctcccgatc ccctatggtg cactctcagt acaatctgct   6420
ctgatgccgc atagttaagc cagtatctgc tccctgcttg tgtgttggag gtcgctgagt   6480
agtgcgcgag caaaatttaa gctacaacaa ggcaaggctt gaccgacaat tgcatgaaga   6540
atctgcttag ggttaggcgt tttgcgctgc ttcgcgatgt acgggccaga tatacgcgtt   6600
gacattgatt attgactagt tattaatagt aatcaattac ggggtcatta gttcatagcc   6660
catatatgga gttccgcgtt acataactta cggtaaatgg cccgcctggc tgaccgccca   6720
acgacccccg cccattgacg tcaataatga cgtatgttcc catagtaacg ccaataggga   6780
ctttccattg acgtcaatgg gtggactatt tacggtaaac tgcccacttg gcagtacatc   6840
aagtgtatca tatgccaagt acgcccccta ttgacgtcaa tgacggtaaa tggcccgcct   6900
ggcattatgc ccagtacatg accttatggg actttcctac ttggcagtac atctacgtat   6960
tagtcatcgc tattaccatg gtgatgcggt tttggcagta catcaatggg cgtggatagc   7020
ggtttgactc acggggattt ccaagtctcc accccattga cgtcaatggg agtttgtttt   7080
ggcaccaaaa tcaacgggac tttccaaaat gtcgtaacaa ctccgcccca ttgacgcaaa   7140
tgggcggtag gcgtgtacgg tgggaggtct atataagcag agctctctgg ctaactagag   7200
aacccactgc ttactggctt atcgaaatta atacgactca ctatagggag acccaagctg   7260
```

```
gtttaaactt aagcttggta ccgagctcac tagtccagtg tggtggcaga tatccagcac   7320
agtggcggcc gctcgagtct agagggcccg tttaaacnnn nngggtctct ctggttagac   7380
cagatctgag cctgggagct ctctggctaa ctagggaacc cactgcttaa gcctcaataa   7440
agcttgcctt gagtgcttca agtagtgtgt gcccgtctgt tgtgtgactc tggtaactag   7500
agatccctca gaccctttta gtcagtgtgg aaaatctcta gcannnnnnn nnnccagcaa   7560
cttatctgtg tctgtccgat tgtctagtgt ctatgtttga tgttatgcgc ctgcgtctgt   7620
actagttagc taactagctc tgtatctggc ggacccgtgg tggaactgac gagttctgaa   7680
cacccggccg caaccctggg agacgtccca gggactttgg gggccgtttt tgtggcccga   7740
cctgaggaag ggagtcgatg tggaatccga ccccgtcagg atatgtggtt ctggtaggag   7800
acgagaacct aaaacagttc ccgcctccgt ctgaattttt gctttcggtt tggaaccgaa   7860
gccgcgcgtc ttgtctgctg cagcgctgca gcatcgttct gtgttgtctc tgtctgactg   7920
tgtttctgta tttgtctgaa aattagggcc agactgttac cactccctta agtttgacct   7980
taggtcactg gaaagatgtc gagcggatcg ctcacaacca gtcggtagat gtcaagaaga   8040
gacgttgggt taccttctgc tctgcagaat ggccaacctt taacgtcgga tggccgcgag   8100
acggcacctt taaccgagac ctcatcaccc aggttaagat caaggtcttt tcacctggcc   8160
cgcatggaca cccagaccag gtcccctaca tcgtgacctg ggaagccttg gcttttgacc   8220
cccctccctg ggtcaagccc tttgtacacc ctaagcctcc gcctcctctt cctccatccg   8280
ccccgtctct ccccccttgaa cctcctcgtt cgaccccgcc tcgatcctcc ctttatccag   8340
ccctcactcc ttctctaggc gccnnnnngg aaaagtttag taaaacacca tatgtatgtt   8400
tcagggaaag ctaggggatg gttttataga catcactatg aaagccctca tccaagaata   8460
agttcagaag tacacatccc actaggggat gctagattgg taataacaac atattggggt   8520
ctgcatacag gagaaagaga ctggcatctg ggtcagggag tctccataga atggaggaaa   8580
aagagatata gcacacaagt agaccctgaa ctagcagacc aactaattca tctgtattac   8640
tttgactgtt tttcagactc tgctataaga aaggccttat taggacatat agttagccct   8700
aggtgtgaat atcaagcagg acataacaag gtaggatctc tacaatactt ggcactagca   8760
gcattaataa caccaaaaaa gataaagcca cctttgccta gtgttacgaa actgacagag   8820
gatagatgga acaagcccca gaagaccaag ggccacagag ggagccacac aatgaatgga   8880
cactagagct tttagaggag cttaagaatg aagctgttag acattttcct aggatttggc   8940
tccatggctt agggcaacat atctatgaaa cttatgggga tacttgggca ggagtggaag   9000
ccataataat gcaacaactg ctgtttatcc atttcagaat tgggtgtcga catagcagaa   9060
taggcgttac tcaacagagg agagcaagaa atggagccag tagatcctag actagagccc   9120
tggaagcatc caggaagtca gcctaaaact gcttgtacca cttgctattg taaaaagtgt   9180
tgctttcatt gccaagtttg tttcacaaca aaagccttag gcatctccta tggcaggaag   9240
aagcggagac agcgacgaag acctcctcaa ggcagtcaga ctcatcaagt ttctctatca   9300
aagcagtaag tagtacatgt aatgcaacct atacaaatag caatagcagc attagtagta   9360
gcaataataa tagcaatagt tgtgtggtcc atagtaatca tagaatatag gaaaatatta   9420
agacaaagaa aaatagacag gttaattgat agactaatnn nnnnnnggcc cgaaggaata   9480
gaagaagaag gtggagagag agacagagac agatccattc gattagtgaa cggatcggca   9540
ctgcgtgcgc caattctgca gacaaatggc agtattcatc cacaatttta aaagaaaagg   9600
ggggattggg gggtacagtg caggggaaag aatagtagac ataatagcaa cagacataca   9660
```

aactaaagaa ttacaaaaac aaattacaaa aattcaaaat tttcgggttt attacaggga 9720
cagcagagat ccagtttggt taattaatgc tgctgagcca cgtgaagcct taagccgcag 9780
ggagaccctg aaaatagact gtaagcaacc ttggggtggg gtaagcctgt tgcagcgtta 9840
gtgtatccat gaactccttt aagatacaag ctatgtgtca ttcctcatgg agacgccgga 9900
gagtcttgag cttacatgat ggtcctgcgg aggccttaaa gtcctgtggg gatgctcagg 9960
gttgtccctg tgtgtcactg agacctccga aagaatttaa atatcacaga aaaaaaaaac 10020
ataaagaaga ccttaagcct ttttaagttc ccaaggagag ccagaagtgg tggtatatag 10080
ctcaacttgg gagactgagg caaaaagact gactgagttt aagaccagcc tagctacacc 10140
acaaagctcc tttctcaaaa gaaaaagctc ccaaggaggt tggatcccca gtgagaccct 10200
cagcaaggcc ctctggcctc actatggtcc tgaggacacc cctccacact gccctgatct 10260
tcttacccca tcctgcctga gctcttcacc tgctctcctc ttgcattcaa atatcttctg 10320
ctacagtagg tccactggag tctcccaggt acccagagtg tgaatgtctg cagcactttc 10380
tgggggacaa ggagcagaga gcaagggacc cacaattcgg gtctagtgtc tgtaaagcct 10440
tgcggagggt agagttctag ttcacacaag gcaccaagtg tttttgctgg ttgcctagga 10500
aacaggacag tgccaaatca ggaacagaaa gagtcaagga acccccaacc actccaagcg 10560
gaggctgaga aaggttttgt agctggaata gagcatgcac taacagatgg agacagctgg 10620
ctttgagctc tgaagcaagt attacatatg gagacttgct ggccttcagg tgcttatctt 10680
gttattggat actgcaggag gatgtaccac agggcttcag ctcagctgac ccccaagtgg 10740
gatatggaaa gagagataga ggaggaggga ccattaagtg ccttgctgcc tgaattctgc 10800
tttccttcta cctctgagag agagctgggg actcggctga gttaagaacc cagctatcaa 10860
ttggaactgt gaaacagtcc aagggacaaa gatactaggt ccccaactgc aacttcctgg 10920
ggaatgatgt ggaaaaatgc tcagccaagg acaaagaaag catcacccac tctggaacaa 10980
tgtcccctgc tgtgaactgg ttcatcaggc catcagggcc ccttgttaag actctaatta 11040
ccctaggact aagtagaggt gttgacgtcc aatgagcgct ttctgcagac ctagcaccag 11100
ggaagtgttt ggaaactgca gcttcagccc ctctggccat ctgctgacct accccacctg 11160
gagcccttaa tgggtcaaac agcaaagtcc agggggcaga gaggaggtgc tttggtctat 11220
aaaggtagtg gggacccagt aaccaccggc gcgccaagct agcaagttaa caaatcgatc 11280
cggatcctcc caccatgaaa ccagtaacgt tatacgatgt cgcagagtat gccggtgtct 11340
cttatcagac cgtttcccgc gtggtgaacc aggccagcca cgtttctgcg aaaacgcggg 11400
aaaaagtgga agcggcgatg gcggagctga attacattcc caaccgcgtg gcacaacaac 11460
tggcgggcaa acagtcgttg ctgattggcg ttgccacctc cagtctggcc ctgcacgcgc 11520
cgtcgcaaat tgtcgcggcg attaaatctc gcgccgatca actgggtgcc agcgtggtgg 11580
tgtcgatggt agaacgaagc ggcgtcgaag cctgtaaagc ggcggtgcac aatcttctcg 11640
cgcaacgcgt cagtgggctg atcattaact atccgctgga tgaccaggat gccattgctg 11700
tggaagctgc ctgcactaat gttccggcgt tatttcttga tgtctctgac cagacaccca 11760
tcaacagtat tattttctcc catgaagacg gtacgcgact gggcgtggag catctggtcg 11820
cattgggtca ccagcaaatc gcgctgttag cgggcccatt aagttctgtc tcggcgcgtc 11880
tgcgtctggc tggctggcat aaatatctca ctcgcaatca aattcagccg atagcggaac 11940
gggaaggcga ctggagtgcc atgtccggtt ttcaacaaac catgcaaatg ctgaatgagg 12000

-continued

```
gcatcgttcc cactgcgatg ctggttgcca acgatcagat ggcgctgggc gcaatgcgcg  12060

ccattaccga gtccgggctg cgcgttggtg cggatatctc ggtagtggga tacgacgata  12120

ccgaagacag ctcatgttat atcccgccgt taaccaccat caaacaggat tttcgcctgc  12180

tggggcaaac cagcgtggac cgcttgctgc aactctctca gggccaggcg gtgaagggca  12240

atcagctgtt gcccgtctca ctggtgaaaa gaaaaaccac cctggcgccc aatacgcaaa  12300

ccgcctctcc ccgcgcgttg gccgattcat taatgcagct ggcacgacag gtttcccgac  12360

tggaaagcgg gcagagaccg ccaaaaaaga agagaaaggt cgacggcggt ggtgctttgt  12420

ctcctcagca ctctgctgtc actcaaggaa gtatcatcaa gaacaaggag ggcatggatg  12480

ctaagtcact aactgcctgg tcccggacac tggtgacctt caaggatgta tttgtggact  12540

tcaccaggga ggagtggaag ctgctggaca ctgctcagca gatcgtgtac agaaatgtga  12600

tgctggagaa ctataagaac ctggtttcct tgggttatca gcttactaag ccagatgtga  12660

tcctccggtt ggagaaggga gaagagccct ggctggtgga gagagaaatt caccaagaga  12720

cccatcctga ttcagagact gcatttgaaa tcaaatcatc agtttgag              12768
```

```
<210> SEQ ID NO 11
<211> LENGTH: 11287
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (39)..(43)
<223> OTHER INFORMATION: n is a, c, g, or t
<220> FEATURE:
<221> NAME/KEY: misc_feature
<222> LOCATION: (7396)..(7400)
<223> OTHER INFORMATION: n is a, c, g, or t
<220> FEATURE:
<221> NAME/KEY: misc_feature
<222> LOCATION: (7582)..(7591)
<223> OTHER INFORMATION: n is a, c, g, or t
<220> FEATURE:
<221> NAME/KEY: misc_feature
<222> LOCATION: (8402)..(8406)
<223> OTHER INFORMATION: n is a, c, g, or t
<220> FEATURE:
<221> NAME/KEY: misc_feature
<222> LOCATION: (9497)..(9504)
<223> OTHER INFORMATION: n is a, c, g, or t

<400> SEQUENCE: 11
```

```
cgcgccaagc tagcaagtta acaaatcgat ccggatccnn nnngcccctc tccctccccc     60

ccccctaacg ttactggccg aagccgcttg gaataaggcc ggtgtgcgtt tgtctatatg    120

ttattttcca ccatattgcc gtcttttggc aatgtgaggg cccggaaacc tggccctgtc    180

ttcttgacga gcattcctag gggtctttcc cctctcgcca aaggaatgca aggtctgttg    240

aatgtcgtga aggaagcagt tcctctggaa gcttcttgaa gacaaacaac gtctgtagcg    300

accctttgca ggcagcggaa ccccccacct ggcgacaggt gcctctgcgg ccaaaagcca    360

cgtgtataag atacacctgc aaaggcggca caaccccagt gccacgttgt gagttggata    420

gttgtggaaa gagtcaaatg gctctcctca agcgtattca acaaggggct gaaggatgcc    480

cagaaggtac cccattgtat gggatctgat ctggggcctc ggtgcacatg ctttacatgt    540

gtttagtcga ggttaaaaaa acgtctaggc cccccgaacc acggggacgt ggttttcctt    600

tgaaaaacac gatgataata tggccacaac catggtgagc aagggcgagg agctgttcac    660

cggggtggtg cccatcctgg tcgagctgga cggcgacgta aacggccaca agttcagcgt    720
```

```
gtccggcgag ggcgagggcg atgccaccta cggcaagctg accctgaagt tcatctgcac    780
caccggcaag ctgcccgtgc cctggcccac cctcgtgacc accctgacct acggcgtgca    840
gtgcttcagc cgctaccccg accacatgaa gcagcacgac ttcttcaagt ccgccatgcc    900
cgaaggctac gtccaggagc gcaccatctt cttcaaggac gacggcaact acaagacccg    960
cgccgaggtg aagttcgagg gcgacaccct ggtgaaccgc atcgagctga agggcatcga   1020
cttcaaggag gacggcaaca tcctggggca caagctggag tacaactaca acagccacaa   1080
cgtctatatc atggccgaca agcagaagaa cggcatcaag gtgaacttca agatccgcca   1140
caacatcgag gacggcagcg tgcagctcgc cgaccactac cagcagaaca cccccatcgg   1200
cgacggcccc gtgctgctgc ccgacaacca ctacctgagc acccagtccg ccctgagcaa   1260
agaccccaac gagaagcgcg atcacatggt cctgctggag ttcgtgaccg ccgccgggat   1320
cactctcggc atggacgagc tgtacaagta agcggccgca atcaacctct ggattacaaa   1380
atttgtgaaa gattgactgg tattcttaac tatgttgctc cttttacgct atgtggatac   1440
gctgctttaa tgcctttgta tcatgctatt acttcccgta cggctttcat tttctcctcc   1500
ttgtataaat cctggttgct gtctctttat gaggagttgt ggcccgttgt caggcaacgt   1560
ggcgtggtgt gcactgtgtt tgctgacgca acccccactg gttggggcat tgccaccacc   1620
tatcaactcc tttccgggac tttcgctttc cccctcccta ttgccacggc ggaactcatt   1680
gccgcctgcc ttgcccgctg ctggacaggg gctcggctgt tgggcactga caattccgtg   1740
gtgttgtcgg ggaagctgac gtcctttcca tggctgctcg cctgtgttgc caactggatt   1800
ctgcgcggga cgtccttctg ctacgtccct tcggccctca atccagcgga ccttccttcc   1860
cgcggcctgc tgccggttct gcggcctctt ccgcgtcttc gccttcgccc tcagacgagt   1920
cggatctccc tttgggccgc ctccccgcct gcctgcaggt ttgtcgagac ctagaaaaac   1980
atggagcaat cacaagtagc aatacagcag ctaccaatgc tgattgtgcc tggctagaag   2040
cacaagagga ggaggaggtg ggttttccag tcacacctca ggtaccttta agaccaatga   2100
cttacaaggc agctgtagat cttagccact ttttaaaaga aaagggggga ctggaagggc   2160
taattcactc ccaacgaaga caagatctgc tttttgcttg tactgggtct ctctggttag   2220
accagatctg agcctgggag ctctctggct aactagggaa cccactgctt aagcctcaat   2280
aaagcttgcc ttgagtgctt caagtagtgt gtgcccgtct gttgtgtgac tctggtaact   2340
agagatccct cagacccttt tagtcagtgt ggaaaatctc tagcagggcc cgtttaaacc   2400
cgctgatcag cctcgactgt gccttctagt tgccagccat ctgttgtttg cccctccccc   2460
gtgccttcct tgaccctgga aggtgccact cccactgtcc tttcctaata aaatgaggaa   2520
attgcatcgc attgtctgag taggtgtcat tctattctgg ggggtggggt ggggcaggac   2580
agcaaggggg aggattggga agacaatagc aggcatgctg gggatgcggt gggctctatg   2640
gcttctgagg cggaaagaac cagctggggc tctagggggt atccccacgc gccctgtagc   2700
ggcgcattaa gcgcggcggg tgtggtggtt acgcgcagcg tgaccgctac acttgccagc   2760
gccctagcgc ccgctccttt cgctttcttc ccttcctttc tcgccacgtt cgccggcttt   2820
ccccgtcaag ctctaaatcg ggcatccct ttagggttcc gatttagtgc tttacggcac   2880
ctcgacccca aaaaacttga ttagggtgat ggttcacgta gtgggccatc gccctgatag   2940
acggtttttc gccctttgac gttggagtcc acgttcttta atagtggact cttgttccaa   3000
actggaacaa cactcaaccc tatctcggtc tattcttttg atttataagg gattttgggg   3060
```

-continued

```
atttcggcct attggttaaa aaatgagctg atttaacaaa aatttaacgc gaattaattc   3120
tgtggaatgt gtgtcagtta gggtgtggaa agtccccagg ctccccaggc aggcagaagt   3180
atgcaaagca tgcatctcaa ttagtcagca accaggtgtg gaaagtcccc aggctcccca   3240
gcaggcagaa gtatgcaaag catgcatctc aattagtcag caaccatagt cccgccccta   3300
actccgccca tcccgcccct aactccgccc agttccgccc attctccgcc ccatggctga   3360
ctaatttttt ttatttatgc agaggccgag gccgcctctg cctctgagct attccagaag   3420
tagtgaggag gcttttttgg aggcctaggc ttttgcaaaa agctcccggg agcttgtata   3480
tccattttcg gatctgatca gcacgtgttg acaattaatc atcggcatag tatatcggca   3540
tagtataata cgacaaggtg aggaactaaa ccatggccaa gttgaccagt gccgttccgg   3600
tgctcaccgc gcgcgacgtc gccggagcgg tcgagttctg gaccgaccgg ctcgggttct   3660
cccgggactt cgtggaggac gacttcgccg gtgtggtccg ggacgacgtg accctgttca   3720
tcagcgcggt ccaggaccag gtggtgccgg acaacaccct ggcctgggtg tgggtgcgcg   3780
gcctggacga gctgtacgcc gagtggtcgg aggtcgtgtc cacgaacttc cgggacgcct   3840
ccgggccggc catgaccgag atcggcgagc agccgtgggg gcgggagttc gccctgcgcg   3900
acccggccgg caactgcgtg cacttcgtgg ccgaggagca ggactgacac gtgctacgag   3960
atttcgattc caccgccgcc ttctatgaaa ggttgggctt cggaatcgtt ttccgggacg   4020
ccggctggat gatcctccag cgcggggatc tcatgctgga gttcttcgcc caccccaact   4080
tgtttattgc agcttataat ggttacaaat aaagcaatag catcacaaat ttcacaaata   4140
aagcattttt ttcactgcat tctagttgtg gtttgtccaa actcatcaat gtatcttatc   4200
atgtctgtat accgtcgacc tctagctaga gcttggcgta atcatggtca tagctgtttc   4260
ctgtgtgaaa ttgttatccg ctcacaattc cacacaacat acgagccgga agcataaagt   4320
gtaaagcctg gggtgcctaa tgagtgagct aactcacatt aattgcgttg cgctcactgc   4380
ccgctttcca gtcgggaaac ctgtcgtgcc agctgcatta atgaatcggc caacgcgcgg   4440
ggagaggcgg tttgcgtatt gggcgctctt ccgcttcctc gctcactgac tcgctgcgct   4500
cggtcgttcg gctgcggcga gcggtatcag ctcactcaaa ggcggtaata cggttatcca   4560
cagaatcagg ggataacgca ggaaagaaca tgtgagcaaa aggccagcaa aaggccagga   4620
accgtaaaaa ggccgcgttg ctggcgtttt tccataggct ccgcccccct gacgagcatc   4680
acaaaaatcg acgctcaagt cagaggtggc gaaacccgac aggactataa agataccagg   4740
cgtttccccc tggaagctcc ctcgtgcgct ctcctgttcc gaccctgccg cttaccggat   4800
acctgtccgc ctttctccct tcgggaagcg tggcgctttc tcaatgctca cgctgtaggt   4860
atctcagttc ggtgtaggtc gttcgctcca agctgggctg tgtgcacgaa ccccccgttc   4920
agcccgaccg ctgcgcctta tccggtaact atcgtcttga gtccaacccg gtaagacacg   4980
acttatcgcc actggcagca gccactggta acaggattag cagagcgagg tatgtaggcg   5040
gtgctacaga gttcttgaag tggtggccta actacggcta cactagaagg acagtatttg   5100
gtatctgcgc tctgctgaag ccagttacct tcggaaaaag agttggtagc tcttgatccg   5160
gcaaacaaac caccgctggt agcggtggtt tttttgtttg caagcagcag attacgcgca   5220
gaaaaaaagg atctcaagaa gatcctttga tcttttctac ggggtctgac gctcagtgga   5280
acgaaaactc acgttaaggg attttggtca tgagattatc aaaaaggatc ttcacctaga   5340
tccttttaaa ttaaaaatga agttttaaat caatctaaag tatatatgag taaacttggt   5400
ctgacagtta ccaatgctta atcagtgagg cacctatctc agcgatctgt ctatttcgtt   5460
```

```
catccatagt tgcctgactc cccgtcgtgt agataactac gatacgggag ggcttaccat   5520
ctggccccag tgctgcaatg ataccgcgag acccacgctc accggctcca gatttatcag   5580
caataaacca gccagccgga agggccgagc gcagaagtgg tcctgcaact ttatccgcct   5640
ccatccagtc tattaattgt tgccgggaag ctagagtaag tagttcgcca gttaatagtt   5700
tgcgcaacgt tgttgccatt gctacaggca tcgtggtgtc acgctcgtcg tttggtatgg   5760
cttcattcag ctccggttcc caacgatcaa ggcgagttac atgatccccc atgttgtgca   5820
aaaaagcggt tagctccttc ggtcctccga tcgttgtcag aagtaagttg gccgcagtgt   5880
tatcactcat ggttatggca gcactgcata attctcttac tgtcatgcca tccgtaagat   5940
gcttttctgt gactggtgag tactcaacca agtcattctg agaatagtgt atgcggcgac   6000
cgagttgctc ttgcccggcg tcaatacggg ataataccgc gccacatagc agaactttaa   6060
aagtgctcat cattggaaaa cgttcttcgg ggcgaaaact ctcaaggatc ttaccgctgt   6120
tgagatccag ttcgatgtaa cccactcgtg cacccaactg atcttcagca tcttttactt   6180
tcaccagcgt ttctgggtga gcaaaaacag gaaggcaaaa tgccgcaaaa aagggaataa   6240
gggcgacacg gaaatgttga atactcatac tcttcctttt tcaatattat tgaagcattt   6300
atcagggtta ttgtctcatg agcggataca tatttgaatg tatttagaaa aataaacaaa   6360
taggggttcc gcgcacattt ccccgaaaag tgccacctga cgtcgacgga tcgggagatc   6420
tcccgatccc ctatggtgca ctctcagtac aatctgctct gatgccgcat agttaagcca   6480
gtatctgctc cctgcttgtg tgttggaggt cgctgagtag tgcgcgagca aaatttaagc   6540
tacaacaagg caaggcttga ccgacaattg catgaagaat ctgcttaggg ttaggcgttt   6600
tgcgctgctt cgcgatgtac gggccagata tacgcgttga cattgattat tgactagtta   6660
ttaatagtaa tcaattacgg ggtcattagt tcatagccca tatatggagt tccgcgttac   6720
ataacttacg gtaaatggcc cgcctggctg accgcccaac gacccccgcc cattgacgtc   6780
aataatgacg tatgttccca tagtaacgcc aatagggact ttccattgac gtcaatgggt   6840
ggactattta cggtaaactg cccacttggc agtacatcaa gtgtatcata tgccaagtac   6900
gccccctatt gacgtcaatg acggtaaatg gcccgcctgg cattatgccc agtacatgac   6960
cttatgggac tttcctactt ggcagtacat ctacgtatta gtcatcgcta ttaccatggt   7020
gatgcggttt tggcagtaca tcaatgggcg tggatagcgg tttgactcac ggggatttcc   7080
aagtctccac cccattgacg tcaatgggag tttgttttgg caccaaaatc aacgggactt   7140
tccaaaatgt cgtaacaact ccgccccatt gacgcaaatg ggcggtaggc gtgtacggtg   7200
ggaggtctat ataagcagag ctctctggct aactagagaa cccactgctt actggcttat   7260
cgaaattaat acgactcact atagggagac ccaagctggt ttaaacttaa gcttggtacc   7320
gagctcacta gtccagtgtg gtggcagata tccagcacag tggcggccgc tcgagtctag   7380
agggcccgtt taaacnnnnn gggtctctct ggttagacca gatctgagcc tgggagctct   7440
ctggctaact agggaaccca ctgcttaagc ctcaataaag cttgccttga gtgcttcaag   7500
tagtgtgtgc ccgtctgttg tgtgactctg gtaactagag atccctcaga cccttttagt   7560
cagtgtggaa aatctctagc annnnnnnnn nccagcaact tatctgtgtc tgtccgattg   7620
tctagtgtct atgtttgatg ttatgcgcct gcgtctgtac tagttagcta actagctctg   7680
tatctggcgg acccgtggtg gaactgacga gttctgaaca cccggccgca accctgggag   7740
acgtcccagg gactttgggg gccgtttttg tggcccgacc tgaggaaggg agtcgatgtg   7800
```

-continued

```
gaatccgacc ccgtcaggat atgtggttct ggtaggagac gagaacctaa aacagttccc   7860
gcctccgtct gaatttttgc tttcggtttg gaaccgaagc cgcgcgtctt gtctgctgca   7920
gcgctgcagc atcgttctgt gttgtctctg tctgactgtg tttctgtatt tgtctgaaaa   7980
ttagggccag actgttacca ctcccttaag tttgacctta ggtcactgga aagatgtcga   8040
gcggatcgct cacaaccagt cggtagatgt caagaagaga cgttgggtta ccttctgctc   8100
tgcagaatgg ccaaccttta acgtcggatg gccgcgagac ggcaccttta accgagacct   8160
catcacccag gttaagatca aggtcttttc acctggcccg catggacacc cagaccaggt   8220
cccctacatc gtgacctggg aagccttggc ttttgacccc cctccctggg tcaagccctt   8280
tgtacaccct aagcctccgc ctcctcttcc tccatccgcc ccgtctctcc cccttgaacc   8340
tcctcgttcg accccgcctc gatcctccct ttatccagcc ctcactcctt ctctaggcgc   8400
cnnnnnggaa aagtttagta aaacaccata tgtatgtttc agggaaagct aggggatggt   8460
tttatagaca tcactatgaa agccctcatc caagaataag ttcagaagta cacatcccac   8520
taggggatgc tagattggta ataacaacat attggggtct gcatacagga gaaagagact   8580
ggcatctggg tcagggagtc tccatagaat ggaggaaaaa gagatatagc acacaagtag   8640
accctgaact agcagaccaa ctaattcatc tgtattactt tgactgtttt tcagactctg   8700
ctataagaaa ggccttatta ggacatatag ttagccctag gtgtgaatat caagcaggac   8760
ataacaaggt aggatctcta caatacttgg cactagcagc attaataaca ccaaaaaaga   8820
taaagccacc tttgcctagt gttacgaaac tgacagagga tagatggaac aagccccaga   8880
agaccaaggg ccacagaggg agccacacaa tgaatggaca ctagagcttt tagaggagct   8940
taagaatgaa gctgttagac attttcctag gatttggctc catggcttag ggcaacatat   9000
ctatgaaact tatggggata cttgggcagg agtggaagcc ataataatgc aacaactgct   9060
gtttatccat ttcagaattg ggtgtcgaca tagcagaata ggcgttactc aacagaggag   9120
agcaagaaat ggagccagta gatcctagac tagagccctg gaagcatcca ggaagtcagc   9180
ctaaaactgc ttgtaccact tgctattgta aaaagtgttg ctttcattgc caagtttgtt   9240
tcacaacaaa agccttaggc atctcctatg gcaggaagaa gcggagacag cgacgaagac   9300
ctcctcaagg cagtcagact catcaagttt ctctatcaaa gcagtaagta gtacatgtaa   9360
tgcaacctat acaaatagca atagcagcat tagtagtagc aataataata gcaatagttg   9420
tgtggtccat agtaatcata gaatatagga aaatattaag acaaagaaaa atagacaggt   9480
taattgatag actaatnnnn nnnnggcccg aaggaataga agaagaaggt ggagagagag   9540
acagagacag atccattcga ttagtgaacg gatcggcact gcgtgcgcca attctgcaga   9600
caaatggcag tattcatcca caattttaaa agaaaagggg ggattggggg gtacagtgca   9660
ggggaaagaa tagtagacat aatagcaaca gacatacaaa ctaaagaatt acaaaaacaa   9720
attacaaaaa ttcaaaattt tcgggtttat tacagggaca gcagagatcc agtttggtta   9780
attaatgctg ctgagccacg tgaagcctta agccgcaggg agaccctgaa aatagactgt   9840
aagcaacctt ggggtggggt aagcctgttg cagcgttagt gtatccatga actcctttaa   9900
gatacaagct atgtgtcatt cctcatggag acgccggaga gtcttgagct tacatgatgg   9960
tcctgcggag gccttaaagt cctgtgggga tgctcagggt tgtccctgtg tgtcactgag  10020
acctccgaaa gaatttaaat atcacagaaa aaaaaaacat aaagaagacc ttaagccttt  10080
ttaagttccc aaggagagcc agaagtggtg gtatatagct caacttggga gactgaggca  10140
aaaagactga ctgagtttaa gaccagccta gctacaccac aaagctcctt tctcaaaaga  10200
```

```
aaaagctccc aaggaggttg gatccccagt gagaccctca gcaaggccct ctggcctcac  10260
tatggtcctg aggacacccc tccacactgc cctgatcttc ttaccccatc ctgcctgagc  10320
tcttcacctg ctctcctctt gcattcaaat atcttctgct acagtaggtc cactggagtc  10380
tcccaggtac ccagagtgtg aatgtctgca gcactttctg gggacaagg agcagagagc  10440
aagggaccca caattcgggt ctagtgtctg taaagccttg cggagggtag agttctagtt  10500
cacacaaggc accaagtgtt tttgctggtt gcctaggaaa caggacagtg ccaaatcagg  10560
aacagaaaga gtcaaggaac ccccaaccac tccaagcgga ggctgagaaa ggttttgtag  10620
ctggaataga gcatgcacta acagatggag acagctggct ttgagctctg aagcaagtat  10680
tacatatgga gacttgctgg ccttcaggtg cttatcttgt tattggatac tgcaggagga  10740
tgtaccacag ggcttcagct cagctgaccc ccaagtggga tatggaaaga gagatagagg  10800
aggagggacc attaagtgcc ttgctgcctg aattctgctt tccttctacc tctgagagag  10860
agctggggac tcggctgagt taagaaccca gctatcaatt ggaactgtga aacagtccaa  10920
gggacaaaga tactaggtcc ccaactgcaa cttcctgggg aatgatgtgg aaaaatgctc  10980
agccaaggac aaagaaagca tcacccactc tggaacaatg tcccctgctg tgaactggtt  11040
catcaggcca tcagggcccc ttgttaagac tctaattacc ctaggactaa gtagaggtgt  11100
tgacgtccaa tgagcgcttt ctgcagacct agcaccaggg aagtgtttgg aaactgcagc  11160
ttcagcccct ctggccatct gctgacctac cccacctgga gcccttaatg ggtcaaacag  11220
caaagtccag gggcagaga ggaggtgctt tggtctataa aggtagtggg gacccagtaa  11280
ccaccgg                                                            11287
```

<210> SEQ ID NO 12
<211> LENGTH: 11178
<212> TYPE: DNA
<213> ORGANISM: Artificial Sequence
<220> FEATURE:
<223> OTHER INFORMATION: Synthetic

<400> SEQUENCE: 12

```
tacagtgcag gggaaagaat agtagacata atagcaacag acatacaaac taaagaatta     60
caaaaacaaa ttacaaaaat tcaaaatttt cgggtttatt acagggacag cagagatcca    120
gtttggttaa ttaattggct ccggtgcccg tcagtgggca gagcgcacat cgcccacagt    180
ccccgagaag ttgggggag gggtcggcaa ttgaaccggt gcctagagaa ggtggcgcgg    240
ggtaaactgg gaaagtgatg tcgtgtactg gctccgcctt tttcccgagg gtgggggaga    300
accgtatata agtgcagtag tcgccgtgaa cgttcttttt cgcaacgggt ttgccgccag    360
aacacaggta agtgccgtgt gtggttcccg cgggcctggc ctctttacgg gttatggccc    420
ttgcgtgcct tgaattactt ccacctggct gcagtacgtg attcttgatc ccgagcttcg    480
ggttggaagt gggtgggaga gttcgaggcc ttgcgcttaa ggagcccctt cgcctcgtgc    540
ttgagttgag gcctggcctg ggcgctgggg ccgccgcgtg cgaatctggt ggcaccttcg    600
cgcctgtctc gctgctttcg ataagtctct agccatttaa aatttttgat gacctgctgc    660
gacgcttttt ttctggcaag atagtcttgt aaatgcgggc caagatctgc acactggtat    720
ttcggttttt ggggccgcgg gcggcgacgg ggcccgtgcg tcccagcgca catgttcggc    780
gaggcggggc ctgcgagcgc ggccaccgag aatcggacgg gggtagtctc aagctggccg    840
gcctgctctg gtgcctggcc tcgcgccgcc gtgtatcgcc ccgccctggg cggcaaggct    900
```

-continued

```
ggcccggtcg gcaccagttg cgtgagcgga aagatggccg cttcccggcc ctgctgcagg    960
gagctcaaaa tggaggacgc ggcgctcggg agagcgggcg ggtgagtcac ccacacaaag   1020
gaaaagggcc tttccgtcct cagccgtcgc ttcatgtgac tccacggagt accgggcgcc   1080
gtccaggcac ctcgattagt tctcgagctt ttggagtacg tcgtctttag gttgggggga   1140
ggggttttat gcgatggagt ttccccacac tgagtgggtg gagactgaag ttaggccagc   1200
ttggcacttg atgtaattct ccttggaatt tgcccttttt gagtttggat cttggttcat   1260
tctcaagcct cagacagtgg ttcaaagttt ttttcttcca tttcaggtgt cgtgaggaat   1320
tcggccatta cggcccgcca ccatggctag attagataaa agtaaagtga ttaacagcgc   1380
attagagctg cttaatgagg tcggaatcga aggtttaaca acccgtaaac tcgcccagaa   1440
gctaggtgta gagcagccta cattgtattg gcatgtaaaa aataagcggg ctttgctcga   1500
cgccttagcc attgagatgt tagataggca ccatactcac ttttgccctt tagaagggga   1560
aagctggcaa gatttttac gtaataacgc taaaagtttt agatgtgctt tactaagtca    1620
tcgcgatgga gcaaaagtac atttaggtac acggcctaca gaaaaacagt atgaaactct   1680
cgaaaatcaa ttagcctttt tatgccaaca aggtttttca ctagagaatg cattatatgc   1740
actcagcgct gtggggcatt ttactttagg ttgcgtattg gaagatcaag agcatcaagt   1800
cgctaaagaa gaaagggaaa cacctactac tgatagtatg ccgccattat tacgacaagc   1860
tatcgaatta tttgatcacc aaggtgcaga gccagccttc ttattcggcc ttgaattgat   1920
catatgcgga ttagaaaaac aacttaaatg tgaaagtggg tcgccaaaaa agaagagaaa   1980
ggtcgacggc ggtggtgctt tgtctcctca gcactctgct gtcactcaag gaagtatcat   2040
caagaacaag gagggcatgg atgctaagtc actaactgcc tggtcccgga cactggtgac   2100
cttcaaggat gtatttgtgg acttcaccag ggaggagtgg aagctgctgg acactgctca   2160
gcagatcgtg tacagaaatg tgatgctgga gaactataag aacctggttt ccttgggtta   2220
tcagcttact aagccagatg tgatcctccg gttggagaag ggagaagagc cctggctggt   2280
ggagagagaa attcaccaag agacccatcc tgattcagag actgcatttg aaatcaaatc   2340
atcagtttaa ggccgcctcg gccatcgata aggatccgga atgcccctct ccctcccccc   2400
cccctaacgt tactggccga agccgcttgg aataaggccg gtgtgcgttt gtctatatgt   2460
tattttccac catattgccg tcttttggca atgtgagggc ccggaaacct ggccctgtct   2520
tcttgacgag cattcctagg ggtctttccc ctctcgccaa aggaatgcaa ggtctgttga   2580
atgtcgtgaa ggaagcagtt cctctggaag cttcttgaag acaaacaacg tctgtagcga   2640
ccctttgcag gcagcggaac cccccacctg gcgacaggtg cctctgcggc caaaagccac   2700
gtgtataaga tacacctgca aaggcggcac aaccccagtg ccacgttgtg agttggatag   2760
ttgtggaaag agtcaaatgg ctctcctcaa gcgtattcaa caaggggctg aaggatgccc   2820
agaaggtacc ccattgtatg ggatctgatc tggggcctcg gtgcacatgc tttacatgtg   2880
tttagtcgag gttaaaaaaa cgtctaggcc ccccgaacca cggggacgtg gttttccttt   2940
gaaaaacacg atgataatat ggccacaacc atgaccgagt acaagcccac ggtgcgcctc   3000
gccacccgcg acgacgtccc ccgggccgta cgcaccctcg ccgccgcgtt cgccgactac   3060
cccgccacgc gccacaccgt cgacccggac cgccacatcg agcgggtcac cgagctgcaa   3120
gaactcttcc tcacgcgcgt cgggctcgac atcggcaagg tgtgggtcgc ggacgacggc   3180
gccgcggtgg cggtctggac cacgccggag agcgtcgaag cgggggcggt gttcgccgag   3240
atcggcccgc gcatggccga gttgagcggt tcccggctgg ccgcgcagca acagatggaa   3300
```

```
ggcctcctgg cgccgcaccg gcccaaggag cccgcgtggt tcctggccac cgtcggcgtc   3360
tcgcccgacc accagggcaa gggtctgggc agcgccgtcg tgctccccgg agtggaggcg   3420
gccgagcgcg ccggggtgcc cgccttcctg gagacctccg cgccccgcaa cctccccttc   3480
tacgagcggc tcggcttcac cgtcaccgcc gacgtcgagg tgcccgaagg accgcgcacc   3540
tggtgcatga cccgcaagcc cggtgcctga gcggccgcaa tcaacctctg gattacaaaa   3600
tttgtgaaag attgactggt attcttaact atgttgctcc ttttacgcta tgtggatacg   3660
ctgctttaat gcctttgtat catgctatta cttcccgtac ggctttcatt ttctcctcct   3720
tgtataaatc ctggttgctg tctctttatg aggagttgtg gcccgttgtc aggcaacgtg   3780
gcgtggtgtg cactgtgttt gctgacgcaa cccccactgg ttggggcatt gccaccacct   3840
atcaactcct ttccgggact ttcgctttcc ccctccctat tgccacggcg gaactcattg   3900
ccgcctgcct tgcccgctgc tggacagggg ctcggctgtt gggcactgac aattccgtgg   3960
tgttgtcggg gaagctgacg tcctttccat ggctgctcgc ctgtgttgcc aactggattc   4020
tgcgcgggac gtccttctgc tacgtccctt cggccctcaa tccagcggac cttccttccc   4080
gcggcctgct gccggttctg cggcctcttc cgcgtcttcg ccttcgccct cagacgagtc   4140
ggatctccct ttgggccgcc tccccgcctg cctgcaggtt tgtcgagacc tagaaaaaca   4200
tggagcaatc acaagtagca atacagcagc taccaatgct gattgtgcct ggctagaagc   4260
acaagaggag gaggaggtgg gttttccagt cacacctcag gtacctttaa gaccaatgac   4320
ttacaaggca gctgtagatc ttagccactt tttaaaagaa aaggggggac tggaagggct   4380
aattcactcc caacgaagac aagatctgct ttttgcttgt actgggtctc tctggttaga   4440
ccagatctga gcctgggagc tctctggcta actagggaac ccactgctta agcctcaata   4500
aagcttgcct tgagtgcttc aagtagtgtg tgcccgtctg ttgtgtgact ctggtaacta   4560
gagatccctc agaccctttt agtcagtgtg gaaaatctct agcagggccc gtttaaaccc   4620
gctgatcagc ctcgactgtg ccttctagtt gccagccatc tgttgtttgc ccctcccccg   4680
tgccttcctt gaccctggaa ggtgccactc ccactgtcct ttcctaataa aatgaggaaa   4740
ttgcatcgca ttgtctgagt aggtgtcatt ctattctggg gggtggggtg gggcaggaca   4800
gcaaggggga ggattgggaa gacaatagca ggcatgctgg ggatgcggtg ggctctatgg   4860
cttctgaggc ggaaagaacc agctggggct ctagggggta tccccacgcg ccctgtagcg   4920
gcgcattaag cgcggcgggt gtggtggtta cgcgcagcgt gaccgctaca cttgccagcg   4980
ccctagcgcc cgctcctttc gctttcttcc cttcctttct cgccacgttc gccggctttc   5040
cccgtcaagc tctaaatcgg ggcatccctt tagggttccg atttagtgct ttacggcacc   5100
tcgaccccaa aaaacttgat tagggtgatg gttcacgtag tgggccatcg ccctgataga   5160
cggtttttcg ccctttgacg ttggagtcca cgttctttaa tagtggactc ttgttccaaa   5220
ctggaacaac actcaaccct atctcggtct attcttttga tttataaggg attttgggga   5280
tttcggccta ttggttaaaa aatgagctga tttaacaaaa atttaacgcg aattaattct   5340
gtggaatgtg tgtcagttag ggtgtggaaa gtccccaggc tccccaggca ggcagaagta   5400
tgcaaagcat gcatctcaat tagtcagcaa ccaggtgtgg aaagtcccca ggctccccag   5460
caggcagaag tatgcaaagc atgcatctca attagtcagc aaccatagtc ccgcccctaa   5520
ctccgcccat cccgccccta actccgccca gttccgccca ttctccgccc catggctgac   5580
taattttttt tatttatgca gaggccgagg ccgcctctgc ctctgagcta ttccagaagt   5640
```

-continued

```
agtgaggagg cttttttgga ggcctaggct tttgcaaaaa gctcccggga gcttgtatat   5700
ccattttcgg atctgatcag cacgtgttga caattaatca tcggcatagt atatcggcat   5760
agtataatac gacaaggtga ggaactaaac catggccaag ttgaccagtg ccgttccggt   5820
gctcaccgcg cgcgacgtcg ccggagcggt cgagttctgg accgaccggc tcgggttctc   5880
ccgggacttc gtggaggacg acttcgccgg tgtggtccgg gacgacgtga ccctgttcat   5940
cagcgcggtc caggaccagg tggtgccgga caacaccctg gcctgggtgt gggtgcgcgg   6000
cctggacgag ctgtacgccg agtggtcgga ggtcgtgtcc acgaacttcc gggacgcctc   6060
cgggccggcc atgaccgaga tcggcgagca gccgtggggg cgggagttcg ccctgcgcga   6120
cccggccggc aactgcgtgc acttcgtggc cgaggagcag gactgacacg tgctacgaga   6180
tttcgattcc accgccgcct tctatgaaag gttgggcttc ggaatcgttt tccgggacgc   6240
cggctggatg atcctccagc gcggggatct catgctggag ttcttcgccc accccaactt   6300
gtttattgca gcttataatg gttacaaata aagcaatagc atcacaaatt tcacaaataa   6360
agcatttttt tcactgcatt ctagttgtgg tttgtccaaa ctcatcaatg tatcttatca   6420
tgtctgtata ccgtcgacct ctagctagag cttggcgtaa tcatggtcat agctgtttcc   6480
tgtgtgaaat tgttatccgc tcacaattcc acacaacata cgagccggaa gcataaagtg   6540
taaagcctgg ggtgcctaat gagtgagcta actcacatta attgcgttgc gctcactgcc   6600
cgctttccag tcgggaaacc tgtcgtgcca gctgcattaa tgaatcggcc aacgcgcggg   6660
gagaggcggt ttgcgtattg ggcgctcttc cgcttcctcg ctcactgact cgctgcgctc   6720
ggtcgttcgg ctgcggcgag cggtatcagc tcactcaaag gcggtaatac ggttatccac   6780
agaatcaggg gataacgcag gaaagaacat gtgagcaaaa ggccagcaaa aggccaggaa   6840
ccgtaaaaag gccgcgttgc tggcgttttt ccataggctc cgcccccctg acgagcatca   6900
caaaaatcga cgctcaagtc agaggtggcg aaacccgaca ggactataaa gataccaggc   6960
gtttccccct ggaagctccc tcgtgcgctc tcctgttccg accctgccgc ttaccggata   7020
cctgtccgcc tttctccctt cgggaagcgt ggcgctttct caatgctcac gctgtaggta   7080
tctcagttcg gtgtaggtcg ttcgctccaa gctgggctgt gtgcacgaac cccccgttca   7140
gcccgaccgc tgcgccttat ccggtaacta tcgtcttgag tccaacccgg taagacacga   7200
cttatcgcca ctggcagcag ccactggtaa caggattagc agagcgaggt atgtaggcgg   7260
tgctacagag ttcttgaagt ggtggcctaa ctacggctac actagaagga cagtatttgg   7320
tatctgcgct ctgctgaagc cagttacctt cggaaaaaga gttggtagct cttgatccgg   7380
caaacaaacc accgctggta gcggtggttt ttttgtttgc aagcagcaga ttacgcgcag   7440
aaaaaaagga tctcaagaag atcctttgat cttttctacg gggtctgacg ctcagtggaa   7500
cgaaaactca cgttaaggga ttttggtcat gagattatca aaaaggatct tcacctagat   7560
ccttttaaat taaaaatgaa gttttaaatc aatctaaagt atatatgagt aaacttggtc   7620
tgacagttac caatgcttaa tcagtgaggc acctatctca gcgatctgtc tatttcgttc   7680
atccatagtt gcctgactcc ccgtcgtgta gataactacg atacgggagg gcttaccatc   7740
tggccccagt gctgcaatga taccgcgaga cccacgctca ccggctccag atttatcagc   7800
aataaaccag ccagccggaa gggccgagcg cagaagtggt cctgcaactt tatccgcctc   7860
catccagtct attaattgtt gccgggaagc tagagtaagt agttcgccag ttaatagttt   7920
gcgcaacgtt gttgccattg ctacaggcat cgtggtgtca cgctcgtcgt ttggtatggc   7980
ttcattcagc tccggttccc aacgatcaag gcgagttaca tgatccccca tgttgtgcaa   8040
```

aaaagcggtt agctccttcg gtcctccgat cgttgtcaga agtaagttgg ccgcagtgtt 8100
atcactcatg gttatggcag cactgcataa ttctcttact gtcatgccat ccgtaagatg 8160
cttttctgtg actggtgagt actcaaccaa gtcattctga gaatagtgta tgcggcgacc 8220
gagttgctct tgcccggcgt caatacggga taataccgcg ccacatagca gaactttaaa 8280
agtgctcatc attggaaaac gttcttcggg gcgaaaactc tcaaggatct taccgctgtt 8340
gagatccagt tcgatgtaac ccactcgtgc acccaactga tcttcagcat cttttacttt 8400
caccagcgtt tctgggtgag caaaaacagg aaggcaaaat gccgcaaaaa agggaataag 8460
ggcgacacgg aaatgttgaa tactcatact cttccttttt caatattatt gaagcattta 8520
tcagggttat tgtctcatga gcggatacat atttgaatgt atttagaaaa ataaacaaat 8580
aggggttccg cgcacatttc cccgaaaagt gccacctgac gtcgacggat cgggagatct 8640
cccgatcccc tatggtgcac tctcagtaca atctgctctg atgccgcata gttaagccag 8700
tatctgctcc ctgcttgtgt gttggaggtc gctgagtagt gcgcgagcaa aatttaagct 8760
acaacaaggc aaggcttgac cgacaattgc atgaagaatc tgcttagggt taggcgtttt 8820
gcgctgcttc gcgatgtacg ggccagatat acgcgttgac attgattatt gactagttat 8880
taatagtaat caattacggg gtcattagtt catagcccat atatggagtt ccgcgttaca 8940
taacttacgg taaatggccc gcctggctga ccgcccaacg acccccgccc attgacgtca 9000
ataatgacgt atgttcccat agtaacgcca atagggactt tccattgacg tcaatgggtg 9060
gactatttac ggtaaactgc ccacttggca gtacatcaag tgtatcatat gccaagtacg 9120
ccccctattg acgtcaatga cggtaaatgg cccgcctggc attatgccca gtacatgacc 9180
ttatgggact ttcctacttg gcagtacatc tacgtattag tcatcgctat taccatggtg 9240
atgcggtttt ggcagtacat caatgggcgt ggatagcggt ttgactcacg gggatttcca 9300
agtctccacc ccattgacgt caatgggagt ttgttttggc accaaaatca acgggacttt 9360
ccaaaatgtc gtaacaactc cgccccattg acgcaaatgg gcggtaggcg tgtacggtgg 9420
gaggtctata taagcagagc ggtttaaact taagcttggt accgagctca ctagtccagt 9480
gtggtggcag atatccagca cagtggcggc cgctcgagtc tagagggccc gttttgcctg 9540
tactgggtct ctctggttag accagatctg agcctgggag ctctctggct aactagggaa 9600
cccactgctt aagcctcaat aaagcttgcc ttgagtgctt caagtagtgt gtgcccgtct 9660
gttgtgtgac tctggtaact agagatccct cagacccttt tagtcagtgt ggaaaatctc 9720
tagcagtggc gcccgaacag ggacttgaaa gcgaaaggga aaccagagga gctctctcga 9780
cgcaggactc ggcttgctga agcgcgcacg gcaagaggcg aggggcggcg actggtgagt 9840
acgccaaaaa ttttgactag cggaggctag aaggagagag atgggtgcga gagcgtcagt 9900
attaagcggg ggagaattag atcgcgatgg gaaaaaattc ggttaaggcc agggggaaag 9960
aaaaaatata aattaaaaca tatagtatgg gcaagcaggg agctagaacg attcgcagtt 10020
aatcctggcc tgttagaaac atcagaaggc tgtagacaaa tactgggaca gctacaacca 10080
tcccttcaga caggatcaga agaacttaga tcattatata atacagtagc aaccctctat 10140
tgtgtgcatc aaaggataga gataaaagac accaaggaag ctttagacaa gatagaggaa 10200
gagcaaaaca aaagtaagac caccgcacag caagcggccg ctgatcttca gacctggagg 10260
aggagatatg agggacaatt ggagaagtga attatataaa tataaagtag taaaaattga 10320
accattagga gtagcaccca ccaaggcaaa gagaagagtg gtgcagagag aaaaaagagc 10380
agtgggaata ggagctttgt tccttgggtt cttgggagca gcaggaagca ctatgggcgc 10440
agcgtcaatg acgctgacgg tacaggccag acaattattg tctggtatag tgcagcagca 10500
gaacaatttg ctgagggcta ttgaggcgca acagcatctg ttgcaactca cagtctgggg 10560
catcaagcag ctccaggcaa gaatcctggc tgtggaaaga tacctaaagg atcaacagct 10620
cctggggatt tggggttgct ctggaaaact catttgcacc actgctgtgc cttggaatgc 10680
tagttggagt aataaatctc tggaacagat ttggaatcac acgacctgga tggagtggga 10740
cagagaaatt aacaattaca caagcttaat acactcctta attgaagaat cgcaaaacca 10800
gcaagaaaag aatgaacaag aattattgga attagataaa tgggcaagtt tgtggaattg 10860
gtttaacata acaaattggc tgtggtatat agaaattatt cataatgata gtaggaggct 10920
tggtaggttt aagaatagtt tttgctgtac tttctatagt gaatagagtt aggcagggat 10980
attcaccatt atcgtttcag acccacctcc caaccccgag gggacccgac aggcccgaag 11040
gaatagaaga agaaggtgga gagagagaca gagacagatc cattcgatta gtgaacggat 11100
cggcactgcg tgcgccaatt ctgcagacaa atggcagtat tcatccacaa ttttaaaaga 11160
aaagggggga ttgggggg 11178

<210> SEQ ID NO 13
<211> LENGTH: 10573
<212> TYPE: DNA
<213> ORGANISM: Artificial Sequence
<220> FEATURE:
<223> OTHER INFORMATION: Synthetic

<400> SEQUENCE: 13
aatgaagcta ctgtcttcta tcgaacaagc atgcgatatt tgccgactta aaaagctcaa 60
gtgctccaaa gaaaaaccga agtgcgccaa gtgtctgaag aacaactggg agtgtcgcta 120
ctctcccaaa accaaaaggt ctccgctgac tagggcacat ctgacagaag tggaatcaag 180
gctagaaaga ctggaacagc tatttctact gatttttcct cgagaagacc ttgacatgat 240
tttgaaaatg gattctttac aggatataaa agcattgtta acaggattat ttgtacaaga 300
taatgtgaat aaagatgccg tcacagatag attggcttca gtggagactg atatgcctct 360
aacattgaga cagcatagaa taagtgcgac atcatcatcg gaagagagta gtaacaaagg 420
tcaaagacag ttgactgtat cgattgactc ggcagctcat catgataact ccacaattcc 480
gttggatttt atgcccaggg atgctcttca tggatttgat tggtctgaag aggatgacat 540
gtcggatggc ttgcccttcc tgaaaacgga ccccaacaat aatgggttct ttggcgacgg 600
ttctctctta tgtattcttc gatctattgg ctttaaaccg gaaaattaca cgaactctaa 660
cgttaacagg ctcccgacca tgattacgga tagatacacg ttggcttcta gatccacaac 720
atcccgttta cttcaaagtt atctcaataa ttttcacccc tactgcccta tcgtgcactc 780
accgacgcta atgatgttgt ataataacca gattgaaatc gcgtcgaagg atcaatggca 840
aatccttttt aactgcatat tagccattgg agcctggtgt atagaggggg aatctactga 900
tatagatgtt ttttactatc aaaatgctaa atctcatttg acgagcaagg tcttcgagtc 960
aggttccata attttggtga cagccctaca tcttctgtcg cgatatacac agtggaggca 1020
gaaaacaaat actagctata attttcacag cttttccata agaatggcca tatcattggg 1080
cttgaatagg gacctcccct cgtccttcag tgatagcagc attctggaac aaagacgccg 1140
aatttggtgg tctgtctact cttgggagat ccaattgtcc ctgctttatg gtcgatccat 1200 ccagcttttct cagaatacaa tctccttccc ttcttctgtc gacgatgtgc agcgtaccac 1260

```
aacaggtccc accatatatc atggcatcat tgaaacagca aggctcttac aagttttcac   1320

aaaaatctat gaactagaca aaacagtaac tgcagaaaaa agtcctatat gtgcaaaaaa   1380

atgcttgatg atttgtaatg agattgagga ggtttcgaga caggcaccaa agtttttaca   1440

aatggatatt tccaccaccg ctctaaccaa tttgttgaag gaacaccctt ggctatcctt   1500

tacaagattc gaactgaagt ggaaacagtt gtctcttatc atttatgtat taagagattt   1560

tttcactaat tttacccaga aaaagtcaca actagaacag gatcaaaatg atcatcaaag   1620

ttatgaagtt aaacgatgct ccatcatgtt aagcgatgca gcacaaagaa ctgttatgtc   1680

tgtaagtagc tatatggaca atcataatgt caccccatat tttgcctgga attgttctta   1740

ttacttgttc aatgcagtcc tagtacccat aaagactcta ctctcaaact caaaatcgaa   1800

tgctgagaat aacgagaccg cacaattatt acaacaaatt aacactgttc tgatgctatt   1860

aaaaaaactg gccactttta aaatccagac ttgtgaaaaa tacattcaag tactggaaga   1920

ggtatgtgcg ccgtttctgt tatcacagtg tgcaatccca ttaccgcata tcagttataa   1980

caatagtaat ggtagcgcca ttaaaaatat tgtcggttct gcaactatcg cccaataccc   2040

tactcttccg gaggaaaatg tcaacaatat cagtgttaaa tatgtttctc ctggctcagt   2100

agggccttca cctgtgccat tgaaatcagg agcaagtttc agtgatctag tcaagctgtt   2160

atctaaccgt ccaccctctc gtaactctcc agtgacaata ccaagaagca caccttcgca   2220

tcgctcagtc acgcctttc tagggcaaca gcaacagctg caatcattag tgccactgac   2280

cccgtctgct ttgtttggtg gcgccaattt taatcaaagt gggaatattg ctgatagctc   2340

attgtccttc actttcacta acagtagcaa cggtccgaac ctcataacaa ctcaaacaaa   2400

ttctcaagcg ctttcacaac caattgcctc ctctaacgtt catgataact tcatgaataa   2460

tgaaatcacg gctagtaaaa ttgatgatgg taataattca aaaccactgt cacctggttg   2520

gacggaccaa actgcgtata acgcgtttgg aatcactaca gggatgttta ataccactac   2580

aatggatgat gtatataact atctattcga tgatgaagat accccaccaa acccaaaaaa   2640

agagtaagaa ttcgatatca agcttatcga taatcaacct ctggattaca aaatttgtga   2700

aagattgact ggtattctta actatgttgc tccttttacg ctatgtggat acgctgcttt   2760

aatgcctttg tatcatgcta ttacttcccg tacggctttc attttctcct ccttgtataa   2820

atcctggttg ctgtctcttt atgaggagtt gtggcccgtt gtcaggcaac gtggcgtggt   2880

gtgcactgtg tttgctgacg caacccccac tggttggggc attgccacca cctatcaact   2940

cctttccggg actttcgctt tccccctccc tattgccacg gcggaactca ttgccgcctg   3000

ccttgcccgc tgctggacag gggctcggct gttgggcact gacaattccg tggtgttgtc   3060

ggggaagctg acgtcctttc catggctgct cgcctgtgtt gccaactgga ttctgcgcgg   3120

gacgtccttc tgctacgtcc cttcggccct caatccagcg gaccttcctt cccgcggcct   3180

gctgccggtt ctgcggcctc ttccgcgtct tcgccttcgc cctcagacga gtcggatctc   3240

cctttgggcc gcctccccgc ctgcctgcag gtttgtcgag acctagaaaa acatggagca   3300

atcacaagta gcaatacagc agctaccaat gctgattgtg cctggctaga agcacaagag   3360

gaggaggagg tgggttttcc agtcacacct caggtacctt taagaccaat gacttacaag   3420

gcagctgtag atcttagcca ctttttaaaa gaaaaggggg gactggaagg gctaattcac   3480

tcccaacgaa gacaagatct gctttttgct tgtactgggt ctctctggtt agaccagatc   3540

tgagcctggg agctctctgg ctaactaggg aacccactgc ttaagcctca ataaagcttg   3600
```

-continued

```
ccttgagtgc ttcaagtagt gtgtgcccgt ctgttgtgtg actctggtaa ctagagatcc   3660
ctcagaccct tttagtcagt gtggaaaatc tctagcaggg cccgtttaaa cccgctgatc   3720
agcctcgact gtgccttcta gttgccagcc atctgttgtt tgcccctccc ccgtgccttc   3780
cttgaccctg gaaggtgcca ctcccactgt cctttcctaa taaaatgagg aaattgcatc   3840
gcattgtctg agtaggtgtc attctattct ggggggtggg gtggggcagg acagcaaggg   3900
ggaggattgg gaagacaata gcaggcatgc tggggatgcg gtgggctcta tggcttctga   3960
ggcggaaaga accagctggg gctctagggg gtatccccac gcgccctgta gcggcgcatt   4020
aagcgcggcg ggtgtggtgg ttacgcgcag cgtgaccgct acacttgcca gcgccctagc   4080
gcccgctcct ttcgctttct tcccttcctt tctcgccacg ttcgccggct ttccccgtca   4140
agctctaaat cggggcatcc ctttagggtt ccgatttagt gctttacggc acctcgaccc   4200
caaaaaactt gattagggtg atggttcacg tagtgggcca tcgccctgat agacggtttt   4260
tcgccctttg acgttggagt ccacgttctt taatagtgga ctcttgttcc aaactggaac   4320
aacactcaac cctatctcgg tctattcttt tgatttataa gggattttgg ggatttcggc   4380
ctattggtta aaaaatgagc tgatttaaca aaaatttaac gcgaattaat tctgtggaat   4440
gtgtgtcagt tagggtgtgg aaagtcccca ggctccccag gcaggcagaa gtatgcaaag   4500
catgcatctc aattagtcag caaccaggtg tggaaagtcc ccaggctccc cagcaggcag   4560
aagtatgcaa agcatgcatc tcaattagtc agcaaccata gtcccgcccc taactccgcc   4620
catcccgccc ctaactccgc ccagttccgc ccattctccg ccccatggct gactaatttt   4680
ttttatttat gcagaggccg aggccgcctc tgcctctgag ctattccaga agtagtgagg   4740
aggctttttt ggaggcctag gcttttgcaa aaagctcccg ggagcttgta tatccatttt   4800
cggatctgat cagcacgtgt tgacaattaa tcatcggcat agtatatcgg catagtataa   4860
tacgacaagg tgaggaacta aaccatggcc aagttgacca gtgccgttcc ggtgctcacc   4920
gcgcgcgacg tcgccggagc ggtcgagttc tggaccgacc ggctcgggtt ctcccgggac   4980
ttcgtggagg acgacttcgc cggtgtggtc cgggacgacg tgaccctgtt catcagcgcg   5040
gtccaggacc aggtggtgcc ggacaacacc ctggcctggg tgtgggtgcg cggcctggac   5100
gagctgtacg ccgagtggtc ggaggtcgtg tccacgaact tccgggacgc ctccgggccg   5160
gccatgaccg agatcggcga gcagccgtgg gggcgggagt tcgccctgcg cgacccggcc   5220
ggcaactgcg tgcacttcgt ggccgaggag caggactgac acgtgctacg agatttcgat   5280
tccaccgccg ccttctatga aaggttgggc ttcggaatcg ttttccggga cgccggctgg   5340
atgatcctcc agcgcgggga tctcatgctg gagttcttcg cccaccccaa cttgtttatt   5400
gcagcttata atggttacaa ataaagcaat agcatcacaa atttcacaaa taaagcattt   5460
ttttcactgc attctagttg tggtttgtcc aaactcatca atgtatctta tcatgtctgt   5520
ataccgtcga cctctagcta gagcttggcg taatcatggt catagctgtt tcctgtgtga   5580
aattgttatc cgctcacaat tccacacaac atacgagccg gaagcataaa gtgtaaagcc   5640
tggggtgcct aatgagtgag ctaactcaca ttaattgcgt tgcgctcact gcccgctttc   5700
cagtcgggaa acctgtcgtg ccagctgcat taatgaatcg gccaacgcgc ggggagaggc   5760
ggtttgcgta ttgggcgctc ttccgcttcc tcgctcactg actcgctgcg ctcggtcgtt   5820
cggctgcggc gagcggtatc agctcactca aaggcggtaa tacggttatc cacagaatca   5880
ggggataacg caggaaagaa catgtgagca aaaggccagc aaaaggccag gaaccgtaaa   5940
aaggccgcgt tgctggcgtt tttccatagg ctccgccccc ctgacgagca tcacaaaaat   6000
```

cgacgctcaa gtcagaggtg gcgaaacccg acaggactat aaagatacca ggcgtttccc 6060
cctggaagct ccctcgtgcg ctctcctgtt ccgaccctgc cgcttaccgg atacctgtcc 6120
gcctttctcc cttcgggaag cgtggcgctt tctcaatgct cacgctgtag gtatctcagt 6180
tcggtgtagg tcgttcgctc caagctgggc tgtgtgcacg aaccccccgt tcagcccgac 6240
cgctgcgcct tatccggtaa ctatcgtctt gagtccaacc cggtaagaca cgacttatcg 6300
ccactggcag cagccactgg taacaggatt agcagagcga ggtatgtagg cggtgctaca 6360
gagttcttga agtggtggcc taactacggc tacactagaa ggacagtatt tggtatctgc 6420
gctctgctga agccagttac cttcggaaaa agagttggta gctcttgatc cggcaaacaa 6480
accaccgctg gtagcggtgg tttttttgtt tgcaagcagc agattacgcg cagaaaaaaa 6540
ggatctcaag aagatccttt gatcttttct acggggtctg acgctcagtg gaacgaaaac 6600
tcacgttaag ggattttggt catgagatta tcaaaaagga tcttcaccta gatcctttta 6660
aattaaaaat gaagttttaa atcaatctaa agtatatatg agtaaacttg gtctgacagt 6720
taccaatgct taatcagtga ggcacctatc tcagcgatct gtctatttcg ttcatccata 6780
gttgcctgac tccccgtcgt gtagataact acgatacggg agggcttacc atctggcccc 6840
agtgctgcaa tgataccgcg agacccacgc tcaccggctc cagatttatc agcaataaac 6900
cagccagccg gaagggccga gcgcagaagt ggtcctgcaa ctttatccgc ctccatccag 6960
tctattaatt gttgccggga agctagagta agtagttcgc cagttaatag tttgcgcaac 7020
gttgttgcca ttgctacagg catcgtggtg tcacgctcgt cgtttggtat ggcttcattc 7080
agctccggtt cccaacgatc aaggcgagtt acatgatccc ccatgttgtg caaaaaagcg 7140
gttagctcct tcggtcctcc gatcgttgtc agaagtaagt tggccgcagt gttatcactc 7200
atggttatgg cagcactgca taattctctt actgtcatgc catccgtaag atgcttttct 7260
gtgactggtg agtactcaac caagtcattc tgagaatagt gtatgcggcg accgagttgc 7320
tcttgcccgg cgtcaatacg ggataatacc gcgccacata gcagaacttt aaaagtgctc 7380
atcattggaa aacgttcttc ggggcgaaaa ctctcaagga tcttaccgct gttgagatcc 7440
agttcgatgt aacccactcg tgcacccaac tgatcttcag catcttttac tttcaccagc 7500
gtttctgggt gagcaaaaac aggaaggcaa aatgccgcaa aaaagggaat aagggcgaca 7560
cggaaatgtt gaatactcat actcttcctt tttcaatatt attgaagcat ttatcagggt 7620
tattgtctca tgagcggata catatttgaa tgtatttaga aaaataaaca aataggggtt 7680
ccgcgcacat ttccccgaaa agtgccacct gacgtcgacg gatcgggaga tctcccgatc 7740
ccctatggtg cactctcagt acaatctgct ctgatgccgc atagttaagc cagtatctgc 7800
tccctgcttg tgtgttggag gtcgctgagt agtgcgcgag caaaatttaa gctacaacaa 7860
ggcaaggctt gaccgacaat tgcatgaaga atctgcttag ggttaggcgt tttgcgctgc 7920
ttcgcgatgt acgggccaga tatacgcgtt gacattgatt attgactagt tattaatagt 7980
aatcaattac ggggtcatta gttcatagcc catatatgga gttccgcgtt acataactta 8040
cggtaaatgg cccgcctggc tgaccgccca acgacccccg cccattgacg tcaataatga 8100
cgtatgttcc catagtaacg ccaataggga ctttccattg acgtcaatgg gtggactatt 8160
tacggtaaac tgcccacttg gcagtacatc aagtgtatca tatgccaagt acgcccccta 8220
ttgacgtcaa tgacggtaaa tggcccgcct ggcattatgc ccagtacatg accttatggg 8280
actttcctac ttggcagtac atctacgtat tagtcatcgc tattaccatg gtgatgcggt 8340

-continued

```
tttggcagta catcaatggg cgtggatagc ggtttgactc acggggattt ccaagtctcc   8400

accccattga cgtcaatggg agtttgtttt ggcaccaaaa tcaacgggac tttccaaaat   8460

gtcgtaacaa ctccgcccca ttgacgcaaa tgggcggtag gcgtgtacgg tgggaggtct   8520

atataagcag agctctctgg ctaactagag aacccactgc ttactggctt atcgaaatta   8580

atacgactca ctatagggag acccaagctg gtttaaactt aagcttggta ccgagctcac   8640

tagtccagtg tggtggcaga tatccagcac agtggcggcc gctcgagggg cccgttttgc   8700

ctgtactggg tctctctggt tagaccagat ctgagcctgg gagctctctg gctaactagg   8760

gaacccactg cttaagcctc aataaagctt gccttgagtg cttcaagtag tgtgtgcccg   8820

tctgttgtgt gactctggta actagagatc cctcagaccc ttttagtcag tgtggaaaat   8880

ctctagcagt ggcgcccgaa cagggacttg aaagcgaaag ggaaaccaga ggagctctct   8940

cgacgcagga ctcggcttgc tgaagcgcgc acggcaagag gcgaggggcg gcgactggtg   9000

agtacgccaa aaattttgac tagcggaggc tagaaggaga gagatgggtg cgagagcgtc   9060

agtattaagc gggggagaat tagatcgcga tgggaaaaaa ttcggttaag gccaggggga   9120

aagaaaaaat ataaattaaa acatatagta tgggcaagca gggagctaga acgattcgca   9180

gttaatcctg gcctgttaga aacatcagaa ggctgtagac aaatactggg acagctacaa   9240

ccatcccttc agacaggatc agaagaactt agatcattat ataatacagt agcaaccctc   9300

tattgtgtgc atcaaaggat agagataaaa gacaccaagg aagctttaga caagatagag   9360

gaagagcaaa acaaaagtaa gaccaccgca cagcaagcgg ccgctgatct tcagacctgg   9420

aggaggagat atgagggaca attggagaag tgaattatat aaatataaag tagtaaaaat   9480

tgaaccatta ggagtagcac ccaccaaggc aaagagaaga gtggtgcaga gagaaaaaag   9540

agcagtggga ataggagctt tgttccttgg gttcttggga gcagcaggaa gcactatggg   9600

cgcagcgtca atgacgctga cggtacaggc cagacaatta ttgtctggta tagtgcagca   9660

gcagaacaat ttgctgaggg ctattgaggc gcaacagcat ctgttgcaac tcacagtctg   9720

gggcatcaag cagctccagg caagaatcct ggctgtggaa agatacctaa aggatcaaca   9780

gctcctgggg atttggggtt gctctggaaa actcatttgc accactgctg tgccttggaa   9840

tgctagttgg agtaataaat ctctggaaca gatttggaat cacacgacct ggatggagtg   9900

ggacagagaa attaacaatt acacaagctt aatacactcc ttaattgaag aatcgcaaaa   9960

ccagcaagaa aagaatgaac aagaattatt ggaattagat aaatgggcaa gtttgtggaa  10020

ttggtttaac ataacaaatt ggctgtggta tataaaatta ttcataatga tagtaggagg  10080

cttggtaggt ttaagaatag tttttgctgt actttctata gtgaatagag ttaggcaggg  10140

atattcacca ttatcgtttc agacccacct cccaaccccg aggggacccg acaggccctt  10200

aattaatccc ctgattctgt ggataaccgt attaccgcct ttgagtgagc tgcacctagt  10260

acggattaga agccgccgag cgggtgacag ccctccgaag gaagactctc ctccgtgcgt  10320

cctcgtcttc accggtcgcg ttcctgaaac gcagatgtgc ctcgcgccgc actgctccga  10380

acaatgtcga ctctagaggt aaactcgacc tatataagca gagctcgttt agtgaaccgt  10440

cagatcgcct ggagacgcca tccacgctgt tttgacctcc atagaagaca ccgggaccga  10500

tccagcctcc gcggccccga attgaattcg aagcaggagt agacgccggc cattacggcc  10560

tgccaccgtt aat                                                     10573
```

<210> SEQ ID NO 14
<211> LENGTH: 11022

<212> TYPE: DNA
<213> ORGANISM: Artificial Sequence
<220> FEATURE:
<223> OTHER INFORMATION: Synthetic

<400> SEQUENCE: 14

```
cgcgatcaca tggtcctgct ggagttcgtg accgccgccg ggatcactct cggcatggac     60
gagctgtaca agtaagcggc cgcaatcaac ctctggatta caaaatttgt gaaagattga    120
ctggtattct taactatgtt gctcctttta cgctatgtgg atacgctgct ttaatgcctt    180
tgtatcatgc tattacttcc cgtacggctt tcattttctc ctccttgtat aaatcctggt    240
tgctgtctct ttatgaggag ttgtggcccg ttgtcaggca acgtggcgtg gtgtgcactg    300
tgtttgctga cgcaaccccc actggttggg gcattgccac cacctatcaa ctcctttccg    360
ggactttcgc tttccccctc cctattgcca cggcggaact cattgccgcc tgccttgccc    420
gctgctggac aggggctcgg ctgttgggca ctgacaattc cgtggtgttg tcggggaagc    480
tgacgtcctt tccatggctg ctcgcctgtg ttgccaactg gattctgcgc gggacgtcct    540
tctgctacgt cccttcggcc ctcaatccag cggaccttcc ttcccgcggc ctgctgccgg    600
ttctgcggcc tcttccgcgt cttcgccttc gccctcagac gagtcggatc tccctttggg    660
ccgcctcccc gcctgcctgc aggtttgtcg agacctagaa aaacatggag caatcacaag    720
tagcaataca gcagctacca atgctgattg tgcctggcta gaagcacaag aggaggagga    780
ggtgggtttt ccagtcacac ctcaggtacc tttaagacca atgacttaca aggcagctgt    840
agatcttagc cactttttaa aagaaaaggg gggactggaa gggctaattc actcccaacg    900
aagacaagat ctgctttttg cttgtactgg gtctctctgg ttagaccaga tctgagcctg    960
ggagctctct ggctaactag ggaacccact gcttaagcct caataaagct tgccttgagt   1020
gcttcaagta gtgtgtgccc gtctgttgtg tgactctggt aactagagat ccctcagacc   1080
cttttagtca gtgtggaaaa tctctagcag ggcccgttta aacccgctga tcagcctcga   1140
ctgtgccttc tagttgccag ccatctgttg tttgcccctc ccccgtgcct tccttgaccc   1200
tggaaggtgc cactcccact gtcctttcct aataaaatga ggaaattgca tcgcattgtc   1260
tgagtaggtg tcattctatt ctggggggtg gggtggggca ggacagcaag ggggaggatt   1320
gggaagacaa tagcaggcat gctggggatg cggtgggctc tatggcttct gaggcggaaa   1380
gaaccagctg gggctctagg gggtatcccc acgcgccctg tagcggcgca ttaagcgcgg   1440
cgggtgtggt ggttacgcgc agcgtgaccg ctacacttgc cagcgcccta gcgcccgctc   1500
ctttcgcttt cttcccttcc tttctcgcca cgttcgccgg ctttccccgt caagctctaa   1560
atcggggcat ccctttaggg ttccgattta gtgctttacg gcacctcgac cccaaaaaac   1620
ttgattaggg tgatggttca cgtagtgggc catcgccctg atagacggtt tttcgccctt   1680
tgacgttgga gtccacgttc tttaatagtg gactcttgtt ccaaactgga acaacactca   1740
accctatctc ggtctattct tttgatttat aagggatttt ggggatttcg gcctattggt   1800
taaaaaatga gctgatttaa caaaaattta acgcgaatta attctgtgga atgtgtgtca   1860
gttagggtgt ggaaagtccc caggctcccc aggcaggcag aagtatgcaa agcatgcatc   1920
tcaattagtc agcaaccagg tgtggaaagt ccccaggctc cccagcaggc agaagtatgc   1980
aaagcatgca tctcaattag tcagcaacca tagtcccgcc cctaactccg cccatcccgc   2040
ccctaactcc gcccagttcc gcccattctc cgccccatgg ctgactaatt ttttttattt   2100
atgcagaggc cgaggccgcc tctgcctctg agctattcca gaagtagtga ggaggctttt   2160
```

-continued ttggaggcct aggcttttgc aaaaagctcc cgggagcttg tatatccatt ttcggatctg 2220
atcagcacgt gttgacaatt aatcatcggc atagtatatc ggcatagtat aatacgacaa 2280
ggtgaggaac taaaccatgg ccaagttgac cagtgccgtt ccggtgctca ccgcgcgcga 2340
cgtcgccgga gcggtcgagt tctggaccga ccggctcggg ttctcccggg acttcgtgga 2400
ggacgacttc gccggtgtgg tccgggacga cgtgaccctg ttcatcagcg cggtccagga 2460
ccaggtggtg ccggacaaca ccctggcctg ggtgtgggtg cgcggcctgg acgagctgta 2520
cgccgagtgg tcggaggtcg tgtccacgaa cttccgggac gcctccgggc cggccatgac 2580
cgagatcggc gagcagccgt gggggcggga gttcgccctg cgcgacccgg ccggcaactg 2640
cgtgcacttc gtggccgagg agcaggactg acacgtgcta cgagatttcg attccaccgc 2700
cgccttctat gaaaggttgg gcttcggaat cgttttccgg gacgccggct ggatgatcct 2760
ccagcgcggg gatctcatgc tggagttctt cgcccacccc aacttgttta ttgcagctta 2820
taatggttac aaataaagca atagcatcac aaatttcaca aataaagcat ttttttcact 2880
gcattctagt tgtggtttgt ccaaactcat caatgtatct tatcatgtct gtataccgtc 2940
gacctctagc tagagcttgg cgtaatcatg gtcatagctg tttcctgtgt gaaattgtta 3000
tccgctcaca attccacaca acatacgagc cggaagcata aagtgtaaag cctggggtgc 3060
ctaatgagtg agctaactca cattaattgc gttgcgctca ctgcccgctt tccagtcggg 3120
aaacctgtcg tgccagctgc attaatgaat cggccaacgc gcggggagag gcggtttgcg 3180
tattgggcgc tcttccgctt cctcgctcac tgactcgctg cgctcggtcg ttcggctgcg 3240
gcgagcggta tcagctcact caaaggcggt aatacggtta tccacagaat caggggataa 3300
cgcaggaaag aacatgtgag caaaaggcca gcaaaaggcc aggaaccgta aaaaggccgc 3360
gttgctggcg tttttccata ggctccgccc ccctgacgag catcacaaaa atcgacgctc 3420
aagtcagagg tggcgaaacc cgacaggact ataaagatac caggcgtttc cccctggaag 3480
ctccctcgtg cgctctcctg ttccgaccct gccgcttacc ggatacctgt ccgcctttct 3540
cccttcggga agcgtggcgc tttctcaatg ctcacgctgt aggtatctca gttcggtgta 3600
ggtcgttcgc tccaagctgg gctgtgtgca cgaacccccc gttcagcccg accgctgcgc 3660
cttatccggt aactatcgtc ttgagtccaa cccggtaaga cacgacttat cgccactggc 3720
agcagccact ggtaacagga ttagcagagc gaggtatgta ggcggtgcta cagagttctt 3780
gaagtggtgg cctaactacg gctacactag aaggacagta tttggtatct gcgctctgct 3840
gaagccagtt accttcggaa aaagagttgg tagctcttga tccggcaaac aaaccaccgc 3900
tggtagcggt ggtttttttg tttgcaagca gcagattacg cgcagaaaaa aaggatctca 3960
agaagatcct ttgatctttt ctacggggtc tgacgctcag tggaacgaaa actcacgtta 4020
agggattttg gtcatgagat tatcaaaaag gatcttcacc tagatccttt taaattaaaa 4080
atgaagtttt aaatcaatct aaagtatata tgagtaaact tggtctgaca gttaccaatg 4140
cttaatcagt gaggcaccta tctcagcgat ctgtctattt cgttcatcca tagttgcctg 4200
actccccgtc gtgtagataa ctacgatacg ggagggctta ccatctggcc ccagtgctgc 4260
aatgataccg cgagacccac gctcaccggc tccagattta tcagcaataa accagccagc 4320
cggaagggcc gagcgcagaa gtggtcctgc aactttatcc gcctccatcc agtctattaa 4380
ttgttgccgg gaagctagag taagtagttc gccagttaat agtttgcgca acgttgttgc 4440
cattgctaca ggcatcgtgg tgtcacgctc gtcgtttggt atggcttcat tcagctccgg 4500
ttcccaacga tcaaggcgag ttacatgatc ccccatgttg tgcaaaaaag cggttagctc 4560

```
cttcggtcct ccgatcgttg tcagaagtaa gttggccgca gtgttatcac tcatggttat   4620
ggcagcactg cataattctc ttactgtcat gccatccgta agatgctttt ctgtgactgg   4680
tgagtactca accaagtcat tctgagaata gtgtatgcgg cgaccgagtt gctcttgccc   4740
ggcgtcaata cgggataata ccgcgccaca tagcagaact ttaaaagtgc tcatcattgg   4800
aaaacgttct tcggggcgaa aactctcaag gatcttaccg ctgttgagat ccagttcgat   4860
gtaacccact cgtgcaccca actgatcttc agcatctttt actttcacca gcgtttctgg   4920
gtgagcaaaa acaggaaggc aaaatgccgc aaaaaaggga ataagggcga cacggaaatg   4980
ttgaatactc atactcttcc tttttcaata ttattgaagc atttatcagg gttattgtct   5040
catgagcgga tacatatttg aatgtattta gaaaaataaa caaatagggg ttccgcgcac   5100
atttccccga aaagtgccac ctgacgtcga cggatcggga gatctcccga tcccctatgg   5160
tgcactctca gtacaatctg ctctgatgcc gcatagttaa gccagtatct gctccctgct   5220
tgtgtgttgg aggtcgctga gtagtgcgcg agcaaaattt aagctacaac aaggcaaggc   5280
ttgaccgaca attgcatgaa gaatctgctt agggttaggc gttttgcgct gcttcgcgat   5340
gtacgggcca gatatacgcg ttgacattga ttattgacta gttattaata gtaatcaatt   5400
acggggtcat tagttcatag cccatatatg gagttccgcg ttacataact tacggtaaat   5460
ggcccgcctg gctgaccgcc caacgacccc cgcccattga cgtcaataat gacgtatgtt   5520
cccatagtaa cgccaatagg gactttccat tgacgtcaat gggtggacta tttacggtaa   5580
actgcccact tggcagtaca tcaagtgtat catatgccaa gtacgccccc tattgacgtc   5640
aatgacggta aatggcccgc ctggcattat gcccagtaca tgaccttatg ggactttcct   5700
acttggcagt acatctacgt attagtcatc gctattacca tggtgatgcg gttttggcag   5760
tacatcaatg ggcgtggata gcggtttgac tcacggggat ttccaagtct ccaccccatt   5820
gacgtcaatg ggagtttgtt ttggcaccaa aatcaacggg actttccaaa atgtcgtaac   5880
aactccgccc cattgacgca aatgggcggt aggcgtgtac ggtgggaggt ctatataagc   5940
agagctctct ggctaactag agaacccact gcttactggc ttatcgaaat taatacgact   6000
cactataggg agacccaagc tggtttaaac ttaagcttgg taccgagctc actagtccag   6060
tgtggtggca gatatccagc acagtggcgg ccgctcgagt ctagagggcc cgttttgcct   6120
gtactgggtc tctctggtta gaccagatct gagcctggga gctctctggc taactaggga   6180
acccactgct taagcctcaa taaagcttgc cttgagtgct tcaagtagtg tgtgcccgtc   6240
tgttgtgtga ctctggtaac tagagatccc tcagaccctt ttagtcagtg tggaaaatct   6300
ctagcagtgg cgcccgaaca gggacttgaa agcgaaaggg aaaccagagg agctctctcg   6360
acgcaggact cggcttgctg aagcgcgcac ggcaagaggc gaggggcggc gactggtgag   6420
tacgccaaaa attttgacta gcggaggcta gaaggagaga gatgggtgcg agagcgtcag   6480
tattaagcgg gggagaatta gatcgcgatg ggaaaaaatt cggttaaggc caggggggaaa   6540
gaaaaaatat aaattaaaac atatagtatg ggcaagcagg gagctagaac gattcgcagt   6600
taatcctggc ctgttagaaa catcagaagg ctgtagacaa atactgggac agctacaacc   6660
atcccttcag acaggatcag aagaacttag atcattatat aatacagtag caaccctcta   6720
ttgtgtgcat caaaggatag agataaaaga caccaaggaa gctttagaca agatagagga   6780
agagcaaaac aaaagtaaga ccaccgcaca gcaagcggcc gctgatcttc agacctggag   6840
gaggagatat gagggacaat tggagaagtg aattatataa atataaagta gtaaaaattg   6900
```

-continued

```
aaccattagg agtagcaccc accaaggcaa agagaagagt ggtgcagaga gaaaaaagag   6960
cagtgggaat aggagctttg ttccttgggt tcttgggagc agcaggaagc actatgggcg   7020
cagcgtcaat gacgctgacg gtacaggcca gacaattatt gtctggtata gtgcagcagc   7080
agaacaattt gctgagggct attgaggcgc aacagcatct gttgcaactc acagtctggg   7140
gcatcaagca gctccaggca agaatcctgg ctgtggaaag atacctaaag gatcaacagc   7200
tcctggggat ttggggttgc tctggaaaac tcatttgcac cactgctgtg ccttggaatg   7260
ctagttggag taataaatct ctggaacaga tttggaatca cacgacctgg atggagtggg   7320
acagagaaat taacaattac acaagcttaa tacactcctt aattgaagaa tcgcaaaacc   7380
agcaagaaaa gaatgaacaa gaattattgg aattagataa atgggcaagt ttgtggaatt   7440
ggtttaacat aacaaattgg ctgtggtata tagaaattat tcataatgat agtaggaggc   7500
ttggtaggtt taagaatagt ttttgctgta ctttctatag tgaatagagt taggcaggga   7560
tattcaccat tatcgtttca gacccacctc ccaaccccga ggggacccga caggcccgaa   7620
ggaatagaag aagaaggtgg agagagagac agagacagat ccattcgatt agtgaacgga   7680
tcggcactgc gtgcgccaat tctgcagaca aatggcagta ttcatccaca attttaaaag   7740
aaaagggggg attggggggt acagtgcagg ggaaagaata gtagacataa tagcaacaga   7800
catacaaact aaagaattac aaaaacaaat tacaaaaatt caaaattttc gggtttatta   7860
cagggacagc agagatccag tttggggttg ctctggaaaa ctcatttgca ccactgctgt   7920
gccttggaat gctagttgga gtaataaatc tctggaacag atttggaatc acacgacctg   7980
gatggagtgg gacagagaaa ttaacaatta cacaagctta atacactcct taattgaaga   8040
atcgcaaaac cagcaagaaa agaatgaaca agaattattg gaattagata aatgggcaag   8100
tttgtggaat tggtttaaca taacaaattg gctgtggtat ataaaattat tcataatgat   8160
agtaggaggc ttggtaggtt taagaatagt ttttgctgta ctttctatag tgaatagagt   8220
taggcaggga tattcaccat tatcgtttca gacccacctc ccaaccccga ggggacccga   8280
caggccctta attaattggc tccggtgccc gtcagtgggc agagcgcaca tcgcccacag   8340
tccccgagaa gttgggggga ggggtcggca attgaaccgg tgcctagaga aggtggcgcg   8400
gggtaaactg ggaaagtgat gtcgtgtact ggctccgcct ttttcccgag ggtgggggag   8460
aaccgtatat aagtgcagta gtcgccgtga agctagctcc ctatcagtga tagagatctc   8520
cctatcagtg atagagagct agccgttctt tttcgcaacg ggtttgccgc cagaacacag   8580
gtaagtgccg tgtgtggttc ccgcgggcct ggcctcttta cgggttatgg cccttgcgtg   8640
ccttgaatta cttccacctg gctgcagtac gtgattcttg atcccgagct tcgggttgga   8700
agtgggtggg agagttcgag gccttgcgct taaggagccc cttcgcctcg tgcttgagtt   8760
gaggcctggc ctgggcgctg gggccgccgc gtgcgaatct ggtggcacct tcgcgcctgt   8820
ctcgctgctt tcgataagtc tctagccatt taaaattttt gatgacctgc tgcgacgctt   8880
tttttctggc aagatagtct tgtaaatgcg ggccaagatc tgcacactgg tatttcggtt   8940
tttggggccg cgggcggcga cggggcccgt gcgtcccagc gcacatgttc ggcgaggcgg   9000
ggcctgcgag cgcggccacc gagaatcgga cgggggtagt ctcaagctgg ccggcctgct   9060
ctggtgcctg gcctcgcgcc gccgtgtatc gccccgccct gggcggcaag gctggcccgg   9120
tcggcaccag ttgcgtgagc ggaaagatgg ccgcttcccg gccctgctgc agggagctca   9180
aaatggagga cgcggcgctc gggagagcgg gcgggtgagt cacccacaca aaggaaaagg   9240
gcctttccgt cctcagccgt cgcttcatgt gactccacgg agtaccgggc gccgtccagg   9300
```

cacctcgatt agttctcgag cttttggagt acgtcgtctt taggttgggg ggaggggttt 9360
tatgcgatgg agtttcccca cactgagtgg gtggagactg aagttaggcc agcttggcac 9420
ttgatgtaat tctccttgga atttgccctt tttgagtttg gatcttggtt cattctcaag 9480
cctcagacag tggttcaaag ttttttcttt ccatttcagg tgaattcggc cattacggcc 9540
tcccaccatg aaaccagtaa cgttatacga tgtcgcagag tatgccggtg tctcttatca 9600
gaccgtttcc cgcgtggtga accaggccag ccacgtttct gcgaaaacgc gggaaaaagt 9660
ggaagcggcg atggcggagc tgaattacat tcccaaccgc gtggcacaac aactggcggg 9720
caaacagtcg ttgctgattg gcgttgccac ctccagtctg gccctgcacg cgccgtcgca 9780
aattgtcgcg gcgattaaat ctcgcgccga tcaactgggt gccagcgtgg tggtgtcgat 9840
ggtagaacga agcggcgtcg aagcctgtaa agcggcggtg cacaatcttc tcgcgcaacg 9900
cgtcagtggg ctgatcatta actatccgct ggatgaccag gatgccattg ctgtggaagc 9960
tgcctgcact aatgttccgg cgttatttct tgatgtctct gaccagacac ccatcaacag 10020
tattattttc tcccatgaag acggtacgcg actgggcgtg gagcatctgg tcgcattggg 10080
tcaccagcaa atcgcgctgt tagcgggccc attaagttct gtctcggcgc gtctgcgtct 10140
ggctggctgg cataaatatc tcactcgcaa tcaaattcag ccgatagcgg aacgggaagg 10200
cgactggagt gccatgtccg gttttcaaca aaccatgcaa atgctgaatg agggcatcgt 10260
tcccactgcg atgctggttg ccaacgatca gatggcgctg ggcgcaatgc gcgccattac 10320
cgagtccggg ctgcgcgttg gtgcggatat ctcggtagtg ggatacgacg ataccgaaga 10380
cagctcatgt tatatcccgc cgttaaccac catcaaacag gattttcgcc tgctggggca 10440
aaccagcgtg gaccgcttgc tgcaactctc tcagggccag gcggtgaagg gcaatcagct 10500
gttgcccgtc tcactggtga aaagaaaaac caccctggcg cccaatacgc aaaccgcctc 10560
tccccgcgcg ttggccgatt cattaatgca gctggcacga caggtttccc gactggaaag 10620
cgggcagcca aaaaagaaga gaaaggtcga cggcggtggt gctttgtctc ctcagcactc 10680
tgctgtcact caaggaagta tcatcaagaa caaggagggc atggatgcta agtcactaac 10740
tgcctggtcc cggacactgg tgaccttcaa ggatgtattt gtggacttca ccagggagga 10800
gtggaagctg ctggacactg ctcagcagat cgtgtacaga aatgtgatgc tggagaacta 10860
taagaacctg gtttccttgg gttatcagct tactaagcca gatgtgatcc tccggttgga 10920
gaagggagaa gagccctggc tggtggagag agaaattcac caagagaccc atcctgattc 10980
agagactgca tttgaaatca aatcatcagt ttaaggccgc ct 11022

<210> SEQ ID NO 15
<211> LENGTH: 9123
<212> TYPE: DNA
<213> ORGANISM: Artificial Sequence
<220> FEATURE:
<223> OTHER INFORMATION: Synthetic

<400> SEQUENCE: 15
ttattgccac catgagcccg aaacgccgca cccaggcgga acgcgcgatg gaaacccagg 60
gcaaactgat tgcggcggcg ctgggcgtgc tgcgcgaaaa aggctatgcg ggctttcgca 120
ttgcggatgt gccgggcgcg gcgggcgtga gccgcggcgc gcagagccat cattttccga 180
ccaaactgga actgctgctg gcgacctttg aatggctgta tgaacagatt accgaacgca 240
gccgcgcgcg cctggcgaaa ctgaaaccgg aagatgatgt gattcagcag atgctggatg 300

-continued

```
atgcggcgga atttttctg gatgatgatt ttagcattag cctggatctg attgtggcgg    360
cggatcgcga tccggcgctg cgcgaaggca ttcagcgcac cgtggaacgc aaccgctttg   420
tggtggaaga tatgtggctg ggcgtgctgg tgagccgcgg cctgagccgc gatgatgcgg   480
aagatattct gtggctgatt tttaacagcg tgcgcggcct ggcggtgcgc agcctgtggc   540
agaaagataa agaacgcttt gaacgcgtgc gcaacagcac cctggaaatt gcgcgcgaac   600
gctatgcgaa atttaaacgc gcgtacagcc gcgcgcgtac gaaaaacaat tacgggtcta   660
ccatcgaggg cctgctcgat ctcccggacg acgacgcccc cgaagaggcg gggctggcgg   720
ctccgcgcct gtcctttctc cccgcgggac acacgcgcag actgtcgacg gcccccccga   780
ccgatgtcag cctgggggac gagctccact tagacggcga ggacgtggcg atggcgcatg   840
ccgacgcgct agacgatttc gatctggaca tgttggggga cggggattcc ccgggtccgg   900
gatttacccc ccacgactcc gccccctacg gcgctctgga tatggccgac ttcgagtttg   960
agcagatgtt taccgatgcc cttggaattg acgagtacgg tgggtaataa gtgtgggagg  1020
gctaagggcg cgccgttcta gagaattcga tatcaagctt atcgataatc aacctctgga  1080
ttacaaaatt tgtgaaagat tgactggtat tcttaactat gttgctcctt ttacgctatg  1140
tggatacgct gctttaatgc ctttgtatca tgctattact tcccgtacgg ctttcatttt  1200
ctcctccttg tataaatcct ggttgctgtc tctttatgag gagttgtggc ccgttgtcag  1260
gcaacgtggc gtggtgtgca ctgtgtttgc tgacgcaacc cccactggtt ggggcattgc  1320
caccacctat caactccttt ccgggacttt cgctttcccc ctccctattg ccacggcgga  1380
actcattgcc gcctgccttg cccgctgctg gacaggggct cggctgttgg gcactgacaa  1440
ttccgtggtg ttgtcgggga agctgacgtc ctttccatgg ctgctcgcct gtgttgccaa  1500
ctggattctg cgcgggacgt ccttctgcta cgtcccttcg gccctcaatc cagcggacct  1560
tccttcccgc ggcctgctgc cggttctgcg gcctcttccg cgtcttcgcc ttcgccctca  1620
gacgagtcgg atctcccttt gggccgcctc cccgcctgcc tgcaggtttg tcgagaccta  1680
gaaaaacatg gagcaatcac aagtagcaat acagcagcta ccaatgctga ttgtgcctgg  1740
ctagaagcac aagaggagga ggaggtgggt tttccagtca cacctcaggt acctttaaga  1800
ccaatgactt acaaggcagc tgtagatctt agccactttt taaaagaaaa ggggggactg  1860
gaagggctaa ttcactccca acgaagacaa gatctgcttt ttgcttgtac tgggtctctc  1920
tggttagacc agatctgagc ctgggagctc tctggctaac tagggaaccc actgcttaag  1980
cctcaataaa gcttgccttg agtgcttcaa gtagtgtgtg cccgtctgtt gtgtgactct  2040
ggtaactaga gatccctcag acccttttag tcagtgtgga aaatctctag cagggcccgt  2100
ttaaacccgc tgatcagcct cgactgtgcc ttctagttgc cagccatctg ttgtttgccc  2160
ctcccccgtg ccttccttga ccctggaagg tgccactccc actgtccttt cctaataaaa  2220
tgaggaaatt gcatcgcatt gtctgagtag gtgtcattct attctggggg gtggggtggg  2280
gcaggacagc aagggggagg attgggaaga caatagcagg catgctgggg atgcggtggg  2340
ctctatggct tctgaggcgg aaagaaccag ctggggctct agggggtatc cccacgcgcc  2400
ctgtagcggc gcattaagcg cggcgggtgt ggtggttacg cgcagcgtga ccgctacact  2460
tgccagcgcc ctagcgcccg ctcctttcgc tttcttccct tcctttctcg ccacgttcgc  2520
cggctttccc cgtcaagctc taaatcgggg catcccttta gggttccgat ttagtgcttt  2580
acggcacctc gaccccaaaa aacttgatta gggtgatggt tcacgtagtg ggccatcgcc  2640
ctgatagacg gtttttcgcc ctttgacgtt ggagtccacg ttctttaata gtggactctt  2700
```

gttccaaact ggaacaacac tcaaccctat ctcggtctat tcttttgatt tataagggat 2760
tttggggatt tcggcctatt ggttaaaaaa tgagctgatt taacaaaaat ttaacgcgaa 2820
ttaattctgt ggaatgtgtg tcagttaggg tgtggaaagt ccccaggctc cccaggcagg 2880
cagaagtatg caaagcatgc atctcaatta gtcagcaacc aggtgtggaa agtccccagg 2940
ctccccagca ggcagaagta tgcaaagcat gcatctcaat tagtcagcaa ccatagtccc 3000
gcccctaact ccgcccatcc cgcccctaac tccgcccagt tccgcccatt ctccgcccca 3060
tggctgacta atttttttta tttatgcaga ggccgaggcc gcctctgcct ctgagctatt 3120
ccagaagtag tgaggaggct tttttggagg cctaggcttt tgcaaaaagc tcccgggagc 3180
ttgtatatcc attttcggat ctgatcagca cgtgttgaca attaatcatc ggcatagtat 3240
atcggcatag tataatacga caaggtgagg aactaaacca tggccaagtt gaccagtgcc 3300
gttccggtgc tcaccgcgcg cgacgtcgcc ggagcggtcg agttctggac cgaccggctc 3360
gggttctccc gggacttcgt ggaggacgac ttcgccggtg tggtccggga cgacgtgacc 3420
ctgttcatca gcgcggtcca ggaccaggtg gtgccggaca acaccctggc ctgggtgtgg 3480
gtgcgcggcc tggacgagct gtacgccgag tggtcggagg tcgtgtccac gaacttccgg 3540
gacgcctccg ggccggccat gaccgagatc ggcgagcagc cgtgggggcg ggagttcgcc 3600
ctgcgcgacc cggccggcaa ctgcgtgcac ttcgtggccg aggagcagga ctgacacgtg 3660
ctacgagatt tcgattccac cgccgccttc tatgaaaggt tgggcttcgg aatcgttttc 3720
cgggacgccg gctggatgat cctccagcgc ggggatctca tgctggagtt cttcgcccac 3780
cccaacttgt ttattgcagc ttataatggt tacaaataaa gcaatagcat cacaaatttc 3840
acaaataaag catttttttc actgcattct agttgtggtt tgtccaaact catcaatgta 3900
tcttatcatg tctgtatacc gtcgacctct agctagagct tggcgtaatc atggtcatag 3960
ctgtttcctg tgtgaaattg ttatccgctc acaattccac acaacatacg agccggaagc 4020
ataaagtgta aagcctgggg tgcctaatga gtgagctaac tcacattaat tgcgttgcgc 4080
tcactgcccg ctttccagtc gggaaacctg tcgtgccagc tgcattaatg aatcggccaa 4140
cgcgcgggga gaggcggttt gcgtattggg cgctcttccg cttcctcgct cactgactcg 4200
ctgcgctcgg tcgttcggct gcggcgagcg gtatcagctc actcaaaggc ggtaatacgg 4260
ttatccacag aatcagggga taacgcagga aagaacatgt gagcaaaagg ccagcaaaag 4320
gccaggaacc gtaaaaaggc cgcgttgctg gcgtttttcc ataggctccg cccccctgac 4380
gagcatcaca aaaatcgacg ctcaagtcag aggtggcgaa acccgacagg actataaaga 4440
taccaggcgt ttccccctgg aagctccctc gtgcgctctc ctgttccgac cctgccgctt 4500
accggatacc tgtccgcctt tctcccttcg ggaagcgtgg cgctttctca atgctcacgc 4560
tgtaggtatc tcagttcggt gtaggtcgtt cgctccaagc tgggctgtgt gcacgaaccc 4620
cccgttcagc ccgaccgctg cgccttatcc ggtaactatc gtcttgagtc caacccggta 4680
agacacgact tatcgccact ggcagcagcc actggtaaca ggattagcag agcgaggtat 4740
gtaggcggtg ctacagagtt cttgaagtgg tggcctaact acggctacac tagaaggaca 4800
gtatttggta tctgcgctct gctgaagcca gttaccttcg gaaaaagagt tggtagctct 4860
tgatccggca aacaaaccac cgctggtagc ggtggttttt ttgtttgcaa gcagcagatt 4920
acgcgcagaa aaaaaggatc tcaagaagat cctttgatct tttctacggg gtctgacgct 4980
cagtggaacg aaaactcacg ttaagggatt ttggtcatga gattatcaaa aaggatcttc 5040

-continued

```
acctagatcc ttttaaatta aaaatgaagt tttaaatcaa tctaaagtat atatgagtaa   5100
acttggtctg acagttacca atgcttaatc agtgaggcac ctatctcagc gatctgtcta   5160
tttcgttcat ccatagttgc ctgactcccc gtcgtgtaga taactacgat acgggagggc   5220
ttaccatctg gccccagtgc tgcaatgata ccgcgagacc cacgctcacc ggctccagat   5280
ttatcagcaa taaaccagcc agccggaagg gccgagcgca gaagtggtcc tgcaacttta   5340
tccgcctcca tccagtctat taattgttgc cgggaagcta gagtaagtag ttcgccagtt   5400
aatagtttgc gcaacgttgt tgccattgct acaggcatcg tggtgtcacg ctcgtcgttt   5460
ggtatggctt cattcagctc cggttcccaa cgatcaaggc gagttacatg atcccccatg   5520
ttgtgcaaaa aagcggttag ctccttcggt cctccgatcg ttgtcagaag taagttggcc   5580
gcagtgttat cactcatggt tatggcagca ctgcataatt ctcttactgt catgccatcc   5640
gtaagatgct tttctgtgac tggtgagtac tcaaccaagt cattctgaga atagtgtatg   5700
cggcgaccga gttgctcttg cccggcgtca atacgggata ataccgcgcc acatagcaga   5760
actttaaaag tgctcatcat tggaaaacgt tcttcggggc gaaaactctc aaggatctta   5820
ccgctgttga gatccagttc gatgtaaccc actcgtgcac ccaactgatc ttcagcatct   5880
tttactttca ccagcgtttc tgggtgagca aaaacaggaa ggcaaaatgc cgcaaaaaag   5940
ggaataaggg cgacacggaa atgttgaata ctcatactct tcctttttca atattattga   6000
agcatttatc agggttattg tctcatgagc ggatacatat ttgaatgtat ttagaaaaat   6060
aaacaaatag gggttccgcg cacatttccc cgaaaagtgc cacctgacgt cgacggatcg   6120
ggagatctcc cgatccccta tggtgcactc tcagtacaat ctgctctgat gccgcatagt   6180
taagccagta tctgctccct gcttgtgtgt tggaggtcgc tgagtagtgc gcgagcaaaa   6240
tttaagctac aacaaggcaa ggcttgaccg acaattgcat gaagaatctg cttagggtta   6300
ggcgttttgc gctgcttcgc gatgtacggg ccagatatac gcgttgacat tgattattga   6360
ctagttatta atagtaatca attacggggt cattagttca tagcccatat atggagttcc   6420
gcgttacata acttacggta aatggcccgc ctggctgacc gcccaacgac ccccgcccat   6480
tgacgtcaat aatgacgtat gttcccatag taacgccaat agggactttc cattgacgtc   6540
aatgggtgga ctatttacgg taaactgccc acttggcagt acatcaagtg tatcatatgc   6600
caagtacgcc ccctattgac gtcaatgacg gtaaatggcc cgcctggcat tatgcccagt   6660
acatgacctt atgggacttt cctacttggc agtacatcta cgtattagtc atcgctatta   6720
ccatggtgat gcggttttgg cagtacatca atgggcgtgg atagcggttt gactcacggg   6780
gatttccaag tctccacccc attgacgtca atgggagttt gttttggcac caaaatcaac   6840
gggactttcc aaaatgtcgt aacaactccg ccccattgac gcaaatgggc ggtaggcgtg   6900
tacggtggga ggtctatata agcagagctc tctggctaac tagagaaccc actgcttact   6960
ggcttatcga aattaatacg actcactata gggagaccca agctggttta aacttaagct   7020
tggtaccgag ctcactagtc cagtgtggtg gcagatatcc agcacagtgg cggccgctcg   7080
aggggcccgt tttgcctgta ctgggtctct ctggttagac cagatctgag cctgggagct   7140
ctctggctaa ctagggaacc cactgcttaa gcctcaataa agcttgcctt gagtgcttca   7200
agtagtgtgt gcccgtctgt tgtgtgactc tggtaactag agatccctca gacccttta    7260
gtcagtgtgg aaaatctcta gcagtggcgc ccgaacaggg acttgaaagc gaaagggaaa   7320
ccagaggagc tctctcgacg caggactcgg cttgctgaag cgcgcacggc aagaggcgag   7380
gggcggcgac tggtgagtac gccaaaaatt ttgactagcg gaggctagaa ggagagagat   7440
```

gggtgcgaga gcgtcagtat taagcggggg agaattagat cgcgatggga aaaaattcgg 7500
ttaaggccag ggggaaagaa aaaatataaa ttaaaacata tagtatgggc aagcagggag 7560
ctagaacgat tcgcagttaa tcctggcctg ttagaaacat cagaaggctg tagacaaata 7620
ctgggacagc tacaaccatc ccttcagaca ggatcagaag aacttagatc attatataat 7680
acagtagcaa ccctctattg tgtgcatcaa aggatagaga taaaagacac caaggaagct 7740
ttagacaaga tagaggaaga gcaaaacaaa agtaagacca ccgcacagca agcggccgct 7800
gatcttcaga cctggaggag gagatatgag ggacaattgg agaagtgaat tatataaata 7860
taaagtagta aaaattgaac cattaggagt agcacccacc aaggcaaaga gaagagtggt 7920
gcagagagaa aaaagagcag tgggaatagg agctttgttc cttgggttct tgggagcagc 7980
aggaagcact atgggcgcag cgtcaatgac gctgacggta caggccagac aattattgtc 8040
tggtatagtg cagcagcaga acaatttgct gagggctatt gaggcgcaac agcatctgtt 8100
gcaactcaca gtctggggca tcaagcagct ccaggcaaga atcctggctg tggaaagata 8160
cctaaaggat caacagctcc tggggatttg gggttgctct ggaaaactca tttgcaccac 8220
tgctgtgcct tggaatgcta gttggagtaa taaatctctg gaacagattt ggaatcacac 8280
gacctggatg gagtgggaca gagaaattaa caattacaca agcttaatac actccttaat 8340
tgaagaatcg caaaaccagc aagaaaagaa tgaacaagaa ttattggaat tagataaatg 8400
ggcaagtttg tggaattggt ttaacataac aaattggctg tggtatataa aattattcat 8460
aatgatagta ggaggcttgg taggtttaag aatagttttt gctgtacttt ctatagtgaa 8520
tagagttagg cagggatatt caccattatc gtttcagacc cacctcccaa ccccgagggg 8580
acccgacagg cccttaatta atcccctgat tctgtggata accgtattac cgcctttgag 8640
tgagctgcac aactgccaga tttcacagga aaagtgaaag gctacaatag gacaactgcc 8700
agatttcaca ggaaaagtga aaggctacaa taggacaact gccagatttc acaggaaaag 8760
tgaaaggcta caataggaca actgccagat ttcacaggaa aagtgaaagg ctacaatagg 8820
acaactgcca gatttcacag gaaaagtgaa aggctacaat aggacaactg ccagatttca 8880
caggaaaagt gaaaggctac aataggacaa agtgaaaggc tacaatagga cggtaaactc 8940
gacctatata agcagagctc gtttagtgaa ccgtcagatc gcctggagac gccatccacg 9000
ctgttttgac ctccatagaa gacaccggga ccgatccagc ctccgcggcc ccgaattgaa 9060
ttcgatgctg gtgttaaaaa catatgatgc tggtgttaaa aacggccatt acggcctgcc 9120
acc 9123

<210> SEQ ID NO 16
<211> LENGTH: 9275
<212> TYPE: DNA
<213> ORGANISM: Artificial Sequence
<220> FEATURE:
<223> OTHER INFORMATION: Synthetic

<400> SEQUENCE: 16
ttatgtgtgg gagggctaag ggcgcgccgt tctagagaat tcgatatcaa gcttatcgat 60
aatcaacctc tggattacaa aatttgtgaa agattgactg gtattcttaa ctatgttgct 120
ccttttacgc tatgtggata cgctgcttta atgcctttgt atcatgctat tacttcccgt 180
acggctttca ttttctcctc cttgtataaa tcctggttgc tgtctcttta tgaggagttg 240
tggcccgttg tcaggcaacg tggcgtggtg tgcactgtgt ttgctgacgc aacccccact 300

-continued

```
ggttggggca ttgccaccac ctatcaactc ctttccggga ctttcgcttt ccccctccct    360

attgccacgg cggaactcat tgccgcctgc cttgcccgct gctggacagg ggctcggctg    420

ttgggcactg acaattccgt ggtgttgtcg gggaagctga cgtcctttcc atggctgctc    480

gcctgtgttg ccaactggat tctgcgcggg acgtccttct gctacgtccc ttcggccctc    540

aatccagcgg accttccttc ccgcggcctg ctgccggttc tgcggcctct tccgcgtctt    600

cgccttcgcc ctcagacgag tcggatctcc ctttgggccg cctccccgcc tgcctgcagg    660

tttgtcgaga cctagaaaaa catggagcaa tcacaagtag caatacagca gctaccaatg    720

ctgattgtgc ctggctagaa gcacaagagg aggaggaggt gggttttcca gtcacacctc    780

aggtaccttt aagaccaatg acttacaagg cagctgtaga tcttagccac tttttaaaag    840

aaaagggggg actggaaggg ctaattcact cccaacgaag acaagatctg ctttttgctt    900

gtactgggtc tctctggtta gaccagatct gagcctggga gctctctggc taactaggga    960

acccactgct taagcctcaa taaagcttgc cttgagtgct tcaagtagtg tgtgcccgtc   1020

tgttgtgtga ctctggtaac tagagatccc tcagaccctt ttagtcagtg tggaaaatct   1080

ctagcagggc ccgtttaaac ccgctgatca gcctcgactg tgccttctag ttgccagcca   1140

tctgttgttt gcccctcccc cgtgccttcc ttgaccctgg aaggtgccac tcccactgtc   1200

ctttcctaat aaaatgagga aattgcatcg cattgtctga gtaggtgtca ttctattctg   1260

gggggtgggg tggggcagga cagcaagggg gaggattggg aagacaatag caggcatgct   1320

ggggatgcgg tgggctctat ggcttctgag gcggaaagaa ccagctgggg ctctaggggg   1380

tatccccacg cgccctgtag cggcgcatta agcgcggcgg gtgtggtggt tacgcgcagc   1440

gtgaccgcta cacttgccag cgccctagcg cccgctcctt tcgctttctt cccttccttt   1500

ctcgccacgt tcgccggctt tccccgtcaa gctctaaatc ggggcatccc tttagggttc   1560

cgatttagtg ctttacggca cctcgacccc aaaaaacttg attagggtga tggttcacgt   1620

agtgggccat cgccctgata gacggttttt cgccctttga cgttggagtc cacgttcttt   1680

aatagtggac tcttgttcca aactggaaca acactcaacc ctatctcggt ctattctttt   1740

gatttataag ggattttggg gatttcggcc tattggttaa aaaatgagct gatttaacaa   1800

aaatttaacg cgaattaatt ctgtggaatg tgtgtcagtt agggtgtgga aagtccccag   1860

gctccccagg caggcagaag tatgcaaagc atgcatctca attagtcagc aaccaggtgt   1920

ggaaagtccc caggctcccc agcaggcaga agtatgcaaa gcatgcatct caattagtca   1980

gcaaccatag tcccgcccct aactccgccc atcccgcccc taactccgcc cagttccgcc   2040

cattctccgc cccatggctg actaattttt tttatttatg cagaggccga ggccgcctct   2100

gcctctgagc tattccagaa gtagtgagga ggcttttttg gaggcctagg cttttgcaaa   2160

aagctcccgg gagcttgtat atccattttc ggatctgatc agcacgtgtt gacaattaat   2220

catcggcata gtatatcggc atagtataat acgacaaggt gaggaactaa accatggcca   2280

agttgaccag tgccgttccg gtgctcaccg cgcgcgacgt cgccggagcg gtcgagttct   2340

ggaccgaccg gctcgggttc tcccgggact tcgtggagga cgacttcgcc ggtgtggtcc   2400

gggacgacgt gaccctgttc atcagcgcgg tccaggacca ggtggtgccg gacaacaccc   2460

tggcctgggt gtgggtgcgc ggcctggacg agctgtacgc cgagtggtcg gaggtcgtgt   2520

ccacgaactt ccgggacgcc tccgggccgg ccatgaccga gatcggcgag cagccgtggg   2580

ggcgggagtt cgccctgcgc gacccggccg gcaactgcgt gcacttcgtg gccgaggagc   2640

aggactgaca cgtgctacga gatttcgatt ccaccgccgc cttctatgaa aggttgggct   2700
```

-continued

```
tcggaatcgt tttccgggac gccggctgga tgatcctcca gcgcggggat ctcatgctgg   2760
agttcttcgc ccaccccaac ttgtttattg cagcttataa tggttacaaa taaagcaata   2820
gcatcacaaa tttcacaaat aaagcatttt tttcactgca ttctagttgt ggtttgtcca   2880
aactcatcaa tgtatcttat catgtctgta taccgtcgac ctctagctag agcttggcgt   2940
aatcatggtc atagctgttt cctgtgtgaa attgttatcc gctcacaatt ccacacaaca   3000
tacgagccgg aagcataaag tgtaaagcct ggggtgccta atgagtgagc taactcacat   3060
taattgcgtt gcgctcactg cccgctttcc agtcgggaaa cctgtcgtgc cagctgcatt   3120
aatgaatcgg ccaacgcgcg gggagaggcg gtttgcgtat tgggcgctct tccgcttcct   3180
cgctcactga ctcgctgcgc tcggtcgttc ggctgcggcg agcggtatca gctcactcaa   3240
aggcggtaat acggttatcc acagaatcag gggataacgc aggaaagaac atgtgagcaa   3300
aaggccagca aaaggccagg aaccgtaaaa aggccgcgtt gctggcgttt ttccataggc   3360
tccgcccccc tgacgagcat cacaaaaatc gacgctcaag tcagaggtgg cgaaacccga   3420
caggactata aagataccag gcgtttcccc ctggaagctc cctcgtgcgc tctcctgttc   3480
cgaccctgcc gcttaccgga tacctgtccg cctttctccc ttcgggaagc gtggcgcttt   3540
ctcaatgctc acgctgtagg tatctcagtt cggtgtaggt cgttcgctcc aagctgggct   3600
gtgtgcacga accccccgtt cagcccgacc gctgcgcctt atccggtaac tatcgtcttg   3660
agtccaaccc ggtaagacac gacttatcgc cactggcagc agccactggt aacaggatta   3720
gcagagcgag gtatgtaggc ggtgctacag agttcttgaa gtggtggcct aactacggct   3780
acactagaag gacagtattt ggtatctgcg ctctgctgaa gccagttacc ttcggaaaaa   3840
gagttggtag ctcttgatcc ggcaaacaaa ccaccgctgg tagcggtggt ttttttgttt   3900
gcaagcagca gattacgcgc agaaaaaaag gatctcaaga agatcctttg atcttttcta   3960
cggggtctga cgctcagtgg aacgaaaact cacgttaagg gattttggtc atgagattat   4020
caaaaaggat cttcacctag atccttttaa attaaaaatg aagttttaaa tcaatctaaa   4080
gtatatatga gtaaacttgg tctgacagtt accaatgctt aatcagtgag gcacctatct   4140
cagcgatctg tctatttcgt tcatccatag ttgcctgact ccccgtcgtg tagataacta   4200
cgatacggga gggcttacca tctggcccca gtgctgcaat gataccgcga gacccacgct   4260
caccggctcc agatttatca gcaataaacc agccagccgg aagggccgag cgcagaagtg   4320
gtcctgcaac tttatccgcc tccatccagt ctattaattg ttgccgggaa gctagagtaa   4380
gtagttcgcc agttaatagt ttgcgcaacg ttgttgccat tgctacaggc atcgtggtgt   4440
cacgctcgtc gtttggtatg gcttcattca gctccggttc ccaacgatca aggcgagtta   4500
catgatcccc catgttgtgc aaaaaagcgg ttagctcctt cggtcctccg atcgttgtca   4560
gaagtaagtt ggccgcagtg ttatcactca tggttatggc agcactgcat aattctctta   4620
ctgtcatgcc atccgtaaga tgcttttctg tgactggtga gtactcaacc aagtcattct   4680
gagaatagtg tatgcggcga ccgagttgct cttgcccggc gtcaatacgg gataataccg   4740
cgccacatag cagaacttta aaagtgctca tcattggaaa acgttcttcg gggcgaaaac   4800
tctcaaggat cttaccgctg ttgagatcca gttcgatgta acccactcgt gcacccaact   4860
gatcttcagc atcttttact ttcaccagcg tttctgggtg agcaaaaaca ggaaggcaaa   4920
atgccgcaaa aaagggaata agggcgacac ggaaatgttg aatactcata ctcttccttt   4980
ttcaatatta ttgaagcatt tatcagggtt attgtctcat gagcggatac atatttgaat   5040
```

-continued

```
gtatttagaa aaataaacaa ataggggttc cgcgcacatt tccccgaaaa gtgccacctg   5100
acgtcgacgg atcgggagat ctcccgatcc cctatggtgc actctcagta caatctgctc   5160
tgatgccgca tagttaagcc agtatctgct ccctgcttgt gtgttggagg tcgctgagta   5220
gtgcgcgagc aaaatttaag ctacaacaag gcaaggcttg accgacaatt gcatgaagaa   5280
tctgcttagg gttaggcgtt ttgcgctgct tcgcgatgta cgggccagat atacgcgttg   5340
acattgatta ttgactagtt attaatagta atcaattacg gggtcattag ttcatagccc   5400
atatatggag ttccgcgtta cataacttac ggtaaatggc ccgcctggct gaccgcccaa   5460
cgacccccgc ccattgacgt caataatgac gtatgttccc atagtaacgc caatagggac   5520
tttccattga cgtcaatggg tggactattt acggtaaact gcccacttgg cagtacatca   5580
agtgtatcat atgccaagta cgccccctat tgacgtcaat gacggtaaat ggcccgcctg   5640
gcattatgcc cagtacatga ccttatggga ctttcctact tggcagtaca tctacgtatt   5700
agtcatcgct attaccatgg tgatgcggtt ttggcagtac atcaatgggc gtggatagcg   5760
gtttgactca cggggatttc caagtctcca ccccattgac gtcaatggga gtttgttttg   5820
gcaccaaaat caacgggact ttccaaaatg tcgtaacaac tccgccccat tgacgcaaat   5880
gggcggtagg cgtgtacggt gggaggtcta tataagcaga gctctctggc taactagaga   5940
acccactgct tactggctta tcgaaattaa tacgactcac tatagggaga cccaagctgg   6000
tttaaactta agcttggtac cgagctcact agtccagtgt ggtggcagat atccagcaca   6060
gtggcggccg ctcgaggggc ccgttttgcc tgtactgggt ctctctggtt agaccagatc   6120
tgagcctggg agctctctgg ctaactaggg aacccactgc ttaagcctca ataaagcttg   6180
ccttgagtgc ttcaagtagt gtgtgcccgt ctgttgtgtg actctggtaa ctagagatcc   6240
ctcagaccct tttagtcagt gtggaaaatc tctagcagtg gcgcccgaac agggacttga   6300
aagcgaaagg gaaaccagag gagctctctc gacgcaggac tcggcttgct gaagcgcgca   6360
cggcaagagg cgaggggcgg cgactggtga gtacgccaaa aattttgact agcggaggct   6420
agaaggagag agatgggtgc gagagcgtca gtattaagcg ggggagaatt agatcgcgat   6480
gggaaaaaat tcggttaagg ccagggggaa agaaaaaata taaattaaaa catatagtat   6540
gggcaagcag ggagctagaa cgattcgcag ttaatcctgg cctgttagaa acatcagaag   6600
gctgtagaca aatactggga cagctacaac catcccttca gacaggatca gaagaactta   6660
gatcattata taatacagta gcaaccctct attgtgtgca tcaaaggata gagataaaag   6720
acaccaagga agctttagac aagatagagg aagagcaaaa caaaagtaag accaccgcac   6780
agcaagcggc cgctgatctt cagacctgga ggaggagata tgagggacaa ttggagaagt   6840
gaattatata aatataaagt agtaaaaatt gaaccattag gagtagcacc caccaaggca   6900
aagagaagag tggtgcagag agaaaaaaga gcagtgggaa taggagcttt gttccttggg   6960
ttcttgggag cagcaggaag cactatgggc gcagcgtcaa tgacgctgac ggtacaggcc   7020
agacaattat tgtctggtat agtgcagcag cagaacaatt tgctgagggc tattgaggcg   7080
caacagcatc tgttgcaact cacagtctgg ggcatcaagc agctccaggc aagaatcctg   7140
gctgtggaaa gatacctaaa ggatcaacag ctcctgggga tttggggttg ctctggaaaa   7200
ctcatttgca ccactgctgt gccttggaat gctagttgga gtaataaatc tctggaacag   7260
atttggaatc acacgacctg gatggagtgg gacagagaaa ttaacaatta cacaagctta   7320
atacactcct taattgaaga atcgcaaaac cagcaagaaa agaatgaaca agaattattg   7380
gaattagata aatgggcaag tttgtggaat tggtttaaca taacaaattg gctgtggtat   7440
```

```
ataaaattat tcataatgat agtaggaggc ttggtaggtt taagaatagt tttgctgta   7500

ctttctatag tgaatagagt taggcaggga tattcaccat tatcgtttca gacccacctc   7560

ccaaccccga ggggacccga caggccctta attaatcccc tgattctgtg gataaccgta   7620

ttaccgcctt tgagtgagct gcacgggagc aattaatcta tagattaaaa agtgaaaggc   7680

tacaatagga cgggagcaat taatctatag attaaaaagt gaaaggctac aataggacgg   7740

gagcaattaa tctatagatt aaaaagtgaa aggctacaat aggacgggag caattaatct   7800

atagattaaa aagtgaaagg ctacaatagg acgggagcaa ttaatctata gattaaaaag   7860

tgaaaggcta caataggacg ggagcaatta atctatagat taaaaagtga aaggctacaa   7920

taggacggga gcaattaatc tatagattaa aaagtgaaag gctacaatag gacggtaaac   7980

tcgacctata taagcagagc tcgtttagtg aaccgtcaga tcgcctggag acgccatcca   8040

cgctgttttg acctccatag aagacaccgg gaccgatcca gcctccgcgg ccccgaattg   8100

aattcggcca ttacggcctg ccaccatgat tgagaatacc tatagcgaaa agttcgagtc   8160

cgcgttcgaa cagatcaagg cggcggccaa cgtggatgcc gccatccgta ttctccaggc   8220

ggaatataac ctcgatttcg tcacctacca tctcgcccag acgatcgcga gcaagatcga   8280

ttcgcccttc gtgcgcacca cctatccgga tgcctgggtt tcccgctacc tcctcaacag   8340

ctatgtgaag gtcgatccga tcgtcaagca gggcttcgaa cgccagctgc ccttcgactg   8400

gagcgaggtc gaaccgacgc cggaggccta tgccatgctg gtcgacgccc agaaacacgg   8460

catcggtggc aatggctact ccatccccgt cgccgacaag gcgcagcgcc gcgccctgct   8520

gtcgctgaat gcccgtatac cggccgacga atggaccgag ctcgtgcgcc gctgccgcaa   8580

cgagtggatc gagatcgccc atctgatcca ccgcaaggcc gtctatgagc tgcatggcga   8640

aaacgatccg gtgccggcat tgtcgccgcg cgagatcgag tgtctgcact ggaccgccct   8700

cggcaaggat tacaaggata tttcggtcat cctgggcata tcagagcata ccacacgcga   8760

ttacctgaag accgcccgct tcaagctcgg ctgcgccacg atctcggccg ccgcgtcgcg   8820

ggctgttcaa ttgcgcatca tcaatcccgc tgcaaacgac gaaaactacg ctttagtagc   8880

tgcgtacagc cgcgcgcgta cgaaaaaacaa ttacgggtct accatcgagg gcctgctcga   8940

tctcccggac gacgacgccc ccgaagaggc ggggctggcg gctccgcgcc tgtcctttct   9000

ccccgcggga cacacgcgca gactgtcgac ggcccccccg accgatgtca gcctggggga   9060

cgagctccac ttagacggcg aggacgtggc gatggcgcat gccgacgcgc tagacgattt   9120

cgatctggac atgttggggg acggggattc cccgggtccg ggatttaccc cccacgactc   9180

cgccccctac ggcgctctgg atatggccga cttcgagttt gagcagatgt ttaccgatgc   9240

ccttggaatt gacgagtacg gtgggtaatg ccacc                              9275
```

<210> SEQ ID NO 17
<211> LENGTH: 9230
<212> TYPE: DNA
<213> ORGANISM: Artificial Sequence
<220> FEATURE:
<223> OTHER INFORMATION: Synthetic

<400> SEQUENCE: 17

```
ttatgtgtgg gagggctaag ggcgcgccgt tctagagaat tcgatatcaa gcttatcgat     60

aatcaacctc tggattacaa aatttgtgaa agattgactg gtattcttaa ctatgttgct    120

ccttttacgc tatgtggata cgctgcttta atgcctttgt atcatgctat tacttcccgt    180
```

-continued

```
acggctttca ttttctcctc cttgtataaa tcctggttgc tgtctcttta tgaggagttg    240
tggcccgttg tcaggcaacg tggcgtggtg tgcactgtgt ttgctgacgc aacccccact    300
ggttggggca ttgccaccac ctatcaactc ctttccggga ctttcgcttt ccccctccct    360
attgccacgg cggaactcat tgccgcctgc cttgcccgct gctggacagg ggctcggctg    420
ttgggcactg acaattccgt ggtgttgtcg gggaagctga cgtcctttcc atggctgctc    480
gcctgtgttg ccaactggat tctgcgcggg acgtccttct gctacgtccc ttcggccctc    540
aatccagcgg accttccttc ccgcggcctg ctgccggttc tgcggcctct tccgcgtctt    600
cgccttcgcc ctcagacgag tcggatctcc ctttgggccg cctccccgcc tgcctgcagg    660
tttgtcgaga cctagaaaaa catggagcaa tcacaagtag caatacagca gctaccaatg    720
ctgattgtgc ctggctagaa gcacaagagg aggaggaggt gggttttcca gtcacacctc    780
aggtaccttt aagaccaatg acttacaagg cagctgtaga tcttagccac tttttaaaag    840
aaaagggggg actggaaggg ctaattcact cccaacgaag acaagatctg ctttttgctt    900
gtactgggtc tctctggtta gaccagatct gagcctggga gctctctggc taactaggga    960
acccactgct taagcctcaa taaagcttgc cttgagtgct tcaagtagtg tgtgcccgtc   1020
tgttgtgtga ctctggtaac tagagatccc tcagaccctt ttagtcagtg tggaaaatct   1080
ctagcagggc ccgtttaaac ccgctgatca gcctcgactg tgccttctag ttgccagcca   1140
tctgttgttt gcccctcccc cgtgccttcc ttgaccctgg aaggtgccac tcccactgtc   1200
ctttcctaat aaaatgagga aattgcatcg cattgtctga gtaggtgtca ttctattctg   1260
gggggtgggg tggggcagga cagcaagggg gaggattggg aagacaatag caggcatgct   1320
ggggatgcgg tgggctctat ggcttctgag gcggaaagaa ccagctgggg ctctaggggg   1380
tatccccacg cgccctgtag cggcgcatta agcgcggcgg gtgtggtggt tacgcgcagc   1440
gtgaccgcta cacttgccag cgccctagcg cccgctcctt tcgctttctt cccttccttt   1500
ctcgccacgt tcgccggctt tccccgtcaa gctctaaatc ggggcatccc tttagggttc   1560
cgatttagtg ctttacggca cctcgacccc aaaaaacttg attagggtga tggttcacgt   1620
agtgggccat cgccctgata gacggttttt cgccctttga cgttggagtc cacgttcttt   1680
aatagtggac tcttgttcca aactggaaca acactcaacc ctatctcggt ctattctttt   1740
gatttataag ggattttggg gatttcggcc tattggttaa aaaatgagct gatttaacaa   1800
aaatttaacg cgaattaatt ctgtggaatg tgtgtcagtt agggtgtgga aagtccccag   1860
gctccccagg caggcagaag tatgcaaagc atgcatctca attagtcagc aaccaggtgt   1920
ggaaagtccc caggctcccc agcaggcaga agtatgcaaa gcatgcatct caattagtca   1980
gcaaccatag tcccgcccct aactccgccc atcccgcccc taactccgcc cagttccgcc   2040
cattctccgc cccatggctg actaattttt tttatttatg cagaggccga ggccgcctct   2100
gcctctgagc tattccagaa gtagtgagga ggcttttttg gaggcctagg cttttgcaaa   2160
aagctcccgg gagcttgtat atccattttc ggatctgatc agcacgtgtt gacaattaat   2220
catcggcata gtatatcggc atagtataat acgacaaggt gaggaactaa accatggcca   2280
agttgaccag tgccgttccg gtgctcaccg cgcgcgacgt cgccggagcg gtcgagttct   2340
ggaccgaccg gctcgggttc tcccgggact tcgtggagga cgacttcgcc ggtgtggtcc   2400
gggacgacgt gaccctgttc atcagcgcgg tccaggacca ggtggtgccg gacaacaccc   2460
tggcctgggt gtgggtgcgc ggcctggacg agctgtacgc cgagtggtcg gaggtcgtgt   2520
ccacgaactt ccgggacgcc tccgggccgg ccatgaccga gatcggcgag cagccgtggg   2580
```

```
ggcgggagtt cgccctgcgc gacccggccg gcaactgcgt gcacttcgtg gccgaggagc   2640
aggactgaca cgtgctacga gatttcgatt ccaccgccgc cttctatgaa aggttgggct   2700
tcggaatcgt tttccgggac gccggctgga tgatcctcca gcgcggggat ctcatgctgg   2760
agttcttcgc ccaccccaac ttgtttattg cagcttataa tggttacaaa taaagcaata   2820
gcatcacaaa tttcacaaat aaagcatttt tttcactgca ttctagttgt ggtttgtcca   2880
aactcatcaa tgtatcttat catgtctgta taccgtcgac ctctagctag agcttggcgt   2940
aatcatggtc atagctgttt cctgtgtgaa attgttatcc gctcacaatt ccacacaaca   3000
tacgagccgg aagcataaag tgtaaagcct ggggtgccta atgagtgagc taactcacat   3060
taattgcgtt gcgctcactg cccgctttcc agtcgggaaa cctgtcgtgc cagctgcatt   3120
aatgaatcgg ccaacgcgcg gggagaggcg gtttgcgtat tgggcgctct tccgcttcct   3180
cgctcactga ctcgctgcgc tcggtcgttc ggctgcggcg agcggtatca gctcactcaa   3240
aggcggtaat acggttatcc acagaatcag gggataacgc aggaaagaac atgtgagcaa   3300
aaggccagca aaaggccagg aaccgtaaaa aggccgcgtt gctggcgttt ttccataggc   3360
tccgcccccc tgacgagcat cacaaaaatc gacgctcaag tcagaggtgg cgaaacccga   3420
caggactata aagataccag gcgtttcccc ctggaagctc cctcgtgcgc tctcctgttc   3480
cgaccctgcc gcttaccgga tacctgtccg cctttctccc ttcgggaagc gtggcgcttt   3540
ctcaatgctc acgctgtagg tatctcagtt cggtgtaggt cgttcgctcc aagctgggct   3600
gtgtgcacga accccccgtt cagcccgacc gctgcgcctt atccggtaac tatcgtcttg   3660
agtccaaccc ggtaagacac gacttatcgc cactggcagc agccactggt aacaggatta   3720
gcagagcgag gtatgtaggc ggtgctacag agttcttgaa gtggtggcct aactacggct   3780
acactagaag gacagtattt ggtatctgcg ctctgctgaa gccagttacc ttcggaaaaa   3840
gagttggtag ctcttgatcc ggcaaacaaa ccaccgctgg tagcggtggt ttttttgttt   3900
gcaagcagca gattacgcgc agaaaaaaag gatctcaaga agatcctttg atcttttcta   3960
cggggtctga cgctcagtgg aacgaaaact cacgttaagg gattttggtc atgagattat   4020
caaaaaggat cttcacctag atccttttaa attaaaaatg aagttttaaa tcaatctaaa   4080
gtatatatga gtaaacttgg tctgacagtt accaatgctt aatcagtgag gcacctatct   4140
cagcgatctg tctatttcgt tcatccatag ttgcctgact ccccgtcgtg tagataacta   4200
cgatacggga gggcttacca tctggcccca gtgctgcaat gataccgcga gacccacgct   4260
caccggctcc agatttatca gcaataaacc agccagccgg aagggccgag cgcagaagtg   4320
gtcctgcaac tttatccgcc tccatccagt ctattaattg ttgccgggaa gctagagtaa   4380
gtagttcgcc agttaatagt ttgcgcaacg ttgttgccat tgctacaggc atcgtggtgt   4440
cacgctcgtc gtttggtatg gcttcattca gctccggttc ccaacgatca aggcgagtta   4500
catgatcccc catgttgtgc aaaaaagcgg ttagctcctt cggtcctccg atcgttgtca   4560
gaagtaagtt ggccgcagtg ttatcactca tggttatggc agcactgcat aattctctta   4620
ctgtcatgcc atccgtaaga tgcttttctg tgactggtga gtactcaacc aagtcattct   4680
gagaatagtg tatgcggcga ccgagttgct cttgcccggc gtcaatacgg gataataccg   4740
cgccacatag cagaacttta aaagtgctca tcattggaaa acgttcttcg gggcgaaaac   4800
tctcaaggat cttaccgctg ttgagatcca gttcgatgta acccactcgt gcacccaact   4860
gatcttcagc atcttttact ttcaccagcg tttctgggtg agcaaaaaca ggaaggcaaa   4920
```

-continued

```
atgccgcaaa aaagggaata agggcgacac ggaaatgttg aatactcata ctcttccttt   4980
ttcaatatta ttgaagcatt tatcagggtt attgtctcat gagcggatac atatttgaat   5040
gtatttagaa aaataaacaa ataggggttc cgcgcacatt tccccgaaaa gtgccacctg   5100
acgtcgacgg atcgggagat ctcccgatcc cctatggtgc actctcagta caatctgctc   5160
tgatgccgca tagttaagcc agtatctgct ccctgcttgt gtgttggagg tcgctgagta   5220
gtgcgcgagc aaaatttaag ctacaacaag gcaaggcttg accgacaatt gcatgaagaa   5280
tctgcttagg gttaggcgtt ttgcgctgct tcgcgatgta cgggccagat atacgcgttg   5340
acattgatta ttgactagtt attaatagta atcaattacg gggtcattag ttcatagccc   5400
atatatggag ttccgcgtta cataacttac ggtaaatggc ccgcctggct gaccgcccaa   5460
cgacccccgc ccattgacgt caataatgac gtatgttccc atagtaacgc caatagggac   5520
tttccattga cgtcaatggg tggactattt acggtaaact gcccacttgg cagtacatca   5580
agtgtatcat atgccaagta cgccccctat tgacgtcaat gacggtaaat ggcccgcctg   5640
gcattatgcc cagtacatga ccttatggga ctttcctact tggcagtaca tctacgtatt   5700
agtcatcgct attaccatgg tgatgcggtt ttggcagtac atcaatgggc gtggatagcg   5760
gtttgactca cggggatttc caagtctcca ccccattgac gtcaatggga gtttgttttg   5820
gcaccaaaat caacgggact ttccaaaatg tcgtaacaac tccgccccat tgacgcaaat   5880
gggcggtagg cgtgtacggt gggaggtcta tataagcaga gctctctggc taactagaga   5940
acccactgct tactggctta tcgaaattaa tacgactcac tatagggaga cccaagctgg   6000
tttaaactta agcttggtac cgagctcact agtccagtgt ggtggcagat atccagcaca   6060
gtggcggccg ctcgaggggc ccgttttgcc tgtactgggt ctctctggtt agaccagatc   6120
tgagcctggg agctctctgg ctaactaggg aacccactgc ttaagcctca ataaagcttg   6180
ccttgagtgc ttcaagtagt gtgtgcccgt ctgttgtgtg actctggtaa ctagagatcc   6240
ctcagaccct tttagtcagt gtggaaaatc tctagcagtg gcgcccgaac agggacttga   6300
aagcgaaagg gaaaccagag gagctctctc gacgcaggac tcggcttgct gaagcgcgca   6360
cggcaagagg cgaggggcgg cgactggtga gtacgccaaa aattttgact agcggaggct   6420
agaaggagag agatgggtgc gagagcgtca gtattaagcg ggggagaatt agatcgcgat   6480
gggaaaaaat tcggttaagg ccagggggaa agaaaaaata taaattaaaa catatagtat   6540
gggcaagcag ggagctagaa cgattcgcag ttaatcctgg cctgttagaa acatcagaag   6600
gctgtagaca aatactggga cagctacaac catcccttca gacaggatca gaagaactta   6660
gatcattata taatacagta gcaaccctct attgtgtgca tcaaaggata gagataaaag   6720
acaccaagga agctttagac aagatagagg aagagcaaaa caaaagtaag accaccgcac   6780
agcaagcggc cgctgatctt cagacctgga ggaggagata tgagggacaa ttggagaagt   6840
gaattatata aatataaagt agtaaaaatt gaaccattag gagtagcacc caccaaggca   6900
aagagaagag tggtgcagag agaaaaaaga gcagtgggaa taggagcttt gttccttggg   6960
ttcttgggag cagcaggaag cactatgggc gcagcgtcaa tgacgctgac ggtacaggcc   7020
agacaattat tgtctggtat agtgcagcag cagaacaatt tgctgagggc tattgaggcg   7080
caacagcatc tgttgcaact cacagtctgg ggcatcaagc agctccaggc aagaatcctg   7140
gctgtggaaa gatacctaaa ggatcaacag ctcctgggga tttggggttg ctctggaaaa   7200
ctcatttgca ccactgctgt gccttggaat gctagttgga gtaataaatc tctggaacag   7260
atttggaatc acacgacctg gatggagtgg gacagagaaa ttaacaatta cacaagctta   7320
```

atacactcct taattgaaga atcgcaaaac cagcaagaaa agaatgaaca agaattattg 7380
gaattagata aatgggcaag tttgtggaat tggtttaaca taacaaattg gctgtggtat 7440
ataaaattat tcataatgat agtaggaggc ttggtaggtt taagaatagt ttttgctgta 7500
ctttctatag tgaatagagt taggcaggga tattcaccat tatcgtttca gacccacctc 7560
ccaaccccga ggggacccga caggccctta attaatcccc tgattctgtg gataaccgta 7620
ttaccgcctt tgagtgagct gcacgggagc aattaatcta tagattaaaa agtgaaaggc 7680
tacaatagga cgggagcaat taatctatag attaaaaagt gaaaggctac aataggacgg 7740
gagcaattaa tctatagatt aaaaagtgaa aggctacaat aggacgggag caattaatct 7800
atagattaaa aagtgaaagg ctacaatagg acgggagcaa ttaatctata gattaaaaag 7860
tgaaaggcta caataggacg ggagcaatta atctatagat taaaaagtga aaggctacaa 7920
taggacggga gcaattaatc tatagattaa aaagtgaaag gctacaatag gacggtaaac 7980
tcgacctata taagcagagc tcgtttagtg aaccgtcaga tcgcctggag acgccatcca 8040
cgctgttttg acctccatag aagacaccgg gaccgatcca gcctccgcgg ccccgaattg 8100
aattcggcca ttacggcctg ccaccatgag cacaaaaaag aaaccattaa cacaagagca 8160
gcttgaggac gcacgtcgcc ttaaagcaat ttatgaaaaa aagaaaaatg aacttggctt 8220
atcccaggaa tctgtcgcag acaagatggg gatggggcag tcaggcgttg gtgctttatt 8280
taatggcatc aatgcattaa atgcttataa cgccgcattg cttgcaaaaa ttctcaaagt 8340
tagcgttgaa gaattcagcc cttcaatcgc cagagagatc tacgagatgt atgaagcggt 8400
tagtatgcag ccgtcactta gaagtgagta tgagtaccct gtttttttctc atgttcaggc 8460 agggatgttc tcacctgagc ttagaacctt taccaaaggt gatgcggaga gatgggtaag 8520
cacaaccaaa aaagccagtg attctgcatt ctggcttgag gttgaaggta attccatgac 8580
cgcaccaaca ggctccaagc caagctttcc tgacggaatg ttaattctcg ttgaccctga 8640
gcaggctgtt gagcccgggg atttctgcat agccagactt gggggtgatg agtttacctt 8700
caagaaactg atcagggata gcggtcaggt gtttttacaa ccactaaacc cacagtaccc 8760
aatgatccca tgcaatgaga gttgttccgt tgtggggaaa gttatcgcta gtcagtggcc 8820
tgaagagacg tttggcccaa aaaagaagag aaaggtcgac ggcggtggtg ctttgtctcc 8880
tcagcactct gctgtcactc aaggaagtat catcaagaac aaggagggca tggatgctaa 8940
gtcactaact gcctggtccc ggacactggt gaccttcaag gatgtatttg tggacttcac 9000
cagggaggag tggaagctgc tggacactgc tcagcagatc gtgtacagaa atgtgatgct 9060
ggagaactat aagaacctgg tttccttggg ttatcagctt actaagccag atgtgatcct 9120
ccggttggag aagggagaag agccctggct ggtggagaga gaaattcacc aagagaccca 9180
tcctgattca gagactgcat ttgaaatcaa atcatcagtt taatgccacc 9230

<210> SEQ ID NO 18
<211> LENGTH: 8874
<212> TYPE: DNA
<213> ORGANISM: Artificial Sequence
<220> FEATURE:
<223> OTHER INFORMATION: Synthetic

<400> SEQUENCE: 18
ttatgtgtgg gagggctaag ggcgcgccgt tctagagaat tcgatatcaa gcttatcgat 60
aatcaacctc tggattacaa aatttgtgaa agattgactg gtattcttaa ctatgttgct 120

-continued

```
ccttttacgc tatgtggata cgctgcttta atgcctttgt atcatgctat tacttcccgt    180
acggctttca ttttctcctc cttgtataaa tcctggttgc tgtctcttta tgaggagttg    240
tggcccgttg tcaggcaacg tggcgtggtg tgcactgtgt ttgctgacgc aacccccact    300
ggttggggca ttgccaccac ctatcaactc ctttccggga ctttcgcttt ccccctccct    360
attgccacgg cggaactcat tgccgcctgc cttgcccgct gctggacagg ggctcggctg    420
ttgggcactg acaattccgt ggtgttgtcg gggaagctga cgtcctttcc atggctgctc    480
gcctgtgttg ccaactggat tctgcgcggg acgtccttct gctacgtccc ttcggccctc    540
aatccagcgg accttccttc ccgcggcctg ctgccggttc tgcggcctct tccgcgtctt    600
cgccttcgcc ctcagacgag tcggatctcc ctttgggccg cctccccgcc tgcctgcagg    660
tttgtcgaga cctagaaaaa catggagcaa tcacaagtag caatacagca gctaccaatg    720
ctgattgtgc ctggctagaa gcacaagagg aggaggaggt gggttttcca gtcacacctc    780
aggtaccttt aagaccaatg acttacaagg cagctgtaga tcttagccac tttttaaaag    840
aaaagggggg actggaaggg ctaattcact cccaacgaag acaagatctg ctttttgctt    900
gtactgggtc tctctggtta gaccagatct gagcctggga gctctctggc taactaggga    960
acccactgct taagcctcaa taaagcttgc cttgagtgct tcaagtagtg tgtgcccgtc   1020
tgttgtgtga ctctggtaac tagagatccc tcagaccctt ttagtcagtg tggaaaatct   1080
ctagcagggc ccgtttaaac ccgctgatca gcctcgactg tgccttctag ttgccagcca   1140
tctgttgttt gcccctcccc cgtgccttcc ttgaccctgg aaggtgccac tcccactgtc   1200
ctttcctaat aaaatgagga aattgcatcg cattgtctga gtaggtgtca ttctattctg   1260
gggggtgggg tggggcagga cagcaagggg gaggattggg aagacaatag caggcatgct   1320
ggggatgcgg tgggctctat ggcttctgag gcggaaagaa ccagctgggg ctctaggggg   1380
tatccccacg cgccctgtag cggcgcatta agcgcggcgg gtgtggtggt tacgcgcagc   1440
gtgaccgcta cacttgccag cgccctagcg cccgctcctt tcgctttctt cccttccttt   1500
ctcgccacgt tcgccggctt tccccgtcaa gctctaaatc ggggcatccc tttagggttc   1560
cgatttagtg ctttacggca cctcgacccc aaaaaacttg attagggtga tggttcacgt   1620
agtgggccat cgccctgata gacggttttt cgccctttga cgttggagtc cacgttcttt   1680
aatagtggac tcttgttcca aactggaaca acactcaacc ctatctcggt ctattctttt   1740
gatttataag ggattttggg gatttcggcc tattggttaa aaaatgagct gatttaacaa   1800
aaatttaacg cgaattaatt ctgtggaatg tgtgtcagtt agggtgtgga aagtccccag   1860
gctccccagg caggcagaag tatgcaaagc atgcatctca attagtcagc aaccaggtgt   1920
ggaaagtccc caggctcccc agcaggcaga agtatgcaaa gcatgcatct caattagtca   1980
gcaaccatag tcccgcccct aactccgccc atcccgcccc taactccgcc cagttccgcc   2040
cattctccgc cccatggctg actaattttt tttatttatg cagaggccga ggccgcctct   2100
gcctctgagc tattccagaa gtagtgagga ggcttttttg gaggcctagg cttttgcaaa   2160
aagctcccgg gagcttgtat atccattttc ggatctgatc agcacgtgtt gacaattaat   2220
catcggcata gtatatcggc atagtataat acgacaaggt gaggaactaa accatggcca   2280
agttgaccag tgccgttccg gtgctcaccg cgcgcgacgt cgccggagcg gtcgagttct   2340
ggaccgaccg gctcgggttc tcccgggact tcgtggagga cgacttcgcc ggtgtggtcc   2400
gggacgacgt gaccctgttc atcagcgcgg tccaggacca ggtggtgccg gacaacaccc   2460
tggcctgggt gtgggtgcgc ggcctggacg agctgtacgc cgagtggtcg gaggtcgtgt   2520
```

```
ccacgaactt ccgggacgcc tccgggccgg ccatgaccga gatcggcgag cagccgtggg   2580
ggcgggagtt cgccctgcgc gacccggccg gcaactgcgt gcacttcgtg gccgaggagc   2640
aggactgaca cgtgctacga gatttcgatt ccaccgccgc cttctatgaa aggttgggct   2700
tcggaatcgt tttccgggac gccggctgga tgatcctcca gcgcggggat ctcatgctgg   2760
agttcttcgc ccaccccaac ttgtttattg cagcttataa tggttacaaa taaagcaata   2820
gcatcacaaa tttcacaaat aaagcatttt tttcactgca ttctagttgt ggtttgtcca   2880
aactcatcaa tgtatcttat catgtctgta taccgtcgac ctctagctag agcttggcgt   2940
aatcatggtc atagctgttt cctgtgtgaa attgttatcc gctcacaatt ccacacaaca   3000
tacgagccgg aagcataaag tgtaaagcct ggggtgccta atgagtgagc taactcacat   3060
taattgcgtt gcgctcactg cccgctttcc agtcgggaaa cctgtcgtgc cagctgcatt   3120
aatgaatcgg ccaacgcgcg gggagaggcg gtttgcgtat tgggcgctct tccgcttcct   3180
cgctcactga ctcgctgcgc tcggtcgttc ggctgcggcg agcggtatca gctcactcaa   3240
aggcggtaat acggttatcc acagaatcag gggataacgc aggaaagaac atgtgagcaa   3300
aaggccagca aaaggccagg aaccgtaaaa aggccgcgtt gctggcgttt ttccataggc   3360
tccgcccccc tgacgagcat cacaaaaatc gacgctcaag tcagaggtgg cgaaacccga   3420
caggactata aagataccag gcgtttcccc ctggaagctc cctcgtgcgc tctcctgttc   3480
cgaccctgcc gcttaccgga tacctgtccg cctttctccc ttcgggaagc gtggcgcttt   3540
ctcaatgctc acgctgtagg tatctcagtt cggtgtaggt cgttcgctcc aagctgggct   3600
gtgtgcacga accccccgtt cagcccgacc gctgcgcctt atccggtaac tatcgtcttg   3660
agtccaaccc ggtaagacac gacttatcgc cactggcagc agccactggt aacaggatta   3720
gcagagcgag gtatgtaggc ggtgctacag agttcttgaa gtggtggcct aactacggct   3780
acactagaag gacagtattt ggtatctgcg ctctgctgaa gccagttacc ttcggaaaaa   3840
gagttggtag ctcttgatcc ggcaaacaaa ccaccgctgg tagcggtggt ttttttgttt   3900
gcaagcagca gattacgcgc agaaaaaaag gatctcaaga agatcctttg atcttttcta   3960
cggggtctga cgctcagtgg aacgaaaact cacgttaagg gattttggtc atgagattat   4020
caaaaaggat cttcacctag atccttttaa attaaaaatg aagttttaaa tcaatctaaa   4080
gtatatatga gtaaacttgg tctgacagtt accaatgctt aatcagtgag gcacctatct   4140
cagcgatctg tctatttcgt tcatccatag ttgcctgact ccccgtcgtg tagataacta   4200
cgatacggga gggcttacca tctggcccca gtgctgcaat gataccgcga gacccacgct   4260
caccggctcc agatttatca gcaataaacc agccagccgg aagggccgag cgcagaagtg   4320
gtcctgcaac tttatccgcc tccatccagt ctattaattg ttgccgggaa gctagagtaa   4380
gtagttcgcc agttaatagt ttgcgcaacg ttgttgccat tgctacaggc atcgtggtgt   4440
cacgctcgtc gtttggtatg gcttcattca gctccggttc ccaacgatca aggcgagtta   4500
catgatcccc catgttgtgc aaaaaagcgg ttagctcctt cggtcctccg atcgttgtca   4560
gaagtaagtt ggccgcagtg ttatcactca tggttatggc agcactgcat aattctctta   4620
ctgtcatgcc atccgtaaga tgcttttctg tgactggtga gtactcaacc aagtcattct   4680
gagaatagtg tatgcggcga ccgagttgct cttgcccggc gtcaatacgg gataataccg   4740
cgccacatag cagaacttta aaagtgctca tcattggaaa acgttcttcg gggcgaaaac   4800
tctcaaggat cttaccgctg ttgagatcca gttcgatgta acccactcgt gcacccaact   4860
```

```
gatcttcagc atcttttact ttcaccagcg tttctgggtg agcaaaaaca ggaaggcaaa   4920
atgccgcaaa aaagggaata agggcgacac ggaaatgttg aatactcata ctcttccttt   4980
ttcaatatta ttgaagcatt tatcagggtt attgtctcat gagcggatac atatttgaat   5040
gtatttagaa aaataaacaa ataggggttc cgcgcacatt tccccgaaaa gtgccacctg   5100
acgtcgacgg atcgggagat ctcccgatcc cctatggtgc actctcagta caatctgctc   5160
tgatgccgca tagttaagcc agtatctgct ccctgcttgt gtgttggagg tcgctgagta   5220
gtgcgcgagc aaaatttaag ctacaacaag gcaaggcttg accgacaatt gcatgaagaa   5280
tctgcttagg gttaggcgtt ttgcgctgct tcgcgatgta cgggccagat atacgcgttg   5340
acattgatta ttgactagtt attaatagta atcaattacg gggtcattag ttcatagccc   5400
atatatggag ttccgcgtta cataacttac ggtaaatggc ccgcctggct gaccgcccaa   5460
cgacccccgc ccattgacgt caataatgac gtatgttccc atagtaacgc caatagggac   5520
tttccattga cgtcaatggg tggactattt acggtaaact gcccacttgg cagtacatca   5580
agtgtatcat atgccaagta cgccccctat tgacgtcaat gacggtaaat ggcccgcctg   5640
gcattatgcc cagtacatga ccttatggga ctttcctact tggcagtaca tctacgtatt   5700
agtcatcgct attaccatgg tgatgcggtt ttggcagtac atcaatgggc gtggatagcg   5760
gtttgactca cggggatttc caagtctcca ccccattgac gtcaatggga gtttgttttg   5820
gcaccaaaat caacgggact ttccaaaatg tcgtaacaac tccgccccat tgacgcaaat   5880
gggcggtagg cgtgtacggt gggaggtcta tataagcaga gctctctggc taactagaga   5940
acccactgct tactggctta tcgaaattaa tacgactcac tatagggaga cccaagctgg   6000
tttaaactta agcttggtac cgagctcact agtccagtgt ggtggcagat atccagcaca   6060
gtggcggccg ctcgaggggc ccgttttgcc tgtactgggt ctctctggtt agaccagatc   6120
tgagcctggg agctctctgg ctaactaggg aacccactgc ttaagcctca ataaagcttg   6180
ccttgagtgc ttcaagtagt gtgtgcccgt ctgttgtgtg actctggtaa ctagagatcc   6240
ctcagaccct tttagtcagt gtggaaaatc tctagcagtg gcgcccgaac agggacttga   6300
aagcgaaagg gaaaccagag gagctctctc gacgcaggac tcggcttgct gaagcgcgca   6360
cggcaagagg cgaggggcgg cgactggtga gtacgccaaa aattttgact agcggaggct   6420
agaaggagag agatgggtgc gagagcgtca gtattaagcg ggggagaatt agatcgcgat   6480
gggaaaaaat tcggttaagg ccagggggaa agaaaaaata taaattaaaa catatagtat   6540
gggcaagcag ggagctagaa cgattcgcag ttaatcctgg cctgttagaa acatcagaag   6600
gctgtagaca aatactggga cagctacaac catcccttca gacaggatca gaagaactta   6660
gatcattata taatacagta gcaaccctct attgtgtgca tcaaaggata gagataaaag   6720
acaccaagga agctttagac aagatagagg aagagcaaaa caaaagtaag accaccgcac   6780
agcaagcggc cgctgatctt cagacctgga ggaggagata tgagggacaa ttggagaagt   6840
gaattatata aatataaagt agtaaaaatt gaaccattag gagtagcacc caccaaggca   6900
aagagaagag tggtgcagag agaaaaaaga gcagtgggaa taggagcttt gttccttggg   6960
ttcttgggag cagcaggaag cactatgggc gcagcgtcaa tgacgctgac ggtacaggcc   7020
agacaattat tgtctggtat agtgcagcag cagaacaatt tgctgagggc tattgaggcg   7080
caacagcatc tgttgcaact cacagtctgg ggcatcaagc agctccaggc aagaatcctg   7140
gctgtggaaa gatacctaaa ggatcaacag ctcctgggga tttggggttg ctctggaaaa   7200
ctcatttgca ccactgctgt gccttggaat gctagttgga gtaataaatc tctggaacag   7260
```

```
atttggaatc acacgacctg gatggagtgg gacagagaaa ttaacaatta cacaagctta   7320
atacactcct taattgaaga atcgcaaaac cagcaagaaa agaatgaaca agaattattg   7380
gaattagata aatgggcaag tttgtggaat tggtttaaca taacaaattg gctgtggtat   7440
ataaaattat tcataatgat agtaggaggc ttggtaggtt taagaatagt ttttgctgta   7500
ctttctatag tgaatagagt taggcaggga tattcaccat tatcgtttca gacccacctc   7560
ccaaccccga ggggacccga caggccctta attaatcccc tgattctgtg gataaccgta   7620
ttaccgcctt tgagtgagct gcacgggagc aattaatcta tagattaaaa agtgaaaggc   7680
tacaatagga cgggagcaat taatctatag attaaaaagt gaaaggctac aataggacgg   7740
gagcaattaa tctatagatt aaaaagtgaa aggctacaat aggacgggag caattaatct   7800
atagattaaa aagtgaaagg ctacaatagg acgggagcaa ttaatctata gattaaaaag   7860
tgaaaggcta caataggacg ggagcaatta atctatagat taaaaagtga aaggctacaa   7920
taggacggga gcaattaatc tatagattaa aaagtgaaag gctacaatag gacggtaaac   7980
tcgacctata taagcagagc tcgtttagtg aaccgtcaga tcgcctggag acgccatcca   8040
cgctgttttg acctccatag aagacaccgg gaccgatcca gcctccgcgg ccccgaattg   8100
aattctccct atcagtgata gagatctccc tatcagtgat agagaggcca ttacggcctg   8160
ccaccatgtt cgttatcatc caggctcacg aataccagaa atacgctgct gttctggacc   8220
agatgttccg tctgcgtaaa aaagttttcg ctgacaccct gtgctgggac gttccggtta   8280
tcggtccgta cgaacgtgac tcctacgact ccctggctcc ggcttacctg gtttggtgca   8340
acgactcccg tacccgtctg tacggtggta tgcgtctgat gccgaccacc ggtccgaccc   8400
tgctgtacga cgttttccgt gaaaccttcc cggacgctgc tgacctgatc gctccgggta   8460
tctgggaagg tacccgtatg tgcatcgacg aagaagctat cgctaaagac ttcccggaaa   8520
tcgacgctgg tcgtgctttc tccatgatgc tgctggctct gtgcgaatgc gctctggacc   8580
acggtatcca caccatgatc tccaactacg aaccgtacct gaaacgtgtt tacaaacgtg   8640
ctggtgctga agttgaagaa ctgggtcgtg ctgacggtta cggtaaatac ccggtttgct   8700
gcggtgcttt cgaagtttcc gaccgtgttc tgcgtaaaat gcgtgctgct ctgggtctga   8760
ccctgccgct gtacgttcgt cacgttccgg ctcgttccgt tgttacccag ttcctggaaa   8820
tggctgctgc tgctaacgac gaaaactacg ctctggttgc ttaataatgc cacc         8874
```

<210> SEQ ID NO 19
<211> LENGTH: 9927
<212> TYPE: DNA
<213> ORGANISM: Artificial Sequence
<220> FEATURE:
<223> OTHER INFORMATION: Synthetic

<400> SEQUENCE: 19

```
cggccatcga taaggatccg cggccgcaat caacctctgg attacaaaat ttgtgaaaga     60
ttgactggta ttcttaacta tgttgctcct tttacgctat gtggatacgc tgctttaatg    120
cctttgtatc atgctattac ttcccgtacg gctttcattt tctcctcctt gtataaatcc    180
tggttgctgt ctctttatga ggagttgtgg cccgttgtca ggcaacgtgg cgtggtgtgc    240
actgtgtttg ctgacgcaac ccccactggt tggggcattg ccaccaccta tcaactcctt    300
tccgggactt tcgctttccc cctccctatt gccacggcgg aactcattgc cgcctgcctt    360
gcccgctgct ggacaggggc tcggctgttg ggcactgaca attccgtggt gttgtcgggg    420
```

-continued

```
aagctgacgt cctttccatg gctgctcgcc tgtgttgcca actggattct gcgcgggacg    480
tccttctgct acgtcccttc ggccctcaat ccagcggacc ttccttcccg cggcctgctg    540
ccggttctgc ggcctcttcc gcgtcttcgc cttcgccctc agacgagtcg gatctccctt    600
tgggccgcct ccccgcctgc ctgcaggttt gtcgagacct agaaaaacat ggagcaatca    660
caagtagcaa tacagcagct accaatgctg attgtgcctg gctagaagca caagaggagg    720
aggaggtggg ttttccagtc acacctcagg tacctttaag accaatgact tacaaggcag    780
ctgtagatct tagccacttt ttaaaagaaa aggggggact ggaagggcta attcactccc    840
aacgaagaca agatctgctt tttgcttgta ctgggtctct ctggttagac cagatctgag    900
cctgggagct ctctggctaa ctagggaacc cactgcttaa gcctcaataa agcttgcctt    960
gagtgcttca agtagtgtgt gcccgtctgt tgtgtgactc tggtaactag agatccctca   1020
gacccttta gtcagtgtgg aaaatctcta gcagggcccg tttaaacccg ctgatcagcc   1080
tcgactgtgc cttctagttg ccagccatct gttgtttgcc cctcccccgt gccttccttg   1140
accctggaag gtgccactcc cactgtcctt tcctaataaa atgaggaaat tgcatcgcat   1200
tgtctgagta ggtgtcattc tattctgggg ggtggggtgg ggcaggacag caagggggag   1260
gattgggaag acaatagcag gcatgctggg gatgcggtgg gctctatggc ttctgaggcg   1320
gaaagaacca gctggggctc tagggggtat ccccacgcgc cctgtagcgg cgcattaagc   1380
gcggcgggtg tggtggttac gcgcagcgtg accgctacac ttgccagcgc cctagcgccc   1440
gctcctttcg ctttcttccc ttcctttctc gccacgttcg ccggctttcc ccgtcaagct   1500
ctaaatcggg gcatcccttt agggttccga tttagtgctt tacggcacct cgaccccaaa   1560
aaacttgatt agggtgatgg ttcacgtagt gggccatcgc cctgatagac ggtttttcgc   1620
cctttgacgt tggagtccac gttctttaat agtggactct tgttccaaac tggaacaaca   1680
ctcaacccta tctcggtcta ttcttttgat ttataaggga ttttggggat ttcggcctat   1740
tggttaaaaa atgagctgat ttaacaaaaa tttaacgcga attaattctg tggaatgtgt   1800
gtcagttagg gtgtggaaag tccccaggct ccccaggcag gcagaagtat gcaaagcatg   1860
catctcaatt agtcagcaac caggtgtgga aagtccccag gctccccagc aggcagaagt   1920
atgcaaagca tgcatctcaa ttagtcagca accatagtcc cgcccctaac tccgcccatc   1980
ccgcccctaa ctccgcccag ttccgcccat tctccgcccc atggctgact aattttttt   2040
atttatgcag aggccgaggc cgcctctgcc tctgagctat tccagaagta gtgaggaggc   2100
ttttttggag gcctaggctt ttgcaaaaag ctcccgggag cttgtatatc cattttcgga   2160
tctgatcagc acgtgttgac aattaatcat cggcatagta tatcggcata gtataatacg   2220
acaaggtgag gaactaaacc atggccaagt tgaccagtgc cgttccggtg ctcaccgcgc   2280
gcgacgtcgc cggagcggtc gagttctgga ccgaccggct cgggttctcc cgggacttcg   2340
tggaggacga cttcgccggt gtggtccggg acgacgtgac cctgttcatc agcgcggtcc   2400
aggaccaggt ggtgccggac aacaccctgg cctgggtgtg ggtgcgcggc ctggacgagc   2460
tgtacgccga gtggtcggag gtcgtgtcca cgaacttccg ggacgcctcc gggccggcca   2520
tgaccgagat cggcgagcag ccgtgggggc gggagttcgc cctgcgcgac ccggccggca   2580
actgcgtgca cttcgtggcc gaggagcagg actgacacgt gctacgagat ttcgattcca   2640
ccgccgcctt ctatgaaagg ttgggcttcg gaatcgtttt ccgggacgcc ggctggatga   2700
tcctccagcg cggggatctc atgctggagt tcttcgccca ccccaacttg tttattgcag   2760
cttataatgg ttacaaataa agcaatagca tcacaaattt cacaaataaa gcattttttt   2820
```

```
cactgcattc tagttgtggt ttgtccaaac tcatcaatgt atcttatcat gtctgtatac   2880
cgtcgacctc tagctagagc ttggcgtaat catggtcata gctgtttcct gtgtgaaatt   2940
gttatccgct cacaattcca cacaacatac gagccggaag cataaagtgt aaagcctggg   3000
gtgcctaatg agtgagctaa ctcacattaa ttgcgttgcg ctcactgccc gctttccagt   3060
cgggaaacct gtcgtgccag ctgcattaat gaatcggcca acgcgcgggg agaggcggtt   3120
tgcgtattgg gcgctcttcc gcttcctcgc tcactgactc gctgcgctcg gtcgttcggc   3180
tgcggcgagc ggtatcagct cactcaaagg cggtaatacg gttatccaca gaatcagggg   3240
ataacgcagg aaagaacatg tgagcaaaag gccagcaaaa ggccaggaac cgtaaaaagg   3300
ccgcgttgct ggcgtttttc cataggctcc gcccccctga cgagcatcac aaaaatcgac   3360
gctcaagtca gaggtggcga aacccgacag gactataaag ataccaggcg tttccccctg   3420
gaagctccct cgtgcgctct cctgttccga ccctgccgct taccggatac ctgtccgcct   3480
ttctcccttc gggaagcgtg gcgctttctc aatgctcacg ctgtaggtat ctcagttcgg   3540
tgtaggtcgt tcgctccaag ctgggctgtg tgcacgaacc ccccgttcag cccgaccgct   3600
gcgccttatc cggtaactat cgtcttgagt ccaacccggt aagacacgac ttatcgccac   3660
tggcagcagc cactggtaac aggattagca gagcgaggta tgtaggcggt gctacagagt   3720
tcttgaagtg gtggcctaac tacggctaca ctagaaggac agtatttggt atctgcgctc   3780
tgctgaagcc agttaccttc ggaaaaagag ttggtagctc ttgatccggc aaacaaacca   3840
ccgctggtag cggtggtttt tttgtttgca agcagcagat tacgcgcaga aaaaaaggat   3900
ctcaagaaga tcctttgatc ttttctacgg ggtctgacgc tcagtggaac gaaaactcac   3960
gttaagggat tttggtcatg agattatcaa aaaggatctt cacctagatc cttttaaatt   4020
aaaaatgaag ttttaaatca atctaaagta tatatgagta aacttggtct gacagttacc   4080
aatgcttaat cagtgaggca cctatctcag cgatctgtct atttcgttca tccatagttg   4140
cctgactccc cgtcgtgtag ataactacga tacgggaggg cttaccatct ggccccagtg   4200
ctgcaatgat accgcgagac ccacgctcac cggctccaga tttatcagca ataaaccagc   4260
cagccggaag ggccgagcgc agaagtggtc ctgcaacttt atccgcctcc atccagtcta   4320
ttaattgttg ccgggaagct agagtaagta gttcgccagt taatagtttg cgcaacgttg   4380
ttgccattgc tacaggcatc gtggtgtcac gctcgtcgtt tggtatggct tcattcagct   4440
ccggttccca acgatcaagg cgagttacat gatcccccat gttgtgcaaa aaagcggtta   4500
gctccttcgg tcctccgatc gttgtcagaa gtaagttggc cgcagtgtta tcactcatgg   4560
ttatggcagc actgcataat tctcttactg tcatgccatc cgtaagatgc ttttctgtga   4620
ctggtgagta ctcaaccaag tcattctgag aatagtgtat gcggcgaccg agttgctctt   4680
gcccggcgtc aatacgggat aataccgcgc cacatagcag aactttaaaa gtgctcatca   4740
ttggaaaacg ttcttcgggg cgaaaactct caaggatctt accgctgttg agatccagtt   4800
cgatgtaacc cactcgtgca cccaactgat cttcagcatc ttttactttc accagcgttt   4860
ctgggtgagc aaaaacagga aggcaaaatg ccgcaaaaaa gggaataagg gcgacacgga   4920
aatgttgaat actcatactc ttcctttttc aatattattg aagcatttat cagggttatt   4980
gtctcatgag cggatacata tttgaatgta tttagaaaaa taaacaaata ggggttccgc   5040
gcacatttcc ccgaaaagtg ccacctgacg tcgacggatc gggagatctc ccgatcccct   5100
atggtgcact ctcagtacaa tctgctctga tgccgcatag ttaagccagt atctgctccc   5160
```

```
tgcttgtgtg ttggaggtcg ctgagtagtg cgcgagcaaa atttaagcta caacaaggca   5220
aggcttgacc gacaattgca tgaagaatct gcttagggtt aggcgttttg cgctgcttcg   5280
cgatgtacgg gccagatata cgcgttgaca ttgattattg actagttatt aatagtaatc   5340
aattacgggg tcattagttc atagcccata tatggagttc cgcgttacat aacttacggt   5400
aaatggcccg cctggctgac cgcccaacga cccccgccca ttgacgtcaa taatgacgta   5460
tgttcccata gtaacgccaa tagggacttt ccattgacgt caatgggtgg actatttacg   5520
gtaaactgcc cacttggcag tacatcaagt gtatcatatg ccaagtacgc cccctattga   5580
cgtcaatgac ggtaaatggc ccgcctggca ttatgcccag tacatgacct tatgggactt   5640
tcctacttgg cagtacatct acgtattagt catcgctatt accatggtga tgcggttttg   5700
gcagtacatc aatgggcgtg gatagcggtt tgactcacgg ggatttccaa gtctccaccc   5760
cattgacgtc aatgggagtt tgttttggca ccaaaatcaa cgggactttc caaaatgtcg   5820
taacaactcc gccccattga cgcaaatggg cggtaggcgt gtacggtggg aggtctatat   5880
aagcagagct ctctggctaa ctagagaacc cactgcttac tggcttatcg aaattaatac   5940
gactcactat agggagaccc aagctggttt aaacttaagc ttggtaccga gctcactagt   6000
ccagtgtggt ggcagatatc cagcacagtg gcggccgctc gagtctagag ggcccgtttt   6060
gcctgtactg ggtctctctg gttagaccag atctgagcct gggagctctc tggctaacta   6120
gggaacccac tgcttaagcc tcaataaagc ttgccttgag tgcttcaagt agtgtgtgcc   6180
cgtctgttgt gtgactctgg taactagaga tccctcagac ccttttagtc agtgtggaaa   6240
atctctagca gtggcgcccg aacagggact tgaaagcgaa agggaaacca gaggagctct   6300
ctcgacgcag gactcggctt gctgaagcgc gcacggcaag aggcgagggg cggcgactgg   6360
tgagtacgcc aaaaattttg actagcggag gctagaagga gagagatggg tgcgagagcg   6420
tcagtattaa gcgggggaga attagatcgc gatgggaaaa aattcggtta aggccagggg   6480
gaaagaaaaa atataaatta aaacatatag tatgggcaag cagggagcta gaacgattcg   6540
cagttaatcc tggcctgtta gaaacatcag aaggctgtag acaaatactg ggacagctac   6600
aaccatccct tcagacagga tcagaagaac ttagatcatt atataataca gtagcaaccc   6660
tctattgtgt gcatcaaagg atagagataa aagacaccaa ggaagcttta gacaagatag   6720
aggaagagca aaacaaaagt aagaccaccg cacagcaagc ggccgctgat cttcagacct   6780
ggaggaggag atatgaggga caattggaga agtgaattat ataaatataa agtagtaaaa   6840
attgaaccat taggagtagc acccaccaag gcaaagagaa gagtggtgca gagagaaaaa   6900
agagcagtgg gaataggagc tttgttcctt gggttcttgg gagcagcagg aagcactatg   6960
ggcgcagcgt caatgacgct gacggtacag gccagacaat tattgtctgg tatagtgcag   7020
cagcagaaca atttgctgag ggctattgag gcgcaacagc atctgttgca actcacagtc   7080
tggggcatca agcagctcca ggcaagaatc ctggctgtgg aaagatacct aaaggatcaa   7140
cagctcctgg ggatttgggg ttgctctgga aaactcattt gcaccactgc tgtgccttgg   7200
aatgctagtt ggagtaataa atctctggaa cagatttgga atcacacgac ctggatggag   7260
tgggacagag aaattaacaa ttacacaagc ttaatacact ccttaattga agaatcgcaa   7320
aaccagcaag aaaagaatga acaagaatta ttggaattag ataaatgggc aagtttgtgg   7380
aattggttta acataacaaa ttggctgtgg tatataaaat tattcataat gatagtagga   7440
ggcttggtag gtttaagaat agtttttgct gtactttcta tagtgaatag agttaggcag   7500
ggatattcac cattatcgtt tcagacccac ctcccaaccc cgaggggacc cgacaggccc   7560
```

-continued

```
ttaattaatt ggctccggtg cccgtcagtg ggcagagcgc acatcgccca cagtccccga   7620
gaagttgggg ggaggggtcg gcaattgaac cggtgcctag agaaggtggc gcggggtaaa   7680
ctgggaaagt gatgtcgtgt actggctccg cctttttccc gagggtgggg gagaaccgta   7740
tataagtgca gtagtcgccg tgaagctagc aattgtgagc ggataacaat tccacagtcg   7800
accctaggtt gtgtcgcgag tgttggatcc cagctgacac caattgtgag cgctcacaat   7860
tgctagaaga atacaaccac gactatataa gaatacaacc acgactccgt tctttttcgc   7920
aacgggtttg ccgccagaac acaggtaagt gccgtgtgtg gttcccgcgg gcctggcctc   7980
tttacgggtt atggcccttg cgtgccttga attacttcca cctggctgca gtacgtgatt   8040
cttgatcccg agcttcgggt tggaagtggg tgggagagtt cgaggccttg cgcttaagga   8100
gccccttcgc ctcgtgcttg agttgaggcc tggcctgggc gctggggccg ccgcgtgcga   8160
atctggtggc accttcgcgc ctgtctcgct gctttcgata agtctctagc catttaaaat   8220
ttttgatgac ctgctgcgac gctttttttc tggcaagata gtcttgtaaa tgcgggccaa   8280
gatctgcaca ctggtatttc ggtttttggg gccgcgggcg gcgacggggc ccgtgcgtcc   8340
cagcgcacat gttcggcgag gcggggcctg cgagcgcggc caccgagaat cggacggggg   8400
tagtctcaag ctggccggcc tgctctggtg cctggcctcg cgccgccgtg tatcgccccg   8460
ccctgggcgg caaggctggc ccggtcggca ccagttgcgt gagcggaaag atggccgctt   8520
cccggccctg ctgcagggag ctcaaaatgg aggacgcggc gctcgggaga gcgggcgggt   8580
gagtcaccca cacaaaggaa aagggccttt ccgtcctcag ccgtcgcttc atgtgactcc   8640
acggagtacc gggcgccgtc caggcacctc gattagttct cgagcttttg gagtacgtcg   8700
tctttaggtt ggggggaggg gttttatgcg atggagtttc cccacactga gtgggtggag   8760
actgaagtta ggccagcttg gcacttgatg taattctcct tggaatttgc cctttttgag   8820
tttggatctt ggttcattct caagcctcag acagtggttc aaagtttttt tcttccattt   8880
caggtgaatt cggccattac ggcccgccac catggctaga ttagataaaa gtaaagtgat   8940
taacagcgca ttagagctgc ttaatgaggt cggaatcgaa ggtttaacaa cccgtaaact   9000
cgcccagaag ctaggtgtag agcagcctac attgtattgg catgtaaaaa ataagcgggc   9060
tttgctcgac gccttagcca ttgagatgtt agataggcac catactcact tttgcccttt   9120
agaaggggaa agctggcaag atttttacg taataacgct aaaagtttta gatgtgcttt   9180
actaagtcat cgcgatggag caaaagtaca tttaggtaca cggcctacag aaaaacagta   9240
tgaaactctc gaaaatcaat tagccttttt atgccaacaa ggtttttcac tagagaatgc   9300
attatatgca ctcagcgctg tggggcattt tactttaggt tgcgtattgg aagatcaaga   9360
gcatcaagtc gctaaagaag aaagggaaac acctactact gatagtatgc cgccattatt   9420
acgacaagct atcgaattat ttgatcacca aggtgcagag ccagccttct tattcggcct   9480
tgaattgatc atatgcggat tagaaaaaca acttaaatgt gaaagtgggt cgccaaaaaa   9540
gaagagaaag gtcgacggcg gtggtgcttt gtctcctcag cactctgctg tcactcaagg   9600
aagtatcatc aagaacaagg agggcatgga tgctaagtca ctaactgcct ggtcccggac   9660
actggtgacc ttcaaggatg tatttgtgga cttcaccagg gaggagtgga agctgctgga   9720
cactgctcag cagatcgtgt acagaaatgt gatgctggag aactataaga acctggtttc   9780
cttgggttat cagcttacta agccagatgt gatcctccgg ttggagaagg gagaagagcc   9840
ctggctggtg gagagagaaa ttcaccaaga gacccatcct gattcagaga ctgcatttga   9900
```

aatcaaatca tcagtttaag gccgcct 9927

<210> SEQ ID NO 20
<211> LENGTH: 8916
<212> TYPE: DNA
<213> ORGANISM: Artificial Sequence
<220> FEATURE:
<223> OTHER INFORMATION: Synthetic

<400> SEQUENCE: 20
agaattcgat atcaagctta tcgataatca acctctggat tacaaaattt gtgaaagatt 60
gactggtatt cttaactatg ttgctccttt tacgctatgt ggatacgctg ctttaatgcc 120
tttgtatcat gctattactt cccgtacggc tttcattttc tcctccttgt ataaatcctg 180
gttgctgtct ctttatgagg agttgtggcc cgttgtcagg caacgtggcg tggtgtgcac 240
tgtgtttgct gacgcaaccc ccactggttg gggcattgcc accacctatc aactcctttc 300
cgggactttc gctttccccc tccctattgc cacggcggaa ctcattgccg cctgccttgc 360
ccgctgctgg acaggggctc ggctgttggg cactgacaat tccgtggtgt tgtcggggaa 420
gctgacgtcc tttccatggc tgctcgcctg tgttgccaac tggattctgc gcgggacgtc 480
cttctgctac gtcccttcgg ccctcaatcc agcggacctt ccttcccgcg gcctgctgcc 540
ggttctgcgg cctcttccgc gtcttcgcct tcgccctcag acgagtcgga tctccctttg 600
ggccgcctcc ccgcctgcct gcaggtttgt cgagacctag aaaaacatgg agcaatcaca 660
agtagcaata cagcagctac caatgctgat tgtgcctggc tagaagcaca agaggaggag 720
gaggtgggtt ttccagtcac acctcaggta cctttaagac caatgactta caaggcagct 780
gtagatctta gccacttttt aaaagaaaag gggggactgg aagggctaat tcactcccaa 840
cgaagacaag atctgctttt tgcttgtact gggtctctct ggttagacca gatctgagcc 900
tgggagctct ctggctaact agggaaccca ctgcttaagc ctcaataaag cttgccttga 960
gtgcttcaag tagtgtgtgc ccgtctgttg tgtgactctg gtaactagag atccctcaga 1020
cccttttagt cagtgtggaa aatctctagc agggcccgtt taaacccgct gatcagcctc 1080
gactgtgcct tctagttgcc agccatctgt tgtttgcccc tcccccgtgc cttccttgac 1140
cctggaaggt gccactccca ctgtcctttc ctaataaaat gaggaaattg catcgcattg 1200
tctgagtagg tgtcattcta ttctgggggg tggggtgggg caggacagca agggggagga 1260
ttgggaagac aatagcaggc atgctgggga tgcggtgggc tctatggctt ctgaggcgga 1320
aagaaccagc tggggctcta gggggtatcc ccacgcgccc tgtagcggcg cattaagcgc 1380
ggcgggtgtg gtggttacgc gcagcgtgac cgctacactt gccagcgccc tagcgcccgc 1440
tcctttcgct ttcttccctt cctttctcgc cacgttcgcc ggctttcccc gtcaagctct 1500
aaatcggggc atccctttag ggttccgatt tagtgcttta cggcacctcg accccaaaaa 1560
acttgattag ggtgatggtt cacgtagtgg gccatcgccc tgatagacgg tttttcgccc 1620
tttgacgttg gagtccacgt tctttaatag tggactcttg ttccaaactg gaacaacact 1680
caaccctatc tcggtctatt cttttgattt ataagggatt ttggggattt cggcctattg 1740
gttaaaaaat gagctgattt aacaaaaatt taacgcgaat taattctgtg gaatgtgtgt 1800
cagttagggt gtggaaagtc cccaggctcc ccaggcaggc agaagtatgc aaagcatgca 1860
tctcaattag tcagcaacca ggtgtggaaa gtccccaggc tccccagcag gcagaagtat 1920
gcaaagcatg catctcaatt agtcagcaac catagtcccg cccctaactc cgcccatccc 1980
gcccctaact ccgcccagtt ccgcccattc tccgccccat ggctgactaa ttttttttat 2040

```
ttatgcagag gccgaggccg cctctgcctc tgagctattc cagaagtagt gaggaggctt   2100
ttttggaggc ctaggctttt gcaaaaagct cccgggagct tgtatatcca ttttcggatc   2160
tgatcagcac gtgttgacaa ttaatcatcg gcatagtata tcggcatagt ataatacgac   2220
aaggtgagga actaaaccat ggccaagttg accagtgccg ttccggtgct caccgcgcgc   2280
gacgtcgccg gagcggtcga gttctggacc gaccggctcg ggttctcccg ggacttcgtg   2340
gaggacgact tcgccggtgt ggtccgggac gacgtgaccc tgttcatcag cgcggtccag   2400
gaccaggtgg tgccggacaa caccctggcc tgggtgtggg tgcgcggcct ggacgagctg   2460
tacgccgagt ggtcggaggt cgtgtccacg aacttccggg acgcctccgg gccggccatg   2520
accgagatcg gcgagcagcc gtgggggcgg gagttcgccc tgcgcgaccc ggccggcaac   2580
tgcgtgcact tcgtggccga ggagcaggac tgacacgtgc tacgagattt cgattccacc   2640
gccgccttct atgaaaggtt gggcttcgga atcgttttcc gggacgccgg ctggatgatc   2700
ctccagcgcg gggatctcat gctggagttc ttcgcccacc ccaacttgtt tattgcagct   2760
tataatggtt acaaataaag caatagcatc acaaatttca caaataaagc atttttttca   2820
ctgcattcta gttgtggttt gtccaaactc atcaatgtat cttatcatgt ctgtataccg   2880
tcgacctcta gctagagctt ggcgtaatca tggtcatagc tgtttcctgt gtgaaattgt   2940
tatccgctca caattccaca caacatacga gccggaagca taaagtgtaa agcctggggt   3000
gcctaatgag tgagctaact cacattaatt gcgttgcgct cactgcccgc tttccagtcg   3060
ggaaacctgt cgtgccagct gcattaatga atcggccaac gcgcggggag aggcggtttg   3120
cgtattgggc gctcttccgc ttcctcgctc actgactcgc tgcgctcggt cgttcggctg   3180
cggcgagcgg tatcagctca ctcaaaggcg gtaatacggt tatccacaga atcaggggat   3240
aacgcaggaa agaacatgtg agcaaaaggc cagcaaaagg ccaggaaccg taaaaaggcc   3300
gcgttgctgg cgtttttcca taggctccgc ccccctgacg agcatcacaa aaatcgacgc   3360
tcaagtcaga ggtggcgaaa cccgacagga ctataaagat accaggcgtt tccccctgga   3420
agctccctcg tgcgctctcc tgttccgacc ctgccgctta ccggatacct gtccgccttt   3480
ctcccttcgg gaagcgtggc gctttctcaa tgctcacgct gtaggtatct cagttcggtg   3540
taggtcgttc gctccaagct gggctgtgtg cacgaacccc ccgttcagcc cgaccgctgc   3600
gccttatccg gtaactatcg tcttgagtcc aacccggtaa gacacgactt atcgccactg   3660
gcagcagcca ctggtaacag gattagcaga gcgaggtatg taggcggtgc tacagagttc   3720
ttgaagtggt ggcctaacta cggctacact agaaggacag tatttggtat ctgcgctctg   3780
ctgaagccag ttaccttcgg aaaaagagtt ggtagctctt gatccggcaa acaaaccacc   3840
gctggtagcg gtggtttttt tgtttgcaag cagcagatta cgcgcagaaa aaaaggatct   3900
caagaagatc ctttgatctt ttctacgggg tctgacgctc agtggaacga aaactcacgt   3960
taagggattt tggtcatgag attatcaaaa aggatcttca cctagatcct tttaaattaa   4020
aaatgaagtt ttaaatcaat ctaaagtata tatgagtaaa cttggtctga cagttaccaa   4080
tgcttaatca gtgaggcacc tatctcagcg atctgtctat ttcgttcatc catagttgcc   4140
tgactccccg tcgtgtagat aactacgata cgggagggct taccatctgg ccccagtgct   4200
gcaatgatac cgcgagaccc acgctcaccg gctccagatt tatcagcaat aaaccagcca   4260
gccggaaggg ccgagcgcag aagtggtcct gcaactttat ccgcctccat ccagtctatt   4320
aattgttgcc gggaagctag agtaagtagt tcgccagtta atagtttgcg caacgttgtt   4380
```

-continued

```
gccattgcta caggcatcgt ggtgtcacgc tcgtcgtttg gtatggcttc attcagctcc   4440
ggttcccaac gatcaaggcg agttacatga tcccccatgt tgtgcaaaaa agcggttagc   4500
tccttcggtc ctccgatcgt tgtcagaagt aagttggccg cagtgttatc actcatggtt   4560
atggcagcac tgcataattc tcttactgtc atgccatccg taagatgctt ttctgtgact   4620
ggtgagtact caaccaagtc attctgagaa tagtgtatgc ggcgaccgag ttgctcttgc   4680
ccggcgtcaa tacgggataa taccgcgcca catagcagaa ctttaaaagt gctcatcatt   4740
ggaaaacgtt cttcggggcg aaaactctca aggatcttac cgctgttgag atccagttcg   4800
atgtaaccca ctcgtgcacc caactgatct tcagcatctt ttactttcac cagcgtttct   4860
gggtgagcaa aaacaggaag gcaaaatgcc gcaaaaaagg gaataagggc gacacggaaa   4920
tgttgaatac tcatactctt cctttttcaa tattattgaa gcatttatca gggttattgt   4980
ctcatgagcg gatacatatt tgaatgtatt tagaaaaata aacaaatagg ggttccgcgc   5040
acatttcccc gaaaagtgcc acctgacgtc gacggatcgg gagatctccc gatcccctat   5100
ggtgcactct cagtacaatc tgctctgatg ccgcatagtt aagccagtat ctgctccctg   5160
cttgtgtgtt ggaggtcgct gagtagtgcg cgagcaaaat ttaagctaca acaaggcaag   5220
gcttgaccga caattgcatg aagaatctgc ttagggttag gcgttttgcg ctgcttcgcg   5280
atgtacgggc cagatatacg cgttgacatt gattattgac tagttattaa tagtaatcaa   5340
ttacggggtc attagttcat agcccatata tggagttccg cgttacataa cttacggtaa   5400
atggcccgcc tggctgaccg cccaacgacc cccgcccatt gacgtcaata atgacgtatg   5460
ttcccatagt aacgccaata gggactttcc attgacgtca atgggtggac tatttacggt   5520
aaactgccca cttggcagta catcaagtgt atcatatgcc aagtacgccc cctattgacg   5580
tcaatgacgg taaatggccc gcctggcatt atgcccagta catgacctta tgggactttc   5640
ctacttggca gtacatctac gtattagtca tcgctattac catggtgatg cggttttggc   5700
agtacatcaa tgggcgtgga tagcggtttg actcacgggg atttccaagt ctccacccca   5760
ttgacgtcaa tgggagtttg ttttggcacc aaaatcaacg ggactttcca aaatgtcgta   5820
acaactccgc cccattgacg caaatgggcg gtaggcgtgt acggtgggag gtctatataa   5880
gcagagctct ctggctaact agagaaccca ctgcttactg gcttatcgaa attaatacga   5940
ctcactatag ggagacccaa gctggtttaa acttaagctt ggtaccgagc tcactagtcc   6000
agtgtggtgg cagatatcca gcacagtggc ggccgctcga ggggcccgtt ttgcctgtac   6060
tgggtctctc tggttagacc agatctgagc ctgggagctc tctggctaac tagggaaccc   6120
actgcttaag cctcaataaa gcttgccttg agtgcttcaa gtagtgtgtg cccgtctgtt   6180
gtgtgactct ggtaactaga gatccctcag acccttttag tcagtgtgga aaatctctag   6240
cagtggcgcc cgaacaggga cttgaaagcg aaagggaaac cagaggagct ctctcgacgc   6300
aggactcggc ttgctgaagc gcgcacggca agaggcgagg ggcggcgact ggtgagtacg   6360
ccaaaaattt tgactagcgg aggctagaag gagagagatg ggtgcgagag cgtcagtatt   6420
aagcggggga gaattagatc gcgatgggaa aaaattcggt taaggccagg gggaaagaaa   6480
aaatataaat taaaacatat agtatgggca agcagggagc tagaacgatt cgcagttaat   6540
cctggcctgt tagaaacatc agaaggctgt agacaaatac tgggacagct acaaccatcc   6600
cttcagacag gatcagaaga acttagatca ttatataata cagtagcaac cctctattgt   6660
gtgcatcaaa ggatagagat aaaagacacc aaggaagctt tagacaagat agaggaagag   6720
caaaacaaaa gtaagaccac cgcacagcaa gcggccgctg atcttcagac ctggaggagg   6780
```

```
agatatgagg gacaattgga gaagtgaatt atataaatat aaagtagtaa aaattgaacc   6840
attaggagta gcacccacca aggcaaagag aagagtggtg cagagagaaa aaagagcagt   6900
gggaatagga gctttgttcc ttgggttctt gggagcagca ggaagcacta tgggcgcagc   6960
gtcaatgacg ctgacggtac aggccagaca attattgtct ggtatagtgc agcagcagaa   7020
caatttgctg agggctattg aggcgcaaca gcatctgttg caactcacag tctggggcat   7080
caagcagctc caggcaagaa tcctggctgt ggaaagatac ctaaaggatc aacagctcct   7140
ggggatttgg ggttgctctg gaaaactcat ttgcaccact gctgtgcctt ggaatgctag   7200
ttggagtaat aaatctctgg aacagatttg gaatcacacg acctggatgg agtgggacag   7260
agaaattaac aattacacaa gcttaataca ctccttaatt gaagaatcgc aaaaccagca   7320
agaaaagaat gaacaagaat tattggaatt agataaatgg gcaagtttgt ggaattggtt   7380
taacataaca aattggctgt ggtatataaa attattcata atgatagtag gaggcttggt   7440
aggtttaaga atagtttttg ctgtactttc tatagtgaat agagttaggc agggatattc   7500
accattatcg tttcagaccc acctcccaac cccgagggga cccgacaggc ccttaattaa   7560
tcccctgatt ctgtggataa ccgtattacc gcctttgagt gagctgcacc tagtacggat   7620
tagaagccgc cgagcgggtg acagccctcc gaaggaagac tctcctccgt gcgtcctcgt   7680
cttcaccggt cgcgttcctg aaacgcagat gtgcctcgcg ccgcactgct ccgaacaatg   7740
tcgactctag aggtaaactc gacctatata agcagagctc gtttagtgaa ccgtcagatc   7800
gcctggagac gccatccacg ctgttttgac ctccatagaa gacaccggga ccgatccagc   7860
ctccgcggcc ccgaattgaa ttcggccatt acggcctgcc accgtgccac catgctggag   7920
cccggcgaga agccctacaa gtgccccgag tgcggcaaga gcttcagcga ctgcagggac   7980
ctggccaggc accagaggac ccacaccggc gagaagccct acaagtgccc cgagtgcggc   8040
aagagcttca gcgaccccgg caacctggtg aggcaccaga ggacccacac cggcgagaag   8100
ccctacaagt gccccgagtg cggcaagagc ttcagccaga gcagcagcct ggtgaggcac   8160
cagaggaccc acaccggcga gaagccctac aagtgccccg agtgcggcaa gagcttcagc   8220
cagagggccc acctggagag gcaccagagg acccacaccg gcgagaagcc ctacaagtgc   8280
cccgagtgcg gcaagagctt cagccagagc ggcgacctga ggaggcacca gaggacccac   8340
accggcgaga agccctacaa gtgccccgag tgcggcaaga gcttcagcca gagcagcaac   8400
ctggtgaggc accagaggac ccacaccggc aagaagacca gcggcccagg cggccgatgc   8460
taagtcactg actgcctggt cccggacact ggtgaccttc aaggatgtgt ttgtggactt   8520
caccagggag gagtggaagc tgctggacac tgctcagcag atcctgtaca gaaatgtgat   8580
gctggagaac tataagaacc tggtttcctt gggttatcag cttactaagc cagatgtgat   8640
cctccggttg gagaagggag aagagccctg gctggtggag agagaaattc accaagagac   8700
ccatcctgat tcagagactg catttgaaat caaatcatca gttgggcgcg ccgacgcgct   8760
ggacgatttc gatctcgaca tgctgggttc tgatgccctc gatgactttg acctggatat   8820
gttgggaagc gacgcattgg atgactttga tctggacatg ctcggctccg atgctctgga   8880
cgatttcgat ctcgatatgt taattaacta attaat                             8916
```

<210> SEQ ID NO 21
<211> LENGTH: 8916
<212> TYPE: DNA
<213> ORGANISM: Artificial Sequence
<220> FEATURE:

<223> OTHER INFORMATION: Synthetic

<400> SEQUENCE: 21
agaattcgat atcaagctta tcgataatca acctctggat tacaaaattt gtgaaagatt 60
gactggtatt cttaactatg ttgctccttt tacgctatgt ggatacgctg ctttaatgcc 120
tttgtatcat gctattactt cccgtacggc tttcattttc tcctccttgt ataaatcctg 180
gttgctgtct ctttatgagg agttgtggcc cgttgtcagg caacgtggcg tggtgtgcac 240
tgtgtttgct gacgcaaccc ccactggttg gggcattgcc accacctatc aactcctttc 300
cgggactttc gctttccccc tccctattgc cacggcggaa ctcattgccg cctgccttgc 360
ccgctgctgg acaggggctc ggctgttggg cactgacaat tccgtggtgt tgtcggggaa 420
gctgacgtcc tttccatggc tgctcgcctg tgttgccaac tggattctgc gcgggacgtc 480
cttctgctac gtcccttcgg ccctcaatcc agcggacctt ccttcccgcg gcctgctgcc 540
ggttctgcgg cctcttccgc gtcttcgcct tcgccctcag acgagtcgga tctccctttg 600
ggccgcctcc ccgcctgcct gcaggtttgt cgagacctag aaaaacatgg agcaatcaca 660
agtagcaata cagcagctac caatgctgat tgtgcctggc tagaagcaca agaggaggag 720
gaggtgggtt ttccagtcac acctcaggta cctttaagac caatgactta caaggcagct 780
gtagatctta gccacttttt aaaagaaaag gggggactgg aagggctaat tcactcccaa 840
cgaagacaag atctgctttt tgcttgtact gggtctctct ggttagacca gatctgagcc 900
tgggagctct ctggctaact agggaaccca ctgcttaagc ctcaataaag cttgccttga 960
gtgcttcaag tagtgtgtgc ccgtctgttg tgtgactctg gtaactagag atccctcaga 1020
cccttttagt cagtgtggaa aatctctagc agggcccgtt taaacccgct gatcagcctc 1080
gactgtgcct tctagttgcc agccatctgt tgtttgcccc tcccccgtgc cttccttgac 1140
cctggaaggt gccactccca ctgtcctttc ctaataaaat gaggaaattg catcgcattg 1200
tctgagtagg tgtcattcta ttctgggggg tggggtgggg caggacagca agggggagga 1260
ttgggaagac aatagcaggc atgctgggga tgcggtgggc tctatggctt ctgaggcgga 1320
aagaaccagc tggggctcta gggggtatcc ccacgcgccc tgtagcggcg cattaagcgc 1380
ggcgggtgtg gtggttacgc gcagcgtgac cgctacactt gccagcgccc tagcgcccgc 1440
tcctttcgct ttcttccctt cctttctcgc cacgttcgcc ggctttcccc gtcaagctct 1500
aaatcggggc atccctttag ggttccgatt tagtgcttta cggcacctcg accccaaaaa 1560
acttgattag ggtgatggtt cacgtagtgg gccatcgccc tgatagacgg tttttcgccc 1620
tttgacgttg gagtccacgt tctttaatag tggactcttg ttccaaactg gaacaacact 1680
caaccctatc tcggtctatt cttttgattt ataagggatt ttggggattt cggcctattg 1740
gttaaaaaat gagctgattt aacaaaaatt taacgcgaat taattctgtg gaatgtgtgt 1800
cagttagggt gtggaaagtc cccaggctcc ccaggcaggc agaagtatgc aaagcatgca 1860
tctcaattag tcagcaacca ggtgtggaaa gtccccaggc tccccagcag gcagaagtat 1920
gcaaagcatg catctcaatt agtcagcaac catagtcccg cccctaactc cgcccatccc 1980
gcccctaact ccgcccagtt ccgcccattc tccgccccat ggctgactaa ttttttttat 2040
ttatgcagag gccgaggccg cctctgcctc tgagctattc cagaagtagt gaggaggctt 2100
ttttggaggc ctaggctttt gcaaaaagct cccgggagct tgtatatcca ttttcggatc 2160
tgatcagcac gtgttgacaa ttaatcatcg gcatagtata tcggcatagt ataatacgac 2220
aaggtgagga actaaaccat ggccaagttg accagtgccg ttccggtgct caccgcgcgc 2280

```
gacgtcgccg gagcggtcga gttctggacc gaccggctcg ggttctcccg ggacttcgtg   2340
gaggacgact tcgccggtgt ggtccgggac gacgtgaccc tgttcatcag cgcggtccag   2400
gaccaggtgg tgccggacaa caccctggcc tgggtgtggg tgcgcggcct ggacgagctg   2460
tacgccgagt ggtcggaggt cgtgtccacg aacttccggg acgcctccgg gccggccatg   2520
accgagatcg gcgagcagcc gtgggggcgg gagttcgccc tgcgcgaccc ggccggcaac   2580
tgcgtgcact tcgtggccga ggagcaggac tgacacgtgc tacgagattt cgattccacc   2640
gccgccttct atgaaaggtt gggcttcgga atcgttttcc gggacgccgg ctggatgatc   2700
ctccagcgcg gggatctcat gctggagttc ttcgcccacc ccaacttgtt tattgcagct   2760
tataatggtt acaaataaag caatagcatc acaaatttca caaataaagc atttttttca   2820
ctgcattcta gttgtggttt gtccaaactc atcaatgtat cttatcatgt ctgtataccg   2880
tcgacctcta gctagagctt ggcgtaatca tggtcatagc tgtttcctgt gtgaaattgt   2940
tatccgctca caattccaca caacatacga gccggaagca taaagtgtaa agcctggggt   3000
gcctaatgag tgagctaact cacattaatt gcgttgcgct cactgcccgc tttccagtcg   3060
ggaaacctgt cgtgccagct gcattaatga atcggccaac gcgcggggag aggcggtttg   3120
cgtattgggc gctcttccgc ttcctcgctc actgactcgc tgcgctcggt cgttcggctg   3180
cggcgagcgg tatcagctca ctcaaaggcg gtaatacggt tatccacaga atcaggggat   3240
aacgcaggaa agaacatgtg agcaaaaggc cagcaaaagg ccaggaaccg taaaaaggcc   3300
gcgttgctgg cgtttttcca taggctccgc ccccctgacg agcatcacaa aaatcgacgc   3360
tcaagtcaga ggtggcgaaa cccgacagga ctataaagat accaggcgtt tccccctgga   3420
agctccctcg tgcgctctcc tgttccgacc ctgccgctta ccggatacct gtccgccttt   3480
ctcccttcgg gaagcgtggc gctttctcaa tgctcacgct gtaggtatct cagttcggtg   3540
taggtcgttc gctccaagct gggctgtgtg cacgaacccc ccgttcagcc cgaccgctgc   3600
gccttatccg gtaactatcg tcttgagtcc aacccggtaa gacacgactt atcgccactg   3660
gcagcagcca ctggtaacag gattagcaga gcgaggtatg taggcggtgc tacagagttc   3720
ttgaagtggt ggcctaacta cggctacact agaaggacag tatttggtat ctgcgctctg   3780
ctgaagccag ttaccttcgg aaaaagagtt ggtagctctt gatccggcaa acaaaccacc   3840
gctggtagcg gtggtttttt tgtttgcaag cagcagatta cgcgcagaaa aaaaggatct   3900
caagaagatc ctttgatctt ttctacgggg tctgacgctc agtggaacga aaactcacgt   3960
taagggattt tggtcatgag attatcaaaa aggatcttca cctagatcct tttaaattaa   4020
aaatgaagtt ttaaatcaat ctaaagtata tatgagtaaa cttggtctga cagttaccaa   4080
tgcttaatca gtgaggcacc tatctcagcg atctgtctat ttcgttcatc catagttgcc   4140
tgactccccg tcgtgtagat aactacgata cgggagggct taccatctgg ccccagtgct   4200
gcaatgatac cgcgagaccc acgctcaccg gctccagatt tatcagcaat aaaccagcca   4260
gccggaaggg ccgagcgcag aagtggtcct gcaactttat ccgcctccat ccagtctatt   4320
aattgttgcc gggaagctag agtaagtagt tcgccagtta atagtttgcg caacgttgtt   4380
gccattgcta caggcatcgt ggtgtcacgc tcgtcgtttg gtatggcttc attcagctcc   4440
ggttcccaac gatcaaggcg agttacatga tcccccatgt tgtgcaaaaa agcggttagc   4500
tccttcggtc ctccgatcgt tgtcagaagt aagttggccg cagtgttatc actcatggtt   4560
atggcagcac tgcataattc tcttactgtc atgccatccg taagatgctt ttctgtgact   4620
```

```
ggtgagtact caaccaagtc attctgagaa tagtgtatgc ggcgaccgag ttgctcttgc   4680
ccggcgtcaa tacgggataa taccgcgcca catagcagaa ctttaaaagt gctcatcatt   4740
ggaaaacgtt cttcggggcg aaaactctca aggatcttac cgctgttgag atccagttcg   4800
atgtaaccca ctcgtgcacc caactgatct tcagcatctt ttactttcac cagcgtttct   4860
gggtgagcaa aaacaggaag gcaaaatgcc gcaaaaaagg gaataagggc gacacggaaa   4920
tgttgaatac tcatactctt cctttttcaa tattattgaa gcatttatca gggttattgt   4980
ctcatgagcg gatacatatt tgaatgtatt tagaaaaata aacaaatagg ggttccgcgc   5040
acatttcccc gaaaagtgcc acctgacgtc gacggatcgg gagatctccc gatcccctat   5100
ggtgcactct cagtacaatc tgctctgatg ccgcatagtt aagccagtat ctgctccctg   5160
cttgtgtgtt ggaggtcgct gagtagtgcg cgagcaaaat ttaagctaca acaaggcaag   5220
gcttgaccga caattgcatg aagaatctgc ttagggttag gcgttttgcg ctgcttcgcg   5280
atgtacgggc cagatatacg cgttgacatt gattattgac tagttattaa tagtaatcaa   5340
ttacggggtc attagttcat agcccatata tggagttccg cgttacataa cttacggtaa   5400
atggcccgcc tggctgaccg cccaacgacc cccgcccatt gacgtcaata atgacgtatg   5460
ttcccatagt aacgccaata gggactttcc attgacgtca atgggtggac tatttacggt   5520
aaactgccca cttggcagta catcaagtgt atcatatgcc aagtacgccc cctattgacg   5580
tcaatgacgg taaatggccc gcctggcatt atgcccagta catgacctta tgggactttc   5640
ctacttggca gtacatctac gtattagtca tcgctattac catggtgatg cggttttggc   5700
agtacatcaa tgggcgtgga tagcggtttg actcacgggg atttccaagt ctccacccca   5760
ttgacgtcaa tgggagtttg ttttggcacc aaaatcaacg ggactttcca aaatgtcgta   5820
acaactccgc cccattgacg caaatgggcg gtaggcgtgt acggtgggag gtctatataa   5880
gcagagctct ctggctaact agagaaccca ctgcttactg gcttatcgaa attaatacga   5940
ctcactatag ggagacccaa gctggtttaa acttaagctt ggtaccgagc tcactagtcc   6000
agtgtggtgg cagatatcca gcacagtggc ggccgctcga ggggcccgtt ttgcctgtac   6060
tgggtctctc tggttagacc agatctgagc ctgggagctc tctggctaac tagggaaccc   6120
actgcttaag cctcaataaa gcttgccttg agtgcttcaa gtagtgtgtg cccgtctgtt   6180
gtgtgactct ggtaactaga gatccctcag acccttttag tcagtgtgga aaatctctag   6240
cagtggcgcc cgaacaggga cttgaaagcg aaagggaaac cagaggagct ctctcgacgc   6300
aggactcggc ttgctgaagc gcgcacggca agaggcgagg ggcggcgact ggtgagtacg   6360
ccaaaaattt tgactagcgg aggctagaag gagagagatg ggtgcgagag cgtcagtatt   6420
aagcggggga gaattagatc gcgatgggaa aaaattcggt taaggccagg gggaaagaaa   6480
aaatataaat taaaacatat agtatgggca agcagggagc tagaacgatt cgcagttaat   6540
cctggcctgt tagaaacatc agaaggctgt agacaaatac tgggacagct acaaccatcc   6600
cttcagacag gatcagaaga acttagatca ttatataata cagtagcaac cctctattgt   6660
gtgcatcaaa ggatagagat aaaagacacc aaggaagctt tagacaagat agaggaagag   6720
caaaacaaaa gtaagaccac cgcacagcaa gcggccgctg atcttcagac ctggaggagg   6780
agatatgagg gacaattgga gaagtgaatt atataaatat aaagtagtaa aaattgaacc   6840
attaggagta gcacccacca aggcaaagag aagagtggtg cagagagaaa aaagagcagt   6900
gggaatagga gctttgttcc ttgggttctt gggagcagca ggaagcacta tgggcgcagc   6960
gtcaatgacg ctgacggtac aggccagaca attattgtct ggtatagtgc agcagcagaa   7020
```

caatttgctg agggctattg aggcgcaaca gcatctgttg caactcacag tctggggcat 7080
caagcagctc caggcaagaa tcctggctgt ggaaagatac ctaaaggatc aacagctcct 7140
ggggatttgg ggttgctctg gaaaactcat ttgcaccact gctgtgcctt ggaatgctag 7200
ttggagtaat aaatctctgg aacagatttg gaatcacacg acctggatgg agtgggacag 7260
agaaattaac aattacacaa gcttaataca ctccttaatt gaagaatcgc aaaaccagca 7320
agaaaagaat gaacaagaat tattggaatt agataaatgg gcaagtttgt ggaattggtt 7380
taacataaca aattggctgt ggtatataaa attattcata atgatagtag gaggcttggt 7440
aggtttaaga atagtttttg ctgtactttc tatagtgaat agagttaggc agggatattc 7500
accattatcg tttcagaccc acctcccaac cccgagggga cccgacaggc ccttaattaa 7560
tcccctgatt ctgtggataa ccgtattacc gcctttgagt gagctgcacc tagtacggat 7620
tagaagccgc cgagcgggtg acagccctcc gaaggaagac tctcctccgt gcgtcctcgt 7680
cttcaccggt cgcgttcctg aaacgcagat gtgcctcgcg ccgcactgct ccgaacaatg 7740
tcgactctag aggtaaactc gacctatata agcagagctc gtttagtgaa ccgtcagatc 7800
gcctggagac gccatccacg ctgttttgac ctccatagaa gacaccggga ccgatccagc 7860
ctccgcggcc ccgaattgaa ttcggccatt acggcctgcc accgtgccac catgctggag 7920
cccggcgaga agccctacaa gtgccccgag tgcggcaaga gcttcagcag gagcgacgag 7980
ctggtgaggc accagaggac ccacaccggc gagaagccct acaagtgccc cgagtgcggc 8040
aagagcttca gcaggagcga caagctggtg aggcaccaga ggacccacac cggcgagaag 8100
ccctacaagt gccccgagtg cggcaagagc ttcagcagga gcgacgacct ggtgaggcac 8160
cagaggaccc acaccggcga gaagccctac aagtgccccg agtgcggcaa gagcttcagc 8220
aggagcgaca acctggtgag gcaccagagg acccacaccg gcgagaagcc ctacaagtgc 8280
cccgagtgcg gcaagagctt cagcgacccc ggcgccctgg tgaggcacca gaggacccac 8340
accggcgaga agccctacaa gtgccccgag tgcggcaaga gcttcagcga ccccggccac 8400
ctggtgaggc accagaggac ccacaccggc aagaagacca gcggcccagg cggccgatgc 8460
taagtcactg actgcctggt cccggacact ggtgaccttc aaggatgtgt ttgtggactt 8520
caccagggag gagtggaagc tgctggacac tgctcagcag atcctgtaca gaaatgtgat 8580
gctggagaac tataagaacc tggtttcctt gggttatcag cttactaagc cagatgtgat 8640
cctccggttg gagaagggag aagagccctg gctggtggag agagaaattc accaagagac 8700
ccatcctgat tcagagactg catttgaaat caaatcatca gttgggcgcg ccgacgcgct 8760
ggacgatttc gatctcgaca tgctgggttc tgatgccctc gatgactttg acctggatat 8820
gttgggaagc gacgcattgg atgactttga tctggacatg ctcggctccg atgctctgga 8880
cgatttcgat ctcgatatgt taattaacta attaat 8916

<210> SEQ ID NO 22
<211> LENGTH: 10562
<212> TYPE: DNA
<213> ORGANISM: Artificial Sequence
<220> FEATURE:
<223> OTHER INFORMATION: Synthetic

<400> SEQUENCE: 22
cgtgccacca tgctggagcc cggcgagaag ccctacaagt gccccgagtg cggcaagagc 60
ttcagcgaca gcggcaacct gagggtgcac cagaggaccc acaccggcga gaagccctac 120

-continued

```
aagtgccccg agtgcggcaa gagcttcagc cagagggcca acctgagggc ccaccagagg    180
acccacaccg gcgagaagcc ctacaagtgc cccgagtgcg gcaagagctt cagcaccagc    240
ggcagcctgg tgaggcacca gaggacccac accggcgaga agccctacaa gtgccccgag    300
tgcggcaaga gcttcagcac cagcggccac ctggtgaggc accagaggac ccacaccggc    360
gagaagccct acaagtgccc cgagtgcggc aagagcttca gcaccagcgg cgagctggtg    420
aggcaccaga ggacccacac cggcgagaag ccctacaagt gccccgagtg cggcaagagc    480
ttcagcacca gcggcaacct ggtgaggcac cagaggaccc acaccggcaa gaagaccagc    540
ggcccaggcg gccgatgcta agtcactgac tgcctggtcc cggacactgg tgaccttcaa    600
ggatgtgttt gtggacttca ccagggagga gtggaagctg ctggacactg ctcagcagat    660
cctgtacaga aatgtgatgc tggagaacta taagaacctg gtttccttgg gttatcagct    720
tactaagcca gatgtgatcc tccggttgga gaagggagaa gagccctggc tggtggagag    780
agaaattcac caagagaccc atcctgattc agagactgca tttgaaatca aatcatcagt    840
tgggcgcgcc gacgcgctgg acgatttcga tctcgacatg ctgggttctg atgccctcga    900
tgactttgac ctggatatgt tgggaagcga cgcattggat gactttgatc tggacatgct    960
cggctccgat gctctggacg atttcgatct cgatatgtta attaactaac gatcacatgg   1020
tcctgctgga gttcgtgacc gccgccggga tcactctcgg catggacgag ctgtacaagt   1080
aagcggccgc aatcaacctc tggattacaa aatttgtgaa agattgactg gtattcttaa   1140
ctatgttgct ccttttacgc tatgtggata cgctgcttta atgcctttgt atcatgctat   1200
tacttcccgt acggctttca ttttctcctc cttgtataaa tcctggttgc tgtctcttta   1260
tgaggagttg tggcccgttg tcaggcaacg tggcgtggtg tgcactgtgt ttgctgacgc   1320
aacccccact ggttggggca ttgccaccac ctatcaactc ctttccggga ctttcgcttt   1380
ccccctccct attgccacgg cggaactcat tgccgcctgc cttgcccgct gctggacagg   1440
ggctcggctg ttgggcactg acaattccgt ggtgttgtcg gggaagctga cgtcctttcc   1500
atggctgctc gcctgtgttg ccaactggat tctgcgcggg acgtccttct gctacgtccc   1560
ttcggccctc aatccagcgg accttccttc ccgcggcctg ctgccggttc tgcggcctct   1620
tccgcgtctt cgccttcgcc ctcagacgag tcggatctcc ctttgggccg cctccccgcc   1680
tgcctgcagg tttgtcgaga cctagaaaaa catggagcaa tcacaagtag caatacagca   1740
gctaccaatg ctgattgtgc ctggctagaa gcacaagagg aggaggaggt gggttttcca   1800
gtcacacctc aggtaccttt aagaccaatg acttacaagg cagctgtaga tcttagccac   1860
tttttaaaag aaaagggggg actggaaggg ctaattcact cccaacgaag acaagatctg   1920
ctttttgctt gtactgggtc tctctggtta gaccagatct gagcctggga gctctctggc   1980
taactaggga acccactgct taagcctcaa taaagcttgc cttgagtgct tcaagtagtg   2040
tgtgcccgtc tgttgtgtga ctctggtaac tagagatccc tcagaccctt ttagtcagtg   2100
tggaaaatct ctagcagggc ccgtttaaac ccgctgatca gcctcgactg tgccttctag   2160
ttgccagcca tctgttgttt gcccctcccc cgtgccttcc ttgaccctgg aaggtgccac   2220
tcccactgtc ctttcctaat aaaatgagga aattgcatcg cattgtctga gtaggtgtca   2280
ttctattctg gggggtgggg tggggcagga cagcaagggg gaggattggg aagacaatag   2340
caggcatgct ggggatgcgg tgggctctat ggcttctgag gcggaaagaa ccagctgggg   2400
ctctaggggg tatccccacg cgccctgtag cggcgcatta agcgcggcgg gtgtggtggt   2460
tacgcgcagc gtgaccgcta cacttgccag cgccctagcg cccgctcctt tcgctttctt   2520
```

-continued cccttccttt ctcgccacgt tcgccggctt tccccgtcaa gctctaaatc ggggcatccc 2580
tttagggttc cgatttagtg ctttacggca cctcgacccc aaaaaacttg attagggtga 2640
tggttcacgt agtgggccat cgccctgata gacggttttt cgccctttga cgttggagtc 2700
cacgttcttt aatagtggac tcttgttcca aactggaaca acactcaacc ctatctcggt 2760
ctattctttt gatttataag ggattttggg gatttcggcc tattggttaa aaaatgagct 2820
gatttaacaa aaatttaacg cgaattaatt ctgtggaatg tgtgtcagtt agggtgtgga 2880
aagtccccag gctccccagg caggcagaag tatgcaaagc atgcatctca attagtcagc 2940
aaccaggtgt ggaaagtccc caggctcccc agcaggcaga agtatgcaaa gcatgcatct 3000
caattagtca gcaaccatag tcccgcccct aactccgccc atcccgcccc taactccgcc 3060
cagttccgcc cattctccgc cccatggctg actaattttt tttatttatg cagaggccga 3120
ggccgcctct gcctctgagc tattccagaa gtagtgagga ggcttttttg gaggcctagg 3180
cttttgcaaa aagctcccgg gagcttgtat atccattttc ggatctgatc agcacgtgtt 3240
gacaattaat catcggcata gtatatcggc atagtataat acgacaaggt gaggaactaa 3300
accatggcca agttgaccag tgccgttccg gtgctcaccg cgcgcgacgt cgccggagcg 3360
gtcgagttct ggaccgaccg gctcgggttc tcccgggact tcgtggagga cgacttcgcc 3420
ggtgtggtcc gggacgacgt gaccctgttc atcagcgcgg tccaggacca ggtggtgccg 3480
gacaacaccc tggcctgggt gtgggtgcgc ggcctggacg agctgtacgc cgagtggtcg 3540
gaggtcgtgt ccacgaactt ccgggacgcc tccgggccgg ccatgaccga gatcggcgag 3600
cagccgtggg ggcgggagtt cgccctgcgc gacccggccg gcaactgcgt gcacttcgtg 3660
gccgaggagc aggactgaca cgtgctacga gatttcgatt ccaccgccgc cttctatgaa 3720
aggttgggct tcggaatcgt tttccgggac gccggctgga tgatcctcca gcgcggggat 3780
ctcatgctgg agttcttcgc ccaccccaac ttgtttattg cagcttataa tggttacaaa 3840
taaagcaata gcatcacaaa tttcacaaat aaagcatttt tttcactgca ttctagttgt 3900
ggtttgtcca aactcatcaa tgtatcttat catgtctgta taccgtcgac ctctagctag 3960
agcttggcgt aatcatggtc atagctgttt cctgtgtgaa attgttatcc gctcacaatt 4020
ccacacaaca tacgagccgg aagcataaag tgtaaagcct ggggtgccta atgagtgagc 4080
taactcacat taattgcgtt gcgctcactg cccgctttcc agtcgggaaa cctgtcgtgc 4140
cagctgcatt aatgaatcgg ccaacgcgcg gggagaggcg gtttgcgtat tgggcgctct 4200
tccgcttcct cgctcactga ctcgctgcgc tcggtcgttc ggctgcggcg agcggtatca 4260
gctcactcaa aggcggtaat acggttatcc acagaatcag gggataacgc aggaaagaac 4320
atgtgagcaa aaggccagca aaaggccagg aaccgtaaaa aggccgcgtt gctggcgttt 4380
ttccataggc tccgcccccc tgacgagcat cacaaaaatc gacgctcaag tcagaggtgg 4440
cgaaacccga caggactata aagataccag gcgtttcccc ctggaagctc cctcgtgcgc 4500
tctcctgttc cgaccctgcc gcttaccgga tacctgtccg cctttctccc ttcgggaagc 4560
gtggcgcttt ctcaatgctc acgctgtagg tatctcagtt cggtgtaggt cgttcgctcc 4620
aagctgggct gtgtgcacga accccccgtt cagcccgacc gctgcgcctt atccggtaac 4680
tatcgtcttg agtccaaccc ggtaagacac gacttatcgc cactggcagc agccactggt 4740
aacaggatta gcagagcgag gtatgtaggc ggtgctacag agttcttgaa gtggtggcct 4800
aactacggct acactagaag gacagtattt ggtatctgcg ctctgctgaa gccagttacc 4860
ttcggaaaaa gagttggtag ctcttgatcc ggcaaacaaa ccaccgctgg tagcggtggt 4920
tttttgttt gcaagcagca gattacgcgc agaaaaaaag gatctcaaga agatcctttg 4980
atcttttcta cggggtctga cgctcagtgg aacgaaaact cacgttaagg gattttggtc 5040
atgagattat caaaaaggat cttcacctag atccttttaa attaaaaatg aagttttaaa 5100
tcaatctaaa gtatatatga gtaaacttgg tctgacagtt accaatgctt aatcagtgag 5160
gcacctatct cagcgatctg tctatttcgt tcatccatag ttgcctgact ccccgtcgtg 5220
tagataacta cgatacggga gggcttacca tctggcccca gtgctgcaat gataccgcga 5280
gacccacgct caccggctcc agatttatca gcaataaacc agccagccgg aagggccgag 5340
cgcagaagtg gtcctgcaac tttatccgcc tccatccagt ctattaattg ttgccgggaa 5400
gctagagtaa gtagttcgcc agttaatagt ttgcgcaacg ttgttgccat tgctacaggc 5460
atcgtggtgt cacgctcgtc gtttggtatg gcttcattca gctccggttc ccaacgatca 5520
aggcgagtta catgatcccc catgttgtgc aaaaaagcgg ttagctcctt cggtcctccg 5580
atcgttgtca gaagtaagtt ggccgcagtg ttatcactca tggttatggc agcactgcat 5640
aattctctta ctgtcatgcc atccgtaaga tgcttttctg tgactggtga gtactcaacc 5700
aagtcattct gagaatagtg tatgcggcga ccgagttgct cttgcccggc gtcaatacgg 5760
gataataccg cgccacatag cagaacttta aaagtgctca tcattggaaa acgttcttcg 5820
gggcgaaaac tctcaaggat cttaccgctg ttgagatcca gttcgatgta acccactcgt 5880
gcacccaact gatcttcagc atcttttact ttcaccagcg tttctgggtg agcaaaaaca 5940
ggaaggcaaa atgccgcaaa aaagggaata agggcgacac ggaaatgttg aatactcata 6000
ctcttccttt ttcaatatta ttgaagcatt tatcagggtt attgtctcat gagcggatac 6060
atatttgaat gtatttagaa aaataaacaa ataggggttc cgcgcacatt tccccgaaaa 6120
gtgccacctg acgtcgacgg atcgggagat ctcccgatcc cctatggtgc actctcagta 6180
caatctgctc tgatgccgca tagttaagcc agtatctgct ccctgcttgt gtgttggagg 6240
tcgctgagta gtgcgcgagc aaaatttaag ctacaacaag gcaaggcttg accgacaatt 6300
gcatgaagaa tctgcttagg gttaggcgtt ttgcgctgct tcgcgatgta cgggccagat 6360
atacgcgttg acattgatta ttgactagtt attaatagta atcaattacg gggtcattag 6420
ttcatagccc atatatggag ttccgcgtta cataacttac ggtaaatggc ccgcctggct 6480
gaccgcccaa cgacccccgc ccattgacgt caataatgac gtatgttccc atagtaacgc 6540
caatagggac tttccattga cgtcaatggg tggactattt acggtaaact gcccacttgg 6600
cagtacatca agtgtatcat atgccaagta cgccccctat tgacgtcaat gacggtaaat 6660
ggcccgcctg gcattatgcc cagtacatga ccttatggga ctttcctact tggcagtaca 6720
tctacgtatt agtcatcgct attaccatgg tgatgcggtt ttggcagtac atcaatgggc 6780
gtggatagcg gtttgactca cggggatttc caagtctcca ccccattgac gtcaatggga 6840
gtttgttttg gcaccaaaat caacgggact ttccaaaatg tcgtaacaac tccgccccat 6900
tgacgcaaat gggcggtagg cgtgtacggt gggaggtcta tataagcaga gctctctggc 6960
taactagaga acccactgct tactggctta tcgaaattaa tacgactcac tatagggaga 7020
cccaagctgg tttaaactta agcttggtac cgagctcact agtccagtgt ggtggcagat 7080
atccagcaca gtggcggccg ctcgagtcta gagggcccgt tttgcctgta ctgggtctct 7140
ctggttagac cagatctgag cctgggagct ctctggctaa ctagggaacc cactgcttaa 7200
gcctcaataa agcttgcctt gagtgcttca agtagtgtgt gcccgtctgt tgtgtgactc 7260
tggtaactag agatccctca gaccctttta gtcagtgtgg aaaatctcta gcagtggcgc 7320
ccgaacaggg acttgaaagc gaaagggaaa ccagaggagc tctctcgacg caggactcgg 7380
cttgctgaag cgcgcacggc aagaggcgag gggcggcgac tggtgagtac gccaaaaatt 7440
ttgactagcg gaggctagaa ggagagagat gggtgcgaga gcgtcagtat taagcggggg 7500
agaattagat cgcgatggga aaaaattcgg ttaaggccag ggggaaagaa aaaatataaa 7560
ttaaaacata tagtatgggc aagcagggag ctagaacgat tcgcagttaa tcctggcctg 7620
ttagaaacat cagaaggctg tagacaaata ctgggacagc tacaaccatc ccttcagaca 7680
ggatcagaag aacttagatc attatataat acagtagcaa ccctctattg tgtgcatcaa 7740
aggatagaga taaaagacac caaggaagct ttagacaaga tagaggaaga gcaaaacaaa 7800
agtaagacca ccgcacagca agcggccgct gatcttcaga cctggaggag gagatatgag 7860
ggacaattgg agaagtgaat tatataaata taaagtagta aaaattgaac cattaggagt 7920
agcacccacc aaggcaaaga gaagagtggt gcagagagaa aaaagagcag tgggaatagg 7980
agctttgttc cttgggttct tgggagcagc aggaagcact atgggcgcag cgtcaatgac 8040
gctgacggta caggccagac aattattgtc tggtatagtg cagcagcaga acaatttgct 8100
gagggctatt gaggcgcaac agcatctgtt gcaactcaca gtctggggca tcaagcagct 8160
ccaggcaaga atcctggctg tggaaagata cctaaaggat caacagctcc tggggatttg 8220
gggttgctct ggaaaactca tttgcaccac tgctgtgcct tggaatgcta gttggagtaa 8280
taaatctctg gaacagattt ggaatcacac gacctggatg gagtgggaca gagaaattaa 8340
caattacaca agcttaatac actccttaat tgaagaatcg caaaaccagc aagaaaagaa 8400
tgaacaagaa ttattggaat tagataaatg ggcaagtttg tggaattggt ttaacataac 8460
aaattggctg tggtatatag aaattattca taatgatagt aggaggcttg gtaggtttaa 8520
gaatagtttt tgctgtactt tctatagtga atagagttag gcagggatat tcaccattat 8580
cgtttcagac ccacctccca accccgaggg gacccgacag gcccgaagga atagaagaag 8640
aaggtggaga gagagacaga gacagatcca ttcgattagt gaacggatcg gcactgcgtg 8700
cgccaattct gcagacaaat ggcagtattc atccacaatt ttaaaagaaa aggggggatt 8760
ggggggtaca gtgcagggga aagaatagta gacataatag caacagacat acaaactaaa 8820
gaattacaaa aacaaattac aaaaattcaa aattttcggg tttattacag ggacagcaga 8880
gatccagttt ggggttgctc tggaaaactc atttgcacca ctgctgtgcc ttggaatgct 8940
agttggagta ataaatctct ggaacagatt tggaatcaca cgacctggat ggagtgggac 9000
agagaaatta acaattacac aagcttaata cactccttaa ttgaagaatc gcaaaaccag 9060
caagaaaaga atgaacaaga attattggaa ttagataaat gggcaagttt gtggaattgg 9120
tttaacataa caaattggct gtggtatata aaattattca taatgatagt aggaggcttg 9180
gtaggtttaa gaatagtttt tgctgtactt tctatagtga atagagttag gcagggatat 9240
tcaccattat cgtttcagac ccacctccca accccgaggg gacccgacag gcccttaatt 9300
aattggctcc ggtgcccgtc agtgggcaga gcgcacatcg cccacagtcc ccgagaagtt 9360
ggggggaggg gtcggcaatt gaaccggtgc ctagagaagg tggcgcgggg taaactggga 9420
aagtgatgtc gtgtactggc tccgcctttt tcccgagggt gggggagaac cgtatataag 9480
tgcagtagtc gccgtgaagc tagcggcgtc gaggcggggg tgatatggcg tcgaggcggg 9540
ggtggctagc cgttcttttt cgcaacgggt ttgccgccag aacacaggta agtgccgtgt 9600

-continued

```
gtggttcccg cgggcctggc ctctttacgg gttatggccc ttgcgtgcct tgaattactt   9660
ccacctggct gcagtacgtg attcttgatc ccgagcttcg ggttggaagt gggtgggaga   9720
gttcgaggcc ttgcgcttaa ggagcccctt cgcctcgtgc ttgagttgag gcctggcctg   9780
ggcgctgggg ccgccgcgtg cgaatctggt ggcaccttcg cgcctgtctc gctgctttcg   9840
ataagtctct agccatttaa aatttttgat gacctgctgc gacgcttttt ttctggcaag   9900
atagtcttgt aaatgcgggc caagatctgc acactggtat ttcggttttt ggggccgcgg   9960
gcggcgacgg ggcccgtgcg tcccagcgca catgttcggc gaggcggggc ctgcgagcgc  10020
ggccaccgag aatcggacgg gggtagtctc aagctggccg gcctgctctg gtgcctggcc  10080
tcgcgccgcc gtgtatcgcc ccgccctggg cggcaaggct ggcccggtcg gcaccagttg  10140
cgtgagcgga aagatggccg cttcccggcc ctgctgcagg gagctcaaaa tggaggacgc  10200
ggcgctcggg agagcgggcg ggtgagtcac ccacacaaag gaaaagggcc tttccgtcct  10260
cagccgtcgc ttcatgtgac tccacggagt accgggcgcc gtccaggcac ctcgattagt  10320
tctcgagctt ttggagtacg tcgtctttag gttgggggga ggggttttat gcgatggagt  10380
ttccccacac tgagtgggtg gagactgaag ttaggccagc ttggcacttg atgtaattct  10440
ccttggaatt tgcccttttt gagtttggat cttggttcat tctcaagcct cagacagtgg  10500
ttcaaagttt ttttcttcca tttcaggtga attcggccat tacggcctcc caccggccgc  10560
ct                                                                 10562
```

```
<210> SEQ ID NO 23
<211> LENGTH: 9215
<212> TYPE: DNA
<213> ORGANISM: Artificial Sequence
<220> FEATURE:
<223> OTHER INFORMATION: Synthetic

<400> SEQUENCE: 23
```

```
ttgccaccat gctggagccc ggcgagaagc cctacaagtg ccccgagtgc ggcaagagct     60
tcagcaccca cctggacctg atcaggcacc agaggaccca caccggcgag aagccctaca    120
agtgccccga gtgcggcaag agcttcagca ggaccgacac cctgagggac caccagagga    180
cccacaccgg cgagaagccc tacaagtgcc ccgagtgcgg caagagcttc agcgacaaga    240
aggacctgac caggcaccag aggacccaca ccggcgagaa gccctacaag tgccccgagt    300
gcggcaagag cttcagcagc cccgccgacc tgaccaggca ccagaggacc cacaccggcg    360
agaagcccta caagtgcccc gagtgcggca agagcttcag caccaccggc aacctgaccg    420
tgcaccagag gacccacacc ggcgagaagc cctacaagtg ccccgagtgc ggcaagagct    480
tcagcaggaa ggacaacctg aagaaccacc agaggaccca caccggcaag aagaccagcg    540
gcccaggcgg ccgatgctaa gtcactgact gcctggtccc ggacactggt gaccttcaag    600
gatgtgtttg tggacttcac cagggaggag tggaagctgc tggacactgc tcagcagatc    660
ctgtacagaa atgtgatgct ggagaactat aagaacctgg tttccttggg ttatcagctt    720
actaagccag atgtgatcct ccggttggag aagggagaag agccctggct ggtggagaga    780
gaaattcacc aagagaccca tcctgattca gagactgcat ttgaaatcaa atcatcagtt    840
gggcgcgccg acgcgctgga cgatttcgat ctcgacatgc tgggttctga tgccctcgat    900
gactttgacc tggatatgtt gggaagcgac gcattggatg actttgatct ggacatgctc    960
ggctccgatg ctctggacga tttcgatctc gatatgttaa ttaactaata tgtgtgggag   1020
ggctaagggc gcgccgttct agagaattcg atatcaagct tatcgataat caacctctgg   1080
```

attacaaaat ttgtgaaaga ttgactggta ttcttaacta tgttgctcct tttacgctat 1140
gtggatacgc tgctttaatg cctttgtatc atgctattac ttcccgtacg gctttcattt 1200
tctcctcctt gtataaatcc tggttgctgt ctctttatga ggagttgtgg cccgttgtca 1260
ggcaacgtgg cgtggtgtgc actgtgtttg ctgacgcaac ccccactggt tggggcattg 1320
ccaccaccta tcaactcctt tccgggactt tcgctttccc cctccctatt gccacggcgg 1380
aactcattgc cgcctgcctt gcccgctgct ggacaggggc tcggctgttg ggcactgaca 1440
attccgtggt gttgtcgggg aagctgacgt cctttccatg gctgctcgcc tgtgttgcca 1500
actggattct gcgcgggacg tccttctgct acgtcccttc ggccctcaat ccagcggacc 1560
ttccttcccg cggcctgctg ccggttctgc ggcctcttcc gcgtcttcgc cttcgccctc 1620
agacgagtcg gatctccctt tgggccgcct ccccgcctgc ctgcaggttt gtcgagacct 1680
agaaaaacat ggagcaatca caagtagcaa tacagcagct accaatgctg attgtgcctg 1740
gctagaagca caagaggagg aggaggtggg ttttccagtc acacctcagg tacctttaag 1800
accaatgact tacaaggcag ctgtagatct tagccacttt ttaaaagaaa aggggggact 1860
ggaagggcta attcactccc aacgaagaca agatctgctt tttgcttgta ctgggtctct 1920
ctggttagac cagatctgag cctgggagct ctctggctaa ctagggaacc cactgcttaa 1980
gcctcaataa agcttgcctt gagtgcttca agtagtgtgt gcccgtctgt tgtgtgactc 2040
tggtaactag agatccctca gaccctttta gtcagtgtgg aaaatctcta gcagggcccg 2100
tttaaacccg ctgatcagcc tcgactgtgc cttctagttg ccagccatct gttgtttgcc 2160
cctcccccgt gccttccttg accctggaag gtgccactcc cactgtcctt tcctaataaa 2220
atgaggaaat tgcatcgcat tgtctgagta ggtgtcattc tattctgggg ggtggggtgg 2280
ggcaggacag caagggggag gattgggaag acaatagcag gcatgctggg gatgcggtgg 2340
gctctatggc ttctgaggcg gaaagaacca gctggggctc taggggggtat ccccacgcgc 2400
cctgtagcgg cgcattaagc gcggcgggtg tggtggttac gcgcagcgtg accgctacac 2460
ttgccagcgc cctagcgccc gctcctttcg ctttcttccc ttcctttctc gccacgttcg 2520
ccggctttcc ccgtcaagct ctaaatcggg gcatcccttt agggttccga tttagtgctt 2580
tacggcacct cgaccccaaa aaacttgatt agggtgatgg ttcacgtagt gggccatcgc 2640
cctgatagac ggtttttcgc cctttgacgt tggagtccac gttctttaat agtggactct 2700
tgttccaaac tggaacaaca ctcaacccta tctcggtcta ttcttttgat ttataaggga 2760
ttttggggat ttcggcctat tggttaaaaa atgagctgat ttaacaaaaa tttaacgcga 2820
attaattctg tggaatgtgt gtcagttagg gtgtggaaag tccccaggct ccccaggcag 2880
gcagaagtat gcaaagcatg catctcaatt agtcagcaac caggtgtgga aagtccccag 2940
gctccccagc aggcagaagt atgcaaagca tgcatctcaa ttagtcagca accatagtcc 3000
cgcccctaac tccgcccatc ccgcccctaa ctccgcccag ttccgcccat tctccgcccc 3060
atggctgact aatttttttt atttatgcag aggccgaggc cgcctctgcc tctgagctat 3120
tccagaagta gtgaggaggc ttttttggag gcctaggctt ttgcaaaaag ctcccgggag 3180
cttgtatatc cattttcgga tctgatcagc acgtgttgac aattaatcat cggcatagta 3240
tatcggcata gtataatacg acaaggtgag gaactaaacc atggccaagt tgaccagtgc 3300
cgttccggtg ctcaccgcgc gcgacgtcgc cggagcggtc gagttctgga ccgaccggct 3360
cgggttctcc cgggacttcg tggaggacga cttcgccggt gtggtccggg acgacgtgac 3420

```
cctgttcatc agcgcggtcc aggaccaggt ggtgccggac aacaccctgg cctgggtgtg   3480
ggtgcgcggc ctggacgagc tgtacgccga gtggtcggag gtcgtgtcca cgaacttccg   3540
ggacgcctcc gggccggcca tgaccgagat cggcgagcag ccgtgggggc gggagttcgc   3600
cctgcgcgac ccggccggca actgcgtgca cttcgtggcc gaggagcagg actgacacgt   3660
gctacgagat ttcgattcca ccgccgcctt ctatgaaagg ttgggcttcg gaatcgtttt   3720
ccgggacgcc ggctggatga tcctccagcg cggggatctc atgctggagt tcttcgccca   3780
ccccaacttg tttattgcag cttataatgg ttacaaataa agcaatagca tcacaaattt   3840
cacaaataaa gcattttttt cactgcattc tagttgtggt ttgtccaaac tcatcaatgt   3900
atcttatcat gtctgtatac cgtcgacctc tagctagagc ttggcgtaat catggtcata   3960
gctgtttcct gtgtgaaatt gttatccgct cacaattcca cacaacatac gagccggaag   4020
cataaagtgt aaagcctggg gtgcctaatg agtgagctaa ctcacattaa ttgcgttgcg   4080
ctcactgccc gctttccagt cgggaaacct gtcgtgccag ctgcattaat gaatcggcca   4140
acgcgcgggg agaggcggtt tgcgtattgg gcgctcttcc gcttcctcgc tcactgactc   4200
gctgcgctcg gtcgttcggc tgcggcgagc ggtatcagct cactcaaagg cggtaatacg   4260
gttatccaca gaatcagggg ataacgcagg aaagaacatg tgagcaaaag gccagcaaaa   4320
ggccaggaac cgtaaaaagg ccgcgttgct ggcgtttttc cataggctcc gcccccctga   4380
cgagcatcac aaaaatcgac gctcaagtca gaggtggcga aacccgacag gactataaag   4440
ataccaggcg tttccccctg gaagctccct cgtgcgctct cctgttccga ccctgccgct   4500
taccggatac ctgtccgcct ttctcccttc gggaagcgtg gcgctttctc aatgctcacg   4560
ctgtaggtat ctcagttcgg tgtaggtcgt tcgctccaag ctgggctgtg tgcacgaacc   4620
ccccgttcag cccgaccgct gcgccttatc cggtaactat cgtcttgagt ccaacccggt   4680
aagacacgac ttatcgccac tggcagcagc cactggtaac aggattagca gagcgaggta   4740
tgtaggcggt gctacagagt tcttgaagtg gtggcctaac tacggctaca ctagaaggac   4800
agtatttggt atctgcgctc tgctgaagcc agttaccttc ggaaaaagag ttggtagctc   4860
ttgatccggc aaacaaacca ccgctggtag cggtggtttt tttgtttgca agcagcagat   4920
tacgcgcaga aaaaaaggat ctcaagaaga tcctttgatc ttttctacgg ggtctgacgc   4980
tcagtggaac gaaaactcac gttaagggat tttggtcatg agattatcaa aaaggatctt   5040
cacctagatc cttttaaatt aaaaatgaag ttttaaatca atctaaagta tatatgagta   5100
aacttggtct gacagttacc aatgcttaat cagtgaggca cctatctcag cgatctgtct   5160
atttcgttca tccatagttg cctgactccc cgtcgtgtag ataactacga tacgggaggg   5220
cttaccatct ggccccagtg ctgcaatgat accgcgagac ccacgctcac cggctccaga   5280
tttatcagca ataaaccagc cagccggaag ggccgagcgc agaagtggtc ctgcaacttt   5340
atccgcctcc atccagtcta ttaattgttg ccgggaagct agagtaagta gttcgccagt   5400
taatagtttg cgcaacgttg ttgccattgc tacaggcatc gtggtgtcac gctcgtcgtt   5460
tggtatggct tcattcagct ccggttccca acgatcaagg cgagttacat gatcccccat   5520
gttgtgcaaa aaagcggtta gctccttcgg tcctccgatc gttgtcagaa gtaagttggc   5580
cgcagtgtta tcactcatgg ttatggcagc actgcataat tctcttactg tcatgccatc   5640
cgtaagatgc ttttctgtga ctggtgagta ctcaaccaag tcattctgag aatagtgtat   5700
gcggcgaccg agttgctctt gcccggcgtc aatacgggat aataccgcgc cacatagcag   5760
aactttaaaa gtgctcatca ttggaaaacg ttcttcgggg cgaaaactct caaggatctt   5820
```

-continued

```
accgctgttg agatccagtt cgatgtaacc cactcgtgca cccaactgat cttcagcatc   5880
ttttactttc accagcgttt ctgggtgagc aaaaacagga aggcaaaatg ccgcaaaaaa   5940
gggaataagg gcgacacgga aatgttgaat actcatactc ttcctttttc aatattattg   6000
aagcatttat cagggttatt gtctcatgag cggatacata tttgaatgta tttagaaaaa   6060
taaacaaata ggggttccgc gcacatttcc ccgaaaagtg ccacctgacg tcgacggatc   6120
gggagatctc ccgatcccct atggtgcact ctcagtacaa tctgctctga tgccgcatag   6180
ttaagccagt atctgctccc tgcttgtgtg ttggaggtcg ctgagtagtg cgcgagcaaa   6240
atttaagcta caacaaggca aggcttgacc gacaattgca tgaagaatct gcttagggtt   6300
aggcgttttg cgctgcttcg cgatgtacgg gccagatata cgcgttgaca ttgattattg   6360
actagttatt aatagtaatc aattacgggg tcattagttc atagcccata tatggagttc   6420
cgcgttacat aacttacggt aaatggcccg cctggctgac cgcccaacga cccccgccca   6480
ttgacgtcaa taatgacgta tgttcccata gtaacgccaa tagggacttt ccattgacgt   6540
caatgggtgg actatttacg gtaaactgcc cacttggcag tacatcaagt gtatcatatg   6600
ccaagtacgc cccctattga cgtcaatgac ggtaaatggc ccgcctggca ttatgcccag   6660
tacatgacct tatgggactt tcctacttgg cagtacatct acgtattagt catcgctatt   6720
accatggtga tgcggttttg gcagtacatc aatgggcgtg gatagcggtt tgactcacgg   6780
ggatttccaa gtctccaccc cattgacgtc aatgggagtt tgttttggca ccaaaatcaa   6840
cgggactttc caaaatgtcg taacaactcc gccccattga cgcaaatggg cggtaggcgt   6900
gtacggtggg aggtctatat aagcagagct ctctggctaa ctagagaacc cactgcttac   6960
tggcttatcg aaattaatac gactcactat agggagaccc aagctggttt aaacttaagc   7020
ttggtaccga gctcactagt ccagtgtggt ggcagatatc cagcacagtg gcggccgctc   7080
gaggggcccg ttttgcctgt actgggtctc tctggttaga ccagatctga gcctgggagc   7140
tctctggcta actagggaac ccactgctta agcctcaata aagcttgcct tgagtgcttc   7200
aagtagtgtg tgcccgtctg ttgtgtgact ctggtaacta gagatccctc agaccctttt   7260
agtcagtgtg gaaaatctct agcagtggcg cccgaacagg gacttgaaag cgaaagggaa   7320
accagaggag ctctctcgac gcaggactcg gcttgctgaa gcgcgcacgg caagaggcga   7380
ggggcggcga ctggtgagta cgccaaaaat tttgactagc ggaggctaga aggagagaga   7440
tgggtgcgag agcgtcagta ttaagcgggg gagaattaga tcgcgatggg aaaaaattcg   7500
gttaaggcca gggggaaaga aaaaatataa attaaaacat atagtatggg caagcaggga   7560
gctagaacga ttcgcagtta atcctggcct gttagaaaca tcagaaggct gtagacaaat   7620
actgggacag ctacaaccat cccttcagac aggatcagaa gaacttagat cattatataa   7680
tacagtagca accctctatt gtgtgcatca aaggatagag ataaaagaca ccaaggaagc   7740
tttagacaag atagaggaag agcaaaacaa aagtaagacc accgcacagc aagcggccgc   7800
tgatcttcag acctggagga ggagatatga gggacaattg gagaagtgaa ttatataaat   7860
ataaagtagt aaaaattgaa ccattaggag tagcacccac caaggcaaag agaagagtgg   7920
tgcagagaga aaaaagagca gtgggaatag gagctttgtt ccttgggttc ttgggagcag   7980
caggaagcac tatgggcgca gcgtcaatga cgctgacggt acaggccaga caattattgt   8040
ctggtatagt gcagcagcag aacaatttgc tgagggctat tgaggcgcaa cagcatctgt   8100
tgcaactcac agtctggggc atcaagcagc tccaggcaag aatcctggct gtggaaagat   8160
```

-continued

```
acctaaagga tcaacagctc ctggggattt ggggttgctc tggaaaactc atttgcacca   8220

ctgctgtgcc ttggaatgct agttggagta ataaatctct ggaacagatt tggaatcaca   8280

cgacctggat ggagtgggac agagaaatta acaattacac aagcttaata cactccttaa   8340

ttgaagaatc gcaaaaccag caagaaaaga atgaacaaga attattggaa ttagataaat   8400

gggcaagttt gtggaattgg tttaacataa caaattggct gtggtatata aaattattca   8460

taatgatagt aggaggcttg gtaggtttaa gaatagtttt tgctgtactt tctatagtga   8520

atagagttag gcagggatat tcaccattat cgtttcagac ccacctccca accccgaggg   8580

gacccgacag gcccttaatt aatcccctga ttctgtggat aaccgtatta ccgcctttga   8640

gtgagctgca caaagaaaca aaccaacctg tctgtattat caaagtgaaa ggctacaata   8700

ggacaaagaa acaaaccaac ctgtctgtat tatcaaagtg aaaggctaca ataggacaaa   8760

gaaacaaacc aacctgtctg tattatcaaa gtgaaaggct acaataggac aaagaaacaa   8820

accaacctgt ctgtattatc aaagtgaaag gctacaatag gacaaagaaa caaaccaacc   8880

tgtctgtatt atcaaagtga aaggctacaa taggacaaag aaacaaacca acctgtctgt   8940

attatcaaag tgaaaggcta caataggaca aagaaacaaa ccaacctgtc tgtattatca   9000

aagtgaaagg ctacaatagg acggtaaact cgacctatat aagcagagct cgtttagtga   9060

accgtcagat cgcctggaga cgccatccac gctgttttga cctccataga agacaccggg   9120

accgatccag cctccgcggc cccgaattga attctaacac cgtgcgtgtt gactatttta   9180

cctctggcgg tgataggcca ttacggcctg ccacc                              9215
```

```
<210> SEQ ID NO 24
<211> LENGTH: 14
<212> TYPE: PRT
<213> ORGANISM: Artificial Sequence
<220> FEATURE:
<223> OTHER INFORMATION: Synthetic

<400> SEQUENCE: 24

Ser Gly Tyr Gly Arg Lys Lys Arg Arg Gln Arg Arg Arg Cys
1               5                   10


<210> SEQ ID NO 25
<211> LENGTH: 19
<212> TYPE: PRT
<213> ORGANISM: Artificial Sequence
<220> FEATURE:
<223> OTHER INFORMATION: Synthetic

<400> SEQUENCE: 25

Ser Gly Arg Gln Ile Lys Ile Trp Phe Gln Asn Arg Arg Met Lys Trp
1               5                   10                  15

Lys Lys Cys


<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Gly Arg Lys Lys Arg Arg Gln Arg Arg Arg Pro Pro Gln Gly
1               5                   10


<210> SEQ ID NO 27
```

<211> LENGTH: 14
<212> TYPE: PRT
<213> ORGANISM: Artificial Sequence
<220> FEATURE:
<223> OTHER INFORMATION: Synthetic

<400> SEQUENCE: 27

Tyr Gly Arg Lys Lys Arg Arg Gln Arg Arg Arg Pro Pro Gln
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Synthetic

<400> SEQUENCE: 28

Cys Arg Gln Ile Lys Ile Trp Phe Gln Asn Arg Arg Met Lys Trp Lys
1               5                   10                  15

Lys

<210> SEQ ID NO 29
<211> LENGTH: 54
<212> TYPE: DNA
<213> ORGANISM: Artificial Sequence
<220> FEATURE:
<223> OTHER INFORMATION: Synthetic

<400> SEQUENCE: 29
gatcccgtaa aaagcgtcgt cgagaaagcc gtaagaaacg tcgacgtgaa agca 54

<210> SEQ ID NO 30
<211> LENGTH: 54
<212> TYPE: DNA
<213> ORGANISM: Artificial Sequence
<220> FEATURE:
<223> OTHER INFORMATION: Synthetic

<400> SEQUENCE: 30
agcttgcttt cacgtcgacg tttcttacgg ctttctcgac gacgcttttt acgg 54

<210> SEQ ID NO 31
<211> LENGTH: 72
<212> TYPE: DNA
<213> ORGANISM: Artificial Sequence
<220> FEATURE:
<223> OTHER INFORMATION: Synthetic

<400> SEQUENCE: 31
gatccggtgc gtatgatctg cgtcgtcgag aacgtcagag ccgtctgcgt cgacgtgaaa 60
gacagagcag aa 72

<210> SEQ ID NO 32
<211> LENGTH: 72
<212> TYPE: DNA
<213> ORGANISM: Artificial Sequence
<220> FEATURE:
<223> OTHER INFORMATION: Synthetic

<400> SEQUENCE: 32
agctttctgc tctgtctttc acgtcgacgc agacggctct gacgttctcg acgacgcaga 60
tcatacgcac cg 72

-continued

```
<210> SEQ ID NO 33
<211> LENGTH: 60
<212> TYPE: DNA
<213> ORGANISM: Artificial Sequence
<220> FEATURE:
<223> OTHER INFORMATION: Synthetic

<400> SEQUENCE: 33

gatccgttaa acgtggactg aaacttcgtc atgttcgtcc gcgtgtgacc cgtgatgtga     60


<210> SEQ ID NO 34
<211> LENGTH: 60
<212> TYPE: DNA
<213> ORGANISM: Artificial Sequence
<220> FEATURE:
<223> OTHER INFORMATION: Synthetic

<400> SEQUENCE: 34

agcttcacat cacgggtcac acgcggacga acatgacgaa gtttcagtcc acgtttaacg     60
```